United States Patent
Burchat et al.

(10) Patent No.: US 9,193,744 B2
(45) Date of Patent: Nov. 24, 2015

(54) HETEROCYCLIC NUCLEAR HORMONE RECEPTOR MODULATORS

(71) Applicants: Andrew Burchat, Shrewsbury, MA (US); Thomas D. Gordon, Medway, MA (US); Kelly D. Mullen, Charlton, MA (US); David C. Ihle, Worcester, MA (US); Michael J. Morytko, Framingham, MA (US); Kevin P. Cusack, Holden, MA (US); Gloria Y. Lo Schiavo, Shrewsbury, MA (US); Lei Wang, Acton, MA (US); Michael Friedman, Brookline, MA (US)

(72) Inventors: Andrew Burchat, Shrewsbury, MA (US); Thomas D. Gordon, Medway, MA (US); Kelly D. Mullen, Charlton, MA (US); David C. Ihle, Worcester, MA (US); Michael J. Morytko, Framingham, MA (US); Kevin P. Cusack, Holden, MA (US); Gloria Y. Lo Schiavo, Shrewsbury, MA (US); Lei Wang, Acton, MA (US); Michael Friedman, Brookline, MA (US)

(73) Assignee: AbbVie Inc., North Chicago, IL (US)

( * ) Notice: Subject to any disclaimer, the term of this patent is extended or adjusted under 35 U.S.C. 154(b) by 3 days.

(21) Appl. No.: 14/019,980

(22) Filed: Sep. 6, 2013

(65) Prior Publication Data

US 2014/0162985 A1   Jun. 12, 2014

Related U.S. Application Data

(60) Provisional application No. 61/698,221, filed on Sep. 7, 2012.

(51) Int. Cl.
| | | |
|---|---|---|
| A61K 31/44 | (2006.01) |
| A61K 31/415 | (2006.01) |
| C07D 471/00 | (2006.01) |
| C07D 491/00 | (2006.01) |
| C07D 498/00 | (2006.01) |
| C07D 513/00 | (2006.01) |
| C07D 515/00 | (2006.01) |
| C07D 231/54 | (2006.01) |
| C07D 487/00 | (2006.01) |
| C07F 9/6503 | (2006.01) |
| C07D 401/06 | (2006.01) |
| C07D 401/14 | (2006.01) |
| C07D 417/08 | (2006.01) |
| C07D 471/04 | (2006.01) |
| C07D 491/044 | (2006.01) |
| C07D 401/04 | (2006.01) |
| C07D 417/06 | (2006.01) |
| C07D 491/113 | (2006.01) |
| C07D 491/20 | (2006.01) |

(52) U.S. Cl.
CPC .......... *C07F 9/65038* (2013.01); *C07D 231/54* (2013.01); *C07D 401/04* (2013.01); *C07D 401/06* (2013.01); *C07D 401/14* (2013.01); *C07D 417/06* (2013.01); *C07D 417/08* (2013.01); *C07D 471/04* (2013.01); *C07D 491/044* (2013.01); *C07D 491/113* (2013.01); *C07D 491/20* (2013.01)

(58) Field of Classification Search
None
See application file for complete search history.

(56) References Cited

U.S. PATENT DOCUMENTS

| | | | |
|---|---|---|---|
| 5,385,947 A | 1/1995 | Godel et al. |
| 6,380,223 B1 | 4/2002 | Dow et al. |
| 6,589,947 B1 | 7/2003 | Hamanaka et al. |
| 6,699,893 B2 | 3/2004 | Dow et al. |
| 6,777,404 B2 | 8/2004 | Hamanaka et al. |
| 6,852,719 B2 | 2/2005 | Liu et al. |
| 7,138,406 B2 | 11/2006 | Chantigny et al. |
| 7,166,593 B2 | 1/2007 | Dow et al. |
| 7,547,714 B2 | 6/2009 | Cheng et al. |
| 7,553,877 B2 | 6/2009 | Chantigny et al. |
| 7,598,231 B2 | 10/2009 | Cheng et al. |
| 7,625,937 B2 | 12/2009 | Ali et al. |
| 7,713,989 B2 | 5/2010 | Dow et al. |
| 7,786,097 B2 | 8/2010 | Cheng et al. |
| 8,067,447 B2 | 11/2011 | Sheppeck et al. |
| 8,093,281 B2 | 1/2012 | Eldred et al. |
| 8,148,409 B2 | 4/2012 | Rucker |
| 8,445,520 B2 | 5/2013 | Cheng et al. |
| 8,658,646 B2 | 2/2014 | Chen et al. |

(Continued)

FOREIGN PATENT DOCUMENTS

| | | |
|---|---|---|
| CN | 102584860 A | 7/2012 |
| EP | 1201660 A1 * | 2/2002 |

(Continued)

OTHER PUBLICATIONS

Greenwald, RB. et al. Drug Delivery Systems: Water Soluble Taxol 2'-Poly(ethylene glycol) Ester Prodrugs-Design and In Vivo Effectiveness. J. Med. Chem. 1996, vol. 39, p. 425.*

(Continued)

*Primary Examiner* — Janet L Andres
*Assistant Examiner* — Ben S Michelson
(74) *Attorney, Agent, or Firm* — McCarter & English, LLP; Elizabeth A. Hanley; Yu Lu

(57) ABSTRACT

The invention provides a compound of Formula (I)

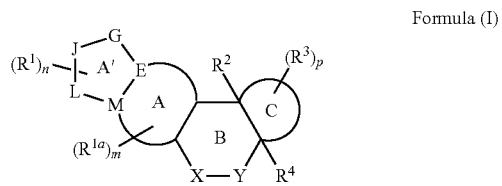

Formula (I)

pharmaceutically acceptable salts, pro-drugs, biologically active metabolites, stereoisomers and isomers thereof wherein the variable are defined herein. The compounds of the invention are useful for treating immunological and oncological conditions.

30 Claims, No Drawings

(56) References Cited

U.S. PATENT DOCUMENTS

| | | |
|---|---|---|
| 2002/0120148 A1 | 8/2002 | Taniguchi et al. |
| 2002/0147336 A1 | 10/2002 | Dow et al. |
| 2003/0105081 A1 | 6/2003 | Yohannes et al. |
| 2003/0199527 A1 | 10/2003 | Hamanaka et al. |
| 2003/0224349 A1 | 12/2003 | Buckbinder |
| 2004/0014741 A1 | 1/2004 | Liu et al. |
| 2004/0110778 A1 | 6/2004 | Yohannes et al. |
| 2004/0138262 A1 | 7/2004 | Chantigny et al. |
| 2004/0176595 A1 | 9/2004 | Dow et al. |
| 2006/0074120 A1 | 4/2006 | Ali et al. |
| 2006/0247264 A1 | 11/2006 | Chantigny et al. |
| 2006/0247266 A1 | 11/2006 | Yamada et al. |
| 2007/0129410 A1 | 6/2007 | Robinson et al. |
| 2008/0188443 A1 | 8/2008 | Cheng et al. |
| 2009/0149445 A1 | 6/2009 | Coghlan et al. |
| 2009/0227548 A1 | 9/2009 | Glossop et al. |
| 2009/0281148 A1 | 11/2009 | Cheng et al. |
| 2010/0069444 A1 | 3/2010 | Rucker |
| 2010/0204239 A1 | 8/2010 | Sui et al. |
| 2010/0286214 A1 | 11/2010 | Cheng et al. |
| 2010/0303758 A1 | 12/2010 | Glossop et al. |
| 2012/0238549 A1 | 9/2012 | Cusack et al. |
| 2014/0179676 A1 | 6/2014 | Cusack et al. |

FOREIGN PATENT DOCUMENTS

| | | |
|---|---|---|
| EP | 1201649 A1 | 5/2002 |
| EP | 1201655 A2 | 5/2002 |
| EP | 1201660 A1 | 5/2002 |
| EP | 2114888 A1 | 11/2009 |
| EP | 2114970 A1 | 11/2009 |
| JP | 2007186480 A | 7/2007 |
| WO | WO-95/18118 A1 | 7/1995 |
| WO | 0020376 A1 | 4/2000 |
| WO | 0066522 A1 | 11/2000 |
| WO | 2004005229 A1 | 1/2004 |
| WO | WO 2004/026248 A2 * | 4/2004 |
| WO | 2004052847 A2 | 6/2004 |
| WO | 2005047254 A1 | 5/2005 |
| WO | WO-2006/081659 A1 | 8/2006 |
| WO | 2008093227 A1 | 8/2008 |
| WO | 2008093236 A1 | 8/2008 |
| WO | 2009069032 A2 | 6/2009 |
| WO | WO-2009/110468 A1 | 9/2009 |
| WO | 2009149139 A1 | 12/2009 |
| WO | 2010013158 A1 | 2/2010 |
| WO | 2010040527 A1 | 4/2010 |
| WO | 2011081173 A1 | 7/2011 |
| WO | WO 2011/081173 A1 * | 7/2011 |

OTHER PUBLICATIONS

Testa, B. et al. Lessons Learned from Marketed and Investigational Prodrugs. J. Med. Chem. 2004, vol. 47(10), p. 2393.*

Carey, FA. Organic Chemistry 6th Ed. McGraw Hill. 2006, chapter 1, p. 9.*

Bungard et al., "Discovery of selective glucocorticoid receptor modulator MK-5932," Bioorg. Med. Chem., 19:7374-7386 (2011).

Akita, H et al., "Diterpeniods. XXXVII. Rearrangement of methyl 13-isopropyl-7-oxo-podocarpa-5,8,11,13-tetraen-15-oate by means of aluminum chloride," Chem. Pharm. Bull. (1975) 23(11):2660-2668.

Bareille, P et al., "Efficacy and safety of once-daily GW870086 a novel selective glucocorticoid in mild-moderate asthmatics: a randomised, two-way crossover, controlled clinical trial," J. Asthma (2013) 50(10):1077-1082.

Bareille, P et al., "Efficacy of a new selective steroid (GW870086) in asthma: an adaptive, randomised, controlled trial," Curr. Drug Therapy (2013) 8(2):69-75.

Barnes, RA et al., "The Stereochemistry of 4a-Methyl-1,2,3,4,4a,9,10,10a-octahydrophenanthrene," J. Am. Chem. Soc. (1955) 77(20):5388-5390.

Brandish, PE et al., "The preclinical efficacy, selectivity and pharmacologic profile of MK-5932, an insulin-sparing selective glucocorticoid receptor modulator," Eur. J. Pharmacology (2014) 724:102-111.

Burnell, RH et al., "The structures of the nellionols. Synthesis of model abieta-8, 11, 13-trien-7-ones. Synthesis of 5-dehydronellionol trimethyl ether," Canadian J. Chem. (1984) 62(12):2822-2829.

Chemical Abstracts Accession No. 1972:448662 & Iresmetov, M et al.: "Synthetic conversions of dehydroabietic acid. II. Synthesis of heterocyclic derivatives of dehydroabietic acid and analogs of D-homo steroids," Sin. Prod. Kanifoli Skipidara (1970) 244-51. From: Ref. Zh., Khim. 1971, Abstr. No. 9Zh546.

CID 11075022 in particular deposit SID 16144193 having a deposit date of Oct. 26, 2006.

CID 11099032 in particular deposit SID 16171282 having a deposit date of Oct. 26, 2006.

Colvin, ES et al., "Glucocorticoid-induced suppression of β-cell proliferation is mediated by Mig6," Endocrinology (2013) 154(3):1039-1046.

Derbenev, AY. et al., "Dexamethasone rapidly increases GABA release in the dorsal motor nucleus of the vagus via retrograde messenger-mediated enhancement of TRPV1 activity," PLoS One (2013) 8(7):e70505.

Erdtman and Malmborg, "Beckmann rearrangement of the oxime of 7-oxodehydroabietate," Acta Chemica Scandinavica (1970) 24(6):2252-2253.

Evans, GB et al., "The Synthesis and Antibacterial Activity of Totarol Derivatives. Part 3: Modification of Ring-B," Bioorg. Med. Chem. (2000) 8:1663-1675.

Fandrick et al., "Zinc Catalyzed and Mediated Propargylations with Propargyl Boronates," Org. Lett., (2010) 12(1):88-91.

Fandrick, DT. et al., "Zinc Catalyzed and Mediated Asymmetric Propargylation of Trifluoromethyl Ketones with a Propargyl Boronate," J. Org. Chem. (2013) 78(8):3592-3615.

Fujita, T et al., "Seven-membered ring compounds. III.Robinson-Mannich reaction to benzocycloheptenones. 3. Synthesis of 3-oxo-11 b-methyl-1 ,2,3,6,7, 11 b-hexahydro-5H-dibenzo-[a,c-]cycloheptatriene," Yakugaku Zasshi (Jan. 1, 1959) pp. 1184-1187.

Fujita, T et al., "Seven-membered ring compounds. IV. Robinson-Mannich reaction to benzocycloheptenones. 4. Synthesis of 3-oxo-11 b-methyl-9 10-dimethoxy- and 9,10,11-trimethoxy-1,2,3,6,7,11 b-hexahydro-5H-dibenzo [a,c]cycloheptatriene," Yakugaku Zasshi (Jan. 1, 1959) pp. 1187-1192.

Fujita, T et al., "Seven-membered ring compounds. VIII. Synthesis of dibenzo[a,c]cyclohepta-1,3-diene," Yakugaku Zasshi (1959) 79:1354-1356.

Harris, PWR et al., "Functionalisation of Alkylalkoxysilanes. Studies Towards Annulations of Diterpenoids," Tetrahedron, Elsevier Science Publishers, Amsterdam, NL, (Jun. 9, 2000) 56(24):4001-4015.

Inamochi, Y. et al., "Histone code of genes induced by co-treatment with a glucocorticoid hormone agonist and a p44/42 MAPK inhibitor in human small intestinal Caco-2 cells," Biochimica et Biophysica Acta, General Subjects (2014) 1840(1):693-700.

Krow, GR., "The Baeyer-Villiger oxidation of ketones and aldehydes," Organic Reactions (Hoboken, NJ, United States) (1993) 43:P251-798.

Kuo, Y-H, et al., "New Diterpenes from the Heartwood of Chamaecyparis obtusa var. formosana," J. Nat. Prod. (1998) 61(6):829-831.

Kuzmich, D et al., "Function-regulating pharmacophores in a sulfonamide class of glucocorticoid receptor agonists," Bioorganic & Medicinal Chemistry Letters (2013) 23:6640-6644.

Pelletier, SW, et al., "The Synthesis of Certain 11,14-Dimethoxydeoxypodocarpic Acid Derivatives. An Application to the Synthesis of (+)-Winterin from Drimys winteri," Tetrahedron, (1977) pp. 1021-1027, URL:http://www.sciencedirect.com/science/article/pii/00404020778022021pdf?md5=80e5526eadf210da5dc578bf28b8b844&pid=1-s2.0-0040402077802202-main.pdf [retrieved on Jul. 4, 2014].

Pettit, GR et al., "Antineoplastic Agents. 529. Isolation and Structure of Nootkastatins 1 and 2 from the Alaskan Yellow Cedar Chamaecyparis nootkatensis," J. Nat. Prod. (2004) 67(9):1476-1482.

(56) References Cited

OTHER PUBLICATIONS

Reeves, JT. et al., "Development of a Large Scale Asymmetric Synthesis of the Glucocorticoid Agonist BI 653048 BS H3PO4," *J. Org. Chem.* (2013) 78(8):3616-3635.

Sanchez and Konopelski, "Phenol Benzylic Epoxide to Quinone Methide Electron Reorganization: Synthesis of (+/−)-Taxodone," *J. Org. Chem.* (1994) 59(18):5445-5452.

Schaffner, K et al., "Triterpenes. CXCI. The stereochemistry of a-onocerin," *Helvetica Chimica Acta* (1956) 39:174-183.

Song, J., "Development of a large scale asymmetric synthesis of the glucocorticoid agonist BI 653048 BS H3PO4," from *Abstracts of Papers, 248th ACS National Meeting & Exposition,* San Francisco, CA, United States, Aug. 10-14, 2014 (2014) ORGN-317.

Steiner, JL. et al., "Glucocorticoids Attenuate the Central Sympathoexcitatory Actions of Insulin," *J. Neurophysiol.* (Sep. 3, 2014) pii: jn.00514.2014. [Epub ahead of print] PubMed PMID: 25185805.

Tanis, SP et al., "Furans in synthesis. 5. Furan-terminated cationic cyclizations in the preparation of fused, spirocyclic and bridged ring systems. An application to the synthesis of nakafuran 9," *J. Org. Chem.* (1985) 50(21):3988-3996.

Tashima, T et al., "Design, synthesis, and BK channel-opening activity of hexahydrodibenzazepinone derivatives," *Bioorganic & Medicinal Chemistry* (2006) 14(23):8014-8031.

Uyanik, M et al., "Supporting INformation for Catalytic Diastereoselective Polycyclization of Homo(polyprenyl)arene Analogues Bearing Terminal Siloxyvinyl Groups," General Procedure for the SnCl 4-Promoted Cyclization S23 Determination of the Relative Sterochemistry of Polycyclic Products S35 References and Notes S40, *Organic Letters* (2006) pp. 5649-5652. Retrieved from the Internet:URL:http://pubs.acs.org/doi/suppl/1 0.1 021/ol062378t/suppl_file/ol062378tsi20061018_123034.pdf [retrieved on Jul. 8, 2014].

Wenkert, E et al., "Condensations of 4-methyl-4-dichloromethyl-2,5-cyclohexadienone," *J. Am. Chem. Soc.* (1969) 91(9):2299-2307.

Wenkert, E et al., "Synthesis of Some Drimanic Sesquiterpenes," *J. Am. Chem. Soc.* (1964) 86(10):2044-2050.

Fujita et al., "Caplus abstract," AN 1960:16868, 1960.

Jung, M., "A Review of Annulation," Tetrahedron, 32:3-31 (1976).

Nathans R., Small-molecule inhibition of HIV-1 VIF. Nature Biotechnology Sep. 2008, vol. 26, No. 10, p. 1188.

Swett R. et al., Pyrazolo[3,4-e][1,4]thiazepines: Synthesis and Structure Proof. Journal of Heterocyclic Chemistry, 1975, vol. 12, No. 6, pp. 1137-1142.

Hudson A et al., "Recent developments in the discovery of the selective glucocorticoid receptor modulators (SGRMs)," 2008, Current Topics in Medicinal Chemistry, 8, 750-765.

* cited by examiner

HETEROCYCLIC NUCLEAR HORMONE RECEPTOR MODULATORS

REFERENCE TO RELATED APPLICATIONS

This application claims the benefit of the filing date of U.S. Provisional Application No. 61/698,221, filed on Sep. 7, 2012, the entire content of which is incorporated herein by reference.

BACKGROUND OF THE INVENTION

The invention provides a novel class of compounds, pharmaceutical compositions comprising such compounds and methods of using such compounds to treat or prevent diseases or disorders associated with modulation of the glucocorticoid receptor. Modulators of the glucocorticoid receptor are useful in the treatment of certain inflammatory related conditions.

Intracellular receptors (IR's) are a class of structurally related proteins involved in the regulation of gene expression. The steroid hormone receptors are a subset of this superfamily whose natural ligands are typically comprised of endogenous steroids such as estradiol, progesterone, and cortisol. Man-made ligands to these receptors play an important role in human health and of these receptors the glucocorticoid receptor (GR) has an essential role in regulating human physiology and immune response.

Steroids which interact with GR have been shown to be potent anti-inflammatory agents. Examples include the glucocorticoid (GC) agonists dexamethasone, prednisone, and prednisolone. The utility of GC agonists in a chronic setting has been limited however due to multiple serious side effects such as osteoporosis, effects on glucose metabolism (diabetogenic), skin thinning, fluid homeostasis and depression for example. (*Expert Opinion on Therapeutic Patents* (2000) 10(1):117). These effects are believed to be the result of cross-reactivity with other steroid receptors such as estrogen, progesterone, androgen, and mineralocorticoid receptors which have somewhat homologous ligand binding domains, and/or the inability to selectively modulate downstream signaling. Identification of a selective glucocorticoid receptor modulator (SGRM) that is efficacious with reduced side-effects could fulfill an unmet medical need.

Selective GR modulators (e.g. repressors, agonists, partial agonists and antagonists) of the present disclosure can be used to influence the basic, life-sustaining systems of the body, including carbohydrate, protein and lipid metabolism, and the functions of the cardiovascular, kidney, central nervous, immune, skeletal muscle, and other organ and tissue systems. In this regard, GR modulators have proven useful in the treatment of inflammation, tissue rejection, auto-immunity, various malignancies, such as leukemias and lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, and Little's syndrome. GR modulators are especially useful in disease states involving systemic inflammation such as inflammatory bowel disease, systemic lupus erythematosus, polyartitis nodosa, Wegener's granulomatosis, giant cell arteritis, rheumatoid arthritis, osteoarthritis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, cirrhosis, juvenile rheumatoid arthritis, juvenile idiopathic arthritis, ankylosing spondylitis, psoriasis, plaque psoriasis, psoriatic arthritis, polymyalgia rheumatica, uveitis and dry eye. GR active compounds have also been used as immunostimulants and repressors, and as wound healing and tissue repair agents.

GR modulators have also found use in a variety of topical diseases such as inflammatory scalp alopecia, panniculitis, psoriasis, discoid lupus erythematosus, inflamed cysts, atopic dermatitis, pyoderma gangrenosum, pemphigus vulgaris, bullous pemphigoid, systemic lupus erythematosus, dermatomyositis, herpes gestationis, eosinophilic fasciitis, relapsing polychondritis, inflammatory vasculitis, sarcoidosis, Sweet's disease, type 1 reactive leprosy, capillary hemangiomas, contact dermatitis, atopic dermatitis, lichen planus, exfoliative dermatitis, erythema nodosum, acne, hirsutism, toxic epidermal necrolysis, erythema multiform, cutaneous T-cell lymphoma and ocular diseases. Selective antagonists of the glucocorticoid receptor have been unsuccessfully pursued for decades. These agents would potentially find application in several disease states associated with Human Immunodeficiency Virus (HIV), cell apoptosis, and cancer including, but not limited to, Kaposi's sarcoma, immune system activation and modulation, desensitization of inflammatory responses, IL-1 expression, anti-retroviral therapy, natural killer cell development, lymphocytic leukemia, and treatment of retinitis pigmentosa. Cogitive and behavioral processes are also susceptible to glucocorticoid therapy where antagonists would potentially be useful in the treatment of processes such as cognitive performance, memory and learning enhancement, depression, addiction, mood disorders, chronic fatigue syndrome, schizophrenia, stroke, sleep disorders, and anxiety.

SUMMARY OF THE INVENTION

One aspect of the invention provides a compound of Formula (I):

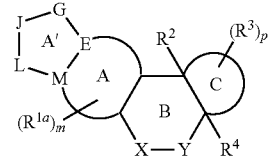

Formula (I)

or a pharmaceutically acceptable salt, pro-drug, biologically active metabolite, isomer, or stereoisomer thereof, wherein:

Ring A' is a heteroaryl ring or an unsaturated or partially unsaturated heterocyclic ring, wherein:
  G is S, O, $CR^1$, $C(R^1)_2$, N, or $NR^1$;
  J is C, $CR^1$, $C(R^1)_2$, O, N, or $NR^1$; and,
  L is C, $CR^1$, $C(R^1)_2$, N, or $NR^1$;
  provided that J is not 0 if G is O or S; and, Ring A is an optionally substituted pyrazine, optionally substituted pyridine, or optionally substituted phenyl;

Ring B is a seven-membered ring optionally substituted with deuterium, wherein:
  X is $-C(R^5)_2-$, $-C(R^5)=$, $-C(=O)-$, $-N(R^a)-$, $-O-$, $-S-$, $-S(O)-$, or $-S(O)_2-$;

or
  when X is —C(R⁵)₂—, both R⁵ substituents, together with the carbon atom to which they are attached, optionally forms a cyclopropyl ring Spiro to Ring B;
Y is —C(R⁵)₂C(R⁵)₂—, =C(R⁵)C(R⁵)₂—, —C(R⁵)₂C(R⁵)=, =C(R⁵)C(R⁵)=, —N(Rᵃ)C(R⁵)₂—, —C(R⁵)₂N(Rᵃ)—, —C(=O)C(R⁵)₂—, —C(R⁵)₂C(=O)—, —O—C(=O)—, —C(=O)—O—, —OC(R⁵)₂—, or —C(R⁵)₂—O—;
  provided that X—Y does not form —N(Rᵃ)—C(R⁵)₂—N(Rᵃ)—, —S—C(R⁵)₂—N(Rᵃ)—, —S—C(R⁵)₂—O—, —O—C(R⁵)₂—N(Rᵃ)—, —C(=O)—C(=O)—C(R₅)₂—, —C(=O)—C(=O)—O—, —N(Rᵃ)—C(R⁵)₂—O—, —O—C(R⁵)₂—O—, —S—C(=O)C(R⁵)₂—, —S—C(=O)—O—, or —S—C(R⁵)₂—O— bonds; and
  provided that X—Y does not result in an oxygen atom adjacent to either a nitrogen atom, a sulfur atom or another oxygen atom; and
  provided that X—Y does not result in two nitrogen atoms adjacent to one another;
Ring C is an optionally substituted, saturated or partially unsaturated, five- or six-membered carbocyclyl or heterocyclyl ring;
R¹ is independently H, deuterium, —Br, —Cl, —F, —CF₃, —CN, —ORᵇ, -optionally substituted (C₁-C₃)alkylene-Rᵇ, optionally substituted (C₁-C₃)alkyl, optionally substituted aryl, optionally substituted (C₃-C₆)cycloalkyl, optionally substituted heteroaryl, optionally substituted heterocyclyl, —S(O)₂Rb—, =O, or —N(Rᵃ)(Rᵇ);
R¹ᵃ is independently H, deuterium, —Br, —Cl, —F, —CF₃, —CN, optionally substituted (C₁-C₆)alkyl, optionally substituted (C₃-C₆)cycloalkyl, optionally substituted heterocyclyl, —S(O)₂—Rᵃ, or —N(Rᵃ)₂;
R² is —CD₃, —CH₂CD₃, —CN, -allyl, —CH₂NHC(=O)(C₁-C₃)alkyl, —CH₂NHSO₂(C₁-C₃)alkyl, —N(R)—SO₂-optionally substituted alkyl; —N(R)(Rᵍ), —N(R)-optionally substituted cycloalkyl, —N(R)-optionally substituted aryl, —N(R)-optionally substituted heteroaryl, —N(R)-optionally substituted heterocyclyl, —N(R)C(O)-optionally substituted alkyl, —N(R)₂, —C(O)N(Rᵃ)₂, —CH₂-optionally substituted aryl, —CH₂-optionally substituted (C₃-C₆)cycloalkyl, optionally substituted (C₁-C₃)alkyl, optionally substituted (C₂-C₃)alkenyl, —CH₂-optionally substituted heteroaryl, —(CH₂)ₙ₁-optionally substituted heterocyclyl, —C(Rᵈ)₂—Rᵉ, or —C(=O)—Rᵉ, provided that when R² is —C(Rᵈ)₂—Rᵉ, only one Rᵈ can be OH;
R³ is independently a bond, deuterium, —CD₃, —CF₃, —N(Rᵃ)SO₂Rᶜ, —N(Rᵃ)CORᶜ, —CON(Rᵃ)Rᶜ, —N(Rᵃ)COORᶜ, —N(Rᵃ)₂, —O—C(O)NR-optionally substituted alkyl, optionally substituted (C₂-C₆)alkynyl, =O, —ORᵃ, —ORᶠ, optionally substituted (C₁-C₄)alkyl, optionally substituted (C₁-C₄)alkyl-O—(C₁-C₄)alkyl, —(C(Rᵃ)₂)ᵣ-optionally substituted (C₃-C₆)cycloalkyl, —(C(Rᵃ)₂)ᵣ-optionally substituted aryl, —(C(Rᵃ)₂)ᵣ-optionally substituted heteroaryl, —(C(Rᵃ)₂)ᵣ—N(Rᵃ)-optionally substituted heteroaryl, —(C(Rᵃ)₂)ᵣ—N(Rᵃ)—(C(Rᵃ)₂)ᵣ-optionally substituted aryl, or a carbocyclic or heterocyclic spirocyclic moiety attached to ring C;

R⁴ is a bond, H, deuterium, —CD₃, —F, optionally substituted (C₁-C₃)alkyl, —OH or —O-optionally substituted (C₁-C₃)alkyl;
R⁵ is independently H, deuterium, —CD₃, —F, —CF₃, —N(Rᵃ), —ORᵃ, or optionally substituted (C₁-C₃) alkyl; and,
Rᵃ is independently H, deuterium, optionally substituted (C₃-C₆)cycloalkyl, or optionally substituted (C₁-C₃) alkyl;
Rᵇ is H, optionally substituted (C₁-C₃)alkyl, optionally substituted aryl, optionally substituted (C₃-C₆)cycloalkyl, optionally substituted heteroaryl, or optionally substituted heterocyclyl;
Rᶜ is optionally substituted (C₁-C₃)alkyl or optionally substituted aryl;
Rᵈ is independently H, deuterium, —OH, or optionally substituted (C₁-C₆) alkyl;
Rᵉ is —CF₃, optionally substituted aryl, optionally substituted (C₁-C₆)alkyl, optionally substituted (C₃-C₆) cycloalkyl, optionally substituted heteroaryl, or optionally substituted heterocyclyl;
Rᶠ is —H, —SO₂NH₂, —CH₂CO₂H, —CH₂CONH₂, —P(=O)(OH)(OH), —C(O)-optionally substituted (C₁-C₆) alkyl, —C(O)N(optionally substituted (C₁-C₆)alkyl)₂, —C(O) (optionally substituted (C₁-C₆) alkyl)₂, —C(O)-optionally substituted aryl, —C(O)-optionally substituted heterocyclyl, —C(O)-optionally substituted (C₃-C₆)cycloalkyl, —C(O)—CR₂-optionally substituted heterocyclyl or —C(O)—CR₂-optionally substituted heteroaryl
Rᵍ is —CH₂-optionally substituted (C₃-C₆)cycloalkyl, —CH₂-optionally substituted heteroaryl, or —CH₂-optionally substituted heterocyclyl;
R is independently H or (C₁-C₃)alkyl;
m is 0, 1, or 2;
n1 is independently 0 or 1;
p is 1, 2, 3 or 4; and
r is independently 0, 1 or 2.

In one embodiment, the compound is represented by any one of the structures shown below:

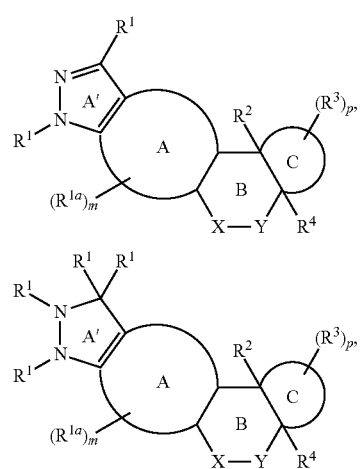

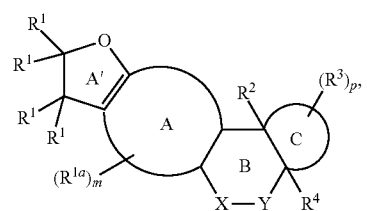
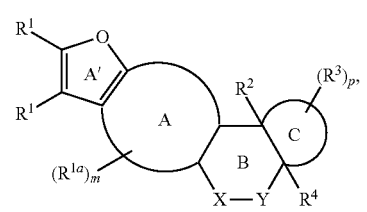
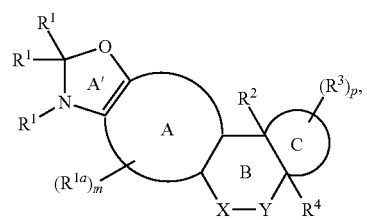
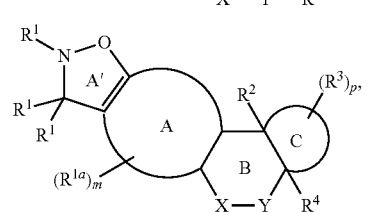
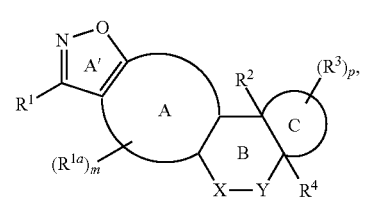
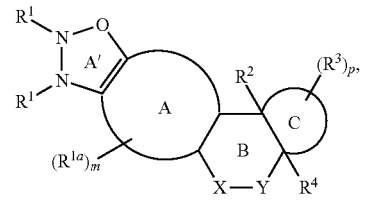
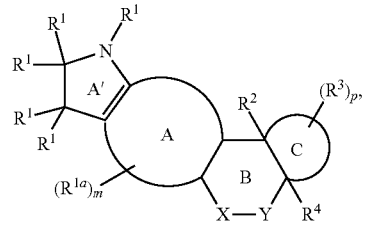
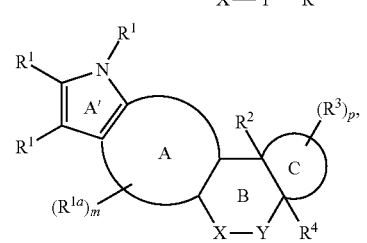
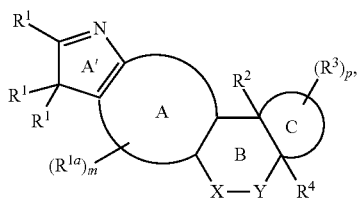
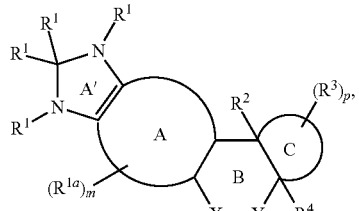
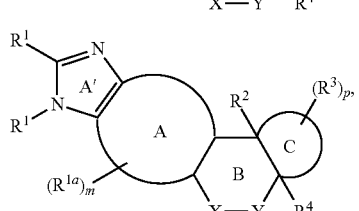
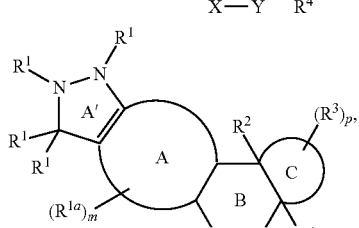
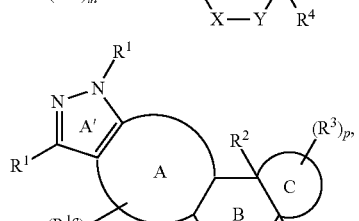
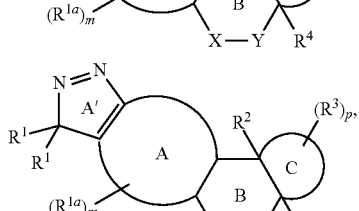
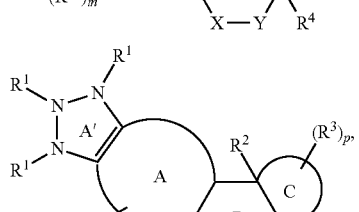
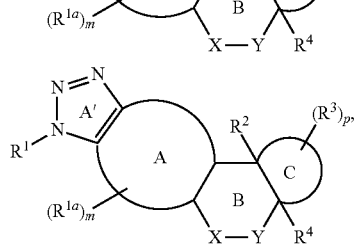

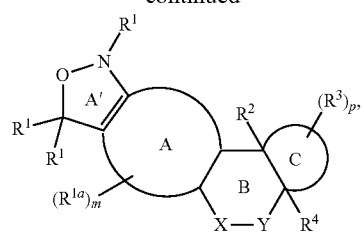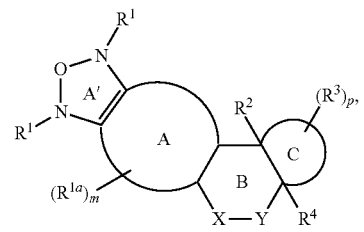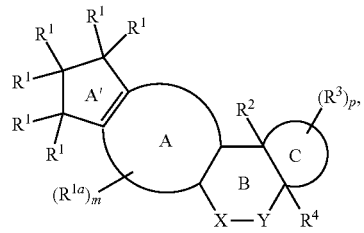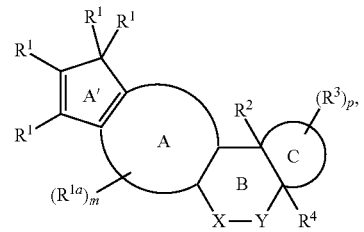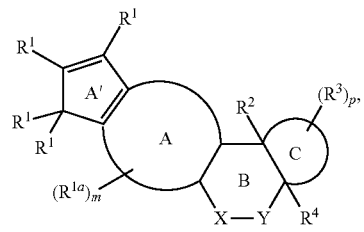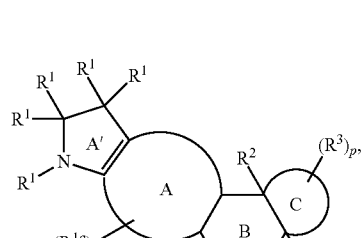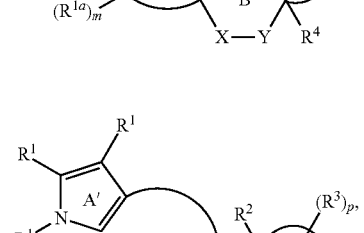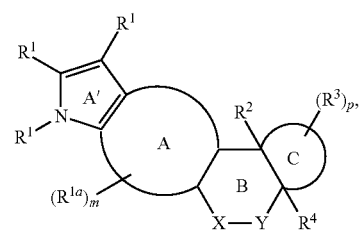
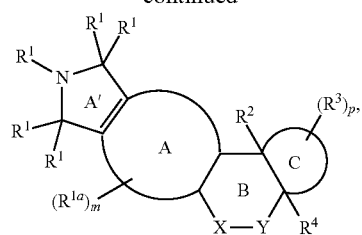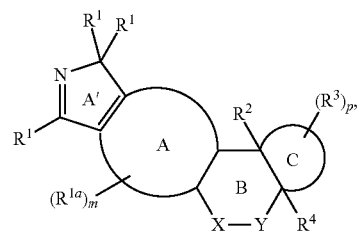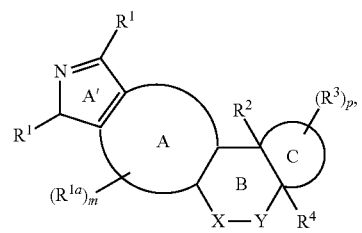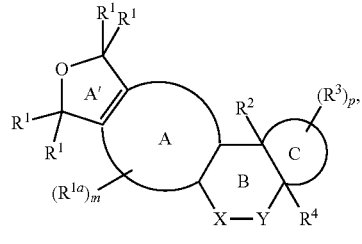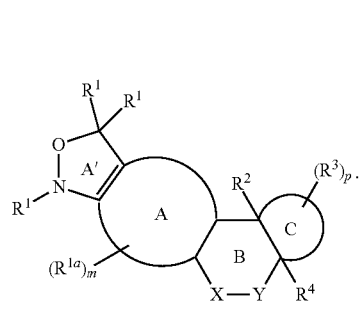
In one embodiment, the compound of any of the preceding embodiments is represented by Formula (I)':
Formula (I)'
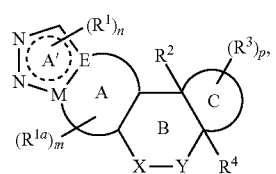
wherein n is 0, 1, 2, or 3.

In one embodiment, the compound of any of the preceding embodiments is represented by Formula (I)A:

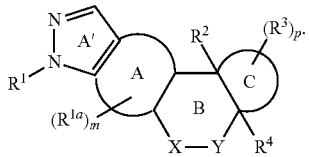

Formula (I)A

In one embodiment, the compound of any of the preceding embodiments is represented by Formula (I)B:

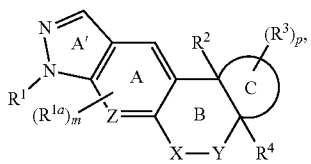

Formula (I)B wherein Z is $CR^{1a}$ or N.

In one embodiment, in the compound of any of the preceding embodiments, Ring C is optionally substituted cyclohexyl.

In one embodiment, in the compound of any of the preceding embodiments, Ring C is represented by Formula (C):

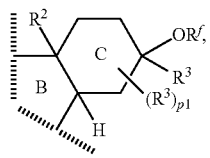

Formula (C)

wherein p1 is 0, 1, or 2; and the ⁞⁞⁞⁞ lines represent the respective Rings A', A, and the remaining portion of Ring B, and substituents thereof.

In one embodiment, in the compound of any of the preceding embodiments, Ring C is optionally substituted cyclopentyl.

In one embodiment, in the compound of any of the preceding embodiments, Ring C is represented by Formula (C'):

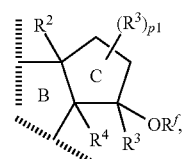

Formula (C')

wherein p1 is 0, 1, or 2; $R^4$ is H or —$CH_2OH$; and the ⁞⁞⁞⁞ lines represent the respective Rings A', A, and the remaining portion of Ring B, and substituents thereof.

In one embodiment, in the compound of any of the preceding embodiments, Ring C is represented by Formula (C"):

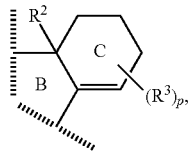

Formula (C")

wherein the ⁞⁞⁞⁞ lines represent the respective Rings A', A, and the remaining portion of Ring B, and substituents thereof.

In one embodiment, in the compound of any of the preceding embodiments, X is —$C(R^5)_2$—, —$C(R^5)$=, —C(=O)—, —O—, or —$N(R^a)$—.

In one embodiment, in the compound of any of the preceding embodiments, X is —$CH_2$—, —C(=O)—, —CH=, —CH(OH)—, or —O—.

In one embodiment, in the compound of any of the preceding embodiments, Y is —$CH_2$—$CH_2$—, =CH—$CH_2$—, or —CH—$CH_2$=.

In one embodiment, the compound of any of the preceding embodiments is represented by Formula (I)D1 or Formula (I)D2, and p2 is 0, 1, or 2:

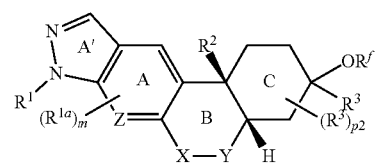

Formula (I)D1

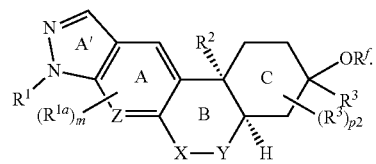

Formula (I)D2

In one embodiment, the compound of any of the preceding embodiments is represented by Formula (I)D1E1 or Formula (I)D1E2, and p2 is 0, 1, or 2:

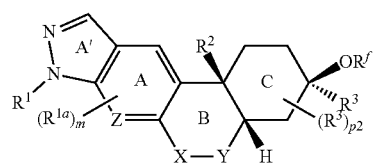

Formula (I)D1E1

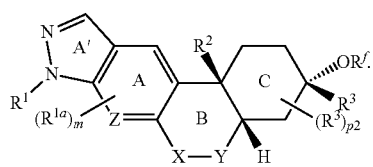

Formula (I)D1E2

In one embodiment, the compound of any of the preceding embodiments is represented by Formula (I)D2E1 or Formula (I)D2E2, and p2 is 0, 1, or 2:

Formula (I)D2E1

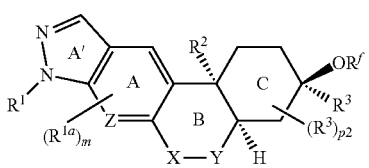

Formula (I)D2E2

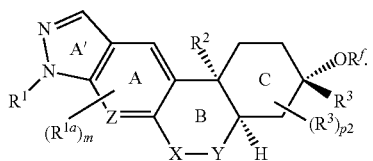

In one embodiment, the compound of any of the preceding embodiments is represented by Formula (I)D3 or Formula (I)D4, and p2 is 0, 1, or 2:

Formula (I)D3

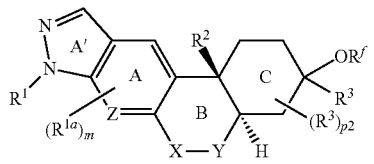

Formula (I)D4

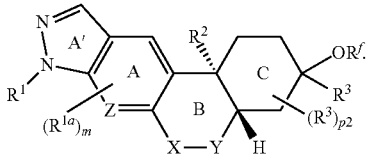

In one embodiment, the compound of any of the preceding embodiments is represented by Formula (I)D3E1 or Formula (I)D3E2, and p2 is 0, 1, or 2:

Formula (I)D3E1

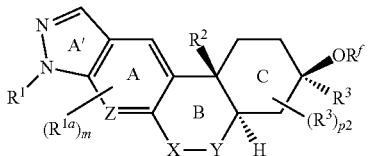

Formula (I)D3E2

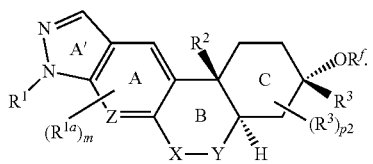

In one embodiment, the compound of any of the preceding embodiments is represented by Formula (I)D4E1 or Formula (I)D4E2, and p2 is 0, 1, or 2:

Formula (I)D4E1

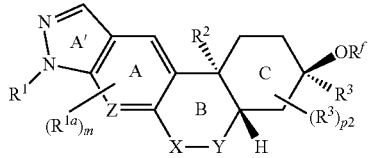

Formula (I)D4E2

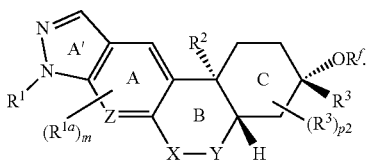

In one embodiment, in the compound of any of the preceding embodiments, $R^1$ is independently H, —$CH_2$-optionally substituted heteroaryl, optionally substituted phenyl, optionally substituted benzyl, or optionally substituted heteroaryl.

In one embodiment, in the compound of any of the preceding embodiments, $R^1$ is optionally substituted azetidinyl, optionally substituted phenyl, optionally substituted piperidinyl, optionally substituted pyrimidinyl, optionally substituted pyridinyl, optionally substituted pyrazolyl, optionally substituted pyrrolidinyl, optionally substituted tetrazolyl or optionally substsituted thiadiazolyl.

In one embodiment, in the compound of any of the preceding embodiments, $R^1$ is optionally substituted phenyl.

In one embodiment, in the compound of any of the preceding embodiments, $R^1$ is 4-fluorophenyl or 4-(methylsulfonyl)phenyl.

In one embodiment, in the compound of any of the preceding embodiments, $R^1$ is optionally substituted heteroaryl.

In one embodiment, in the compound of any of the preceding embodiments, $R^1$ is 2-, 3-, or 4-pyridine, or 2-, 4-, or 5-pyrimidine, optionally substituted by $C_{1-3}$ alkyl or $C_{1-3}$ alkoxy.

In one embodiment, in the compound of any of the preceding embodiments, $R^{1a}$ is independently H, deuterium, Br, Cl, F, or optionally substituted ($C_1$-$C_3$)alkyl.

In one embodiment, in the compound of any of the preceding embodiments, $R^3$ is independently H, —$CF_3$, —C≡$CCH_3$, optionally substituted ($C_1$-$C_4$)alkyl, optionally substituted —($C_1$-$C_4$)alkyl-O—($C_1$-$C_4$)alkyl, —$C(R^a)_2)_r$-optionally substituted ($C_3$-$C_6$)cycloalkyl, optionally substituted aryl, optionally substituted heteroaryl, or —$(CH_2)_r$-optionally substituted aryl.

In one embodiment, in the compound of any of the preceding embodiments, $R^3$ is independently H, —$CF_3$, =O, —$OR^f$, optionally substituted ($C_1$-$C_4$)alkyl, optionally substituted ($C_2$-$C_6$)alkynyl, optionally substituted —($C_1$-$C_4$)alkyl-O—($C_1$-$C_4$)alkyl, optionally substituted aryl.

In one embodiment, in the compound of any of the preceding embodiments, —$OR^f$ is independently —OH, —$OSO_2NH_2$, —$OCH_2CO_2H$, —$OCH_2CONH_2$, or —OP(=O)(OH)(OH).

In one embodiment, in the compound of any of the preceding embodiments, —$OR^f$ is attached to a carbon additionally substituted by an $R^3$ selected from: —$C_{1-3}$ alkyl, —$(CH_2)_{0-3}$—CN, —$CH_2$—O—$C_{1-3}$ alkyl, —$CF_3$, —$CH_2$—NH—CH($CH_3$)-phenyl, -phenyl, —C≡CH, or —C≡C—$C_{1-3}$ alkyl.

In one embodiment, in the compound of any of the preceding embodiments, $R^2$ is —$CH_2$—$CH_3$, —$CH_2$—$CF_3$, —$(CH_2)_r$-optionally substituted aryl, or optionally substituted ($C_1$-$C_3$)alkyl.

In one embodiment, in the compound of any of the preceding embodiments, R² is —CN, —CH₂-optionally substituted (C₃-C₆)cycloalkyl, —C(=O)—Rᵉ, —(CH₂)ᵣ-optionally substituted heteroaryl, —CH₂-optionally substituted heterocyclyl, or optionally substituted (C₁-C₃)alkyl.

In one embodiment, in the compound of any of the preceding embodiments, R² is —CN, —CH₂CH₃, —CH₂OH, —CH₂CN, —CH₂NHC(=O)CH₃, —CH₂NHSO₂(C₁-C₃)alkyl, —CH₂-2-pyridinyl, —CH₂-2-pyrimidinyl, —C(=O)-2-pyridinyl, —CH₂-cyclopropyl, or

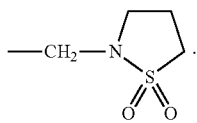

In one embodiment, in the compound of any of the preceding embodiments, Z is N.

In one embodiment, in the compound of any of the preceding embodiments, Z is CR¹ᵃ; m is 1; and R¹ᵃ is H, deuterium, C₁₋₃ alkyl (e.g., Me), Cl, Br, or F.

In one embodiment, the compound is selected from:
(3S,4aS,12bR)-12b-Ethyl-9-(4-fluoro-phenyl)-3-trifluoromethyl-1,2,3,4,4a,5,6,7,9,12b-decahydro-9,10-diaza-benzo[3,4]cyclohepta[1,2-f]inden-3-ol; compound with (3R,4aR,12bS)-12b-ethyl-9-(4-fluoro-phenyl)-3-trifluoromethyl-1,2,3,4,4a,5,6,7,9,12b-decahydro-9,10-diaza-benzo[3,4]cyclohepta[1,2-f]inden-3-ol;
(3R,4aR,12bS)-12b-Ethyl-9-(4-fluoro-phenyl)-3-trifluoromethyl-1,2,3,4,4a,5,6,7,9,12b-decahydro-9,10-diaza-benzo[3,4]cyclohepta[1,2-f]inden-3-ol;
(3S,4aS,12bR)-12b-Ethyl-9-(4-fluoro-phenyl)-3-trifluoromethyl-1,2,3,4,4a,5,6,7,9,12b-decahydro-9,10-diaza-benzo[3,4]cyclohepta[1,2-f]inden-3-ol;
(3S,4aR,12bR)-12b-Ethyl-9-(4-fluoro-phenyl)-3-propyl-1,2,3,4,4a,5,6,7,9,12b-decahydro-9,10-diaza-benzo[3,4]cyclohepta[1,2-f]inden-3-ol; compound with (3R,4aS,12bS)-12b-ethyl-9-(4-fluoro-phenyl)-3-propyl-1,2,3,4,4a,5,6,7,9,12b-decahydro-9,10-diaza-benzo[3,4]cyclohepta[1,2-f]inden-3-ol;
(3R,4aS,12bR)-12b-Ethyl-3-methoxymethyl-1,2,3,4,4a,5,6,7,9,12b-decahydro-9,10-diaza-benzo[3,4]cyclohepta[1,2-f]inden-3-ol; compound with (3S,4aR,12bS)-12b-ethyl-3-methoxymethyl-1,2,3,4,4a,5,6,7,9,12b-decahydro-9,10-diaza-benzo[3,4]cyclohepta[1,2-f]inden-3-ol;
(3R,4aS,12bS)-9-(4-fluorophenyl)-3-methyl-12b-(pyridin-2-ylmethyl)-1,2,3,4,4a,5,6,7,9,12b-decahydrobenzo[6,7]cyclohepta[1,2-f]indazol-3-ol;
(3S,4aR,12bR)-9-(4-fluorophenyl)-3-methyl-12b-(pyridin-2-ylmethyl)-1,2,3,4,4a,5,6,7,9,12b-decahydrobenzo[6,7]cyclohepta[1,2-f]indazol-3-ol;
2-((3R,4aS,12bS)-9-(4-fluorophenyl)-3-hydroxy-12b-(pyridin-2-ylmethyl)-1,2,3,4,4a,5,6,7,9,12b-decahydrobenzo[6,7]cyclohepta[1,2-f]indazol-3-yl)acetonitrile;
2-((3S,4aR,12bR)-9-(4-fluorophenyl)-3-hydroxy-12b-(pyridin-2-ylmethyl)-1,2,3,4,4a,5,6,7,9,12b-decahydrobenzo[6,7]cyclohepta[1,2-f]indazol-3-yl)acetonitrile;
(3S,4aS,12bS)-9-(4-fluorophenyl)-12b-(pyridin-2-ylmethyl)-3-(trifluoromethyl)-1,2,3,4,4a,5,6,7,9,12b-decahydrobenzo[6,7]cyclohepta[1,2-f]indazol-3-ol;
(3R,4aR,12bR)-9-(4-fluorophenyl)-12b-(pyridin-2-ylmethyl)-3-(trifluoromethyl)-1,2,3,4,4a,5,6,7,9,12b-decahydrobenzo[6,7]cyclohepta[1,2-f]indazol-3-ol;
(3S,4aS,12bR)-12b-(cyclopropylmethyl)-9-(4-fluorophenyl)-3-(trifluoromethyl)-1,2,3,4,4a,5,6,7,9,12b-decahydrobenzo[6,7]cyclohepta[1,2-f]indazol-3-ol;
(3R,4aR,12bS)-12b-(cyclopropylmethyl)-9-(4-fluorophenyl)-3-(trifluoromethyl)-1,2,3,4,4a,5,6,7,9,12b-decahydrobenzo[6,7]cyclohepta[1,2-f]indazol-3-ol;
rac-(3R,4aR,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol;
((3S,4aR,12bR)-12b-Ethyl-9-(4-fluoro-phenyl)-3-propyl-1,2,3,4,4a,5,6,7,9,12b-decahydro-9,10-diaza-benzo[3,4]cyclohepta[1,2-f]inden-3-ol;
(3R,4aS,12bS)-12b-ethyl-9-(4-fluoro-phenyl)-3-propyl-1,2,3,4,4a,5,6,7,9,12b-decahydro-9,10-diaza-benzo[3,4]cyclohepta[1,2-f]inden-3-ol;
(3S,4aR,12bR)-12b-Ethyl-9-(4-fluoro-phenyl)-3-methoxymethyl-1,2,3,4,4a,5,6,7,9,12b-decahydro-9,10-diaza-benzo[3,4]cyclohepta[1,2-f]inden-3-ol;
(3R,4aS,12bS)-12b-Ethyl-9-(4-fluoro-phenyl)-3-methoxymethyl-1,2,3,4,4a,5,6,7,9,12b-decahydro-9,10-diaza-benzo[3,4]cyclohepta[1,2-f]inden-3-ol;
(3S,4aR,12bR)-3-Ethoxymethyl-12b-ethyl-9-(4-fluoro-phenyl)-1,2,3,4,4a,5,6,7,9,12b-decahydro-9,10-diaza-benzo[3,4]cyclohepta[1,2-f]inden-3-ol;
(3R,4aS,12bS)-3-Ethoxymethyl-12b-ethyl-9-(4-fluoro-phenyl)-1,2,3,4,4a,5,6,7,9,12b-decahydro-9,10-diaza-benzo[3,4]cyclohepta[1,2-f]inden-3-ol;
(3R,4aS,12bS)-9-(4-fluoro-phenyl)-3-methoxymethyl-12b-pyridin-2-ylmethyl-1,2,3,4,4a,5,6,7,9,12b-decahydro-9,10-diaza-benzo[3,4]cyclohepta[1,2-f]inden-3-ol;
(3S,4aR,12bR)-9-(4-Fluoro-phenyl)-3-methoxymethyl-12b-pyridin-2-ylmethyl-1,2,3,4,4a,5,6,7,9,12b-decahydro-9,10-diaza-benzo[3,4]cyclohepta[1,2-f]inden-3-ol;
(3R,4aS,12bR)-12b-Ethyl-3-methoxymethyl-1,2,3,4,4a,5,6,7,9,12b-decahydro-9,10-diaza-benzo[3,4]cyclohepta[1,2-f]inden-3-ol;
compound with (3S,4aR,12bS)-12b-ethyl-3-methoxymethyl-1,2,3,4,4a,5,6,7,9,12b-decahydro-9,10-diaza-benzo[3,4]cyclohepta[1,2-f]inden-3-ol;
(3R,4aS,12bS)-9-(4-fluorophenyl)-3-methyl-12b-(pyridin-2-ylmethyl)-1,2,3,4,4a,5,6,7,9,12b-decahydrobenzo[6,7]cyclohepta[1,2-f]indazol-3-ol;
(3S,4aR,12bR)-9-(4-fluorophenyl)-3-methyl-12b-(pyridin-2-ylmethyl)-1,2,3,4,4a,5,6,7,9,12b-decahydrobenzo[6,7]cyclohepta[1,2-f]indazol-3-ol;
2-((3R,4aS,12bS)-9-(4-fluorophenyl)-3-hydroxy-12b-(pyridin-2-ylmethyl)-1,2,3,4,4a,5,6,7,9,12b-decahydrobenzo[6,7]cyclohepta[1,2-f]indazol-3-yl)acetonitrile;
2-((3S,4aR,12bR)-9-(4-fluorophenyl)-3-hydroxy-12b-(pyridin-2-ylmethyl)-1,2,3,4,4a,5,6,7,9,12b-decahydrobenzo[6,7]cyclohepta[1,2-f]indazol-3-yl)acetonitrile;
(3S,4aS,12bS)-9-(4-fluorophenyl)-12b-(pyridin-2-ylmethyl)-3-(trifluoromethyl)-1,2,3,4,4a,5,6,7,9,12b-decahydrobenzo[6,7]cyclohepta[1,2-f]indazol-3-ol;
(3R,4aR,12bR)-9-(4-fluorophenyl)-12b-(pyridin-2-ylmethyl)-3-(trifluoromethyl)-1,2,3,4,4a,5,6,7,9,12b-decahydrobenzo[6,7]cyclohepta[1,2-f]indazol-3-ol;
(3S,4aS,12bR)-12b-(cyclopropylmethyl)-9-(4-fluorophenyl)-3-(trifluoromethyl)-1,2,3,4,4a,5,6,7,9,12b-decahydrobenzo[6,7]cyclohepta[1,2-f]indazol-3-ol;
(3R,4aR,12bS)-12b-(cyclopropylmethyl)-9-(4-fluorophenyl)-3-(trifluoromethyl)-1,2,3,4,4a,5,6,7,9,12b-decahydrobenzo[6,7]cyclohepta[1,2-f]indazol-3-ol;
rac-(3R,4aR,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol;

(3S,4aS,12bS)-12b-ethyl-9-(4-fluorophenyl)-3-(trifluorom-ethyl)-1,2,3,4,4a,5,6,7,9,12b-decahydrobenzo[6,7]cyclohepta[1,2-f]indazol-3-ol;

(3R,4aR,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol;

(3S,4aR,12bR)-3-ethyl-9-(4-fluorophenyl)-12b-(pyridin-2-ylmethyl)-1,2,3,4,4a,5,6,7,9,12b-decahydrobenzo[6,7]cyclohepta[1,2-f]indazol-3-ol;

(3R,4aS,12bS)-3-ethyl-9-(4-fluorophenyl)-12b-(pyridin-2-ylmethyl)-1,2,3,4,4a,5,6,7,9,12b-decahydrobenzo[6,7]cyclohepta[1,2-f]indazol-3-ol;

(3R,4aS,12bS)-3-ethyl-9-(4-fluorophenyl)-12b-(pyrimidin-2-ylmethyl)-1,2,3,4,4a,5,6,7,9,12b-decahydrobenzo[6,7]cyclohepta[1,2-f]indazol-3-ol;

(3S,4aR,12bR)-3-ethyl-9-(4-fluorophenyl)-12b-(pyrimidin-2-ylmethyl)-1,2,3,4,4a,5,6,7,9,12b-decahydrobenzo[6,7]cyclohepta[1,2-f]indazol-3-ol;

(3R,4aS,12bS)-3-methyl-12b-(pyridin-2-ylmethyl)-9-(pyridin-4-yl)-1,2,3,4,4a,5,6,7,9,12b-decahydrobenzo[6,7]cyclohepta[1,2-f]indazol-3-ol;

(3S,4aR,12bR)-3-methyl-12b-(pyridin-2-ylmethyl)-9-(pyridin-4-yl)-1,2,3,4,4a,5,6,7,9,12b-decahydrobenzo[6,7]cyclohepta[1,2-f]indazol-3-ol;

(3R,4aS,12bS)-3-(ethoxymethyl)-9-(4-fluorophenyl)-12b-(pyridin-2-ylmethyl)-1,2,3,4,4a,5,6,7,9,12b-decahydrobenzo[6,7]cyclohepta[1,2-f]indazol-3-ol;

(3S,4aR,12bR)-3-(ethoxymethyl)-9-(4-fluorophenyl)-12b-(pyridin-2-ylmethyl)-1,2,3,4,4a,5,6,7,9,12b-decahydrobenzo[6,7]cyclohepta[1,2-f]indazol-3-ol;

(3S,4aR,12bS)-12b-ethyl-9-(4-fluorophenyl)-3-(methoxymethyl)-1,2,3,4,4a,5,6,7,9,12b-decahydrobenzo[6,7]cyclohepta[1,2-f]indazol-3-ol;

(3R,4aS,12bR)-12b-ethyl-9-(4-fluorophenyl)-3-(methoxymethyl)-1,2,3,4,4a,5,6,7,9,12b-decahydrobenzo[6,7]cyclohepta[1,2-f]indazol-3-ol;

(3S,4aR,12bR)-9-(4-fluorophenyl)-3-(methoxymethyl)-12b-(pyrimidin-2-ylmethyl)-1,2,3,4,4a,5,6,7,9,12b-decahydrobenzo[6,7]cyclohepta[1,2-f]indazol-3-ol;

(3R,4aR,12bR)-12b-ethyl-9-(4-fluorophenyl)-3-(methoxymethyl)-1,2,3,4,4a,5,6,7,9,12b-decahydrobenzo[6,7]cyclohepta[1,2-f]indazol-3-ol;

(3S,4aS,12bS)-12b-ethyl-9-(4-fluorophenyl)-3-(methoxymethyl)-1,2,3,4,4a,5,6,7,9,12b-decahydrobenzo[6,7]cyclohepta[1,2-f]indazol-3-ol;

(3S,4aR,12bR)-12b-(cyclopropylmethyl)-9-(4-fluorophenyl)-3-(methoxymethyl)-1,2,3,4,4a,5,6,7,9,12b-decahydrobenzo[6,7]cyclohepta[1,2-f]indazol-3-ol;

(3R,4aS,12bS)-12b-(cyclopropylmethyl)-9-(4-fluorophenyl)-3-(methoxymethyl)-1,2,3,4,4a,5,6,7,9,12b-decahydrobenzo[6,7]cyclohepta[1,2-f]indazol-3-ol;

(3R,4aS,12bS)-9-(4-fluorophenyl)-3-(methoxymethyl)-12b-(pyrimidin-2-ylmethyl)-1,2,3,4,4a,5,6,7,9,12b-decahydrobenzo[6,7]cyclohepta[1,2-f]indazol-3-ol;

rac-(3R,4aS,12bR)-12b-ethyl-3-(methoxymethyl)-9-(pyridin-4-yl)-1,2,3,4,4a,5,6,7,9,12b-decahydrobenzo[6,7]cyclohepta[1,2-f]indazol-3-ol;

(3S,4aR,12bS)-12b-ethyl-3-(methoxymethyl)-9-(pyridin-3-yl)-1,2,3,4,4a,5,6,7,9,12b-decahydrobenzo[6,7]cyclohepta[1,2-f]indazol-3-ol;

(3R,4aS,12bR)-12b-ethyl-3-(methoxymethyl)-9-(pyridin-3-yl)-rac-(3R,4aS,12bR)-12b-ethyl-3-(methoxymethyl)-9-(2-methylpyridin-4-yl)-1,2,3,4,4a,5,6,7,9,12b-decahydrobenzo[6,7]cyclohepta[1,2-f]indazol-3-ol;

1,2,3,4,4a,5,6,7,9,12b-decahydrobenzo[6,7]cyclohepta[1,2-f]indazol-3-ol;

(3S,4aR,12bS)-12b-ethyl-3-(methoxymethyl)-9-(pyridin-2-yl)-1,2,3,4,4a,5,6,7,9,12b-decahydrobenzo[6,7]cyclohepta[1,2-f]indazol-3-ol;

(3R,4aS,12bR)-12b-ethyl-3-(methoxymethyl)-9-(pyridin-2-yl)-1,2,3,4,4a,5,6,7,9,12b-decahydrobenzo[6,7]cyclohepta[1,2-f]indazol-3-ol;

(3S,4aR,12bR)-3-(methoxymethyl)-12b-(pyridin-2-ylmethyl)-9-(pyridin-4-yl)-1,2,3,4,4a,5,6,7,9,12b-decahydrobenzo[6,7]cyclohepta[1,2-f]indazol-3-ol;

(3R,4aS,12bS)-3-(methoxymethyl)-12b-(pyridin-2-ylmethyl)-9-(pyridin-4-yl)-1,2,3,4,4a,5,6,7,9,12b-decahydrobenzo[6,7]cyclohepta[1,2-f]indazol-3-ol;

(3S,4aR,12bS)-12b-ethyl-3-(methoxymethyl)-9-(pyridin-4-yl)-1,2,3,4,4a,5,6,7,9,12b-decahydrobenzo[6,7]cyclohepta[1,2-f]indazol-3-ol;

(3R,4aS,12bS)-3-(methoxymethyl)-9-(2-methylpyridin-4-yl)-12b-(pyridin-2-ylmethyl)-1,2,3,4,4a,5,6,7,9,12b-decahydrobenzo[6,7]cyclohepta[1,2-f]indazol-3-ol;

(3S,4aR,12bR)-3-(methoxymethyl)-9-(2-methylpyridin-4-yl)-12b-(pyridin-2-ylmethyl)-1,2,3,4,4a,5,6,7,9,12b-decahydrobenzo[6,7]cyclohepta[1,2-f]indazol-3-ol;

(3S,4aR,12bS)-12b-ethyl-9-(4-fluorophenyl)-3-methyl-1,2,3,4,4a,5,6,7,9,12b-decahydrobenzo[6,7]cyclohepta[1,2-f]indazol-3-ol;

(3R,4aS,12bR)-12b-ethyl-9-(4-fluorophenyl)-3-methyl-1,2,3,4,4a,5,6,7,9,12b-decahydrobenzo[6,7]cyclohepta[1,2-f]indazol-3-ol;

(3R,4aS,12bS)-9-(4-fluorophenyl)-3-methyl-12b-(pyrimidin-2-ylmethyl)-1,2,3,4,4a,5,6,7,9,12b-decahydrobenzo[6,7]cyclohepta[1,2-f]indazol-3-ol;

(3S,4aR,12bR)-9-(4-fluorophenyl)-3-methyl-12b-(pyrimidin-2-ylmethyl)-1,2,3,4,4a,5,6,7,9,12b-decahydrobenzo[6,7]cyclohepta[1,2-f]indazol-3-ol;

(3S,4aR,12bR)-12b-(cyclopropylmethyl)-9-(4-fluorophenyl)-3-methyl-1,2,3,4,4a,5,6,7,9,12b-decahydrobenzo[6,7]cyclohepta[1,2-f]indazol-3-ol;

rac-(3R,4aS,12bS)-9-(4-fluorophenyl)-3-methyl-12b-(pyridin-2-ylmethyl)-1,2,3,4,4a,5,6,7,9,12b-decahydrobenzo[6,7]cyclohepta[1,2-f]indazol-3-ol;

(3R,4aS,12bS)-3-methyl-9-(2-methylpyridin-4-yl)-12b-(pyridin-2-ylmethyl)-1,2,3,4,4a,5,6,7,9,12b-decahydrobenzo[6,7]cyclohepta[1,2-f]indazol-3-ol;

(3S,4aR,12bR)-3-methyl-9-(2-methylpyridin-4-yl)-12b-(pyridin-2-ylmethyl)-1,2,3,4,4a,5,6,7,9,12b-decahydrobenzo[6,7]cyclohepta[1,2-f]indazol-3-ol;

2-((3R,4aS,12bS)-9-(4-fluorophenyl)-3-hydroxy-12b-(pyrimidin-2-ylmethyl)-1,2,3,4,4a,5,6,7,9,12b-decahydrobenzo[6,7]cyclohepta[1,2-f]indazol-3-yl)acetonitrile;

2-((3R,4aS,12bS)-9-(4-fluorophenyl)-3-hydroxy-12b-(pyrimidin-2-ylmethyl)-1,2,3,4,4a,5,6,7,9,12b-decahydrobenzo[6,7]cyclohepta[1,2-f]indazol-3-yl)acetonitrile;

2-((3S,4aR,12bR)-9-(4-fluorophenyl)-3-hydroxy-12b-(pyrimidin-2-ylmethyl)-1,2,3,4,4a,5,6,7,9,12b-decahydrobenzo[6,7]cyclohepta[1,2-f]indazol-3-yl)acetonitrile;

2-((3S,4aR,12bS)-12b-ethyl-9-(4-fluorophenyl)-3-hydroxy-1,2,3,4,4a,5,6,7,9,12b-decahydrobenzo[6,7]cyclohepta[1,2-f]indazol-3-yl)acetonitrile;

2-((3R,4aS,12bR)-12b-ethyl-9-(4-fluorophenyl)-3-hydroxy-1,2,3,4,4a,5,6,7,9,12b-decahydrobenzo[6,7]cyclohepta[1,2-f]indazol-3-yl)acetonitrile;

2-((3S,4aR,12bR)-12b-(cyclopropylmethyl)-9-(4-fluorophenyl)-3-hydroxy-1,2,3,4,4a,5,6,7,9,12b-decahydrobenzo[6,7]cyclohepta[1,2-f]indazol-3-yl)acetonitrile;

2-((3R,4aS,12bS)-12b-(cyclopropylmethyl)-9-(4-fluorophenyl)-3-hydroxy-1,2,3,4,4a,5,6,7,9,12b-decahydrobenzo[6,7]cyclohepta[1,2-f]indazol-3-yl)acetonitrile;

2-((3R,4aS,12bS)-3-hydroxy-12b-(pyridin-2-ylmethyl)-9-(pyridin-4-yl)-1,2,3,4,4a,5,6,7,9,12b-decahydrobenzo[6,7]cyclohepta[1,2-f]indazol-3-yl)acetonitrile;

2-((3S,4aR,12bR)-3-hydroxy-12b-(pyridin-2-ylmethyl)-9-(pyridin-4-yl)-1,2,3,4,4a,5,6,7,9,12b-decahydrobenzo[6,7]cyclohepta[1,2-f]indazol-3-yl)acetonitrile;

2-((3R,4aS,12bS)-3-hydroxy-9-(2-methylpyridin-4-yl)-12b-(pyridin-2-ylmethyl)-1,2,3,4,4a,5,6,7,9,12b-decahydrobenzo[6,7]cyclohepta[1,2-f]indazol-3-yl)acetonitrile;

2-((3S,4aR,12bR)-3-hydroxy-9-(2-methylpyridin-4-yl)-12b-(pyridin-2-ylmethyl)-1,2,3,4,4a,5,6,7,9,12b-decahydrobenzo[6,7]cyclohepta[1,2-f]indazol-3-yl)acetonitrile;

(3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carbonitrile;

(3S,4aS,12bR)-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carbonitrile;

N-(((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)methanesulfonamide;

2-(((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)isothiazolidine 1,1-dioxide;

N-(((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)ethanesulfonamide;

N-(((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)methanesulfonamide;

(3R,4aR,12bS)-9-(4-fluorophenyl)-12b-(hydroxymethyl)-3-(trifluoromethyl)-1,2,3,4,4a,5,6,7,9,12b-decahydrobenzo[6,7]cyclohepta[1,2-f]indazol-3-ol;

(3S,4aS,12bR)-9-(4-fluorophenyl)-12b-(hydroxymethyl)-(trifluoromethyl)-1,2,3,4,4a,5,6,7,9,12b-decahydrobenzo[6,7]cyclohepta[1,2-f]indazol-3-ol;

rac-(3R,4aR,12bS)-9-(4-fluorophenyl)-12b-(hydroxymethyl)-3-(trifluoromethyl)-1,2,3,4,4a,5,6,7,9,12b-decahydrobenzo[6,7]cyclohepta[1,2-f]indazol-3-ol;

2-((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)acetonitrile;

2-((3S,4aS,12bR)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)acetonitrile;

N-(43S,4aS,12bR)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)acetamide;

N-(((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)acetamide;

((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)(pyridin-2-yl)methanone compound with 43R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)(pyridin-2-yl)methanone;

(3R,4aR,12bS)—N-Cyclopropyl-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carboxamide;

(3S,4aS,12bR)—N-cyclopropyl-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carboxamide;

(3R,4aR,12bS)-8-Bromo-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol;

(3R,4aR,12bS)-12b-Ethyl-9-(4-fluorophenyl)-3-(trifluoromethyl)-1,2,3,4,4a,5,9,12b-octahydrobenzo[6,7]cyclohepta[1,2-f]indazol-3-ol;

(3R,4aS,12bS)-3-Ethyl-9-(4-fluorophenyl)-3-hydroxy-12b-(pyridin-2-ylmethyl)-1,2,3,4,4a,5,6,12b-octahydrobenzo[6,7]cyclohepta[1,2-f]indazol-7(9H)-one;

rac-(3S,4aR,12bR)-3-ethyl-9-(4-fluorophenyl)-3-hydroxy-12b-(pyridin-2-ylmethyl)-1,2,3,4,4a,5,6,12b-octahydrobenzo[6,7]cyclohepta[1,2-f]indazol-7(9H)-one;

(3R,4S,4aR,12bR)-12b-Ethyl-9-(4-fluorophenyl)-3-(trifluoromethyl)-1,2,3,4,4a,5,6,7,9,12b-decahydrobenzo[6,7]cyclohepta[1,2-f]indazole-3,4-diol;

(3S,4R,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazole-3,4-diol;

(2R,3S,4aS,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol;

(2S,3R,4aR,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol;

rac-(3R,4aS,12bR)-12b-Ethyl-9-(4-fluorophenyl)-3-hydroxy-3-methyl-1,3,4,4a,5,6,7,12b-octahydrobenzo[6,7]cyclohepta[1,2-f]indazol-2(9H)-one;

(3S,4aS,12bS)-12b-Ethyl-9-(4-fluorophenyl)-3-(trifluoromethyl)-1,2,3,4,4a,5,6,7,9,12b-decahydrobenzo[6,7]cyclohepta[1,2-f]indazol-3-yl dihydrogen phosphate;

(3R,4aR,12bR)-8-Bromo-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol;

(3R,4aR,12bR)-12b-Ethyl-9-(4-fluorophenyl)-8-methyl-3-(trifluoromethyl)-1,2,3,4,4a,5,6,7,9,12b-decahydrobenzo[6,7]cyclohepta[1,2-f]indazol-3-ol;

(3R,4aR,7 S,12bR)-12b-Ethyl-9-(4-fluorophenyl)-3-(trifluoromethyl)-1,2,3,4,4a,5,6,7,9,12b-decahydrobenzo[6,7]cyclohepta[1,2-f]indazole-3,7-diol;

(3R,4aR,12bR)-12b-Ethyl-9-(4-fluorophenyl)-3-hydroxy-3-(trifluoromethyl)-1,2,3,4,4a,5,6,12b-octahydrobenzo[6,7]cyclohepta[1,2-f]indazol-7 (9H)-one;

(3R,12bR)-12b-ethyl-9-(4-fluorophenyl)-3-(trifluoromethyl)-1,2,3,5,6,7,9,12b-octahydrobenzo[6,7]cyclohepta[1,2-f]indazol-3-ol;

(3S,12bS)-12b-ethyl-9-(4-fluorophenyl)-3-(trifluoromethyl)-1,2,3,5,6,7,9,12b-octahydrobenzo[6,7]cyclohepta[1,2-f]indazol-3-ol;

(2S,3R,4aR,12bR)-12b-Ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol;

(3R,4aR,12bR)-12b-Ethyl-3-ethynyl-9-(4-fluorophenyl)-1,2,3,4,4a,5,6,7,9,12b-decahydrobenzo[6,7]cyclohepta[1,2-f]indazol-3-ol;

(3S,4aS,12bS)-12b-ethyl-3-ethynyl-9-(4-fluorophenyl)-1,2,3,4,4a,5,6,7,9,12b-decahydrobenzo[6,7]cyclohepta[1,2-f]indazol-3-ol;

(3R,4aR,12bR)-12b-ethyl-9-(4-fluorophenyl)-3-(prop-1-yn-1-yl)-1,2,3,4,4a,5,6,7,9,12b-decahydrobenzo[6,7]cyclohepta[1,2-f]indazol-3-ol;

(3S,4aS,12bS)-12b-ethyl-9-(4-fluorophenyl)-3-(prop-1-yn-1-yl)-1,2,3,4,4a,5,6,7,9,12b-decahydrobenzo[6,7]cyclohepta[1,2-f]indazol-3-ol;

(3R,4aR,12bR)-3,12b-Diethyl-9-(4-fluorophenyl)-1,2,3,4,4a,5,6,7,9,12b-decahydrobenzo[6,7]cyclohepta[1,2-f]indazol-3-ol;

(3S,4aS,12bS)-3,12b-diethyl-9-(4-fluorophenyl)-1,2,3,4,4a,5,6,7,9,12b-decahydrobenzo[6,7]cyclohepta[1,2-f]indazol-3-ol;

(3S,4aR,12bR)-12b-Ethyl-9-(4-fluorophenyl)-3-hydroxy-3-(trifluoromethyl)-1,3,4,4a,5,6,7,12b-octahydrobenzo[6,7]cyclohepta[1,2-f]indazol-2(9H)-one;

(3R,4aS,12bS)-12b-ethyl-9-(4-fluorophenyl)-3-hydroxy-3-(trifluoromethyl)-1,3,4,4a,5,6,7,12b-octahydrobenzo[6,7]cyclohepta[1,2-f]indazol-2(9H)-one;

(2R,3S,4aR,12bR)-12b-Ethyl-9-(4-fluorophenyl)-2-methyl-3-(trifluoromethyl)-1,2,3,4,4a,5,6,7,9,12b-decahydrobenzo[6,7]cyclohepta[1,2-f]indazole-2,3-diol;

(2S,3R,4aS,12bS)-12b-ethyl-9-(4-fluorophenyl)-2-methyl-3-(trifluoromethyl)-1,2,3,4,4a,5,6,7,9,12b-decahydrobenzo[6,7]cyclohepta[1,2-f]indazole-2,3-diol;

(2R,3S,4aR,12bR)-12b-Ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol;

(2S,3R,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol;

(2S,3S,4aR,12bR)-12b-Ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol;

(2R,3R,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol;

(3R,4aS,12bR)-12b-Ethyl-3-(methoxymethyl)-9-(pyridin-4-yl)-1,2,3,4,4a,5,6,7,9,12b-decahydrobenzo[6,7]cyclohepta[1,2-f]indazol-3-ol;

rac-(3R,4aS,12bS)-3-(methoxymethyl)-9-(2-methylpyridin-4-yl)-12b-(pyridin-2-ylmethyl)-1,2,3,4,4a,5,6,7,9,12b-decahydrobenzo[6,7]cyclohepta[1,2-f]indazol-3-ol;

(3R,4aS,12bS)-12b-ethyl-9-(4-fluorophenyl)-3-((((R)-1-phenylethyl)amino)methyl)-1,2,3,4,4a,5,6,7,9,12b-decahydrobenzo[6,7]cyclohepta[1,2-f]indazol-3-ol;

(3S,4aR,12bR)-12b-ethyl-9-(4-fluorophenyl)-3-((((R)-1-phenylethyl)amino)methyl)-1,2,3,4,4a,5,6,7,9,12b-decahydrobenzo[6,7]cyclohepta[1,2-f]indazol-3-ol;

(3S,4aR,12bS)-12b-ethyl-3-(methoxymethyl)-9-(2-methylpyridin-4-yl)-2,3,4,4a,5,6,9,12b-octahydro-1H-benzo[4,5]oxepino[3,2-f]indazol-3-ol;

(3R,4aS,12bR)-12b-ethyl-3-(methoxymethyl)-9-(2-methylpyridin-4-yl)-2,3,4,4a,5,6,9,12b-octahydro-1H-benzo[4,5]oxepino[3,2-f]indazol-3-ol;

rac-(3R,4aS,12bR)-12b-ethyl-9-(4-fluorophenyl)-3-(methoxymethyl)-2,3,4,4a,5,6,9,12b-octahydro-1H-benzo[4,5]oxepino[3,2-f]indazol-3-ol;

(3S,4aR,12bS)-12b-ethyl-9-(4-fluorophenyl)-3-(methoxymethyl)-2,3,4,4a,5,6,9,12b-octahydro-1H-benzo[4,5]oxepino[3,2-f]indazol-3-ol;

(3R,4aS,12bR)-12b-ethyl-9-(4-fluorophenyl)-3-(methoxymethyl)-2,3,4,4a,5,6,9,12b-octahydro-1H-benzo[4,5]oxepino[3,2-f]indazol-3-ol;

rac-(3R,4aS,12bR)-12b-ethyl-3-(methoxymethyl)-9-(pyridin-4-yl)-2,3,4,4a,5,6,9,12b-octahydro-1H-benzo[4,5]oxepino[3,2-f]indazol-3-ol;

(3S,4aR,12bS)-12b-ethyl-3-(methoxymethyl)-9-(pyridin-4-yl)-2,3,4,4a,5,6,9,12b-octahydro-1H-benzo[4,5]oxepino[3,2-f]indazol-3-ol;

(3R,4aS,12bR)-12b-ethyl-3-(methoxymethyl)-9-(pyridin-4-yl)-2,3,4,4a,5,6,9,12b-octahydro-1H-benzo[4,5]oxepino[3,2-f]indazol-3-ol;

(3S,4aR,12bS)-12b-ethyl-3-(methoxymethyl)-9-(pyrimidin-4-yl)-2,3,4,4a,5,6,9,12b-octahydro-1H-benzo[4,5]oxepino[3,2-f]indazol-3-ol;

(3R,4aS,12bR)-12b-ethyl-3-(methoxymethyl)-9-(pyrimidin-4-yl)-2,3,4,4a,5,6,9,12b-octahydro-1H-benzo[4,5]oxepino[3,2-f]indazol-3-ol;

(3S,4aR,12bS)-12b-ethyl-3-(methoxymethyl)-9-(2-methoxypyridin-4-yl)-2,3,4,4a,5,6,9,12b-octahydro-1H-benzo[4,5]oxepino[3,2-f]indazol-3-ol;

(3R,4aS,12bR)-12b-ethyl-3-(methoxymethyl)-9-(2-methoxypyridin-4-yl)-2,3,4,4a,5,6,9,12b-octahydro-1H-benzo[4,5]oxepino[3,2-f]indazol-3-ol;

rac-(3R,4aS,12bR)-12b-ethyl-3-(methoxymethyl)-9-(5-methyl-1,3,4-thiadiazol-2-yl)-2,3,4,4a,5,6,9,12b-octahydro-1H-benzo[4,5]oxepino[3,2-f]indazol-3-ol;

(3S,4aR,12bS)-12b-ethyl-3-(methoxymethyl)-9-(2-(trifluoromethyl)pyridin-4-yl)-2,3,4,4a,5,6,9,12b-octahydro-1H-benzo[4,5]oxepino[3,2-f]indazol-3-ol;

(3R,4aS,12bR)-12b-ethyl-3-(methoxymethyl)-9-(2-(trifluoromethyl)pyridin-4-yl)-2,3,4,4a,5,6,9,12b-octahydro-1H-benzo[4,5]oxepino[3,2-f]indazol-3-ol;

(3S,4aR,12bS)-12b-ethyl-3-methyl-9-(2-methylpyridin-4-yl)-2,3,4,4a,5,6,9,12b-octahydro-1H-benzo[4,5]oxepino[3,2-f]indazol-3-ol;

(3R,4aS,12bR)-12b-ethyl-3-methyl-9-(2-methylpyridin-4-yl)-2,3,4,4a,5,6,9,12b-octahydro-1H-benzo[4,5]oxepino[3,2-f]indazol-3-ol;

2-((3S,4aR,12bS)-12b-ethyl-3-hydroxy-9-(2-methylpyridin-4-yl)-2,3,4,4a,5,6,9,12b-octahydro-1H-benzo[4,5]oxepino[3,2-f]indazol-3-yl)acetonitrile;

2-((3R,4aS,12bR)-12b-ethyl-3-hydroxy-9-(2-methylpyridin-4-yl)-2,3,4,4a,5,6,9,12b-octahydro-1H-benzo[4,5]oxepino[3,2-f]indazol-3-yl)acetonitrile;

(3R,4aR,12bR)-12b-Ethyl-9-(4-fluorophenyl)-3-(trifluoromethyl)-2,3,4,4a,5,6,9,12b-octahydro-1H-benzo[4,5]oxepino[3,2-f]indazol-3-ol;

(3S,4aS,12bS)-12b-ethyl-9-(4-fluorophenyl)-3-(trifluoromethyl)-2,3,4,4a,5,6,9,12b-octahydro-1H-benzo[4,5]oxepino[3,2-f]indazol-3-ol;

rac-(3R,4aS,12bS)-9-(4-Fluorophenyl)-3-methyl-12b-(pyridin-2-ylmethyl)-1,2,3,4,4a,5,6,7,9,12b-decahydrobenzo[3,4]cyclohepta[1,2-b]pyrazolo[4,3-e]pyridin-3-ol;

(3R,4aS,12bS)-9-(4-Fluorophenyl)-3-methyl-12b-(pyridin-2-ylmethyl)-1,2,3,4,4a,5,6,7,9,12b-decahydrobenzo[3,4]cyclohepta[1,2-b]pyrazolo[4,3-e]pyridin-3-ol;

(3S,4aR,12bR)-9-(4-Fluorophenyl)-3-methyl-12b-(pyridin-2-ylmethyl)-1,2,3,4,4a,5,6,7,9,12b-decahydrobenzo[3,4]cyclohepta[1,2-b]pyrazolo[4,3-e]pyridin-3-ol;

rac-(3R,4aS,12bS)-12b-Ethyl-9-(4-fluorophenyl)-3-(trifluoromethyl)-1,2,3,4,4a,5,6,7,9,12b-decahydrobenzo[3,4]cyclohepta[1,2-b]pyrazolo[4,3-e]pyridin-3-ol;

rac-(3R,4aR,12bR)-12b-ethyl-9-(4-fluorophenyl)-3-(trifluoromethyl)-1,2,3,4,4a,5,6,7,9,12b-decahydrobenzo[3,4]cyclohepta[1,2-b]pyrazolo[4,3-e]pyridin-3-ol;

(3S,4aS,12bS)-12b-Ethyl-9-(4-fluorophenyl)-3-(trifluoromethyl)-1,2,3,4,4a,5,6,7,9,12b-decahydrobenzo[3,4]cyclohepta[1,2-b]pyrazolo[4,3-e]pyridin-3-ol;

(3R,4aR,12bR)-12b-ethyl-9-(4-fluorophenyl)-3-(trifluoromethyl)-1,2,3,4,4a,5,6,7,9,12b-decahydrobenzo[3,4]cyclohepta[1,2-b]pyrazolo[4,3-e]pyridin-3-ol;

rac-(3R,4aR,12bR)-9-(4-Fluorophenyl)-12b-(pyridin-2-ylmethyl)-3-(trifluoromethyl)-1,2,3,4,4a,5,6,7,9,12b-decahydrobenzo[3,4]cyclohepta[1,2-b]pyrazolo[4,3-e]pyridin-3-ol;

(3R,4aS,12bS)-9-(4-fluorophenyl)-3-(methoxymethyl)-12b-(pyridin-2-ylmethyl)-1,2,3,4,4a,5,6,7,9,12b-decahydrobenzo[3,4]cyclohepta[1,2-b]pyrazolo[4,3-e]pyridin-3-ol;

(3S,4aR,12bR)-9-(4-fluorophenyl)-3-(methoxymethyl)-12b-(pyridin-2-ylmethyl)-1,2,3,4,4a,5,6,7,9,12b-decahydrobenzo[3,4]cyclohepta[1,2-b]pyrazolo[4,3-e]pyridin-3-ol;

(3R,4aS,12bS)-9-(4-fluorophenyl)-3-(methoxymethyl)-12b-(pyridin-2-ylmethyl)-1,2,3,4,4a,5,6,7,9,12b-decahydrobenzo[3,4]cyclohepta[1,2-b]pyrazolo[4,3-e]pyridin-3-ol;

(3S,4aR,12bR)-9-(4-fluorophenyl)-3-(methoxymethyl)-12b-(pyridin-2-ylmethyl)-1,2,3,4,4a,5,6,7,9,12b-decahydrobenzo[3,4]cyclohepta[1,2-b]pyrazolo[4,3-e]pyridin-3-ol;

2-((3S,4aR,12bR)-9-(4-fluorophenyl)-3-hydroxy-12b-(pyrimidin-2-ylmethyl)-1,2,3,4,4a,5,6,7,9,12b-decahydrobenzo[3,4]cyclohepta[1,2-b]pyrazolo[4,3-e]pyridin-3-yl)acetonitrile;

(3R,4aS,12bS)-9-(4-fluorophenyl)-3-methyl-12b-(pyrimidin-2-ylmethyl)-1,2,3,4,4a,5,6,7,9,12b-decahydrobenzo[3,4]cyclohepta[1,2-b]pyrazolo[4,3-e]pyridin-3-ol;

(3S,4aR,12bR)-9-(4-fluorophenyl)-3-methyl-12b-(pyrimidin-2-ylmethyl)-1,2,3,4,4a,5,6,7,9,12b-decahydrobenzo[3,4]cyclohepta[1,2-b]pyrazolo[4,3-e]pyridin-3-ol;

2-((3R,4aS,12bS)-9-(4-fluorophenyl)-3-hydroxy-12b-(pyrimidin-2-ylmethyl)-1,2,3,4,4a,5,6,7,9,12b-decahydrobenzo[3,4]cyclohepta[1,2-b]pyrazolo[4,3-e]pyridin-3-yl)acetonitrile;

2-((3R,4aR,12bR)-9-(4-fluorophenyl)-3-hydroxy-12b-(pyridin-2-ylmethyl)-1,2,3,4,4a,5,6,7,9,12b-decahydrobenzo[3,4]cyclohepta[1,2-b]pyrazolo[4,3-e]pyridin-3-yl)acetonitrile;

2-((3R,4aS,12bS)-9-(4-fluorophenyl)-3-hydroxy-12b-(pyridin-2-ylmethyl)-1,2,3,4,4a,5,6,7,9,12b-decahydrobenzo[3,4]cyclohepta[1,2-b]pyrazolo[4,3-e]pyridin-3-yl)acetonitrile;

rac-(3R,4aR,13bS)-9-(4-fluorophenyl)-13b-(pyridin-2-ylmethyl)-3-(trifluoromethyl)-2,3,4,4a,5,6,7,13b-octahydro-1H-benzo[3,4]cyclohepta[1,2-d]imidazo[1,5-a]pyridin-3-ol;

rac-(3R,4aS,13bS)-9-(4-Fluorophenyl)-3-(methoxymethyl)-13b-(pyridin-2-ylmethyl)-2,3,4,4a,5,6,7,13b-octahydro-1H-benzo[3,4]cyclohepta[1,2-d]imidazo[1,5-a]pyridin-3-ol;

(3R,4aR,12bR)-12b-ethyl-9-(4-(methylsulfonyl)phenyl)-3-(trifluoromethyl)-1,2,3,4,4a,5,6,7,9,12b-decahydrobenzo[6,7]cyclohepta[1,2-f]indazol-3-ol;

(3S,4aS,12bS)-12b-ethyl-9-(4-(methylsulfonyl)phenyl)-3-(trifluoromethyl)-1,2,3,4,4a,5,6,7,9,12b-decahydrobenzo[6,7]cyclohepta[1,2-f]indazol-3-ol;

(3S,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-yl sulfamate;

2-(((3S,4aS,12bS)-12b-Ethyl-9-(4-fluorophenyl)-3-(trifluoromethyl)-1,2,3,4,4a,5,6,7,9,12b-decahydrobenzo[6,7]cyclohepta[1,2-f]indazol-3-yl)oxy)acetamide;

2-(((3S,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-yl)oxy)acetic acid;

(3R,4aS,13bS)-9-(4-fluorophenyl)-3-(methoxymethyl)-13b-(pyridin-2-ylmethyl)-2,3,4,4a,5,6,7,13b-octahydro-1H-benzo[3,4]cyclohepta[1,2-d]imidazo[1,5-a]pyridin-3-ol;

(3S,4aR,13bR)-9-(4-fluorophenyl)-3-(methoxymethyl)-13b-(pyridin-2-ylmethyl)-2,3,4,4a,5,6,7,13b-octahydro-1H-benzo[3,4]cyclohepta[1,2-d]imidazo[1,5-a]pyridin-3-ol; or rac-(3R,4aR,13bS)-9-(4-fluorophenyl)-13b-(pyridin-2-ylmethyl)-3-(trifluoromethyl)-2,3,4,4a,5,6,7,13b-octahydro-1H-benzo[3,4]cyclohepta[1,2-d][1,2,3]triazolo[1,5-a]pyridin-3-ol.

Another aspect of the invention provides a pharmaceutical composition comprising the compound of any one of the preceding embodiments, and a pharmaceutically acceptable carrier or excipient.

The present invention also comprises the use of a compound of Formula (I) as a medicament.

Thus another aspect of the invention provides a method of treating a disease or condition comprising administering a therapeutically effective amount of the compound of any one of the preceding embodiments, or the pharmaceutical composition thereof.

In one embodiment, the disease or condition to be treated is acquired immunodeficiency syndrome (AIDS), acute adrenal insufficiency, addiction, Addison's Disease, adrenal function, allergic rhinitis, allergies, Alzheimer's, anorexia, angioneurotic edema, ankylosing spondylitis, anxiety, asthma, autoimmunity, autoimmune chronic active hepatitis, autoimmune diseases, blepharitis, bursitis, cachexia, cardiovascular disease, cerebral edema, choroidal neovascularization due to age-related macular degeneration, chronic kidney disease, chronic obstructive pulmonary disease, chronic primary adrenal insufficiency, chronic retinal detachment, compulsive behavior, congenital adrenal hyperplasia, cognitive dysfunction, conjunctivitis, cirrhosis, Crohn's disease, Cushing's syndrome, depression, diabetes, diabetes mellitus, diabetic microangiopathy, diabetic neuropathy, diabetic retinopathy, dry eye syndrome, frailty, giant cell arteritis, glaucoma, granulomatous polyarteritis, hay fever, hepatitis, HPA axis suppression and regulation, human immunodeficiency virus (HIV), hypercalcemia, hypercortisolemia, hypergylcemia, hypertension, immune proliferation/apoptosis, immunodeficiency, immunomodulation, inflammation, inflammation of the eye, inflammatory bowel disease, inhibition of myeloid cell lines, insulin dependent diabetes mellitus, insulin-dependent diabetes mellitus glaucoma, insulin resistance, iridocyclitis, juvenile idiopathic arthritis, juvenile rheumatoid arthritis, leukemia, Little's syndrome, lupus, lymphoma, macular degeneration, macular edema, a malignancy, medical catabolism, multi-drug resistance, multiple sclerosis, neurodgeneration, obesity, ocular or macular edema, ocular neovascular disease, organ transplantation, modulation of the Th1/Th2 cytokine balance, optic neuritis, optic pits, neuropathy, osteoarthritis, osteoporosis, Parkinson's, plaque psoriasis, polyarteritis nodosa, post-laser treatment complications, post-surgical bone fracture, post-traumatic stress syndrome, prevention of muscle frailty, psoriasis, psoriatic arthritis, psychosis, regulation of carbohydrate, protein and lipid metabolism, regulation of electrolyte and water balance, regulation of functions of the cardiovascular, kidney, central nervous, immune, or skeletal muscle systems, retinopathy of prematurity, rheumatic fever, rheumatoid arthritis, rhinitis, scleritis, secondary adrenal insufficiency, stroke and spinal cord injury, sympathetic ophthalmia, systemic lupus erythematosus, Syndrome X, tendonitis, thrombocytopenia, tissue rejection, ulcerative colitis, urticaria, uveitis, viral infection, or Wegener's granulomatosis or wound healing.

In one embodiment, the disease or condition to be treated is ankylosing spondylitis, Crohn's disease, inflammatory bowel disease, juvenile idiopathic arthritis, juvenile rheumatoid arthritis, plaque psoriasis, psoriasis, psoriatic arthritis, rheumatoid arthritis, ulcerative colitis, or uveitis.

DETAILED DESCRIPTION OF THE INVENTION

The glucocorticoid receptor (GR) is present in glucocorticoid responsive cells where it resides in the cytosol in an inactive state until it is stimulated by an agonist. Upon stimulation the glucocorticoid receptor translocates to the cell nucleus where it specifically interacts with DNA and/or protein(s) and regulates transcription in a glucocorticoid responsive manner. Two examples of proteins that interact with the glucocorticoid receptor are the transcription factors, API and NFK-B. Such interactions result in inhibition of API- and NFK-B-mediated transcription and are believed to be responsible for some of the anti-inflammatory activity of endogenously administered glucocorticoids. In addition, glucocorticoids may also exert physiologic effects independent of nuclear transcription. Biologically relevant glucocorticoid receptor agonists include Cortisol and corticosterone. Many synthetic glucocorticoid receptor agonists exist including dexamethasone, prednisone and prednisilone. By definition, glucocorticoid receptor antagonists bind to the receptor and prevent glucocorticoid receptor agonists from binding and eliciting GR mediated events, including transcription. RU486 is an example of a non-selective glucocorticoid receptor antagonist.

Although there are glucocorticoid receptor therapies in the art, there is a continuing need for and a continuing search in this field of art for selective glucocorticoid receptor therapies. Thus, the identification of non-steroidal compounds which have specificity for one or more steroid receptors, but which have reduced or no cross-reactivity for other steroid or intracellular receptors, is of significant value in this field.

Many autoimmune diseases and disease associated with chronic inflammation, as well as acute responses, have been linked to excessive or unregulated production or activity of one or more cytokines.

The compounds of the invention are also useful in the treatment of rheumatoid arthritis, ankylosing spondilitis, a solid tumor, a sarcoma, fibrosarcoma, osteoma, melanoma, retinoblastoma, an ocular disease, a cancer, a rhabdomyosarcoma, glioblastoma, neuroblastoma, teratocarcinoma, hypersensitivity reactions, hyperkinetic movement disorders, hypersensitivity pneumonitis, hypertension, hypokinetic movement disorders, aordic and peripheral aneurysisms, hypothalamic-pituitary-adrenal axis evaluation, aortic dissection, arterial hypertension, arteriosclerosis, arteriovenous fistula, ataxia, spinocerebellar degenerations, streptococcal myositis, structural lesions of the cerebellum, subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, telangiectasia, thromboangitis obliterans, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, heart transplant rejection, hemachromatosis, hemodialysis, hemolytic uremic syndrome/thrombolytic thrombocytopenic purpura, hemorrhage, idiopathic pulmonary fibrosis, antibody mediated cytotoxicity, Asthenia, infantile spinal muscular atrophy, inflammation of the aorta, influenza A, ionizing radiation exposure, iridocyclitis/uveitis/optic neuritis, juvenile spinal muscular atrophy, lymphoma, myeloma, leukaemia, malignant ascites, hematopoietic cancers, a diabetic condition such as insulin-dependent diabetes mellitus glaucoma, diabetic retinopathy or microangiopathy, sickle cell anaemia, chronic inflammation, glomerulonephritis, graft rejection, Lyme disease, von Hippel Lindau disease, pemphigoid, Paget's disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, stroke, hypoxia, ischemia, ovarian hyperstimulation syndrome, post perfusion syndrome, post pump syndrome, post-MI cardiotomy syndrome, preeclampsia, menometrorrhagia, endometriosis, pulmonary hypertension, infantile hemangioma, or infection by Herpes simplex, Herpes Zoster, human immunodeficiency virus, parapoxvirus, protozoa or toxoplasmosis, progressive supranucleo palsy, primary pulmonary hypertension, radiation therapy, Raynaud's phenomenon, Raynaud's disease, Refsum's disease, regular narrow QRS tachycardia, renovascular hypertension, restrictive cardiomyopathy, sarcoma, senile chorea, senile dementia of Lewy body type, shock, skin allograft, skin changes syndrome, ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy, macular degeneration, restenosis, ischemia/reperfusion injury, ischemic stroke, vascular occlusion, carotid obstructive disease, ulcerative colitis, inflammatory bowel disease, diabetes, diabetes mellitus, insulin dependent diabetes mellitus, allergic diseases, dermatitis scleroderma, graft versus host disease, organ transplant rejection (including but not limited to bone marrow and solid organ rejection), acute or chronic immune disease associated with organ transplantation, sarcoidosis, disseminated intravascular coagulation, Kawasaki's disease, nephrotic syndrome, chronic fatigue syndrome, Wegener's granulomatosis, Henoch-Schoenlein purpurea, microscopic vasculitis of the kidneys, chronic active hepatitis, septic shock, toxic shock syndrome, sepsis syndrome, cachexia, infectious diseases, parasitic diseases, acquired immunodeficiency syndrome, acute transverse myelitis, Huntington's chorea, stroke, primary biliary cirrhosis, hemolytic anemia, malignancies, Addison's disease, idiopathic Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, *yersinia* and *salmonella* associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, peripheral vascular disorders, peritonitis, pernicious anemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis A, Hepatitis B, Hepatitis C, His bundle arrythmias, HIV infection/HIV neuropathy, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, *pneumocystis carinii* pneumonia, pneumonia, connective tissue disease associated interstitial lung disease, mixed connective tissue disease, associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthritis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, acute and chronic pain (different forms of pain), Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, toxicity, transplants, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as ascites, effusions, and exudates, including for example macular edema, cerebral edema, acute lung injury, adult respiratory distress syndrome (ARDS), proliferative disorders such as restenosis, fibrotic disorders such as hepatic cirrhosis and atherosclerosis, mesangial cell proliferative disorders such as diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, preeclampsia, menometrorrhagia, cat scratch fever, rubeosis, neovascular glaucoma and retinopathies such as those associated with diabetic retinopathy, retinopathy of prematurity, or age-related macular degeneration. In addition, these compounds can be used as active agents against hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

Compounds of Formula (I) of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the compound of the present invention. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the compounds of this invention. Non-limiting examples of therapeutic agents for rheumatoid arthritis with which a compound of Formula (I) of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. Compounds of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, adalimumab OR D2E7 (U.S. Pat. No. 6,090,382, HUMIRA™), CA2 (REMICADE™), SIMPONI™ (golimumab), CIMZIA™, ACTEMRA™, CDP 571, and soluble p55 or p75 TNF receptors, derivatives, thereof, p75TNFR1gG (ENBREL™) or p55TNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination is non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of Formula (I) of the invention may also be combined with agents, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as TNFα or IL-1 (e.g., NIK, IKK, p38 or MAP kinase inhibitors), IL-1β converting enzyme inhibitors, T-cell signaling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™) and p55TNFRIgG (Lenercept), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, S1P1 agonists (such as Fingolimod), and Mesopram. Preferred combinations include methotrexate or leflunomide and in moderate or severe rheumatoid arthritis cases, cyclosporin and anti-TNF antibodies as noted above.

Non-limiting examples of therapeutic agents for inflammatory bowel disease with which a compound of Formula (I) of the invention can be combined include the following: budenoside; epidermal growth factor; corticosteroids; cyclosporin, sulfasalazine; amino salicylates; 6-mercaptopurine; azathioprine; metronidazole; lip oxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signaling by proinflammatory cytokines such as TNFα or IL-1 (e.g. NIK, IKK, or MAP kinase inhibitors); IL-1β converting enzyme inhibitors; TNFα converting enzyme inhibitors; T-cell signaling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of Formula (I) can be combined include the following: TNF antagonists, for example, anti-TNF antibodies, adalimumab OR D2E7 (U.S. Pat. No. 6,090,382, HUMIRA™), CA2 (REMICADE™), CDP 571, TNFR-Ig constructs, (p75TNFRIgG (ENBREL™) and p55TNFRIgG (LENERCEPT™) inhibitors and PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α-2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

Preferred examples of therapeutic agents for multiple sclerosis in which a compound of Formula (I) can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

A compound of Formula (I) may also be combined with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of Formula (I) can be combined include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, adalimumab OR D2E7 (U.S. Pat. No. 6,090,382; HUMIRA™), CA2 (REMICADE™), CDP 571, TNFR-Ig constructs, (p75TNFRIgG (ENBREL™) and p55TNFRIgG (LENERCEPT™)

Non-limiting examples of therapeutic agents for psoriasis with which a compound of Formula (I) can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of Formula (I) can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, adalimumab OR D2E7 (U.S. Pat. No. 6,090,382, HUMIRA™), and efalizumab.

Preferred examples of therapeutic agents for SLE (Lupus) with which a compound of Formula (I) can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with LW 394 (abetimus), agents that deplete or inactivate B-cells, for example, Rituximab (anti-CD20 antibody), lymphostat-B (anti-BlyS antibody), TNF antagonists, for example, anti-TNF antibodies, adalimumab OR D2E7 (U.S. Pat. No. 6,090,382; HUMIRA™), CA2 (REMICADE™), CDP 571, TNFR-Ig constructs, (p75TNFRIgG (ENBREL™) and p55TNFRIgG (LENERCEPT™).

In this invention, the following definitions are applicable:

A "therapeutically effective amount" is an amount of a compound of Formula (I) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of Formula (I) which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of Formula (I) and their salts may exist in more than one crystal form and the present invention includes each crystal form and mixtures thereof.

Certain compounds of Formula (I) and their salts may also exist in the form of solvates, for example hydrates, and the present invention includes each solvate and mixtures thereof.

Certain compounds of Formula (I) may contain one or more chiral centers, and exist in different optically active forms. When compounds of Formula (I) contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of Formula (I) contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of Formula (I), and mixtures thereof. Certain compounds of Formula (I) may exist in different tautomeric forms or as different geometric isomers, and the present invention includes each tautomer and/or geometric isomer of compounds of Formula (I) and mixtures thereof. Certain compounds of Formula (I) may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Formula (I) and mixtures thereof. Certain compounds of Formula (I) may exist in zwitterionic form and the present invention includes each zwitterionic form of compounds of Formula (I) and mixtures thereof.

As used herein the term "pro-drug" refers to an agent which is converted into the parent drug in vivo by some physiological chemical process (e.g., a pro-drug on being brought to the physiological pH is converted to the desired drug form). Pro-drugs are often useful because, in some situations, they may be easier to administer than the parent drug. They may, for instance, be bioavailable by oral administration whereas the parent drug is not. The pro-drug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial.

Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the pro-drug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to phosphates, phosphate esters, and carboxylic acid substituents wherein the free hydrogen is replaced by ($C_1$-$C_4$) alkyl, ($C_1$-$C_{12}$)alkanoyloxymethyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)-alkylcarbamoyl-($C_1$-$C_2$)alkyl and piperidino-, pyrrolidino- or morpholino($C_2$-$C_3$)alkyl.

Other exemplary pro-drugs release an alcohol of Formula (I) wherein the free hydrogen of the hydroxyl substituent is replaced by ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_{12}$) alkoxycarbonyloxymethyl, N—($C_1$-$C_6$)alkoxycarbonylamino-methyl, succinoyl, ($C_1$-$C_6$)alkanoyl, α-amino($C_1$-$C_4$)alkanoyl, arylacetyl and α-aminoacyl, or α-aminoacyl-α-aminoacyl wherein said α-aminoacyl moieties are independently any of the naturally occurring L-amino acids found in proteins, $P(O)(OH)_2$, —$P(O)(O(C_1$-$C_6)alkyl)_2$ or glycosyl (the radical resulting from detachment of the hydroxyl of the hemiacetal of a carbohydrate).

Other exemplary pro-drugs release an amine of Formula (I) wherein the free hydrogen of the amine group is replaced by —C(O)alkyl, —C(O)O-alkyl, N-phosphonoxyalkyl, alkyl, cycloalkyl, aryl, heteroaryl or heterocyclyl, wherein the alkyl, cycloalkyl, aryl, heteroaryl or heterocyclyl can be optionally substituted with, for example, halogen and hydroxyl.

As used herein "solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

As used herein, "spirocyclic ($C_2$-$C_{10}$) heterocyclyl" means bicyclic or polycyclic hydrocarbon group having two or three ($C_3$-$C_{10}$) rings at least one of which contains a heteroatom such as nitrogen, oxygen or sulfur. For purposes of exemplification, which should not be construed as limiting the scope of this invention, spirocyclic ($C_2$-$C_{10}$) heterocyclyl may include diazaspiro[3.5]nonane and diazaspiro[4.5]decane.

As used herein, "spirocyclic ($C_5$-$C_{11}$) carbocyclyl" means a saturated or unsaturated, bicyclic or polycyclic hydrocarbon group having two or three ($C_3$-$C_{10}$) cycloalkyl rings. For purposes of exemplification, which should not be construed as limiting the scope of this invention, spirocyclic ($C_5$-$C_{11}$) carbocyclyl includes spiro[5.5]undecane, spiro[4.5]decane and spiro[4.4]nonane.

The term "heterocyclic," "heterocyclyl" or "heterocyclylene," as used herein, include non-aromatic ring systems, including, but not limited to, monocyclic, bicyclic, and tricyclic rings, which can be completely saturated or which can contain one or more units of unsaturation. (for the avoidance of doubt, the degree of unsaturation does not result in an aromatic ring system) and have 5 to 12 atoms including at least one heteroatom, such as nitrogen, oxygen, or sulfur. For purposes of exemplification, which should not be construed as limiting the scope of this invention, the following are examples of heterocyclic rings: azepinyl, azetidinyl, indolinyl, isoindolinyl, morpholinyl, piperazinyl, piperidinyl, pyrrolidinyl, quinucludinyl, thiomorpholinyl, tetrahydropyranyl, tetrahydrofuranyl, tetrahydroindolyl, thiomorpholinyl and tropanyl.

The term "heteroaryl" or "heteroarylene" as used herein, include aromatic ring systems, including, but not limited to, monocyclic, bicyclic and tricyclic rings, and have 5 to 12 atoms including at least one heteroatom, such as nitrogen, oxygen, or sulfur. For purposes of exemplification, which should not be construed as limiting the scope of this invention: azaindolyl, benzo[b]thienyl, benzimidazolyl, benzofuranyl, benzoxazolyl, benzothiazolyl, benzothiadiazolyl, benzoxadiazolyl, 6,7-dihydro-5H-cyclopentapyrimidinyl, furanyl, imidazolyl, imidazopyridinyl, indolyl, indazolyl, isoxazolyl, isothiazolyl, octahydro-pyrrolopyrrolyl, oxadiazolyl, oxazolyl, phthalazinyl, pteridinyl, purinyl, pyranyl, 5,8-dihydro-6H-pyrano[3,4-d]pyridinyl, pyrazinyl, pyrazolyl, pyridinyl, pyrido[2,3-d]pyrimidinyl, pyrido[4,3-d]pyrimidinyl, pyrido[3,4-d]$_p$ yrimidinyl, pyrimidinyl, pyrimido[4,5-d]pyrimidinyl, pyrrolyl, pyrrolo[2,3-d]pyrimidinyl, pyrazolo[3,4-d]$_p$ yrimidinyl, quinolinyl, quinazolinyl, 5,6,7,8-tetrahydroquinaz olinyl, triazolyl, thiazolyl, thieno[2,3-d]pyrimidinyl, thieno[3,2-d]pyrimidinyl, thiophenyl, tetrazolyl, thiadiazolyl, thienyl, [1,3,5]triazinyl, 5,6,7,8-tetrahydro-imidazo[1,5-a]pyrazinyl, and 5,6,7,8-tetrahydro-triazolo[1,2,4]pyrazinyl.

As used herein, "alkyl" and "alkylene" include straight chained or branched hydrocarbons which are completely saturated. For purposes of exemplification, which should not be construed as limiting the scope of this invention, examples of alkyls are methyl, ethyl, propyl, isopropyl, butyl, pentyl, hexyl and isomers thereof.

As used herein, "alkenyl," "alkenylene," "alkynylene" and "alkynyl" mean hydrocarbon moieties containing two to eight carbons and include straight chained or branched hydrocarbons which contain one or more units of unsaturation, one or more double bonds for alkenyl and one or more triple bonds for alkynyl. For purposes of exemplification, which should not be construed as limiting the scope of this invention, examples of alkenyl are ethenyl, propenyl and butenyl, and examples of alkynyl are ethynyl, propynyl and butynyl.

As used herein, "aryl" or "arylene" groups include aromatic carbocyclic ring systems (e.g. phenyl) and fused polycyclic aromatic ring systems. For purposes of exemplification, which should not be construed as limiting the scope of this invention, aryl groups include naphthyl, biphenyl and 1,2,3,4-tetrahydronaphthyl.

As used herein, "cycloalkyl," "cycloalkylene," "carbocycle" or "carbocyclyl" means $C_3$-$C_{12}$ monocyclic or multicyclic (e.g., bicyclic, tricyclic, etc.) hydrocarbons that are completely saturated or have one or more unsaturated bonds but do not amount to an aromatic group. For purposes of exemplification, which should not be construed as limiting the scope of this invention, examples of a cycloalkyl group are cyclopropyl, cyclobutyl, cyclopentyl, cyclopentenyl, cyclohexyl and cyclohexenyl.

As used herein, many moieties or substituents are termed as being either "substituted" or "optionally substituted." When a moiety is modified by one of these terms, unless otherwise noted, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: deuterium, $CD_3$, optionally substituted ($C_1$-$C_8$)alkyl groups, optionally substituted ($C_2$-$C_8$)alkenyl groups, ($C_2$-$C_8$)alkynyl groups, optionally substituted ($C_3$-$C_{10}$)cycloalkyl groups, halogen (F, Cl, Br or I), halogenated ($C_1$-$C_8$)alkyl groups (for example but not limited to —$CF_3$), —O—($C_1$-$C_8$)alkyl groups, —OH, —S—($C_1$-$C_8$)alkyl groups, —SH, —NH($C_1$-$C_8$)alkyl groups, —N(($C_1$-$C_8$)alkyl)$_2$ groups, —NH$_2$, —NH—($C_1$-$C_6$)alkyl-optionally substituted heterocycle, —NH-heterocycle, —C(O)NH$_2$, —C(O)NH($C_1$-$C_8$)alkyl groups, —C(O)N(($C_1$-$C_8$)alkyl)$_2$, —NHC(O)H, —NHC(O)($C_1$-$C_8$)alkyl groups, —NHC(O)($C_3$-$C_8$)cycloalkyl groups, —N(($C_1$-$C_8$)alkyl)C(O)H, —N(($C_1$-$C_8$)alkyl)C(O)($C_1$-$C_8$)alkyl groups, —NHC(O)NH$_2$, —NHC(O)NH($C_1$-$C_8$)alkyl groups, —N(($C_1$-$C_8$)alkyl)C(O)NH$_2$ groups, —NHC(O)N(($C_1$-$C_8$)alkyl)$_2$ groups, —N(($C_1$-$C_8$)alkyl)C(O)N(($C_1$-$C_8$)alkyl)$_2$ groups, —N(($C_1$-$C_8$)alkyl)C(O)NH(($C_1$-$C_8$)alkyl), —C(O)H, —C(O)($C_1$-$C_8$)alkyl groups, —CN, —NO$_2$, —S(O)($C_1$-$C_8$)alkyl groups, —S(O)$_2$($C_1$-$C_8$)alkyl groups, —S(O)$_2$N(($C_1$-$C_8$)alkyl)$_2$ groups, —S(O)$_2$NH($C_1$-$C_8$)alkyl groups, —S(O)$_2$NH($C_3$-$C_8$)cycloalkyl groups, —S(O)$_2$NH$_2$ groups, —NHS(O)$_2$($C_1$-$C_8$)alkyl groups, —N(($C_1$-$C_8$)alkyl)S(O)$_2$($C_1$-$C_8$)alkyl groups, —($C_1$-$C_8$)alkyl-O—($C_1$-$C_8$)alkyl groups, —O—($C_1$-$C_8$)alkyl-O—($C_1$-$C_8$)alkyl groups, —C(O)OH, —C(O)O($C_1$-$C_8$)alkyl groups, —NHOH, —NHO($C_1$-$C_8$)alkyl groups, —O-halogenated ($C_1$-$C_8$)alkyl groups (for example but not limited to —$OCF_3$), —S(O)$_2$-halogenated ($C_1$-$C_8$)alkyl groups (for example but not limited to S(O)$_2$$CF_3$), —S-halogenated ($C_1$-$C_8$)alkyl groups (for example but not limited to $SCF_3$), —($C_1$-$C_6$)alkyl-optionally substituted heterocycle (for example but not limited to azetidine, piperidine, piperazine, pyrrolidine, tetrahydrofuran, pyran or morpholine), —($C_1$-$C_6$)alkyl-heteroaryl (for example but not limited to tetrazole, imidazole, furan, pyrazine or pyrazole), -optionally substituted phenyl, —NHC(O)O—($C_1$-$C_6$)alkyl groups, —N(($C_1$-$C_6$)alkyl)C(O)O—($C_1$-$C_6$)alkyl groups, —C(=NH)—($C_1$-$C_6$)alkyl groups, —C(=NOH)—($C_1$-$C_6$)alkyl groups, —NH—($C_1$-$C_6$)alkyl-optionally substituted aryl groups, or —C(=N—O—($C_1$-$C_6$)alkyl)-($C_1$-$C_6$)alkyl groups.

One or more compounds of this invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as *Remington's Pharmaceutical Sciences*, Mack Publishing Co., Easton, Pa., latest edition.

Suitable routes of administration may, for example, include oral, eyedrop, rectal, transmucosal, topical, inhaled or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few hours up to over several days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in a method of the present invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition (see e.g. Fingl et al., 1975, in *The Pharmacological Basis of Therapeutics*, Ch. 1, p. 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the following Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients.

| Parts by weight | |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PI3 kinase inhibitors, calcineurin inhibitors and immunosuppressants. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deletrious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present invention.

The present invention also comprises the use of a compound of Formula (I) as a medicament.

Purification Methods

Intermediate and final compounds may be purified by any technique or combination of techniques known to one skilled in the art. Some examples that are not limiting include flash chromatography with a solid phase (i.e. silica gel, alumina, etc.) and a solvent (or combination of solvents, i.e. heptane, EtOAc, DCM, MeOH, MeCN, water, etc.) that elutes the desired compounds; preparatory TLC with a solid phase (i.e. silica gel, alumina etc.) and a solvent (or combination of solvents, i.e. heptane, EtOAc, DCM, MeOH, MeCN, water, etc.) that elutes the desired compounds; reverse phase HPLC (see Table 1 for some non-limiting conditions); recrystallization from an appropriate solvent (i.e. MeOH, EtOH, i-PrOH, EtOAc, toluene, etc.) or combination of solvents (i.e. EtOAc/heptane, EtOAc/MeOH, etc.); chiral chromatography with a solid phase and an appropriate solvent (i.e. EtOH/heptane, MeOH/heptane, i-PrOH/heptane, etc. with or without a modifier such as DEA, Tfa, etc.) to elute the desired compound; precipitation from a combination of solvents (i.e. DMF/water, DMSO/DCM, EtOAc/heptane, etc.); trituration with an appropriate solvent (i.e. EtOAc, DCM, MeCN, MeOH, EtOH, i-PrOH, n-PrOH, etc.); extractions by dissolving a compound in a liquid and washing with an appropriately immiscible liquid (i.e. DCM/water, EtOAc/water, DCM/sat. $NaHCO_3$, EtOAc/sat. $NaHCO_3$, DCM/10% aqueous HCl, EtOAc/10% aqueous HCl, etc.); distillation (i.e. simple, fractional, Kugelrohr, etc.); gas chromatography using an appropriate temperature, carrier gas and flow rate; sublimation at an appropriate temperature and pressure; filtration through a media (i.e. Florosil®, alumina, Celite®, silica gel, etc.) with a solvent (i.e. heptane, hexanes, EtOAc, DCM, MeOH, etc.) or combination of solvents; salt formation with solid support (resin based, i.e. ion exchange) or without. Descriptions of these techniques can be found in the following references: Gordon, A. J. and Ford, R. A. *The Chemist's Companion*, 1972; Palleros, D. R. *Experimental Organic Chemistry*, 2000; Still, W. C., Kahn and M. Mitra, A. *J. Org. Chem.* 1978, 43:2923; Yan, B. *Analysis and Purification Methods in Combinatorial Chemistry*, 2003; Harwood, L. M., Moody, C. J. and Percy, J. M. *Experimental Organic Chemistry: Standard and Microscale*, $2^{nd}$ Edition, 1999; Stichlmair, J. G. and Fair, J. R. *Distillation; Principles and Practices*, 1998; Beesley T. E. and Scott, R. P. W. *Chiral Chromatography*, 1999; Landgrebe, J. A. *Theory and Practice in the Organic Laboratory*, $4^{th}$ Ed., 1993; Skoog, D. A. and Leary, J. J. *Principles of Instrumental Analysis*, $4^{th}$ Ed., 1992; G. Subramanian, *Chiral Separation Techniques*, $3^{rd}$ Edition 2007; Y. Kazakevich, R. Lobrutto, *HPLC for Pharmaceutical Scientists*, 2007.

Degassing Methods

Preparations of intermediate and final compounds obtained via the General Procedures can be optionally degassed using one or more of the Degassing Methods described below. The reaction mixtures may be degassed by a single or multiple applications of any technique or combination of techniques known to one skilled in the art. Some examples that are not limiting include bubbling a continuous stream of an inert gas (e.g. nitrogen, argon, etc.) through a mixture of reagents and a solvent suitable for the transformation (e.g. THF, 1,4-dioxane, EtOAc, DCM, toluene, MeOH, EtOH, DMF, MeCN, water, etc.); freeze-thawing of a mixture of reagents in a solvent (e.g. THF, 1,4-dioxane, EtOAc, DCM, toluene, MeOH, EtOH, DMF, MeCN, water, etc.) where the resulting solution is cooled below its freezing point and evacuated under reduced pressure, then allowed to warm above the freezing point and purged with an atmosphere of inert gas (e.g. nitrogen, argon, etc.); evacuation under reduced pressure of a mixture of reagents with or without a suitable solvent for the transformation (e.g. THF, 1,4-dioxane, EtOAc, DCM, toluene, MeOH, EtOH, DMF, MeCN, water, etc.) followed by purging of the mixture with an inert gas (e.g. nitrogen, argon, etc.); evacuation under reduced pressure of a mixture of reagents in a suitable solvent for the transformation (e.g. THF, 1,4-dioxane, EtOAc, DCM, toluene, MeOH, EtOH, DMF, MeCN, water, etc.) with the aid of mechanical agitation (e.g. stirring, shaking, sonication, etc.) followed by purging of the mixture with an inert gas (e.g. nitrogen, argon, etc.). Some descriptions of these techniques can be found in the following references, Gordon, A. J. and Ford, R. A. *The Chemist's Companion*, 1972; Palleros, D. R. *Experimental Organic Chemistry*, 2000; Harwood, L. M., Moody, C. J. and Percy, J. M. *Experimental Organic Chemistry: Standard and Microscale*, $2^{nd}$ Edition, 1999; Landgrebe, J. A. *Theory and*

Practice in the Organic Laboratory, 4th Edition, 1993; Leonard, J., Lygo, B. and Procter, G. Advanced Practical Organic Chemistry, 2nd Edition, 1998; Meyers, A. G.; Dragovich, P. S. Organic Syntheses, 1995, 72:104; Hajos, Z. G., Parrish, D. R. Organic Syntheses, 1985, 63:26.

EXAMPLES

None of the specific conditions and reagents noted herein are to be construed as limiting the scope of the invention and are provided for illustrative purposes only. All starting materials are commercially available from Sigma-Aldrich (including Fluka and Discovery CPR) unless otherwise noted after the chemical name. Reagent/reactant names given are as named on the commercial bottle or as generated by IUPAC conventions, CambridgeSoft® Chemdraw Ultra 9.0.7 or AutoNom 2000. Compounds designated as salts (e.g. hydrochloride, acetate) may contain more than one molar equivalent of the salt. Schemes represent racemic mixtures.

ABBREVIATIONS

Ac Acetyl
AcOH Glacial acetic acid
AIBN 2,2'-Azobis(2-methylpropionitrile)
Aq. Aqueous
Brine Saturated aqueous sodium chloride
bs Broad singlet
BuLi Butyllithium
d Doublet
DAD Diode array detection
DCM Dichloromethane (methylene chloride)
dd Doublet of doublets
DEA Diethylamine
DIEA Diisopropylethylamine
DIBAL-H Diisobutylaluminum hydride
DME 1,2-Dimethoxyethane
DMEM/F12 Dulbecco's Modified Eagle's Medium: Nutrient Mixture F-12
DMF N,N-Dimethylformamide
DMSO Dimethyl sulfoxide
ELSD Evaporative light scattering detection
EtOAc Ethyl acetate
$Et_2O$ Diethyl ether
EtOH Ethanol
FBS Fetal bovine serum
g Gram(s)
GR Glucocorticoid receptor
h Hour(s)
HEPES N-2-Hydroxyethylpiperazine-N'-2-ethanesulfonic acid
Hz Hertz
IPrOH Isopropanol
KOAc Potassium acetate
LAH Lithium aluminum hydride
LC Liquid chromatography
LiHMDS Lithium Hexamethyldisilazide
LiOH Lithium hydroxide
m Multiplet
M Molar
MeCN Acetonitrile
MeOH Methyl alcohol
mg Milligram(s)
min Minute(s)
mL Milliliter(s)
mmol Millimole(s)
mM Millimolar
mm Millimeter(s)
MS Mass spectrometry
N Normal
$NaBH_4$ Sodium borohydride
NBS N-Bromosuccinimide
nd not done
ng Nanogram(s)
$NH_4OAc$ Ammonium acetate
nM Nanomolar
NMO 4-Methylmorpholine N-oxide
NMR Nuclear magnetic resonance
OCN Osteocalcin
psi Pounds per square inch
pTSA p-toluenesulfonic acid monohydrate
rac racemic
rpm Revolutions per minute
$R_t$ Retention time
rt Room temperature
sat. Saturated
s Singlet
SFC Supercritical fluid chromatography
t Triplet
TBAF Tetra-n-butylammonium fluoride
Tfa Trifluoroacetic acid
TEA Triethylamine
TES Triethylsilyl
Tf Trifluoromethanesulfonyl
THF Tetrahydrofuran
TMS Trimethylsilyl
U Unit(s)
Wt Weight
Xantphos 4,5-Bis(diphenylphosphino)-9,9-dimethylxanthene
µL Microliter(s)
µg Microgram(s)
µM Micromolar
µm Micrometer(s)

Methods:
GR Fluorescence Polarization Assay

Fluorescence polarization assays were carried out using the PolarScreen™ Glucocorticoid Receptor Competitor Assay, Red from Invitrogen (P2893). The assay buffer was prepared according to the manufacturer's protocol and used to dilute the fluorescent glucocorticoid and GR. Compounds were prepared and serial diluted 1:4 in DMSO. Compound, fluorescent glucocorticoid and GR were added in a final volume of 20 µL and incubated overnight at 4° C. Fluorescent polarization was measured on the PerkinElmer Envision®.

A549 Cell Assay to Measure Inflammation Markers

A549 cells were seeded (3E4 cells/well) in 96-well assay plates in culture medium (100 µL/well., F-12 K base media, supplemented with 10% FBS and 100 µ/mL-100 µg/mL Pen-Strep.) After overnight culture in an incubator set to 37° C., 4.9% $CO_2$, and 90% humidity, media was removed from adherent cells by aspiration and replaced with 100 µL/well Assay Medium (F-12 K base media supplemented with 5% charcoal stripped calf sera and 100 U/mL-100 µg/mL Pen-Strep.) Compounds were prepared in DMSO and serial diluted (1:3, 1:4, or 1:5) with DMSO in Dilution Plate(s) to give 10 dilution points for each compound tested. Further dilution (1:250) of compound was made into assay medium and 50 µL/well diluted drug or DMSO/media control was applied to cells. After a 1 h pre-incubation in a temperature, $CO_2$, and humidity controlled incubator, set to 37° C., 50 µL/well of 4 ng/mL IL-1β diluted in assay media, was applied to cultures. Assay plates, with a final volume of 200 µL/well and final concentrations of 0.1% DMSO and 1 ng/mL IL-1β were returned to incubator for a four h incubation period. Next, plates were spun at 183 g (1000 rpm in Beckman/Coulter Allegra 6KR centrifuge) for 10 min. Cell-free supernatant (150 µL/well) was collected and IL-6 was measured by MSD kit, following protocol of manufacturer, and using MSD SECTOR Imager 6000 instrument. Potency of compounds to inhibit IL-6 was determined using the percent reduction of measured IL-6 in wells with compound compared to control wells without drug, and relative to (100% inhibition) positive control compound of 1 µM prednisolone. Results were represented as $IC_{50}$ and Emax values. To verify that viable cell numbers were similar across plate(s), and not confounding compound $IC_{50}$ data interpretation, the remaining 50 µL/well of cells and media (after removal of supernatant) were used to run Cell Titer-Glo Assay per directions of manufacturer.

MG-63 Cell Assay to Measure Bone Markers

MG-63 cells were cultured in culture media containing ascorbic acid (DMEM/F12 supplemented with 10% FBS, 1% HEPES, 100 U/mL-100 µg/mL Pen-Strep, and 100 µg/mL of ascorbic acid) for, minimally, 1 week before study. MG-63 cells were seeded (4E4 cells/well) in 96-well assay plates in culture medium (200 µL/well.) After overnight culture in an incubator set to 37° C., 4.9% $CO_2$, and 90% humidity, media was removed from adherent cells by aspiration and replaced with 100 µL/well assay medium, DMEM/F12 supplemented with 5% Charcoal Stripped Serum, 1% HEPES, 100 U/mL-100 µg/mL Pen-Strep, and 100 µg/mL of ascorbic acid. Compounds were prepared with DMSO and serial diluted (1:3, 1:4, or 1:5) with DMSO in dilution plate(s) to give 10 dilution points for each compound tested. Further dilution (1:250) of compound was made into assay medium and 50 µL/well diluted drug or DMSO/media control was applied to cells. After a 1 h pre-incubation in a temperature, $CO_2$, and humidity controlled incubator, set to 37° C., 50 µL/well of 40 nM Vitamin K and 400 nM Vitamin D that were diluted in assay media were applied to plates. Assay plates, with a final volume of 200 µL/well and final concentrations of 0.1% DMSO, 10 nM Vitamin K, and 100 nM Vitamin D, were returned to incubator for overnight culture. Next, plates were spun at 183 g (1000 rpm in Beckman/Coulter Allegra 6KR centrifuge) for 10 min. Cell-free supenatant (150 µL/well) was collected and OCN was measured by MSD kit, following protocol of manufacturer, and using MSD SECTOR Imager 6000 instrument. Potency of drug to inhibit OCN was determined using the percent reduction of measured OCN in wells with drug compared to control wells without drug, and relative to (100% inhibition) positive control sample of 10 µM prednisolone. Results were represented as $IC_{50}$ and Emax values. To verify that viable cell numbers were similar across plate(s), and not confounding compound $IC_{50}$ data interpretation, the remaining 50 µL/well of cells and media (after removal of supernatant) were used to run Cell Titer-Glo Assay per directions of manufacturer.

LC/MS methods

Method 1: UPLC 2 min method: The gradient was 5-60% B in 0.60 min then 60-95% B to 1.0 min with a hold at 95% B for 0.30 (1.25 mL/min flow rate). The column used for the chromatography was 2.1×30 mm Acquity UPLC HSS T3 column (1.8 µm particles). The gradient was 5-60% B in 0.60 min then 60-95% B to 1.0 min with a hold at 95% B for 0.30 (1.25 mL/min flow rate). The mobile phase A was 10 mM $NH_4OAc$, mobile phase B was HPLC grade MeCN. Detection methods are diode array (DAD) and evaporative light scattering (ELSD) detection as well as pos/neg electrospray ionization.

Method 2: Halo Purity QC method: The gradient was 5-60% B in 1.5 min then 60-95% B to 2.5 min with a hold at 95% B for 1.2 min (1.3 mL/min flow rate). The mobile phase A was 10 mM $NH_4OAc$, mobile phase B was HPLC grade MeCN. The column used for the chromatography is a 4.6×50 mm MAC-MOD Halo C18 column (2.7 µm particles). Detection methods are diode array (DAD) and evaporative light scattering (ELSD) detection as well as positive/negative electrospray ionization.

Method 3: Halo 4 min method: The gradient was 5-60% B in 1.5 min then 60-95% B to 2.5 min with a hold at 95% B for 1.2 min (1.3 mL/min flow rate). The mobile phase A was 10 mM $NH_4OAc$, mobile phase B was HPLC grade MeCN. The column used for the chromatography is a 4.6×50 mm MAC-MOD Halo C8 column (2.7 µm particles). Detection methods are diode array (DAD) and evaporative light scattering (ELSD) detection as well as positive/negative electro spray ionization.

Method 4: Halo test 4 min nonpolar; (30-95%: 4 min gradient for highly nonpolar): The gradient was 30-60% B in 1.50 min then 60-95% B to 2.5 min with a hold at 95% B for 1.2 min (1.3 mL/min flow rate). The mobile phase A was 10 mM ammonium acetate, mobile phase B was HPLC grade MeCN. The column used for the chromatography is a 4.6×50 mm MAC-MOD Halo C8 column (2.7 µm particles). Detection methods are diode array (DAD) and evaporative light scattering (ELSD) detection as well as positive/negative electrospray ionization.

Preparative Chiral Chromatography Methods

Method 1: The gradient was 4-12% A in 22 min (20 mL/min flow rate) then re-equilibrated at 4% for 8 min. Mobile phase A was HPLC grade isopropanol, mobile phase B was HPLC grade heptane with 0.12% DEA added. The column used for the chromatography was a Daicel IA, 20×250 mm column (5 µm particles).

Method 2: (LC) Isocratic 5% A (20 mL/min flow rate). Mobile phase A was EtOH (200 proof), mobile phase B was HPLC grade heptane with 0.1% DEA added. The chromatography used a Daicel IB, 20×250 mm column (5 µm particles).

Method 3: (LC) Isocratic 6% A (20 mL/min flow rate). Mobile phase A was EtOH (200 proof), mobile phase B was HPLC grade heptane with 0.1% DEA added. The chromatography used a Daicel IB, 20×250 mm column (5 µm particles).

Method 4: (LC) Isocratic 15% A (20 mL/min flow rate). Mobile phase A was IPA (HPLC grade), mobile phase B was HPLC grade heptane with 0.125% DEA added. The chromatography used a Daicel IA, 20×250 mm column (5 µm particles).

Method 5: (LC) Gradient 7-35% A (20 mL/min flow rate). Mobile phase A was (EtOH w/0.1% DEA as cosolvent), mobile phase B was HPLC grade heptane with 0.125% DEA added. The chromatography used a Daicel IA, 20×250 mm column (5 µm particles).

Method 6: (LC) Gradient 15-55% A (20 mL/min flow rate). Mobile phase A was (IPA w/0.1% DEA as cosolvent), mobile phase B was HPLC grade heptane with 0.125% DEA added. The chromatography used a Daicel IA, 20×250 mm column (5 µm particles).

Method 7: (LC) Isocratic 2% A (20 mL/min flow rate). Mobile phase A was (EtOH w/0.1% DEA as cosolvent), mobile phase B was HPLC grade heptane with 0.125% DEA added. The chromatography used a Daicel IB, 20×250 mm column (5 µm particles).

Method 8: (LC) Isocratic 40% A (20 mL/min flow rate). Mobile phase A was EtOH (200 proof), mobile phase B was HPLC grade heptane with 0.12% DEA added. The chromatography used a Daicel IA, 20×250 mm column (5 μm particles).

Method 9: (LC) Isocratic 20% A (20 mL/min flow rate). Mobile phase A was EtOH (200 proof), mobile phase B was HPLC grade heptane with 0.12% DEA added. The chromatography used a Daicel IA, 20×250 mm column (5 μm particles).

Method 10: (LC) Isocratic 10% A (20 mL/min flow rate). Mobile phase A was EtOH (200 proof), mobile phase B was HPLC grade heptane with 0.12% DEA added. The chromatography used a Daicel IA, 20×250 mm column (5 μm particles).

Method 11: (LC) Isocratic 20% B (20 mL/min flow rate). Mobile phase B was iPrOH, mobile phase A was HPLC grade heptane with 0.12% DEA added. The chromatography used a Daicel ID, 20×250 mm column (5 μm particles).

Method 12: (LC) Gradient 5-35% B (20 mL/min flow rate). Mobile phase A was heptane (no modifier), mobile phase B was EtOH (no modifier). The chromatography used a Daicel IA, 20×250 mm column (5 μm particles).

Method 13: (LC) Gradient 15-55% B (20 mL/min flow rate). Mobile phase A was heptane with 0.1% DEA added, mobile phase B was EtOH (no modifier). The chromatography used a Welko SS, column.

Method 14: (LC) Isocratic 9% A (20 mL/min flow rate). Mobile phase A was EtOH (200 proof), mobile phase B was HPLC grade heptane with 0.1% DEA added. The chromatography used a Daicel IC, 20×250 mm column (5 μm particles).

Method 15: (LC) Gradient 4% B for 19 min, 4-50% B over 5 min, 50% B for 6 min (20 mL/min flow rate). Mobile phase A was heptane with 0.12% DEA added and mobile phase B was isopropanol. The chromatography used a Daicel IA, 20×250 mm column (5 μm particles).

Method 16: (LC) Gradient 8% B for 14 min, 8-40% B over 10 sec, 40% B for 6 min (20 mL/min flow rate). Mobile phase A was heptane with 0.12% DEA added and mobile phase B was isopropanol. The chromatography used a Daicel IA, 20×250 mm column (5 μm particles).

Method 17: (LC) Isocratic 4% B (24 mL/min flow rate). Mobile phase A was heptane with 0.1% DEA added, mobile phase B was isopropanol. The chromatography used a Daicel IC, 20×250 mm column (5 μm particles).

Method 18: (LC) Isocratic 10% B (20 mL/min flow rate). Mobile phase A was heptane with 0.1% DEA added, mobile phase B was ethanol. The chromatography used a Daicel IA, 20×250 mm column (5 μm particles).

Method 19: (LC) Gradient 3-14% B (20 mL/min flow rate). Mobile phase A was heptane with 0.1% DEA added, mobile phase B was ethanol. The chromatography used a Daicel IA, 20×250 mm column (5 μm particles).

Method 20: (LC) Isocratic 3% B (20 mL/min flow rate). Mobile phase A was heptane with 0.1% DEA added, mobile phase B was ethanol. The chromatography used a Daicel IB, 20×250 mm column (5 μm particles).

Method 21: (LC) Gradient 3-14% B (20 mL/min flow rate). Mobile phase A was heptane with 0.1% DEA added, mobile phase B was ethanol. The chromatography used a Daicel IA, 20×250 mm column (5 μm particles).

Method 22: (LC) Gradient 5-55% A (20 mL/min flow rate). Mobile phase A was ethanol, mobile phase B was heptane with 0.1% DEA added. The chromatography used a Daicel IA, 20×250 mm column (5 μm particles).

Method 23: (LC) Isocratic 8% A (20 mL/min flow rate). Mobile phase A was ethanol, mobile phase B was heptane with 0.1% DEA added. The chromatography used a Daicel IA, 20×250 mm column (5 μm particles).

Method 24: (LC) Gradient 10-60% B (20 mL/min flow rate). Mobile phase B was EtOH, mobile phase A was HPLC grade heptane with 0.12% DEA added. The chromatography used a Daicel ID column, 20×250 mm column (5 μm particles).

Method 25: (LC) Isocratic 15% B (20 mL/min flow rate). Mobile phase B was EtOH, mobile phase A was heptane with 0.12% DEA added. The chromatography used a Daicel IB, 20×250 mm column (5 μm particles).

Method 26: (LC) Gradient 15-25% B (20 mL/min flow rate). Mobile phase B was IPA, mobile phase A was HPLC grade heptane with 0.12% DEA added. The chromatography used a Daicel IC column, 20×250 mm column (5 μm particles).

Method 27: (LC) Isocratic 20% B (20 mL/min flow rate). Mobile phase B was EtOH, mobile phase A was heptane with 0.12% DEA added. The chromatography used a Daicel IA, 20×250 mm column (5 μm particles).

Method 28: (LC) Isocratic 15% B (20 mL/min flow rate). Mobile phase B was EtOH, mobile phase A was heptane with 0.12% DEA added. The chromatography used a Daicel IA, 20×250 mm column (5 μm particles).

Method 29: (LC) Gradient 15-40% B (20 mL/min flow rate). Mobile phase B was IPA, mobile phase A was HPLC grade heptane with 0.12% DEA added. The chromatography used a Daicel ID column, 20×250 mm column (5 μm particles).

Method 30: (LC) Isocratic 30% A (20 mL/min flow rate). Mobile phase A was HPLC grade EtOH (200 proof) with 0.1% DEA added, mobile phase B was HPLC grade heptane with 0.125% DEA added. The chromatography used a Daicel IC, 20×250 mm column (5 μm particles).

Method 31: The gradient was 2-15% A in 36 min (20 mL/min flow rate) then re-equilibrated at 2% for 4 min. Mobile phase A was HPLC grade isopropanol, mobile phase B was HPLC grade heptane with 0.2% DEA added. The column used for the chromatography was a Daicel IA, 20×250 mm column (5 μm particles).

Method 32: (LC) Isocratic 15% A (20 mL/min flow rate) for 18 min, then step to 45% A to elute the second component. Mobile phase A was EtOH (200 proof), mobile phase B was HPLC grade heptane with 0.2% DEA added. The column used for the chromatography was a Daicel IA, 20×250 mm column (5 μm particles).

Method 33: (LC) Isocratic 20% A (20 mL/min flow rate) for 16 min, then step to 60% A to elute the second component. Mobile phase A was HPLC grade isopropanol, mobile phase B was HPLC grade heptane with 0.12% DEA added. The column used for the chromatography was a Daicel ID, 20×250 mm column (5 μm particles).

Method 34: The gradient was 25-45% A in 22 min (20 mL/min flow rate) then re-equilibrated at 25% for 5 min. Mobile phase A was 200 proof EtOH, mobile phase B was HPLC grade heptane with 0.12% DEA added. The column used for the chromatography was a Daicel IC, 20×250 mm column (5 μm particles).

Method 35: (LC) Isocratic 2% A (20 mL/min flow rate). Mobile phase A was (EtOH w/0.1% DEA as co-solvent), mobile phase B was HPLC grade heptane with 0.125% DEA added. The chromatography used a Daicel IC, 20×250 mm column (5 μm particles).

Method 36: (LC) Gradient 20-30% A (20 mL/min flow rate). Mobile phase A was EtOH (no modifier). Mobile phase B was heptane with 0.125% DEA. The chromatography used a Daicel IA, 20×250 mm column (5 μm particles).

Method 37: (LC) Gradient 20-50% A (20 mL/min flow rate). Mobile phase A was IPA (no modifier). Mobile phase B was heptane with 0.125% DEA. The chromatography used a Daicel IA, 20×250 mm column (5 µm particles).

Method 38: (LC) Gradient 2-6% A (20 mL/min flow rate). Mobile phase A was EtOH (no modifier). Mobile phase B was heptane (0.12% DEA modifier). The chromatography used a Daicel ID, 20×250 mm column (5 µm particles).

Method 39: (LC) Gradient 0-10% A (20 mL/min flow rate). Mobile phase A was EtOH (no modifier). Mobile phase B was heptane (0.12% DEA modifier). The chromatography used a Daicel IA, 20×250 mm column (5 µm particles).

Method 40: (LC) Gradient 1-4% A (20 mL/min flow rate). Mobile phase A was IPA (no modifier). Mobile phase B was heptane (0.12% DEA modifier). The chromatography used a Daicel IB, 20×250 mm column (5 µm particles).

Method 41: (LC) Gradient 10-30% A (20 mL/min flow rate). Mobile phase A was EtOH (no modifier). Mobile phase B was heptane (0.12% DEA modifier). The chromatography used a Daicel IC, 20×250 mm column (5 µm particles).

Method 42: (LC) Isocratic 5% A then gradient 5-70% A (20 mL/min flow rate). Mobile phase A was EtOH (no modifier). Mobile phase B was heptane (0.12% DEA modifier). The chromatography used a Daicel IC, 20×250 mm column (5 µm particles).

Method 43: (LC) Isocratic 30% B. Mobile phase B was iPrOH (no modifier). Mobile phase B was heptane (0.2% DEA modifier added). The chromatography used a Daicel ID, 20×250 mm column (5 µm particles).

Method 44: (LC) Isocratic 5% A (20 mL/min flow rate). Mobile phase A was EtOH, mobile phase B was HPLC grade heptane with 0.125% DEA added. The chromatography used a Daicel IA, 20×250 mm column (5 µm particles).

Method 45: (LC) Gradient 5-14% A (20 mL/min flow rate). Mobile phase A was IPA (no modifier). Mobile phase B was heptane (0.12% DEA modifier). The chromatography used a Daicel IC, 20×250 mm column (5 µm particles).

Method 46: (LC) Isocratic 35% B for 17 min (20 mL/min flow rate). Mobile phase A was heptane with 0.12% DEA added, mobile phase B was isopropanol. The chromatography used a Daicel IA, 20×250 mm column (5 µm particles).

Method 47: (LC) Isocratic 35% B for 26 min and then 50% B for 9 min (20 mL/min flow rate). Mobile phase A was heptane with 0.12% DEA added, mobile phase B was isopropanol. The chromatography used a Daicel IA, 20×250 mm column (5 µm particles).

Method 48: (LC) Isocratic 20% B for 18 min (20 mL/min flow rate). Mobile phase A was heptane with 0.12% DEA added, mobile phase B was EtOH. The chromatography used a Daicel IA, 20×250 mm column (5 µm particles).

Method 49: (LC) Isocratic 20% B for 17 min (20 mL/min flow rate). Mobile phase A was heptane with 0.12% DEA added, mobile phase B was isopropanol. The chromatography used a Daicel IA, 20×250 mm column (5 µm particles).

Method 50: (LC) Isocratic 20% B for 15.5 min and then 45% B for 5 min (20 mL/min flow rate). Mobile phase A was heptane with 0.12% DEA added, mobile phase B was EtOH. The chromatography used a Daicel IA, 20×250 mm column (5 µm particles).

Method 51: (LC) Isocratic 25% B (20 mL/min flow rate) for 22 min. Mobile phase B was EtOH (200 proof), mobile phase A was HPLC grade heptane with 0.12% DEA added. The chromatography used a Daicel ID, 20×250 mm column (5 µm particles).

Method 52: (LC) Isocratic 25% B (20 mL/min flow rate) for 25 min. Mobile phase B was iPrOH, mobile phase A was HPLC grade heptane with 0.12% DEA added. The chromatography used a Daicel IA, 20×250 mm column (5 µm particles).

Method 53: (LC) Gradient 22% A (20 mL/min flow rate) for 16.5 min, then step to 40% A to elute the second component. Mobile phase A was HPLC grade isopropanol, mobile phase B was HPLC grade heptane with 0.12% DEA added. The column used for the chromatography was a Daicel IA, 20×250 mm column (5 µm particles).

Method 54: (LC) Gradient 15% A (20 mL/min flow rate) for 23 min then step to 50% A and hold at 50% for 8 min. Mobile phase A was EtOH (200 proof), mobile phase B was HPLC grade heptane with 0.2% DEA added. The column used for the chromatography was a Daicel IA, 20×250 mm column (5 µm particles).

Method 55: (LC) Isocratic 25% B (20 mL/min flow rate) for 19.5 min then step to 55% B and hold at 55% for 7 min. Mobile phase B was EtOH (200 proof), mobile phase A was HPLC grade heptane with 0.1% DEA added. The column used for the chromatography was a Daicel ID, 20×250 mm column (5 µm particles).

Method 56: (LC) Isocratic 5% B (20 mL/min flow rate) for 12.5 min then gradient of 5-45% B and over 13.5 min. Mobile phase B was EtOH (200 proof), mobile phase A was HPLC grade heptane with 0.1% DEA added. The column used for the chromatography was a Daicel IB, 20×250 mm column (5 µm particles).

Scheme 1:

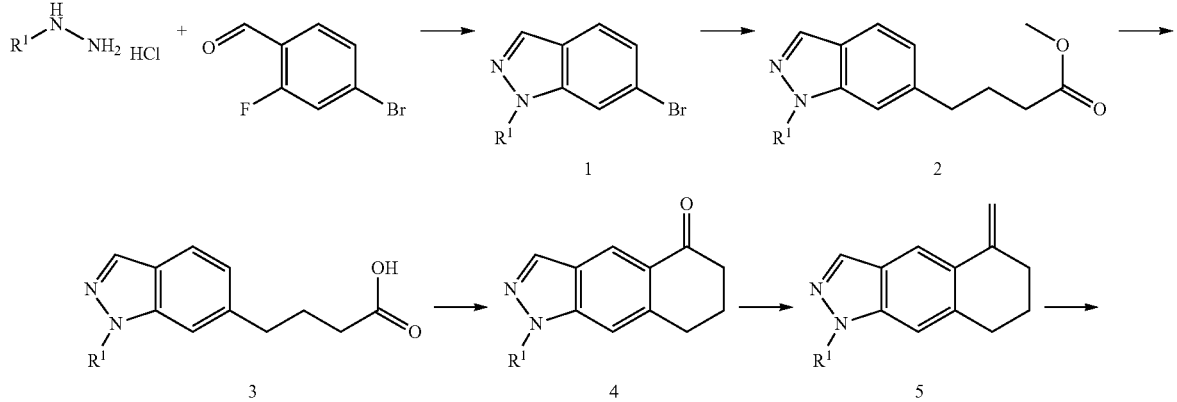

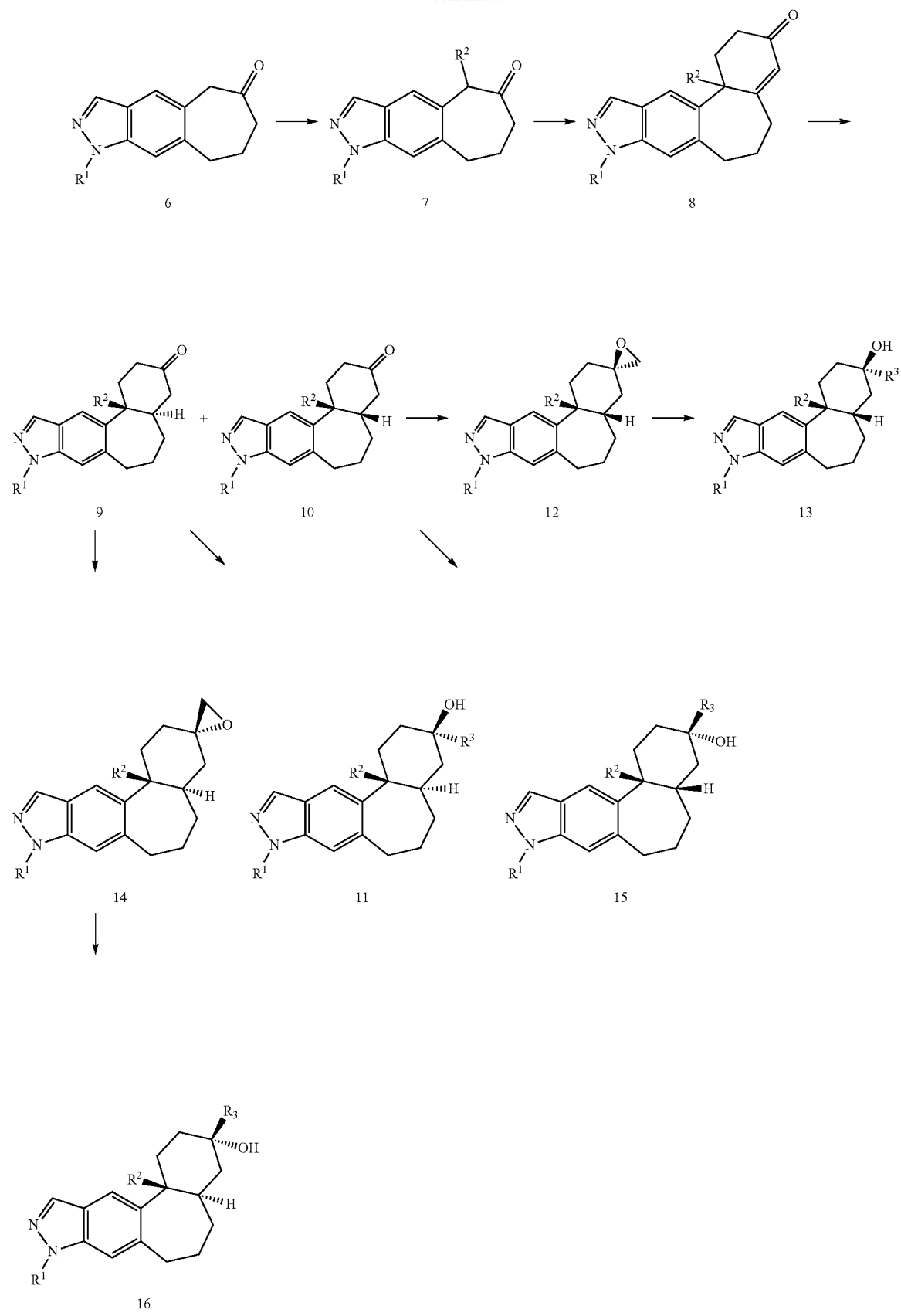

Example #1

(3S,4aS,12bR)-12b-Ethyl-9-(4-fluoro-phenyl)-3-trifluoromethyl-1,2,3,4,4a, 5,6,7,9,12b-decahydro-9,10-diaza-benzo[3,4]cyclohepta[1,2-f]inden-3-ol; compound with (3R,4aR,12bS)-12b-ethyl-9-(4-fluoro-phenyl)-3-trifluoromethyl-1,2,3,4,4a,5,6,7,9,12b-decahydro-9,10-diaza-benzo[3,4]cyclohepta[1,2-f]inden-3-ol (15, R¹=4-Fluorophenyl, R²=Ethyl, R³=Trifluoromethyl)

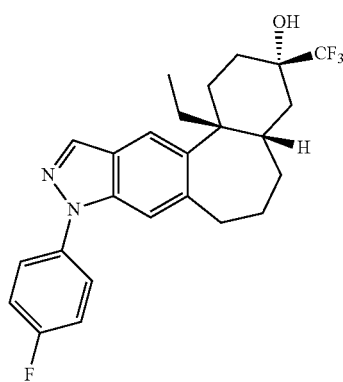 [SMILES: CC[C@@]12CC[C@@](O)(C(F)(F)F)C[C@@H]1CCCc1cc3c(cnn3-c3ccc(F)cc3)cc12]

Step 1: 6-Bromo-1-(4-fluorophenyl)-1H-indazole (1, R¹=4-Fluorophenyl)

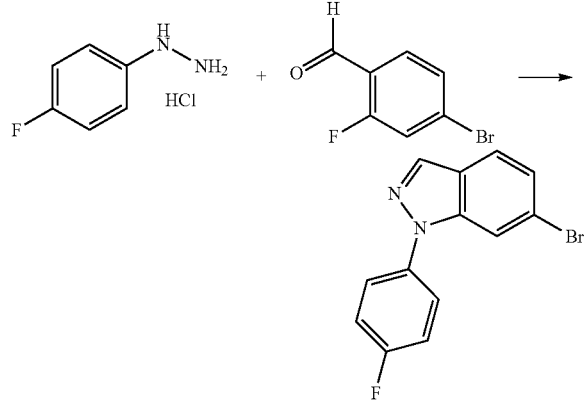

A flask was charged with (4-fluorophenyl)hydrazine hydrochloride (25.0 g, 154 mmol), 1-methyl-2-pyrrolidinone (500 mL) and 4-bromo-2-fluorobenzaldehyde (31.2 g, 154 mmol). The mixture was stirred at rt for about 14 h then potassium 2-methylpropan-2-olate (18.98 g, 169 mmol) was added. The mixture was stirred for about 1 h then a second portion of potassium 2-methylpropan-2-olate (17.25 g, 154 mmol) was added. The mixture was stirred for about 15 min then warmed in an oil bath heated to about 160° C. for about 24 h. The mixture was cooled to rt then about 250 mL solvent was removed under reduced pressure. The mixture was diluted with about 750 mL water then allowed to stand overnight. The supernatant was decanted and the resulting residue was stirred with EtOAc (350 mL) for about 1 h. The solids were collected by filtration. The filtrate was concentrated then stirred in a mixture of DCM (350 mL), water (250 mL) and 6 N HCl (25 mL) for about 3 h. The layers were separated then the organic layer was dried over MgSO₄, filtered and the filtrate concentrated under reduced pressure. The residue was purified on silica gel (330 g) using a gradient of 0-10% EtOAc in DCM. Product fractions were combined and concentrated under reduced pressure to give a solid which was treated with heptane (100 mL) and stirred overnight at room rt. The solids were collected by filtration and washed with heptane (25 mL). The solids from the initial EtOAc trituration and the material from the column and heptane trituration were combined to yield 6-bromo-1-(4-fluorophenyl)-1H-indazole (1, R¹=4-fluorophenyl) (23.94 g, 54%); LC/MS, method 3, $R_t$=2.83 min, MS m/z 291, 293 (M+H)⁺. ¹H NMR (400 MHz, DMSO) δ 8.41 (s, 1H), 7.97 (s, 1H), 7.88-7.79 (m, 3H), 7.46-7.42 (m, 3H).

Step #2: Ethyl 4-(1-(4-fluorophenyl)-1H-indazol-6-yl)butanoate (2, R¹=4-Fluorophenyl)

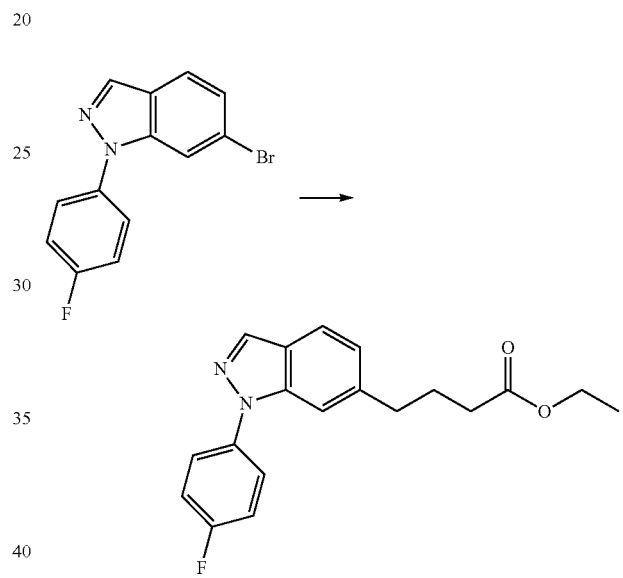

A flask with stir bar and nitrogen line was charged with the 6-bromo-1-(4-fluorophenyl)-1H-indazole (1, R¹=4-Fluorophenyl) (23.8 g, 82 mmol), THF (300 mL) and palladium tetrakistriphenylphospine (5.0 g, 4.33 mmol). Zinc(II) 4-ethoxy-4-oxobutan-1-ide bromide (0.5 M solution in THF, 200 mL, 82 mmol) was added over about 20 min and then the mixture was stirred at rt for about 30 min. The mixture was heated in an oil bath to about 75° C. for about 1 h. The mixture was cooled to rt then concentrated under reduced pressure. The material was partitioned between EtOAc (250 mL) and sat. aq. NH₄Cl (150 mL). The organic layer was washed with brine (100 mL), dried over MgSO₄, filtered and concentrated under reduced pressure. The residue was purified on silica gel (330 g) using a gradient of 0-50% EtOAc in heptane. Pure product fractions were combined and concentrated. Impure product fractions were combined, concentrated under reduced pressure then dissolved in EtOAc (20 mL) and heptane (70 mL). The mixture was cooled to about 0° C. with stirring. After about 30 min the solids were removed by filtration and discarded. The filtrate was concentrated under reduced pressure. The residue was purified on silica gel (220 g) using a gradient of 0-50% EtOAc in heptane. Pure product fractions were combined with those from the first column then concentrated to yield ethyl 4-(1-(4-fluorophenyl)-1H-indazol-6-yl)butanoate (2, R¹=4-Fluorophenyl) (17.95 g, 67%); LC/MS, method 3, $R_t$=2.76 min, MS m/z 327 (M+H)+. 1H NMR (400 MHz, DMSO) δ 8.31 (s, 1H), 7.86-7.75 (m, 3H), 7.57 (s, 1H), 7.46-7.41 (m, 2H), 7.14-7.12 (m, 1H), 4.02 (q, J=10.0 Hz, 2H), 2.76 (t, J=7.6 Hz, 2H), 2.30 (t, J=7.4 Hz, 2H), 1.95-1.82 (m, 2H), 1.14 (t, J=10.0 Hz, 3H).

Step #3: 4-(1-(4-Fluorophenyl)-1H-indazol-6-yl)butanoic acid (3, $R^1$=4-Fluorophenyl)

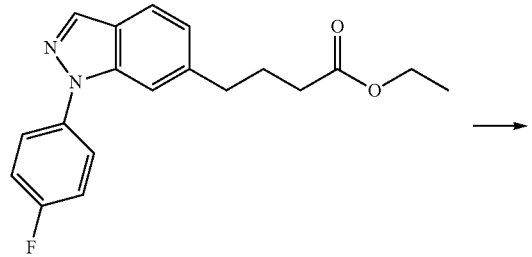

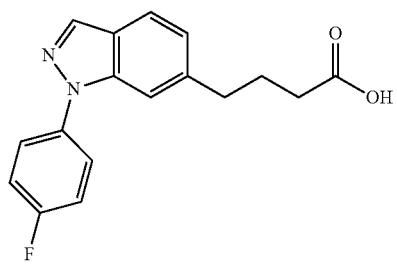

A mixture of ethyl 4-(1-(4-fluorophenyl)-1H-indazol-6-yl)butanoate (2, $R^1$=4-Fluorophenyl) (17.95 g, 55.0 mmol), LiOH (3.95 g, 165 mmol), 1,4-dioxane (150 mL) and water (30 mL) was warmed in an oil bath heated to about 80° C. for about 16 h. The mixture was cooled to rt then concentrated under reduced pressure to give a solid. The material was dissolved in water (200 mL) then the mixture was acidified to about pH 1 with hydrochloric acid (6 N) (30 mL, 180 mmol). The mixture was extracted twice with EtOAc (150 mL, then 50 mL) then the combined organic solutions were dried over MgSO4, filtered and the filtrate concentrated under reduced pressure to yield 4-(1-(4-fluorophenyl)-1H-indazol-6-yl)butanoic acid (3, $R^1$=4-Fluorophenyl) (15.87 g, 97%); LC/MS, method 3, $R_t$=2.19 min, MS m/z 299 (M+H)+. 1H NMR (400 MHz, DMSO) δ 12.03 (s, 1H), 8.30 (d, J=0.9 Hz, 1H), 7.84-7.74 (m, 3H), 7.57 (s, 1H), 7.48-7.39 (m, 2H), 7.13 (dd, J=8.3, 1.2 Hz, 1H), 2.79-2.72 (m, 2H), 2.26-2.22 (m, 2H), 1.91-1.81 (m, 2H).

Step #4: 1-(4-Fluorophenyl)-7,8-dihydro-1H-benzo[f]indazol-5(6H)-one (4, $R^1$=4-Fluorophenyl)

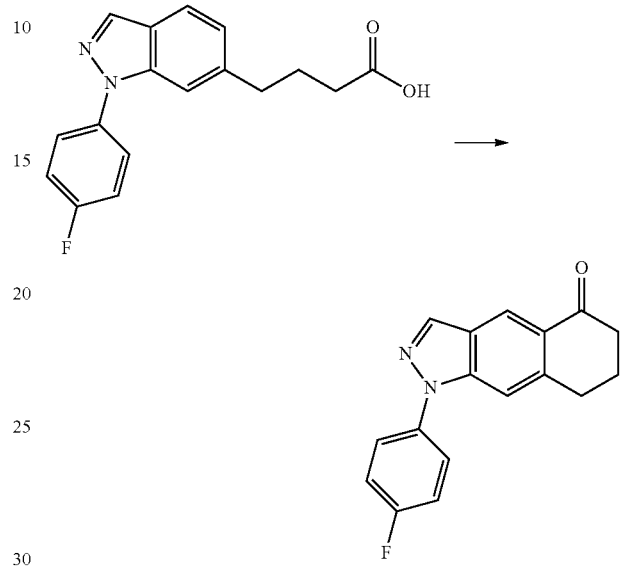

A solution of 4-(1-(4-fluorophenyl)-1H-indazol-6-yl)butanoic acid (3, $R^1$=4-Fluorophenyl) (13.86 g, 46.5 mmol) in DCM (225 mL) was treated with oxalyl dichloride (2M in DCM) (25.6 mL, 51.1 mmol). Two drops of DMF were added and the mixture was stirred for about 45 min at rt. A second portion of oxalyl dichloride (2M in DCM) (4.65 mL, 9.29 mmol) was added followed by 1 drop DMF. After about 15 min the solvent was removed under reduced pressure. The material was dissolved in DCM (225 mL) and the flask was fitted with a reflux condenser. Aluminum trichloride (8.2 g, 61.5 mmol) was added and the mixture was stirred for about 30 min. A second portion of aluminum trichloride (7.67 g, 57.5 mmol) was added to the mixture and stirring was continued for about 30 min. The reaction was quenched by slow addition of ice in small portions over about 30-45 min with vigorous stirring. After addition of about 50 g of ice, the biphasic mixture was transferred to a separatory funnel and the layers were separated. The aqueous layer was extracted with DCM (30 mL) and the combined organic solutions were washed with water (75 mL), 0.5 N aq. sodium hydroxide (100 mL) and brine (50 mL). The organic mixture was dried over MgSO4, filtered and concentrated under reduced pressure to a solid. The material was purified on silica gel (330 g) using a gradient of 0-15% EtOAc in DCM. Fractions containing >95% desired product were combined and concentrated under reduced pressure. Fractions containing desired product contaminated with the minor regioisomer [1-(4-fluorophenyl)-7,8-dihydro-1H-benzo[g]indazol-9(6H)-one] were combined and concentrated under reduced pressure separately. The residue was purified on silica gel (80 g) using a gradient of 0-10% EtOAc in DCM. Fractions containing >95% desired product were combined with those from the first column and concentrated under reduced pressure to yield 1-(4-fluorophenyl)-7,8-dihydro-1H-benzo[f]indazol-5(6H)-one (4, $R^1$=4-Fluorophenyl) (8.73 g, 67%); LC/MS, method 3, $R_t$=2.43 min, MS m/z 281 (M+H)+. 1H NMR (400 MHz, DMSO) δ 8.52 (d, J=0.9 Hz, 1H), 8.49 (s, 1H), 7.86-7.78 (m, 2H), 7.69 (s, 1H), 7.51-7.41 (m, 2H), 3.12-3.09 (m, 2H), 2.70-2.63 (m, 2H), 2.11-2.02 (m, 2H). Note: ¹H NMR shows ~4% minor regioisomer.

Step #5: 1-(4-Fluorophenyl)-5-methylene-5,6,7,8-tetrahydro-1H-benzo[f]indazole (5, R¹=4-Fluorophenyl)

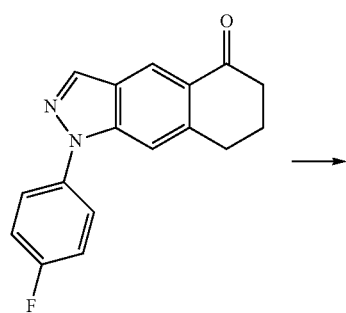

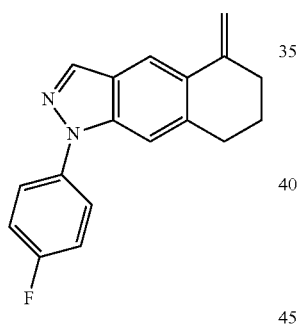

A round bottom flask with nitrogen line and stir bar was charged with sodium hydride (60 wt % in oil, 2.49 g, 62.3 mmol) and DMSO (40 mL) then the mixture was heated to about 60° C. for about 1 h. The mixture was cooled to rt and diluted with THF (40 mL) and then methyltriphenylphosphonium bromide (22.81 g, 63.8 mmol) was added in one portion. The slurry was stirred for about 30 min and then 1-(4-fluorophenyl)-7,8-dihydro-1H-benzo[f]indazol-5(6H)-one (4, R¹=4-Fluorophenyl) (8.73 g, 31.1 mmol) suspended in THF (100 mL) was added. The mixture was stirred at rt for about 14 h then the solids were collected by filtration and the filter cake was washed with EtOAc (2×25 mL). The filtrate was concentrated under reduced pressure. The residue was purified on silica gel (330 g) using a gradient of 0-15% EtOAc in heptane. Product fractions were combined and concentrated under reduced pressure to yield 1-(4-fluorophenyl)-5-methylene-5, 6,7,8-tetrahydro-M-benzo[f]indazole (5, R¹=4-Fluorophenyl) (8.52 g, 98%); LC/MS, method 3, R$_f$=3.01 min, MS m/z 279 (M+H)⁺. ¹H NMR (400 MHz, DMSO) δ 8.31 (d, J=0.9 Hz, 1H), 8.20 (s, 1H), 7.83-7.76 (m, 2H), 7.55 (s, 1H), 7.47-

7.38 (m, 2H), 5.60 (d, J=1.1 Hz, 1H), 4.98 (d, J=1.3 Hz, 1H), 3.00-2.97 (m, 2H), 2.59-2.53 (m, 2H), 1.87-1.77 (m, 2H).

Step #6: 1-(4-Fluorophenyl)-5,7,8,9-tetrahydrocyclohepta[f]indazol-6(1H)-one (6, R¹=4-Fluorophenyl)

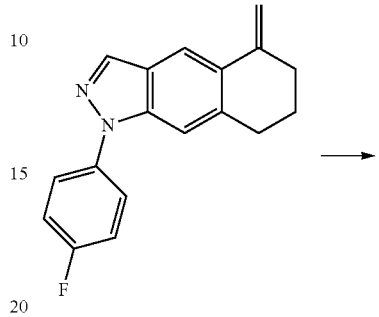

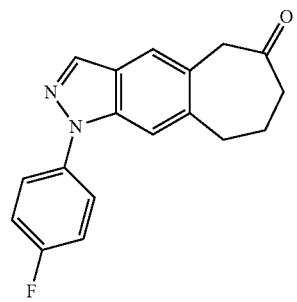

To a stirred mixture of 1-(4-fluorophenyl)-5-methylene-5, 6,7,8-tetrahydro-1H-benzo[f]indazole (5, R¹=4-Fluorophenyl) (8.5 g, 30.5 mmol), MeOH (204 mL) and water (17 mL) was added a solution of [hydroxyl(tosyloxy)iodo]benzene (11.98 g, 30.5 mmol) in MeOH (31 mL) over about 30 min maintaining the internal temperature of the mixture between about 15 and 20° C. The mixture was stirred for about 15 min then diluted with brine (300 mL) and extracted three times with DCM (2×100 mL, 1×30 mL). The combined organic solutions were extracted with 5 N hydrochloric acid (~30 mL), dried over MgSO₄ and filtered. The filtrate was concentrated under reduced pressure and the material was dissolved in hot EtOAc (~30 mL). The mixture was cooled in an ice/water bath and the solids were collected by filtration and dried under vacuum at rt to yield 5.44 grams of material. The filtrate was concentrated under reduced pressure then the residue was purified on silica gel (120 g) using a gradient of 10-50% EtOAc in heptane. Product fractions were combined and concentrated under reduced pressure to yield an additional 2.34 grams of material. The solids were combined to yield 1-(4-fluorophenyl)-5,7,8,9-tetrahydrocyclohepta[f]indazol-6 (1H)-one (6, R¹=4-Fluorophenyl) (7.78 g, 86.6%); LC/MS, method 3, R$_f$=2.40 min, MS m/z 295 (M+H)⁺. ¹H NMR (400 MHz, DMSO) δ 8.28 (d, J=0.9 Hz, 1H), 7.83-7.76 (m, 2H), 7.68 (s, 1H), 7.67 (s, 1H), 7.47-7.39 (m, 2H), 3.86 (s, 2H), 3.13-3.10 (m, 2H), 2.54-2.46 (m, 2H), 1.96-1.84 (m, 2H).

Step #7: 5-Ethyl-1-(4-fluorophenyl)-5,7,8,9-tetrahydrocyclohepta[f]indazol-6(1H)-one (7, R$^1$=4-Fluorophenyl, R$^2$=Ethyl)

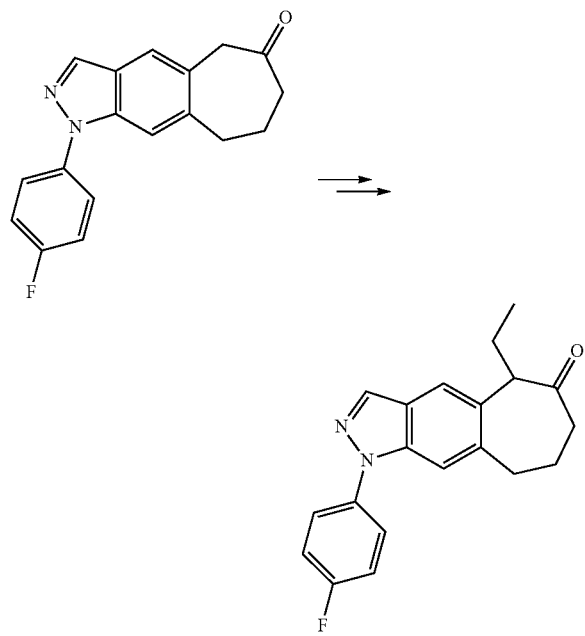

Step #7a: (E)-5-ethylidene-1-(4-fluorophenyl)-5,7,8,9-tetrahydrocyclohepta[f]indazol-6(1H)-one

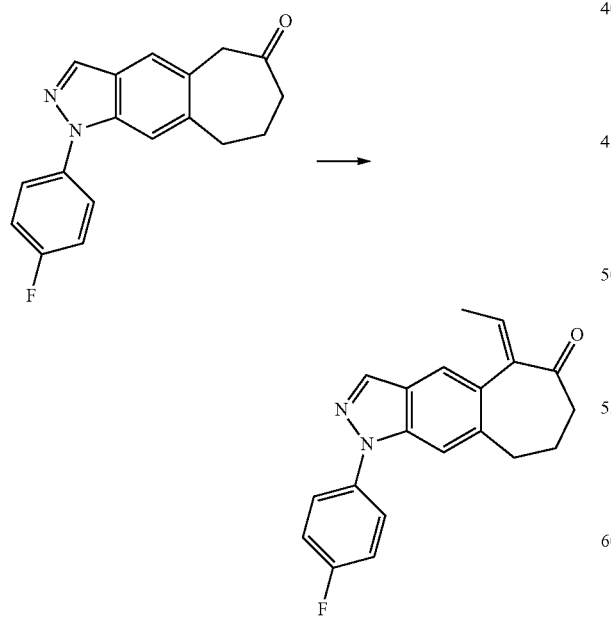

A three necked round bottom flask with septum, nitrogen line, thermometer and stir bar was charged with the 1-(4-fluorophenyl)-5,7,8,9-tetrahydrocyclohepta[f]indazol-6 (1H)-one (6, R$^1$=4-Fluorophenyl) (3.75 g, 12.74 mmol) and THF (50 mL). The solution was cooled to about −70° C. then LiHMDS (12.74 mL, 12.74 mmol) was added keeping the internal temp below about −60° C. The mixture was warmed to about 0° C. over about 5 min then cooled to about −70° C. Acetaldehyde (0.786 g, 17.84 mmol) was added in one portion. The mixture was stirred for about 2 h at about −78° C. then the cold bath was removed and the mixture was allowed to warm to about 10° C. Brine (25 mL), water (25 mL) and EtOAc (100 mL) were added and the layers were separated. The aqueous layer was extracted with EtOAc (50 mL) then the organic solutions were combined, extracted with brine (50 mL), dried over MgSO$_4$, filtered and concentrated under reduced pressure. The residue was purified on silica gel (120 g) using a gradient of 0-50% EtOAc in heptane. Product fractions were combined and concentrated under reduced pressure to yield (E)-5-ethylidene-1-(4-fluorophenyl)-5,7,8,9-tetrahydrocyclohepta[f]indazol-6(1H)-one (3.23 g, 79%); LC/MS, method 3, R$_t$=2.68 min, MS m/z 321 (M+H)$^+$. $^1$H NMR (400 MHz, DMSO) δ 8.36 (d, J=0.8 Hz, 1H), 7.87-7.80 (m, 2H), 7.75 (s, 1H), 7.70 (s, 1H), 7.50-7.40 (m, 2H), 7.12 (q, J=7.4 Hz, 1H), 2.82 (t, J=7.0 Hz, 2H), 2.28 (t, J=7.1 Hz, 2H), 2.01-1.91 (m, 2H), 1.87 (d, J=7.4 Hz, 3H).

Step #7b: 5-Ethyl-1-(4-fluorophenyl)-5,7,8,9-tetrahydrocyclohepta[f]indazol-6(1H)-one (7, R$^1$=4-Fluorophenyl, R$^2$=Ethyl)

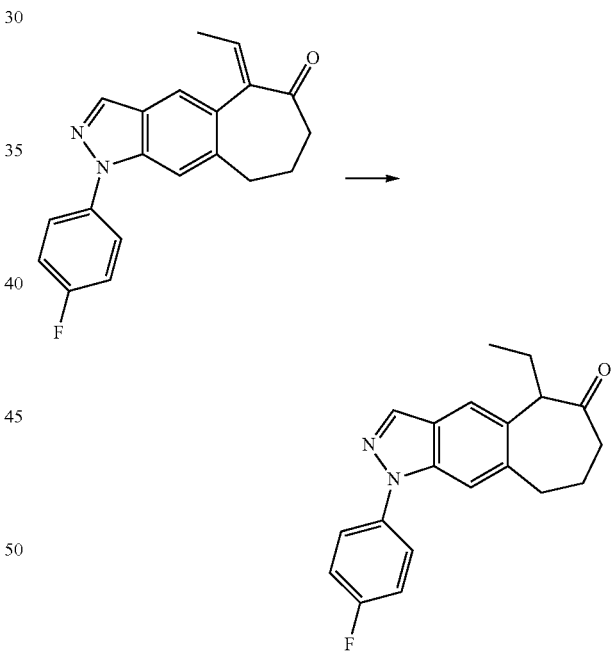

A solution of (E)-5-ethylidene-1-(4-fluorophenyl)-5,7,8,9-tetrahydrocyclohepta[f]indazol-6(1H)-one (3.27 g, 10.21 mmol) in toluene (75 mL) containing 20% Pd(OH)$_2$ on carbon (0.300 g, 0.427 mmol) was evacuated and placed under hydrogen. The reaction was shaken under about 50 psi of hydrogen for about 1 h, then the catalyst was removed by filtration through Celite® and the filtrate concentrated under reduced pressure to yield 5-ethyl-1-(4-fluorophenyl)-5,7,8,9-tetrahydrocyclohepta[f]indazol-6(1H)-one (7, R$^1$=4-Fluorophenyl, R$^2$=Ethyl) (3.25 g, 99%); LC/MS, method 3, R$_t$=2.69 min, MS m/z 323 (M+H)$^+$. $^1$H NMR (400 MHz, DMSO) δ 8.29 (d, J=0.9 Hz, 1H), 7.84-7.77 (m, 2H), 7.65 (s, 1H), 7.62 (s, 1H), 7.47-7.38 (m, 2H), 4.08 (t, J=7.0 Hz, 1H), 3.33-3.24 (m, 1H), 3.03-2.97 (m, 1H), 2.79-2.72 (m, 1H), 2.43-2.35 (m, 1H), 2.33-2.05 (m, 2H), 1.83-1.59 (m, 2H), 0.90 (t, J=7.3 Hz, 3H).

Step #8: 12b-Ethyl-9-(4-fluorophenyl)-1,2,6,7,9,12b-hexahydro-5H-9,10-diaza-benzo[3,4]cyclohepta[1,2-f]inden-3-one (8, R$^1$=4-Fluorophenyl, R$^2$=Ethyl)

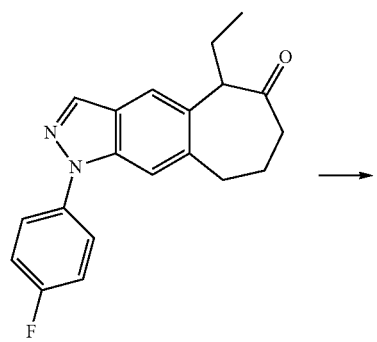

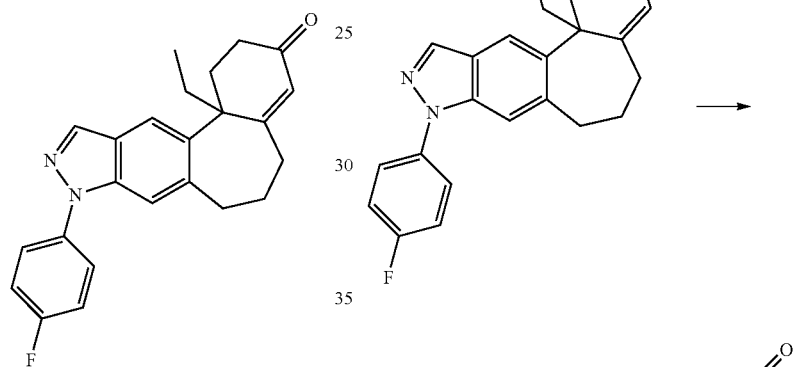

A three necked round bottom flask with septum, nitrogen line, thermometer and stir bar was charged with EtOH (50 mL) and sodium (0.348 g, 15.1 mmol). The mixture was stirred until the reaction was complete, then 5-ethyl-1-(4-fluorophenyl)-5,7,8,9-tetrahydrocyclohepta[f]indazol-6(1H)-one (7, R$^1$=4-Fluorophenyl, R$^2$=Ethyl) (3.25 g, 10.1 mmol) suspended in EtOH (50 mL) was added. The mixture was heated to about 35° C. for about 10 min then methyl vinyl ketone (0.777 g, 11.09 mmol) was added. The mixture was stirred for about 45 min at about 35° C. then heated to about 60° C. for about 1 h. Methyl vinyl ketone (0.27 g, 3.85 mmol) was added and stirring was continued for about 30 min. Methyl vinyl ketone (0.22 g, 3.14 mmol) was added then heating was continued for about 45 min. The mixture was cooled to rt then concentrated under reduced pressure. Water (100 mL) and EtOAc (100 mL) were added then the mixture was acidified to about pH 1 with 6 N aq. HCl. The layers were separated then the aqueous layer was extracted with EtOAc (20 mL). The combined organic solutions were dried over MgSO$_4$, filtered and concentrated under reduced pressure. The residue was purified on silica gel (120 g) using a gradient of 10-50% EtOAc in heptane. Product fractions were combined and concentrated under reduced pressure to yield 12b-Ethyl-9-(4-fluorophenyl)-1,2,6,7,9,12b-hexahydro-5H-9,10-diaza-benzo[3,4]cyclohepta[1,2-f]inden-3-one (8, R$^1$=4-Fluorophenyl, R$^2$=Ethyl) (3.03 g, 80%); LC/MS, method 3, R$_t$=2.73 min, MS m/z 375 (M+H)$^+$. $^1$H NMR (400 MHz, DMSO) δ 8.32 (s, 1H), 7.89 (s, 1H), 7.85-7.78 (m, 2H), 7.63 (s, 1H), 7.47-7.38 (m, 2H), 5.89 (s, 1H), 3.03-2.95 (m, 1H), 2.88-2.63 (m, 2H), 2.58-2.27 (m, 4H), 2.21-2.00 (m, 2H), 1.93-1.73 (m, 3H), 0.92-0.84 (t, J=7.2 Hz, 3H).

Step #9: (4aR,12bR)-12b-Ethyl-9-(4-fluoro-phenyl)-1,2,4a,5,6,7,9,12b-octahydro-4H-9,10-diaza-benzo[3,4]cyclohepta[1,2-f]inden-3-one; compound with (4aS,12bS)-12b-ethyl-9-(4-fluoro-phenyl)-1,2,4a,5,6,7,9,12b-octahydro-4H-9,10-diaza-benzo[3,4]cyclohepta[1,2-f]inden-3-one (9, R$^1$=4-Fluorophenyl, R$^2$=Ethyl) and (4aS,12bR)-12b-ethyl-9-(4-fluoro-phenyl)-1,2,4a,5,6,7,9,12b-octahydro-4H-9,10-diaza-benzo[3,4]cyclohepta[1,2-f]inden-3-one; compound with (4aR,12bS)-12b-ethyl-9-(4-fluoro-phenyl)-1,2,4a,5,6,7,9,12b-octahydro-4H-9,10-diaza-benzo[3,4]cyclohepta[1,2-f]inden-3-one (10, R$^1$=4-Fluorophenyl, R$^2$=Ethyl)

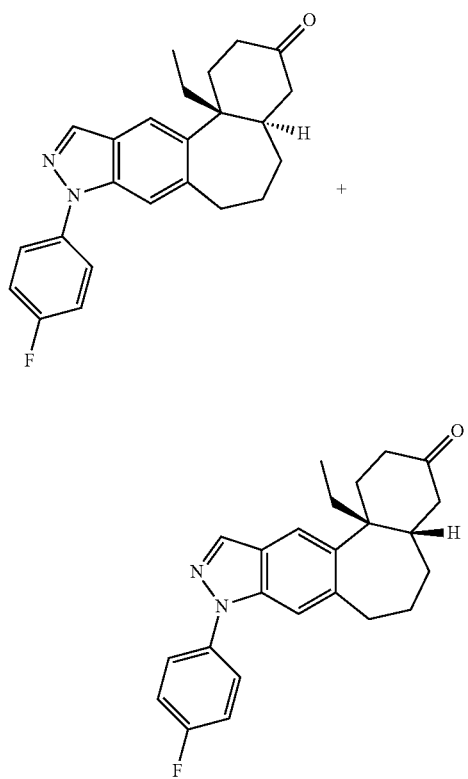

A solution of (12b-ethyl-9-(4-fluorophenyl)-1,2,6,7,9,12b-hexahydro-5H-9,10-diaza-benzo[3,4]cyclohepta[1,2-f]inden-3-one (8, $R^1$=4-Fluorophenyl, $R^2$=Ethyl) (3.03 g, 8.09 mmol) in toluene (75 mL) containing 20% Pd(OH)$_2$ on carbon (0.290 g, 0.413 mmol) was evacuated and placed under hydrogen. The reaction was shaken under about 55 psi of hydrogen for about 12 h then at about 55° C. for about 6 h. The catalyst was removed by filtration through Celite® and the filtrate was concentrated under reduced pressure. The residue was treated with EtOAc (20 mL) and the solids which formed upon standing were collected by filtration and washed with EtOAc (3 mL). The filtrate was retained. The solid was recrystallized from EtOAc (25 mL) to yield (4aR,12bR)-12b-ethyl-9-(4-fluorophenyl)-1,2,4a,5,6,7,9,12b-octahydro-4H-9,10-diaza-benzo[3,4]cyclohepta[1,2-f]inden-3-one; compound with (4aS,12bS)-12b-ethyl-9-(4-fluoro-phenyl)-1,2,4a,5,6,7,9,12b-octahydro-4H-9,10-diaza-benzo[3,4]cyclohepta[1,2-f]inden-3-one (10, $R^1$=4-Fluorophenyl, $R^2$=Ethyl) (1.26 g, 41%); LC/MS, method 2, $R_t$=3.05 min, MS m/z 377 (M+H)$^+$. $^1$H NMR (400 MHz, DMSO) δ 8.27 (d, J=0.8 Hz, 1H), 7.86 (s, 1H), 7.83-7.77 (m, 2H), 7.59 (s, 1H), 7.45-7.37 (m, 2H), 3.29-3.24 (m, 1H), 2.99-2.94 (m, 1H), 2.55-2.43 (m, 3H), 2.40-2.11 (m, 3H), 2.09-1.85 (m, 5H), 1.64-1.57 (m, 1H), 1.37-1.28 (m, 1H), 0.49 (t, J=7.3 Hz, 3H).

The filtrates were combined and concentrated under reduced pressure. The residue was enriched in the later eluting isomer on silica gel (120 g) using a gradient of 0-10% EtOAc in DCM. Product fractions containing >90% of the later eluting isomer were combined and concentrated under reduced pressure to yield a solid (0.355 g). Fractions containing both product isomers were combined and concentrated, then further enriched in the later eluting isomer on silica gel (80 g) using a gradient of 0-15% EtOAc in DCM. Product fractions containing >90% of the later eluting isomer were combined with the enriched material from the first column and concentrated under reduced pressure to yield a solid (0.650 g). The material was crystallized from EtOH (10 mL) to yield (4aS,12bR)-12b-ethyl-9-(4-fluoro-phenyl)-1,2,4a,5,6,7,9,12b-octahydro-4H-9,10-diaza-benzo[3,4]cyclohepta[1,2-f]inden-3-one; compound with (4aR,12bS)-12b-ethyl-9-(4-fluoro-phenyl)-1,2,4a,5,6,7,9,12b-octahydro-4H-9,10-diaza-benzo[3,4]cyclohepta[1,2-f]inden-3-one (9, $R^1$=4-Fluorophenyl, $R^2$=Ethyl) (0.44 g, 14%); LC/MS, method 3, $R_t$=2.94 min, MS m/z 377 (M+H)$^+$. $^1$H NMR (400 MHz, DMSO) δ 8.27 (d, J=0.7 Hz, 1H), 7.83 (s, 1H), 7.82-7.79 (m, 2H), 7.62 (s, 1H), 7.46-7.37 (m, 2H), 3.16-3.09 (m, 1H), 3.02-2.97 (m, 1H), 2.82-2.77 (m, 1H), 2.63-2.47 (m, 1H), 2.41-2.16 (m, 4H), 2.09-2.02 (m, 1H), 1.92-1.88 (m, 1H), 1.80-1.72 (m, 2H), 1.61-1.45 (m, 3H), 0.64 (t, J=7.4 Hz, 3H).

Step #10: (3S,4aS,12bR)-12b-Ethyl-9-(4-fluoro-phenyl)-3-trifluoromethyl-1,2,3,4,4a,5,6,7,9,12b-decahydro-9,10-diaza-benzo[3,4]cyclohepta[1,2-f]inden-3-ol; compound with (3R,4aR,12bS)-12b-ethyl-9-(4-fluoro-phenyl)-3-trifluoromethyl-1,2,3,4,4a,5,6,7,9,12b-decahydro-9,10-diaza-benzo[3,4]cyclohepta[1,2-f]inden-3-ol (15, $R^1$=4-Fluorophenyl, $R^2$=Ethyl, $R^3$=Trifluoromethyl)

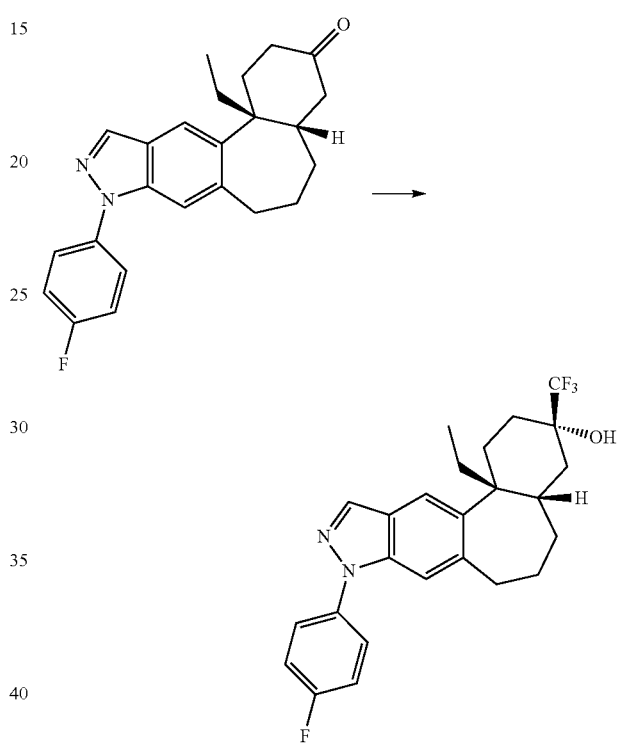

A 3 necked round bottom flask with stir bar, nitrogen line, septum and thermometer was charged with (4aR,12bR)-12b-ethyl-9-(4-fluoro-phenyl)-1,2,4a,5,6,7,9,12b-octahydro-4H-9,10-diaza-benzo[3,4]cyclohepta[1,2-f]inden-3-one; compound with (4aS,12bS)-12b-ethyl-9-(4-fluoro-phenyl)-1,2,4a,5,6,7,9,12b-octahydro-4H-9,10-diaza-benzo[3,4]cyclohepta[1,2-f]inden-3-one (10, $R^1$=4-Fluorophenyl, $R^2$=Ethyl) (0.41 g, 1.089 mmol) and DME (10 mL). Cesium fluoride (0.025 g, 0.163 mmol) was added, the mixture was stirred for about 10 min at rt, then cooled to an internal temperature of about −50° C. Trimethyl(trifluoromethyl)silane (0.275 g, 1.934 mmol) was added and the mixture was allowed to warm slowly to about 0° C. TBAF (1 M in THF, 1.2 mL, 1.2 mmol) was added and the mixture was warmed to rt. After about 1 h the mixture was concentrated under reduced pressure. The residue was partitioned between EtOAc (25 mL) and water (35 mL). The organic layer was washed with water (3×25 mL) then brine (25 mL), dried over MgSO$_4$, filtered and concentrated under reduced pressure. The residue was purified on silica gel (25 g) using a gradient of 0-10% EtOAc in DCM. Product fractions were combined and concentrated under reduced pressure to yield (3S,4aS,12bR)-12b-Ethyl-9-(4-fluoro-phenyl)-3-trifluoromethyl-1,2,3,4,4a,5,6,7,9,12b-decahydro-9,10-diaza-benzo[3,4]cyclohepta[1, 2-f]inden-3-ol; compound with (3R,4aR,12bS)-12b-ethyl-9-(4-fluoro-phenyl)-3-trifluoromethyl-1,2,3,4,4a,5,6,7,9,12b-decahydro-9,10-diaza-benzo[3,4]cyclohepta[1,2-f]inden-3-ol (15, R¹=4-Fluorophenyl, R²=Ethyl, R³=Trifluoromethyl) (Example 1) (0.395 g, 81%)); LC/MS, method 2, $R_t$=3.35 min, MS m/z 447 (M+H)⁺. ¹H NMR (400 MHz, DMSO) δ 8.28 (s, 1H), 7.84-7.77 (m, 3H), 7.56 (s, 1H), 7.46-7.37 (m, 2H), 5.59 (s, 1H), 3.23-3.03 (m, 1H), 2.97-2.87 (m, 1H), 2.55-2.39 (m, 1H), 2.30-1.94 (m, 4H), 1.91-1.37 (m, 8H), 0.62 (t, J=7.4 Hz, 3H).

Examples #2 and #3

(3R,4aR,12bS)-12b-Ethyl-9-(4-fluoro-phenyl)-3-trifluoromethyl-1,2,3,4,4a,5,6,7,9,12b-decahydro-9,10-diaza-benzo[3,4]cyclohepta[1,2-f]inden-3-ol (15, R¹=4-Fluorophenyl, R²=Ethyl, R³=Trifluoromethyl) and (3S,4aS,12bR)-12b-Ethyl-9-(4-fluoro-phenyl)-3-trifluoromethyl-1,2,3,4,4a,5,6,7,9,12b-decahydro-9,10-diaza-benzo[3,4]cyclohepta[1,2-f]inden-3-ol (15, R¹=4-Fluorophenyl, R²=Ethyl, R³=Trifluoromethyl)

The Example #1 enantiomers were separated using Preparative Chiral Purification Method 1. Fractions from the first peak eluted were combined and concentrated under reduced pressure. The residue was dissolved in MeOH (1.5 mL), treated with water (25 mL) then concentrated under reduced pressure to remove MeOH. Solids were collected by filtration and washed with water (4 mL) and dried under vacuum at about 70° C. to yield (3R,4aR,12bS)-12b-Ethyl-9-(4-fluoro-phenyl)-3-trifluoromethyl-1,2,3,4,4a,5,6,7,9,12b-decahydro-9,10-diaza-benzo[3,4]cyclohepta[1,2-f]inden-3-ol (15, R¹=4-Fluorophenyl, R²=Ethyl, R³=Trifluoromethyl) (Example 2) (0.132 g, 37%). LC/MS, method 2, $R_t$=3.35 min, MS m/z 447 (M+H)⁺. ¹H NMR (400 MHz, DMSO) δ 8.28 (s, 1H), 7.84-7.77 (m, 3H), 7.56 (s, 1H), 7.46-7.37 (m, 2H), 5.59 (s, 1H), 3.23-3.03 (m, 1H), 2.97-2.87 (m, 1H), 2.55-2.39 (m, 1H), 2.30-1.94 (m, 4H), 1.91-1.37 (m, 8H), 0.62 (t, J=7.4 Hz, 3H).

Fractions from the second peak eluted were combined and concentrated under reduced pressure. The residue was dissolved in MeOH (1.5 mL), treated with water (25 mL) and concentrated under reduced pressure to remove MeOH. Solids were collected by filtration and washed with water (4 mL) and dried under vacuum at about 70° C. to yield (3S,4aS,12bR)-12b-Ethyl-9-(4-fluoro-phenyl)-3-trifluoromethyl-1,2,3,4,4a,5,6,7,9,12b-decahydro-9,10-diaza-benzo[3,4]cyclohepta[1,2-f]inden-3-ol (15, R¹=4-Fluorophenyl, R²=Ethyl, R³=Trifluoromethyl) (Example 3) (0.126 g, 35%). LC/MS, method 2, $R_t$=3.35 min, MS m/z 447 (M+H)⁺. ¹H NMR (400 MHz, DMSO) δ 8.28 (s, 1H), 7.84-7.77 (m, 3H), 7.56 (s, 1H), 7.46-7.37 (m, 2H), 5.59 (s, 1H), 3.23-3.03 (m, 1H), 2.97-2.87 (m, 1H), 2.55-2.39 (m, 1H), 2.30-1.94 (m, 4H), 1.91-1.37 (m, 8H), 0.62 (t, J=7.4 Hz, 3H).

Example #4

(3S,4aR,12bR)-12b-Ethyl-9-(4-fluoro-phenyl)-3-propyl-1,2,3,4,4a,5,6,7,9,12b-decahydro-9,10-diaza-benzo[3,4]cyclohepta[1,2-f]inden-3-ol; compound with (3R,4aS,12bS)-12b-ethyl-9-(4-fluoro-phenyl)-3-propyl-1,2,3,4,4a,5,6,7,9,12b-decahydro-9,10-diaza-benzo[3,4]cyclohepta[1,2-f]inden-3-ol (16, R¹=4-Fluorophenyl, R²=Ethyl, R³=Propyl)

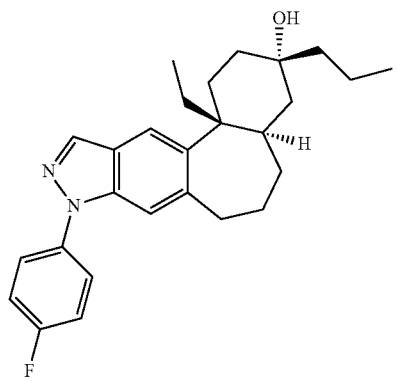 [SMILES: CCC[C@]1(O)CC[C@@]2(CC)c3cc4cnn(-c5ccc(F)cc5)c4cc3CCC[C@@H]2C1]

Step #1: rac-(2'R,4aS,12bS)-12b-ethyl-9-(4-fluorophenyl)-2,4,4a,5,6,7,9,12b-octahydro-1H-spiro[benzo[6,7]cyclohepta[1,2-f]indazole-3,2'-oxirane] (14, R¹=4-Fluorophenyl, R²=Ethyl)

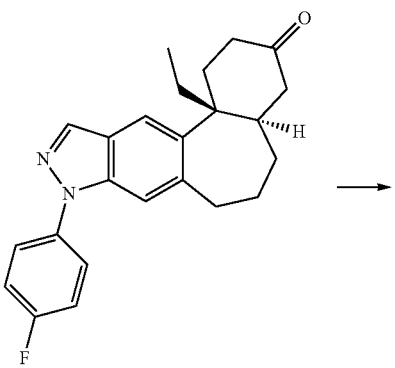

-continued

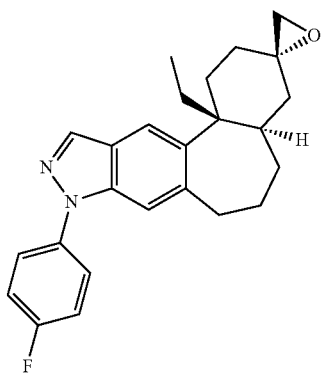

A flask with stir bar and nitrogen line was charged with sodium hydride (60% in oil 0.106 g, 2.66 mmol) and DMSO (7 mL). The mixture was warmed in an oil bath heated to about 65° C. for about 45 min. The mixture was cooled to rt, diluted with THF (7 mL) then cooled to about 0° C. Trimethylsulfoxonium iodide (0.585 g, 2.66 mmol) was added and the mixture was stirred for about 15 min. (4aR,12bR)-12b-Ethyl-9-(4-fluoro-phenyl)-1,2,4a,5,6,7,9,12b-octahydro-4H-9,10-diaza-benzo[3,4]cyclohepta[1,2-f]inden-3-one; compound with (4aS,12bS)-12b-ethyl-9-(4-fluoro-phenyl)-1,2,4a,5,6,7,9,12b-octahydro-4H-9,10-diaza-benzo[3,4]cyclohepta[1,2-f]inden-3-one (9, $R^1$=4-Fluorophenyl, $R^2$=Ethyl) (0.500 g, 1.328 mmol) suspended in THF (9 mL) was added to the reaction mixture. After about 15 min the ice bath was removed and the mixture was allowed to warm to rt for about 6 h. The mixture was concentrated under reduced pressure and the residue was partitioned between EtOAc (100 mL) and water (50 mL). The layers were separated and the aqueous layer was extracted with EtOAc (25 mL). The combined organic layers were washed with water (2×50 mL) and brine (30 mL). The organic solution was dried over $MgSO_4$, filtered and concentrated under reduced pressure. The residue was purified on silica gel (25 g) using a gradient of 0-20% EtOAc in DCM. Product fractions were combined and concentrated under reduced pressure to yield rac-(2'R,4aS,12bS)-12b-ethyl-9-(4-fluorophenyl)-2,4,4a,5,6,7,9,12b-octahydro-1H-spiro[benzo[6,7]cyclohepta[1,2-f]indazole-3,2'-oxirane] (14, $R^1$=4-Fluorophenyl, $R^2$=Ethyl) (0.462 g, 1.183 mmol, 89% yield); LC/MS, method 3, $R_t$=3.14 min, MS m/z 391 (M+H)+. $^1$H NMR (400 MHz, DMSO) δ 8.27 (d, J=0.8 Hz, 1H), 7.93 (s, 1H), 7.85-7.78 (m, 2H), 7.56 (s, 1H), 7.45-7.37 (m, 2H), 3.26-3.19 (m, 1H), 2.97-2.92 (m, 1H), 2.67 (d, J=4.7 Hz, 1H), 2.62 (d, J=4.7 Hz, 1H), 2.36-2.32 (m, 1H), 2.23-2.14 (m, 1H), 2.12-1.91 (m, 4H), 1.91-1.68 (m, 3H), 1.62-1.54 (m, 1H), 1.32-1.28 (m, 1H), 1.26-1.16 (m, 1H), 1.07-0.94 (m, 1H), 0.40 (t, J=7.3 Hz, 3H).

Step #2: (3S,4aR,12bR)-12b-Ethyl-9-(4-fluoro-phenyl)-3-propyl-1,2,3,4,4a,5,6,7,9,12b-decahydro-9,10-diaza-benzo[3,4]cyclohepta[1,2-f]inden-3-ol; compound with (3R,4aS,12bS)-12b-ethyl-9-(4-fluoro-phenyl)-3-propyl-1,2,3,4,4a,5,6,7,9,12b-decahydro-9,10-diaza-benzo[3,4]cyclohepta[1,2-f]inden-3-ol (16, $R^1$=4-Fluorophenyl, $R^2$=Ethyl, $R^3$=Propyl)

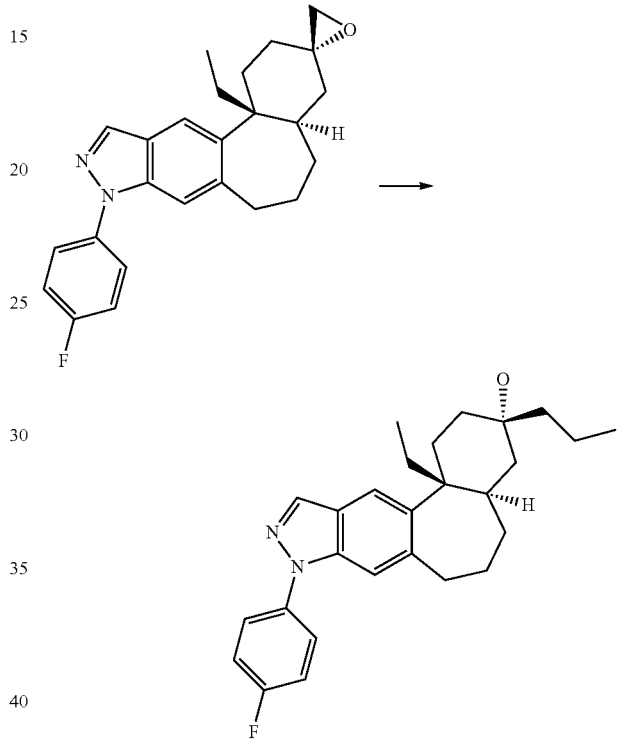

A 50 mL 3 necked round bottom flask with stir bar, nitrogen line, septum and thermometer was charged with rac-(2'R,4aS,12bS)-12b-ethyl-9-(4-fluorophenyl)-2,4,4a,5,6,7,9,12b-octahydro-1H-spiro[benzo[6,7]cyclohepta[1,2-f]indazole-3,2'-oxirane](14, $R^1$=4-Fluorophenyl, $R^2$=Ethyl) (0.225 g, 0.576 mmol), THF (10 mL) and copper(I) iodide (0.016 g, 0.086 mmol). The mixture was stirred for about 10 min then cooled to about −5° C. Ethylmagnesium bromide (3 M in ether, 0.576 mL, 1.73 mmol) was added keeping the internal temperature below about 0° C. After about 15 min sat. aqueous $NH_4Cl$ (3 mL), water (25 mL) and EtOAc (25 mL) were added to the mixture. The layers were separated then the organic solution was dried over $MgSO_4$, filtered and concentrated under reduced pressure. The residue was purified on silica gel (12 g) using a gradient of 0-20% EtOAc in DCM. Product fractions were combined and concentrated under reduced pressure to yield (3S,4aR,12bR)-12b-Ethyl-9-(4-fluoro-phenyl)-3-propyl-1,2,3,4,4a,5,6,7,9,12b-decahydro-9,10-diaza-benzo[3,4]cyclohepta[1,2-f]inden-3-ol; compound with (3R,4aS,12bS)-12b-ethyl-9-(4-fluoro-phenyl)-3-propyl-1,2,3,4,4a,5,6,7,9,12b-decahydro-9,10-diaza-benzo[3,4]cyclohepta[1,2-f]inden-3-ol (16, $R^1$=4-Fluorophenyl, $R^2$=Ethyl, $R^3$=Propyl) (Example 4) (0.187 g, 77%); LC/MS, method 2, $R_t$=3.84 min, MS m/z 421 (M+H)+. $^1$H NMR (400

MHz, DMSO) δ 8.27 (d, J=0.6 Hz, 1H), 7.92 (s, 1H), 7.83-7.77 (m, 2H), 7.54 (s, 1H), 7.45-7.35 (m, 2H), 3.83 (s, 1H), 3.22-3.15 (m, 1H), 2.95-2.89 (m, 1H), 2.22-2.14 m, 1H), 2.12-1.93 (m, 3H), 1.88-1.71 (m, 2H), 1.68-1.59 (m, 1H), 1.56-1.48 (m, 2H), 1.44-1.24 (m, 8H), 0.88 (t, J=6.6 Hz, 3H), 0.35 (t, J=7.3 Hz, 3H)

Examples #5 and #6

(3S,4aR,12bR)-12b-Ethyl-9-(4-fluoro-phenyl)-3-propyl-1,2,3,4,4a,5,6,7,9,12b-decahydro-9,10-diaza-benzo[3,4]cyclohepta[1,2-f]inden-3-ol (16, $R^1$=4-Fluorophenyl, $R^2$=Ethyl, $R^3$=Propyl) and (3R,4aS,12bS)-12b-Ethyl-9-(4-fluoro-phenyl)-3-propyl-1,2,3,4,4a,5,6,7,9,12b-decahydro-9,10-diaza-benzo[3,4]cyclohepta[1,2-f]inden-3-ol (16, $R^1$=4-Fluorophenyl, $R^2$=Ethyl, $R^3$=Propyl)

The Example #4 enantiomers were separated using Preparative Chiral Purification Method 2. Fractions from the first peak eluted were combined and concentrated under reduced pressure. The residue was dissolved in MeOH (1.5 mL), treated with water (25 mL), concentrated under reduced pressure to remove MeOH. Solids were collected by filtration and washed with water (4 mL) then dried under vacuum at about 70° C. to yield (3S,4aR,12bR)-12b-Ethyl-9-(4-fluoro-phenyl)-3-propyl-1,2,3,4,4a,5,6,7,9,12b-decahydro-9,10-diaza-benzo[3,4]cyclohepta[1,2-f]inden-3-ol (16, $R^1$=4-Fluorophenyl, $R^2$=Ethyl, $R^3$=Propyl) (Example 5) (0.045 g, 30%). LC/MS, method 2, $R_t$=3.84 min, MS m/z 421 (M+H)$^+$. $^1$H NMR (400 MHz, DMSO) δ 8.27 (d, J=0.6 Hz, 1H), 7.92 (s, 1H), 7.83-7.77 (m, 2H), 7.54 (s, 1H), 7.45-7.35 (m, 2H), 3.83 (s, 1H), 3.22-3.15 (m, 1H), 2.95-2.89 (m, 1H), 2.22-2.14 m, 1H), 2.12-1.93 (m, 3H), 1.88-1.71 (m, 2H), 1.68-1.59 (m, 1H), 1.56-1.48 (m, 2H), 1.44-1.24 (m, 8H), 0.88 (t, J=6.6 Hz, 3H), 0.35 (t, J=7.3 Hz, 3H)

Fractions from the second peak eluted were combined and concentrated under reduced pressure. The residue was dissolved in MeOH (1.5 mL), treated with water (25 mL) and concentrated under reduced pressure to remove MeOH. Solids were collected by filtration, washed with water (4 mL) and dried under vacuum at about 70° C. to yield (3R,4aS,12bS)-12b-Ethyl-9-(4-fluoro-phenyl)-3-propyl-1,2,3,4,4a,5,6,7,9,12b-decahydro-9,10-diaza-benzo[3,4]cyclohepta[1,2-f]inden-3-ol (16, $R^1$=4-Fluorophenyl, $R^2$=Ethyl, $R^3$=Propyl) (Example 6) (0.045 g, 30%). LC/MS, method 2, $R_t$=3.84 min, MS m/z 421 (M+H)$^+$. $^1$H NMR (400 MHz, DMSO) δ 8.27 (d, J=0.6 Hz, 1H), 7.92 (s, 1H), 7.83-7.77 (m, 2H), 7.54 (s, 1H), 7.45-7.35 (m, 2H), 3.83 (s, 1H), 3.22-3.15 (m, 1H), 2.95-2.89 (m, 1H), 2.22-2.14 m, 1H), 2.12-1.93 (m, 3H), 1.88-1.71 (m, 2H), 1.68-1.59 (m, 1H), 1.56-1.48 (m, 2H), 1.44-1.24 (m, 8H), 0.88 (t, J=6.6 Hz, 3H), 0.35 (t, J=7.3 Hz, 3H)

Example #7 and Example #8

(3S,4aR,12bR)-12b-Ethyl-9-(4-fluoro-phenyl)-3-methoxymethyl-1,2,3,4,4a,5,6,7,9,12b-decahydro-9,10-diaza-benzo[3,4]cyclohepta[1,2-f]inden-3-ol (16, $R^1$=4-Fluorophenyl, $R^2$=Ethyl, $R^3$=Methoxymethyl) and (3R,4aS,12bS)-12b-Ethyl-9-(4-fluoro-phenyl)-3-methoxymethyl-1,2,3,4,4a,5,6,7,9,12b-decahydro-9,10-diaza-benzo[3,4]cyclohepta[1,2-f]inden-3-ol (16, $R^1$=4-Fluorophenyl, $R^2$=Ethyl, $R^3$=Methoxymethyl)

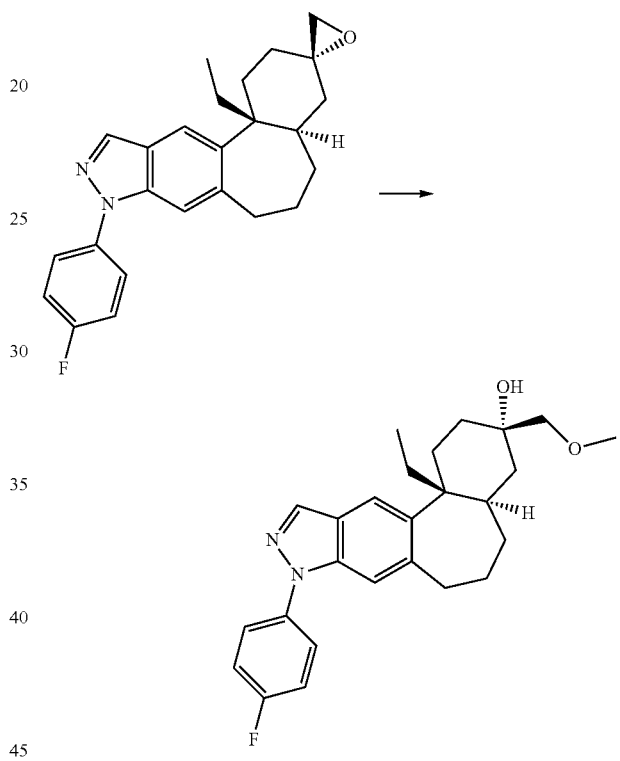

A vial was charged with MeOH (3 mL, 74.9 mmol) and sodium (67 mg, 2.91 mmol) then the mixture was stirred until a solution had formed. rac-(2'S,4aR,12bR)-12b-ethyl-9-(4-fluorophenyl)-2,4,4a,5,6,7,9,12b-octahydro-1H-spiro[benzo[6,7]cyclohepta[1,2-f]indazole-3,2'-oxirane ($R^1$=4-Fluorophenyl, $R^2$=Ethyl) (110 mg, 0.282 mmol) was added and the mixture was warmed in an oil bath heated to about 70° C. for about 1 hr. The solution was cooled to rt then added slowly to a stirring mixture of water (25 mL) and sat. aq. NH$_4$Cl (3 mL). The mixture was concentrated under reduced pressure to remove MeOH then the solid was collected by filtration and washed with water (~5 mL). The material was dried under vacuum to give (3S,4aR,12bR)-12b-Ethyl-9-(4-fluoro-phenyl)-3-methoxymethyl-1,2,3,4,4a,5,6,7,9,12b-decahydro-9,10-diaza-benzo[3,4]cyclohepta[1,2-f]inden-3-ol; compound with (3R,4aS,12bS)-12b-Ethyl-9-(4-fluoro-phenyl)-3-methoxymethyl-1,2,3,4,4a,5,6,7,9,12b-decahydro-9,10-diaza-benzo[3,4]cyclohepta[1,2-f]inden-3-ol (16, $R^1$=4-Fluorophenyl, $R^2$=Ethyl, $R^3$=Methoxymethyl) (0.114 g, 96%).

The enantiomers were separated using Preparative Chiral Purification Method 2. Fractions from the first peak eluted were combined and concentrated under reduced pressure. The residue was dissolved in MeOH (1.5 mL), treated with water (25 mL) and concentrated under reduced pressure to remove MeOH. Solids were collected by filtration, washed with water (4 mL and dried under vacuum at about 70° C. to yield (3S,4aR,12bR)-12b-Ethyl-9-(4-fluoro-phenyl)-3-methoxymethyl-1,2,3,4,4a,5,6,7,9,12b-decahydro-9,10-diaza-benzo[3,4]cyclohepta[1,2-f]inden-3-ol (16, $R^1$=4-Fluorophenyl, $R^2$=Ethyl, $R^3$=Methoxymethyl) (Example 7) (38 mg, 32%); LC/MS, method 2, $R_t$=3.24 min, MS m/z 423 (M+H)$^+$. $^1$H NMR (400 MHz, DMSO) δ 8.27 (d, J=0.7 Hz, 1H), 7.93 (s, 1H), 7.84-7.77 (m, 2H), 7.54 (s, 1H), 7.44-7.36 (m, 2H), 4.15 (s, 1H), 3.29 (s, 3H), 3.24-3.09 (m, 1H), 3.13 (s, 2H), 2.95-2.90 (m, 1H), 2.21-2.14 (m, 1H), 2.11-1.96 (m, 3H), 1.89-1.70 (m, 2H), 1.67-1.41 (m, 5H), 1.36-1.25 (m, 2H), 0.35 (t, J=7.3 Hz, 3H).

Fractions from the second peak eluted were combined and concentrated under reduced pressure. The residue was dissolved in MeOH (1.5 mL), treated with water (25 mL) and concentrated under reduced pressure to remove MeOH. Solids were collected by filtration, washed with water (4 mL) and dried under vacuum at about 70° C. to yield (3R,4aS,12bS)-12b-Ethyl-9-(4-fluoro-phenyl)-3-methoxymethyl-1,2,3,4,4a,5,6,7,9,12b-decahydro-9,10-diaza-benzo[3,4]cyclohepta[1,2-f]inden-3-ol (16, $R^1$=4-Fluorophenyl, $R^2$=Ethyl, $R^3$=Methoxymethyl) (Example 8) (32 mg, 27%); LC/MS, method 2, $R_t$=3.24 min, MS m/z 423 (M+H)$^+$. $^1$H NMR (400 MHz, DMSO) δ 8.27 (d, J=0.7 Hz, 1H), 7.93 (s, 1H), 7.84-7.77 (m, 2H), 7.54 (s, 1H), 7.44-7.36 (m, 2H), 4.15 (s, 1H), 3.29 (s, 3H), 3.24-3.09 (m, 1H), 3.13 (s, 2H), 2.95-2.90 (m, 1H), 2.21-2.14 (m, 1H), 2.11-1.96 (m, 3H), 1.89-1.70 (m, 2H), 1.67-1.41 (m, 5H), 1.36-1.25 (m, 2H), 0.35 (t, J=7.3 Hz, 3H).

Example #9 and Example #10

(3S,4aR,12bR)-3-Ethoxymethyl-12b-ethyl-9-(4-fluoro-phenyl)-1,2,3,4,4a,5,6,7,9,12b-decahydro-9,10-diaza-benzo[3,4]cyclohepta[1,2-f]inden-3-ol (16, $R^1$=4-Fluorophenyl, $R^2$=Ethyl, $R^3$=Ethoxymethyl) and (3R,4aS,12bS)-3-Ethoxymethyl-12b-ethyl-9-(4-fluoro-phenyl)-1,2,3,4,4a,5,6,7,9,12b-decahydro-9,10-diaza-benzo[3,4]cyclohepta[1,2-f]inden-3-ol (16, $R^1$=4-Fluorophenyl, $R^2$=Ethyl, $R^3$=Ethoxymethyl)

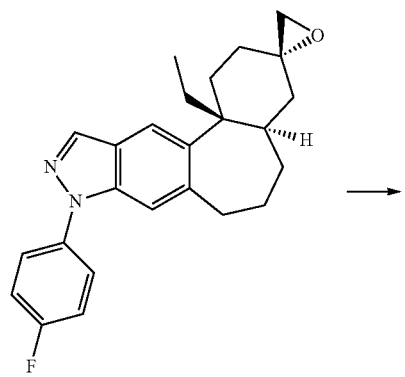

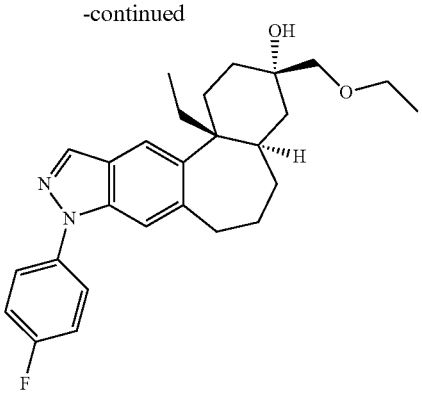

A vial was charged with ethanol (3 mL, 74.9 mmol) and sodium (68 mg, 2.91 mmol) then the mixture was stirred until a solution had formed. +/−Compound 14 ($R^1$=4-Fluorophenyl, $R^2$=Ethyl) (110 mg, 0.282 mmol) was added and the mixture was warmed in an oil bath heated to about 70° C. for about 1 hr. The solution was cooled to rt and added slowly to a stirring mixture of water (25 mL) and sat. aq. NH$_4$Cl (3 mL). The mixture was concentrated under reduced pressure to remove MeOH, then the solid was collected by filtration and washed with water (~5 mL). The material was dried under vacuum to give (3S,4aR,12bR)-3-Ethoxymethyl-12b-ethyl-9-(4-fluoro-phenyl)-1,2,3,4,4a,5,6,7,9,12b-decahydro-9,10-diaza-benzo[3,4]cyclohepta[1,2-f]inden-3-ol compound with (3R,4aS,12bS)-3-Ethoxymethyl-12b-ethyl-9-(4-fluoro-phenyl)-1,2,3,4,4a,5,6,7,9,12b-decahydro-9,10-diaza-benzo[3,4]cyclohepta[1,2-f]inden-3-ol (16, $R^1$=4-Fluorophenyl, $R^2$=Ethyl, $R^3$=Ethoxymethyl) (0.117 g, 95%).

The enantiomers were separated using Preparative Chiral Purification Method 3. Fractions from the first peak eluted were combined and concentrated under reduced pressure. The residue was dissolved in MeOH (1.5 mL), treated with water (25 mL. and concentrated under reduced pressure to remove MeOH. Solids were collected by filtration, washed with water (4 mL) and dried under vacuum at about 70° C. to yield (3S,4aR,12bR)-3-Ethoxymethyl-12b-ethyl-9-(4-fluoro-phenyl)-1,2,3,4,4a,5,6,7,9,12b-decahydro-9,10-diaza-benzo[3,4]cyclohepta[1,2-f]inden-3-ol (16, $R^1$=4-Fluorophenyl, $R^2$=Ethyl, $R^3$=Ethoxymethyl) (Example 9) (34 mg, 28%); LC/MS, method 2, $R_t$=3.53 min, MS m/z 437 (M+H)$^+$. $^1$H NMR (400 MHz, DMSO) δ 8.27 (d, J=0.7 Hz, 1H), 7.93 (s, 1H), 7.83-7.78 (m, 2H), 7.54 (s, 1H), 7.44-7.36 (m, 2H), 4.09 (s, 1H), 3.47 (q, J=7.0 Hz, 2H), 3.24-3.11 (m, 1H), 3.16 (s, 2H), 2.95-2.90 (m, 1H), 2.22-1.94 (m, 4H), 1.89-1.71 (m, 2H), 1.66-1.45 (m, 5H), 1.36-1.29 (m, 2H), 1.13 (t, J=7.0 Hz, 3H), 0.35 (t, J=7.3 Hz, 3H).

Fractions from the second peak eluted were combined and concentrated under reduced pressure. The residue was dissolved in MeOH (1.5 mL) treated with water (25 mL) and concentrated under reduced pressure to remove MeOH. Solids were collected by filtration, washed with water (4 mL and dried under vacuum at about 70° C. to yield (3R,4aS,12bS)-3-Ethoxymethyl-12b-ethyl-9-(4-fluoro-phenyl)-1,2,3,4,4a,5,6,7,9,12b-decahydro-9,10-diaza-benzo[3,4]cyclohepta[1,2-f]inden-3-ol (Example 10) (16, $R^1$=4-Fluorophenyl, $R^2$=Ethyl, $R^3$=Ethoxymethyl) (16 mg, 13%); LC/MS, method 2, $R_t$=3.53 min, MS m/z 437 (M+H)$^+$.)$^+$. $^1$H NMR (400 MHz, DMSO) δ 8.27 (d, J=0.7 Hz, 1H), 7.93 (s, 1H), 7.83-7.78 (m, 2H), 7.54 (s, 1H), 7.44-7.36 (m, 2H), 4.09 (s, 1H), 3.47 (q, J=7.0 Hz, 2H), 3.24-3.11 (m, 1H), 3.16 (s, 2H), 2.95-2.90 (m, 1H), 2.22-1.94 (m, 4H), 1.89-1.71 (m, 2H), 1.66-1.45 (m, 5H), 1.36-1.29 (m, 2H), 1.13 (t, J=7.0 Hz, 3H), 0.35 (t, J=7.3 Hz, 3H).

Example 11

3R,4aS,12bS)-9-(4-Fluoro-phenyl)-3-methoxymethyl-12b-pyridin-2-ylmethyl-1,2,3,4,4a,5,6,7,9,12b-decahydro-9,10-diaza-benzo[3,4]cyclohepta[1,2-f]inden-3-ol; compound with 3S,4aR,12bR)-9-(4-fluoro-phenyl)-3-methoxymethyl-12b-pyridin-2-ylmethyl-1,2,3,4,4a,5,6,7,9,12b-decahydro-9,10-diaza-benzo[3,4]cyclohepta[1,2-f]inden-3-ol (13, R¹=4-Fluorophenyl, R²=Pyridin-2-ylmethyl, R³=Methoxymethyl)

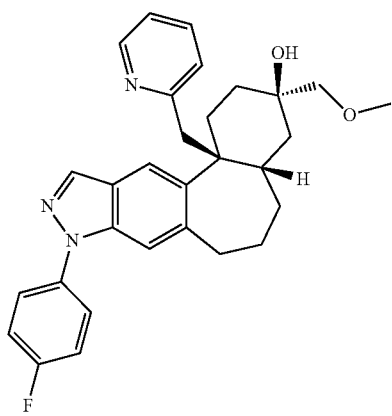 [SMILES: COC[C@@]1(O)CC[C@@]2(Cc3ccccn3)c3cc4cnn(-c5ccc(F)cc5)c4cc3CCC[C@H]2C1]

Step #1: (1-(4-Fluorophenyl)-5-(pyridin-2-ylmethyl)-5,7,8,9-tetrahydrocyclohepta[f]indazol-6(1H)-one (7, R¹=4-Fluorophenyl, R²=Pyridin-2-ylmethyl)

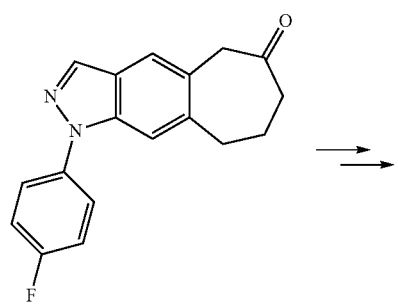

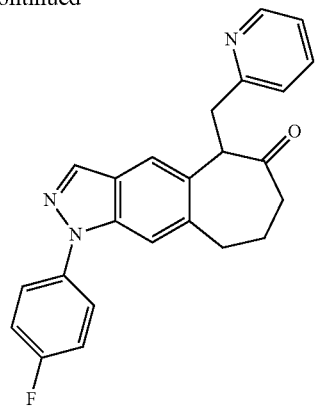

Step #1a: (E)-1-(4-Fluorophenyl)-5-(pyridin-2-ylmethylene)-5,7,8,9-tetrahydrocyclohepta[f]indazol-6(1H)-one A 3 neck round bottom flask with stir bar, nitrogen line and thermometer was charged with 1-(4-fluorophenyl)-5,7,8,9-tetrahydrocyclohepta[f]indazol-6 (1H)-one (6, R¹=4-Fluorophenyl) (0.500 g, 1.699 mmol) and THF (15 mL). The solution was cooled to about −60° C. then LiHMDS (1M in THF, 2.0 mL, 2.0 mmol) was added. After complete addition the mixture was removed from the cold bath and allowed to warm to about 0° C. The mixture was cooled to about −65° C. then picolinaldehyde (0.546 g, 5.10 mmol) was added and the temperature of the mixture was raised to about −5° C. After about 15 min the reaction was quenched with AcOH (1 mL) and stirred for about 15 min. The mixture was transferred to a separatory funnel with the aid of EtOAc (25 mL) and sat. aq. NaHCO₃ (25 mL). The layers were separated then the aq. layer was extracted with EtOAc (25 mL). The combined organic layers were washed with brine (15 mL) then dried over MgSO₄, filtered and concentrated under reduced pressure. The residue was purified on silica gel (12 g) using a gradient of 0-40% EtOAc in DCM. Product fractions were combined and concentrated under reduced pressure to yield (E)-1-(4-fluorophenyl)-5-(pyridin-2-ylmethylene)-5,7,8,9-tetrahydrocyclohepta[f]indazol-6(1H)-one (0.519 g, 80%); LC/MS, method 3, R$_t$=2.54 min, MS m/z 384 (M+H)⁺. ¹H NMR (400 MHz, DMSO) δ 8.56-8.54 (m, 1H), 8.23 (d, J=0.8 Hz, 1H), 7.89-7.83 (m, 3H), 7.69 (s, 1H), 7.59-7.51 (m, 1H), 7.53 (s, 1H), 7.51-7.41 (m, 2H), 7.22-7.20 (m, 1H), 6.97 (d, J=8.0 Hz, 1H), 2.99 (t, J=7.0 Hz, 2H), 2.38 (t, J=6.9 Hz, 2H), 2.09-1.95 (m, 2H).

Step #1b: (1-(4-Fluorophenyl)-5-(pyridin-2-ylmethyl)-5,7,8,9-tetrahydrocyclohepta[f]indazol-6(1H)-one (7, R¹=4-Fluorophenyl, R²=Pyridin-2-ylmethyl)

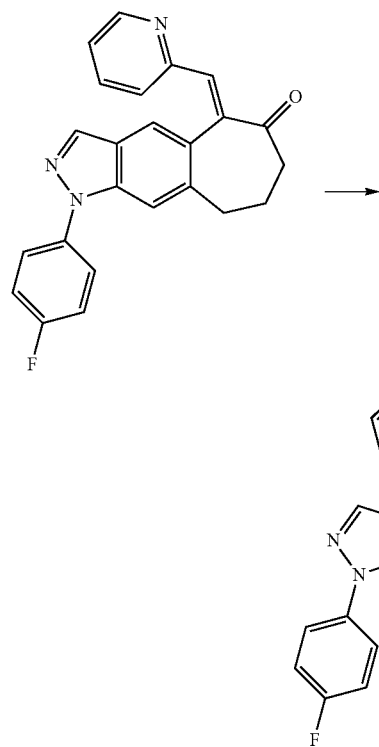

A solution of (E)-1-(4-fluorophenyl)-5-(pyridin-2-ylmethylene)-5,7,8,9-tetrahydrocyclohepta[f]indazol-6(1H)-one (0.519 g, 1.354 mmol) in toluene (25 mL) containing 20% Pd(OH)₂ (0.090 g, 0.128 mmol) was evacuated and placed under hydrogen. The mixture was stirred under an atmosphere of hydrogen provided via a balloon at rt for about 11 h then the catalyst was removed by filtration through Celite®. The filtrate was concentrated under reduced pressure to yield 1-(4-fluorophenyl)-5-(pyridin-2-ylmethyl)-5,7,8,9-tetrahydrocyclohepta[f]indazol-6(1H)-one (7, R¹=4-Fluorophenyl, R²=Pyridin-2-ylmethyl) (0.52 g, 100%); LC/MS, method 3, R$_t$=2.06 min, MS m/z 386 (M+H)⁺. ¹H NMR (400 MHz, DMSO) δ 8.48-8.46 (m, 1H), 8.27 (d, J=0.8 Hz, 1H), 7.84-7.75 (m, 2H), 7.72-7.63 (m, 3H), 7.47-7.38 (m, 2H), 7.36 (d, J=7.8 Hz, 1H), 7.21-7.17 (m, 1H), 4.95-4.92 (m, 1H), 3.88-3.81 (m, 1H), 3.44-3.36 (m, 1H), 3.34-3.27 (m, 1H), 3.12-3.06 (m, 1H), 2.98-2.90 (m, 1H), 2.47-2.40 (m, 1H), 2.27-2.17 (m, 1H), 1.60-1.57 (m, 1H).

Step #2: 9-(4-Fluorophenyl)-12b-pyridin-2-ylmethyl-1,2,6,7,9,12b-hexahydro-5H-9,10-diaza-benzo[3,4]cyclohepta[1,2-f]inden-3-one (8, R¹=4-Fluorophenyl, R²=Pyridin-2-ylmethyl)

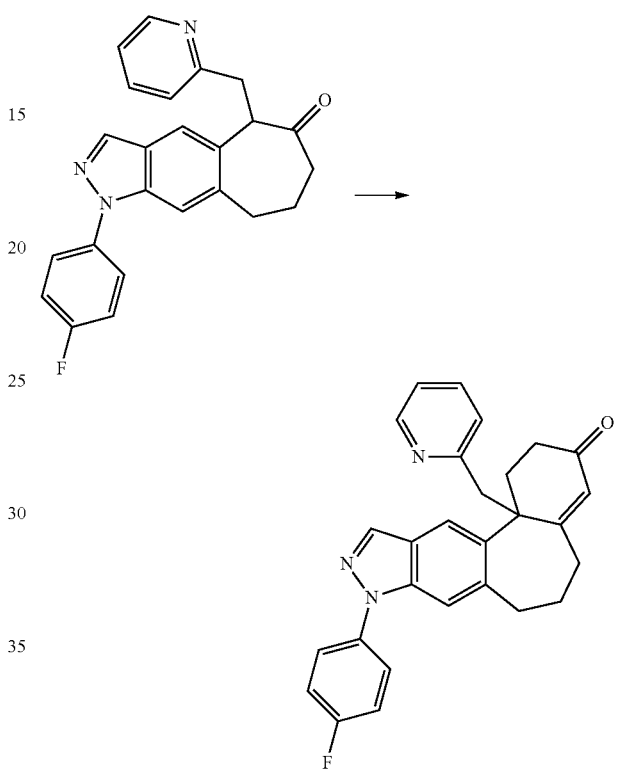

Sodium (0.042 g, 1.827 mmol) was added to EtOH (2 mL) then the mixture was stirred until a solution was obtained. The solution was added to 1-(4-fluorophenyl)-5-(pyridin-2-ylmethyl)-5,7,8,9-tetrahydrocyclohepta[f]indazol-6(1H)-one (7, R¹=4-Fluorophenyl, R²=Pyridin-2-ylmethyl) (0.280 g, 0.726 mmol) suspended in EtOH (2 mL). The mixture was warmed in an oil bath heated to about 60° C. But-3-en-2-one (0.083 g, 1.184 mmol) was added to the mixture dropwise over about 5 min then the mixture was stirred at about 60° C. for about 14 h. The mixture was concentrated under reduced pressure and the residue pardoned between water (15 mL), brine (10 mL) and EtOAc (25 mL). The layers were separated then the aqueous layer was extracted with EtOAc (15 mL). The combined organic layers were dried over MgSO₄, filtered and concentrated under reduced pressure. The residue was purified on silica gel (12 g) using 100% EtOAc. Product fractions were combined and concentrated under reduced pressure to yield (4-fluorophenyl)-12b-pyridin-2-ylmethyl-1,2,6,7,9,12b-hexahydro-5H-9,10-diaza-benzo[3,4]cyclohepta[1,2-f]inden-3-one (8, R¹=4-Fluorophenyl, R²=Pyridin-2-ylmethyl) (0.100 g, 32%); LC/MS, method 3, R$_t$=2.40 min, MS m/z 438 (M+H)⁺. ¹H NMR (400 MHz, DMSO) δ 8.39-8.35 (m, 3H), 7.82-7.78 (m, 2H), 7.59-7.54 (m, 2H), 7.45-7.36 (m, 2H), 7.18 (d, J=7.8 Hz, 1H), 7.14-7.11 (m, 1H), 5.90 (s, 1H), 3.90 (d, J=13.3 Hz, 1H), 3.64 (d, J=13.4 Hz, 1H), 3.07-2.92

(m, 1H), 2.85-2.73 (m, 2H), 2.46-2.27 (m, 2H), 2.23-2.03 (m, 2H), 1.79-1.71 (m, 2H), 1.58-1.46 (m, 1H).

Step #3: (4aS,12bS)-9-(4-Fluorophenyl)-12b-pyridin-2-ylmethyl-1,2,4a,5,6,7,9,12b-octahydro-4H-9,10-diaza-benzo[3,4]cyclohepta[1,2-f]inden-3-one; compound with (4aR,12bR)-9-(4-fluorophenyl)-12b-pyridin-2-ylmethyl-1,2,4a,5,6,7,9,12b-octahydro-4H-9,10-diaza-benzo[3,4]cyclohepta[1,2-f]inden-3-one (10, R¹=4-Fluorophenyl, R²=Pyridin-2-ylmethyl)

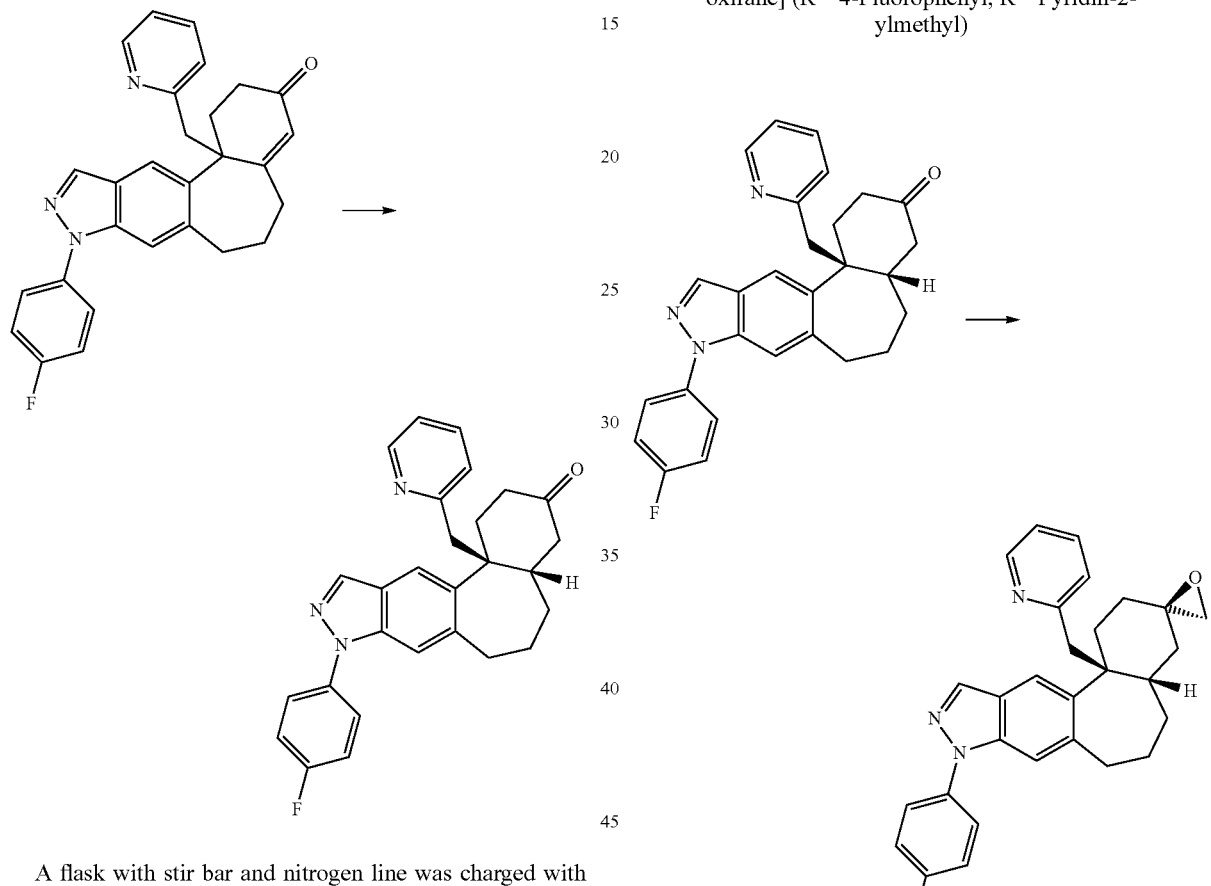

A flask with stir bar and nitrogen line was charged with (4-fluorophenyl)-12b-pyridin-2-ylmethyl-1,2,6,7,9,12b-hexahydro-5H-9,10-diaza-benzo[3,4]cyclohepta[1,2-f]inden-3-one (8, R¹=4-Fluorophenyl, R²=Pyridin-2-ylmethyl) (0.288 g, 0.658 mmol), Aliquat 336® (0.219 g, 0.542 mmol) and toluene (11 mL). The mixture was stirred for about 5 min then sodium hydrogencarbonate (0.332 g, 3.95 mmol) and water (1 mL) were added. The mixture was stirred for about 5 min then sodium dithionite (0.687 g, 3.95 mmol) and water (10 mL) were added. The mixture was warmed in an oil bath heated to about 95° C. for about 25 min, then the mixture was cooled to rt and the layers separated. The aqueous layer was extracted with toluene (10 mL) then the organic layers were combined and dried over MgSO₄, filtered and concentrated under reduced pressure. The residue was purified on silica gel (12 g) using a gradient of 50-100% EtOAc in heptane. Product fractions were combined and concentrated under reduced pressure to yield (4aS,12bS)-9-(4-Fluorophenyl)-12b-pyridin-2-ylmethyl-1,2,4a,5,6,7,9,12b-octahydro-4H-9,10-diaza-benzo[3,4]cyclohepta[1,2-f]inden-3-one; compound with (4aR,12bR)-9-(4-fluoro-phenyl)-12b-pyridin-2-ylmethyl-1,2,4a,5,6,7,9,12b-octahydro-4H-9,10-diaza-benzo[3,4]cyclohepta[1,2-f]inden-3-one (10, R¹=4-Fluorophenyl, R²=Pyridin-2-ylmethyl (0.090 g, 31%); LC/MS, method 3, R$_t$=2.48 min, MS m/z 440 (M+H)⁺. ¹H NMR (400 MHz, DMSO) δ 8.39-8.36 (m, 1H), 8.15 (d, J=0.8 Hz, 1H), 7.87-7.79 (m, 2H), 7.71 (s, 1H), 7.44-7.35 (m, 4H), 7.13-7.05 (m, 1H), 6.41 (d, J=7.8 Hz, 1H), 3.76 (d, J=12.9 Hz, 1H), 3.42-3.34 (m, 1H), 3.16-3.10 (m, 1H), 2.97 (d, J=12.9 Hz, 1H), 2.57-2.27 (m, 5H), 2.11-1.83 (m, 4H), 1.69-1.54 (m, 2H).

Step #4: rac-(2'R,4aS,12bS)-9-(4-fluorophenyl)-12b-(pyridin-2-ylmethyl)-2,4,4a,5,6,7,9,12b-octahydro-1H-spiro[benzo[6,7]cyclohepta[1,2-f]indazole-3,2'-oxirane] (R¹=4-Fluorophenyl, R²=Pyridin-2-ylmethyl)

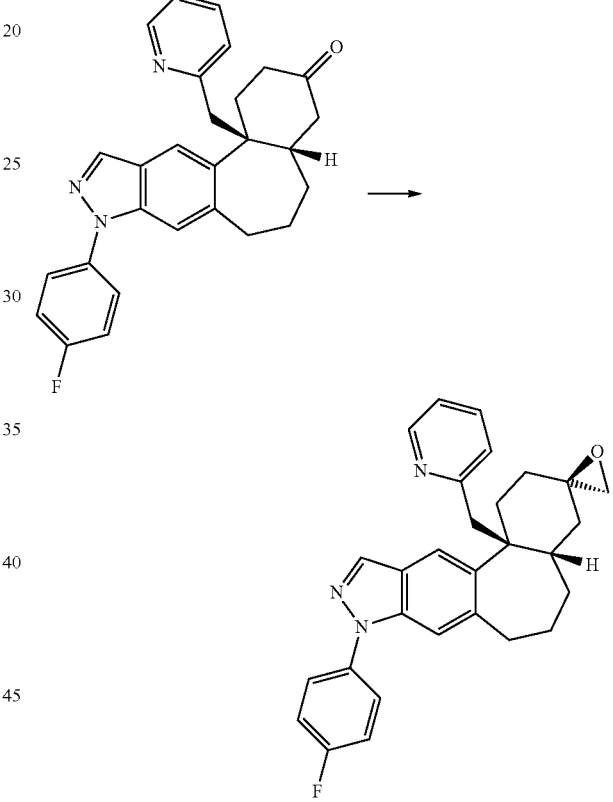

A flask with stir bar and nitrogen line was charged with DMSO (2 mL) and sodium hydride (60 wt % in oil, 0.021 g, 0.523 mmol). The mixture was warmed in an oil bath heated to about 65° C. for about 30 min then cooled to rt. THF (1 mL) was added and the mixture was cooled to about 0° C. Trimethylsulfoxonium iodide (0.115 g, 0.523 mmol) was added and the mixture was stirred for about 15 min. (4aS,12bS)-9-(4-Fluorophenyl)-12b-pyridin-2-ylmethyl-1,2,4a,5,6,7,9,12b-octahydro-4H-9,10-diaza-benzo[3,4]cyclohepta[1,2-f]inden-3-one; compound with (4aR,12bR)-9-(4-fluorophenyl)-12b-pyridin-2-ylmethyl-1,2,4a,5,6,7,9,12b-octahydro-4H-9,10-diaza-benzo[3,4]cyclohepta[1,2-f]inden-3-one (10, R¹=4-Fluorophenyl, R²=Pyridin-2-ylmethyl) (0.115 g, 0.262 mmol) in THF (3 mL) was added and the mixture was allowed to warm to rt for about 18 h. The mixture was diluted with EtOAc (25 mL) and washed with water (25 mL). The aqueous layer was extracted with EtOAc (25 mL) then the combined organic layers were washed with water (2×25 mL) and brine (25 mL), dried over MgSO$_4$, filtered and concentrated under reduced pressure to yield rac-(2'R,4aS,12bS)-9-(4-fluorophenyl)-12b-(pyridin-2-ylmethyl)-2,4,4a,5,6,7,9,12b-octahydro-1H-spiro[benzo[6,7]cyclohepta[1,2-f]indazole-3,2'-oxirane] (R$^1$=4-Fluorophenyl, R$^2$=Pyridin-2-ylmethyl) (0.115 g, 97%); LC/MS, method 3, R$_t$=2.63 min, MS m/z 454 (M+H)$^+$. $^1$H NMR (400 MHz, DMSO) δ 8.37-8.35 (m, 1H), 8.14 (d, J=0.7 Hz, 1H), 7.85-7.77 (m, 2H), 7.65 (s, 1H), 7.44-7.32 (m, 4H), 7.08-7.04 (m, 1H), 6.48 (d, J=7.8 Hz, 1H), 3.61 (d, J=12.7 Hz, 1H), 3.34-3.26 (m, 1H), 3.13-3.06 (m, 1H), 3.01 (d, J=12.8 Hz, 1H), 2.60-2.43 (m, 1H), 2.39-2.25 (m, 2H), 2.21-2.12 (m, 1H), 1.87-1.78 (m, 2H), 1.75-1.56 (m, 3H), 1.54-1.50 (m, 1H), 1.28-1.19 (m, 1H), 1.17-1.09 (m, 1H), 0.88-0.74 (m, 1H).

Step #5: (3R,4aS,12bS)-9-(4-Fluorophenyl)-3-methoxymethyl-12b-pyridin-2-ylmethyl-1,2,3,4,4a,5,6,7,9,12b-decahydro-9,10-diaza-benzo[3,4]cyclohepta[1,2-f]inden-3-ol; compound with (3S,4aR,12bR)-9-(4-fluorophenyl)-3-methoxymethyl-12b-pyridin-2-ylmethyl-1,2,3,4,4a,5,6,7,9,12b-decahydro-9,10-diaza-benzo[3,4]cyclohepta[1,2-f]inden-3-ol (13, R$^1$=4-Fluorophenyl, R$^2$=Pyridin-2-ylmethyl, R$^3$=Methoxymethyl)

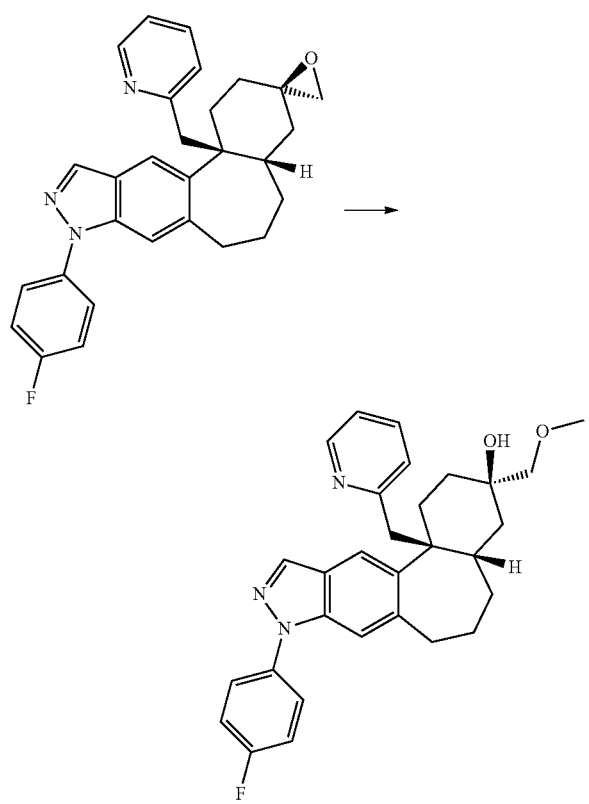

Sodium (0.057 g, 2.469 mmol) and MeOH (3 mL) were stirred until a solution was obtained. The solution was added to rac-(2'R,4aS,12bS)-9-(4-fluorophenyl)-12b-(pyridin-2-ylmethyl)-2,4,4a,5,6,7,9,12b-octahydro-1H-spiro[benzo[6,7]cyclohepta[1,2-f]indazole-3,2'-oxirane] (R$^1$=4-Fluorophenyl, R$^2$=Pyridin-2-ylmethyl) (0.112 g, 0.247 mmol) then the suspension was warmed in an oil bath heated to about 70° C. for about 3 h. The mixture was cooled to rt then concentrated under reduced pressure. Water (12 mL) was added to the residue and the resulting solid was collected by filtration and dried under reduced pressure to yield (3R,4aS,12bS)-9-(4-Fluoro-phenyl)-3-methoxymethyl-12b-pyridin-2-ylmethyl-1,2,3,4,4a,5,6,7,9,12b-decahydro-9,10-diaza-benzo[3,4]cyclohepta[1,2-f]inden-3-ol; compound with (3S,4aR,12bR)-9-(4-fluoro-phenyl)-3-methoxymethyl-12b-pyridin-2-ylmethyl-1,2,3,4,4a,5,6,7,9,12b-decahydro-9,10-diaza-benzo[3,4]cyclohepta[1,2-f]inden-3-ol (Example 11) (13, R$^1$=4-Fluorophenyl, R$^2$=Pyridin-2-ylmethyl, R$^3$=Methoxymethyl) (0.119 g, 99%); LC/MS, method 2, R$_t$=2.51 min, MS m/z 486 (M+H)$^+$.

Examples #12 and #13

(3R,4aS,12bS)-9-(4-fluoro-phenyl)-3-methoxymethyl-12b-pyridin-2-ylmethyl-1,2,3,4,4a,5,6,7,9,12b-decahydro-9,10-diaza-benzo[3,4]cyclohepta[1,2-f]inden-3-ol (13, R$^1$=4-Fluorophenyl, R$^2$=Pyridin-2-ylmethyl, R$^3$=Methoxymethyl) and (3S,4aR,12bR)-9-(4-Fluoro-phenyl)-3-methoxymethyl-12b-pyridin-2-ylmethyl-1,2,3,4,4a,5,6,7,9,12b-decahydro-9,10-diaza-benzo[3,4]cyclohepta[1,2-f]inden-3-ol (13, R$^1$=4-Fluorophenyl, R$^2$=Pyridin-2-ylmethyl, R$^3$=Methoxymethyl)

The enantiomers from Example #11 were separated using Preparative Chiral Purification Method 4. Fractions from the first peak eluted were combined and concentrated under reduced pressure. The residue was dissolved in MeOH (1.5 mL), treated with water (25 mL) and Concentrated under reduced pressure to remove MeOH. Solids were collected by filtration, washed with water (4 mL) and dried under vacuum at about 70° C. to yield (3R,4aS,12bS)-9-(4-fluoro-phenyl)-3-methoxymethyl-12b-pyridin-2-ylmethyl-1,2,3,4,4a,5,6,7,9,12b-decahydro-9,10-diaza-benzo[3,4]cyclohepta[1,2-f]inden-3-ol (Example 12) (13, R$^1$=4-Fluorophenyl, R$^2$=Pyridin-2-ylmethyl, R$^3$=Methoxymethyl) (0.022 g, 20%); $^1$H NMR (400 MHz, DMSO) δ 8.37-8.33 (m, 1H), 8.14 (d, J=0.7 Hz, 1H), 7.88-7.78 (m, 2H), 7.65 (s, 1H), 7.46-7.37 (m, 2H), 7.36-7.31 (m, 1H), 7.27 (s, 1H), 7.06-7.02 (m, 1H), 6.33 (d, J=7.8 Hz, 1H), 4.16 (s, 1H), 3.57 (d, J=12.7 Hz, 1H), 3.34-3.26 (m, 1H), 3.13-2.80 (m, 1H), 3.07 (s, 3H), 2.91-2.87 (m, 1H), 2.89 (s, 2H) 2.58-2.44 (m, 1H), 2.06-2.01 (m, 1H), 1.95-1.89 (m, 1H), 1.86-1.79 (m, 1H), 1.67-1.46 (m, 3H), 1.39-1.36 (m, 1H), 1.27-1.21 (m, 2H), 1.05-1.01 (m, 1H).

Fractions from the second peak eluted were combined and concentrated under reduced pressure. The residue was dissolved in MeOH (1.5 mL), treated with water (25 mL) and concentrated under reduced pressure to remove MeOH. Solids were collected by filtration, washed with water (4 mL) and dried under vacuum at about 70° C. to yield (3S,4aR,12bR)-9-(4-Fluoro-phenyl)-3-methoxymethyl-12b-pyridin-2-ylmethyl-1,2,3,4,4a,5,6,7,9,12b-decahydro-9,10-diaza-benzo[3,4]cyclohepta[1,2-f]inden-3-ol (Example 13) (13, R$^1$=4-Fluorophenyl, R$^2$=Pyridin-2-ylmethyl, R$^3$=Methoxymethyl) (0.030 g, 27%). $^1$H NMR (400 MHz, DMSO) δ 8.37-8.33 (m, 1H), 8.14 (d, J=0.7 Hz, 1H), 7.88-7.78 (m, 2H), 7.65 (s, 1H), 7.46-7.37 (m, 2H), 7.36-7.31 (m, 1H), 7.27 (s, 1H), 7.06-7.02 (m, 1H), 6.33 (d, J=7.8 Hz, 1H), 4.16 (s, 1H), 3.57 (d, J=12.7 Hz, 1H), 3.34-3.26 (m, 1H), 3.13-2.80 (m, 1H), 3.07 (s, 3H), 2.91-2.87 (m, 1H), 2.89 (s, 2H) 2.58-2.44 (m, 1H), 2.06-2.01 (m, 1H), 1.95-1.89 (m, 1H), 1.86-1.79 (m, 1H), 1.67-1.46 (m, 3H), 1.39-1.36 (m, 1H), 1.27-1.21 (m, 2H), 1.05-1.01 (m, 1H).

Scheme 2:
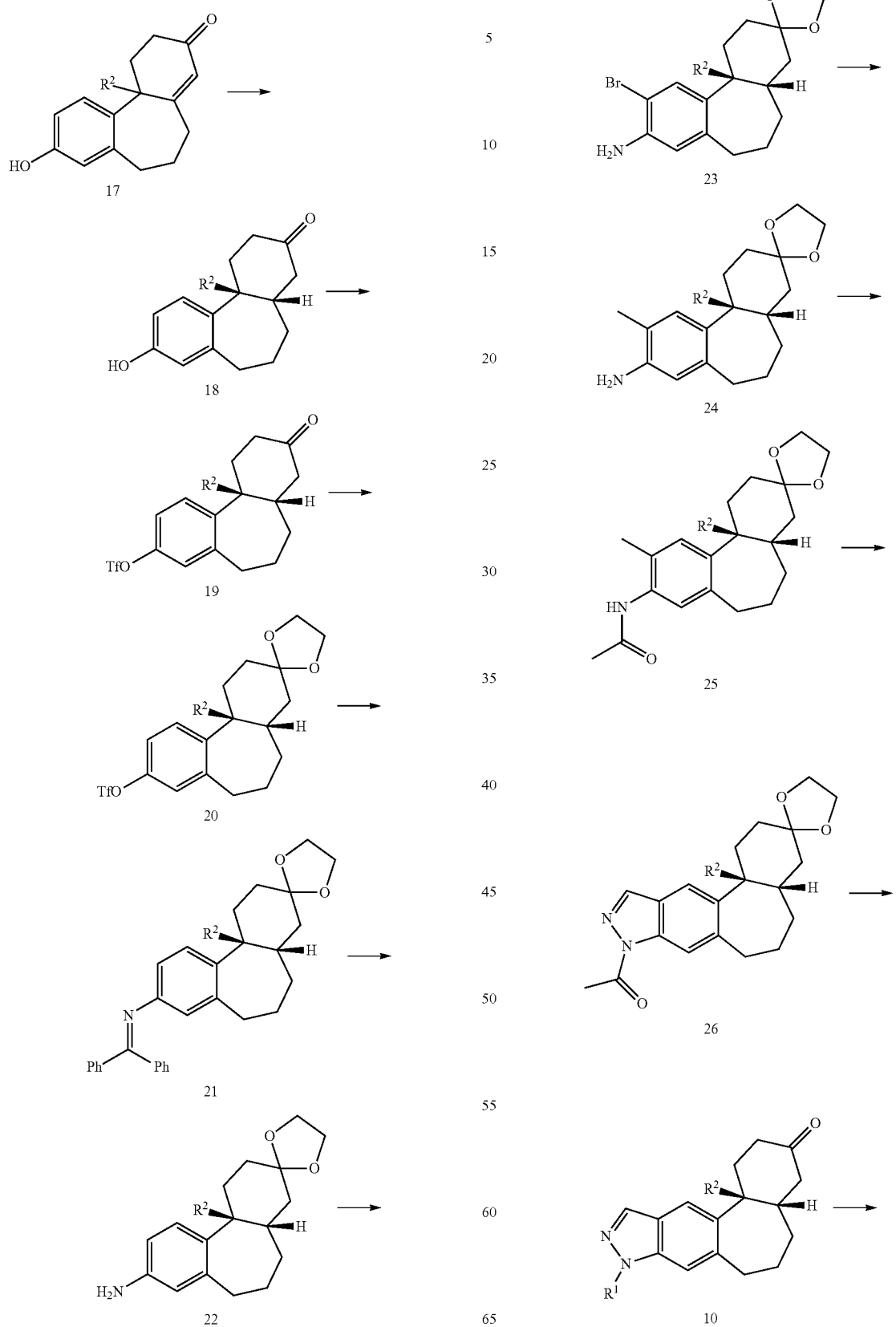

-continued

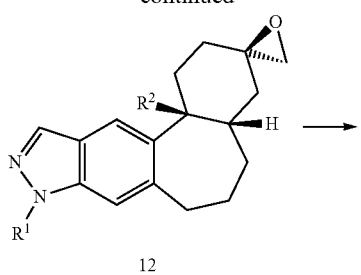

12

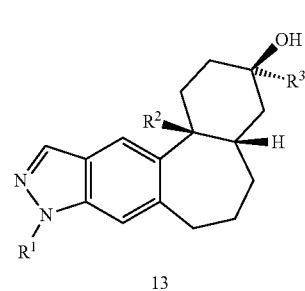

13

Example 14

(3R,4aS,12bR)-12b-Ethyl-3-methoxymethyl-1,2,3,4,
4a,5,6,7,9,12b-decahydro-9,10-diaza-benzo[3,4]
cyclohepta[1,2-f]inden-3-ol; compound with (3S,
4aR,12bS)-12b-ethyl-3-methoxymethyl-1,2,3,4,4a,5,
6,7,9,12b-decahydro-9,10-diaza-benzo[3,4]
cyclohepta[1,2-f]inden-3-ol (13, R¹=H, R²=Ethyl,
R³=Methoxymethyl)

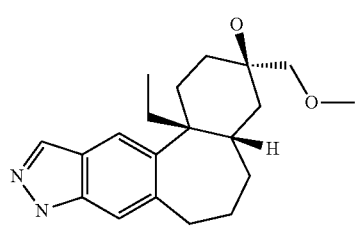 [SMILES: CC[C@@]12CC[C@](O)(COC)C[C@@H]1CCCc1cc3[nH]ncc3cc12]

Step #1: 11b-Ethyl-9-hydroxy-1,2,5,6,7,11b-hexahy-
dro-dibenzo[a,c]cyclohepten-3-one (17, R²=Ethyl)

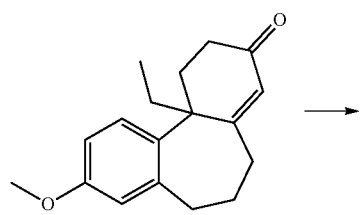

-continued

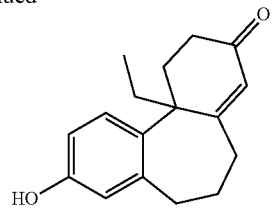

A mixture containing 11b-ethyl-9-methoxy-1,2,5,6,7,11b-hexahydro-dibenzo[a,c]cyclohepten-3-one (10.2 g, 37.7 mmol) [prepared as described in US2012/238549 A1] and DL-methionine (18.3 g, 123 mmol) in methanesulfonic acid (100 mL, 1.54 mol) was mechanically stirred under nitrogen at rt over about 3 days. The reaction was diluted with DCM (700 mL) and poured carefully onto ice water (700 mL). The layers were separated and the aqueous layer was extracted again with DCM (500 mL). The combined organic layers were washed with water (2×500 mL), dried over $Na_2SO_4$, filtered and concentrated under reduced pressure. The residue was purified on silica gel (220 g) using a gradient from 0-50% EtOAc in DCM. Product fractions were combined and concentrated under reduced pressure to yield 11b-ethyl-9-hydroxy-1,2,5,6,7,11b-hexahydro-dibenzo[a,c]cyclohepten-3-one (17, R²=Ethyl) (8.54 g, 88%) as an off-white solid. LC/MS, method 1, 0.73 min, 319 (M+H)⁺. ¹H NMR (400 MHz, DMSO) δ 9.19 (s, 1H), 7.11 (d, J=8.6 Hz, 1H), 6.62 (dd, J=8.5, 2.7 Hz, 1H), 6.51 (d, J=2.7 Hz, 1H), 5.81 (s, 1H), 2.79-2.70 (m, 1H), 2.67-2.52 (m, 1H), 2.44-2.35 (m, 2H), 2.33-2.18 (m, 3H), 2.14-2.04 (m, 1H), 2.01-1.90 (m, 1H), 1.86-1.66 (m, 3H), 0.78 (t, J=7.4 Hz, 3H).

Step #2: (4aS,11bR)-11b-Ethyl-9-hydroxy-1,2,4,4a,
5,6,7,11b-octahydro-dibenzo[a,c]cyclohepten-3-one;
compound with (4aR,11bS)-11b-ethyl-9-hydroxy-1,
2,4,4a,5,6,7,11b-octahydro-dibenzo[a,c]cyclohepten-
3-one (18, R²=Ethyl)

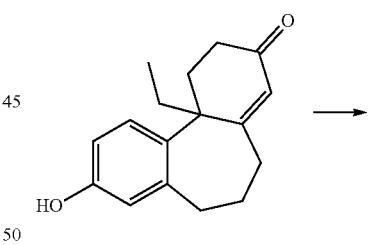

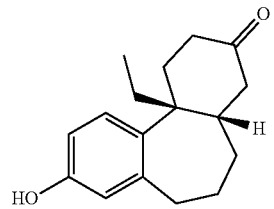

To a suspension of 11b-ethyl-9-hydroxy-1,2,5,6,7,11b-hexahydro-dibenzo[a,c]cyclohepten-3-one (17, R²=Ethyl) (11.25 g, 43.9 mmol) and 10% Pd—C (1.40 g, 1.32 mmol) in THF (80 mL) was added pyridine (20 mL) and the mixture was hydrogenated at rt under about 40 psi of hydrogen for about 18 h. The catalyst was removed by filtration through Celite®, and the filtrate was concentrated. The residue was dissolved in DCM (200 mL) and washed with 2N aq. HCl (100 mL), dried over $Na_2SO_4$, filtered and concentrated under reduced pressure. The residue was re-dissolved in EtOAc (100 mL) and DCM (100 mL), filtered through a short pad of silica gel, and concentrated until product began to precipitate. Product was collected by filtration, rinsed with EtOAc (10 mL) and dried under reduced pressure to yield (4aS,11bR)-11b-ethyl-9-hydroxy-1,2,4,4a,5,6,7,11b-octahydro-dibenzo[a,c]cyclohepten-3-one; compound with (4aR,11bS)-11b-ethyl-9-hydroxy-1,2,4,4a,5,6,7,11b-octahydro-dibenzo[a,c]cyclohepten-3-one (18, $R^2$=Ethyl) (6.45 g, 57%) as a white solid. LC/MS, method 1, 0.80 min, 319 (M−H)⁻. $^1$H NMR (400 MHz, DMSO) 9.14 (s, 1H), 7.11-7.05 (m, 1H), 6.60-6.54 (m, 2H), 2.96-2.86 (m, 1H), 2.65-2.54 (m, 2H), 2.47-2.36 (m, 1H), 2.29-2.20 (m, 1H), 2.20-2.05 (m, 4H), 1.89-1.79 (m, 1H), 1.71-1.51 (m, 3H), 1.49-1.31 (m, 2H), 0.61 (t, J=7.4 Hz, 3H).

Step #3: Trifluoro-methanesulfonic acid (7aR,11aS)-11a-ethyl-9-oxo-6,7,7a,8,9,10,11,11a-octahydro-5H-dibenzo[a,c]cyclohepten-3-yl ester; compound with trifluoro-methanesulfonic acid (7aS,11aR)-11a-ethyl-9-oxo-6,7,7a,8,9,10,11,11a-octahydro-5H-dibenzo[a,c]cyclohepten-3-yl ester (19, $R^2$=Ethyl)

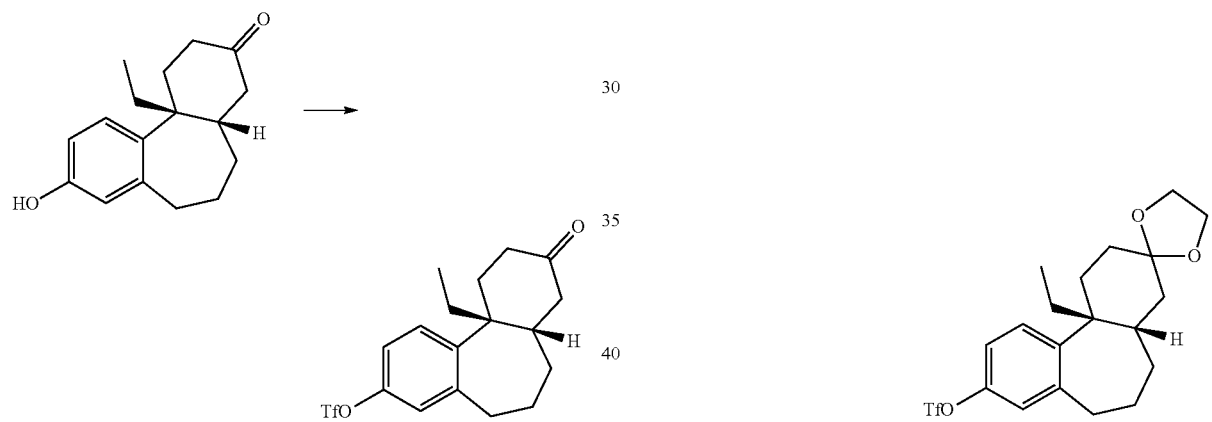

A solution of (4aS,11bR)-11b-ethyl-9-hydroxy-1,2,4,4a,5,6,7,11b-octahydro-dibenzo[a,c]cyclohepten-3-one; compound with (4aR,11bS)-11b-ethyl-9-hydroxy-1,2,4,4a,5,6,7,11b-octahydro-dibenzo[a,c]cyclohepten-3-one (18, $R^2$=Ethyl (6.45 g, 25.0 mmol) in DCM (100.0 mL) was treated with N-phenylbis(trifluoromethanesulfonimide) (8.92 g, 25.0 mmol) and DIEA (8.72 mL, 49.9 mmol) at rt. The reaction was stirred at rt for about 72 h. Silica gel (30 g) was added and solvents were removed under reduced pressure. The residue was applied to a silica gel column (220 g) and purified using a gradient from 10-30% EtOAc in heptane. Product fractions were combined and concentrated to yield trifluoro-methanesulfonic acid (7aR,11aS)-11a-ethyl-9-oxo-6,7,7a,8,9,10,11,11a-octahydro-5H-dibenzo[a,c]cyclohepten-3-yl ester; compound with trifluoro-methanesulfonic acid (7 aS,11aR)-11a-ethyl-9-oxo-6,7,7a,8,9,10,11,11a-octahydro-5H-dibenzo[a,c]cyclohepten-3-yl ester (19, $R^2$=Ethyl) (8.82 g, 90%) as an oil. LC/MS, method 4, 2.53 min, 449 (M+OAc)⁻. $^1$H NMR (400 MHz, DMSO) δ 7.48 (d, J=8.8 Hz, 1H), 7.29 (d, J=2.9 Hz, 1H), 7.25 (dd, J=8.7, 2.9 Hz, 1H), 3.05-2.95 (m, 1H), 2.91-2.82 (m, 1H), 2.68-2.59 (m, 1H), 2.44-2.24 (m, 2H), 2.24-2.11 (m, 3H), 2.08-1.96 (m, 1H), 1.94-1.86 (m, 1H), 1.78-1.64 (m, 2H), 1.61-1.51 (m, 1H), 1.51-1.37 (m, 2H), 0.59 (t, J=7.4 Hz, 3H).

Step #4: rac-(4aR,11bS)-11b-ethyl-1,2,4,4a,5,6,7,11b-octahydro spiro[dibenzo[a,c][7]annulene-3,2'-[1,3]dioxolan]-9-yl trifluoromethanesulfonate (20, $R^2$=Ethyl)

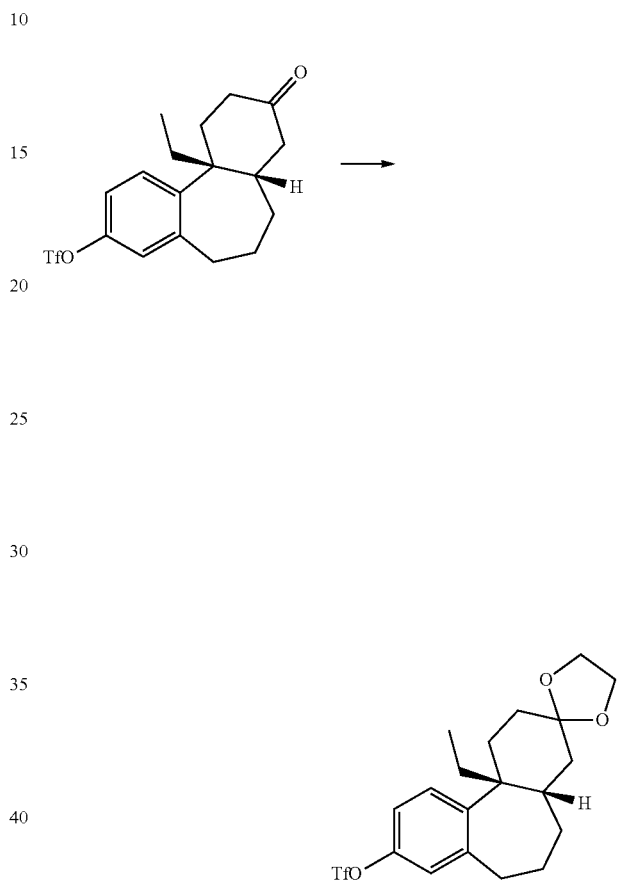

A flask equipped with a Dean-Stark apparatus was charged with trifluoro-methanesulfonic acid (7aR,11aS)-11a-ethyl-9-oxo-6,7,7a,8,9,10,11,11a-octahydro-5H-dibenzo[a,c]cyclohepten-3-yl ester; compound with trifluoro-methanesulfonic acid (7 aS,11aR)-11a-ethyl-9-oxo-6,7,7a,8,9,10,11,11a-octahydro-5H-dibenzo[a,c]cyclohepten-3-yl ester (19, $R^2$=Ethyl) (2.2 g, 5.63 mmol), ethane-1,2-diol (1.571 mL, 28.2 mmol), pTSA (0.107 g, 0.563 mmol) and toluene (44 mL). The mixture was heated to reflux for about 21 h. The mixture was cooled to rt, EtOAc (20 mL), sat. aq. NaHCO₃ (10 mL) were added and the layers were separated. The organic layer was washed with brine (15 mL), dried over MgSO₄, filtered and concentrated under reduced pressure. The residue was purified on silica gel (12 g) using a gradient of 0-40% EtOAc in heptane. Product fractions were combined and concentrated under reduced pressure to yield rac-(4aR,11bS)-11b-ethyl-1,2,4,4a,5,6,7,11b-octahydrospiro[dibenzo[a,c][7]annulene-3,2'-[1,3]dioxolan]-9-yl trifluoromethanesulfonate (20, $R^2$=Ethyl) (2.2 g, 90%); LC/MS, method 3, $R_t$=3.05 min, MS m/z 435 (M+H)⁺. $^1$H NMR (400 MHz, DMSO) δ 7.42-7.35 (m, 1H), 7.26-7.22 (m, 2H), 3.91-3.69 (m, 4H), 3.04-2.77 (m, 2H), 2.43-2.37 (m, 1H), 2.22-2.13 (m, 1H), 2.11-1.94 (m, 2H), 1.71-1.62 (m, 2H), 1.61-1.54 (m, 2H), 1.52-1.35 (m, 3H), 1.32-1.17 (m, 2H), 0.59 (t, J=7.4 Hz, 3H).

Step #5: rac-(4aR,11bS)—N-(diphenylmethylene)-11b-ethyl-1,2,4,4a,5,6,7,11b-octahydrospiro[dibenzo[a,c][7]annulene-3,2'-[1,3]dioxolan]-9-amine (21, R²=Ethyl)

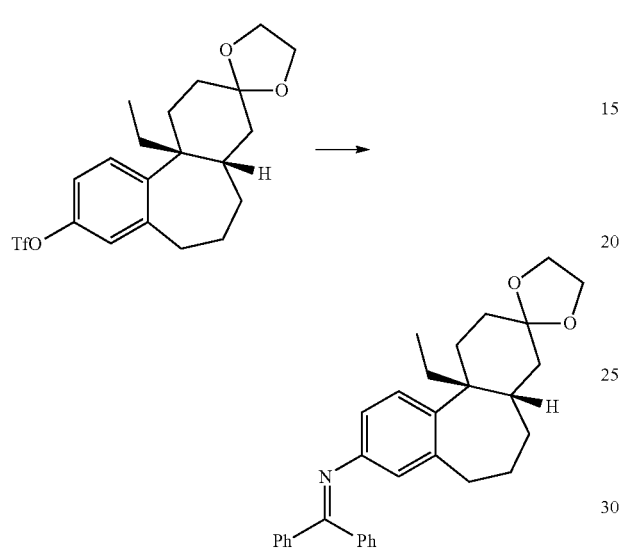

A reaction vial equipped with septa cap fitted with nitrogen inlet needle was charged with palladium(II) acetate (0.029 g, 0.128 mmol), cesium carbonate (1.460 g, 4.48 mmol) and Xantphos (0.111 g, 0.192 mmol). The vial was purged with nitrogen and 1,4-dioxane (8.7 mL) was added. The suspension was allowed to stir at about rt for about 10 min then TEA (0.027 ml, 0.192 mmol) was added dropwise. The mixture was stirred at rt for about 10 min and heated to about 80° C. for about 10 min. To the mixture was added a solution of rac-(4aR,11bS)-11b-ethyl-1,2,4,4a,5,6,7,11b-octahydrospiro[dibenzo[a,c][7]annulene-3,2'-[1,3]dioxolan]-9-yl trifluoromethanesulfonate (20, R²=Ethyl) (1.391 g, 3.20 mmol) and benzophenone imine (0.645 ml, 3.84 mmol) in Dioxane (4 mL). The mixture was heated at about 100° C. for about 3 h. The reaction was allowed to cool to rt and partitioned between EtOAc (50 mL) and water (50 mL). The layers were separated and the organic layer was washed with brine (50 mL) and then filtered through a pad of Celite®. The filter pad was washed with a 9:1 mixture of DCM/MeOH (50 mL) then the filtrate was concentrated under reduced pressure to give a solid on standing. The material was triturated with three portions of EtOAc (5 mL, then 2×2 mL) to give a yellow solid. The EtOAc supenatants were combined and concentrated under reduced pressure. The residue was triturated with Et₂O (10 mL) then the solid was collected by filtration. The solids from both triturations were combined and dried under vacuum to yield rac-(4aR,11bS)—N-(diphenylmethylene)-11b-ethyl-1,2,4,4a,5,6,7,11b-octahydrospiro[dibenzo[a,c][7]annulene-3,2'-[1,3]-dioxolan]-9-amine (21, R²=Ethyl) (1.205 g, 81%); LC/MS, method 3, R$_f$=3.53 min, MS m/z 466 (M+H)⁺. ¹H NMR (400 MHz, CDCl₃) δ 7.77 (d, J=7.6 Hz, 2H), 7.53-7.37 (m, 3H), 7.33-7.20 (m, 3H), 7.10 (d, J=7.2 Hz, 2H), 6.96 (d, J=8.4 Hz, 1H), 6.50 (bs, 2H), 3.98-3.84 (m, 4H), 2.86-2.79 (m, 1H), 2.54-2.48 (m, 1H), 2.38-2.32 (m, 1H), 2.27-2.12 (m, 1H), 2.10-2.01 (m, 2H), 1.90-1.72 (m, 1H), 1.68-1.52 (m, 4H), 1.51-1.40 (m, 2H), 1.39-1.23 (m, 2H), 0.57 (t, J=7.4 Hz, 3H).

Step #6: rac-(4aR,11bS)-11b-ethyl-1,2,4,4a,5,6,7,11b-octahydrospiro[dibenzo[a,c][7]annulene-3,2'-[1,3]dioxolan]-9-amine (22, R²=Ethyl)

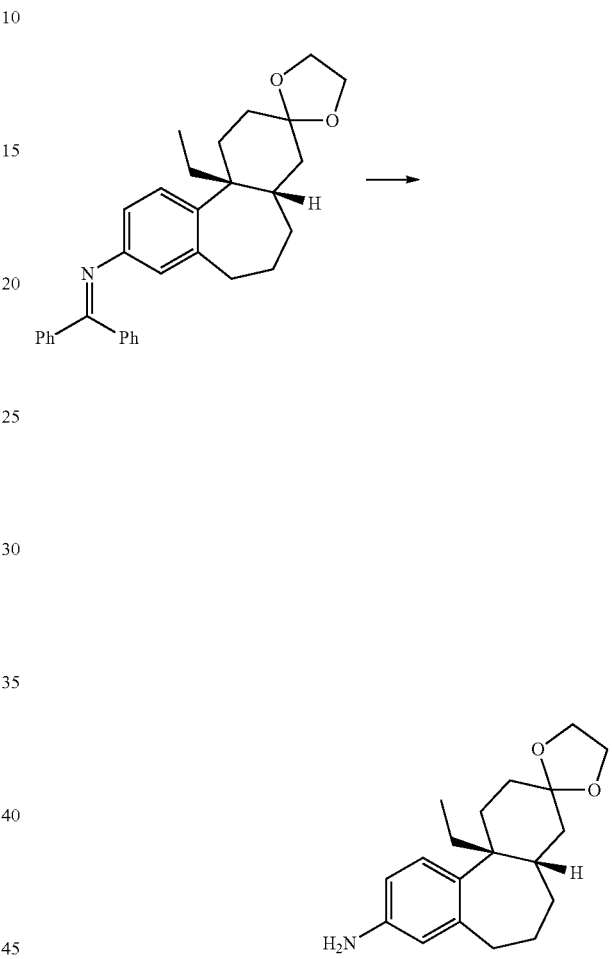

A flask with stir bar, condenser and nitrogen line was charged with rac-(4aR,11bS)—N-(diphenylmethylene)-11b-ethyl-1,2,4,4a,5,6,7,11b-octahydrospiro[dibenzo[a,c][7]annulene-3,2'-[1,3]dioxolan]-9-amine (21, R²=Ethyl) (0.550 g, 1.181 mmol), 10% Pd on carbon (0.094 g, 0.089 mmol) and MeOH (25 mL). Ammonium formate (1.12 g, 17.7 mmol) was added and the mixture was heated to about 65° C. After about 15 min the mixture was cooled to rt and filtered through a pad of Celite®. The pad was washed with MeOH (15 mL) then the filtrate was concentrated under reduced pressure. The residue was partitioned between EtOAc (20 mL), water (5 mL) and sat. aq. NaHCO₃ (15 mL). The layers were separated and the aqueous layer was extracted with EtOAc (15 mL). The combined organic layers were dried over MgSO₄, filtered and concentrated under reduced pressure to yield rac-(4aR,11bS)-11b-ethyl-1,2,4,4a,5,6,7,11b-octahydrospiro[dibenzo[a,c][7]annulene-3,2'-[1,3]dioxolan]-9-amine (22, R²=Ethyl) (0.345 g, 97%); LC/MS, method 3, R$_f$=2.50 min, MS m/z 302 (M+H)⁺. ¹H NMR (400 MHz, DMSO) δ 6.83 (d, J=8.3 Hz, 1H), 6.36-6.28 (m, 2H), 4.75 (bs, 2H), 3.87-3.72

(m, 4H), 2.82-2.75 (m, 1H), 2.57-2.45 (m, 1H), 2.30-2.26 (m, 1H), 2.14-2.05 (m, 1H), 2.00-1.89 (m, 2H), 1.72-1.15 (m, 9H), 0.58 (t, J=7.4 Hz, 3H).

Step #7: rac-(4aR,11bS)-10-bromo-11b-ethyl-1,2,4,4a,5,6,7,11b-octahydrospiro[dibenzo[a,c][7]annulene-3,2'-[1,3]dioxolan]-9-amine (23, R²=Ethyl)

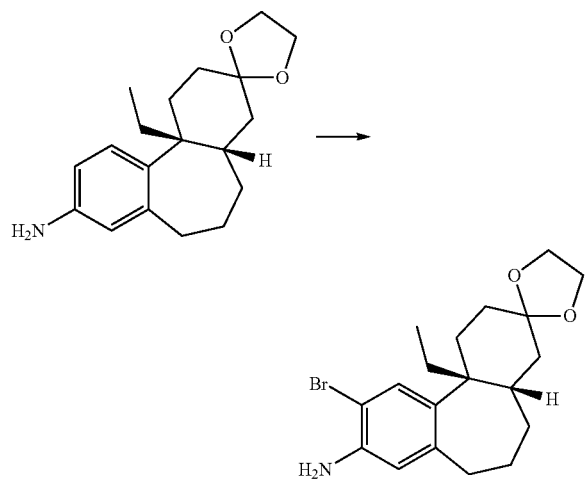

rac-(4aR,11bS)-11b-ethyl-1,2,4,4a,5,6,7,11b-octahydrospiro[dibenzo[a,c][7]annulene-3,2'-[1,3]dioxolan]-9-amine (22, R²=Ethyl) (0.345 g, 1.145 mmol) in THF (8 mL) was cooled to about 0° C. then NBS (0.204 g, 1.145 mmol) was added. After about 10 min, sat. aq. NaHCO₃ (20 mL) and EtOAc (25 mL) were added. The mixture was warmed to rt and the layers were separated. The aqueous layer was extracted with EtOAc (15 mL). The combined organic layers were dried over MgSO₄, filtered and concentrated under reduced pressure. The residue was purified on silica gel (12 g) using a gradient of 0-10% EtOAc in DCM. Product fractions were combined and concentrated under reduced pressure to yield rac-(4aR,11bS)-10-bromo-11b-ethyl-1,2,4,4a,5,6,7,11b-octahydrospiro[dibenzo[a,c][7]annulene-3,2'-[1,3]dioxolan]-9-amine (23, R²=Ethyl) (0.255 g, 59%); LC/MS, method 3, R$_t$=2.85 min, MS m/z 380, 382 (M+H)⁺. ¹H NMR (400 MHz, DMSO) δ 7.03 (s, 1H), 6.55 (s, 1H), 5.04 (s, 2H), 3.89-3.73 (m, 4H), 2.80-2.73 (m, 1H), 2.58-2.46 (m, 1H), 2.26-2.19 (m, 1H), 2.14-2.05 (m, 1H), 2.02-1.88 (m, 2H), 1.72-1.45 (m, 4H), 1.43-1.18 (m, 5H), 0.60 (t, J=7.4 Hz, 3H).

Step #8: rac-(4aR,11bS)-11b-ethyl-10-methyl-1,2,4,4a,5,6,7,11b-octahydrospiro[dibenzo[a,c][7]annulene-3,2'-[1,3]dioxolan]-9-amine (24, R²=Ethyl)

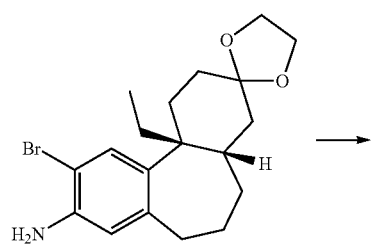

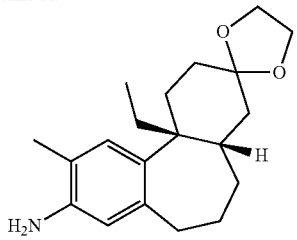

A mixture of rac-(4aR,11bS)-10-bromo-11b-ethyl-1,2,4,4a,5,6,7,11b-octahydrospiro[dibenzo[a,c][7]annulene-3,2'-[1,3]dioxolan]-9-amine (23, R²=Ethyl) (0.255 g, 0.670 mmol) in DME (6 mL) and water (2 mL) was degassed by bubbling nitrogen through the mixture for about 15 min. Cesium carbonate (0.655 g, 2.011 mmol), 2,4,6-trimethyl-1,3,5,2,4,6-trioxatriborinane (0.168 g, 1.341 mmol) and PdCl₂(PPh₃)₂ (0.024 g, 0.034 mmol) were added and the mixture was heated to about 90° C. for about 22 h. The mixture was cooled to rt, diluted with EtOAc (25 mL) and washed with sat. aq. NaHCO₃ (10 mL). The organic layer was dried over MgSO₄, filtered and concentrated under reduced pressure. The residue was purified on silica gel (4 g) using a gradient of 0-15% EtOAc in DCM. Product fractions were combined and concentrated under reduced pressure to yield rac-(4aR,11bS)-11b-ethyl-10-methyl-1,2,4,4a,5,6,7,11b-octahydrospiro[dibenzo[a,c][7]annulene-3,2'-[1,3]dioxolan]-9-amine (24, R²=Ethyl) (0.112 g, 53%); LC/MS, method 3, R$_t$=2.53 min, MS m/z 316 (M+H)⁺. ¹H NMR (400 MHz, DMSO) δ 6.72 (s, 1H), 6.35 (s, 1H), 4.61 (s, 2H), 3.88-3.70 (m, 4H), 2.79-2.72 (m, 1H), 2.54-2.47 (m, 1H), 2.33-2.27 (m, 1H), 2.13-2.04 (m, 1H), 2.00 (s, 3H), 1.97-1.88 (m, 2H), 1.72-1.57 (m, 3H), 1.53-1.46 (m, 1H), 1.41-1.14 (m, 5H), 0.59 (t, J=7.4 Hz, 3H).

Step #9: rac-N-((4aR,11bS)-11b-ethyl-10-methyl-1,2,4,4a,5,6,7,11b-octahydrospiro[dibenzo[a,c][7]annulene-3,2'-[1,3]dioxolan]-9-yl)acetamide (25, R²=Ethyl)

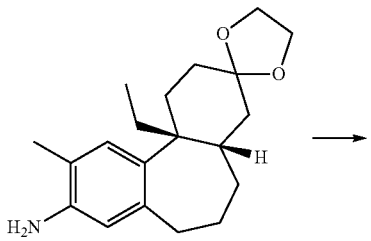

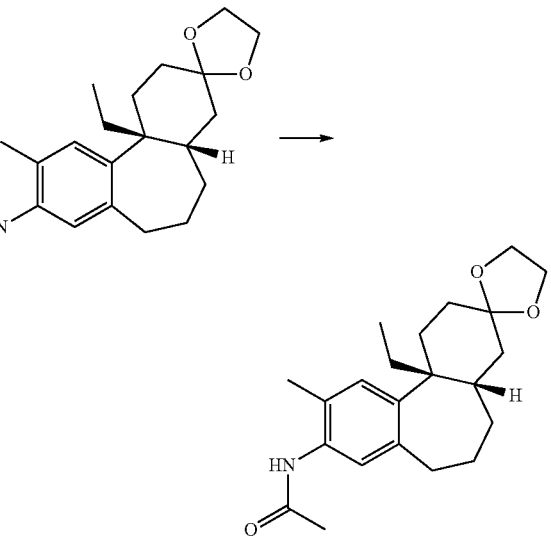

rac-(4aR,11bS)-11b-ethyl-10-methyl-1,2,4,4a,5,6,7,11b-octahydrospiro[dibenzo[a,c][7]annulene-3,2'-[1,3]dioxolan]-9-amine (24, R²=Ethyl) (0.178 g, 0.563 mmol) was dissolved in DCM (4 mL) then potassium acetate (0.138 g, 1.408 mmol) and acetic anhydride (0.115 g, 1.126 mmol) were added. After about 10 min sat. aq. NaHCO₃ (3 mL) was added and the mixture was diluted with DCM (15 mL). The layers were separated and the organic layer was dried over MgSO₄, filtered and concentrated under reduced pressure. The residue was purified on silica gel (12 g) using a gradient of 0-50% EtOAc in DCM. Product fractions were combined and concentrated under reduced pressure to yield rac-N-((4aR,11bS)-11b-ethyl-10-methyl-1,2,4,4a,5,6,7,11b-octahydrospiro[dibenzo[a,c][7]annulene-3,2'-[1,3]dioxolan]-9-yl)acetamide (25, R²=Ethyl) (0.125 g, 62%); LC/MS, method 3, R$_t$=2.36 min, MS m/z 358 (M+H)⁺. ¹H NMR (400 MHz, DMSO) δ 9.12 (s, 1H), 7.13 (s, 1H), 6.99 (s, 1H), 3.89-3.73 (m, 4H), 2.87-2.81 (m, 1H), 2.67-2.59 (m, 1H), 2.39-2.32 (m, 1H), 2.22-2.06 (m, 1H), 2.15 (s, 3H) 2.02 (s, 3H), 2.01-1.91 (m, 2H), 1.69-161 (m, 3H), 1.58-1.51 (m, 1H), 1.49-1.20 (m, 5H), 0.61 (t, J=7.5 Hz, 3H).

Step #10: rac-1-((4aR,12bS)-12b-ethyl-4a,5,6,7-tetrahydro-1H-spiro[benzo[6,7]cyclohepta[1,2-f]indazole-3,2'-[1,3]dioxolan]-9(2H,4H,12bH)-yl)ethanone (26, R²=Ethyl)

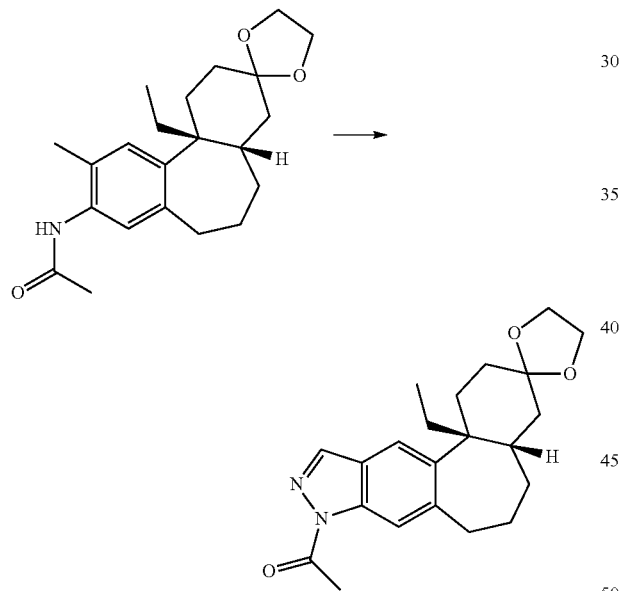

rac-N-((4aR,11bS)-11b-ethyl-10-methyl-1,2,4,4a,5,6,7,11b-octahydrospiro[dibenzo[a,c][7]annulene-3,2'-[1,3]dioxolan]-9-yl)acetamide (25, R²=Ethyl) (0.125 g, 0.350 mmol) in CHCl₃ (8 mL) was treated with potassium acetate (0.069 g, 0.699 mmol), AcOH (0.042 g, 0.699 mmol), 18-Crown-6 (15 mg, 0.057 mmol), acetic anhydride (0.071 g, 0.699 mmol) and isopentyl nitrite (0.123 g, 1.049 mmol). The mixture was warmed to about 70° C. for about 3 h then a second portion of isopentyl nitrite (0.200 g, 1.707 mmol) and acetic anhydride (0.110 g, 1.077 mmol) were added. After about 11 h the mixture was cooled to rt and treated with sat. aq. NaHCO₃ (3 mL) and water (10 mL). The mixture was extracted with DCM (30 mL) then the organic layer was dried over MgSO₄, filtered and concentrated under reduced pressure. The residue was purified on silica gel (12 g) using a gradient of 0-20% EtOAc in DCM. Product fractions were combined and concentrated under reduced pressure to yield rac-1-((4aR,12bS)-12b-ethyl-4a,5,6,7-tetrahydro-1H-spiro[benzo[6,7]cyclohepta[1,2-f]indazole-3,2'-[1,3]dioxolan]-9(2H,4H,12bH)-yl)ethanone (26, R²=Ethyl) (0.083 g, 64%); LC/MS, method 3, R$_t$=2.87 min, MS m/z 369 (M+H)⁺. ¹H NMR (400 MHz, DMSO) δ 8.37 (d, J=0.6 Hz, 1H), 8.06 (s, 1H), 7.75 (s, 1H), 3.95-3.68 (m, 4H), 3.11-3.04 (m, 1H), 2.98-2.92 (m, 1H), 2.69 (s, 3H), 2.57-2.48 (m, 1H), 2.32-1.13 (m, 12H), 0.59 (t, J=7.4 Hz, 3H).

Step #11: (4aS,12bR)-9-Acetyl-12b-ethyl-1,2,4a,5,6,7,9,12b-octahydro-4H-9,10-diaza-benzo[3,4]cyclohepta[1,2-f]inden-3-one; compound with (4aR,12bS)-9-Acetyl-12b-ethyl-1,2,4a,5,6,7,9,12b-octahydro-4H-9,10-diaza-benzo[3,4]cyclohepta[1,2-f]inden-3-one (10, R¹=Acetyl, R²=Ethyl)

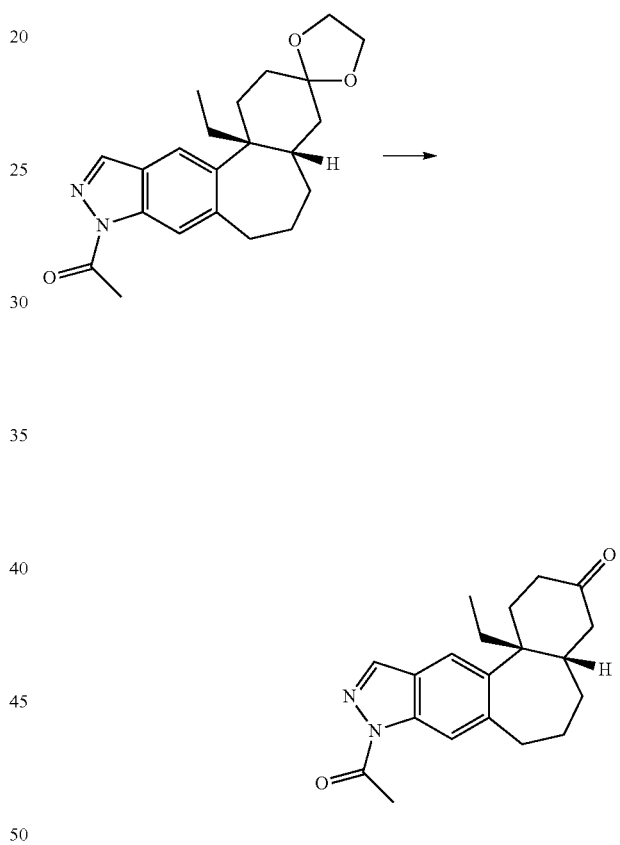

rac-1-((4aR,12bS)-12b-ethyl-4a,5,6,7-tetrahydro-1H-spiro[benzo[6,7]cyclohepta[1,2-f]indazole-3,2'-[1,3]dioxolan]-9(2H,4H,12bH)-yl)ethanone (26, R²=Ethyl) (0.083 g, 0.225 mmol) in a mixture of DCM (4 mL) and water (2 mL) was treated with TFA (0.25 mL, 0.225 mmol) then heated to about 40° C. After about 15 min the mixture was cooled to rt then concentrated under reduced pressure. The residue was partitioned between EtOAc (25 mL) and sat. aq. NaHCO₃ (15 mL). The organic layer was dried over MgSO₄, filtered and concentrated under reduced pressure to yield (4aS,12bR)-9-Acetyl-12b-ethyl-1,2,4a,5,6,7,9,12b-octahydro-4H-9,10-diaza-benzo[3,4]cyclohepta[1,2-f]inden-3-one; compound with (4aR,12bS)-9-acetyl-12b-ethyl-1,2,4a,5,6,7,9,12b-octahydro-4H-9,10-diaza-benzo[3,4]cyclohepta[1,2-f]inden-3-one (10, R¹=Acetyl, R²=Ethyl) (0.066 g, 90%); LC/MS, method 3, R$_t$=2.58 min, MS m/z 325 (M+H)⁺. ¹H NMR (400 MHz, DMSO) δ 8.36 (d, J=0.7 Hz, 1H), 8.11 (s, 1H), 7.86 (s, 1H), 3.19-3.13 (m, 1H), 2.99-2.92 (m, 1H), 2.79-2.73 (m, 1H), 2.69 (s, 3H), 2.43-1.40 (m, 12H), 0.61 (t, J=7.4 Hz, 3H).

Step #12: rac-(2'R,4aS,12bR)-12b-ethyl-2,4,4a,5,6,7,9,12b-octahydro-1H-spiro[benzo[6,7]cyclohepta[1,2-f]indazole-3,2'-oxirane] (12, R¹=H, R²=Ethyl)

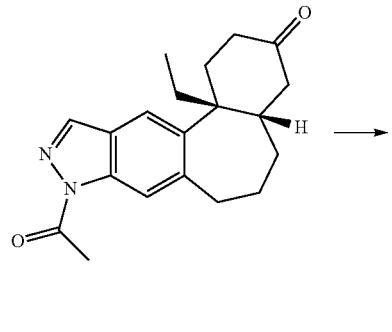

A mixture of DMSO (1 mL) and sodium hydride (60 wt % in oil, 0.020 g, 0.51 mmol) was heated to about 65° C. for about 45 min then cooled to rt and diluted with THF (1 mL). The mixture was cooled to about 0° C. and trimethylsulfoxonium iodide (0.112 g, 0.509 mmol) was added. The mixture was stirred for about 15 min and (4aS,12bR)-9-acetyl-12b-ethyl-1,2,4a,5,6,7,9,12b-octahydro-4H-9,10-diaza-benzo[3,4]cyclohepta[1,2-f]inden-3-one; compound with (4aR,12bS)-9-Acetyl-12b-ethyl-1,2,4a,5,6,7,9,12b-octahydro-4H-9,10-diaza-benzo[3,4]cyclohepta[1,2-f]inden-3-one (10, R¹=Acetyl, R²=Ethyl) (0.066 g, 0.203 mmol) dissolved in THF (1.5 mL) was added. The mixture was warmed to rt and stirred for about 14 h. In a separate flask a mixture of DMSO (1 mL) and sodium hydride (60 wt % in oil, 0.020 g, 0.51 mmol) was heated to about 65° C. for about 45 min then cooled to rt and diluted with THF (0.5 mL). The mixture was cooled to about 0° C., trimethylsulfoxonium iodide (0.112 g, 0.51 mmol) was added and the mixture was stirred for about 15 min. The mixture was added to the epoxidation reaction and stirring was continued for about 2 h at rt. The reaction mixture was diluted with EtOAc (25 mL) and washed successively with sat. aq. NH₄Cl (15 mL), water (15 mL), and brine (15 mL). The organic solution was died over MgSO₄, filtered and concentrated under reduced pressure to provide crude rac-(2'R,4aS,12bR)-12b-ethyl-2,4,4a,5,6,7,9,12b-octahydro-1H-spiro[benzo[6,7]cyclohepta[1,2-f]indazole-3,2'-oxirane] (12, R¹=H, R²=Ethyl) (0.084 g); LC/MS, method 3, $R_t$=2.32 min, MS m/z 297 (M+H)⁺. The material was used directly in Step #13 without further purification Step #13: (3R,4aS,12bR)-12b-Ethyl-3-methoxymethyl-1,2,3,4,4a,5,6,7,9,12b-decahydro-9,10-diaza-benzo[3,4]cyclohepta[1,2-f]inden-3-ol; compound with (3S,4aR,12bS)-12b-ethyl-3-methoxymethyl-1,2,3,4,4a,5,6,7,9,12b-decahydro-9,10-diaza-benzo[3,4]cyclohepta[1,2-f]inden-3-ol (13, R¹=H, R²=Ethyl, R³=Methoxymethyl)

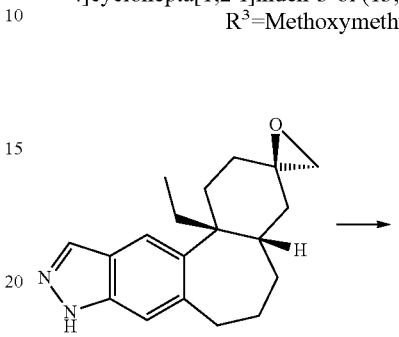

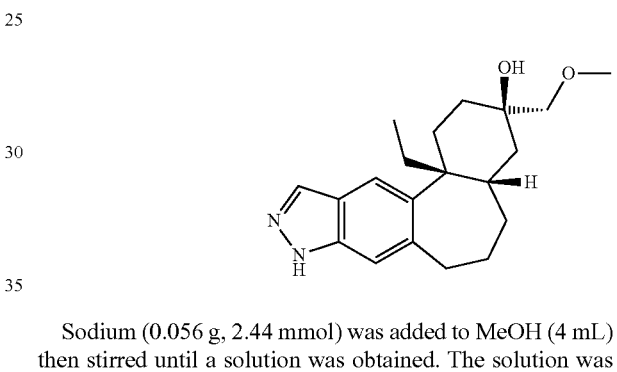

Sodium (0.056 g, 2.44 mmol) was added to MeOH (4 mL) then stirred until a solution was obtained. The solution was added to a flask containing crude rac-(2'R,4aS,12bR)-12b-ethyl-2,4,4a,5,6,7,9,12b-octahydro-1H-spiro[benzo[6,7]cyclohepta[1,2-f]indazole-3,2'-oxirane] (12, R¹=H, R²=Ethyl) (0.084 g obtained in Step #12). The mixture was heated to about 70° C. for about 45 min. The mixture was cooled to rt then acetic acid (0.146 g, 2.436 mmol) was added. The mixture was purified by preparative reverse phase HPLC; Hypersil HS C18 column, 250 mm×21.2 mm, 8 μm particle size, flow rate 21 mL/min, detection 254 nm, Å=0.05 N ammonium acetate ph 4.5 buffer, B=MeCN, 15 to 100% over 25 min. Product fractions were collected and concentrated to remove MeCN. The solids were collected by filtration, washed with water and dried under vacuum to yield (3R,4aS,12bR)-12b-ethyl-3-methoxymethyl-1,2,3,4,4a,5,6,7,9,12b-decahydro-9,10-diaza-benzo[3,4]cyclohepta[1,2-f]inden-3-ol; compound with (3S,4aR,12bS)-12b-ethyl-3-methoxymethyl-1,2,3,4,4a,5,6,7,9,12b-decahydro-9,10-diaza-benzo[3,4]cyclohepta[1,2-f]inden-3-ol (13, R¹=H, R²=Ethyl, R³=Methoxymethyl) (0.015 g, 23% from (4aS,12bR)-9-Acetyl-12b-ethyl-1,2,4a,5,6,7,9,12b-octahydro-4H-9,10-diaza-benzo[3,4]cyclohepta[1,2-f]inden-3-one; compound with (4aR,12bS)-9-Acetyl-12b-ethyl-1,2,4a,5,6,7,9,12b-octahydro-4H-9,10-diaza-benzo[3,4]cyclohepta[1,2-f]inden-3-one (10, R¹=Acetyl, R²=Ethyl) (Example 14) (0.066 g)); LC/MS, method 2, $R_t$=2.07 min, MS m/z 329 (M+H)⁺. ¹H NMR (400 MHz, DMSO) δ 12.73 (s, 1H), 7.94 (s, 1H), 7.57 (s, 1H), 7.22 (s, 1H), 4.15 (s, 1H), 3.09 (s, 3H), 3.07-2.97 (m, 1H), 2.96-2.85 (m, 1H), 2.92 (s, 2H), 2.36-2.29

(m, 2H), 2.26-2.18 (m, 1H), 2.16-2.02 (m, 1H), 1.83-1.60 (m, 3H), 1.57-1.31 (m, 4H), 1.25-1.18 (m, 1H), 1.01-0.98 (m, 1H), 0.56 (t, J=7.4 Hz, 3H).

Example #15 and #16

(3R,4aS,12bS)-9-(4-fluorophenyl)-3-methyl-12b-(pyridin-2-ylmethyl)-1,2,3,4,4a,5,6,7,9,12b-decahydrobenzo[6,7]cyclohepta[1,2-f]indazol-3-ol (13, $R^1$=4-Fluorophenyl, $R^2$=Pyridin-2-ylmethyl 1, $R^3$=Methyl) and (3S,4aR,12bR)-9-(4-fluorophenyl)-3-methyl-12b-(pyridin-2-ylmethyl)-1,2,3,4,4a,5,6,7,9,12b-decahydrobenzo[6,7]cyclohepta[1,2-f]indazol-3-ol (13, $R^1$=4-Fluorophenyl, $R^2$=Pyridin-2-ylmethyl, $R^3$=Methyl)

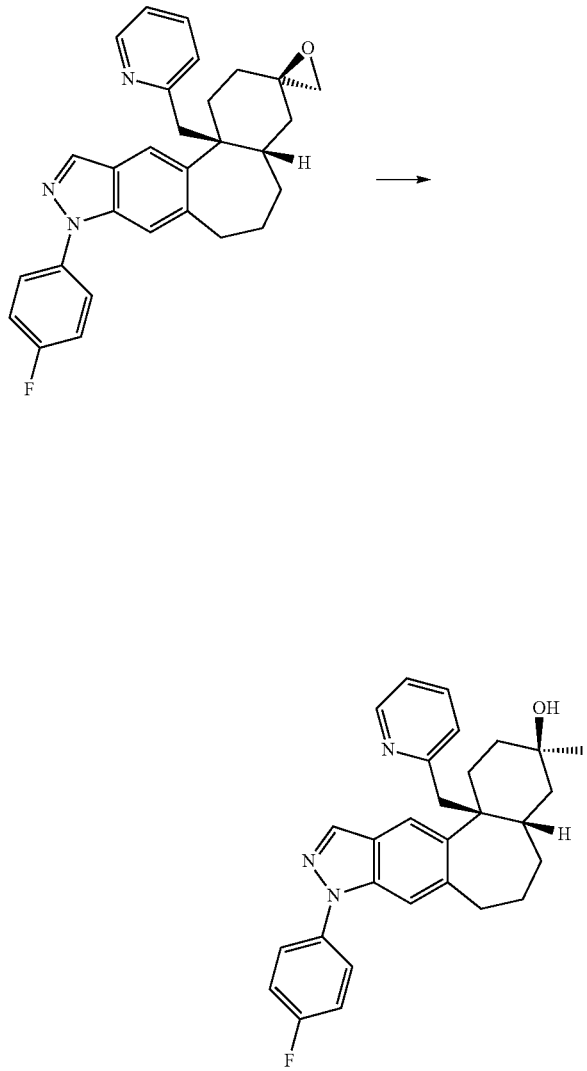

A solution of (2'R,4aS,12bS)-9-(4-fluorophenyl)-12b-(pyridin-2-ylmethyl)-2,4,4a,5,6,7,9,12b-octahydro-1H-spiro[benzo[6,7]cyclohepta[1,2-f]indazole-3,2'-oxirane]compound with (2'S,4aR,12bR)-9-(4-fluorophenyl)-12b-(pyridin-2-ylmethyl)-2,4,4a,5,6,7,9,12b-octahydro-1H-spiro[benzo[6,7]cyclohepta[1,2-f]indazole-3,2'-oxirane] (12, $R^1$=4-Fluorophenyl, $R^2$=Pyridin-2-ylmethyl) (500 mg, 1.10 mmol) in EtOH (10 mL) was treated with NaBH$_4$ (104 mg, 2.76 mmol). The reaction was warmed to 60° C. for about 20 min and then allowed to stir at rt for about 18 h. The reaction was concentrated under reduced pressure, then sat. aq. NH$_4$Cl (25 mL) was added and the product was extracted with EtOAc (2×25 mL). The organic solution was dried over Na$_2$SO$_4$, filtered and concentrated under reduced pressure. The residue was purified on silica gel (25 g) using EtOAc as eluent. Product fractions were combined and concentrated to yield (3R,4aS,12bS)-9-(4-fluorophenyl)-3-methyl-12b-(pyridin-2-ylmethyl)-1,2,3,4,4a,5,6,7,9,12b-decahydrobenzo[6,7]cyclohepta[1,2-f]indazol-3-ol; compound with (3S,4aR,12bR)-9-(4-fluorophenyl)-3-methyl-12b-(pyridin-2-ylmethyl)-1,2,3,4,4a,5,6,7,9,12b-decahydrobenzo[6,7]cyclohepta[1,2-f]indazol-3-ol (13, $R^1$=4-Fluorophenyl, $R^2$=Pyridin-2-ylmethyl, $R^3$=Methyl) (503 mg, 100%) as a white solid.

The enantiomers were separated using Preparative Chiral Purification Method 5. Fractions from the first peak eluted were combined and concentrated under reduced pressure. The residue was dissolved in MeOH (5 mL), treated with water (25 mL) and concentrated under reduced pressure to remove MeOH. Solids were collected by filtration, washed with water (2 mL) and dried under vacuum at about 70° C. to yield (3R,4aS,12bS)-9-(4-fluorophenyl)-3-methyl-12b-(pyridin-2-ylmethyl)-1,2,3,4,4a,5,6,7,9,12b-decahydrobenzo[6,7]cyclohepta[1,2-f]indazol-3-ol (Example 15) (13, $R^1$=4-Fluorophenyl, $R^2$=Pyridin-2-ylmethyl, $R^3$=Methyl) (0.179 g, 35%); LC/MS, method 2, R$_f$=2.54 min, MS m/z 456 (M+H)$^+$. $^1$H NMR (400 MHz, DMSO) δ 1H NMR (400 MHz, DMSO) δ 8.37-8.33 (m, 1H), 8.14 (d, J=0.8 Hz, 1H), 7.86-7.76 (m, 2H), 7.64 (s, 1H), 7.45-7.37 (m, 2H), 7.37-7.31 (m, 1H), 7.26 (s, 1H), 7.07-7.02 (m, 1H), 6.36 (d, J=7.8 Hz, 1H), 4.04 (s, 1H), 3.59 (d, J=12.6 Hz, 1H), 3.37-3.24 (m, 1H), 3.17-3.05 (m, 1H), 2.91 (d, J=12.6 Hz, 1H), 2.52-2.44 (m, 2H), 2.09-1.99 (m, 1H), 1.99-1.75 (m, 2H), 1.65-1.38 (m, 4H), 1.29-1.02 (m, 2H), 0.91 (s, 3H).

Fractions from the second peak eluted were combined and concentrated under reduced pressure. The residue was dissolved in MeOH (5 mL), treated with water (25 mL) and concentrated under reduced pressure to remove MeOH. Solids were collected by filtration, washed with water (2 mL) and dried under vacuum at about 70° C. to yield (3S,4aR,12bR)-9-(4-fluorophenyl)-3-methyl-12b-(pyridin-2-ylmethyl)-1,2,3,4,4a,5,6,7,9,12b-decahydrobenzo[6,7]cyclohepta[1,2-f]indazol-3-ol (Example 16) (13, $R^1$=4-Fluorophenyl, $R^2$=Pyridin-2-ylmethyl, $R^3$=Methyl) (0.168 g, 33%). LC/MS, method 2, R$_f$=2.54 min, MS m/z 456 (M+H)$^+$. $^1$H NMR (400 MHz, DMSO) δ 1H NMR (400 MHz, DMSO) δ 8.37-8.33 (m, 1H), 8.14 (d, J=0.8 Hz, 1H), 7.86-7.76 (m, 2H), 7.64 (s, 1H), 7.45-7.37 (m, 2H), 7.37-7.31 (m, 1H), 7.26 (s, 1H), 7.07-7.02 (m, 1H), 6.36 (d, J=7.8 Hz, 1H), 4.04 (s, 1H), 3.59 (d, J=12.6 Hz, 1H), 3.37-3.24 (m, 1H), 3.17-3.05 (m, 1H), 2.91 (d, J=12.6 Hz, 1H), 2.52-2.44 (m, 2H), 2.09-1.99 (m, 1H), 1.99-1.75 (m, 2H), 1.65-1.38 (m, 4H), 1.29-1.02 (m, 2H), 0.91 (s, 3H).

Example #17 and #18

2-((3R,4aS,12bS)-9-(4-fluorophenyl)-3-hydroxy-12b-(pyridin-2-ylmethyl)-1,2,3,4,4a,5,6,7,9,12b-decahydrobenzo[6,7]cyclohepta[1,2-f]indazol-3-yl)acetonitrile (13, $R^1$=4-Fluorophenyl, $R^2$=Pyridin-2-ylmethyl 1, $R^3$=Cyanomethyl) and 2-((3S,4aR,12bR)-9-(4-fluorophenyl)-3-hydroxy-12b-(pyridin-2-ylmethyl)-1,2,3,4,4a,5,6,7,9,12b-decahydrobenzo[6,7]cyclohepta[1,2-f]indazol-3-yl)acetonitrile (13, $R^1$=4-Fluorophenyl, $R^2$=Pyridin-2-ylmethyl, $R^3$=Cyanomethyl)

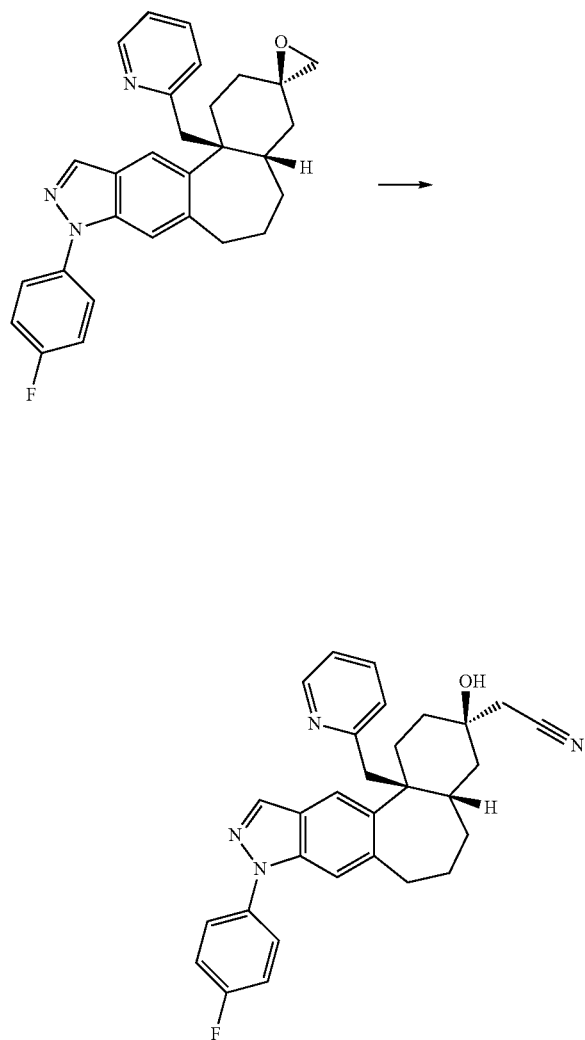

A solution of (2'R,4aS,12bS)-9-(4-fluorophenyl)-12b-(pyridin-2-ylmethyl)-2,4,4a,5,6,7,9,12b-octahydro-1H-spiro[benzo[6,7]cyclohepta[1,2-f]indazole-3,2'-oxirane] compound with (2'S,4aR,12bR)-9-(4-fluorophenyl)-12b-(pyridin-2-ylmethyl)-2,4,4a,5,6,7,9,12b-octahydro-1H-spiro[benzo[6,7]cyclohepta[1,2-f]indazole-3,2'-oxirane] (12, $R^1$=4-Fluorophenyl, $R^2$=Pyridin-2-ylmethyl) (500 mg, 1.10 mmol) in toluene (10 mL) was stirred at rt under nitrogen. Cyanodiethylaluminum (6.61 mL, 6.61 mmol) was added over about 5 min resulting in a slight exotherm. Stirring was continued at rt for about 1 h, then the mixture was warmed to 40° C. for about 4 h. The mixture was treated with aq. sat. solution of sodium potassium tartrate-ethyl acetate (1:1) (20 mL) and stirring was continued for 15 min at rt. The aqueous layer was extracted with EtOAc (4×40 mL) and the combined organic layers were dried over $Na_2SO_4$, filtered and concentrated under reduced pressure to yield an oil (250 mg). The crude material was purified on silica gel (4 g) using EtOAc as the eluant. Product fractions were combined and concentrated under reduced pressure, then dried under vacuum at about 50° C. to provide 2-((3R,4aS,12bS)-9-(4-fluorophenyl)-3-hydroxy-12b-(pyridin-2-ylmethyl)-1,2,3,4,4a,5,6,7,9,12b-decahydrobenzo[6,7]cyclohepta[1,2-f]indazol-3-yl)acetonitrile (13, $R^1$=4-Fluorophenyl, $R^2$=Pyridin-2-ylmethyl 1, $R^3$=Cyanomethyl); compound with 2-((3S,4aR,12bR)-9-(4-fluorophenyl)-3-hydroxy-12b-(pyridin-2-ylmethyl)-1,2,3,4,4a,5,6,7,9,12b-decahydrobenzo[6,7]cyclohepta[1,2-f]indazol-3-yl)acetonitrile (13, $R^1$=4-Fluorophenyl, $R^2$=Pyridin-2-ylmethyl, $R^3$=Cyanomethyl) (155 mg, 29%) of as an off-white solid.

The enantiomers were separated using Preparative Chiral Purification Method 6. Fractions from the first peak eluted were combined and concentrated under reduced pressure. The residue was dissolved in MeOH (5 mL), treated with water (25 mL) and concentrated under reduced pressure to remove MeOH. Solids were collected by filtration, washed with water (2 mL) and dried under vacuum at about 70° C. to yield 2-((3R,4aS,12bS)-9-(4-fluorophenyl)-3-hydroxy-12b-(pyridin-2-ylmethyl)-1,2,3,4,4a,5,6,7,9,12b-decahydrobenzo[6,7]cyclohepta[1,2-f]indazol-3-yl)acetonitrile (Example 17) (13, $R^1$=4-Fluorophenyl, $R^2$=Pyridin-2-ylmethyl 1, $R^3$=Cyanomethyl) (0.053 g, 34%); LC/MS, method 2, $R_t$=2.36 min, MS m/z 481 $(M+H)^+$. $^1$H NMR (400 MHz, DMSO) δ $^1$H NMR (400 MHz, DMSO) δ 8.39-8.33 (m, 1H), 8.14 (d, J=0.8 Hz, 1H), 7.86-7.77 (m, 2H), 7.66 (s, 1H), 7.46-7.34 (m, 3H), 7.28 (s, 1H), 7.08-7.02 (m, 1H), 6.35 (d, J=7.8 Hz, 1H), 4.90 (s, 1H), 3.61 (d, J=12.6 Hz, 1H), 3.36-3.26 (m, 1H), 3.18-3.08 (m, 1H), 2.91 (d, J=12.7 Hz, 1H), 2.63-2.52 (m, 1H), 2.48-2.40 (m, 1H), 2.38 (bs, 2H), 2.17-2.08 (m, 1H), 2.02-1.81 (m, 2H), 1.67-1.41 (m, 4H), 1.30-1.19 (m, 2H)

Fractions from the second peak eluted were combined and concentrated under reduced pressure. The residue was dissolved in MeOH (5 mL), treated with water (25 mL) and concentrated under reduced pressure to remove MeOH. Solids were collected by filtration, washed with water (2 mL) and dried under vacuum at about 70° C. to yield 2-((3S,4aR,12bR)-9-(4-fluorophenyl)-3-hydroxy-12b-(pyridin-2-ylmethyl)-1,2,3,4,4a,5,6,7,9,12b-decahydrobenzo[6,7]cyclohepta[1,2-f]indazol-3-yl)acetonitrile (Example 18) (13, $R^1$=4-Fluorophenyl, $R^2$=Pyridin-2-ylmethyl 1, $R^3$=Cyanomethyl) (0.048 g, 31%); LC/MS, method 2, $R_t$=2.36 min, MS m/z 481 $(M+H)^+$.)$^+$. $^1$H NMR (400 MHz, DMSO) δ $^1$H NMR (400 MHz, DMSO) δ 8.39-8.33 (m, 1H), 8.14 (d, J=0.8 Hz, 1H), 7.86-7.77 (m, 2H), 7.66 (s, 1H), 7.46-7.34 (m, 3H), 7.28 (s, 1H), 7.08-7.02 (m, 1H), 6.35 (d, J=7.8 Hz, 1H), 4.90 (s, 1H), 3.61 (d, J=12.6 Hz, 1H), 3.36-3.26 (m, 1H), 3.18-3.08 (m, 1H), 2.91 (d, J=12.7 Hz, 1H), 2.63-2.52 (m, 1H), 2.48-2.40 (m, 1H), 2.38 (bs, 2H), 2.17-2.08 (m, 1H), 2.02-1.81 (m, 2H), 1.67-1.41 (m, 4H), 1.30-1.19 (m, 2H)

Additional examples, prepared in a manner similar to the preparation of Example #1, 2 or 3 are listed in Table 1.

TABLE 1

| Ex. # | Reactant | Reagent | Product structure | LC/MS method/ $R_T$ M/Z | Chiral method | Order of elution/ sign of rotation |
|---|---|---|---|---|---|---|
| 19 | 10 ($R^1$ = 4-Fluorophenyl, $R^2$ = Pyridin-2-ylmethyl) | CsF/CF$_3$ TMS/TBAF | 15 (3S,4aS,12bS)- (4-Fluorophenyl, $R^2$ = Pyridin-2-ylmethyl, $R^3$ = Trifluoromethyl) | 2 2.74 min 510 MH$^+$ | 10 | $1^{st}$/pos |
| 20 | 10 ($R^1$ = 4-Fluorophenyl, $R^2$ = Pyridin-2-ylmethyl) | CsF/CF$_3$ TMS/TBAF | 15 (3R,4aR,12bR)- (4-Fluorophenyl, $R^2$ = Pyridin-2-ylmethyl, $R^3$ = Trifluoromethyl) | 2 2.74 min 510 MH$^+$ | 10 | 2nd/neg |
| 21 | 9 ($R^1$ = 4-Fluorophenyl, $R^2$ = Cyclopropyl-methyl) | CsF/CF$_3$ TMS/TBAF | 11 (3S,4aS,12bR)- (4-Fluorophenyl, $R^2$ = Cyclopropylmethyl, $R^3$ = Trifluoromethyl) | 2 3.06 min 473 MH$^+$ | 42 | $1^{st}$/nd |
| 22 | 9 ($R^1$ = 4-Fluorophenyl, $R^2$ = Cyclopropyl-methyl) | CsF/CF$_3$ TMS/TBAF | 11 (3S,4aS,12bR)- (4-Fluorophenyl, $R^2$ = Cyclopropylmethyl, $R^3$ = Trifluoromethyl) | 2 3.06 min 473 MH$^+$ | 42 | $2^{nd}$/nd |
| 23 | 9 ($R^1$ = 4-Fluorophenyl, $R^2$ = Ethyl) | CsF/CF$_3$ TMS/TBAF | 11 (3S,4aS,12bS)- (4-Fluorophenyl, $R^2$ = Ethyl, $R^3$ = Trifluoromethyl); cmpd with (3R,4aR,12bR)- (4-Fluorophenyl, $R^2$ = Ethyl, $R^3$ = Trifluoromethyl) | 2 2.96 min 447 MH$^+$ | NA | NA |
| 24 | 9 ($R^1$ = 4-Fluorophenyl, $R^2$ = Ethyl) | CsF/CF$_3$ TMS/TBAF | 11 (3S,4aS,12bS)- (4-Fluorophenyl, $R^2$ = Ethyl, $R^3$ = Trifluoromethyl) | 2 2.96 min 447 MH$^+$ | 45 | $1^{st}$/neg |
| 25 | 9 ($R^1$ = 4-Fluorophenyl, $R^2$ = Ethyl) | CsF/CF$_3$ TMS/TBAF | 11 (3R,4aR,12bR)- (4-Fluorophenyl, $R^2$ = Ethyl, $R^3$ = Trifluoromethyl) | 2 2.96 min 447 MH$^+$ | 45 | 2nd/pos |

Additional examples, prepared in a manner similar to the preparation of Example #4 are listed in Table 2.

TABLE 2

| Ex. # | Reactant | Reagent | Product structure | LC/MS method/ $R_T$ M/Z | Chiral method | Order of elution/ sign of rotation |
|---|---|---|---|---|---|---|
| 26 | 12 ($R^1$ = 4-Fluorophenyl, $R^2$ = Pyridin-2-ylmethyl) | methyl-magnesium bromide | 13 (3S,4aR,12bR) ($R^1$ = 4-Fluorophenyl, $R^2$ = Pyridin-2-ylmethyl, $R^3$ = Ethyl) | 2 2.69 min 470 MH$^+$ | 7 | $1^{st}$/pos |
| 27 | 12 ($R^1$ = 4-Fluorophenyl, $R^2$ = Pyridin-2-ylmethyl) | methyl-magnesium bromide | 13 (3R,4aS,12bS) ($R^1$ = 4-Fluorophenyl, $R^2$ = Pyridin-2-ylmethyl, $R^3$ = Ethyl) | 2 2.69 min 470 MH$^+$ | 7 | $2^{nd}$/neg |
| 28 | 12 ($R^1$ = 4-Fluorophenyl, $R^2$ = Pyrimidin-2-ylmethyl) | methyl-magnesium bromide | 13 (3R,4aS,12bS) ($R^1$ = 4-Fluorophenyl, $R^2$ = Pyrimidin-2-ylmethyl, $R^3$ = Ethyl) | 2 2.52 min 471 MH$^+$ | 9 | $1^{st}$/nd |
| 29 | 12 ($R^1$ = 4-Fluorophenyl, $R^2$ = Pyrimidin-2-ylmethyl) | methyl-magnesium bromide | 13 (3S,4aR,12bR) ($R^1$ = 4-Fluorophenyl, $R^2$ = Pyrimidin-2-ylmethyl, $R^3$ = Ethyl) | 2 2.52 min 471 MH$^+$ | 9 | $2^{nd}$/nd |
| 30 | 12 ($R^1$ = 4-Pyridyl, $R^2$ = Pyridin-2yl-methyl) | methyl-magnesium bromide | 13 (3R,4aS,12bS) ($R^1$ = 4-Pyridyl, $R^2$ = Pyridin-2-ylmethyl, $R^3$ = Methyl) | 2 1.83 min 439 MH$^+$ | 28 | $1^{st}$/NA |

TABLE 2-continued

| Ex. # | Reactant | Reagent | Product structure | LC/MS method/ $R_T$ M/Z | Chiral method | Order of elution/ sign of rotation |
|---|---|---|---|---|---|---|
| 31 | 12 ($R^1$ = 4-Pyridyl, $R^2$ = Pyridin-2yl-methyl) | methyl-magnesium bromide | 13 (3S,4aR,12bR) ($R^1$ = 4-Pyridyl, $R^2$ = Pyridin-2yl-methyl, $R^3$ = Methyl) | 2 1.83 min 439 MH$^+$ | 28 | 2$^{nd}$/NA |

Additional examples, prepared in a manner similar to the preparation of Example #12 are listed in Table 3.

TABLE 3

| Ex. # | Reactant | Reagent | Product structure | LC/MS method/ $R_t$ M/Z | Chiral method | Order of elution/ sign of rotation |
|---|---|---|---|---|---|---|
| 32 | 12 ($R^1$ = 4-Fluorophenyl, $R^2$ = Pyridin-2-ylmethyl) | Sodium ethoxide | 13 (3R,4aS,12bS) ($R^1$ = 4-Fluorophenyl, $R^2$ = Pyridin-2-ylmethyl, $R^3$ = Ethoxymethyl) | 2 2.67 min 500 MH$^+$ | 10 | 1$^{st}$/neg |
| 33 | 12 ($R^1$ = 4-Fluorophenyl, $R^2$ = Pyridin-2-ylmethyl) | Sodium ethoxide | 13 (3S,4aR,12bR) ($R^1$ = 4-Fluorophenyl, $R^2$ = Pyridin-2-ylmethyl, $R^3$ = EthoxyMethyl) | 2 2.67 min 500 MH$^+$ | 10 | 2$^{nd}$/pos |
| 34 | 12 ($R^1$ = 4-Fluorophenyl, $R^2$ = Ethyl) | Sodium methoxide | 13 (3S,4aR,12bS)-(4-Fluorophenyl, $R^2$ = Ethyl, $R^3$ = Methoxymethyl) | 2 2.96 min 423 MH$^+$ | 35 | 1$^{st}$/neg |
| 35 | 12 ($R^1$ = 4-Fluorophenyl, $R^2$ = Ethyl) | Sodium methoxide | 13 (3R,4aS,12bR)-(4-Fluorophenyl, $R^2$ = Ethyl, $R^3$ = Methoxymethyl) | 2 2.96 min 423 MH$^+$ | 35 | 2$^{nd}$/pos |
| 36 | 12 ($R^1$ = 4-Fluorophenyl, $R^2$ = Pyrimidin-2-ylmethyl) | Sodium methoxide | 13 (3S,4aR,12bR)-($R^1$ = 4-Fluorophenyl, $R^2$ = Pyrimidin-2-ylmethyl, $R^3$ = Methoxymethyl) | 2 2.32 min 487 MH$^+$ | 37 | 2$^{nd}$/pos |
| 37 | 11 ($R^1$ = 4-Fluorophenyl, $R^2$ = Ethyl) | Sodium methoxide | 11 (3R,4aR,12bR)-($R^1$ = 4-Fluorophenyl, $R^2$ = Ethyl, $R^3$ = Methoxymethyl) | 2 2.79 min 423 MH$^+$ | 38 | 1$^{st}$/nd |
| 38 | 11 ($R^1$ = 4-Fluorophenyl, $R^2$ = Ethyl) | Sodium methoxide | 11 (3S,4aS,12bS)-($R^1$ = 4-Fluorophenyl, $R^2$ = Ethyl, $R^3$ = Methoxymethyl) | 2 2.79 min 423 MH$^+$ | 38 | 2$^{nd}$/nd |
| 39 | 12 ($R^1$ = 4-Fluorophenyl, $R^2$ = Cyclopropyl-methyl) | Sodium methoxide | 13 (3S,4aR,12bR)-($R^1$ = 4-Fluorophenyl, $R^2$ = Cyclopropylmethyl, $R^3$ = Methoxymethyl) | 2 3.08 min 449 MH$^+$ | 40 | 1$^{st}$/neg |
| 40 | 12 ($R^1$ = 4-Fluorophenyl, $R^2$ = Cyclopropyl-methyl) | Sodium methoxide | 13 (3R,4aS,12bS)-($R^1$ = 4-Fluorophenyl, $R^2$ = Cyclopropylmethyl, $R^3$ = Methoxymethyl) | 2 3.08 min 449 MH$^+$ | 40 | 2$^{nd}$/pos |
| 41 | 12 ($R^1$ = 4-Fluorophenyl, $R^2$ = Pyrimidin-2-ylmethyl) | Sodium methoxide | 13 (3R,4aS,12bS)-($R^1$ = 4-Fluorophenyl, $R^2$ = Pyrimidin-2-ylmethyl, $R^3$ = Methoxymethyl) | 2 2.32 min 487 MH$^+$ | 37 | 1$^{st}$/neg |
| 42 | 12 ($R^1$ = 4-Pyridyl, $R^2$ = Ethyl) | Sodium methoxide | 13 (3R,4aS,12bR) with (3S,4aR,12bS) ($R^1$ = 4-Pyridyl, $R^2$ = Ethyl, $R^3$ = Methoxymethyl) | 2 2.37 min 406 MH$^+$ | NA | NA |
| 43 | 12 ($R^1$ = 3-Pyridyl, $R^2$ = Ethyl) | Sodium methoxide | 13 (3S,4aR,12bS) ($R^1$ = 3-Pyridyl, $R^2$ = Ethyl, $R^3$ = Methoxymethyl) | 2 2.42 min 406 MH$^+$ | 25 | 1$^{st}$/NA |

TABLE 3-continued

| Ex. # | Reactant | Reagent | Product structure | LC/MS method/ $R_t$, M/Z | Chiral method | Order of elution/ sign of rotation |
|---|---|---|---|---|---|---|
| 44 | 12 ($R^1$ = 3-Pyridyl, $R^2$ = Ethyl) | Sodium methoxide | 13 (3R,4aS,12bR) ($R^1$ = 3-Pyridyl, $R^2$ = Ethyl, $R^3$ = Methoxymethyl) | 2<br>2.42 min<br>406 MH$^+$ | 25 | $2^{nd}$/NA |
| 45 | 12 ($R^1$ = 2-Methylpyridin-4-yl, $R^2$ = Ethyl) | Sodium methoxide | 13 (3R,4aS,12bR) with (3S,4aR,12bS) ($R^1$ = 2-Methylpyridin-4-yl, $R^2$ = Ethyl, $R^3$ = Methoxymethyl) | 2<br>2.52 min<br>420 MH$^+$ | NA | NA |
| 46 | 12 ($R^1$ = 2-Pyridyl, $R^2$ = Ethyl) | Sodium methoxide | 13 (3S,4aR,12bS) ($R^1$ = 2-Pyridyl, $R^2$ = Ethyl, $R^3$ = Methoxymethyl) | 3<br>2.80 min<br>406 MH$^+$ | 26 | $1^{st}$/NA |
| 47 | 12 ($R^1$ = 2-Pyridyl, $R^2$ = Ethyl) | Sodium methoxide | 13 (3S,4aR,12bS) ($R^1$ = 2-Pyridyl, $R^2$ = Ethyl, $R^3$ = Methoxymethyl) | 2<br>3.03 min<br>406 MH$^+$ | 26 | $2^{nd}$/NA |
| 48 | 12 ($R^1$ = 4-Pyridyl, $R^2$ = Pyridin-2-ylmethyl) | Sodium methoxide | 13 (3S,4aR,12bR) ($R^1$ = 4-Pyridyl, $R^2$ = Pyridin-2-ylmethyl, $R^3$ = Methoxymethyl) | 2<br>1.95 min<br>469 MH$^+$ | 27 | $2^{nd}$/NA |
| 49 | 12 ($R^1$ = 4-Pyridyl, $R^2$ = Pyridin-2-ylmethyl) | Sodium methoxide | 13 (3S,4aR,12bS) ($R^1$ = 4-Pyridyl, $R^2$ = Pyridin-2-ylmethyl, $R^3$ = Methoxymethyl) | 2<br>1.95 min<br>469 MH$^+$ | 27 | $1^{st}$/NA |
| 50 | 12 ($R^1$ = 4-Pyridyl, $R^2$ = Ethyl) | Sodium methoxide | 13 (3S,4aR,12bS) ($R^1$ = 4-Pyridyl, $R^2$ = Ethyl, $R^3$ = Methoxymethyl) | 2<br>2.48 min<br>406 MH$^+$ | 24 | $2^{nd}$/neg |
| 51 | 12 ($R^1$ = 2-Methyl-pyridin-4-yl, $R^2$ = Pyridin-2-ylmethyl) | Sodium methoxide | 13 (3S,4aR,12bS) ($R^1$ = 2-methylpyridin-4-yl, $R^2$ = Pyridin-2-ylmethyl, $R^3$ = methoxymethyl) | 2<br>1.83 min<br>483 MH$^+$ | 52 | $1^{st}$/nd |
| 52 | 12 ($R^1$ = 2-Methyl-pyridin-4-yl, $R^2$ = Pyridin-2-ylmethyl) | Sodium methoxide | 13 (3S,4aR,12bR) ($R^1$ = 2-methylpyridin-4-yl, $R^2$ = Pyridin-2-ylmethyl, $R^3$ = methoxymethyl) | 2<br>1.83 min<br>483 MH$^+$ | 52 | $2^{nd}$/pos |

Additional examples, prepared in a manner similar to the preparation of Example #15 are listed in Table 4.

TABLE 4

| Ex. # | Epoxide | Reagent | Product structure | LC/MS method/ $R_t$, MH$^+$ | Chiral method | Order of elution/ sign of rotation |
|---|---|---|---|---|---|---|
| 53 | 12 ($R^1$ = 4-Fluorophenyl, $R^2$ = Ethyl) | NaBH$_4$ | 13 (3S,4aR,12bS) (4-Fluorophenyl, $R^2$ = Ethyl, $R^3$ = Methyl) | 2<br>2.96 min<br>393 MH$^+$ | 35 | $1^{st}$/neg |
| 54 | 12 ($R^1$ = 4-Fluorophenyl, $R^2$ = Ethyl) | NaBH$_4$ | 13 (3R,4aS,12bR) (4-Fluorophenyl, $R^2$ = Ethyl, $R^3$ = Methyl) | 2<br>2.96 min<br>393 MH$^+$ | 35 | $2^{nd}$/pos |
| 55 | 12 ($R^1$ = 4-Fluorophenyl, $R^2$ = Pyrimidin-2-ylmethyl) | NaBH$_4$ | 13 (3S,4aR,12bS) ($R^1$ = 4-Fluorophenyl, $R^2$ = Pyrimidin-2-ylmethyl, $R^3$ = Methyl) | 2<br>2.36 min<br>457 MH$^+$ | 36 | $1^{st}$/neg |
| 56 | 12 ($R^1$ = 4-Fluorophenyl, $R^2$ = Pyrimidin-2-ylmethyl) | NaBH$_4$ | 13 (3S,4aR,12bR) ($R^1$ = 4-Fluorophenyl, $R^2$ = Pyrimidin-2-ylmethyl, $R^3$ = Methyl) | 2<br>2.36 min<br>457 MH$^+$ | 36 | $2^{nd}$/pos |
| 57 | 12 ($R^1$ = 4-Fluorophenyl, $R^2$ = Cyclopropyl-methyl) | NaBH$_4$ | 13 (3R,4aS,12bS) ($R^1$ = 4-Fluorophenyl, $R^2$ = Cyclopropylmethyl, $R^3$ = Methyl) | 2<br>3.08 min<br>419 MH$^+$ | 39 | $1^{st}$/pos |

TABLE 4-continued

| Ex. # | Epoxide | Reagent | Product structure | LC/MS method/ $R_t$, MH$^+$ | Chiral method | Order of elution/ sign of rotation |
|---|---|---|---|---|---|---|
| 58 | 12 (R$^1$ = 4-Fluorophenyl, R$^2$ = Cyclopropyl-methyl) | NaBH$_4$ | 13 (3S,4aR,12bR) (R$^1$ = 4-Fluorophenyl, R$^2$ = Cyclopropylmethyl, R$^3$ = Methyl) | 2 3.08 min 419 MH$^+$ | 39 | 2$^{nd}$/neg |
| 59 | 12 (R$^1$ = 4-Fluorophenyl, R$^2$ = Pyridin-2-ylmethyl) | NaBH$_4$ | 13 (3R,4aS,12bS) with (3S,4aR,12bR) (R$^1$ = 4-Fluorophenyl, R$^2$ = Pyridin-2-ylmethyl, R$^3$ = Methyl) | 2, 2.51 min 456 MH$^+$ | NA | NA |
| 60 | 12 (R$^1$ = 2-Methyl-pyridin-4-yl, R$^2$ = Pyridin-2-ylmethyl) | NaBH$_4$ | 13 (3R,4aS,12bS)-(R$^1$ = 2-methylpyridin-4-yl, R$^2$ = Pyridin-2-ylmethyl, R$^3$ = Methyl) | 2 1.86 min 453 MH$^+$ | 51 | 1$^{st}$/neg |
| 61 | 12 (R$^1$ = 2-Methyl-pyridin-4-yl, R$^2$ = Pyridin-2-ylmethyl) | NaBH$_4$ | 13 (3S,4aR,12bR)- (R$^1$ = 2-methylpyridin-4-yl, R$^2$ = Pyridin-2-ylmethyl, R$^3$ = Methyl) | 2 1.86 min 453 MH$^+$ | 51 | 2$^{nd}$/pos |

Additional examples, prepared in a manner similar to the preparation of Example #17 are listed in Table 5.

TABLE 5

| Ex. # | Epoxide | Reagent | Product structure | LC/MS method/ $R_t$, MH$^+$ | Chiral method | Order of elution/ sign of rotation |
|---|---|---|---|---|---|---|
| 62 | 12 (R$^1$ = 4-Fluorophenyl, R$^2$ = Pyrimidin-2-ylmethyl) | cyanodiethyl aluminum | 13 (3R,4aS,12bS) (R$^1$ = 4-Fluorophenyl, R$^2$ = Pyrimidin-2-ylmethyl, R$^3$ = Cyanomethyl) | 2 2.19 min 482 MH$^+$ | 8 | 1$^{st}$/nd |
| 63 | 12 (R$^1$ = 4-Fluorophenyl, R$^2$ = Pyrimidin-2-ylmethyl) | cyanodiethyl aluminum | 13 (3S,4aR,12bR) (R$^1$ = 4-Fluorophenyl, R$^2$ = Pyrimidin-2-ylmethyl, R$^3$ = Cyanomethyl) | 2 2.19 min 482 MH$^+$ | 8 | 2$^{nd}$/nd |
| 64 | 12 (R$^1$ = 4-Fluorophenyl, R$^2$ = Ethyl) | Cyanodiethyl aluminum | 13 (3S,4aR,12bS) (4-Fluorophenyl, R$^2$ = Ethyl, R$^3$ = Cyanomethyl) | 2 2.75 min 418 MH$^+$ | 36 | 1$^{st}$/neg |
| 65 | 12 (R$^1$ = 4-Fluorophenyl, R$^2$ = Ethyl) | Cyanodiethyl aluminum | 13 (3R,4aS,12bR) (4-Fluorophenyl, R$^2$ = Ethyl, R$^3$ = Cyanomethyl) | 2 2.75 min 418 MH$^+$ | 36 | 2$^{nd}$/pos |
| 66 | 12 (R$^1$ = 4-Fluorophenyl, R$^2$ = Cyclopropyl-methyl) | Cyanodiethyl aluminum | 13 (3S,4aR,12bR) (R$^1$ = 4-Fluorophenyl, R$^2$ = Cyclopropylmethyl), R$^3$ = Cyanomethyl | 2 2.87 min 444 MH$^+$ | 41 | 1$^{st}$/neg |
| 67 | 12 (R$^1$ = 4-Fluorophenyl, R$^2$ = Cyclopropyl-methyl) | Cyanodiethyl aluminum | 13 (3R,4aS,12bS) (R$^1$ = 4-Fluorophenyl, R$^2$ = Cyclopropylmethyl, R$^3$ = Cyanomethyl) | 2 2.87 min 444 MH$^+$ | 41 | 2$^{nd}$/pos |
| 68 | 13 (R$^1$ = 4-Pyridyl, R$^2$ = Pyridin-2-ylmethyl) | KCN | 13 (3R,4aS,12bS) (R$^1$ = 4-Pyridyl, R$^2$ = Pyridin-2-ylmethyl, R$^3$ = Cyanomethyl) | 2 1.71 min 464 MH$^+$ | 29 | 1$^{st}$/NA |

TABLE 5-continued

| Ex. # | Epoxide | Reagent | Product structure | LC/MS method/ $R_t$ MH⁺ | Chiral method | Order of elution/ sign of rotation |
|---|---|---|---|---|---|---|
| 69 | 13 (R¹ = 4-Pyridyl, R² = Pyridin-2-ylmethyl) | KCN | 13 (3S,4aR,12bR) (R¹ = 4-Pyridyl, R² = Pyridin-2-ylmethyl, R³ = Cyanomethyl) | 2 1.71 min 464 MH⁺ | 29 | 2$^{nd}$/NA |
| 70 | 6 (R¹ = 2-Methyl-pyridin-4-yl, R² = Pyridin-2-ylmethyl) | KCN | (3R,4aS,12bS)-(R¹ = 2-methylpyridin-4-yl, R² = pyridin-2-yl-methyl, R³ = cyanomethyl) | 2 1.74 min 478 MH⁺ | 53 | 1$^{st}$/neg |
| 71 | 12 (R¹ = 2-Methyl-pyridin-4-yl, R² = Pyridin-2-ylmethyl) | KCN | (3S,4aR,12bR)-(R¹ = 2-methylpyridin-4-yl, R² = pyridin-2-yl-methyl, R³ = cyanomethyl) | 2 1.74 min 478 MH⁺ | 53 | 2$^{nd}$/pos |

Scheme 3:

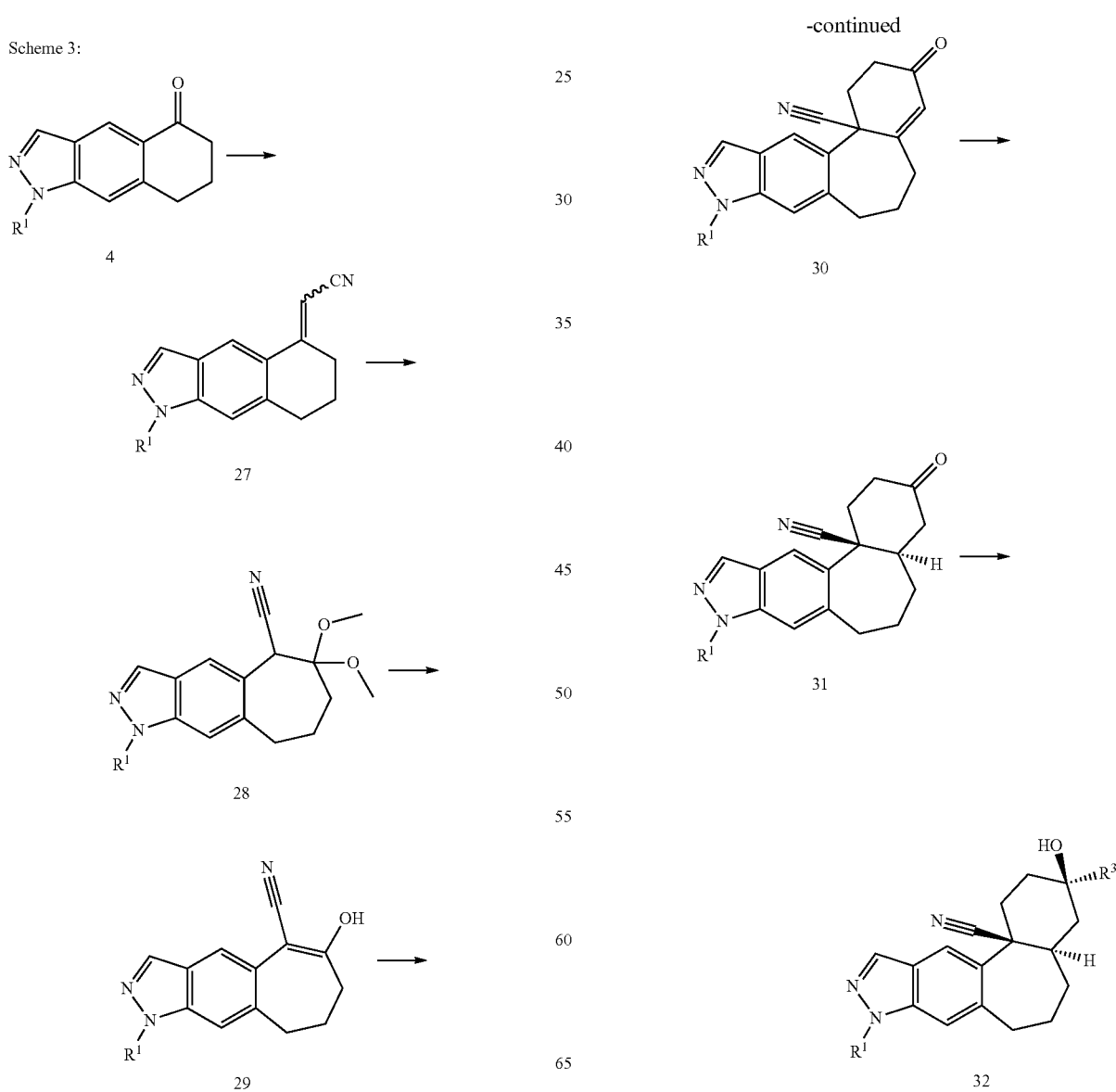

Example #72 and #73

(3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carbonitrile (32, R$^1$=4-Fluorophenyl, R$^3$=Trifluoromethyl) and (3S,4aS,12bR)-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carbonitrile (32, R$^1$=4-Fluorophenyl, R$^3$=Trifluoromethyl)

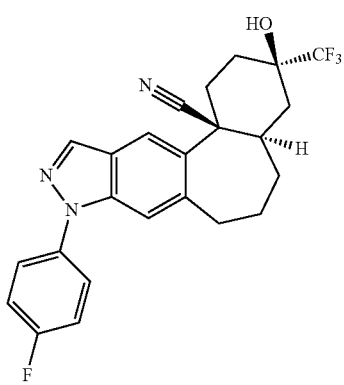

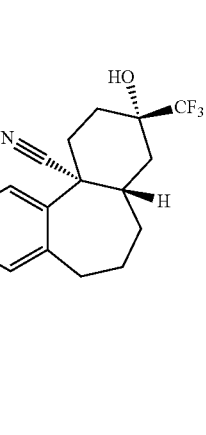

Step 1: 2-(1-(4-Fluorophenyl)-7,8-dihydro-1H-benzo[f]indazol-5(6H)-ylidene)acetonitrile (27, R$^1$=4-Fluorophenyl)

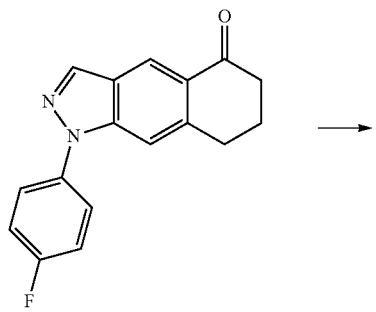

-continued

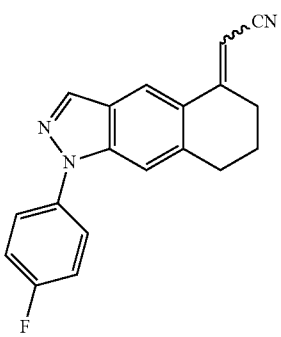

To a stirred suspension of sodium hydride (60% in oil, 12.0 g, 300 mmol) in DME (600 mL) was added diethyl (cyanomethyl)phosphonate (53.1 g, 300 mmol) at a dropwise rate under nitrogen. After gas evolution ceases (about 30 min), 1-(4-fluorophenyl)-7,8-dihydro-1H-benzo[f]indazol-5(6H)-one (4, R$^1$=4-Fluorophenyl) (42.0 g, 150 mmol) was added in portions. The reaction was stirred at rt for about 3 h, then the reaction was concentrated under reduced pressure and the residue was dissolved with EtOAc (1000 mL) and sat. aq. NH$_4$Cl (500 mL). The organic layer was dried over Na$_2$SO$_4$, filtered and concentrated under reduced pressure. The residue was purified on silica gel (330 g) using a gradient of 70-100% DCM in heptane. Product fractions were combined and concentrated under reduced pressure to yield 2-(1-(4-fluorophenyl)-7,8-dihydro-1H-benzo[f]indazol-5(6H)-ylidene)acetonitrile (27, R$^1$=4-Fluorophenyl) as a 2:1 mixture of isomers (42.9 g, 94%); LC/MS, method 3, R$_t$=2.57 min, MS m/z 304 (M+H)$^+$. $^1$H NMR (400 MHz, DMSO) δ 8.60 (bs, 0.33H), 8.50 (d, J=0.9 Hz, 0.33H), 8.42 (bs, 0.67H), 8.40 (d, J=0.9 Hz, 0.67H), 7.88-7.76 (m, 2H), 7.67 (bs, 0.33H), 7.64 (bs, 0.67H), 7.52-7.36 (m, 2H), 6.32 (t, J=1.6 Hz, 0.67H), 5.73 (t, J=1.5 Hz, 0.33H), 3.03-2.95 (m, 2H), 2.90-2.83 (m, 1H), 2.71-2.64 (m, 1H), 1.93-1.81 (m, 2H).

Step 2: 1-(4-Fluorophenyl)-6,6-dimethoxy-1,5,6,7,8,9-hexahydrocyclohepta[f]indazole-5-carbonitrile (28, R$^1$=4-Fluorophenyl)

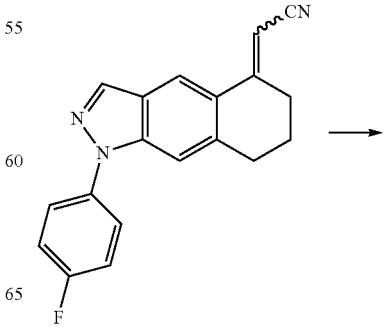

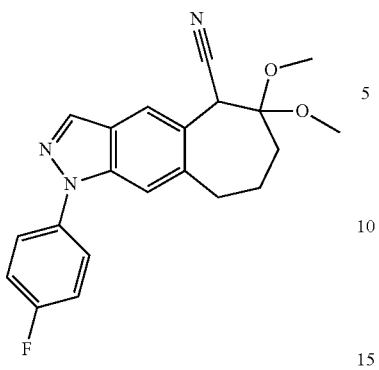

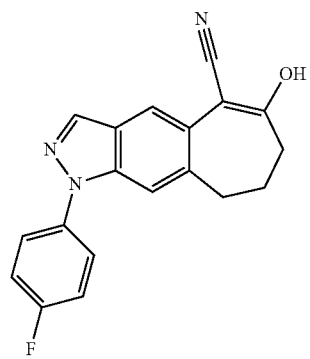

A suspension of silver(I) nitrate (55.3 g, 325 mmol) and 2-(1-(4-fluorophenyl)-7,8-dihydro-1H-benzo[f]indazol-5(6H)-ylidene)acetonitrile (27, R¹=4-Fluorophenyl) (42.9 g, 141 mmol) in MeOH (1350 mL) was heated to about 65° C. and a solution of iodine (39.5 g, 156 mmol) in MeOH (500 mL) was added dropwise over about 60 min. The reaction was cooled to rt and filtered to remove solids, rinsing with MeOH (2×100 mL). The filtrate was concentrated under reduced pressure, then redissolved with EtOAc (700 mL), sat. aq. NaCl (250 mL), and water (100 mL). The organic layer was washed again with water (500 mL), dried over $Na_2SO_4$, filtered and concentrated to a foam then further dried under vacuum to yield 1-(4-fluorophenyl)-6,6-dimethoxy-1,5,6,7,8,9-hexahydrocyclohepta[f]indazole-5-carbonitrile (28, R¹=4-Fluorophenyl) (54.9 g, 100%); LC/MS, method 3, $R_t$=2.51 min, MS m/z 366 (M+H)⁺. ¹H NMR (400 MHz, DMSO) δ 8.34 (d, J=0.9 Hz, 1H), 8.00 (s, 1H), 7.97-7.72 (m, 2H), 7.62 (s, 1H), 7.47-7.36 (m, 2H), 4.99 (d, J=1.6 Hz, 1H), 3.26 (s, 3H), 3.16-2.99 (m, 5H), 2.30-2.20 (m, 1H), 2.10-1.99 (m, 1H), 1.85-1.97 (m, 1H), 1.53-1.38 (m, 1H).

A solution of 1-(4-fluorophenyl)-6,6-dimethoxy-1,5,6,7,8,9-hexahydrocyclohepta[f]indazole-5-carbonitrile (28, R¹=4-Fluorophenyl) (54.8 g, 141 mmol) in THF (1000 mL) and 3N aq. HCl (170 mL) was heated at reflux for about 5 h. The reaction was cooled to rt and concentrated to about 200 mL volume. The product was extracted with ether (500 mL) and EtOAc (100 mL). The organic layer was washed with water (150 mL) and sat. aq. NaCl (150 mL). The organic layer was dried over $Na_2SO_4$, filtered and concentrated to about 100 mL volume and diluted with heptane (about 100 mL). The product was filtered off and rinsed with 1:1/EtOAc:heptane (2×100 mL) and dried under vacuum at about 50° C. for about 18 h to yield 1-(4-fluorophenyl)-6-hydroxy-1,7,8,9-tetrahydrocyclohepta[f]indazole-5-carbonitrile (29, R¹=4-Fluorophenyl) (23.1 g, 51%) as a solid: LC/MS, method 3, $R_t$=2.19 min, MS m/z 318 (M–H)—. ¹H NMR (400 MHz, DMSO) δ 11.35 (s, 1H), 8.34 (s, 1H), 7.85-7.77 (m, 2H), 7.76 (s, 1H), 7.71 (s, 1H), 7.47-7.38 (m, 2H), 2.82-2.74 (m, 2H), 2.31-2.22 (m, 2H), 2.19-2.07 (m, 2H).

Step 3: 1-(4-Fluorophenyl)-6-hydroxy-1,7,8,9-tetrahydrocyclohepta[f]indazole-5-carbonitrile (29, R¹=4-Fluorophenyl)

Step 4: 9-(4-Fluorophenyl)-3-oxo-1,2,3,5,6,7,9,12b-octahydrobenzo[6,7]cyclohepta[1,2-f]indazole-12b-carbonitrile (30, R¹=4-Fluorophenyl)

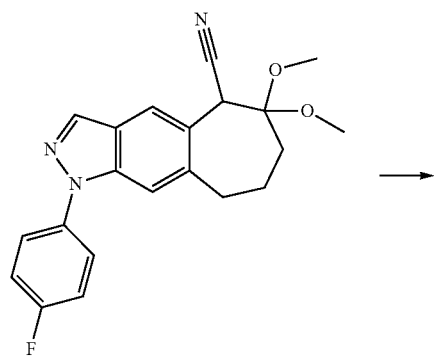

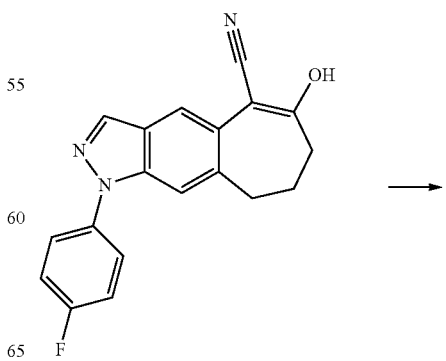

111

-continued

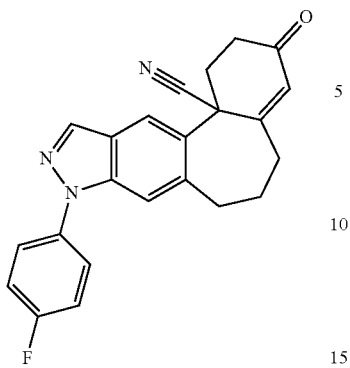

A solution of 1-(4-fluorophenyl)-6-hydroxy-1,7,8,9-tetrahydrocyclohepta[f]indazole-5-carbonitrile (29, $R^1$=4-Fluorophenyl) (30.0 g, 94 mmol) in EtOH (640 mL) was treated with TEA (3.93 mL, 28.2 mmol) and but-3-en-2-one (15.5 mL, 188 mmol) and the mixture was stirred mechanically at rt for about 18 h. The volume of the reaction was reduced to about 300 mL under reduced pressure and the intermediate was filtered off and washed with heptane (50 mL). The solid intermediate is taken up in toluene (1500 mL), treated with pTSA (0.894 g, 4.70 mmol) and heated at reflux with a Dean-Stark trap for about 5 h, then stirred at about 90° C. for about 16 h. The reaction was cooled to rt, washed with sat. aq. NaHCO$_3$ (300 mL), dried over Na$_2$SO$_4$, filtered and concentrated under reduced pressure to yield rac-9-(4-fluorophenyl)-3-oxo-1,2,3,5,6,7,9,12b-octahydrobenzo[6,7]cyclohepta[1,2-f]indazole-12b-carbonitrile (30, $R^1$=4-Fluorophenyl) (28.0 g, 72%) as a tan foam. LC/MS, method 3, $R_t$=2.42 min, $^1$H NMR (400 MHz, DMSO) δ 8.45 (d, J=0.9 Hz, 1H), 8.20 (s, 1H), 7.84-7.78 (m, 2H), 7.69 (s, 1H), 7.48-7.39 (m, 2H), 6.18 (s, 1H), 3.01-2.59 (m, 6H), 2.46-2.37 (m, 1H), 2.24-2.12 (m, 1H), 2.02-1.87 (m, 2H).

Step 5: (4aR,12bS)-9-(4-Fluorophenyl)-3-oxo-1,2,3,4,4a,5,6,7,9,12b-decahydrobenzo[6,7]cyclohepta[1,2-f]indazole-12b-carbonitrile; compound with (4aS,12bR)-9-(4-fluorophenyl)-3-oxo-1,2,3,4,4a,5,6,7,9,12b-decahydrobenzo[6,7]cyclohepta[1,2-f]indazole-12b-carbonitrile (31, $R^1$=4-Fluorophenyl)

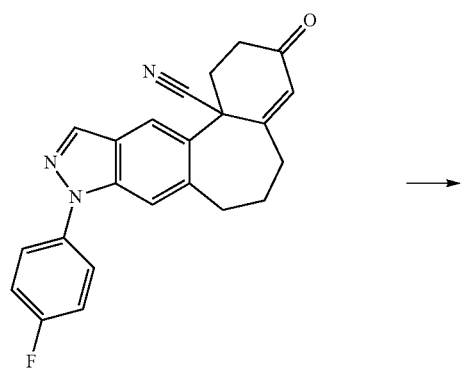

112

-continued

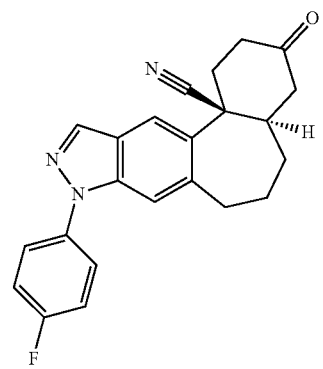

A solution of 9-(4-fluorophenyl)-3-oxo-1,2,3,5,6,7,9,12b-octahydrobenzo[6,7]cyclohepta[1,2-f]indazole-12b-carbonitrile (30, $R^1$=4-Fluorophenyl) (28.0 g, 67.9 mmol) in toluene (600 mL) containing dihydroxypalladium (4.29 g, 3.05 mmol) was hydrogenated on a Parr shaker at about 55° C. and about 50 psi of hydrogen for about 10 h. The reaction was cooled to rt and filtered (Celite®), rinsing with DCM (3×200 mL). The combined organics were concentrated to about 100 mL, the product was filtered off and dried under reduced pressure to yield (4aR,12bS)-9-(4-fluorophenyl)-3-oxo-1,2,3,4,4a,5,6,7,9,12b-decahydrobenzo[6,7]cyclohepta[1,2-f]indazole-12b-carbonitrile; compound with (4aS,12bR)-9-(4-fluorophenyl)-3-oxo-1,2,3,4,4a,5,6,7,9,12b-decahydrobenzo[6,7]cyclohepta[1,2-f]indazole-12b-carbonitrile (31, $R^1$=4-Fluorophenyl) (18.2 g, 72%) as an off-white solid. LC/MS, method 3, $R_t$=2.41 min, MS m/z 374 (M+H)$^+$, $^1$H NMR (400 MHz, DMSO) δ 8.36 (s, 1H), 8.06 (s, 1H), 7.85-7.79 (m, 2H), 7.71 (s, 1H), 7.47-7.40 (m, 2H), 3.47-3.36 (m, 1H), 3.15-3.04 (m, 1H), 2.93-2.63 (m, 4H), 2.44-2.30 (m, 2H), 2.26-2.14 (m, 1H), 2.10-1.99 (m, 1H), 1.95-1.84 (m, 2H), 1.40-1.27 (m, 1H).

Step 6: (3R,4aR,12bS)-9-(4-Fluorophenyl)-3-hydroxy-3-(trifluoromethyl)-1,2,3,4,4a,5,6,7,9,12b-decahydrobenzo[6,7]cyclohepta[1,2-f]indazole-12b-carbonitrile; compound with (3S,4aS,12bR)-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carbonitrile (32, $R^1$=4-Fluorophenyl, $R^3$=Trifluoromethyl)

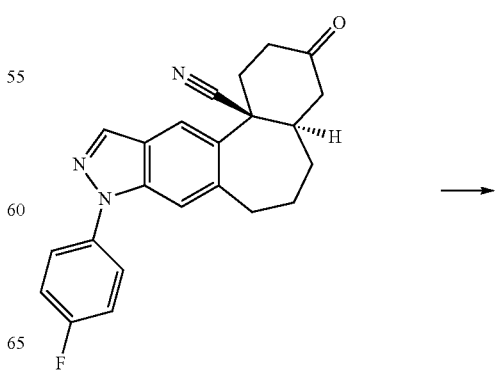

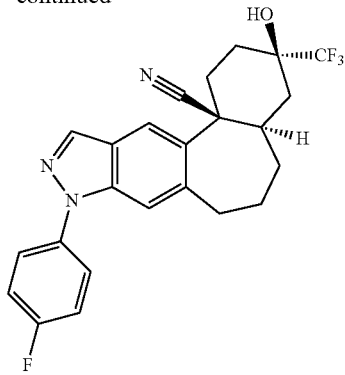

A suspension of (4aR,12bS)-9-(4-fluorophenyl)-3-oxo-1,2,3,4,4a,5,6,7,9,12b-decahydrobenzo[6,7]cyclohepta[1,2-f]indazole-12b-carbonitrile; compound with (4aS,12bR)-9-(4-fluorophenyl)-3-oxo-1,2,3,4,4a,5,6,7,9,12b-decahydrobenzo[6,7]cyclohepta[1,2-f]indazole-12b-carbonitrile (31, $R^1$=4-Fluorophenyl) (19.7 g, 52.8 mmol) in DME (1000 mL) was treated with CsF (1.20 g, 7.91 mmol) and the mixture was stirred at rt for about 10 min. The mixture was cooled to about 0° C. and treated dropwise with trimethyl (trifluoromethyl)silane (11.7 mL, 79 mmol), maintaining the reaction temperature below 1° C. The mixture was stirred for about 30 min at about 0° C., then TBAF (79 mL, 79 mmol) was added over about 5 min. The reaction was allowed to warm to rt, then solvents were removed under reduced pressure. The residue was taken up in EtOAc (400 mL) and washed with water (2×400 mL) and brine (200 mL). The organic layer was dried over $Na_2SO_4$, filtered and concentrated under vacuum to yellow foam. The crude was divided into 4 portions and each portion was dissolved in a minimum amount of DCM for injection and purified on silica gel (220 g) using a gradient of 25-50% EtOAc in heptane. The product peaks from each run were combined and concentrated to a white solid. The solid was further dried under reduced pressure to yield: (3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carbonitrile; compound with (3S,4aS,12bR)-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carbonitrile (32, $R^1$=4-Fluorophenyl, $R^3$=Trifluoromethyl) (13.5 g, 58%) as a white solid. LC/MS, method 3, $R_t$=2.60 min, MS m/z 502 (M+OAc$^-$)$^-$, $^1$H NMR (400 MHz, DMSO) δ 8.33 (s, 1H), 8.09 (s, 1H), 7.84-7.77 (m, 2H), 7.69 (s, 1H), 7.47-7.38 (m, 2H), 6.25 (s, 1H), 3.41-3.28 (m, 1H), 3.11-3.01 (m, 1H), 2.69-2.56 (m, 1H), 2.33-2.22 (m, 1H), 2.13-1.67 (m, 7H), 1.62-1.52 (m, 1H), 1.40-1.25 (m, 1H).

The enantiomers were separated using Preparative Chiral Purification Method 11. Fractions from the first peak eluted were combined and concentrated under reduced pressure. The residue was dissolved in MeOH (5 mL), treated with water (25 mL) and concentrated under reduced pressure to remove MeOH. Solids were collected by filtration, washed with water (2 mL) and dried under vacuum at about 50° C. to yield (3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carbonitrile (32, $R^1$=4-Fluorophenyl, $R^3$=Trifluoromethyl) (Example 72) LC/MS, method 3, $R_t$=2.60 min, MS m/z 502 (M+OAC$^-$)$^-$, $^1$H NMR (400 MHz, DMSO) δ 8.33 (s, 1H), 8.09 (s, 1H), 7.84-7.77 (m, 2H), 7.69 (s, 1H), 7.47-7.38 (m, 2H), 6.25 (s, 1H), 3.41-3.28 (m, 1H), 3.11-3.01 (m, 1H), 2.69-2.56 (m, 1H), 2.33-2.22 (m, 1H), 2.13-1.67 (m, 7H), 1.62-1.52 (m, 1H), 1.40-1.25 (m, 1H).

Fractions from the second peak eluted were combined and concentrated under reduced pressure. The residue was dissolved in MeOH (5 mL), treated with water (25 mL) and concentrated under reduced pressure to remove MeOH. Solids were collected by filtration, washed with water (2 mL) and dried under vacuum at about 50° C. to yield (3S,4aS,12bR)-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carbonitrile (32, $R^1$=4-Fluorophenyl, $R^3$=Trifluoromethyl) (Example 73) LC/MS, method 3, $R_t$=2.60 min, MS m/z 502 (M+OAc$^-$)$^-$, $^1$H NMR (400 MHz, DMSO) δ 8.33 (s, 1H), 8.09 (s, 1H), 7.84-7.77 (m, 2H), 7.69 (s, 1H), 7.47-7.38 (m, 2H), 6.25 (s, 1H), 3.41-3.28 (m, 1H), 3.11-3.01 (m, 1H), 2.69-2.56 (m, 1H), 2.33-2.22 (m, 1H), 2.13-1.67 (m, 7H), 1.62-1.52 (m, 1H), 1.40-1.25 (m, 1H).

Scheme 4:

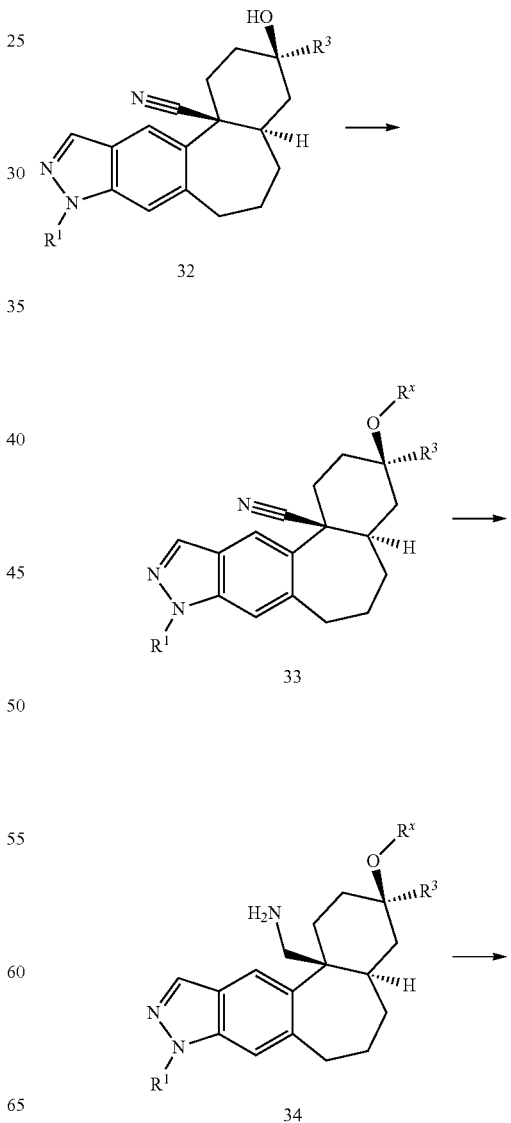

-continued

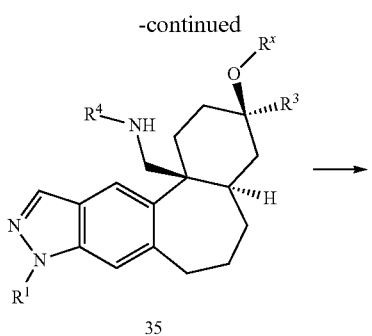

35

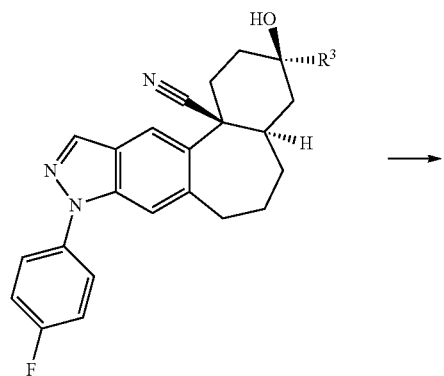

36 wherein R$^x$ is a protecting group.

Example 74

N-(((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)methanesulfonamide (36, R$^1$=4-Fluorophenyl, R$^3$=Trifluoromethyl, R$^4$=Methanesulfonyl)

Step 1: (3R,4aR,12bS)-3-(Benzyloxy)-9-(4-fluorophenyl)-3-(trifluoromethyl)-1,2,3,4,4a,5,6,7,9,12b-decahydrobenzo[6,7]cyclohepta[1,2-f]indazole-12b-carbonitrile (33, R$^1$=4-Fluorophenyl, R$^3$=Trifluoromethyl)

-continued

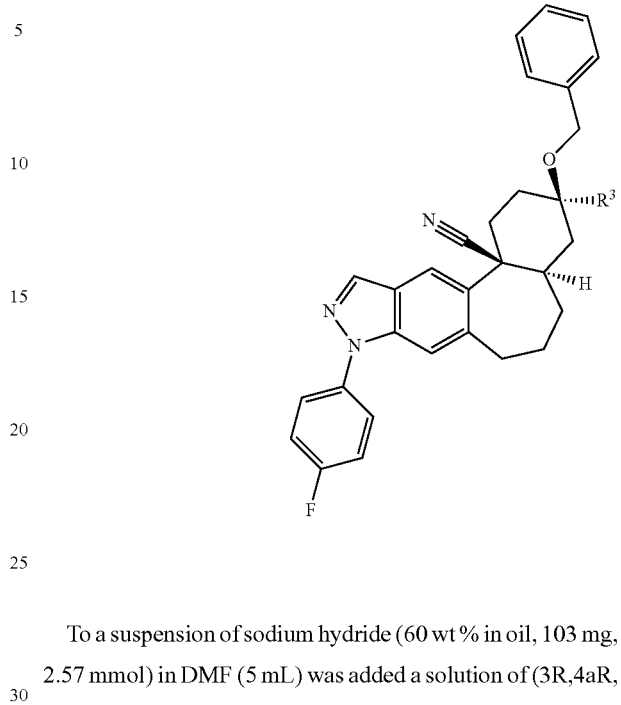

To a suspension of sodium hydride (60 wt % in oil, 103 mg, 2.57 mmol) in DMF (5 mL) was added a solution of (3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carbonitrile (32, R$^1$=4-Fluorophenyl, R$^3$=Trifluoromethyl) (760 mg, 1.71 mmol) in DMF (15 mL) at a dropwise rate. The reaction was stirred for about 10 min at rt, then (bromomethyl)benzene (0.26 mL, 2.14 mmol) was added. The mixture was stirred for about 1 h. Solvents were removed under reduced pressure. The residue was dissolved in DCM (50 mL) and washed with water (25 mL). The organic layer was dried over Na$_2$SO$_4$, filtered and concentrated onto silica gel (10 g). The crude product was purified on silica gel (40 g) using a gradient of 20-40% EtOAc in heptane. Product fractions were combined and concentrated under reduced pressure to yield (3R,4aR,12bS)-3-(benzyloxy)-9-(4-fluorophenyl)-3-(trifluoromethyl)-1,2,3,4,4a,5,6,7,9,12b-decahydrobenzo[6,7]cyclohepta[1,2-f]indazole-12b-carbonitrile (33, R$^1$=4-Fluorophenyl, R$^3$=Trifluoromethyl, R$_x$=Benzyl) (890 mg, 97%) as a white solid; LC/MS, method 3, R$_t$=3.08 min, MS m/z 534 (M+H)$^+$, $^1$H NMR (400 MHz, DMSO) δ 8.35 (d, J=0.8 Hz, 1H), 8.12 (s, 1H), 7.86-7.78 (m, 2H), 7.71 (s, 1H), 7.48-7.29 (m, 7H), 4.80-4.66 (m, 2H), 3.41-3.31 (m, 1H), 3.13-3.01 (m, 1H), 2.74-2.62 (m, 1H), 2.61-2.51 (m, 1H), 2.29-2.22 (m, 1H), 2.18-1.93 (m, 4H), 1.89-1.70 (m, 3H), 1.42-1.27 (m, 1H).

117

Step #2: ((3R,4aR,12bS)-3-(benzyloxy)-9-(4-fluorophenyl)-3-(trifluoromethyl)-1,2,3,4,4a,5,6,7,9,12b-decahydrobenzo[6,7]cyclohepta[1,2-f]indazol-12b-yl)methanamine (34, R¹=4-Fluorophenyl, R³=Trifluoromethyl, Rᵍ=Benzyl)

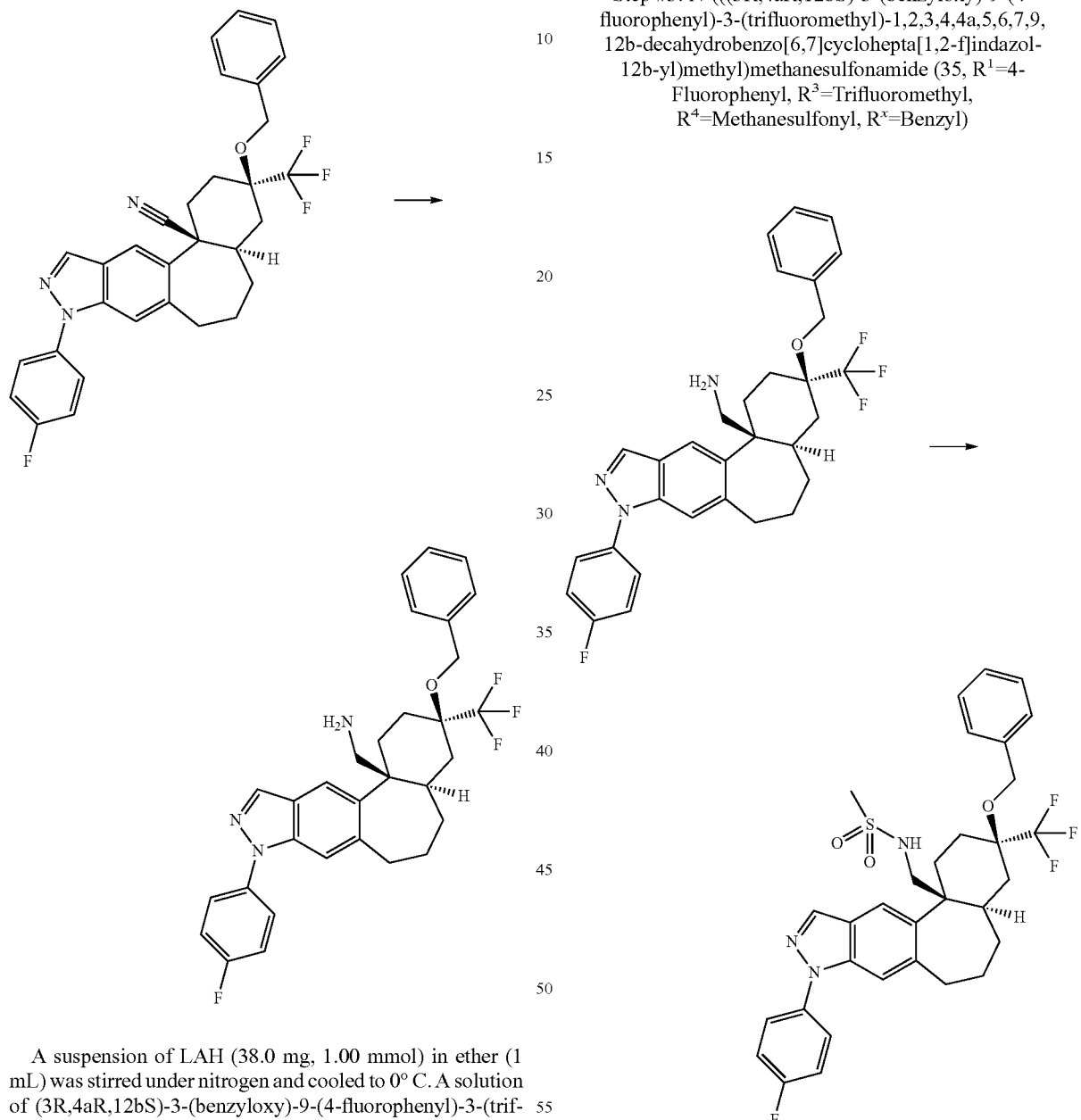

A suspension of LAH (38.0 mg, 1.00 mmol) in ether (1 mL) was stirred under nitrogen and cooled to 0° C. A solution of (3R,4aR,12bS)-3-(benzyloxy)-9-(4-fluorophenyl)-3-(trifluoromethyl)-1,2,3,4,4a,5,6,7,9,12b-decahydrobenzo[6,7]cyclohepta[1,2-f]indazole-12b-carbonitrile (33, R¹=4-Fluorophenyl, R³=Trifluoromethyl, Rˣ=Benzyl) (89 mg, 0.167 mmol) in THF (3 mL) was added maintaining reaction temperature under 5° C. and the mixture was allowed to stir at rt for about 54 h. The reaction was diluted with THF (2 mL) and quenched by addition of water (40 μL), then 2N NaOH (40 μL) and then water (80 μL). The reaction was stirred overnight at rt. The mixture was dried with Na₂SO₄ and filtered through Celite®, rinsing with THF (5 mL) and EtOAc (10 mL). The combined organics were concentrated under reduced pressure to yield crude ((3R,4aR,12bS)-3-(benzy-

118 loxy)-9-(4-fluorophenyl)-3-(trifluoromethyl)-1,2,3,4,4a,5,6,7,9,12b-decahydrobenzo[6,7]cyclohepta[1,2-f]indazol-12b-yl)methanamine (34, R¹=4-Fluorophenyl, R³=Trifluoromethyl, Rₓ=Benzyl). LC/MS, method 3, R_f=2.41 min, MS m/z 538 (M+H)⁺. The residue was used in step #3 without further purification.

Step #3: N-(((3R,4aR,12bS)-3-(benzyloxy)-9-(4-fluorophenyl)-3-(trifluoromethyl)-1,2,3,4,4a,5,6,7,9,12b-decahydrobenzo[6,7]cyclohepta[1,2-f]indazol-12b-yl)methyl)methanesulfonamide (35, R¹=4-Fluorophenyl, R³=Trifluoromethyl, R⁴=Methanesulfonyl, Rˣ=Benzyl)

Crude ((3R,4aR,12bS)-3-(benzyloxy)-9-(4-fluorophenyl)-3-(trifluoromethyl)-1,2,3,4,4a,5,6,7,9,12b-decahydrobenzo[6,7]cyclohepta[1,2-f]indazol-12b-yl)methanamine (34, R¹=4-Fluorophenyl, R³=Trifluoromethyl, R⁴=H, R³=Benzyl) (0.135 mmol) was dissolved in DCM (3 mL) and methanesulfonyl chloride (0.026 mL, 0.334 mmol) and TEA (0.023 mL, 0.167 mmol) were added at rt. The reaction was stirred at rt for about 30 min, then diluted with DCM (10 mL) and concentrated with silica gel (3 g). The residue was purified on silica gel using a gradient of 0-10% EtOAc in DCM.

Product fractions were combined and concentrated to yield N-(((3R,4aR,12bS)-3-(benzyloxy)-9-(4-fluorophenyl)-3-(trifluoromethyl)-1,2,3,4,4a,5,6,7,9,12b-decahydrobenzo[6,7]cyclohepta[1,2-f]indazol-12b-yl)methyl)methanesulfonamide (35, $R^1$=4-Fluorophenyl, $R^3$=Trifluoromethyl, $R^4$=Methanesulfonyl, $R^g$=Benzyl) (40 mg, 39%) as a clear glass; LC/MS, method 3, $R_t$=2.95 min, MS m/z 616 (M+H)$^+$.) The residue was used in step #4 without further purification.

Step #4: N-(((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)methanesulfonamide (36, $R^1$=4-Fluorophenyl, $R^3$=Trifluoromethyl, $R^4$=Methanesulfonyl) (Example 74)

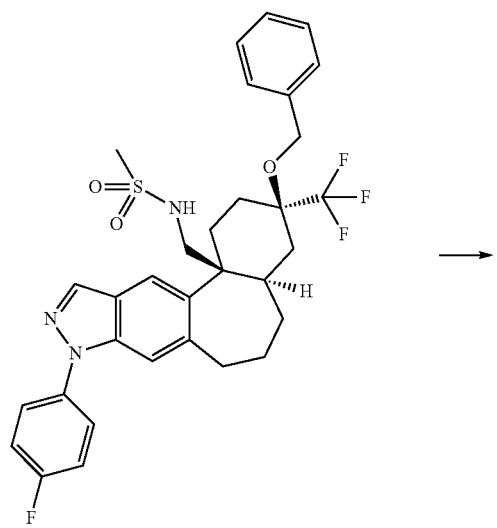

A solution of N-(((3R,4aR,12bS)-3-(benzyloxy)-9-(4-fluorophenyl)-3-(trifluoromethyl)-1,2,3,4,4a,5,6,7,9,12b-decahydrobenzo[6,7]cyclohepta[1,2-f]indazol-12b-yl)methyl)methanesulfonamide (35, $R^1$=4-Fluorophenyl, $R^3$=Trifluoromethyl, $R^4$=Methanesulfonyl, $R_x$=Benzyl) (40 mg, 0.065 mmol) in DCM (3 mL) was cooled to about 0° C. and treated with BBr$_3$ (1M in hexane, 0.23 mL, 0.23 mmol). The mixture was stirred for about 30 min at rt. The reaction was quenched by addition of MeOH (5 mL) and warmed to rt for about 90 min. Solvents were removed under reduced pressure and the residue was dissolved in DCM (20 mL) and concentrated onto silica gel (1 g). The residue was purified on silica gel (12 g) using a gradient of 30-100% EtOAc in DCM. Product fractions were combined and concentrated under reduced pressure. The residue was dissolved in MeOH (5 mL), diluted with water (3 mL) and reduced in volume to about 3 mL under reduced pressure. The product was filtered off and dried under vacuum at about 50° C. to yield N-(((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)methanesulfonamide (36, $R^1$=4-Fluorophenyl, $R^3$=Trifluoromethyl, $R^4$=Methanesulfonyl) (23 mg, 67%) as an off-white solid. LC/MS, method 2, $R_t$=2.49 min, MS m/z 526 (M+H)$^+$, $^1$H NMR (400 MHz, DMSO) δ 8.25 (d, J=0.6 Hz, 1H), 7.84 (s, 1H), 7.79-7.72 (m, 2H), 7.55 (s, 1H), 7.42-7.34 (m, 2H), 6.29 (t, J=6.7 Hz, 1H), 5.89 (s, 1H), 3.90-3.81 (m, 1H), 3.36-3.30 (m, 1H), 3.28-3.20 (m, 1H), 3.00-2.90 (m, 1H), 2.61 (s, 3H), 2.28-2.20 (m, 1H), 2.14-2.03 (m, 1H), 2.02-1.73 (m, 5H), 1.72-1.53 (m, 3H), 1.44-1.30 (m, 1H).

Example 75

2-(((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)isothiazolidine 1,1-dioxide (11, $R^1$=4-Fluorophenyl, $R^3$=Trifluoromethyl)

Step 1: 2-(((3R,4aR,12bS)-3-(benzyloxy)-9-(4-fluorophenyl)-3-(trifluoromethyl)-1,2,3,4,4a,5,6,7,9,12b-decahydrobenzo[6,7]cyclohepta[1,2-f]indazol-12b-yl)methyl)isothiazolidine 1,1-dioxide (35, $R^1$=4-Fluorophenyl, $R^3$=Trifluoromethyl, $R^g$=Benzyl)

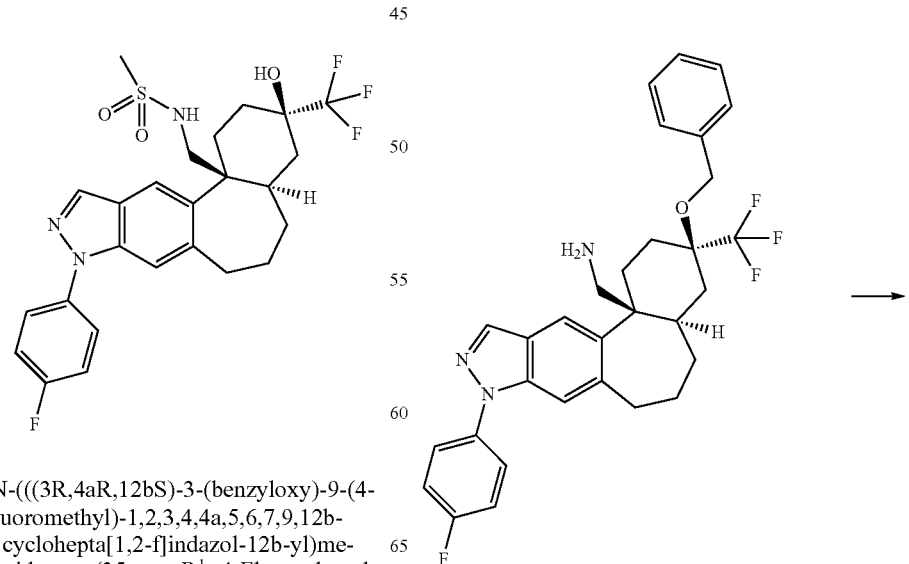

121
-continued

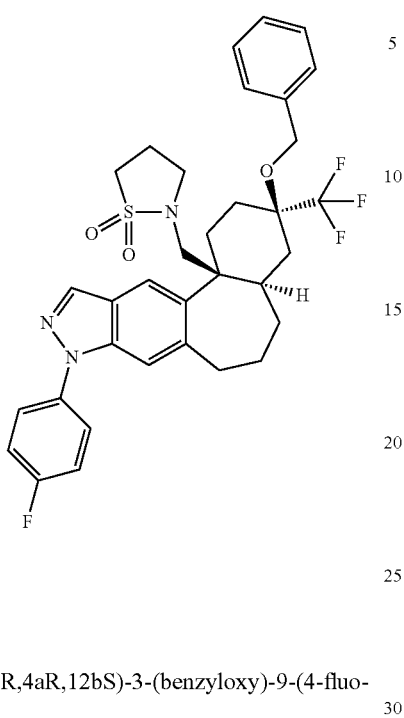

A solution of ((3R,4aR,12bS)-3-(benzyloxy)-9-(4-fluorophenyl)-3-(trifluoromethyl)-1,2,3,4,4a,5,6,7,9,12b-decahydrobenzo[6,7]cyclohepta[1,2-f]indazol-12b-yl)methanamine (34, $R^1$=4-Fluorophenyl, $R^3$=Trifluoromethyl, $R^g$=Benzyl) (82 mg, 0.153 mmol) in DCM (3 mL) was treated with TEA (0.021 mL, 0.153 mmol) and 3-chloro-propane-1-sulfonyl chloride (0.023 mL, 0.19 mmol) at rt under nitrogen for about 1 h. The organic layer was washed with 2N aq. HCl (2 mL), dried over $Na_2SO_4$, filtered and concentrated under reduced pressure. The residue was dissolved in DMF (2 mL) and added dropwise to a suspension of sodium hydride (60 wt % in oil, 7.6 mg, 0.30 mmol) in DMF (1 mL). The reaction was heated at about 50° C. for 2 h and then cooled to rt and concentrate under reduced pressure. The residue was purified on silica gel (4 g) using a gradient of 0-30% EtOAc in DCM. Product fractions were combined and concentrated to yield 2-(((3R,4aR,12bS)-3-(benzyloxy)-9-(4-fluorophenyl)-3-(trifluoromethyl)-1,2,3,4,4a,5,6,7,9,12b-decahydrobenzo[6,7]cyclohepta[1,2-f]indazol-12b-yl)methyl)isothiazolidine 1,1-dioxide (35, $R^1$=4-Fluorophenyl, $R^3$=Trifluoromethyl, $R^g$=Benzyl) (63 mg, 64%) as an oil. LC/MS, method 3, $R_t$=3.01 min, MS m/z 642 (M+H)$^+$. The oil was used in step #2 without further purification.

122

Step #2: 2-(((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)isothiazolidine 1,1-dioxide (11, $R^1$=4-Fluorophenyl, $R^2$=1,1-dioxidoisothiazolidin-2-yl) methyl, $R^3$=Trifluoromethyl)

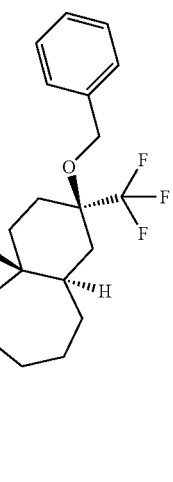

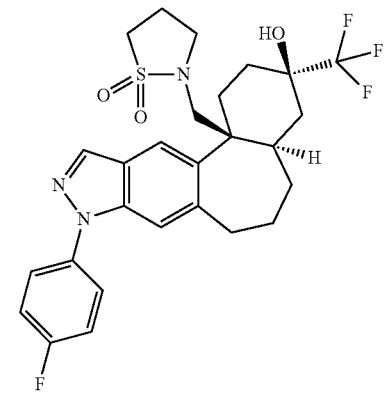

A solution of 2-(((3R,4aR,12bS)-3-(benzyloxy)-9-(4-fluorophenyl)-3-(trifluoromethyl)-1,2,3,4,4a,5,6,7,9,12b-decahydrobenzo[6,7]cyclohepta[1,2-f]indazol-12b-yl)methyl)isothiazolidine 1,1-dioxide (35, $R^1$=4-Fluorophenyl, $R^3$=Trifluoromethyl, $R^g$=Benzyl) (63 mg, 0.10 mmol) in DCM (3 mL) was cooled to about 0° C. and treated with $BBr_3$ (0.40 mL, 0.40 mmol). The mixture was stirred for about 30 min, then the reaction was quenched by dropwise addition of MeOH (5 mL) and warmed to rt. The reaction was concentrated under reduced pressure, then dissolved in MeOH (5 mL) and stirred at 35° C. for about 15 min. DCM (5 mL) was added and the mixture was concentrated onto silica gel (1 g). The residue was purified on silica gel column (4 g) using a gradient of 30-100% EtOAc in DCM. Product fractions were combined and concentrated. The residue was dissolved in MeOH (5 mL) and water (3 mL), then concentrate under reduced pressure to about (3 mL) volume. The product was filtered off and dried under reduced pressure to yield 2-(((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)isothiazolidine 1,1-dioxide (11, R¹=4-Fluorophenyl, R²=1,1-dioxidoisothiazolidin-2-yl)methyl, R³=Trifluoromethyl) (22 mg, 41%) as an off-white solid; LC/MS, method 2, $R_t$=2.59 min, MS m/z 552 (M+H)⁺, ¹H NMR (400 MHz, DMSO) δ 8.29 (s, 1H), 7.90 (s, 1H), 7.85-7.76 (m, 2H), 7.62 (s, 1H), 7.45-7.37 (m, 2H), 5.98 (s, 1H), 3.65 (q, J=14.6 Hz, 2H), 3.41-3.32 (m, 1H), 3.14-2.99 (m, 2H), 2.96-2.86 (m, 1H), 2.36-2.25 (m, 1H), 2.20-2.08 (m, 1H), 2.08-1.55 (m, 12H), 1.49-1.35 (m, 1H). (Example 75)

Additional examples, prepared in a manner similar to the preparation of Examples #74 are listed in Table 6.

TABLE 6

| Ex. # | Amine structure | Product structure | LC/MS method | $R_t$/MH⁺ |
|---|---|---|---|---|
| 76 | 34, (3R,4aR,12bS) R¹ = 4-Fluorophenyl, R³ = Trifluoromethyl | 36 (3R,4aR,12bS) (R¹ = 4-Fluorophenyl, R³ = Trifluoromethyl, R⁴ = Ethanesulfonyl) | 2 | 2.42 min 526 |
| 77 | 34, (3R,4aR,12bS) R¹ = 4-Fluorophenyl, R³ = Trifluoromethyl | 36 (3R,4aR,12bS) (R¹ = 4-Fluorophenyl, R³ = Trifloromethyl, R⁴ = Methanesulfonyl) | 2 | 2.56 min 540 |

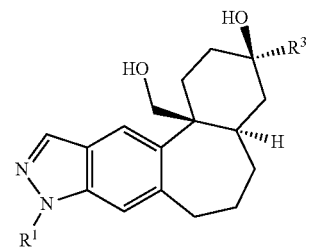

38

Example #78

(3R,4aR,12bS)-9-(4-fluorophenyl)-12b-(hydroxymethyl)-3-(trifluoromethyl)-1,2,3,4,4a,5,6,7,9,12b-decahydrobenzo[6,7]cyclohepta[1,2-f]indazol-3-ol (38, R¹=4-Fluorophenyl, R³=Trifluoromethyl)

Scheme 5:

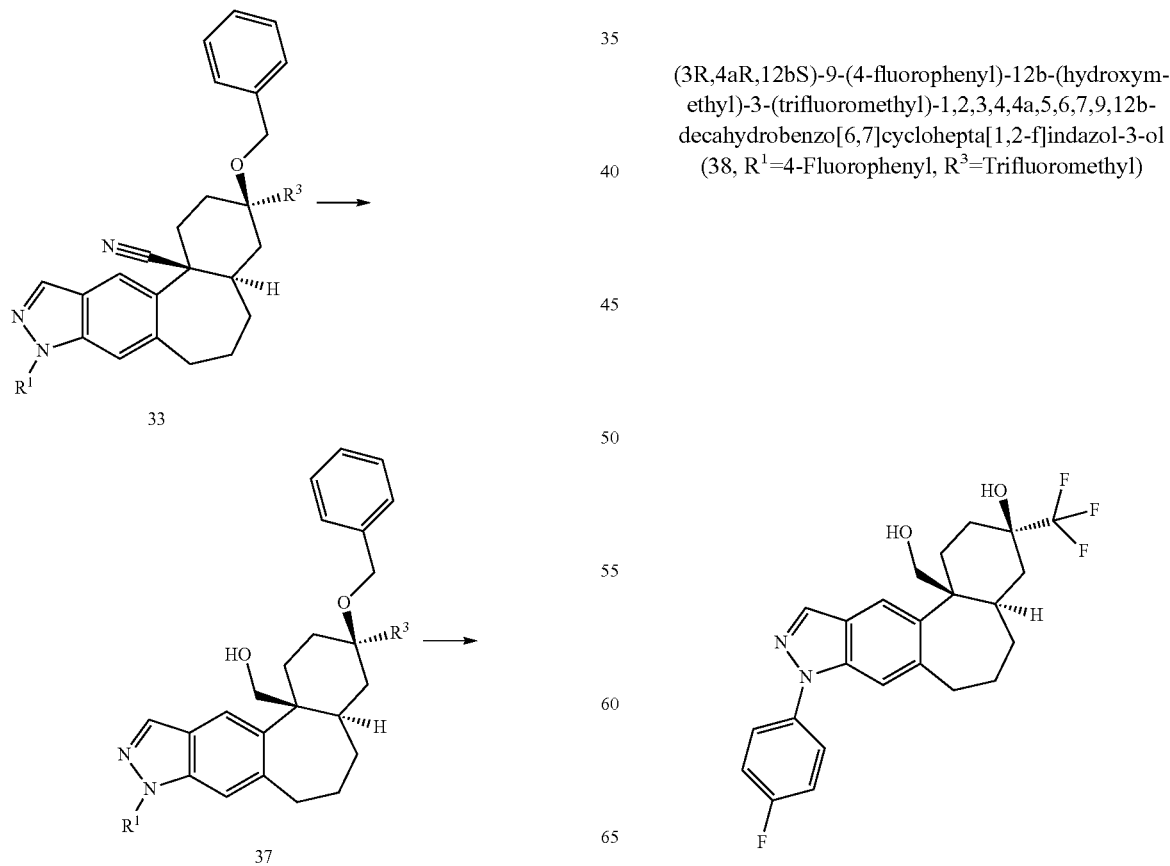

Step #1: ((3R,4aR,12bS)-3-(benzyloxy)-9-(4-fluorophenyl)-3-(trifluoromethyl)-1,2,3,4,4a,5,6,7,9,12b-decahydrobenzo[6,7]cyclohepta[1,2-f]indazol-12b-yl)methanol (37, $R^1$=4-Fluorophenyl, $R^3$=Trifluoromethyl)

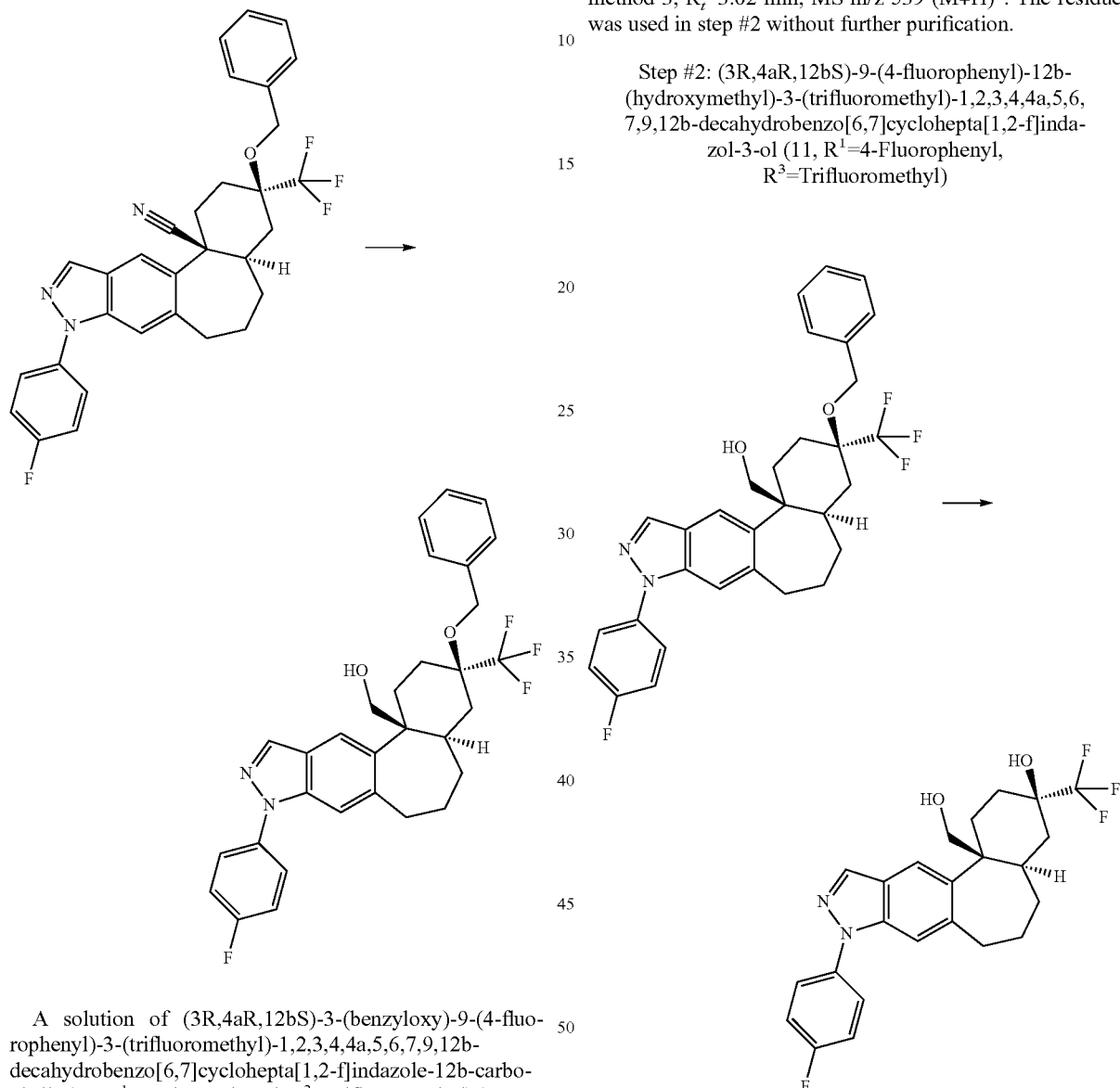

A solution of (3R,4aR,12bS)-3-(benzyloxy)-9-(4-fluorophenyl)-3-(trifluoromethyl)-1,2,3,4,4a,5,6,7,9,12b-decahydrobenzo[6,7]cyclohepta[1,2-f]indazole-12b-carbonitrile (33, $R^1$=4-Fluorophenyl, $R^3$=Trifluoromethyl) (79 mg, 0.158 mmol) was dissolved in THF (2 mL) and cooled to about 0° C. under nitrogen. The mixture was treated dropwise with DIBAL-H (1M in cyclohexane, 0.90 mL, 0.90 mmol). The reaction was stirred at about 0° C. for about 2 h, then quenched by addition of 6% acetic acid in sat. aq. sodium acetate solution (3 mL). The reaction was concentrated to about 3 mL volume and extracted with DCM (2×20 mL). The organic extracts were dried over $Na_2SO_4$, filtered and concentrated under reduced pressure. Intermediate LC/MS, method 3, $R_t$=3.14 min, MS m/z 537 (M+H)$^+$. The residue was dissolved in EtOH (3 mL) and treated with $NaBH_4$ (18 mg, 0.47 mmol) at rt for about 1 h. The reaction was quenched with aq. $NH_4Cl$ solution (2 mL) and stirred about 15 min at rt. The mixture was further diluted with water (2 mL) and extracted with DCM (2×5 mL). The combined DCM layers were washed with water, dried over $Na_2SO_4$, filtered and concentrated under reduced pressure to yield (3R,4aR,12bS)-9-(4-fluorophenyl)-12b-(hydroxymethyl)-3-(trifluoromethyl)-1,2,3,4,4a,5,6,7,9,12b-decahydrobenzo[6,7]cyclohepta[1,2-f]indazol-3-ol), (37, $R^1$=4-Fluorophenyl, $R^3$=Trifluoromethyl) (85 mg, 100%) as a glass: LC/MS, method 3, $R_t$=3.02 min, MS m/z 539 (M+H)$^+$. The residue was used in step #2 without further purification.

Step #2: (3R,4aR,12bS)-9-(4-fluorophenyl)-12b-(hydroxymethyl)-3-(trifluoromethyl)-1,2,3,4,4a,5,6,7,9,12b-decahydrobenzo[6,7]cyclohepta[1,2-f]indazol-3-ol (11, $R^1$=4-Fluorophenyl, $R^3$=Trifluoromethyl)

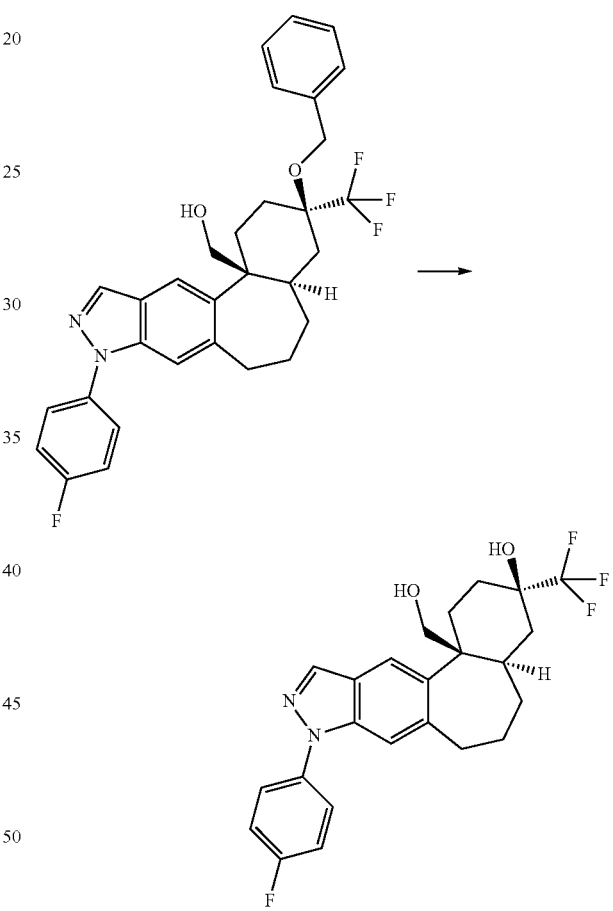

Crude ((3R,4aR,12bS)-3-(benzyloxy)-9-(4-fluorophenyl)-3-(trifluoromethyl)-1,2,3,4,4a,5,6,7,9,12b-decahydrobenzo[6,7]cyclohepta[1,2-f]indazol-12b-yl)methanol (37, $R^1$=4-Fluorophenyl, $R^3$=Trifluoromethyl) (85 mg, 0.158 mmol) was dissolved in DCM (3 mL), cooled to about 0° C. and tribromoborane (0.553 mL, 0.553 mmol) was added at a dropwise rate. The mixture was stirred for about 30 min, MeOH (10 mL) was added and the reaction was allowed to warm to rt for 90 min. The solvents were removed under reduced pressure and the residue was dissolved in DCM (20 mL), then concentrated onto silica gel (about 1 g). The residue was purified on silica gel column (12 g) using a gradient of 30-90% EtOAc in heptane. Product fractions were combined and concentrated under reduced pressure. The residue was dissolved in MeOH (5 mL) and water (3 mL), then concentrated under reduced pressure to about (3 mL) volume. The product was filtered off and dried under reduced pressure to yield: (3R,4aR,12bS)-9-(4-fluorophenyl)-12b-(hydroxymethyl)-3-(trifluoromethyl)-1,2,3,4,4a,5,6,7,9,12b-decahydrobenzo[6,7]cyclohepta[1,2-f]indazol-3-ol (38, $R^1$=4-Fluorophenyl, $R^3$=Trifluoromethyl) (27 mg, 38%) as an off-white solid; LC/MS, method 2, $R_t$=2.47 min, MS m/z 449 (M+H)$^+$, $^1$H NMR (400 MHz, DMSO) δ 8.25 (d, J=0.8 Hz, 1H), 7.86 (s, 1H), 7.83-7.75 (m, 2H), 7.56 (s, 1H), 7.45-7.36 (m, 2H), 5.82 (s, 1H), 4.42 (t, J=4.9 Hz, 1H), 4.01-3.86 (m, 2H), 3.27-3.18 (m, 1H), 3.08-2.96 (m, 1H), 2.48-2.37 (m, 1H), 2.10-1.53 (m, 9H), 1.50-1.34 (m, 1H).

Additional examples, prepared in a manner similar to the preparation of Example 78 are listed in Table 7.

TABLE 7

| Ex. # | Nitrile structure | Product structure | LC/MS method | $R_t$/MH$^+$ |
|---|---|---|---|---|
| 79 | 33, (3S,4aS,12bR) $R^1$ = 4-Fluorophenyl, $R^3$ = Trifluoromethyl | 38 (3S,4aS,12bR) ($R^1$ = 4-Fluorophenyl, $R^3$ = Trifluoromethyl) | 2 | 449 |
| 80 | 33, (3R,4aR,12bS); compound with (3S,4aS,12bR), $R^1$ = 4-Fluorophenyl, $R^3$ = Trifluoromethyl | 38 (3R,4aR,12bS); compound with (3S,4aS,12bR), ($R^1$ = 4-Fluorophenyl, $R^3$ = Trifluoromethyl) | 2 | 449 |

Scheme 6:

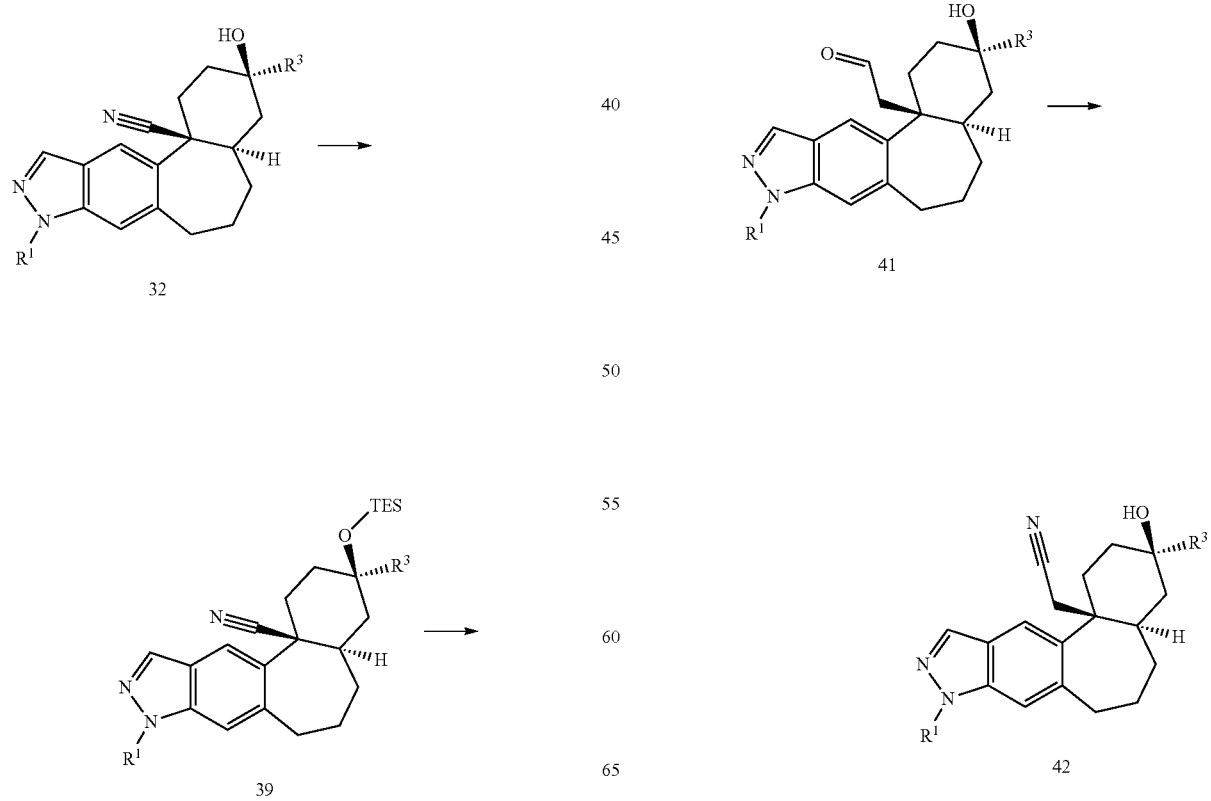
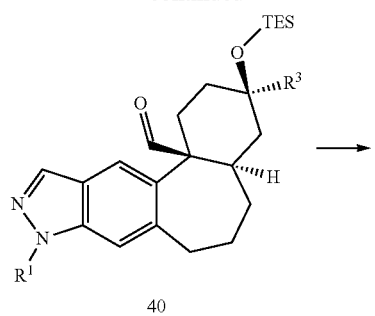

Examples #81 and #82

2-((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)acetonitrile (42, ($R^1$=4-Fluorophenyl, $R^3$=Trifluoromethyl) and 2-43S,4aS,12bR)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)acetonitrile (42, ($R^1$=4-Fluorophenyl, $R^3$=Trifluoromethyl)

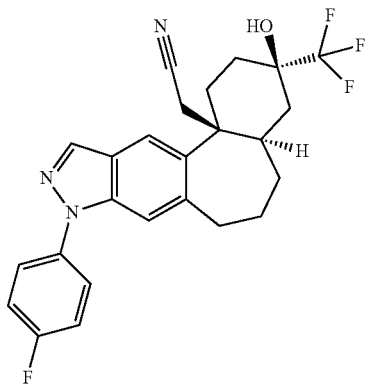 [SMILES: OC[C@@]12CC[C@](O)(C(F)(F)F)C[C@H]1CCCc1cc3c(cnn3-c3ccc(F)cc3)cc12]

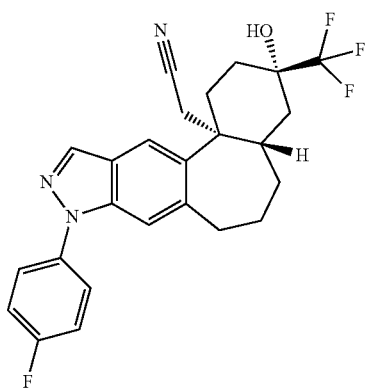

Step 1: (3S,4aS,12bR)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carbonitrile; compound with (3R,4aR,12bS)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carbonitrile (39, ($R^1$=4-Fluorophenyl, $R^3$=Trifluoromethyl)

A solution of (3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carbonitrile; compound with (3S,4aS,12bR)-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carbonitrile (32, $R^1$=4-Fluorophenyl, $R^3$=Trifluoromethyl) (3.0 g, 6.77 mmol) in THF (60 mL) was cooled to about 0° C. under nitrogen. LiHMDS (1M solution in hexane, 8.12 mL, 8.12 mmol) was added dropwise, maintaining the reaction temperature below about 3° C. and the anion was stirred for an additional 10 min at 0° C. Triethylchlorosilane (1.72 mL, 10.2 mmol) was added and the reaction was stirred at about 0° C. for 6 h. The reaction was quenched by addition of sat. aq. NH$_4$Cl (50 mL), and extracted with EtOAc (100 mL). The organic layer was dried over Na$_2$SO$_4$ and filtered. The filterate was treated with silica gel (10 g) and concentrated to dryness. The residue was purified on silica gel (120 g) using a gradient of 5-20% EtOAc in heptane. Product fractions were combined and concentrated to about 50 mL volume. Product was filtered off, rinsed with heptane (10 mL) and dried under reduced pressure to yield (3S,4aS,12bR)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b- carbonitrile; compound with (3R,4aR,12bS)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carbonitrile (39, R¹=4-Fluorophenyl, R³=Trifluoromethyl) as a white solid (2.88 g, 76%); LC/MS, method 4, R$_t$=2.47 min, MS m/z 558 (M+H)$^+$, ¹H NMR (400 MHz, DMSO) δ 8.32 (d, J=0.8 Hz, 1H), 8.09 (s, 1H), 7.83-7.77 (m, 2H), 7.67 (s, 1H), 7.45-7.38 (m, 2H), 3.37-3.25 (m, 1H), 2.12-3.00 (m, 1H), 2.62-2.52 (m, 2H), 2.47-2.38 (m, 1H), 2.27-2.16 (m, 1H), 2.07-1.92 (m, 3H), 1.86-1.54 (m, 3H), 1.38-1.24 (m, 1H), 0.99-0.92 (m, 9H), 0.72-0.62 (m, 6H).

Step 2: (3R,4aR,12bS)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carbaldehyde; compound with (3S,4aS,12bR)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carb aldehyde (40, R¹=4-Fluorophenyl, R³=Trifluoromethyl)

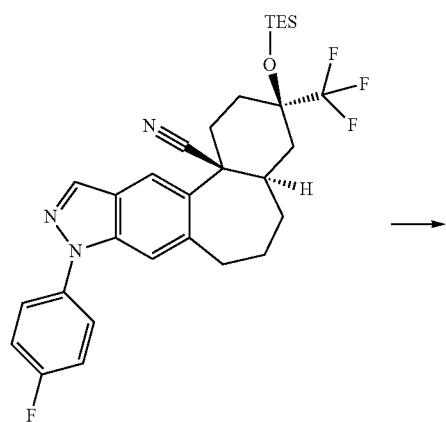

A solution of (3R,4aR,12bS)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carbonitrile; compound with (3S,4aS,12bR)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carbonitrile (39, R¹=4-Fluorophenyl, R³=Trifluoromethyl) (600 mg, 1.08 mmol) in Toluene (24 mL) was cooled to about 0° C. and DIBAL-H (1M solution in cyclohexane, 6.5 mL, 6.5 mmol) was added dropwise while maintaining the reaction temperature below about 1° C. The reaction was stirred at about 0° C. for about 1 h. The reaction was quenched by addition of 6% HOAc in sat. aq. NaOAc (25 mL) while maintaining the reaction temperature below 5° C. The mixture was allowed to warm to rt, water (10 mL) was added and stirring was continued for about 2 h. The layers were separated and the organic layer was stirred with sat. aq. NH$_4$Cl (25 mL) for about 2 h. The organic layer was dried with Na$_2$SO$_4$, filtered and concentrated to a waxy solid (730 mg). The crude was purified on silica gel (40 g) using a gradient of 5-20% EtOAc in heptane. Product fractions were combine and concentrated under reduced pressure to yield (3R,4aR,12bS)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carbaldehyde; compound with (3S,4aS,12bR)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carbaldehyde (40, R¹=4-Fluorophenyl, R³=Trifluoromethyl) as a viscous oil (566 mg, 94%); LC/MS, method 4, R$_t$=2.58 min, MS m/z 561 (M+H)$^+$, ¹H NMR (400 MHz, DMSO) δ 9.37 (d, J=1.9 Hz, 1H), 8.32 (d, J=0.9 Hz, 1H), 8.04 (s, 1H), 7.82-7.77 (m, 2H), 7.63 (s, 1H), 7.44-7.37 (m, 2H), 3.00-2.91 (m, 1H), 2.71-2.58 (m, 1H), 2.29-1.90 (m, 6H), 1.86-1.58 (m, 4H), 1.36-1.21 (m, 1H), 0.99-0.90 (m, 9H), 0.67-0.58 (m, 6H).

Step 3: 2-((3R,4aR,12bR)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazol-12b-yl)acetaldehyde; compound with 2-((3S,4aS,12bR)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazol-12b-yl)acetaldehyde (41, R¹=4-Fluorophenyl, R³=Trifluoromethyl)

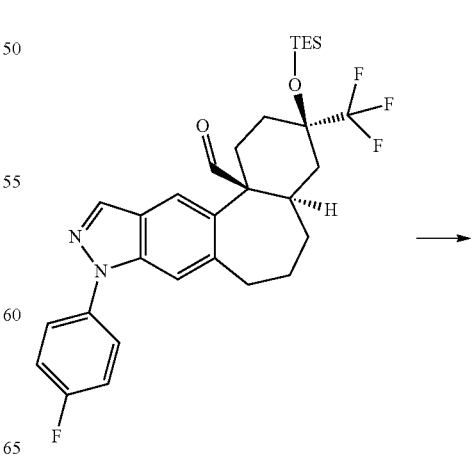

-continued

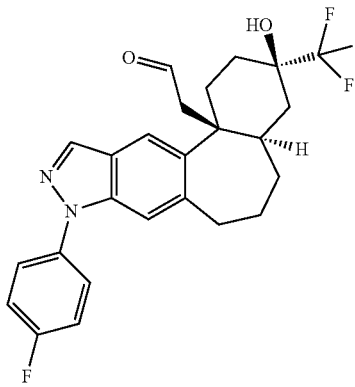

A suspension of methoxymethyl-triphenyl-phosphonium; chloride (1.10 g, 3.20 mmol) in THF (10 mL) was cooled to about 0° C. under nitrogen. A solution of LHMDS (1M in hexane, 3.20 mL, 3.20 mmol) was added dropwise maintaining the reaction temperature at 0-2° C. and then the reaction was stirred an additional 10 min. A solution of (3R,4aR, 12bS)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carbaldehyde; compound with (3S,4aS,12bR)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carb aldehyde (40, $R^1$=4-Fluorophenyl, $R^3$=Trifluoromethyl) (560 mg, 0.999 mmol) in THF (5 mL) was added dropwise maintaining the reaction temperature at about 0-2° C. The reaction was stirred at about 0° C. for about 30 min, then warmed to rt for about 18 h. Silica gel (4 g) was added and the solvents were removed under reduced pressure. The residue was purified on silica gel (40 g) silica gel using a gradient of 2-25% EtOAc in heptane. Product fractions were combined and concentrated under reduced pressure to a foam (524 mg, LC/MS, method 4, $R_t$=2.75 and 2.77 min, MS m/z 589 (M+H)$^+$. The residue was dissolved in THF (10 mL) and treated with TBAF (1M solution in THF, 0.89 mL, 0.89 mmol) at rt for about 30 min. The reaction was diluted with EtOAc (25 mL) and washed with water (3×25 mL). The organic layer was dried over $Na_2SO_4$, filtered and concentrated under reduced pressure. The residue was dissolved in THF (10 mL) and 4N HCl (5 mL). The reaction was heated at about 60° C. for about 90 min. The reaction was cooled to rt and concentrated to about 5 mL volume under reduced pressure. The product was extracted with EtOAc (25 mL), washed with water (3×25 mL), dried over $Na_2SO_4$, filtered and concentrated under reduced pressure. The residue was dissolved in EtOAc (about 4 mL) and precipitated by addition of heptane. Product was filtered off and dried under reduced pressure to yield 2-((3R,4aR,12bS)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazol-12b-yl)acetaldehyde; compound with 2-((3S,4aS,12bR)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazol-12b-yl)acetaldehyde (41, $R^1$=4-Fluorophenyl, $R^3$=Trifluoromethyl) (320 mg, 79%); LC/MS, method 4, $R_t$=1.73 min, MS m/z 459 (M–H), $^1$H NMR (400 MHz, DMSO) δ 9.14 (d, J=2.8 Hz, 1H), 8.27 (d, J=0.7 Hz, 1H), 7.97 (s, 1H), 7.82-7.76 (m, 2H), 7.62 (s, 1H), 7.45-7.37 (m, 2H), 5.93 (s, 1H), 3.32-3.21 (m, 1H), 3.05-2.94 (m, 2H), 2.73-2.64 (m, 1H), 2.41-2.30 (m, 1H), 2.24-2.13 (m, 1H), 2.11-1.97 (m, 2H), 1.87-1.70 (m, 3H), 1.69-1.51 (m, 3H), 1.44-1.28 (m, 1H).

Step #4: 2-((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)acetonitrile; compound with 2-((3S,4aS,12bR)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)acetonitrile (42, $R^1$=4-Fluorophenyl, $R^3$=Trifluoromethyl)

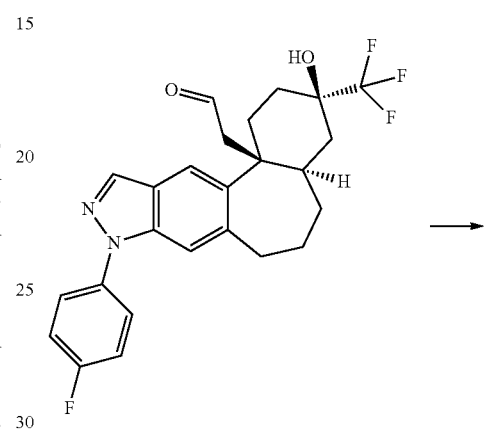

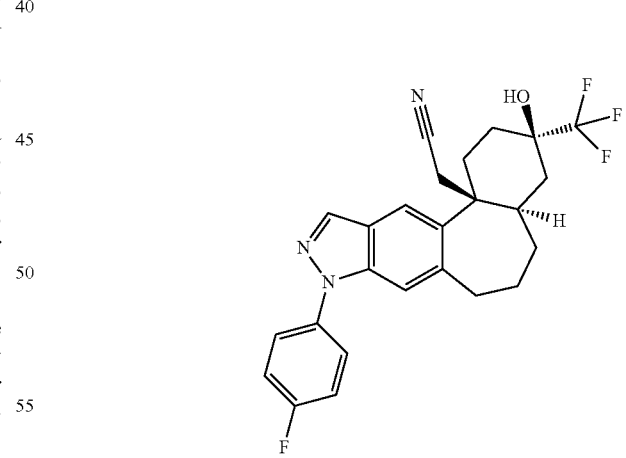

A solution of 2-((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)acetaldehyde; compound with 2-((3S,4aS,12bR)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)acetaldehyde (41, $R^1$=4-Fluorophenyl, $R^3$=Trifluoromethyl) (320 mg, 0.695 mmol) in pyridine (10 mL) was treated with hydroxylamine hydrochloride (53 mg, 0.76 mmol) and the mixture was heated to about 60° C. for about 15 min, then cooled to rt. Acetic anhydride (0.33 mL, 3.47 mmol) was added dropwise then the mixture was heated to about 60° C. for about 3 h. The reaction was cooled and concentrated under reduced pressure. The residue was dissolved in EtOAc (25 mL) and washed with 2N aq. NaOH and 2N aq. HCl. The organic layer was dried over $Na_2SO_4$ and filtered. Silica gel (~2 g) was added and the solvent removed under reduced pressure. The residue was purified on silica gel (12 g) using a gradient of 10-50% EtOAc in heptane as eluant. Product fractions were combined and concentrated under reduced pressure to yield 2-((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)acetonitrile; compound with 2-((3S,4aS,12bR)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)acetonitrile (42, $R^1$=4-Fluorophenyl, $R^3$=Trifluoromethyl) as a foam (255 mg, 79%); LC/MS, method 4, $R_t$=1.69 min, MS m/z 458 (M+H)$^+$, $^1$H NMR (400 MHz, DMSO) δ 8.29 (d, J=0.8 Hz, 1H), 7.99 (s, 1H), 7.83-7.75 (m, 2H), 7.61 (s, 1H), 7.44-7.36 (m, 2H), 5.93 (s, 1H), 3.37 (d, J=17.4 Hz, 1H), 3.28-3.27 (m, 1H), 3.10 (d, J=17.4 Hz, 1H), 3.05-2.94 (m, 1H), 2.41-2.29 (m, 1H), 2.26-2.16 (m, 1H), 2.10-2.01 (m, 1H), 2.01-1.92 (m, 1H), 1.87-1.55 (m, 6H), 1.42-1.29 (m, 1H).

The enantiomers were separated using Preparative Chiral Purification Method 12. Fractions from the first peak eluted were combined and concentrated under reduced pressure. The residue was dissolved in MeOH (3 mL), treated with water (10 mL) and concentrated under reduced pressure to remove MeOH. Solids were collected by filtration, washed with water (2 mL) and dried under vacuum at about 50° C. to 2-((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)acetonitrile (42, $R^1$=4-Fluorophenyl, $R^3$=Trifluoromethyl) (Example 81)

Fractions from the second peak eluted were combined and concentrated under reduced pressure. The residue was dissolved in MeOH (3 mL), treated with water (10 mL) and concentrated under reduced pressure to remove MeOH. Solids were collected by filtration, washed with water (2 mL) and dried under vacuum at about 50° C. to yield 2-((3S,4aS,12bR)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)acetonitrile (42, $R^1$=4-Fluorophenyl, $R^3$=Trifluoromethyl) (Example 82) LC/MS, method 4, $R_t$=1.69 min, MS m/z 458 (M+H)$^+$, $^1$H NMR (400 MHz, DMSO) δ 8.29 (d, J=0.8 Hz, 1H), 7.99 (s, 1H), 7.83-7.75 (m, 2H), 7.61 (s, 1H), 7.44-7.36 (m, 2H), 5.93 (s, 1H), 3.37 (d, J=17.4 Hz, 1H), 3.28-3.27 (m, 1H), 3.10 (d, J=17.4 Hz, 1H), 3.05-2.94 (m, 1H), 2.41-2.29 (m, 1H), 2.26-2.16 (m, 1H), 2.10-2.01 (m, 1H), 2.01-1.92 (m, 1H), 1.87-1.55 (m, 6H), 1.42-1.29 (m, 1H).

Examples #83 and #84

N-(((3S,4aS,12bR)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)acetamide (36, ($R^1$=4-Fluorophenyl, $R^3$=Trifluoromethyl, $R^4$=Acetyl) and N-(((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)acetamide (36, ($R^1$=4-Fluorophenyl, $R^3$=Trifluoromethyl, $R^4$=acetyl)

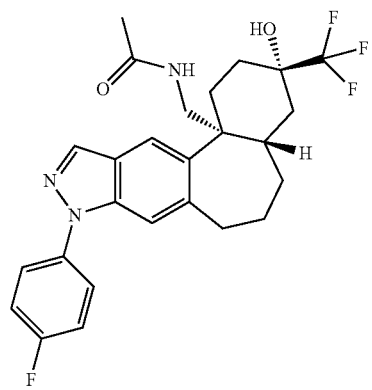

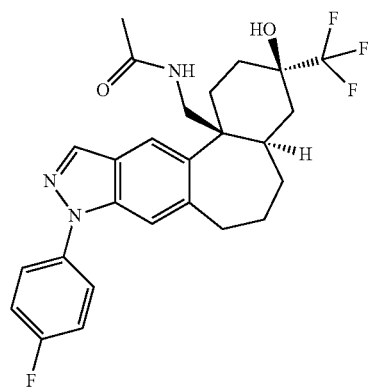

Step #1: ((3R,4aR,12bS)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazol-12b-yl)methanamine compound with ((3S,4aS,12bR)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazol-12b-yl)methanamine (34, $R^1$=4-Fluorophenyl, $R^3$=Trifluoromethyl, $R^4$=acetyl$R^x$=TES)

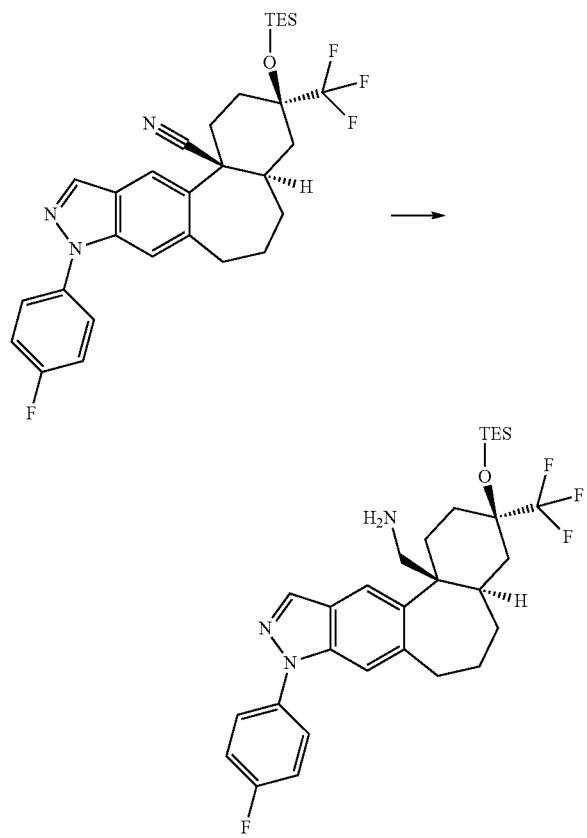

((3R,4aR,12bS)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazol-12b-yl)methanamine compound with ((3S,4aS,12bR)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazol-12b-yl)methanamine was prepared in a manner similar to Example 2, step 2, starting with (3S,4aS,12bR)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carbonitrile; compound with (3R,4aR,12bS)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carbonitrile (39, ($R^1$=4-Fluorophenyl, $R^3$=Trifluoromethyl) to yield a 3R,4aR,12bS)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazol-12b-yl)methanamine compound with ((3S,4aS,12bR)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazol-12b-yl)methanamine (34, $R^1$=4-Fluorophenyl, $R^3$=Trifluoromethyl, $R^4$=Acetyl$R^x$=TES) (530 mg, 100%)

which was used without further purification; LC/MS, method 3, $R_t$=2.84 min, MS m/z 562 (M+H)$^+$, $^1$H NMR (400 MHz, DMSO) δ 8.25 (d, J=0.7 Hz, 1H), 7.85 (s, 1H), 7.80-7.76 (m, 2H), 7.56 (s, 1H), 7.43-7.35 (m, 2H), 3.38 (d, J=13.2 Hz, 1H), 3.27-3.15 (m, 1H), 3.02-2.92 (m, 1H), 2.84 (d, J=13.3 Hz, 1H), 2.18-2.07 (m, 1H), 2.03-1.55 (m, 9H), 1.44-1.31 (m, 1H), 0.99-0.91 (m, 9H), 0.69-0.60 (m, 6H).

Step #2: N-(((3R,4aR,12bS)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazol-12b-yl)methyl)acetamide compound with N-(((3S,4aS,12bR)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazol-12b-yl)methyl)acetamide (35, $R^1$=4-Fluorophenyl, $R^3$=Trifluoromethyl, $R^x$=TES)

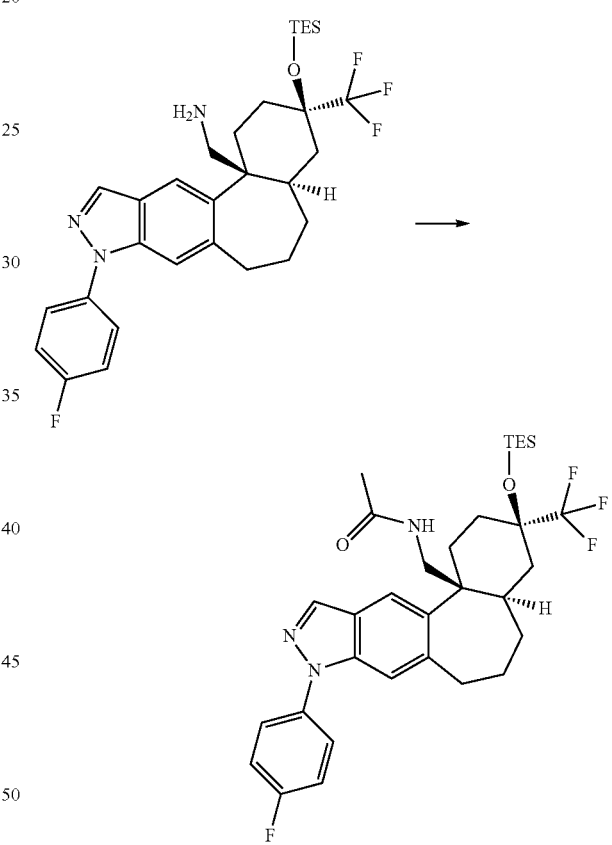

To a solution of ((3R,4aR,12bS)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazol-12b-yl)methanamine compound with ((3S,4aS,12bR)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazol-12b-yl)methanamine (34, $R^1$=4-Fluorophenyl, $R^3$=Trifluoromethyl, $R^4$=Acetyl, $R^x$=TES) (175 mg, 0.31 mmol) in DCM (5 mL) was added TEA (0.087 mL, 0.62 mmol) and Ac$_2$O (0.059 mL, 0.62 mmol) and the reaction was stirred at rt for about 1 h. The reaction was washed with 2N aq. NaOH (5 mL) and water (5 mL), then dried over Na$_2$SO$_4$, filtered and concentrated under reduced pressure to yield N-(((3R,4aR,12bS)-9-(4-fluorophenyl)-3-((triethylsilyl)

oxy)-3-(trifluoromethyl)-1,2,3,4,4a,5,6,7,9,12b-decahydrobenzo[6,7]cyclohepta[1,2-f]indazol-12b-yl)methyl)acetamide compound with N-(((3S,4aS,12bR)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazol-12b-yl)methyl)acetamide (35, $R^1$=4-Fluorophenyl, $R^3$=Trifluoromethyl, $R^4$=Acetyl, $R^x$=TES) as a foam (197 mg, 99%); LC/MS, method 4, $R_t$=2.36 min, MS m/z 604 (M+H)$^+$, $^1$H NMR (400 MHz, DMSO) δ 8.25 (d, J=0.7 Hz, 1H), 7.82-7.74 (m, 3H), 7.55 (s, 1H), 7.43-7.37 (m, 2H), 7.07-7.00 (m, 1H), 3.92-3.84 (m, 1H), 3.77-3.68 (m, 1H), 3.38-3.30 (m, 1H), 3.03-2.91 (m, 1H), 2.22-2.11 (m, 2H), 2.11-1.80 (m, 5H), 1.80-1.62 (m, 3H), 3.12 (s, 3H), 1.46-1.33 (m, 1H), 0.98-0.92 (m, 9H), 0.70-0.63 (m, 6H).

Step #3: N-(((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)acetamide; compound with N-(((3S,4aS,12bR)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)acetamide (36, $R^1$=4-Fluorophenyl, $R^3$=Trifluoromethyl, $R^4$=Acetyl)

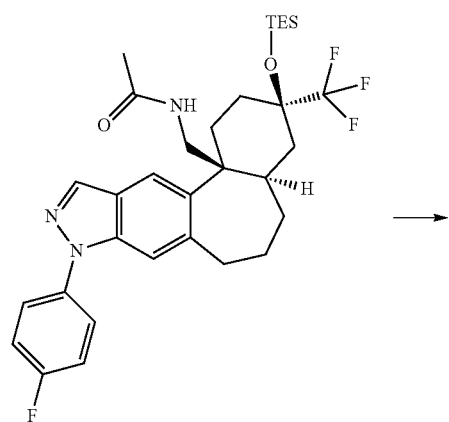

A solution of N-(((3R,4aR,12bS)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazol-12b-yl)methyl)acetamide compound with N-(43 S,4aS,12bR)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazol-12b-yl)methyl)acetamide (35, $R^1$=4-Fluorophenyl, $R^3$=Trifluoromethyl, $R^g$=TES) (195 mg, 0.32 mmol) in DCM (5 mL) was treated with TBAF (1M solution in THF, 0.32 mL, 0.32 mmol) at rt for about 30 min. The reaction was diluted with DCM (10 mL), washed with water (3×5 mL), dried over Na$_2$SO$_4$, filtered and concentrated to solids under reduced pressure. The residue was triturated in EtOAc (~2 mL), filtered, rinsed with heptane and dried under vacuum to yield N-(((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)acetamide; compound with N-(((3S,4aS,12bR)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)acetamide (36, $R^1$=4-Fluorophenyl, $R^3$=Trifluoromethyl, $R^4$=Acetyl) as a white solid (125 mg, 72%); LC/MS, method 4, $R_t$=1.55 min, MS m/z 490 (M+H)$^+$, $^1$H NMR (400 MHz, DMSO) δ 8.25 (d, J=0.7 Hz, 1H), 7.81-7.73 (m, 3H), 7.55 (s, 1H), 7.44-7.35 (m, 2H), 7.07 (t, J=5.9 Hz, 1H), 5.88 (s, 1H), 4.00-3.91 (m, 1H), 3.65-3.56 (m, 1H), 3.42-3.31 (m, 1H), 3.00-2.90 (m, 1H), 2.13-1.94 (m, 3H), 1.95-1.77 (m, 4H), 1.71-1.61 (m, 3H), 1.59 (s, 3H), 1.45-1.32 (m, 1H).

The enantiomers were separated using Preparative Chiral Purification Method 13. Fractions from the first peak eluted were combined and concentrated under reduced pressure. The residue was dissolved in MeOH (3 mL), treated with water (10 mL) and concentrated under reduced pressure to remove MeOH. Solids were collected by filtration, washed with water (2 mL) and dried under vacuum at about 50° C. to yield N-(a 3 S,4aS,12bR)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)acetamide (36, $R^1$=4-Fluorophenyl, $R^3$=Trifluoromethyl), $R^4$=Acetyl) as a white solid (40 mg, 25%) (Example 83) LC/MS, method 4, $R_t$=1.55 min, MS m/z 490 (M+H)$^+$, $^1$H NMR (400 MHz, DMSO) δ 8.25 (d, J=0.7 Hz, 1H), 7.81-7.73 (m, 3H), 7.55 (s, 1H), 7.44-7.35 (m, 2H), 7.07 (t, J=5.9 Hz, 1H), 5.88 (s, 1H), 4.00-3.91 (m, 1H), 3.65-3.56 (m, 1H), 3.42-3.31 (m, 1H), 3.00-2.90 (m, 1H), 2.13-1.94 (m, 3H), 1.95-1.77 (m, 4H), 1.71-1.61 (m, 3H), 1.59 (s, 3H), 1.45-1.32 (m, 1H).

Fractions from the second peak eluted were combined and concentrated under reduced pressure. The residue was dissolved in MeOH (3 mL), treated with water (10 mL) and concentrated under reduced pressure to remove MeOH. Solids were collected by filtration, washed with water (2 mL) and dried under vacuum at about 50° C. to yield N-(((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)acetamide as a white solid (38 mg, 24%) (36, $R^1$=4-Fluorophenyl, $R^3$=Trifluoromethyl, $R^4$=Acetyl)

(Example 84) LC/MS, method 4, $R_t$=1.55 min, MS m/z 490 (M+H)$^+$, $^1$H NMR (400 MHz, DMSO) δ 8.25 (d, J=0.7 Hz, 1H), 7.81-7.73 (m, 3H), 7.55 (s, 1H), 7.44-7.35 (m, 2H), 7.07 (t, J=5.9 Hz, 1H), 5.88 (s, 1H), 4.00-3.91 (m, 1H), 3.65-3.56 (m, 1H), 3.42-3.31 (m, 1H), 3.00-2.90 (m, 1H),

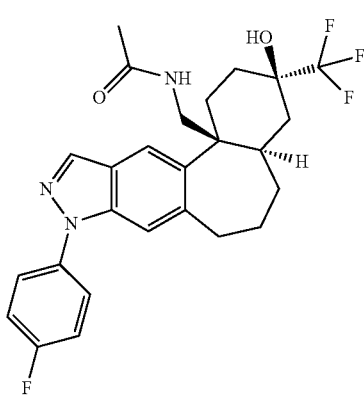

2.13-1.94 (m, 3H), 1.95-1.77 (m, 4H), 1.71-1.61 (m, 3H), 1.59 (s, 3H), 1.45-1.32 (m, 1H).

Examples 85

((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)(pyridin-2-yl)methanone compound with 43R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)(pyridin-2-yl)methanone

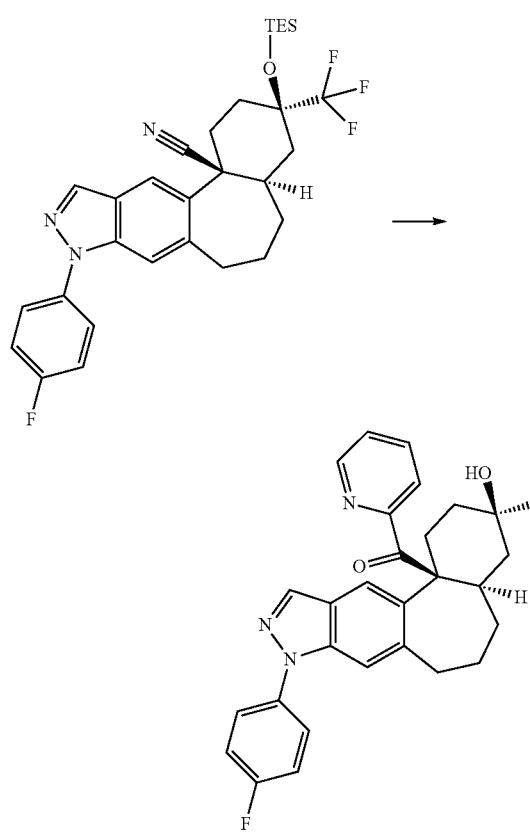

A solution of 2-bromopyridine (506 mg, 3.20 mmol) in THF (6 mL) was cooled to about −78° C. under nitrogen. A solution of BuLi (2.5M solution in hexanes, 1.26 mL, 3.14 mmol) was added dropwise while maintaining reaction temperature below −75° C. The reaction was stirred for about 15 min at about −78° C. then a solution of (3R,4aR,12bS)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carbonitrile; compound with (3R,4aR,12bS)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carbonitrile (33, $R^1$=4-Fluorophenyl, $R^3$=Trifluoromethyl, $R^g$=TES) (350 mg, 0.628 mmol) in THF (2.5 mL) was added dropwise maintaining reaction temperature below −74° C. The reaction was stirred for about 30 min and then quenched by addition of 2 N aq. HCl (5 mL). The mixture was stirred about 6 h at rt and then cooled to rt. The reaction was neutralized by addition of sat. aq. NaHCO₃ (20 mL) and the products extracted with EtOAc (2×20 mL), dried over Na₂SO₄, filtered and concentrated under reduced pressure. The product was purified on silica gel (25 g) using a gradient of 25-50% EtOAc in heptane. Product fractions were combined and concentrated under reduced pressure. The residue was dissolved in MeOH (10 mL), water (5 mL) was added and the mixture was concentrated to about 5 mL volume. The product was filtered off and dried under reduced pressure at about 50° C. to yield ((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)(pyridin-2-yl)methanone compound with ((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)(pyridin-2-yl)methanone (11, $R^1$=4-Fluorophenyl, $R^2$=2-Pyridylcarbonyl, $R^3$=Trifluoromethyl) (49 mg, 15%) as a yellow solid; Major isomer: LC/MS, method 2, $R_t$=2.80 min, MS m/z 524 (M+H)⁺, ¹H NMR (400 MHz, DMSO) δ 9.90 (s, 1H), 8.63 (d, J=4.0 Hz, 1H), 8.09-8.02 (m, 1H), 7.94-7.88 (m, 2H), 7.66-7.60 (m, 1H), 7.35-7.29 (m, 2H), 7.25-7.18 (m, 2H), 6.98 (s, 1H), 6.19 (s, 1H), 3.16-3.05 (m, 1H), 2.77-2.65 (m, 1H), 2.19-1.86 (m, 6H), 1.77-1.58 (m, 3H), 1.53-1.39 (m, 1H), 1.37-1.23 (m, 1H). Evidence of two hemi-ketal forms is observed in both the NMR and the LC/MS.

Scheme 7:

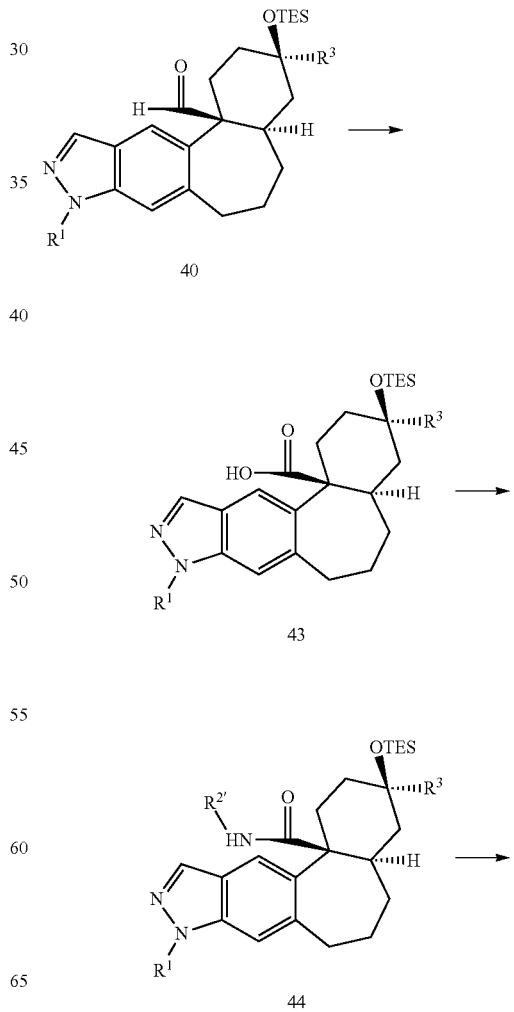

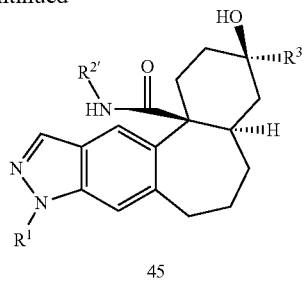

Example #86 and #87: (3R,4aR,12bS)—N-Cyclopropyl-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carboxamide (45, R¹=4-Fluorophenyl, R³=Trifluoromethyl, R²'=Cyclopropyl) and (3S,4aS,12bR)—N-cyclopropyl-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carboxamide (45, R¹=4-Fluorophenyl, R³=Trifluoromethyl, R²'=Cyclopropyl)

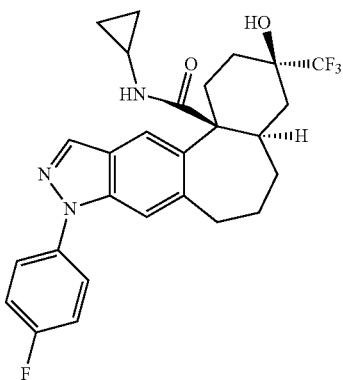 [SMILES: O=C(NC1CC1)[C@@]12CC[C@](O)(C(F)(F)F)C[C@H]1CCCc1cc3c(cnn3-c3ccc(F)cc3)cc12]

Step 1: rac-(3R,4aR,12bS)-9-(4-Fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carboxylic acid (43, R¹=4-Fluorophenyl, R³=Trifluoromethyl)

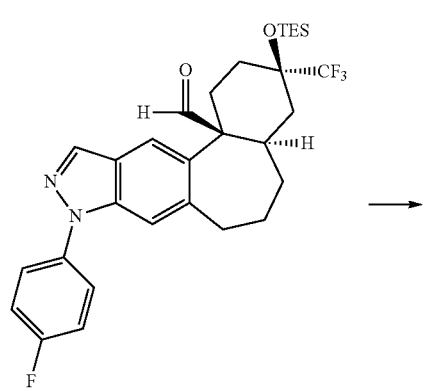

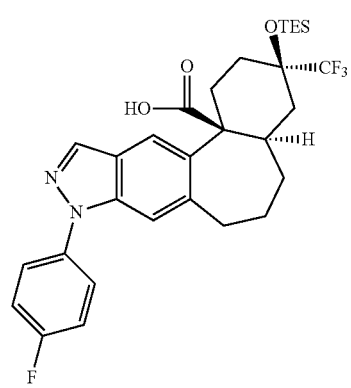

t-Butanol (20 mL) and water (4 mL) were added to rac-(3R,4aR,12bS)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carb aldehyde (40, R¹=4-Fluorophenyl, R³=Trifluoromethyl) (0.360 g, 0.642 mmol). After cooling to about 0° C., sodium dihydrogenphosphate (0.770 g, 6.42 mmol), 2-methyl-but-2-ene (0.270 g, 3.85 mmol), and sodium chlorite (0.348 g, 3.85 mmol) were added sequentially. After about 30 min, the ice bath was removed and the reaction was allowed to warm to rt. After about 3 h, a 1:1 solution of sat. aq. $Na_2SO_3$ and sat. aq. NaCl (50 mL) was added. Water (30 mL) was added. The mixture was extracted with EtOAc (3×50 mL). The combined organics were dried over $MgSO_4$, filtered, and concentrated under reduced pressure. The residue was purified on silica gel (40 g) using a gradient of 0-20% EtOAc in heptane. The product fractions were combined and concentrated under reduced pressure to give rac-(3R,4aR,12bS)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carboxylic acid (43, R¹=4-Fluorophenyl, R³=Trifluoromethyl) (0.267 g, 72% yield); LC/MS, method 4, $R_t$=2.39 min.; MS m/z: 577 (M+H)⁺. ¹H NMR (400 MHz, DMSO) δ 12.57 (s, 1H), 8.26 (d, J=0.7 Hz, 1H), 7.90 (s, 1H), 7.82-7.75 (m, 2H), 7.54 (s, 1H), 7.45-7.35 (m, 2H), 2.95-2.71 (m, 2H), 2.60-2.48 (m, 1H), 2.42-2.15 (m, 4H), 2.03-1.78 (m, 3H), 1.73-1.52 (m, 2H), 1.34-1.20 (m, 1H), 0.99-0.90 (m, 9H), 0.69-0.59 (m, 6H).

Step 2: rac-(3R,4aR,12bS)—N-Cyclopropyl-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carboxamide (44, R¹=4-Fluorophenyl, R²'=Cyclopropyl, R³=Trifluoromethyl)

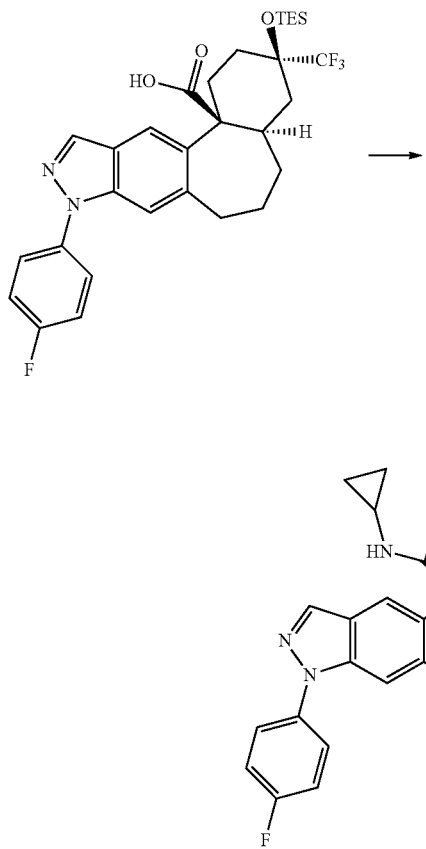

1-[Bis(dimethylamino)methylene]-1H-1,2,3-triazolo[4,5-b]pyridinium 3-oxide hexafluorophosphate (0.201 g, 0.530 mmol) was added to a solution of rac-(3R,4aR,12bS)-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carb oxylic acid (43, R¹=4-Fluorophenyl, R³=Trifluoromethyl) (0.235 g, 0.407 mmol), cyclopropanamine (0.093 g, 1.6 mmol), N-ethyl-N,N-diisopropylethylamine (0.285 mL, 1.63 mmol), DCM (5 mL), and DMF (1 mL). After about 24 h, 1-[bis(dimethylamino)methylene]-1H-1,2,3-triazolo[4,5-b]pyridinium 3-oxide hexafluorophosphate (0.020 g, 0.053 mmol) was added. After about 24 h, the reaction mixture was partitioned between DCM (50 mL) and sat. aq. NaHCO₃ (10 mL). The organic layer was washed with water (10 mL), dried over MgSO₄, filtered, and concentrated under reduced pressure. The residue was purified on silica gel (40 g) using a gradient of 0-17% EtOAc in heptane. The product fractions were combined and concentrated under reduced pressure to give rac-(3R,4aR,12bS)—N-cyclopropyl-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carboxamide (44, R¹=4-Fluorophenyl, R²'=Cyclopropyl, R³=Trifluoromethyl) (0.230 g. 92% yield); LC/MS, method 4, R$_t$=2.65 min.; MS m/z: 616 (M+H)⁺. ¹H NMR (400 MHz, CDCl₃) δ 8.16 (d, J=0.9 Hz 1H), 7.86 (s, 1H), 7.73-7.65 (m, 2H), 7.45 (s, 1H), 7.29-7.22 (m, 2H), 4.99 (s, 1H), 2.93-2.72 (m, 2H), 2.72-2.46 (m, 4H), 2.26-2.08 (m, 2H), 2.08-1.87 (m, 3H), 1.75-1.63 (m, 2H), 1.42-1.29 (m, 1H), 1.05-0.96 (m, 9H), 0.78-0.60 (m, 8H), 0.32-0.15 (m, 2H).

Step 3: (3R,4aR,12bS)—N-Cyclopropyl-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carb oxamide (45, R¹=4-Fluorophenyl, R²'=Cyclopropyl, R³=Trifluoromethyl) and (3S,4aS,12bR)—N-cyclopropyl-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carboxamide (45, R¹=4-Fluorophenyl, R²'=cyclopropyl, R³=Trifluoromethyl)

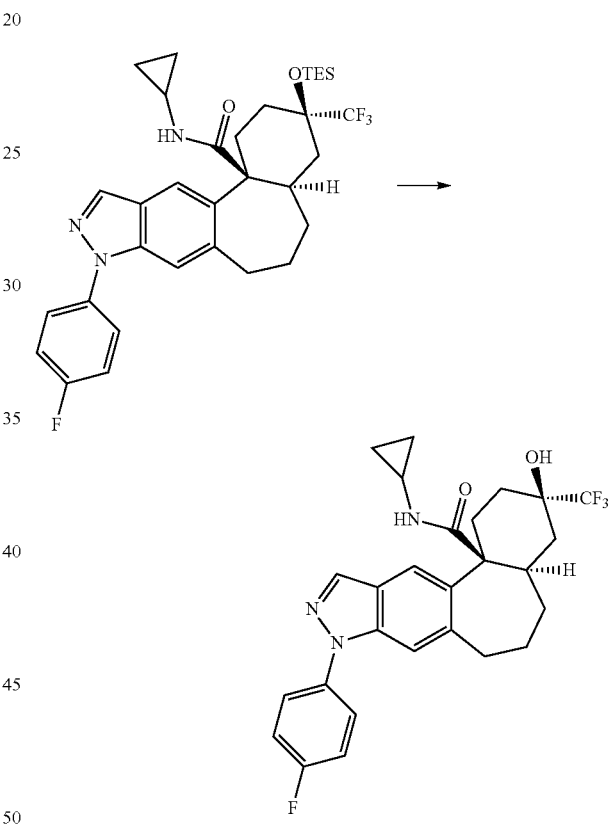

TBAF (1 M solution in THF, 0.560 mL, 0.560 mmol) was added to a solution of rac-(3R,4aR,12bS)—N-cyclopropyl-9-(4-fluorophenyl)-3-((triethylsilyl)oxy)-3-(trifluoromethyl)-1,2,3,4,4a,5,6,7,9,12b-decahydrobenzo[6,7]cyclohepta[1,2-f]indazole-12b-carboxamide (44, R¹=4-Fluorophenyl, R²'=Cyclopropyl, R³=Trifluoromethyl) (0.230 g, 0.374 mmol) and DCM (6 mL). After about 1 h, TBAF (1 M solution in THF, 0.30 mL, 0.30 mmol) was added. After about 30 min, DCM (50 mL) was added. The solution was washed with water (4×20 mL) and sat. aq. NaCl (20 mL). The organic layer was dried over MgSO₄, filtered, and concentrated under reduced pressure. The residue was loaded onto silica gel (6 g) and purified on silica gel (40 g) using a gradient of 0-30% EtOAc in DCM. The product fractions were combined and concentrated to give rac-(3R,4aR,12bS)—N-cyclopropyl-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carboxamide (45, R¹=4-Fluorophenyl, R²'=Cyclopropyl, R³=Trifluoromethyl) (0.150 g, 78% yield); LC/MS, method 3, $R_f$=2.46 min.; MS m/z: 502 (M+H)⁺. ¹H NMR (400 MHz, DMSO) δ 8.31 (d, J=0.8 Hz, 1H), 7.88 (s, 1H), 7.84-7.74 (m, 2H), 7.57 (s, 1H), 7.45-7.36 (m, 2H), 6.37 (d, J=3.8 Hz, 1H), 5.89 (s, 1H), 2.90-2.64 (m, 2H), 2.63-2.50 (m, 2H), 2.50-2.36 (m, 2H), 2.17-2.06 (m, 1H), 2.03-1.88 (m, 2H), 1.81-1.66 (m, 2H), 1.58-1.35 (m, 2H), 1.32-1.13 (m, 1H), 0.56-0.40 (m, 2H), 0.37-0.15 (m, 2H).

The enantiomers were separated using Preparative Chiral Purification method 14. Fractions from the first peak eluted were combined and concentrated under reduced pressure then lyophilized to give (3R,4aR,12bS)—N-cyclopropyl-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carboxamide (45, R¹=4-Fluorophenyl, R²'=Cyclopropyl, R³=Trifluoromethyl) (0.070 g, 40% yield); LC/MS, method 2, $R_f$=2.56 min.; MS m/z: 502 (M+H)⁺. Sign of rotation is negative. LC/MS, method 3, $R_f$=2.46 min.; MS m/z: 502 (M+H)⁺. ¹H NMR (400 MHz, DMSO) δ 8.31 (d, J=0.8 Hz, 1H), 7.88 (s, 1H), 7.84-7.74 (m, 2H), 7.57 (s, 1H), 7.45-7.36 (m, 2H), 6.37 (d, J=3.8 Hz, 1H), 5.89 (s, 1H), 2.90-2.64 (m, 2H), 2.63-2.50 (m, 2H), 2.50-2.36 (m, 2H), 2.17-2.06 (m, 1H), 2.03-1.88 (m, 2H), 1.81-1.66 (m, 2H), 1.58-1.35 (m, 2H), 1.32-1.13 (m, 1H), 0.56-0.40 (m, 2H), 0.37-0.15 (m, 2H).

Fractions from the second peak eluted were combined and concentrated under reduced pressure then lyophilized to give (3S,4aS,12bR)—N-cyclopropyl-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carboxamide (45, R¹=4-Fluorophenyl, R²'=Cyclopropyl, R³=Trifluoromethyl) (0.070 g, 40% yield); LC/MS, method 2, $R_f$=2.56 min.; MS m/z: 502 (M+H)⁺. Sign of rotation is positive. LC/MS, method 3, $R_f$=2.46 min.; MS m/z: 502 (M+H)⁺. ¹H NMR (400 MHz, DMSO) δ 8.31 (d, J=0.8 Hz, 1H), 7.88 (s, 1H), 7.84-7.74 (m, 2H), 7.57 (s, 1H), 7.45-7.36 (m, 2H), 6.37 (d, J=3.8 Hz, 1H), 5.89 (s, 1H), 2.90-2.64 (m, 2H), 2.63-2.50 (m, 2H), 2.50-2.36 (m, 2H), 2.17-2.06 (m, 1H), 2.03-1.88 (m, 2H), 1.81-1.66 (m, 2H), 1.58-1.35 (m, 2H), 1.32-1.13 (m, 1H), 0.56-0.40 (m, 2H), 0.37-0.15 (m, 2H).

Scheme 8:

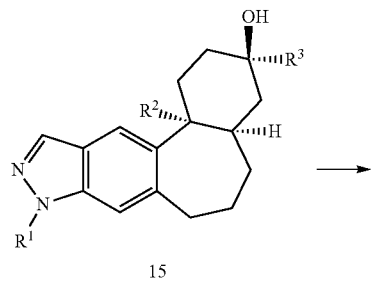

15

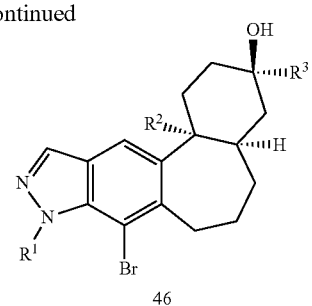

46

Example #92

(3R,4aR,12bS)-8-Bromo-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol (46, R¹=4-Fluorophenyl, R²=Ethyl, R³=Trifluoromethyl)

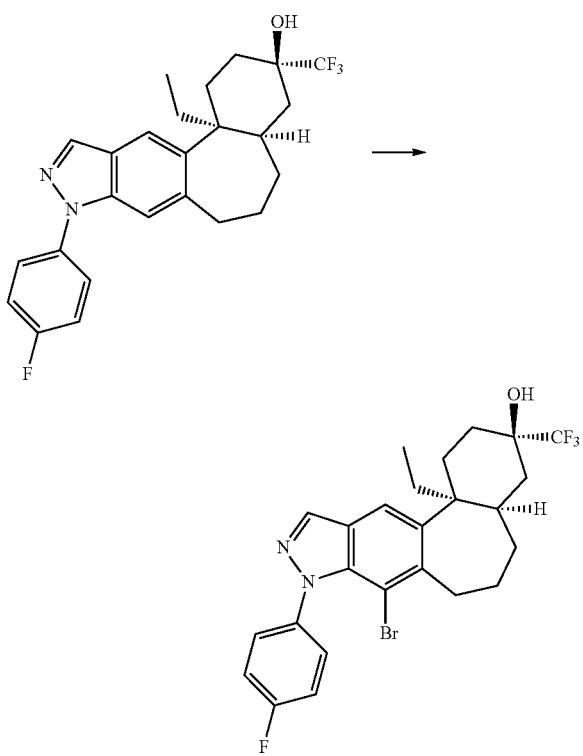

NBS (0.011 g, 0.064 mmol) was added to a solution of (3R,4aR,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol (15, R¹=4-Fluorophenyl, R²=Ethyl, R³=Trifluoromethyl) (0.022 g, 0.049 mmol) in DMF (0.5 mL) and the mixture was heated to about 60° C. for about 3 h. After cooling to rt, the reaction was quenched with ice (5 g). Sat. Aq. Na₂CO₃ (10 mL) and EtOAc (20 mL) were added. The layers were separated and the organic layer was washed with water (10 mL) then dried over MgSO₄, filtered and concentrated under reduced pressure. The residue was purified on silica gel (4 g) using a gradient of 0-27% EtOAc in heptane. Product fractions were combined and concentrated under reduced pressure. The residue was lyophilized to yield (3R, 4aR,12bS)-8-bromo-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol (46, R¹=4-Fluorophenyl, R²=Ethyl, R³=Trifluoromethyl) (0.013 g, 49% yield); LC/MS, method 2, $R_t$=3.13 min.; MS m/z: 525 and 527 (M+H)⁺. ¹H NMR (400 MHz, DMSO) δ 8.29 (s, 1H), 7.90 (s, 1H), 7.57-7.50 (m, 2H), 7.38-7.30 (m, 2H), 5.56 (s, 1H), 3.56-3.44 (m, 1H), 3.03-2.88 (m, 1H), 2.43-2.18 (m, 2H), 2.16-1.66 (m, 7H), 1.64-1.38 (m, 4H), 0.68 (t, J=7.3 Hz, 3H).

Scheme 9:

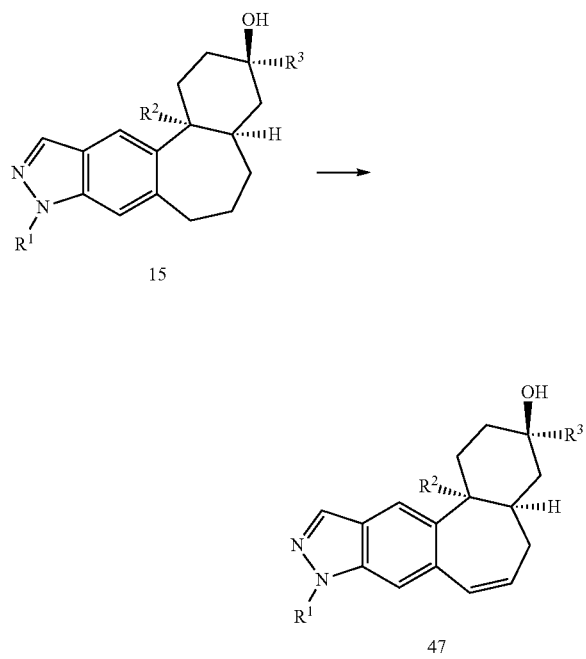

Example #93

(3R,4aR,12bS)-12b-Ethyl-9-(4-fluorophenyl)-3-(trifluoromethyl)-1,2,3,4,4a,5,9,12b-octahydrobenzo[6,7]cyclohepta[1,2-f]indazol-3-ol (47, R¹=4-Fluorophenyl, R²=Ethyl, R³=Trifluoromethyl)

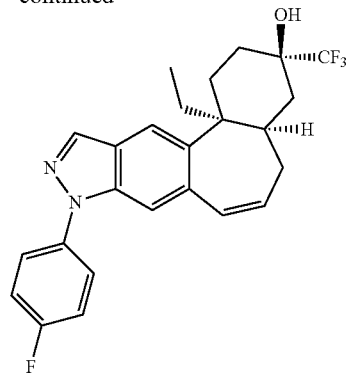

(3R,4aR,12bS)-12b-Ethyl-9-(4-fluorophenyl)-3-(trifluoromethyl)-1,2,3,4,4a,5,6,7,9,12b-decahydrobenzo[6,7]cyclohepta[1,2-f]indazol-3-ol (15, R¹=4-Fluorophenyl, R²=Ethyl, R³=Trifluoromethyl) (0.030 g, 0.067 mmol), NBS (0.013 g, 0.074 mmol), and AIBN (0.0011 g, 0.0067 mmol) were dissolved in CCl₄ (1 mL) and then mixed at reflux for about 2 h. The reaction was diluted with DCM (10 mL) and then washed with water (2×3 mL). The organic layer was dried over MgSO₄, filtered and concentrated under reduced pressure. The residue was purified on silica gel (4 g) using a gradient of 0-30% EtOAc in heptane. Product fractions were combined and concentrated under reduced pressure to dryness. The residue was purified on silica gel (12 g) using a gradient of 0-20% EtOAc in heptane. Product fractions were combined and concentrated under reduced pressure to dryness. The residue was further purified by reverse phase HPLC (Atlantis Prep T3 OBD (Waters), 5 μm particle size 19×100 mm) using a gradient of 10-95% MeCN in aq. NH₄OAc (50 mM). The fractions containing product were combined and concentrated under reduced pressure to remove the organic volatiles. The resulting mixture was frozen then lyophilized to give (3R,4aR,12bS)-12b-ethyl-9-(4-fluorophenyl)-3-(trifluoromethyl)-1,2,3,4,4a,5,9,12b-octahydrobenzo[6,7]cyclohepta[1,2-f]indazol-3-ol (47, R¹=4-Fluorophenyl, R²=Ethyl, R³=Trifluoromethyl) (0.0050 g, 16% yield); LC/MS, method 2, $R_t$=3.00 min.; MS m/z: 445 (M+H)⁺. ¹H NMR (400 MHz, DMSO) δ 8.33 (s, 1H), 7.87 (s, 1H), 7.85-7.79 (m, 2H), 7.72 (s, 1H), 7.44-7.37 (m, 2H), 6.58 (dd, J=12.4, 2.5 Hz, 1H), 5.84-5.76 (m, 1H), 5.59 (s, 1H), 2.84-2.73 (m, 1H), 2.64-2.56 (m, 1H), 2.23-2.08 (m, 2H), 2.06-1.96 (m, 1H), 1.78-1.38 (m, 6H), 0.65 (t, J=7.3 Hz, 3H).

Scheme 10:

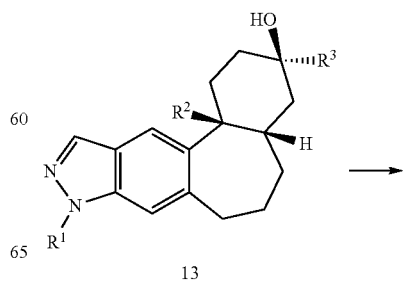

-continued

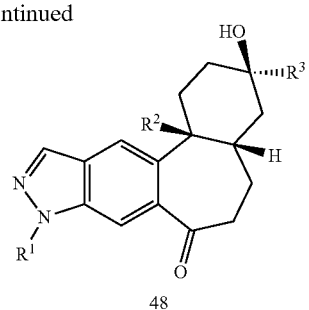

48

Example #94

(3R,4aS,12bS)-3-Ethyl-9-(4-fluorophenyl)-3-hydroxy-12b-(pyridin-2-ylmethyl)-1,2,3,4,4a,5,6,12b-octahydrobenzo[6,7]cyclohepta[1,2-f]indazol-7(9H)-one (48, R$^1$=4-Fluorophenyl, R$^2$=Pyridyin-2-ylmethyl, R$^3$=Ethyl)

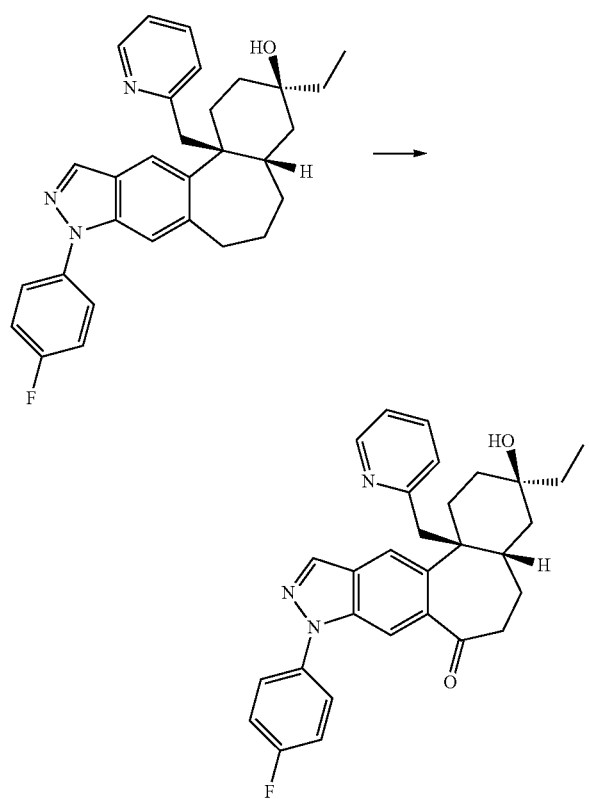

Potassium iodide (1 M solution in water, 0.365 mL, 0.365 mmol) was added to a solution of (3R,4aS,12bS)-3-ethyl-9-(4-fluorophenyl)-12b-(pyridin-2-ylmethyl)-1,2,3,4,4a,5,6,7,9,12b-decahydrobenzo[6,7]cyclohepta[1,2-f]indazol-3-ol (13, R$^1$=4-Fluorophenyl, R$^2$=Pyridyin-2-ylmethyl, R$^3$=Ethyl) (0.143 g, 0.305 mmol) and MeCN (3 mL) under air. 2-Hydroperoxy-2-methylpropane (0.717 mL, 5.18 mmol) was added dropwise over about 5 min. The reaction was mixed at rt for about 24 h. The reaction was quenched with sat. aq. sodium sulfite (5 mL) and then a 1:1 solution of sat. aq. NaHCO$_3$/water (5 mL) was added. The solution was extracted with EtOAc (3×5 mL). The combined organics were dried over MgSO$_4$, filtered, and concentrated under reduced pressure. The residue was purified on silica gel (12 g) using a gradient of 50-86% EtOAc in heptane. Product fractions were combined and concentrated under reduced pressure. The residue was further purified by reverse phase HPLC (Atlantis Prep T3 OBD (Waters), 5 µm particle size 19×100 mm) using a gradient of 0-95% MeCN in aqueous NH$_4$OAc (50 mM). The fractions containing product were combined and concentrated under reduced pressure to remove the organic volatiles. The resulting mixture was frozen then lyophilized to give (3R,4aS,12bS)-3-ethyl-9-(4-fluorophenyl)-3-hydroxy-12b-(pyridin-2-ylmethyl)-1,2,3,4,4a,5,6,12b-octahydrobenzo[6,7]cyclohepta[1,2-f]indazol-7(9H)-one (48, R$^1$=4-Fluorophenyl, R$^2$=Pyridin-2-ylmethyl, R$^3$=Ethyl) (0.008 g, 6% yield). LC/MS, method 2, R$_t$=2.32 min.; MS m/z: 484 (M+H)$^+$. $^1$H NMR (400 MHz, DMSO) δ 8.38 (d, J=4.8 Hz, 1H), 8.30 (d, J=0.9 Hz, 1H), 7.88-7.78 (m, 2H), 7.69 (s, 1H), 7.54 (s, 1H), 7.48-7.41 (m, 2H), 7.35 (td, J=7.6, 1.8 Hz, 1H), 7.10-7.04 (m, 1H), 6.34-6.30 (m, 1H), 3.95 (s, 1H), 3.02-2.86 (m, 3H), 2.74-2.64 (m, 2H), 2.47-2.43 (m, 1H), 2.12-2.03 (m, 1H), 2.02-1.90 (m, 1H), 1.73-1.62 (m, 1H), 1.55-1.46 (m, 2H), 1.39-1.25 (m, 2H), 1.20 (q, J=7.8 Hz, 2H), 0.73 (t, J=7.4 Hz, 3H).

An additional example, prepared in a manner similar to the preparation of Example #92 is listed in Table 8.

TABLE 8

| Ex. # | Reactant | Reagent | Product structure | LC/MS method/ R$_t$ MH$^+$ |
|---|---|---|---|---|
| 95 | 13 (R$^1$ = 4-Fluorophenyl, R$^2$ = Pyridin-2-ylmethyl, R$^3$ = Ethyl) | 2-Hydroperoxy-2-methylpropane and potassium iodide | 48 (3S,4aR,12bR) (R$^1$ = 4-Fluorophenyl, R$^2$ = Pyridin-2-ylmethyl, R$^3$ = Ethyl) | 2 2.32 min 484 MH$^+$ |

Scheme 11:

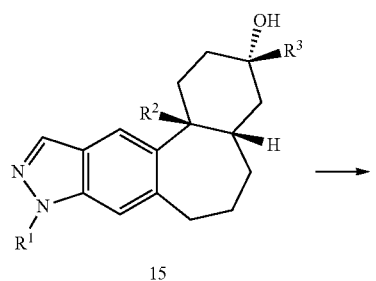

15

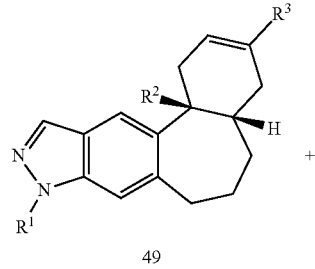

49

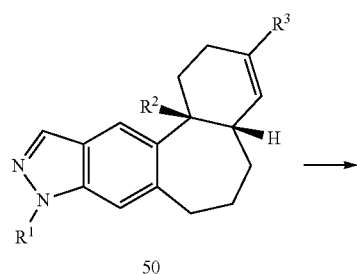

50

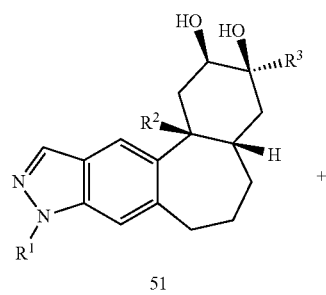

51

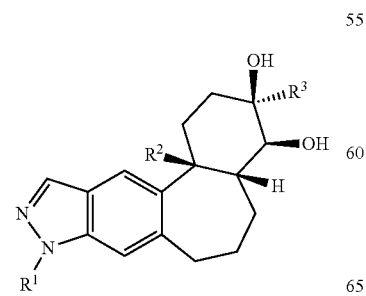

52

Example #96, #97, #98 and #99

(3R,4S,4aR,12bR)-12b-Ethyl-9-(4-fluorophenyl)-3-(trifluoromethyl)-1,2,3,4,4a,5,6,7,9,12b-decahydrobenzo[6,7]cyclohepta[1,2-f]indazole-3,4-diol (52, R¹=4-Fluorophenyl, R²=Ethyl, R³=Trifluoromethyl), (3S,4R,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazole-3,4-diol (52, R¹=4-Fluorophenyl, R²=Ethyl, R³=Trifluoromethyl), (2R,3S,4aS,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol (51, R¹=4-Fluorophenyl, R²=Ethyl, R³=Trifluoromethyl), and (2S,3R,4aR,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol (51, R¹=4-Fluorophenyl, R²=Ethyl, R³=Trifluoromethyl)

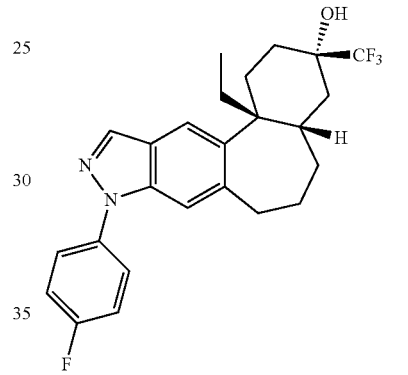

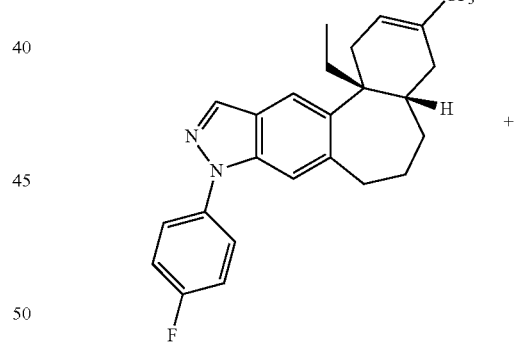

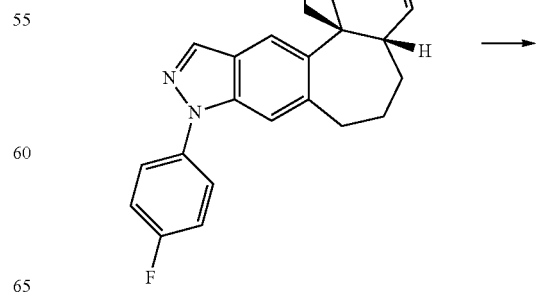

-continued

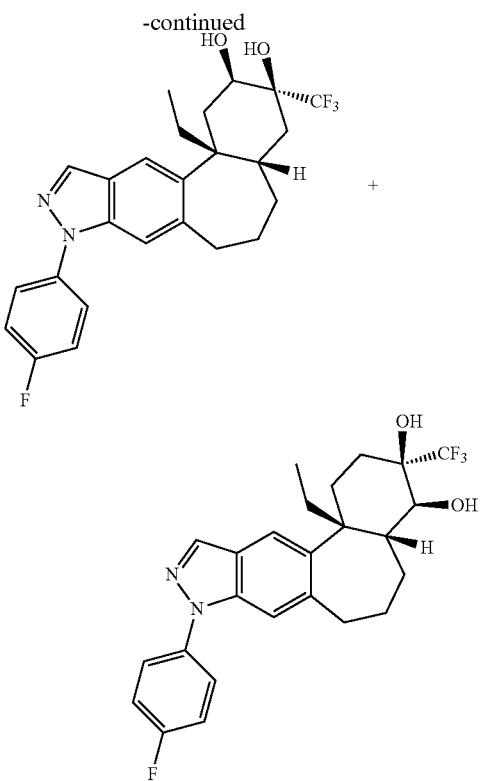

To a vessel containing pyridine (0.886 g, 11.2 mmol) was added rac-(3S,4aS,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol (15, R$^1$=4-Fluorophenyl, R$^2$=Ethyl, R$^3$=Trifluoromethyl) (0.100 g, 0.224 mmol), and thionyl chloride (0.480 g, 4.03 mmol). The reaction was warmed to about 80° C. for about 3 h. The reaction was cooled to rt, slowly quenched with sat. aq. NaHCO$_3$ (10 mL) and then extracted with EtOAc (3×10 mL). The combined organics were dried over MgSO$_4$, filtered and concentrated under reduced pressure. The residue was purified on silica gel (12 g) using a gradient of 0-30% EtOAc in heptane. The product fractions were concentrated to give about a 2.5:1 mixture of rac-(4aS,12bR)-12b-ethyl-9-(4-fluorophenyl)-3-(trifluoromethyl)-1,4,4a,5,6,7,9,12b-octahydrobenzo[6,7]cyclohepta[1,2-f]indazole and rac-(4aS,12bR)-12b-ethyl-9-(4-fluorophenyl)-3-(trifluoromethyl)-1,2,4a,5,6,7,9,12b-octahydrobenzo[6,7]cyclohepta[1,2-f]indazole as a colorless oil (0.048 g, 50% yield). LC/MS, method 3, R$_f$=3.21 min.; MS m/z: 429 (M+H)$^+$. Potassium osmate dihydrate (0.081 g, 0.22 mmol) and 4-methylmorpholine N-oxide (0.771 g, 6.58 mmol) were added sequentially, each in one portion, to a biphasic solution of a mixture of rac-(4aS,12bR)-12b-ethyl-9-(4-fluorophenyl)-3-(trifluoromethyl)-1,4,4a,5,6,7,9,12b-octahydrobenzo[6,7]cyclohepta[1,2-f]indazole and rac-(4aS,12bR)-12b-ethyl-9-(4-fluorophenyl)-3-(trifluoromethyl)-1,2,4a,5,6,7,9,12b-octahydrobenzo[6,7]cyclohepta[1,2-f]indazole (0.940 g, 2.194 mmol), THF (15 mL), and water (7.5 mL). After about 20 h, potassium osmate dihydrate (0.081 g, 0.22 mmol) and 4-methylmorpholine N-oxide (0.771 g, 6.58 mmol) were added sequentially, each in one portion. The reaction was warmed to about 40° C. for about 30 h. The reaction was allowed to cool to rt and after about 3 days at rt, water (300 mL) was added. The solution was extracted with DCM (2×200 mL). The combined organics were dried over MgSO$_4$, filtered, and concentrated under reduced pressure. The residue was purified on silica gel (120 g) using a gradient of 0-15% EtOAc in DCM. The product fractions were concentrated under reduced pressure to afford rac-(3R,4S,4aR,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazole-3,4-diol (52, R$^1$=4-Fluorophenyl, R$^2$=Ethyl, R$^3$=Trifluoromethyl) (0.520 g, 51% yield) LC/MS, method 3, R$_f$=2.71 min.; MS m/z: 463 (M+H)$^+$. $^1$H NMR (400 MHz, DMSO) δ 8.27 (s, 1H), 7.85-7.78 (m, 2H), 7.71 (s, 1H), 7.60 (s, 1H), 7.44-7.37 (m, 2H), 5.48 (s, 1H), 4.68 (d, J=9.0 Hz, 1H), 3.30-3.27 (m, 1H), 3.12-2.98 (m, 2H), 2.46-2.36 (m, 1H), 2.28-2.16 (m, 2H), 2.15-2.04 (m, 1H), 1.96-1.77 (m, 3H), 1.77-1.42 (m, 4H), 0.59 (t, J=7.3 Hz, 3H) and rac-(2R,3S,4aS,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol (51, R$^1$=4-Fluorophenyl, R$^2$=Ethyl, R$^3$=Trifluoromethyl) (0.280 g, 27%, yield) LC/MS, method 3, R$_f$=2.74 min.; MS m/z: 463 (M+H)$^+$. $^1$H NMR (400 MHz, DMSO) δ 8.31 (s, 1H), 7.87-7.75 (m, 3H), 7.59 (s, 1H), 7.45-7.36 (m, 2H), 5.52 (s, 1H), 4.96 (d, J=6.6 Hz, 1H), 4.11-3.99 (m, 1H), 3.09-2.93 (m, 2H), 2.56-2.51 (m, 1H), 2.35-2.17 (m, 2H), 2.16-2.03 (m, 1H), 1.83-1.71 (m, 1H), 1.71-1.58 (m, 2H), 1.54-1.20 (m, 4H), 0.61 (t, J=7.3 Hz, 3H).

The enantiomers of rac-(3R,4S,4aR,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazole-3,4-diol (52, R$^1$=4-Fluorophenyl, R$^2$=Ethyl, R$^3$=Trifluoromethyl) were separated using Preparative Chiral Purification method 15.

Fractions from the first peak eluted were combined and concentrated under reduced pressure then lyophilized to give (3S,4R,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazole-3,4-diol (52, R$^1$=4-Fluorophenyl, R$^2$=Ethyl, R$^3$=Trifluoromethyl) (0.018 g, 36% yield). LC/MS, method 2, R$_f$=2.72 min.; MS m/z: 463 (M+H)$^+$. $^1$H NMR (400 MHz, DMSO) δ 8.31 (s, 1H), 7.87-7.75 (m, 3H), 7.59 (s, 1H), 7.45-7.36 (m, 2H), 5.52 (s, 1H), 4.96 (d, J=6.6 Hz, 1H), 4.11-3.99 (m, 1H), 3.09-2.93 (m, 2H), 2.56-2.51 (m, 1H), 2.35-2.17 (m, 2H), 2.16-2.03 (m, 1H), 1.83-1.71 (m, 1H), 1.71-1.58 (m, 2H), 1.54-1.20 (m, 4H), 0.61 (t, J=7.3 Hz, 3H).

Fractions from the second peak eluted were combined and concentrated under reduced pressure then lyophilized to give (3R,4S,4aR,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazole-3,4-diol (52, R$^1$=4-Fluorophenyl, R$^2$=Ethyl, R$^3$=Trifluoromethyl) (0.014 g, 28% yield). LC/MS, method 2, R$_f$=2.72 min.; MS m/z: 463 (M+H)$^+$. $^1$H NMR (400 MHz, DMSO) δ 8.31 (s, 1H), 7.87-7.75 (m, 3H), 7.59 (s, 1H), 7.45-7.36 (m, 2H), 5.52 (s, 1H), 4.96 (d, J=6.6 Hz, 1H), 4.11-3.99 (m, 1H), 3.09-2.93 (m, 2H), 2.56-2.51 (m, 1H), 2.35-2.17 (m, 2H), 2.16-2.03 (m, 1H), 1.83-1.71 (m, 1H), 1.71-1.58 (m, 2H), 1.54-1.20 (m, 4H), 0.61 (t, J=7.3 Hz, 3H).

The enantiomers of rac-(2R,3S,4aS,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol (51, R$^1$=4-Fluorophenyl, R$^2$=Ethyl, R$^3$=Trifluoromethyl) were separated using Preparative Chiral Purification method 16.

Fractions from the first peak eluted were combined and concentrated under reduced pressure then lyophilized to give (2S,3R,4aR,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol (51, R$^1$=4-Fluorophenyl, R$^2$=Ethyl, R$^3$=Trifluoromethyl) (0.009 g, 10% yield). LC/MS, method 2, R$_f$=2.74 min.; MS m/z: 463 (M+H)$^+$. $^1$H NMR (400 MHz, DMSO) δ 8.31 (s, 1H), 7.87-7.75 (m, 3H), 7.59 (s, 1H), 7.45-7.36 (m, 2H), 5.52 (s, 1H), 4.96 (d, J=6.6 Hz, 1H), 4.11-3.99 (m, 1H), 3.09-2.93 (m, 2H), 2.56-2.51 (m, 1H), 2.35-2.17 (m, 2H), 2.16-2.03 (m, 1H), 1.83-1.71 (m, 1H), 1.71-1.58 (m, 2H), 1.54-1.20 (m, 4H), 0.61 (t, J=7.3 Hz, 3H).

Fractions from the second peak eluted were combined and concentrated under reduced pressure then lyophilized to give (2R,3S,4aS,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol (51, $R^1$=4-Fluorophenyl, $R^2$=Ethyl, $R^3$=Trifluoromethyl) (0.017 g, 19% yield). LC/MS, method 2, $R_t$=2.74 min.; MS m/z: 463 (M+H)⁺. ¹H NMR (400 MHz, DMSO) δ 8.31 (s, 1H), 7.87-7.75 (m, 3H), 7.59 (s, 1H), 7.45-7.36 (m, 2H), 5.52 (s, 1H), 4.96 (d, J=6.6 Hz, 1H), 4.11-3.99 (m, 1H), 3.09-2.93 (m, 2H), 2.56-2.51 (m, 1H), 2.35-2.17 (m, 2H), 2.16-2.03 (m, 1H), 1.83-1.71 (m, 1H), 1.71-1.58 (m, 2H), 1.54-1.20 (m, 4H), 0.61 (t, J=7.3 Hz, 3H).

Scheme 12:

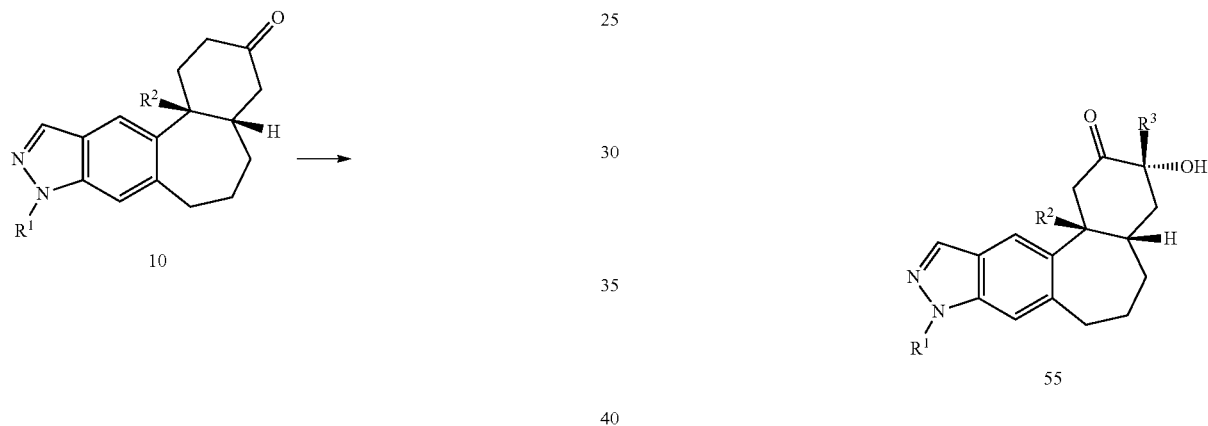

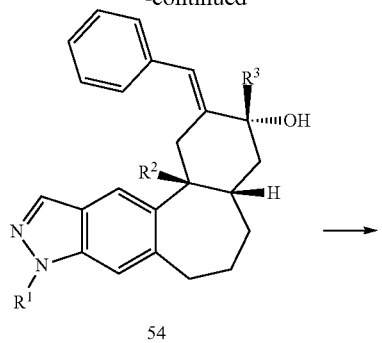

Example 100 rac-(3R,4aS,12bR)-12b-Ethyl-9-(4-fluorophenyl)-3-hydroxy-3-methyl-1,3,4,4a,5,6,7,12b-octahydrobenzo[6,7]cyclohepta[1,2-f]indazol-2(9H)-one (55, $R^1$=4-Fluorophenyl, $R^2$=Ethyl, $R^3$=Methyl)

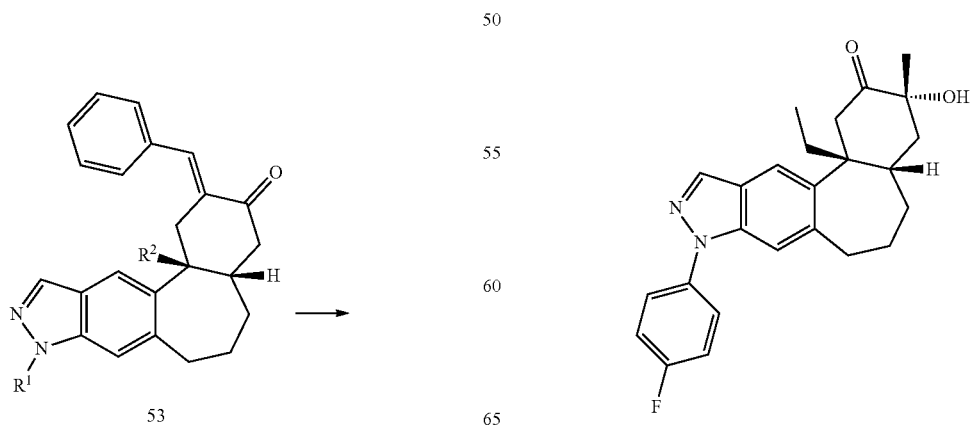

Step 1: rac-(4aS,12bR,E)-2-Benzylidene-12b-ethyl-9-(4-fluorophenyl)-1,4,4a,5,6,7,9,12b-octahydrobenzo[6,7]cyclohepta[1,2-f]indazol-3(2H)-one (53, R¹=4-Fluorophenyl, R²=Ethyl)

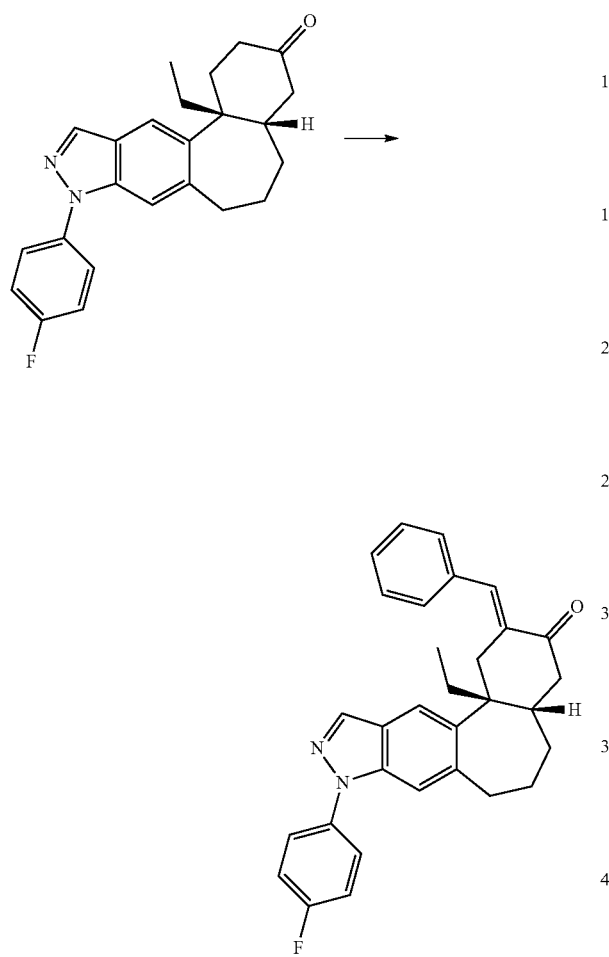

Sodium (0.092 g, 4.0 mmol) was added to ethanol (20 mL) and mixed at rt until the sodium was completely consumed. A solution of rac-(4aS,12bR)-12b-ethyl-9-(4-fluorophenyl)-1,4,4a,5,6,7,9,12b-octahydrobenzo[6,7]cyclohepta[1,2-f]indazol-3 (2H)-one (10, R¹=4-Fluorophenyl, R²=Ethyl) (1.00 g, 2.66 mmol) in THF (10 mL) was added in one portion. Benzaldehyde (0.310 g, 2.92 mmol) was added and the reaction mixture was stirred at rt for about 3 h. The organic volatiles were removed under reduced pressure. The residue was partitioned between EtOAc (70 mL) and water (50 mL). The organic layer was dried over MgSO₄, filtered, and concentrated under reduced pressure. The residue was purified on silica gel (40 g) using a gradient of 5-18% EtOAc in heptane. The product fractions were combined and concentrated under reduced pressure to give rac-(4aS,12bR,E)-2-benzylidene-12b-ethyl-9-(4-fluorophenyl)-1,4,4a,5,6,7,9,12b-octahydrobenzo[6,7]cyclohepta[1,2-f]indazol-3(2H)-one (53, R¹=4-Fluorophenyl, R²=Ethyl) (1.00 g, 81% yield); LC/MS, method 3, R$_f$=3.11 min.; MS m/z: 465 (M+H)⁺. ¹H NMR (400 MHz, DMSO) δ 7.98-7.96 (m, 1H), 7.80-7.73 (m, 2H), 7.73-7.67 (m, 2H), 7.62-7.55 (m, 3H), 7.53-7.46 (m, 2H), 7.44-7.35 (m, 2H), 6.99 (s, 1H), 3.72-3.62 (m, 1H), 3.27-3.15 (m, 1H), 3.01-2.91 (m, 1H), 2.90-2.81 (m, 1H), 2.58-2.52 (m, 1H), 2.48-2.37 (m, 1H), 2.36-2.25 (m, 1H), 2.25-2.14 (m, 1H), 2.11-1.97 (m, 1H), 1.87-1.45 (m, 4H), 0.65 (t, J=7.3 Hz, 3H).

Step 2: rac-(3R,4aS,12bR,E)-2-Benzylidene-12b-ethyl-9-(4-fluorophenyl)-3-methyl-1,2,3,4,4a,5,6,7,9,12b-decahydrobenzo[6,7]cyclohepta[1,2-f]indazol-3-ol (54, R¹=4-Fluorophenyl, R²=Ethyl, R³=Methyl)

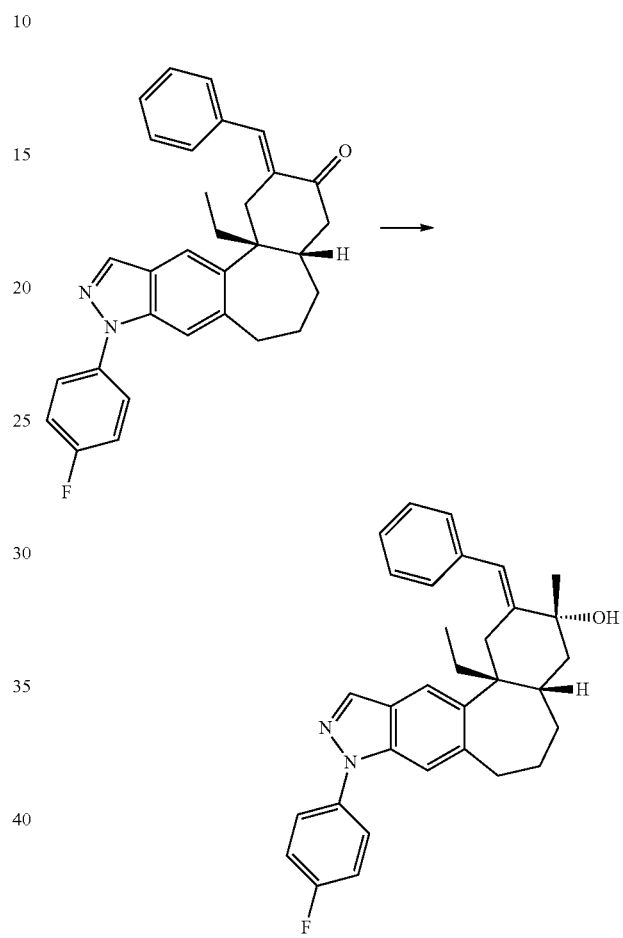

THF (2 mL) was added to cerium(III) chloride (0.130 g, 0.527 mmol). The suspension was warmed to about 50° C. for about 30 min then cooled to about −78° C. A solution of methylmagnesium bromide (3.0 M solution in Et₂O, 0.165 mL, 0.495 mmol) and THF (2 mL) was added dropwise and the reaction mixture was stirred for about 15 min. A solution of rac-(4aS,12bR,E)-2-benzylidene-12b-ethyl-9-(4-fluorophenyl)-1,4,4a,5,6,7,9,12b-octahydrobenzo[6,7]cyclohepta[1,2-f]indazol-3 (2H)-one (53, R¹=4-Fluorophenyl, R²=Ethyl) (0.100 g, 0.215 mmol) and THF (2 mL) was added dropwise via syringe and the reaction was stirred at about −78° C. for about 1 h. Methylmagnesium bromide (3.0 M solution in Et₂O, 0.16 mL, 0.48 mmol) was added. After about 1 h, methylmagnesium bromide (3.0 M solution in Et₂O, 0.1 mL, 0.3 mmol) was added. After about 1 h, the reaction was quenched with MeOH (1 mL) maintaining an internal temperature of less than about −60° C. Sat. aq. NH₄Cl (2 mL), water (2 mL), and EtOAc (20 mL) were added and the mixture was allowed to warm to rt. EtOAc (50 mL) and water (20 mL) were added. The layers were separated and the aqueous layer was extracted with EtOAc (20 mL). The combined organics were dried over MgSO₄, filtered, and concentrated under reduced pressure. The residue was purified on silica gel (25 g) using a gradient of 0-10% EtOAc in heptane. The product fractions were combined and concentrated under reduced pressure to give rac-(3R,4aS,12bR,E)-2-benzylidene-12b-ethyl-9-(4-fluorophenyl)-3-methyl-1,2,3,4,4a, 5,6,7,9,12b-decahydrobenzo[6,7]cyclohepta[1,2-f]indazol-3-ol (54, R¹=4-Fluorophenyl, R²=Ethyl, R³=Methyl) (0.057 g, 55% yield); LC/MS, method 3, $R_t$=3.16 min.; MS m/z: 481 (M+H)⁺. ¹H NMR (400 MHz, DMSO) δ 7.76-7.70 (m, 2H), 7.64 (s, 1H), 7.62-7.55 (m, 2H), 7.46 (s, 1H), 7.43-7.35 (m, 5H), 6.86 (s, 1H), 6.80 (s, 1H), 4.57 (s, 1H), 3.63-3.53 (m, 1H), 3.06-2.86 (m, 2H), 2.36-1.99 (m, 4H), 1.81-1.61 (m, 2H), 1.61-1.42 (m, 3H), 1.39 (s, 3H), 1.30-1.22 (m, 1H), 0.51 (t, J=7.3 Hz, 3H).

Step 3: rac-(3R,4aS,12bR)-12b-Ethyl-9-(4-fluorophenyl)-3-hydroxy-3-methyl-1,3,4,4a,5,6,7,12b-octahydrobenzo[6,7]cyclohepta[1,2-f]indazol-2(9H)-one (55, R¹=4-Fluorophenyl, R²=Ethyl, R³=Methyl)

MgSO₄ and concentrated under reduced pressure. The residue was purified on silica gel (12 g) using a gradient of 5-25% EtOAc in heptane. The product fractions were combined and concentrated under reduced pressure. The residue was purified on silica gel (12 g) using a gradient of 5-25% EtOAc in heptane. The product fractions were combined, concentrated under reduced pressure, and lyophilized to give rac-(3R,4aS, 12bR)-12b-ethyl-9-(4-fluorophenyl)-3-hydroxy-3-methyl-1, 3,4,4a,5,6,7,12b-octahydrobenzo[6,7]cyclohepta[1,2-f]indazol-2(9H)-one (55, R¹=4-Fluorophenyl, R²=Ethyl, R³=Methyl) (0.010 g, 21% yield); LC/MS, method 2, $R_t$=2.78 min.; MS m/z: 407 (M+H)⁺. ¹H NMR (400 MHz, DMSO) δ 8.24 (d, J=0.5 Hz, 1H), 7.82-7.73 (m, 2H), 7.57 (s, 1H), 7.57 (s, 1H), 7.44-7.34 (m, 2H), 4.75 (s, 1H), 3.18-3.06 (m, 2H), 3.02-2.92 (m, 1H), 2.77-2.67 (m, 1H), 2.49-2.41 (m, 1H), 2.41-2.29 (m, 1H), 2.29-2.17 (m, 1H), 1.88-1.65 (m, 3H), 1.60-1.38 (m, 3H), 1.32 (s, 3H), 0.62 (t, J=7.4 Hz, 3H).

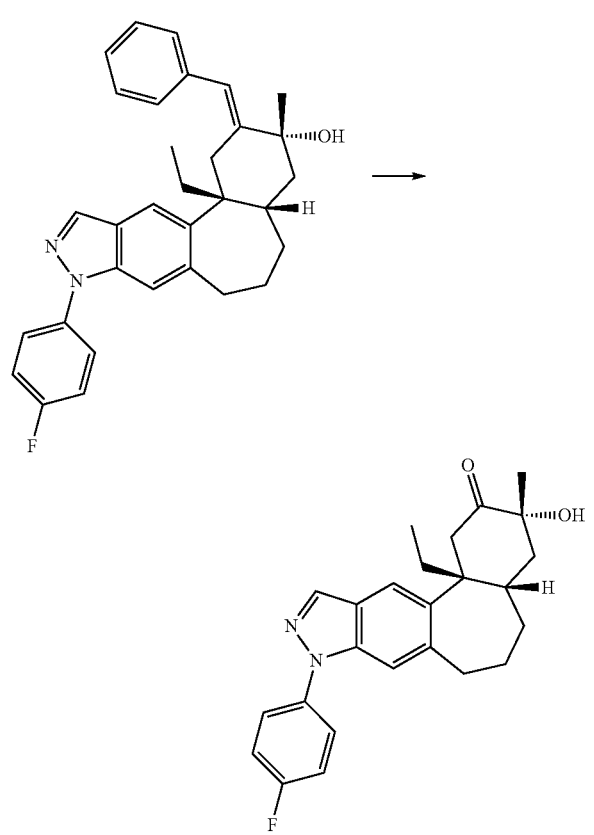

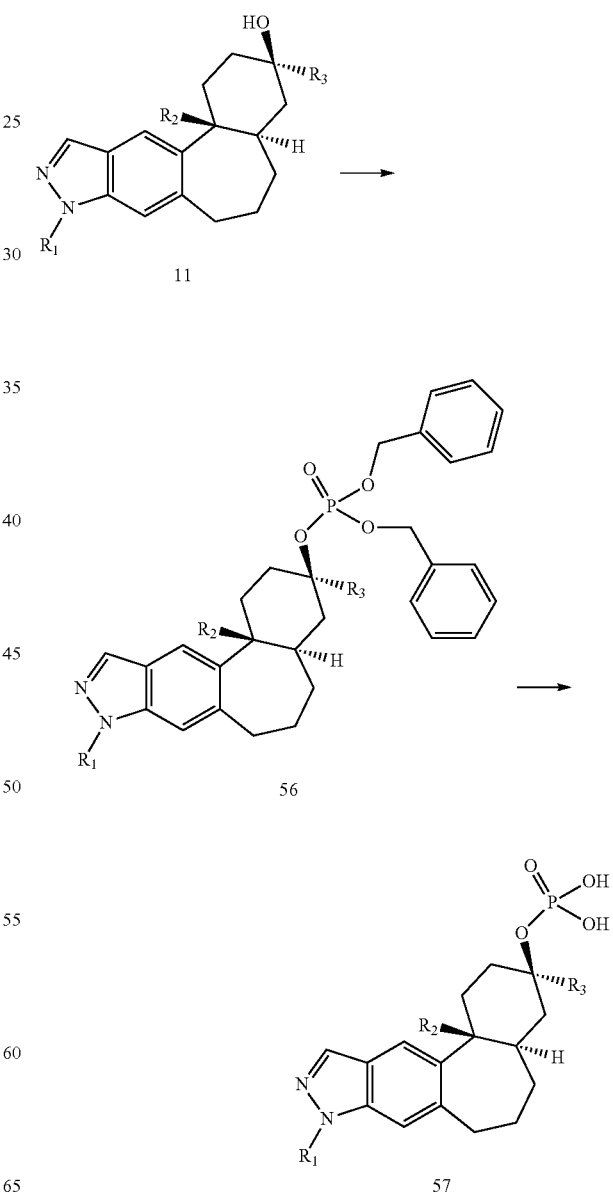

Scheme 13

DCM (5 mL) was added to rac-(3S,4aS,12bR,E)-2-benzylidene-12b-ethyl-9-(4-fluorophenyl)-3-methyl-1,2,3,4,4a, 5,6,7,9,12b-decahydrobenzo[6,7]cyclohepta[1,2-f]indazol-3-ol (54, R¹=4-Fluorophenyl, R²=Ethyl, R³=Methyl) (0.055 g, 0.11 mmol). The reaction was cooled to about −78° C. Ozone was bubbled through for about 2 min. A slurry of polymer bound triphenylphosphine (3 mmol/g, 0.25 g) in DCM (5 mL) was added. The cold bath was allowed to thaw to rt. After about 16 h, the mixture was filtered rinsing with 50% MeOH in DCM (40 mL). The filtrate was dried over

Example #101

(3S,4aS,12bS)-12b-Ethyl-9-(4-fluorophenyl)-3-(trifluoromethyl)-1,2,3,4,4a,5,6,7,9,12b-decahydrobenzo[6,7]cyclohepta[1,2-f]indazol-3-yl dihydrogen phosphate (57, R$^1$=4-Fluorophenyl, R$^2$=Ethyl, R$^3$=Trifluoromethyl)

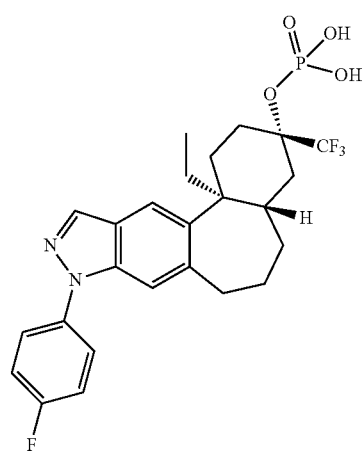 [SMILES: CC[C@]12CC[C@@](OP(=O)(O)O)(C(F)(F)F)C[C@@H]1CCCc1cc3c(cnn3-c3ccc(F)cc3)cc12]

Step #1: Dibenzyl((3S,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-yl)phosphate (56, R$^1$=4-Fluorophenyl, R$^2$=Ethyl, R$^3$=Trifluoromethyl)

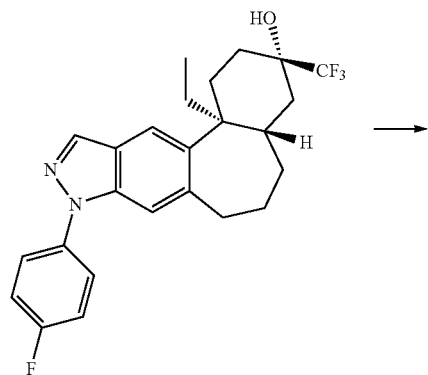

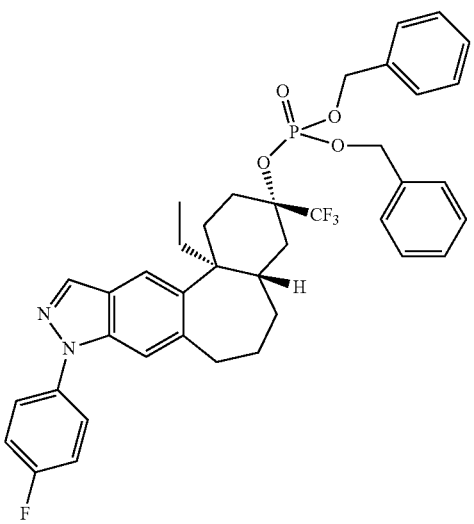

Dibenzyl diisopropylphosphoramidite (0.380 mL, 1.13 mmol) was added dropwise over about 10 min to a solution of (3S,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol (11, R$^1$=4-Fluorophenyl, R$^2$=Ethyl, R$^3$=Trifluoromethyl) (0.250 g, 0.560 mmol), 5-methyl-1H-tetrazole (0.169 g, 2.02 mmol), and DCM (3.10 mL) under a nitrogen atmosphere.

After 2 h, the solution was cooled to about 0° C. under air. H$_2$O$_2$ (30% aq. solution, 0.570 mL, 5.58 mmol) was added dropwise over about 20 min. After about 30 min, the ice bath was removed. After about 2 h, the reaction was diluted with DCM (20 mL) and water (20 mL), then the layers were separated. The organics were washed with water (10 mL) and sat. aq. NaCl (10 mL). The aqueous layers were extracted with DCM (5 mL). The combined organics were dried over Na$_2$SO$_4$, filtered and concentrated. The residue was purified on silica gel (40 g) using a gradient of 0-30% EtOAc in heptane. The fractions containing product were combined and concentrated under reduced pressure to afford dibenzyl ((3S,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-yl)phosphate (56, R$^1$=4-Fluorophenyl, R$^2$=Ethyl, R$^3$=Trifluoromethyl) (0.372 g, 94% yield) as a stick ivory foam. LC/MS, method 3, R$_t$=3.49 min, MS m/z 691 (M+H)$^+$. $^1$H NMR (400 MHz, DMSO) δ 8.24 (d, J=0.7 Hz, 1H), 7.84-7.75 (m, 2H), 7.82 (s, 1H), 7.56 (s, 1H), 7.49-7.29 (m, 12H), 5.17-5.01 (m, 4H), 3.22-3.10 (m, 1H), 2.98-2.88 (m, 1H), 2.38-1.87 (m, 8H), 1.86-1.54 (m, 4H), 1.40-1.25 (m, 1H), 0.34 (t, J=7.3 Hz, 3H).

Step #2: (3S,4aS,12bS)-12b-Ethyl-9-(4-fluorophenyl)-3-(trifluoromethyl)-1,2,3,4,4a,5,6,7,9,12b-decahydrobenzo[6,7]cyclohepta[1,2-f]indazol-3-yl dihydrogen phosphate (57, R¹= 4-Fluorophenyl, R²=Ethyl, R³=Trifluoromethyl)

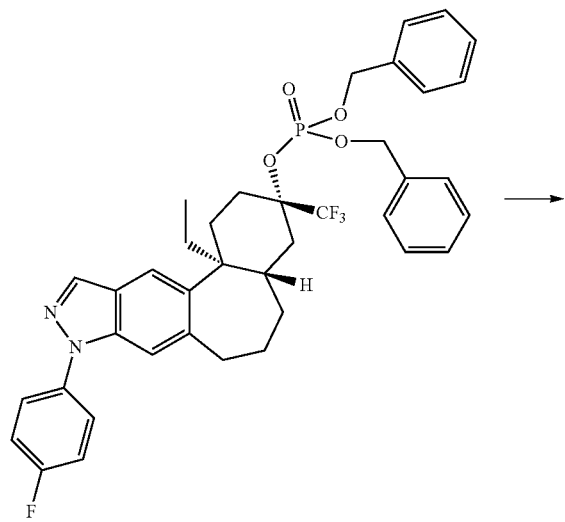

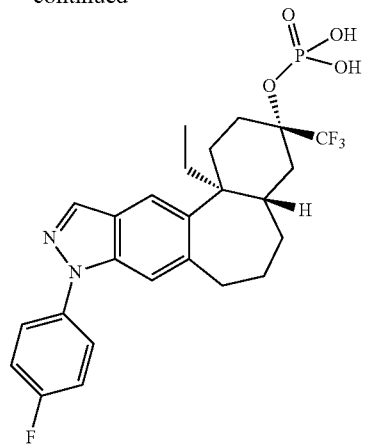

A solution of dibenzyl((3S,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-yl)phosphate (56, R¹=4-Fluorophenyl, R²=Ethyl, R³=Trifluoromethyl) (0.372 g, 0.526 mmol) and MeOH (10.0 mL) was added to 10% palladium on carbon (wet, 50% water, 0.112 g). The mixture was shaken at rt under hydrogen (50 psi) for about 17 h. The mixture was filtered through Celite® rinsing with 50% DCM/MeOH (50 mL). The volatiles were removed under reduced pressure. The residue was slurried in MeOH (0.5 mL) then the solid was collected by filtration rinsing with MeOH (0.5 mL). The material was dried in a vacuum oven at about 65° C. for about 16 h to afford (3S,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-yl dihydrogen phosphate (57, R¹=4-Fluorophenyl, R²=Ethyl, R³=Trifluoromethyl) (0.155 g, 53% yield) as an ivory solid. LC/MS, method 2, $R_f$=1.96 min, MS m/z 527 (M+H)⁺. ¹H NMR (400 MHz, DMSO) 8.25 (d, J=0.7 Hz, 1H), 7.85 (s, 1H), 7.83-7.76 (m, 2H), 7.56 (s, 1H), 7.44-7.36 (m, 2H), 3.27-3.15 (m, 1H), 3.00-2.89 (m, 1H), 2.58-1.55 (m, 12H), 1.42-1.26 (m, 1H), 0.40 (t, J=7.3 Hz, 3H).

Scheme 14

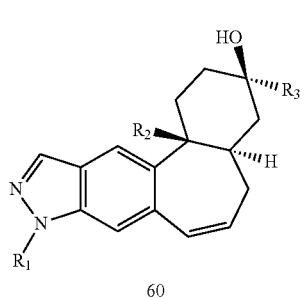 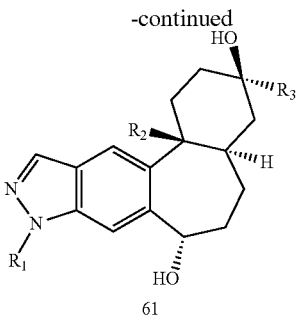 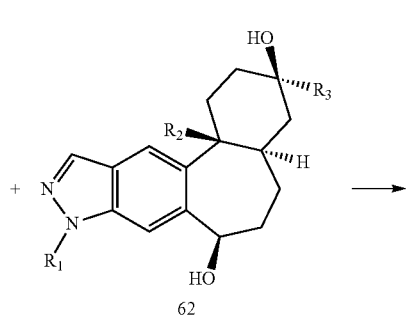

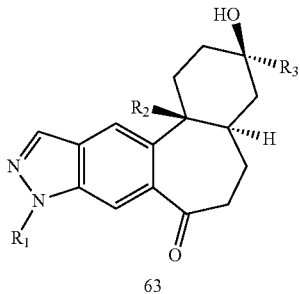

Example #102

(3R,4aR,12bR)-8-Bromo-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol (58, R¹=4-Fluorophenyl, R²=Ethyl, R³=Trifluoromethyl)

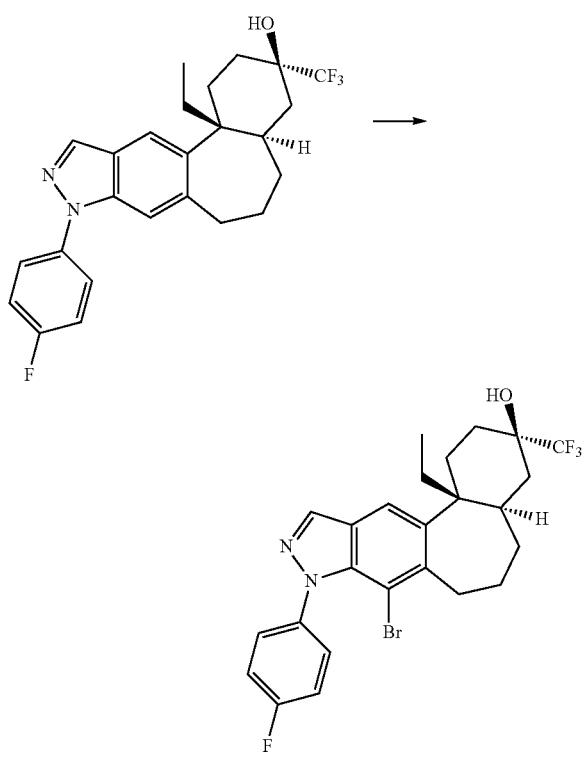

NBS (0.052 g, 0.29 mmol) was added in one portion to a solution of (3R,4aR,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol (11, R¹=4-Fluorophenyl, R²=Ethyl, R³=Trifluoromethyl) (0.100 g, 0.224 mmol) and DMF (2.20 mL) under a nitrogen atmosphere. The solution was warmed to about 60° C. for about 2 h. A solution of NBS (0.0040 g, 0.022 mmol) and DMF (0.10 mL) was added. After about 1 h, a solution of NBS (0.0040 g, 0.022 mmol) and DMF (0.10 mL) was added. After about 30 min, the light yellow solution was allowed to cool to rt. Sat. aq. NaHCO$_3$ (5 mL), water (5 mL), and EtOAc (10 mL) were added. The layers were separated and the organics were washed with water (10 mL) and sat. aq. NaCl (10 mL). The aqueous layers were extracted with EtOAc (10 mL). The combined organics were dried over Na$_2$SO$_4$, filtered, and concentrated. The residue was purified on silica gel (12 g) using a gradient of 0-7% EtOAc in heptane. The fractions containing product were combined and concentrated under reduced pressure to afford a sticky ivory solid. The residue was dissolved in MeCN, treated with water, and concentrated under reduced pressure to remove MeCN. The mixture was frozen then lyophilized to afford (3R,4aR,12bR)-8-bromo-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol (58, R¹=4-Fluorophenyl, R²=Ethyl, R³=Trifluoromethyl) (0.0809 g, 69% yield) as a fluffy white solid. LC/MS, method 2, R$_t$=3.00 min, MS m/z 525 and 527 (M+H)⁺. ¹H NMR (400 MHz, DMSO) δ 8.29 (s, 1H), 7.91 (s, 1H), 7.55-7.48 (m, 2H), 7.37-7.29 (m, 2H), 5.87 (s, 1H), 3.73-3.63 (m, 1H), 3.04-2.90 (m, 1H), 2.42-2.27 (m, 1H), 2.22-1.52 (m, 11H), 1.29-1.10 (m, 1H), 0.46 (t, J=7.3 Hz, 3H).

Example #103

(3R,4aR,12bR)-12b-Ethyl-9-(4-fluorophenyl)-8-methyl-3-(trifluoromethyl)-1,2,3,4,4a,5,6,7,9,12b-decahydrobenzo[6,7]cyclohepta[1,2-f]indazol-3-ol (59, R$^1$=4-Fluorophenyl, R$^2$=Ethyl, R$^3$=Trifluoromethyl)

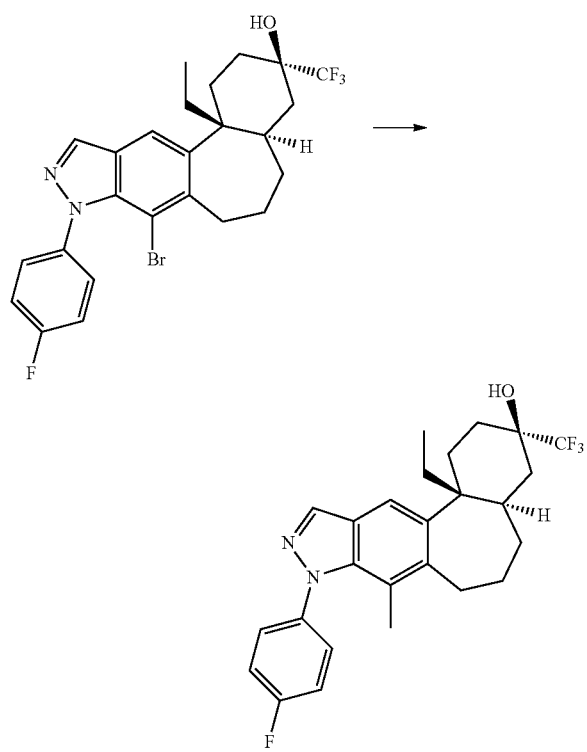

[1,1'-Bis(diphenylphosphino)ferrocene]dichloropalladium(II)-CH$_2$Cl$_2$ adduct (0.012 g, 0.015 mmol) was added to a mixture of (3R,4aR,12bR)-8-bromo-12b-ethyl-9-(4-fluorophenyl)-3-(trifluoromethyl)-1,2,3,4,4a,5,6,7,9,12b-decahydrobenzo[6,7]cyclohepta[1,2-f]indazole-3-ol (58, R$^1$=4-Fluorophenyl, R$^2$=Ethyl, R$^3$=Trifluoromethyl) (0.0393 g, 0.0750 mmol), methylboronic acid (0.0090 g, 0.15 mmol), Na$_2$CO$_3$ (0.020 g, 0.19 mmol), 1,4-dioxane (0.400 mL), and water (0.100 mL) under a nitrogen atmosphere. The reaction vessel was evacuated then back-filled with nitrogen three times. The mixture was warmed to about 80° C. for about 9 h. After cooling to rt, water (2 mL) and EtOAc (5 mL) were added. The layers were separated and the aqueous layer was extracted with EtOAc (5 mL). The combined organics were dried over Na$_2$SO$_4$, filtered, and concentrated under reduced pressure. The residue was purified on silica gel (12 g) using a gradient of 0-20% EtOAc in heptane. The fractions containing product were combined and concentrated under reduced pressure. The residue was purified by reverse phase HPLC (Synergy Max-RP column) using a gradient of 10-95% MeCN in aqueous NH$_4$OAc (50 mM). The fractions containing product were combined and concentrated under reduced pressure to remove the organic volatiles. The resulting mixture was frozen then lyophilized to afford (3R,4aR,12bR)-12b-ethyl-9-(4-fluorophenyl)-8-methyl-3-(trifluoromethyl)-1,2,3,4,4a,5,6,7,9,12b-decahydrobenzo[6,7]cyclohepta[1,2-f]indazol-3-ol (59, R$^1$=4-Fluorophenyl, R$^2$=Ethyl, R$^3$=Trifluoromethyl) (0.0119 g, 34% yield) of a fluffy white solid. LC/MS, method 2, R$_f$=2.85 mM, MS m/z 461 (M+H)$^+$. $^1$H NMR (400 MHz, DMSO) δ 8.17 (s, 1H), 7.70 (s, 1H), 7.56-7.47 (m, 2H), 7.40-7.31 (m, 2H), 5.84 (bs, 1H), 3.23-3.12 (m, 1H), 2.87-2.73 (m, 1H), 2.42-2.26 (m, 1H), 2.22-1.51 (m, 10H), 2.03 (s, 3H), 1.31-1.11 (m, 2H), 0.46 (t, J=7.4 Hz, 3H).

Example #104

(3R,4aR,7S,12bR)-12b-Ethyl-9-(4-fluorophenyl)-3-(trifluoromethyl)-1,2,3,4,4a,5,6,7,9,12b-decahydrobenzo[6,7]cyclohepta[1,2-f]indazole-3,7-diol (61, R$^1$=4-Fluorophenyl, R$^2$=Ethyl, R$^3$=Trifluoromethyl)

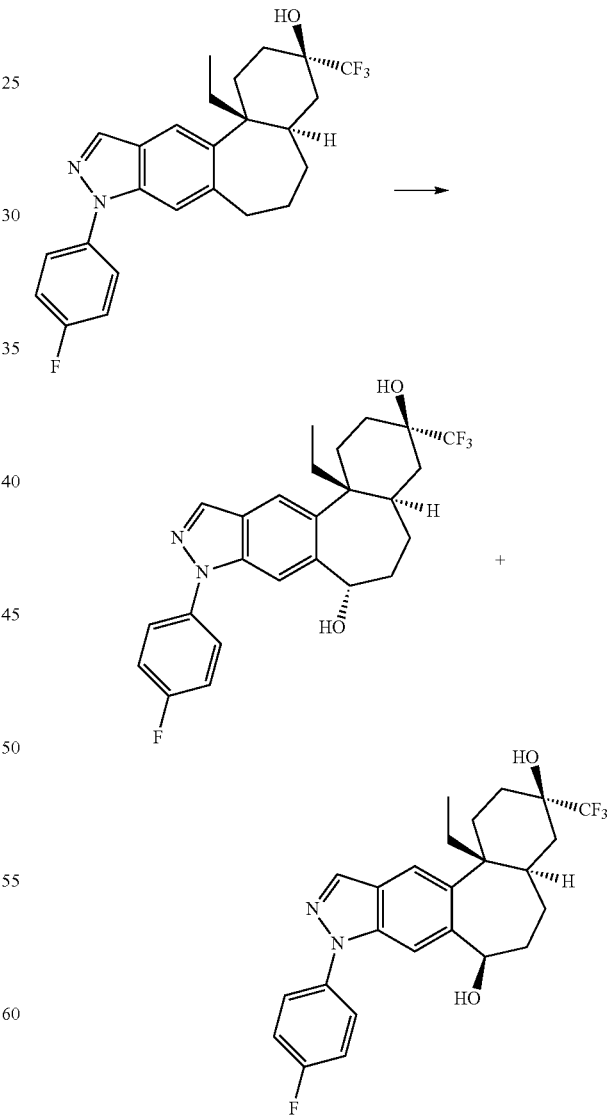

NBS (0.110 g, 0.618 mmol) was added in one portion to a solution of (3R,4aR,12bR)-12b-ethyl-9-(4-fluorophenyl)-3-

(trifluoromethyl)-1,2,3,4,4a,5,6,7,9,12b-decahydrobenzo[6,7]cyclohepta[1,2-f]indazol-3-ol (11, $R^1$=4-Fluorophenyl, $R^2$=Ethyl, $R^3$=Trifluoromethyl) (0.248 g, 0.555 mmol) and $CCl_4$ (9.5 mL) under a nitrogen atmosphere. AIBN (0.009 g, 0.055 mmol) was added in one portion. The reaction vessel was evacuated and back-filled with nitrogen three times then the solution was warmed to reflux. After 2 h, the solution was cooled to rt. NBS (0.020 g, 0.11 mmol) and AIBN (0.001 g, 0.006 mmol) were added sequentially. The reaction vessel was evacuated and back-filled with nitrogen three times then the solution was warmed to reflux. After 45 min, the mixture was allowed to cool to rt. 75% Sat. aq. $NaHCO_3$ (20 mL), water (5 mL), and DCM (25 mL) were added. The layers were separated and the aqueous layer was extracted with DCM (25 mL). The combined organics were dried over $Na_2SO_4$, filtered, and concentrated. The residue was purified on silica gel (40 g) using a gradient of 0-20% EtOAc in heptane. The fractions containing product were combined and concentrated under reduced pressure to afford (3R,4aR,12bR)-12b-ethyl-9-(4-fluorophenyl)-3-(trifluoromethyl)-1,2,3,4,4a,5,9,12b-octahydrobenzo[6,7]cyclohepta[1,2-f]indazol-3-ol (60, $R^1$=4-Fluorophenyl, $R^2$=Ethyl, $R^3$=Trifluoromethyl) (0.0671 g, 27% yield). LC/MS, method 3, $R_t$=2.83 min, MS m/z 445 $(M+H)^+$. Borane tetrahydrofuran complex (1 M solution in THF, 0.750 mL, 0.750 mmol) was added dropwise to a solution of (3R,4aR,12bR)-12b-ethyl-9-(4-fluorophenyl)-3-(trifluoromethyl)-1,2,3,4,4a,5,9,12b-octahydrobenzo[6,7]cyclohepta[1,2-f]indazol-3-ol (60, $R^1$=4-Fluorophenyl, $R^2$=Ethyl, $R^3$=Trifluoromethyl) (0.0671 g, 0.151 mmol) and THF (1.5 mL) under a nitrogen atmosphere at about 0° C. After about 15 min, the ice bath was removed and the solution was left to stir at rt for about 18 h. The reaction was cooled to about 0° C. NaOH (3.8 M aq. solution, 0.800 mL, 3.04 mmol) was added dropwise over about 5 min). $H_2O_2$ (30% aq. solution, 0.770 mL, 7.54 mmol) was added dropwise over about 5 min. After about 15 min, the ice bath was removed and the mixture was stirred at rt for about 2 h. The mixture was warmed to about 40° C. After about 1 h, the mixture was allowed to cool to rt. Water (10 mL), EtOAc (10 mL) and MeOH (1 mL) were added. The layers were separated and the aqueous layer was extracted with EtOAc (2×10 mL). The combined organics were washed with sat. aq. NaCl (5 mL), dried over $Na_2SO_4$, filtered, and concentrated. The residue was purified on silica gel (40 g) using a gradient of 0-30% EtOAc in heptane. The fractions containing each product were combined and concentrated under reduced pressure. The first eluting band afforded (3R,4aR,7R,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazole-3,7-diol (62, $R^1$=4-Fluorophenyl, $R^2$=Ethyl, $R^3$=Trifluoromethyl) (0.0061 g, 9% yield). LC/MS, method 2, $R_t$=2.44 min, MS m/z 463 $(M+H)^+$. The second eluting band afforded (3R,4aR,7 S,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazole-3,7-diol (61, $R^1$=4-Fluorophenyl, $R^2$=Ethyl, $R^3$=Trifluoromethyl) (0.024 g, 35% yield) of an ivory solid. LC/MS, method 3, $R_t$=2.36 min, MS m/z 463 $(M+H)^+$. $^1H$ NMR (400 MHz, DMSO) δ 8.27-8.25 (m, 1H), 8.20 (s, 1H), 7.84 (s, 1H), 7.81-7.72 (m, 2H), 7.50-7.41 (m, 2H), 5.87 (s, 1H), 5.47 (d, J=6.28 Hz, 1H), 5.12-5.03 (m, 1H), 2.19-1.37 (m, 13H), 0.42 (t, J=7.2 Hz, 3H).

Example #105

(3R,4aR,12bR)-12b-Ethyl-9-(4-fluorophenyl)-3-hydroxy-3-(trifluoromethyl)-1,2,3,4,4a,5,6,12b-octahydrobenzo[6,7]cyclohepta[1,2-f]indazol-7(9H)-one (63, $R^1$=4-Fluorophenyl, $R^2$=Ethyl, $R^3$=Trifluoromethyl)

Dess-Martin periodinane (0.017 g, 0.039 mmol) was added to a solution of (3R,4aR,7 S,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazole-3,7-diol (61, $R^1$=4-Fluorophenyl, $R^2$=Ethyl, $R^3$=Trifluoromethyl) (0.0079 g, 0.017 mmol), (3R,4aR,7R,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazole-3,7-diol (62, $R^1$=4-Fluorophenyl, $R^2$=Ethyl, $R^3$=Trifluoromethyl) (0.0061 g, 0.013 mmol), and DCM (0.300 mL) under a nitrogen atmosphere. After about 90 min, sat. aq. NaHCO₃ (2 mL) and water (1 mL) were added. The mixture was extracted with EtOAc (2×5 mL). The combined organics were dried over Na₂SO₄, filtered, and concentrated. The residue was purified on silica gel (4 g) using a gradient of 0-25% EtOAc in heptane. The fractions containing product were combined and concentrated under reduced pressure to afford an ivory foam. The residue was dissolved in MeCN, treated with water, and concentrated under reduced pressure to remove MeCN. The mixture was frozen then lyophilized to afford (3R,4aR,12bR)-12b-ethyl-9-(4-fluorophenyl)-3-hydroxy-3-(trifluoromethyl)-1,2,3,4,4a,5,6,12b-octahydrobenzo[6,7]cyclohepta[1,2-f]indazol-7(9H)-one (63, R¹=4-Fluorophenyl, R²=Ethyl, R³=Trifluoromethyl) (0.0124 g, 89% yield) of an ivory solid. LC/MS, method 2, R$_t$=2.54 min, MS m/z 461 (M+H)⁺. ¹H NMR (400 MHz, DMSO) δ 8.41-8.38 (m, 1H), 7.93 (s, 1H), 7.84-7.75 (m, 2H), 7.54 (s, 1H), 7.48-7.39 (m, 2H), 5.94 (s, 1H), 2.86-2.74 (m, 1H), 2.70-2.59 (m, 1H), 2.26-2.14 (m, 1H), 2.09-1.84 (m, 5H), 1.81-1.59 (m, 4H), 1.54-1.40 (m, 1H), 0.37 (t, J=7.2 Hz, 3H).

Scheme 15

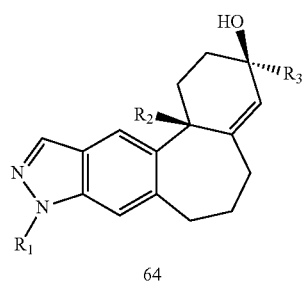

Example #106 and #107

(3R,12bR)-12b-ethyl-9-(4-fluorophenyl)-3-(trifluoromethyl)-1,2,3,5,6,7,9,12b-octahydrobenzo[6,7]cyclohepta[1,2-f]indazol-3-ol (64, R¹=4-Fluorophenyl, R²=Ethyl, R³=Trifluoromethyl) and (3S,12bS)-12b-ethyl-9-(4-fluorophenyl)-3-(trifluoromethyl)-1,2,3,5,6,7,9,12b-octahydrobenzo[6,7]cyclohepta[1,2-f]indazol-3-ol (64, R¹=4-Fluorophenyl, R²=Ethyl, R³=Trifluoromethyl)

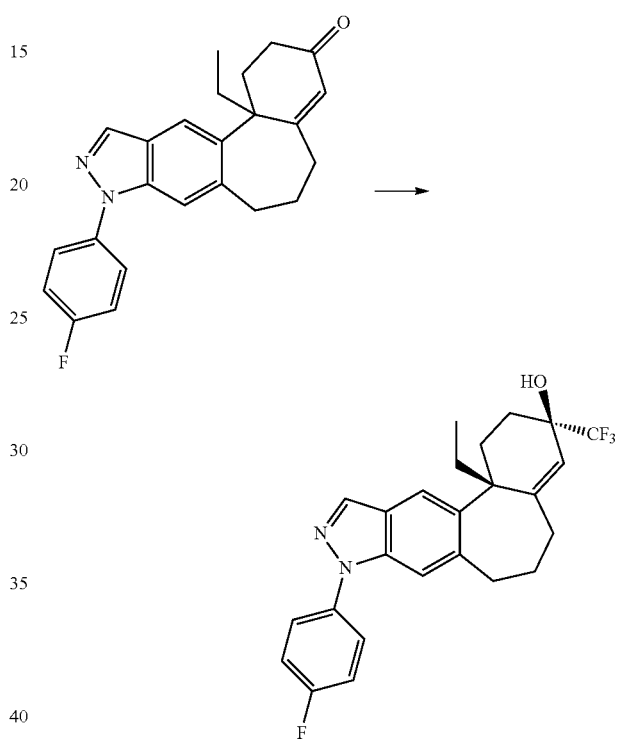

CsF (0.101 g, 0.668 mmol) was added in one portion to a solution of (R)-12b-ethyl-9-(4-fluorophenyl)-1,5,6,7,9,12b-hexahydrobenzo[6,7]cyclohepta[1,2-f]indazol-3 (2H)-one; compound with (S)-12b-ethyl-9-(4-fluorophenyl)-1,5,6,7,9,12b-hexahydrobenzo[6,7]cyclohepta[1,2-f]indazol-3(2H)-one (8, R¹=4-Fluorophenyl, R²=Ethyl) (1.00 g, 2.67 mmol) and DME (30.0 mL) under a nitrogen atmosphere. After stirring at rt for about 15 min, the mixture was cooled to about 0° C. Trimethyl(trifluoromethyl)silane (0.670 mL, 4.53 mmol) was added dropwise over about 15 min. After about 1 h, the organic volatiles were removed under reduced pressure. The residue was dissolved in DME (30.0 mL) and TBAF (1 M solution in THF, 3.00 mL, 3.00 mmol) was added in one portion. After about 1 h, the reaction solution was poured into EtOAc (100 mL) and water (100 mL). The layers were separated and the organics were washed with sat. aq. NaCl (50 mL), dried over Na₂SO₄, filtered, and concentrated. The residue was purified on silica gel (80 g) using a gradient of 0-25% EtOAc in heptane. The fractions containing product were combined and concentrated under reduced pressure to afford (3R,12bR)-12b-ethyl-9-(4-fluorophenyl)-3-(trifluoromethyl)-1,2,3,5,6,7,9,12b-octahydrobenzo[6,7]cyclohepta[1,2-f]indazol-3-ol; compound with (3S,12bS)-12b-ethyl-9-(4-fluorophenyl)-3-(trifluoromethyl)-1,2,3,5,6,7,9,12b-octahydrobenzo[6,7]cyclohepta[1,2-f]indazol-3-ol (64, $R^1$=4-Fluorophenyl, $R^2$=Ethyl, $R^3$=Trifluoromethyl) (0.918 g, 77% yield) as a light tan solid. LC/MS, method 2, $R_t$=2.83 min, MS m/z 445 (M+H)$^+$. $^1$H NMR (400 MHz, DMSO) δ 8.27 (d, J=0.8 Hz, 1H), 7.85 (s, 1H), 7.83-7.75 (m, 2H), 7.54 (s, 1H), 7.45-7.36 (m, 2H), 6.05 (s, 1H), 5.50 (s, 1H), 3.09-2.94 (m, 1H), 2.89-2.79 (m, 1H), 2.41-2.27 (m, 2H), 2.28-2.14 (m, 1H), 2.05 (q, J=7.3 Hz, 2H), 1.95-1.67 (m, 5H), 0.83 (t, J=7.3 Hz, 3H).

The enantiomers were separated using Preparative Chiral Purification Method 17 (0.145 g, 3.26 mmol).

Fractions from the first peak eluted were combined and concentrated under reduced pressure. The residue was dissolved in MeOH, treated with water, and concentrated under reduced pressure to remove MeOH. The mixture was frozen then lyophilized to afford (3R,12bR)-12b-ethyl-9-(4-fluorophenyl)-3-(trifluoromethyl)-1,2,3,5,6,7,9,12b-octahydrobenzo[6,7]cyclohepta[1,2-f]indazol-3-ol (64, $R^1$=4-Fluorophenyl, $R^2$=Ethyl, $R^3$=Trifluoromethyl) (0.0596 g, 41% yield) as an ivory solid. Sign of rotation is positive. LC/MS, method 2, $R_t$=2.83 min, MS m/z 445 (M+H)$^+$. $^1$H NMR (400 MHz, DMSO) δ 8.27 (d, J=0.8 Hz, 1H), 7.85 (s, 1H), 7.83-7.75 (m, 2H), 7.54 (s, 1H), 7.45-7.36 (m, 2H), 6.05 (s, 1H), 5.50 (s, 1H), 3.09-2.94 (m, 1H), 2.89-2.79 (m, 1H), 2.41-2.27 (m, 2H), 2.28-2.14 (m, 1H), 2.05 (q, J=7.3 Hz, 2H), 1.95-1.67 (m, 5H), 0.83 (t, J=7.3 Hz, 3H).

Fractions from the second peak eluted were combined and concentrated under reduced pressure. The residue was dissolved in MeOH, treated with water, and concentrated under reduced pressure to remove MeOH. The mixture was frozen then lyophilized to afford (3S,12bS)-12b-ethyl-9-(4-fluorophenyl)-3-(trifluoromethyl)-1,2,3,5,6,7,9,12b-octahydrobenzo[6,7]cyclohepta[1,2-f]indazol-3-ol (64, $R^1$=4-Fluorophenyl, $R^2$=Ethyl, $R^3$=Trifluoromethyl) (0.0588 g, 41% yield) as an ivory solid. Sign of rotation is negative. LC/MS, method 2, $R_t$=2.83 min, MS m/z 445 (M+H)$^+$. $^1$H NMR (400 MHz, DMSO) δ 8.27 (d, J=0.8 Hz, 1H), 7.83-7.75 (m, 2H), 7.54 (s, 1H), 7.45-7.36 (m, 2H), 6.05 (s, 1H), 5.50 (s, 1H), 3.09-2.94 (m, 1H), 2.89-2.79 (m, 1H), 2.41-2.27 (m, 2H), 2.28-2.14 (m, 1H), 2.05 (q, J=7.3 Hz, 2H), 1.95-1.67 (m, 5H), 0.83 (t, J=7.3 Hz, 3H).

Scheme 16

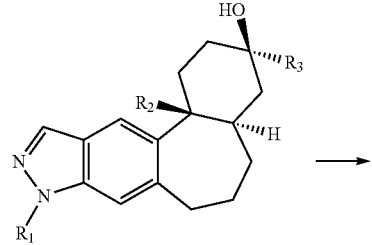

11

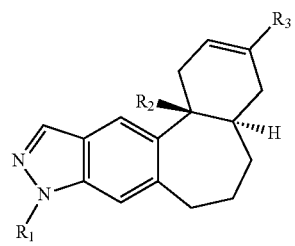

65

+

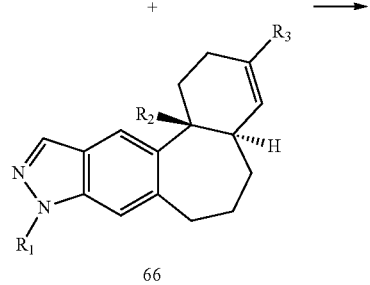

66

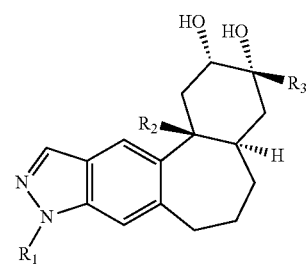

67

Example #108

(2S,3R,4aR,12bR)-12b-Ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol (67, $R^1$=4-Fluorophenyl, $R^2$=Ethyl, $R^3$=Trifluoromethyl)

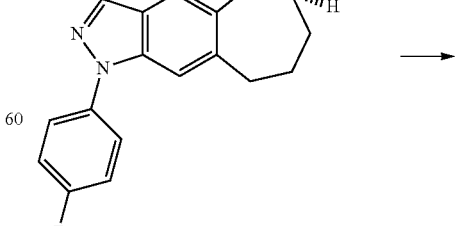

-continued

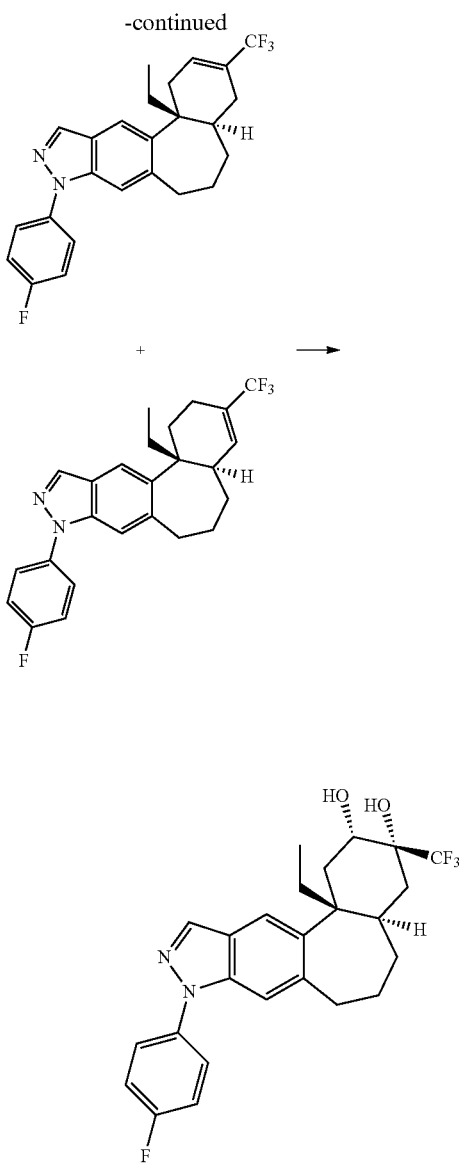

Thionyl chloride (0.120 mL, 1.645 mmol) was added dropwise to a solution of (3R,4aR,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol (11, R¹=4-Fluorophenyl, R²=Ethyl, R³=Trifluoromethyl) (0.0720 g, 0.161 mmol), pyridine (0.200 mL, 2.473 mmol), and toluene (0.300 mL) under a nitrogen atmosphere. The mixture was warmed to about 80° C. After about 4 h, the mixture was allowed to cool to rt. The volatiles were removed under reduced pressure. Saturated aq. NaHCO₃ (2 mL) and EtOAc (5 mL) were added. The layers were separated and the aqueous layer was extracted with EtOAc (5 mL). The combined organics were dried over Na₂SO₄, filtered, and concentrated. The residue was purified on silica gel (80 g) using a gradient of 0-10% EtOAc in heptane. The fractions containing product were combined and concentrated under reduced pressure to afford a 2:1 mixture of (4aR,12bR)-12b-ethyl-9-(4-fluorophenyl)-3-(trifluoromethyl)-1,2,4a,5,6,7,9,12b-octahydrobenzo[6,7]cyclohepta[1,2-f]indazole (66, R¹=4-Fluorophenyl, R²=Ethyl, R³=Trifluoromethyl) and (4 aR,12bR)-12b-ethyl-9-(4-fluorophenyl)-3-(trifluoromethyl)-1,4,4a,5,6,7,9,12b-octahydrobenzo[6,7]cyclohepta[1,2-f]indazole (65, R¹=4-Fluorophenyl, R²=Ethyl, R³=Trifluoromethyl) (0.0599 g, 0.140 mmol) as a light yellow film. LC/MS, method 3, R$_t$=3.23 min, MS m/z 429 (M+H)⁺. Potassium osmate dihydrate (0.0040 g, 0.011 mmol) was added in one portion to a biphasic solution of a 2:1 mixture of (4aR,12bR)-12b-ethyl-9-(4-fluorophenyl)-3-(trifluoromethyl)-1,2,4a,5,6,7,9,12b-octahydrobenzo[6,7]cyclohepta[1,2-f]indazole (66, R¹=4-Fluorophenyl, R²=Ethyl, R³=Trifluoromethyl) and (4aR,12bR)-12b-ethyl-9-(4-fluorophenyl)-3-(trifluoromethyl)-1,4,4a,5,6,7,9,12b-octahydrobenzo[6,7]cyclohepta[1,2-f]indazole (65, R¹=4-Fluorophenyl, R²=Ethyl, R³=Trifluoromethyl) (0.0560 g, 0.131 mmol), THF (1.0 mL), and water (0.50 mL). NMO (0.046 g, 0.392 mmol) was added in one portion. After about 16 h, the mixture was warmed to about 40° C. After about 33 h, the mixture was allowed to cool to rt. Water (3 mL) was added. The solution was extracted with DCM (2×5 mL). The combined organics were dried over Na₂SO₄, filtered, and concentrated under reduced pressure. The material was dissolved in DCM/MeOH and 0.4 g of silica gel was added. The volatiles were removed under reduced pressure. The resulting solid was purified on silica gel (12 g) using a gradient of 0-20% EtOAc in heptane. The fractions containing product were combined and concentrated under reduced pressure to afford (2S,3R,4aR,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol (67, R¹=4-Fluorophenyl, R²=Ethyl, R³=Trifluoromethyl) (0.0116 g, 19% yield) as an ivory solid. LC/MS, method 2, R$_t$=2.75 min, MS m/z 463 (M+H)⁺. ¹H NMR (400 MHz, DMSO) δ 8.32 (s, 1H), 7.85 (s, 1H), 7.84-7.76 (m, 2H), 7.56 (s, 1H), 7.46-7.35 (m, 2H), 5.52 (s, 1H), 4.90 (d, J=6.7 Hz, 1H), 3.90-3.79 (m, 1H), 3.22-3.09 (m, 1H), 3.00-2.89 (m, 1H), 2.24-2.06 (m, 3H), 2.06-1.94 (m, 1H), 1.92-1.70 (m, 2H), 1.69-1.51 (m, 4H), 1.40-1.20 (m, 1H), 0.45 (t, J=7.3 Hz, 3H).

Example #109 and #110

(3R,4aR,12bR)-12b-Ethyl-3-ethynyl-9-(4-fluorophenyl)-1,2,3,4,4a,5,6,7,9,12b-decahydrobenzo[6,7]cyclohepta[1,2-f]indazol-3-ol (11, R¹=4-Fluorophenyl, R²=Ethyl, R³=Ethynyl) and (3S,4aS,12bS)-12b-ethyl-3-ethynyl-9-(4-fluorophenyl)-1,2,3,4,4a,5,6,7,9,12b-decahydrobenzo[6,7]cyclohepta[1,2-f]indazol-3-ol (11, R¹=4-Fluorophenyl, R²=Ethyl, R³=Ethynyl)

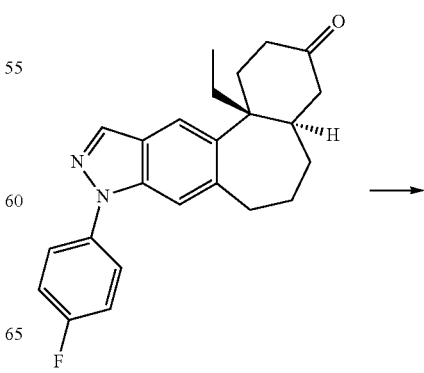

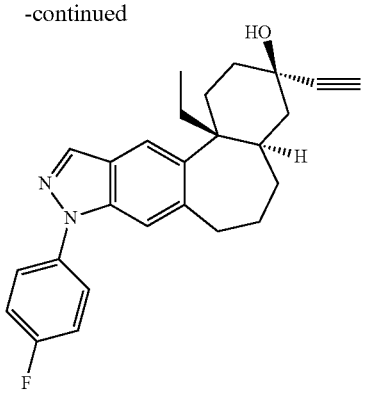

Ethynylmagnesium bromide (0.5 M solution in THF, 6.00 mL, 3.00 mmol) was added dropwise over about 15 min to a mixture of (4aR,12bR)-12b-ethyl-9-(4-fluorophenyl)-1,4,4a,5,6,7,9,12b-octahydrobenzo[6,7]cyclohepta[1,2-f]indazole-3 (2H)-one; compound with (4aS,12bS)-12b-ethyl-9-(4-fluorophenyl)-1,4,4a,5,6,7,9,12b-octahydrobenzo[6,7]cyclohepta[1,2-f]indazol-3 (2H)-one (9, R¹=4-Fluorophenyl, R²=Ethyl) (0.200 g, 0.531 mmol) and THF (2.5 mL) under a nitrogen atmosphere at about 0° C. After about 90 min, the ice bath was removed and the solution was stirred at rt for about 1 h. Sat. aq. NH₄Cl (10 mL) and water (10 mL) were added. The solution was extracted with DCM (2×20 mL). The combined organics were dried over Na₂SO₄ and filtered. Silica gel (2 g) was added and the organic volatiles were removed under reduced pressure. The resulting solid was purified on silica gel (12 g) using a gradient of 0-3% EtOAc in DCM. The fractions containing product were combined and concentrated under reduced pressure to afford (3R,4aR,12bR)-12b-ethyl-3-ethynyl-9-(4-fluorophenyl)-1,2,3,4,4a,5,6,7,9,12b-decahydrobenzo[6,7]cyclohepta[1,2-f]indazol-3-ol; compound with (3S,4aS,12bS)-12b-ethyl-3-ethynyl-9-(4-fluorophenyl)-1,2,3,4,4a,5,6,7,9,12b-decahydrobenzo[6,7]cyclohepta[1,2-f]indazol-3-ol (11, R¹=4-Fluorophenyl, R²=Ethyl, R³=Ethynyl) (0.116 g, 54% yield). LC/MS, method 2, $R_t$=2.78 min, MS m/z 403 (M+H)⁺. ¹H NMR (400 MHz, DMSO) δ 8.26 (d, J=0.7 Hz, 1H), 7.91 (s, 1H), 7.83-7.76 (m, 2H), 7.55 (s, 1H), 7.45-7.36 (m, 2H), 5.48 (s, 1H), 3.24 (s, 1H), 3.22-3.11 (m, 1H), 2.98-2.88 (m, 1H), 2.32-2.23 (m, 1H), 2.20-1.48 (m, 11H), 1.41-1.26 (m, 1H), 0.37 (t, J=7.3 Hz, 3H).

The enantiomers were separated using Preparative Chiral Purification Method 18 (0.177 g, 4.40 mmol).

Fractions from the first peak eluted were combined and concentrated under reduced pressure. The residue was dissolved in MeCN and MeOH, treated with water, and concentrated under reduced pressure to remove the organic volatiles. The mixture was frozen then lyophilized to afford (3S,4aS,12bS)-12b-ethyl-3-ethynyl-9-(4-fluorophenyl)-1,2,3,4,4a,5,6,7,9,12b-decahydrobenzo[6,7]cyclohepta[1,2-f]indazol-3-ol (11, R¹=4-Fluorophenyl, R²=Ethyl, R³=Ethynyl) (0.0778 g, 44% yield) as an ivory solid. Sign of rotation is negative. LC/MS, method 2, $R_t$=2.78 min, MS m/z 403 (M+H)⁺. ¹H NMR (400 MHz, DMSO) δ 8.26 (d, J=0.7 Hz, 1H), 7.91 (s, 1H), 7.83-7.76 (m, 2H), 7.55 (s, 1H), 7.45-7.36 (m, 2H), 5.48 (s, 1H), 3.24 (s, 1H), 3.22-3.11 (m, 1H), 2.98-2.88 (m, 1H), 2.32-2.23 (m, 1H), 2.20-1.48 (m, 11H), 1.41-1.26 (m, 1H), 0.37 (t, J=7.3 Hz, 3H).

Fractions from the second peak eluted were combined and concentrated under reduced pressure. The residue was dissolved in MeOH, treated with water, and concentrated under reduced pressure to remove MeOH. The mixture was frozen then lyophilized to afford (3R,4aR,12bR)-12b-ethyl-3-ethynyl-9-(4-fluorophenyl)-1,2,3,4,4a,5,6,7,9,12b-decahydrobenzo[6,7]cyclohepta[1,2-f]indazol-3-ol (11, R¹=4-Fluorophenyl, R²=Ethyl, R³=Ethynyl) (0.0783 g, 44% yield) as an ivory solid. Sign of rotation is positive. LC/MS, method 2, $R_t$=2.78 min, MS m/z 403 (M+H)⁺. ¹H NMR (400 MHz, DMSO) δ 8.26 (d, J=0.7 Hz, 1H), 7.91 (s, 1H), 7.83-7.76 (m, 2H), 7.55 (s, 1H), 7.45-7.36 (m, 2H), 5.48 (s, 1H), 3.24 (s, 1H), 3.22-3.11 (m, 1H), 2.98-2.88 (m, 1H), 2.32-2.23 (m, 1H), 2.20-1.48 (m, 11H), 1.41-1.26 (m, 1H), 0.37 (t, J=7.3 Hz, 3H).

Additional examples, prepared in a manner similar to the preparation of Examples #109 and 110 are listed in Table 9.

TABLE 9

| Ex. # | Ketone | Reagent | Product structure | LC/MS method/ $R_t$, MH⁺ | Chiral method | Order of elution/ sign of rotation |
|---|---|---|---|---|---|---|
| 111 | 9 (4aR,12bR)- (R¹ = 4-Fluorophenyl, R² = Ethyl) | 1-Propynyl magnesium bromide | 11 (3R,4aR,12bR)- (R¹ = 4-Fluorophenyl, R² = Ethyl, R³ = 1-Propynyl) | 2 2.86 min 417 MH⁺ | 19 | 1ˢᵗ/pos |
| 112 | 9 (R¹ = 4-Fluorophenyl, R² = Ethyl) | 1-Propynyl magnesium bromide | 11 (3S,4aS,12bS) (R¹ = 4-Fluorophenyl, R² = Ethyl, R³ = 1-Propynyl) | 2 2.86 min 417 MH⁺ | 19 | 2ⁿᵈ/neg |

Example #113

(3R,4aR,12bR)-3,12b-Diethyl-9-(4-fluorophenyl)-1,2,3,4,4a,5,6,7,9,12b-decahydrobenzo[6,7]cyclohepta[1,2-f]indazol-3-ol (11, R¹=4-Fluorophenyl, R²=Ethyl, R³=Ethyl)

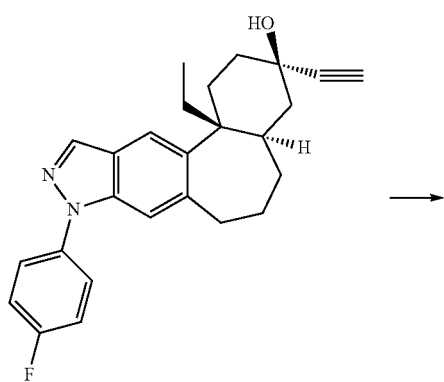

A solution of (3R,4aR,12bR)-12b-ethyl-3-ethynyl-9-(4-fluorophenyl)-1,2,3,4,4a,5,6,7,9,12b-decahydrobenzo[6,7]cyclohepta[1,2-f]indazol-3-ol (11, R¹=4-Fluorophenyl, R²=Ethyl, R³=Ethynyl) (0.0331 g, 0.082 mmol) and THF (1.00 mL) was added to 10 wt % Pd/C (wet) (0.006 g). The mixture was placed under a hydrogen atmosphere using a balloon. After about 2 h, the hydrogen was evacuated. The mixture was filtered through Celite® rinsing with DCM (20 mL). The organic volatiles were removed under reduced pressure. The residue was purified on silica gel (4 g) using a gradient of 0-4% EtOAc in DCM. The fractions containing product were combined and concentrated under reduced pressure. The residue was dissolved in MeCN and MeOH, treated with water, and concentrated under reduced pressure to remove the organic volatiles. The mixture was frozen then lyophilized to afford (3R,4aR,12bR)-3,12b-diethyl-9-(4-fluorophenyl)-1,2,3,4,4a,5,6,7,9,12b-decahydrobenzo[6,7]cyclohepta[1,2-f]indazol-3-ol (11, R¹=4-Fluorophenyl, R²=Ethyl, R³=Ethyl) (0.031 g, 91%) as an ivory solid. LC/MS, method 2, $R_t$=3.07 min, MS m/z 407 (M+H)⁺. ¹H NMR (400 MHz, DMSO) δ 8.25 (s, 1H), 7.87 (s, 1H), 7.84-7.74 (m, 2H), 7.54 (s, 1H), 7.45-7.35 (m, 2H), 4.03 (s, 1H), 3.24-3.12 (m, 1H), 2.98-2.86 (m, 1H), 2.20-2.03 (m, 2H), 2.03-1.92 (m, 1H), 1.91-1.62 (m, 4H), 1.61-1.20 (m, 8H), 0.83 (t, J=7.3 Hz, 3H), 0.37 (t, J=7.1 Hz, 3H). Sign of rotation is positive.

Additional example, prepared in a manner similar to the preparation of Example #113 is listed in Table 10.

TABLE 10

| Ex. # | Reactant | Reagent | Product structure | LC/MS method/ $R_t$ MH⁺ | Order of elution/ sign of rotation |
|---|---|---|---|---|---|
| 114 | 11(3S,4aS,12bS) - (R¹ = 4-Fluorophenyl, R² = Ethyl, R³ = 1-Ethynyl) | H₂ and 10% Pd/C | 11 (3S,4aS,12bS)- (R¹ = 4-Fluorophenyl, R² = Ethyl, R³ = Ethyl) | 2 2.98 min 407 MH⁺ | nd/Neg |

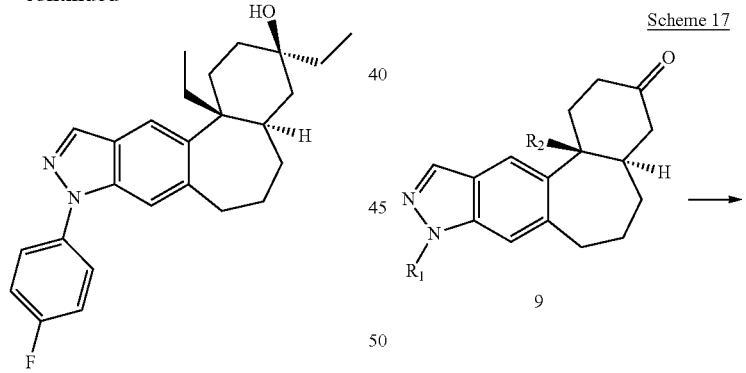

Scheme 17

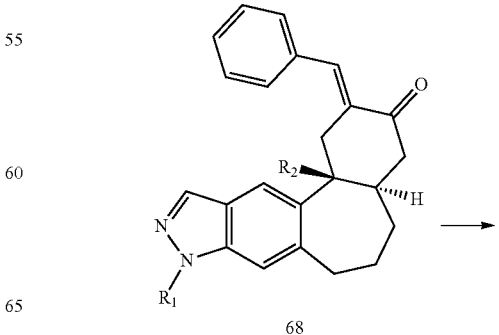

-continued

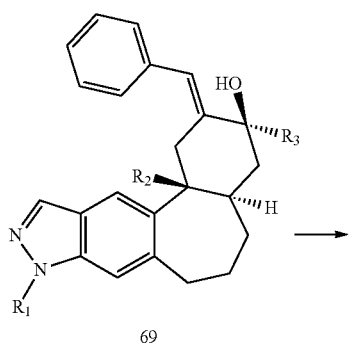

69

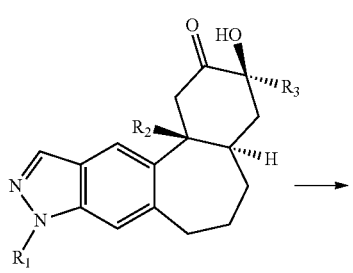

70

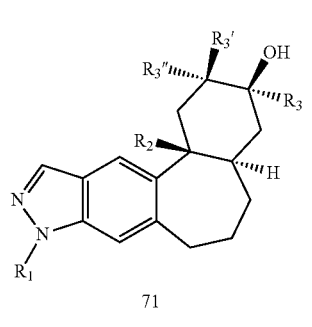

71

Example #115 and #116

(3S,4aR,12bR)-12b-Ethyl-9-(4-fluorophenyl)-3-hydroxy-3-(trifluoromethyl)-1,3,4,4a,5,6,7,12b-octahydrobenzo[6,7]cyclohepta[1,2-f]indazol-2(9H)-one (70, $R^1$=4-Fluorophenyl, $R^2$=Ethyl, $R^3$=Trifluoromethyl) and (3R,4aS,12bS)-12b-ethyl-9-(4-fluorophenyl)-3-hydroxy-3-(trifluoromethyl)-1,3,4,4a,5,6,7,12b-octahydrobenzo[6,7]cyclohepta[1,2-f]indazol-2(9H)-one (70, $R^1$=4-Fluorophenyl, $R^2$=Ethyl, $R^3$=Trifluoromethyl)

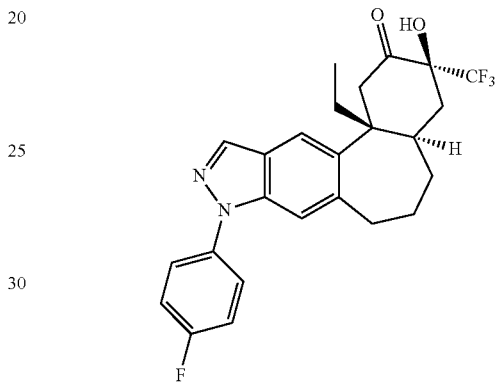

Step #1: (4aR,12bR,E)-2-Benzylidene-12b-ethyl-9-(4-fluorophenyl)-1,4,4a,5,6,7,9,12b-octahydrobenzo[6,7]cyclohepta[1,2-f]indazol-3 (2H)-one; compound with (4aS,12bS,E)-2-benzylidene-12b-ethyl-9-(4-fluorophenyl)-1,4,4a,5,6,7,9,12b-octahydrobenzo[6,7]cyclohepta[1,2-f]indazol-3 (2H)-one (68, $R^1$=4-Fluorophenyl, $R^2$=Ethyl)

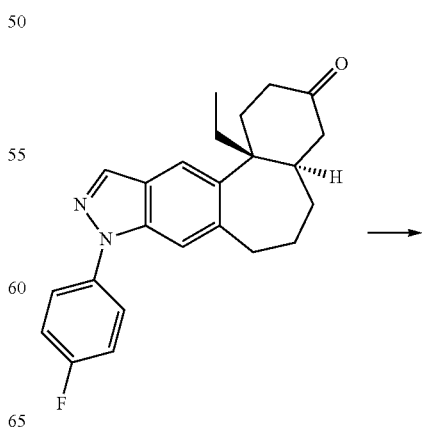

-continued

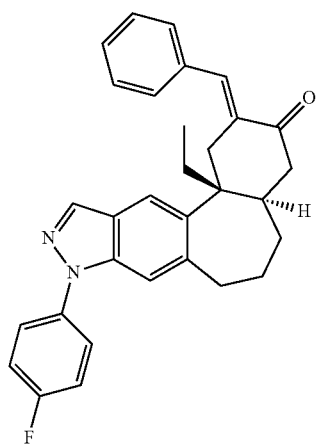

Freshly prepared sodium ethoxide (1 M solution in EtOH, 3.00 mL, 3.00 mmol) was added to a mixture of (4aR,12bR)-12b-ethyl-9-(4-fluorophenyl)-1,4,4a,5,6,7,9,12b-octahydrobenzo[6,7]cyclohepta[1,2-f]indazol-3 (2H)-one; compound with (4aS,12bS)-12b-ethyl-9-(4-fluorophenyl)-1,4,4a,5,6,7,9,12b-octahydrobenzo[6,7]cyclohepta[1,2-f]indazol-3 (2H)-one (4aR,12bR)-12b-ethyl-9-(4-fluorophenyl)-1,4,4a,5,6,7,9,12b-octahydrobenzo[6,7]cyclohepta[1,2-f]indazol-3 (2H)-one (9, R$^1$=4-Fluorophenyl, R$^2$=Ethyl) (0.750 g, 1.99 mmol), THF (6.50 mL) and EtOH (13.0 mL) under a nitrogen atmosphere. Benzaldehyde (0.220 mL, 2.17 mmol) was added. After about 3 h, sodium ethoxide (1 M solution in EtOH, 3.00 mL, 3.00 mmol) was added. After about 15 h, the mixture was warmed to about 60° C. After about 30 min, the mixture was allowed to cool to rt. AcOH (0.500 mL) was added. The volatiles were removed under reduced pressure. Water (25 mL) and DCM (50 mL) were added. The layers were separated and the organics were washed with sat. aq. NaCl (25 mL) then dried over Na$_2$SO$_4$, filtered, and concentrated under reduced pressure. The residue was purified on silica gel (80 g) using a gradient of 0-25% EtOAc in heptane. The fractions containing product were combined and concentrated under reduced pressure to afford (4aR,12bR,E)-2-benzylidene-12b-ethyl-9-(4-fluorophenyl)-1,4,4a,5,6,7,9,12b-octahydrobenzo[6,7]cyclohepta[1,2-f]indazol-3(2H)-one; compound with (4aS,12bS,E)-2-benzylidene-12b-ethyl-9-(4-fluorophenyl)-1,4,4a,5,6,7,9,12b-octahydrobenzo[6,7]cyclohepta[1,2-f]indazol-3(2H)-one (68, R$^1$=4-Fluorophenyl, R$^2$=Ethyl) (0.545 g, 59% yield) as an ivory solid. LC/MS, method 3, R$_t$=3.05 min, MS m/z 465 (M+H)$^+$. $^1$H NMR (400 MHz, DMSO) δ 7.98 (s, 1H), 7.81-7.74 (m, 2H), 7.67-7.62 (m, 2H), 7.62-7.53 (m, 4H), 7.53-7.45 (m, 2H), 7.44-7.35 (m, 2H), 3.37-3.32 (m, 2H), 3.28-3.17 (m, 1H), 2.98-2.87 (m, 1H), 2.62-2.43 (m, 2H), 2.38-2.25 (m, 1H), 2.16-1.89 (m, 3H), 1.75-1.64 (m, 1H), 1.51-1.23 (m, 2H), 0.19 (t, J=7.2 Hz, 3H).

Step #2: (3R,4aS,12bS,E)-2-Benzylidene-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol; compound with (3S,4aR,12bR,E)-2-benzylidene-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol (69, R$^1$=4-Fluorophenyl, R$^2$=Ethyl, R$^3$=Trifluoromethyl)

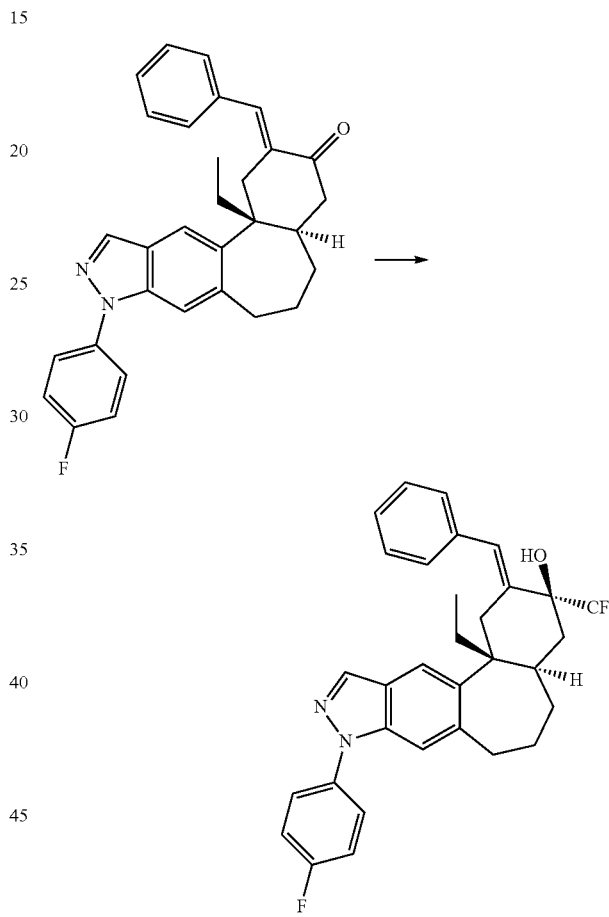

CsF (0.050 g, 0.33 mmol) was added to a mixture of (4aR,12bR,E)-2-benzylidene-12b-ethyl-9-(4-fluorophenyl)-1,4,4a,5,6,7,9,12b-octahydrobenzo[6,7]cyclohepta[1,2-f]indazol-3 (2H)-one; compound with (4aS,12bS,E)-2-benzylidene-12b-ethyl-9-(4-fluorophenyl)-1,4,4a,5,6,7,9,12b-octahydrobenzo[6,7]cyclohepta[1,2-f]indazol-3 (2H)-one (68, R$^1$=4-Fluorophenyl, R$^2$=Ethyl) (0.617 g, 1.33 mmol) and DME (13.0 mL) under nitrogen. After stirring for about 15 min, the mixture was cooled to about 0° C. (Trifluoromethyl)trimethylsilane (0.300 mL, 2.03 mmol) was added dropwise. After about 45 min, the ice bath was removed and the volatiles were removed under reduced pressure. DME (13.0 mL) was added. TBAF (1 M solution in THF, 1.50 mL, 1.50 mmol) was added in one portion. After about 1 h, water (25 mL) and EtOAc (25 mL) were added. The layers were separated and the organics were washed with water (2×25 mL) then dried over Na$_2$SO$_4$, filtered, and concentrated under reduced pressure. The residue was purified on silica gel (40 g) using a gradient of 0-20% EtOAc in heptane. The fractions containing product were combined and concentrated under reduced pressure to afford (3R,4aS,12bS,E)-2-Benzylidene-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol; compound with (3S,4aR,12bR,E)-2-benzylidene-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol (69, $R^1$=4-Fluorophenyl, $R^2$=Ethyl, $R^3$=Trifluoromethyl) (0.489 g, 69% yield) as an ivory solid. LC/MS, method 3, $R_t$=3.03 min, MS m/z 535 (M+H)$^+$. $^1$H NMR (400 MHz, DMSO) δ 8.27 (d, J=0.8 Hz, 1H), 7.86 (s, 1H), 7.83-7.72 (m, 2H), 7.51 (s, 1H), 7.46-7.34 (m, 6H), 7.31-7.23 (m, 1H), 7.21-7.17 (m, 1H), 6.29 (s, 1H), 3.56-3.45 (m, 1H), 3.11-2.99 (m, 1H), 2.93-2.81 (m, 1H), 2.70-2.59 (m, 1H), 2.17-1.89 (m, 4H), 1.86-1.60 (m, 3H), 1.52-1.23 (m, 2H), −0.21 (t, J=7.2 Hz, 3H).

Step #3: (3S,4aR,12bR)-12b-Ethyl-9-(4-fluorophenyl)-3-hydroxy-3-(trifluoromethyl)-1,3,4,4a,5,6,7,12b-octahydrobenzo[6,7]cyclohepta[1,2-f]indazole-2(9H)-one; compound with (3R,4aS,12bS)-12b-ethyl-9-(4-fluorophenyl)-3-hydroxy-3-(trifluoromethyl)-1,3,4,4a,5,6,7,12b-octahydrobenzo[6,7]cyclohepta[1,2-f]indazol-2(9H)-one (70, $R^1$=4-Fluorophenyl, $R^2$=Ethyl, $R^3$=Trifluoromethyl)

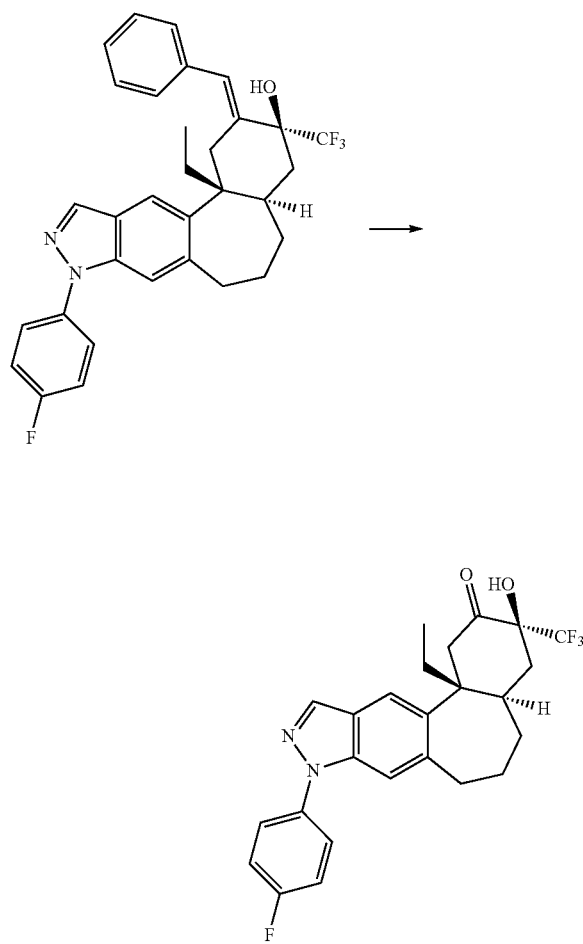

A solution of (3R,4aS,12bS,E)-2-benzylidene-12b-ethyl-9-(4-fluorophenyl)-3-(trifluoromethyl)-1,2,3,4,4a,5,6,7,9,12b-decahydrobenzo[6,7]cyclohepta[1,2-f]indazole-3-ol; compound with (3S,4aR,12bR,E)-2-benzylidene-12b-ethyl-9-(4-fluorophenyl)-3-(trifluoromethyl)-1,2,3,4,4a,5,6,7,9,12b-decahydrobenzo[6,7]cyclohepta[1,2-f]indazole-3-ol (69, $R^1$=4-Fluorophenyl, $R^2$=Ethyl, $R^3$=Trifluoromethyl) (0.489 g, 0.915 mmol), DCM (13.5 mL), and MeOH (1.5 mL) was cooled to −78° C. while purging with $O_2$. After about 10 min, ozone was bubbled through the reaction for about 14 min. The solution was purged with oxygen for about 10 min. Polymer bound triphenylphosphine (3 mmol/g, 0.915 g, 3.50 mmol) was added in one portion. The reaction mixture was allowed to warm to rt over about 30 min. After about 3 h, the mixture was filtered rinsing with DCM. The organic volatiles were removed under reduced pressure. The residue was purified on silica gel (40 g) using a gradient of 0-20% EtOAc in heptane. The fractions containing product were combined and concentrated under reduced pressure to afford (3S,4aR,12bR)-12b-ethyl-9-(4-fluorophenyl)-3-hydroxy-3-(trifluoromethyl)-1,3,4,4a,5,6,7,12b-octahydrobenzo[6,7]cyclohepta[1,2-f]indazol-2(9H)-one; compound with (3R,4aS,12bS)-12b-ethyl-9-(4-fluorophenyl)-3-hydroxy-3-(trifluoromethyl)-1,3,4,4a,5,6,7,12b-octahydrobenzo[6,7]cyclohepta[1,2-f]indazol-2(9H)-one (70, $R^1$=4-Fluorophenyl, $R^2$=Ethyl, $R^3$=Trifluoromethyl) (0.371 g, 88% yield) as an ivory solid. LC/MS, method 2, $R_t$=2.93 min, MS m/z 461 (M+H)$^+$. $^1$H NMR (400 MHz, DMSO) δ 8.24 (s, 1H), 7.86-7.74 (m, 3H), 7.58 (s, 1H), 7.47-7.35 (m, 2H), 6.62 (s, 1H), 3.27-3.19 (m, 1H), 3.18-3.04 (m, 2H), 3.00-2.90 (m, 1H), 2.41-2.18 (m, 3H), 2.06-1.94 (m, 1H), 1.91-1.74 (m, 3H), 1.46-1.16 (m, 2H), 0.41 (t, J=7.3 Hz, 3H).

The enantiomers were separated using Preparative Chiral Purification Method 20 (0.127 g, 0.276 mmol).

Fractions from the first peak eluted were combined and concentrated under reduced pressure. The residue was dissolved in MeCN, treated with water, and concentrated under reduced pressure to remove the organic volatiles. The mixture was frozen then lyophilized to afford (3R,4aS,12bS)-12b-ethyl-9-(4-fluorophenyl)-3-hydroxy-3-(trifluoromethyl)-1,3,4,4a,5,6,7,12b-octahydrobenzo[6,7]cyclohepta[1,2-f]indazol-2(9H)-one (70, $R^1$=4-Fluorophenyl, $R^2$=Ethyl, $R^3$=Trifluoromethyl) (0.0570 g, 45% yield) as an ivory solid. Sign of rotation is negative. LC/MS, method 2, $R_t$=2.93 min, MS m/z 461 (M+H)$^+$. $^1$H NMR (400 MHz, DMSO) δ 8.24 (s, 1H), 7.86-7.74 (m, 3H), 7.58 (s, 1H), 7.47-7.35 (m, 2H), 6.62 (s, 1H), 3.27-3.19 (m, 1H), 3.18-3.04 (m, 2H), 3.00-2.90 (m, 1H), 2.41-2.18 (m, 3H), 2.06-1.94 (m, 1H), 1.91-1.74 (m, 3H), 1.46-1.16 (m, 2H), 0.41 (t, J=7.3 Hz, 3H).

Fractions from the second peak eluted were combined and concentrated under reduced pressure. The residue was dissolved in MeCN, treated with water, and concentrated under reduced pressure to remove MeOH. The mixture was frozen then lyophilized to afford (3S,4aR,12bR)-12b-ethyl-9-(4-fluorophenyl)-3-hydroxy-3-(trifluoromethyl)-1,3,4,4a,5,6,7,12b-octahydrobenzo[6,7]cyclohepta[1,2-f]indazol-2(9H)-one (70, $R^1$=4-Fluorophenyl, $R^2$=Ethyl, $R^3$=Trifluoromethyl) (0.0584 g, 46% yield) as an ivory solid. Sign of rotation is positive. LC/MS, method 2, $R_t$=2.93 min, MS m/z 461 (M+H)$^+$. $^1$H NMR (400 MHz, DMSO) δ 8.24 (s, 1H), 7.86-7.74 (m, 3H), 7.58 (s, 1H), 7.47-7.35 (m, 2H), 6.62 (s, 1H), 3.27-3.19 (m, 1H), 3.18-3.04 (m, 2H), 3.00-2.90 (m, 1H), 2.41-2.18 (m, 3H), 2.06-1.94 (m, 1H), 1.91-1.74 (m, 3H), 1.46-1.16 (m, 2H), 0.41 (t, J=7.3 Hz, 3H).

Example #117 and #118

(2R,3S,4aR,12bR)-12b-Ethyl-9-(4-fluorophenyl)-2-methyl-3-(trifluoromethyl)-1,2,3,4,4a,5,6,7,9,12b-decahydrobenzo[6,7]cyclohepta[1,2-f]indazole-2,3-diol (71, R¹=4-Fluorophenyl, R²=Ethyl, R³=Trifluoromethyl, R³'=Hydroxyl, R³"=Methyl) and (2S,3R,4aS,12bS)-12b-ethyl-9-(4-fluorophenyl)-2-methyl-3-(trifluoromethyl)-1,2,3,4,4a,5,6,7,9,12b-decahydrobenzo[6,7]cyclohepta[1,2-f]indazole-2,3-diol (71, R¹=4-Fluorophenyl, R²=Ethyl, R³=Trifluoromethyl, R³'=Hydroxyl, R³"=Methyl)

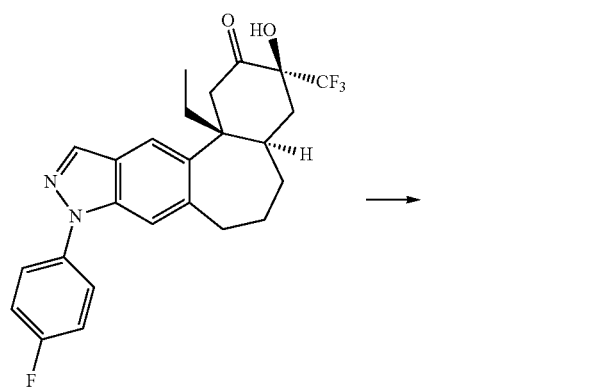

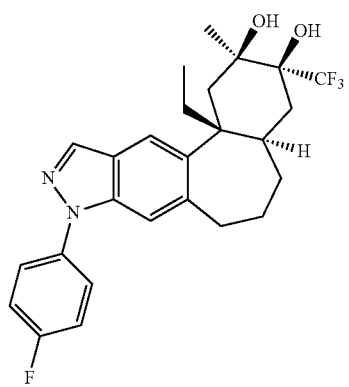

Methylmagnesium bromide (3.0 M solution in diethyl ether, 1.30 mL, 1.30 mmol) was added dropwise over about 15 min to a solution of (3S,4aR,12bR)-12b-ethyl-9-(4-fluorophenyl)-3-hydroxy-3-(trifluoromethyl)-1,3,4,4a,5,6,7,12b-octahydrobenzo[6,7]cyclohepta[1,2-f]indazol-2(9H)-one; compound with (3R,4aS,12bS)-12b-ethyl-9-(4-fluorophenyl)-3-hydroxy-3-(trifluoromethyl)-1,3,4,4a,5,6,7,12b-octahydrobenzo[6,7]cyclohepta[1,2-f]indazol-2(9H)-one (70, R¹=4-Fluorophenyl, R²=Ethyl, R³=Trifluoromethyl) (0.184 g, 0.399 mmol) and THF (8.0 mL) under a nitrogen atmosphere maintaining an internal temperature between about −40° C. and −50° C. The cold bath was allowed to thaw to about 0° C. over about 30 min. After about 3.5 h, the ice bath was removed. After about 30 min at rt, the solution was poured into sat. aq. NH₄Cl (25 mL), water (5 mL) and DCM (25 mL). The layers were separated and the aqueous layer was extracted with DCM (2×25 mL). The combined organics were dried over Na₂SO₄, filtered, and concentrated under reduced pressure. The residue was purified on silica gel (25 g) using a gradient of 0-6% EtOAc in DCM. The fractions containing product were combined and concentrated under reduced pressure to afford (2R,3 S,4aR,12bR)-12b-ethyl-9-(4-fluorophenyl)-2-methyl-3-(trifluoromethyl)-1,2,3,4,4a,5,6,7,9,12b-decahydrobenzo[6,7]cyclohepta[1,2-f]indazole-2,3-diol; compound with (2S,3R,4aS,12bS)-12b-ethyl-9-(4-fluorophenyl)-2-methyl-3-(trifluoromethyl)-1,2,3,4,4a,5,6,7,9,12b-decahydrobenzo[6,7]cyclohepta[1,2-f]indazole-2,3-diol (71, R¹=4-Fluorophenyl, R²=Ethyl, R³=Trifluoromethyl, R³'=Hydroxyl, R³"=Methyl) (0.192 g, quantitative yield) as an ivory solid. LC/MS, method 2, R$_t$=2.89 min, MS m/z 477 (M+H)⁺. ¹H NMR (400 MHz, DMSO) δ 8.29 (s, 1H), 7.83 (s, 1H), 7.83-7.75 (m, 2H), 7.54 (s, 1H), 7.44-7.36 (m, 2H), 5.70 (s, 1H), 4.49 (s, 1H), 3.24-3.10 (m, 1H), 3.00-2.88 (m, 1H), 2.45-2.30 (m, 2H), 2.22-2.09 (m, 1H), 2.06-1.71 (m, 5H), 1.67-1.56 (m, 2H), 1.48-1.31 (m, 1H), 1.33 (s, 3H), 0.48 (t, J=7.1 Hz, 3H).

The enantiomers were separated using Preparative Chiral Purification Method 21 (0.208 g, 0.437 mmol).

Fractions from the first peak eluted were combined and concentrated under reduced pressure. The residue was dissolved in MeCN, treated with water, and concentrated under reduced pressure to remove the organic volatiles. The mixture was frozen then lyophilized to afford (3R,4aS,12bS)-12b-ethyl-9-(4-fluorophenyl)-3-hydroxy-3-(trifluoromethyl)-1,3,4,4a,5,6,7,12b-octahydrobenzo[6,7]cyclohepta[1,2-f]indazol-2(9H)-one (71, R¹=4-Fluorophenyl, R²=Ethyl, R³=Trifluoromethyl, R³'=Hydroxyl, R³"=Methyl) (0.0913 g, 44% yield) as an ivory solid. Sign of rotation is positive. LC/MS, method 2, R$_t$=2.89 min, MS m/z 477 (M+H)⁺. ¹H NMR (400 MHz, DMSO) δ 8.29 (s, 1H), 7.83 (s, 1H), 7.83-7.75 (m, 2H), 7.54 (s, 1H), 7.44-7.36 (m, 2H), 5.70 (s, 1H), 4.49 (s, 1H), 3.24-3.10 (m, 1H), 3.00-2.88 (m, 1H), 2.45-2.30 (m, 2H), 2.22-2.09 (m, 1H), 2.06-1.71 (m, 5H), 1.67-1.56 (m, 2H), 1.48-1.31 (m, 1H), 1.33 (s, 3H), 0.48 (t, J=7.1 Hz, 3H).

Fractions from the second peak eluted were combined and concentrated under reduced pressure. The residue was dissolved in MeCN, treated with water, and concentrated under reduced pressure to remove MeOH. The mixture was frozen then lyophilized to afford (2S,3R,4aS,12bS)-12b-ethyl-9-(4-fluorophenyl)-2-methyl-3-(trifluoromethyl)-1,2,3,4,4a,5,6,7,9,12b-decahydrobenzo[6,7]cyclohepta[1,2-f]indazole-2,3-diol (71, R¹=4-Fluorophenyl, R²=Ethyl, R³=Trifluoromethyl, R³'=Hydroxyl, R³"=Methyl) (0.0932 g, 45% yield) as an ivory solid. Sign of rotation is negative. LC/MS, method 2, R$_t$=2.89 min, MS m/z 477 (M+H)⁺. ¹H NMR (400 MHz, DMSO) δ 8.29 (s, 1H), 7.83 (s, 1H), 7.83-7.75 (m, 2H), 7.54 (s, 1H), 7.44-7.36 (m, 2H), 5.70 (s, 1H), 4.49 (s, 1H), 3.24-3.10 (m, 1H), 3.00-2.88 (m, 1H), 2.45-2.30

(m, 2H), 2.22-2.09 (m, 1H), 2.06-1.71 (m, 5H), 1.67-1.56 (m, 2H), 1.48-1.31 (m, 1H), 1.33 (s, 3H), 0.48 (t, J=7.1 Hz, 3H).

Example #119, #120, #121 and #122

(2R,3S,4aR,12bR)-12b-Ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol (71, R¹=4-Fluorophenyl, R²=Ethyl, R³=Trifluoromethyl, R³'=Hydroxyl, R³''=H), (2S,3R,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol (71, R¹=4-Fluorophenyl, R²=Ethyl, R³=Trifluoromethyl, R³'=Hydroxyl, R³''=H), (2S,3S,4aR,12bR)-12b-Ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol (71, R¹=4-Fluorophenyl, R²=Ethyl, R³=Trifluoromethyl, R³'=H, R³''=Hydroxyl), and (2R,3R,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol (71, R¹=4-Fluorophenyl, R²=Ethyl, R³=Trifluoromethyl, R³'=H, R³''=Hydroxyl)

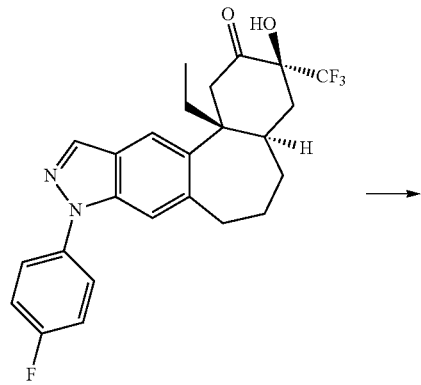

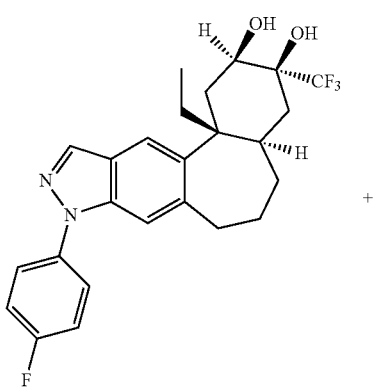

+

-continued

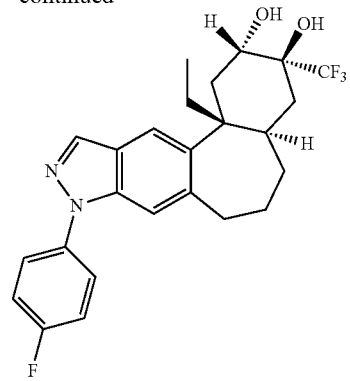

NaBH₄ (0.060 g, 1.6 mmol) was added in one portion to a solution of (3S,4aR,12bR)-12b-ethyl-9-(4-fluorophenyl)-3-hydroxy-3-(trifluoromethyl)-1,3,4,4a,5,6,7,12b-octahydrobenzo[6,7]cyclohepta[1,2-f]indazol-2 (9H)-one; compound with (3R,4aS,12bS)-12b-ethyl-9-(4-fluorophenyl)-3-hydroxy-3-(trifluoromethyl)-1,3,4,4a,5,6,7,12b-octahydrobenzo[6,7]cyclohepta[1,2-f]indazol-2 (9H)-one (70, R¹=4-Fluorophenyl, R²=Ethyl, R³=Trifluoromethyl) (0.500 g, 1.09 mmol), THF (4.0 mL), and MeOH (8.0 mL). After about 30 min, the volatiles were removed under reduced pressure. Sat. aq. NH₄Cl (20 mL), water (20 mL) and DCM (50 mL) were added. 2 M aq. HCl was added dropwise to adjust to about pH 1. After stirring vigorously for about 15 min, the layers were separated and the organic layer was washed with 40 mL of sat. aq. NaCl (40 mL). The combined organics were dried over Na₂SO₄, filtered, and concentrated under reduced pressure. The residue was purified on silica gel (80 g) using a gradient of 10-50% EtOAc in heptane. The fractions containing the first eluting diastereomer were combined and concentrated under reduced pressure to afford (2R,3S,4aR,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol; compound with (2S,3R,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol (71, R¹=4-Fluorophenyl, R²=Ethyl, R³=Trifluoromethyl, R³'=Hydroxyl, R³''=H) (0.270 g, 54% yield) as an ivory solid. LC/MS, method 2, R_t=2.84 min, MS m/z 463 (M+H)⁺. ¹H NMR (400 MHz, DMSO) δ 8.28 (d, J=0.7 Hz, 1H), 7.84 (s, 1H), 7.84-7.76 (m, 2H), 7.60 (s, 1H), 7.46-7.35 (m, 2H), 5.37 (d, J=5.3 Hz, 1H), 5.30 (s, 1H), 3.99-3.90 (m, 1H), 3.38-3.23 (m, 1H), 2.96-2.85 (m, 1H), 2.46-2.29 (m, 2H), 2.07-1.73 (m, 4H), 1.73-1.63 (m, 1H), 1.63-1.45 (m, 3H), 1.44-1.27 (m, 1H), 0.53 (t, J=7.3 Hz, 3H). The fractions containing the second eluting diastereomer were combined and concentrated under reduced pressure to afford (2S,3S,4aR,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol; compound with (2R,3R,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol (71, R¹=4-Fluorophenyl, R²=Ethyl, R³=Trifluoromethyl, R³'=H, R³''=Hydroxyl) (0.171 g, 34% yield) as an ivory solid. LC/MS, method 2, R_t=2.61 min, MS m/z 463 (M+H)⁺. ¹H NMR (400 MHz, DMSO) δ 8.30 (d, J=0.8 Hz, 1H), 7.82 (s, 1H), 7.89-7.75 (m, 2H), 7.55 (s, 1H), 7.46-7.35 (m, 2H), 5.82 (s, 1H), 5.16 (d, J=4.1 Hz, 1H), 3.89-3.78 (m, 1H), 3.21-3.08 (m, 1H), 2.99-2.88 (m, 1H), 2.36-2.26 (m, 1H), 2.21-2.08 (m, 2H), 2.03-1.93 (m, 1H), 1.89-1.58 (m, 6H), 1.43-1.25 (m, 1H), 0.45 (t, J=7.3 Hz, 3H).

The enantiomers were separated using Preparative Chiral Purification Method 22 on (2R,3S,4aR,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol; compound with (2S,3R,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol (71, $R^1$=4-Fluorophenyl, $R^2$=Ethyl, $R^3$=Trifluoromethyl, $R^{3'}$=Hydroxyl, $R^{3''}$=H) (0.134 g, 0.290 mmol). LC/MS, method 2, $R_t$=2.61 min, MS m/z 463 (M+H)$^+$. $^1$H NMR (400 MHz, DMSO) δ 8.30 (d, J=0.8 Hz, 1H), 7.82 (s, 1H), 7.89-7.75 (m, 2H), 7.55 (s, 1H), 7.46-7.35 (m, 2H), 5.82 (s, 1H), 5.16 (d, J=4.1 Hz, 1H), 3.89-3.78 (m, 1H), 3.21-3.08 (m, 1H), 2.99-2.88 (m, 1H), 2.36-2.26 (m, 1H), 2.21-2.08 (m, 2H), 2.03-1.93 (m, 1H), 1.89-1.58 (m, 6H), 1.43-1.25 (m, 1H), 0.45 (t, J=7.3 Hz, 3H).

Fractions from the first peak eluted were combined and concentrated under reduced pressure. The residue was dissolved in MeCN, treated with water, and concentrated under reduced pressure to remove the organic volatiles. The mixture was frozen then lyophilized to afford (2R,3S,4aR,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol (71, $R^1$=4-Fluorophenyl, $R^2$=Ethyl, $R^3$=Trifluoromethyl, $R^{3'}$=Hydroxyl, $R^{3''}$=H) (0.0451 g, 34% yield) as an ivory solid. Sign of rotation is positive. LC/MS, method 2, $R_t$=2.61 min, MS m/z 463 (M+H)$^+$. $^1$H NMR (400 MHz, DMSO) δ 8.30 (d, J=0.8 Hz, 1H), 7.82 (s, 1H), 7.89-7.75 (m, 2H), 7.55 (s, 1H), 7.46-7.35 (m, 2H), 5.82 (s, 1H), 5.16 (d, J=4.1 Hz, 1H), 3.89-3.78 (m, 1H), 3.21-3.08 (m, 1H), 2.99-2.88 (m, 1H), 2.36-2.26 (m, 1H), 2.21-2.08 (m, 2H), 2.03-1.93 (m, 1H), 1.89-1.58 (m, 6H), 1.43-1.25 (m, 1H), 0.45 (t, J=7.3 Hz, 3H).

Fractions from the second peak eluted were combined and concentrated under reduced pressure. The residue was dissolved in MeCN, treated with water, and concentrated under reduced pressure to remove the organic volatiles. The mixture was frozen then lyophilized to afford (2S,3R,4aS,12bS)-12b-ethyl-9-(4-fluorophenyl)-2-methyl-3-(trifluoromethyl)-1,2,3,4,4a,5,6,7,9,12b-decahydrobenzo[6,7]cyclohepta[1,2-f]indazole-2,3-diol (71, $R^1$=4-Fluorophenyl, $R^2$=Ethyl, $R^3$=Trifluoromethyl, $R^{3'}$=Hydroxyl, $R^{3''}$=H) (0.0623 g, 46% yield) as an ivory solid. Sign of rotation is negative. LC/MS, method 2, $R_t$=2.61 min, MS m/z 463 (M+H)$^+$. $^1$H NMR (400 MHz, DMSO) δ 8.30 (d, J=0.8 Hz, 1H), 7.82 (s, 1H), 7.89-7.75 (m, 2H), 7.55 (s, 1H), 7.46-7.35 (m, 2H), 5.82 (s, 1H), 5.16 (d, J=4.1 Hz, 1H), 3.89-3.78 (m, 1H), 3.21-3.08 (m, 1H), 2.99-2.88 (m, 1H), 2.36-2.26 (m, 1H), 2.21-2.08 (m, 2H), 2.03-1.93 (m, 1H), 1.89-1.58 (m, 6H), 1.43-1.25 (m, 1H), 0.45 (t, J=7.3 Hz, 3H).

The enantiomers were separated using Preparative Chiral Purification Method 23 on (2S,3S,4aR,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol; compound with (2R,3R,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol (71, $R^1$=4-Fluorophenyl, $R^2$=Ethyl, $R^3$=Trifluoromethyl, $R^{3'}$=H, $R^{3''}$=Hydroxyl) (0.169 g, 0.365 mmol).

Fractions from the first peak eluted were combined and concentrated under reduced pressure. The residue was dissolved in MeCN, treated with water, and concentrated under reduced pressure to remove the organic volatiles. The mixture was frozen then lyophilized to afford (2S,3S,4aR,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol (71, $R^1$=4-Fluorophenyl, $R^2$=Ethyl, $R^3$=Trifluoromethyl, $R^{3'}$=H, $R^{3''}$=Hydroxyl) (0.0741 g, 44% yield) as an ivory solid. Sign of rotation is positive. LC/MS, method 2, $R_t$=2.61 min, MS m/z 463 (M+H)$^+$. $^1$H NMR (400 MHz, DMSO) δ 8.30 (d, J=0.8 Hz, 1H), 7.82 (s, 1H), 7.89-7.75 (m, 2H), 7.55 (s, 1H), 7.46-7.35 (m, 2H), 5.82 (s, 1H), 5.16 (d, J=4.1 Hz, 1H), 3.89-3.78 (m, 1H), 3.21-3.08 (m, 1H), 2.99-2.88 (m, 1H), 2.36-2.26 (m, 1H), 2.21-2.08 (m, 2H), 2.03-1.93 (m, 1H), 1.89-1.58 (m, 6H), 1.43-1.25 (m, 1H), 0.45 (t, J=7.3 Hz, 3H).

Fractions from the second peak eluted were combined and concentrated under reduced pressure. The residue was dissolved in MeCN, treated with water, and concentrated under reduced pressure to remove the organic volatiles. The mixture was frozen then lyophilized to afford (2R,3R,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol (71, $R^1$=4-Fluorophenyl, $R^2$=Ethyl, $R^3$=Trifluoromethyl, $R^{3'}$=H, $R^{3''}$=Hydroxyl) (0.0741 g, 44% yield) as an ivory solid. Sign of rotation is negative. LC/MS, method 2, $R_t$=2.61 min, MS m/z 463 (M+H)$^+$. $^1$H NMR (400 MHz, DMSO) δ 8.30 (d, J=0.8 Hz, 1H), 7.82 (s, 1H), 7.89-7.75 (m, 2H), 7.55 (s, 1H), 7.46-7.35 (m, 2H), 5.82 (s, 1H), 5.16 (d, J=4.1 Hz, 1H), 3.89-3.78 (m, 1H), 3.21-3.08 (m, 1H), 2.99-2.88 (m, 1H), 2.36-2.26 (m, 1H), 2.21-2.08 (m, 2H), 2.03-1.93 (m, 1H), 1.89-1.58 (m, 6H), 1.43-1.25 (m, 1H), 0.45 (t, J=7.3 Hz, 3H).

Scheme 18:

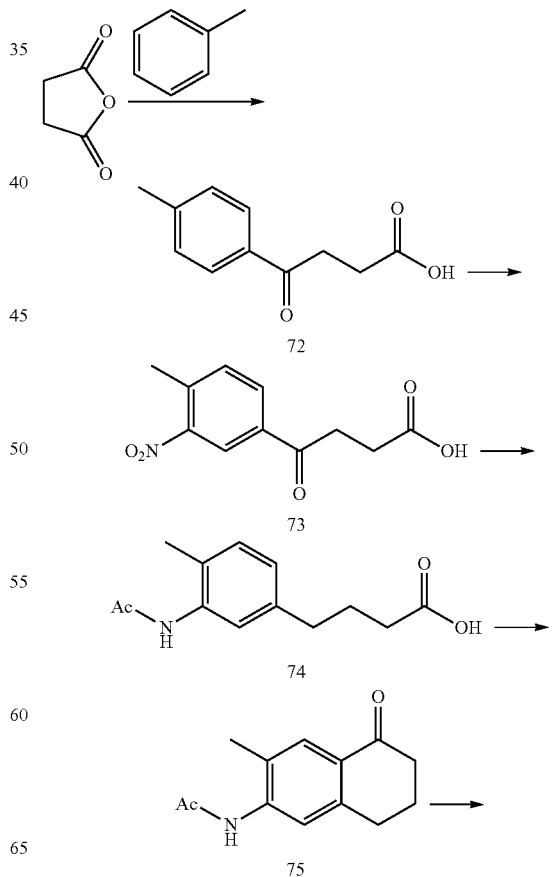

195

-continued

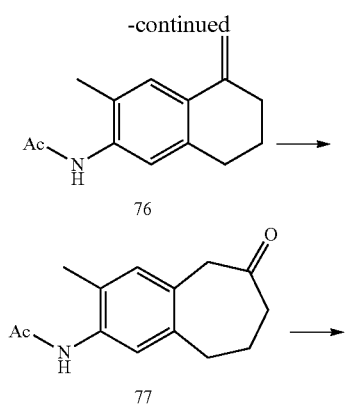

196

Step 1: 4-Oxo-4-(p-tolyl)butanoic acid (72)

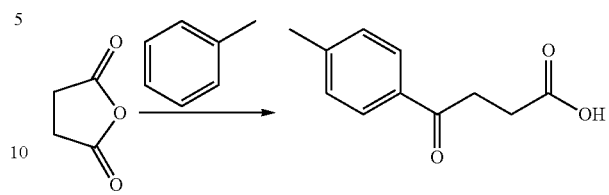

Succinic anhydride (2.25 kg, 22.5 mol) was added to toluene (12.5 L, 118 mol). The mixture was heated to between 40-50° C. AlCl₃ (6.75 kg, 50.6 mol) was added portionwise maintaining an internal temperature of about 90° C. After completion of addition, the brown solution/syrup was stirred for about 30 min at about 95-105° C. The mixture was cooled to about 30° C. then poured onto crushed ice (45 L). After stirring for about 15 min, EtOAc (18 L) and MeOH (2.5 L) were added. The layers were separated and the aqueous phase was extracted with EtOAc (2×10 L). The combined organic layers were washed with water (15 L) and sat. aq. NaCl (15 L), dried over Na₂SO₄ and concentrated under reduced pressure.

The residue was stirred with tert-butyl methyl ether (8 L) overnight at rt. The precipitate was collected by filtration rinsing with tert-butyl methyl ether (2×1.5 L). The material was dried overnight at rt to afford 4-oxo-4-(p-tolyl)butanoic acid (72) (2000 g, 46% yield) as a white solid. ¹H NMR (300 MHz, DMSO): δ 7.92 (d, J=8.4 Hz, 2H), 7.28 (d, J=8.0 Hz, 2H), 3.34 (m, 2H), 2.82 (m, 2H), 2.43 (s, 3H).

Step 2: 4-(4-Methyl-3-nitrophenyl)-4-oxobutanoic acid (73)

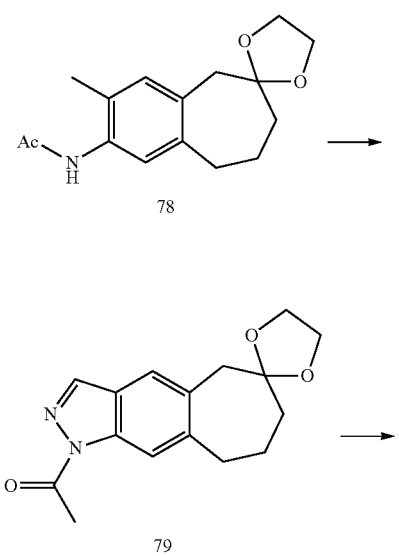

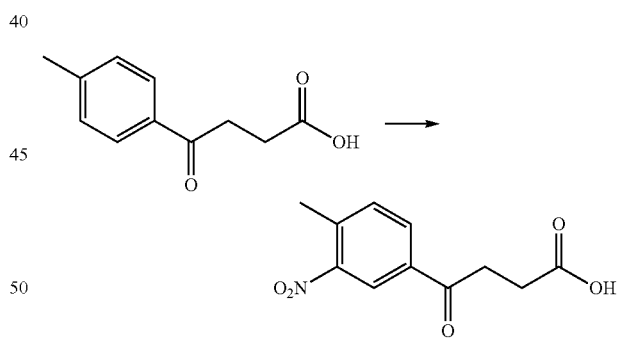

Preparation 1: 5,7,8,9-tetrahydro-1H-spiro[cyclohepta[f]indazole-6,2'[1,3]dioxolane] (80)

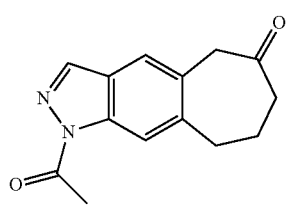 [SMILES: CC(=O)n1ncc2cc3c(cc21)CCCC(=O)C3]

HNO₃ (65%) (2300 mL) was cooled to about 0° C. Fuming HNO₃ (5700 mL) was carefully added maintaining an internal temperature of less than 15° C. The solution was cooled to about –5° C. and H₂SO₄ (800 mL) was added maintaining an internal temperature of less than 5° C. After cooling to about –8° C., 4-oxo-4-(p-tolyl)butanoic acid (72) (4000 g, 20.8 mol) was added portionwise maintaining the temperature below about 0° C. After completion of addition the mixture was allowed to warm to about 15-17° C. The solution was poured onto crushed ice with stirring. After about 2 h at rt, the solid was collected by filtration washing with water (3×10 L) and then dried to afford 4-(4-methyl-3-nitrophenyl)-4-oxobutanoic acid (73) (3400 g, 69% yield). ¹H NMR (300 MHz, DMSO): δ 8.46 (s, 1H), 8.20 (d, J=8.4 Hz, 1H), 7.64 (d, J=8.0 Hz, 1H), 3.25 (m, 2H), 2.62 (m, 2H), 2.60 (s, 3H).

Step 3:
4-(3-Acetamido-4-methylphenyl)-4-oxobutanoic acid (74)

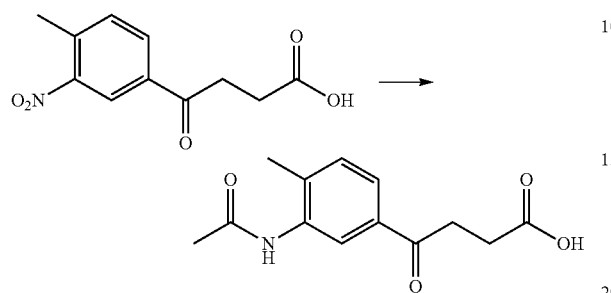

10% Pd/C (100 g) was added to a solution of 4-(4-methyl-3-nitrophenyl)-4-oxobutanoic acid (73) (3.40 kg, 14.3 mol) and EtOAc (20 L) in 40 L Parr reactor. Acetic anhydride (2.40 L, 25.4 mol) was added. The mixture was stirred under about 5 bar H₂ atmosphere overnight. The reaction was concentrated under reduced pressure. To the resulting grey solid was added EtOH (14 L) and H₂SO₄ (~35 mL). The mixture was stirred in the 40 L Parr vessel under about 5 bar H₂ pressure overnight at rt. The reaction mixture was poured into 2 N aqueous NaOH (35 L), stirred overnight at rt, and then filtered through of Celite® rinsing with water. The filtrate and washings were combined and concentrated under reduced pressure to remove EtOH. The aqueous residue was washed with tert-butyl methyl ether (7 L). The aqueous layer was acidified with 2 N aq. HCl. The precipitate was collected by filtration rinsing with water (2×14 L) and dried to afford 4-(3-acetamido-4-methylphenyl)-4-oxobutanoic acid (74) (2.70 kg, 76% yield). ¹H NMR (300 MHz, DMSO): δ 12.03 (s, 1H), 9.25 (s, 1H), 7.50 (s, 1H), 7.30 (d, J=7.6 Hz, 2H), 6.88 (d, J=7.6 Hz, 2H), 2.56 (m, 2H), 2.28 (m, 2H), 2.16 (s, 3H), 2.04 (s, 3H), 1.74 (m, 2H).

Step 4: N-(3-Methyl-5-oxo-5,6,7,8-tetrahydronaphthalen-2-yl)acetamide (75)

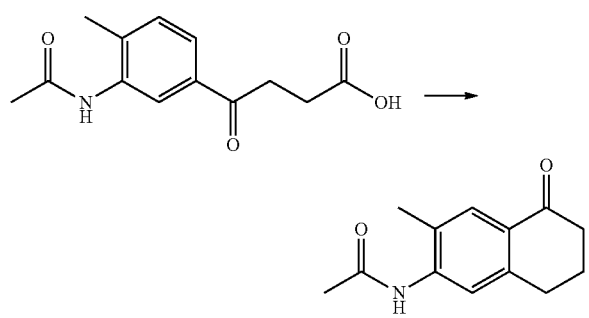

In a mechanically stirred 50 L vessel, 4-(3-acetamido-4-methylphenyl)-4-oxobutanoic acid (74) (675 g, 2.87 mol) was dissolved in nitromethane (13.75 L). Thionyl chloride (255 mL, 3.49 mol) was added. The resulting mixture was stirred for about 1.5 h at rt. AlCl₃ (973 g, 7.30 mol) was added maintaining a temperature of about 25° C. The resulting mixture was stirred for another about 30 min and then poured onto ice water (30 L). The resulting mixture was extracted with EtOAc (1×60 L then 2×20 L). The organic layers were combined and washed with sat. aq. NaCl (1×10 L), 1 M aq. NaOH (15 L) and sat. aq. NaCl (1×10 L). The organic layer was dried over Na₂SO₄, filtered, and concentrated to afford N-(3-Methyl-5-oxo-5,6,7,8-tetrahydronaphthalen-2-yl)acetamide (380 g, 65% yield). ¹H NMR (300 MHz, DMSO): δ 9.36 (s, 1H), 7.68 (s, 1H), 7.62 (s, 1H), 2.86 (m, 2H), 2.55 (m, 2H), 2.23 (s, 3H), 2.06 (s, 3H), 2.00 (m, 2H).

Step 5: N-(3-Methyl-5-methylene-5,6,7,8-tetrahydronaphthalen-2-yl)acetamide (76)

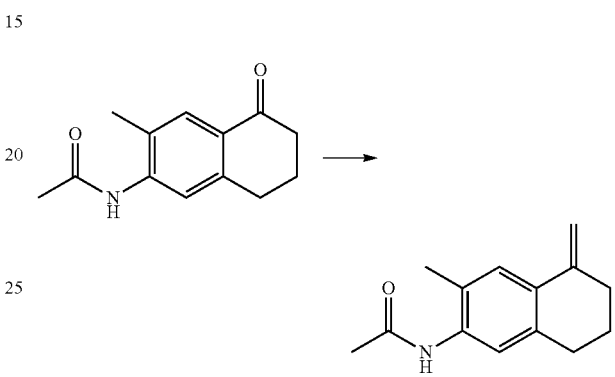

In a mechanically stirred 50 L vessel, Et₂O (12.5 L) was added to methyltriphenylphosphonium bromide (1.81 kg, 5.06 mol). KOtBu (566 g, 5.06 mol) was added. The mixture was heated to reflux for about 1 h. THF (5 L) was added followed by addition of N-(3-methyl-5-oxo-5,6,7,8-tetrahydronaphthalen-2-yl)acetamide (75) (475 g, 2.19 mol). The mixture was warmed to reflux overnight. The reaction was diluted with Et₂O (5 L). The resulting mixture was cooled to rt and then poured into water (30 L). After stirring for about 1 h at rt, the layers were left standing to separate. The aqueous layer was removed and the organic mixture was filtered rinsing with Et₂O. The solids were dried in vacuo to afford N-(3-methyl-5-methylene-5,6,7,8-tetrahydronaphthalen-2-yl)acetamide (76) (284 g, 60% yield). ¹H NMR (300 MHz, DMSO): δ 9.24 (s, 1H), 7.49 (s, 1H), 7.24 (s, 1H), 5.48 (m, 1H), 4.86 (m, 1H), 2.65 (m, 2H), 2.49 (m, 2H), 2.35 (s, 3H), 2.06 (s, 3H), 1.75 (m, 2H).

Step 6: N-(3-Methyl-6-oxo-6,7,8,9-tetrahydro-5H-benzo[7]annulen-2-yl)acetamide (77)

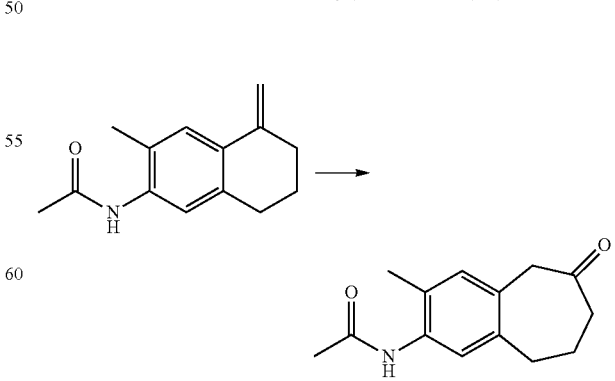

In a 50 L mechanically stirred vessel, N-(3-methyl-5-methylene-5,6,7,8-tetrahydronaphthalen-2-yl)acetamide (76)

(710 g, 3.30 mol) was suspended in MeOH (22.5 L) and water (1.875 L). A solution of hydroxy(tosyloxy)iodobenzene (1.30 kg, 3.30 mol) in MeOH (3.50 L) was added maintaining the internal temperature below about 20° C. After completion of addition, the solution was stirred for about 15 min and then poured into saturated aqueous NaCl (35 L). The aqueous mixture was extracted with DCM (2×12 L). The combined organic layers were washed with 5 N aqueous HCl (3.50 L), dried with Na$_2$SO$_4$, filtered, and concentrated to afford N-(3-methyl-6-oxo-6,7,8,9-tetrahydro-5H-benzo[7]annulen-2-yl)acetamide (77) (520 g, 68% yield). $^1$H NMR (300 MHz, DMSO): δ 9.24 (s, 1H), 7.20 (s, 1H), 6.98 (s, 1H), 3.68 (s, 2H), 2.88 (m, 2H), 2.52 (m, 2H), 2.16 (s, 3H), 2.04 (s, 3H), 1.82 (m, 2H).

Step 7: N-(3-Methyl-5,7,8,9-tetrahydrospiro[benzo[7]annulene-6,2'-[1,3]dioxolan]-2-yl)acetamide (78)

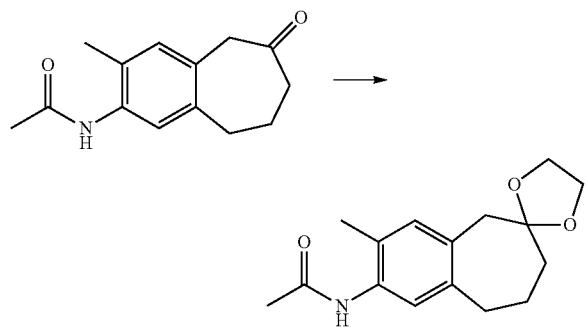

In a 50 L mechanically stirred vessel with Dean-Stark trap, toluene (22 L) was added to N-(3-methyl-6-oxo-6,7,8,9-tetrahydro-5H-benzo[7]annulen-2-yl)acetamide (77) (1.04 kg, 4.50 mol). TosOH (84.0 g, 442 mmol) and ethylene glycol (750 mL, 13.4 mol) were added. The resulting mixture was heated to reflux overnight, cooled to rt, diluted with EtOAc (12 L) and washed with sat. aq. NaHCO$_3$ (12 L) and sat. aq.s NaCl (12 L). The combined aq. washes were extracted with DCM (2×8 L). The combined organic layers were dried over Na$_2$SO$_4$, filtered, and concentrated under reduced pressure. The residue was purified on silica gel. The product containing fractions were combined and concentrated under reduced pressure to afford N-(3-methyl-5,7,8,9-tetrahydrospiro[benzo[7]annulene-6,2'-[1,3]dioxolan]-2-yl)acetamide (78) (900 g, 73% yield). $^1$H NMR (300 MHz, CDCl$_3$): δ 7.45 (s, 1H), 7.03 (s, 1H), 6.92 (s, 1H), 3.96 (m, 4H), 3.02 (s, 2H), 2.76 (m, 2H), 2.20 (s, 3H), 2.18 (s, 3H), 1.98 (m, 2H), 1.74 (m, 2H).

Step 8: 1-(5,7,8,9-Tetrahydro-1H-spiro[cyclohepta[f]indazole-6,2'-[1,3]dioxolan]-1-yl)ethanone (79)

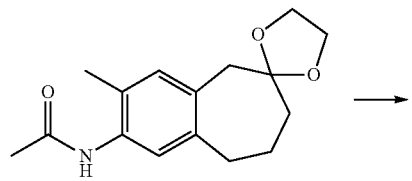

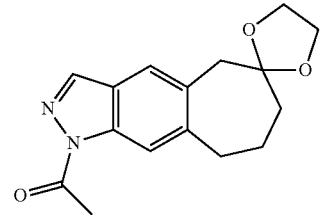

In a 20 L 3 necked flask, N-(3-Methyl-5,7,8,9-tetrahydrospiro[benzo[7]annulene-6,2'-[1,3]dioxolan]-2-yl)acetamide (78) (900 g, 3.27 mol) was dissolved in chloroform (10 L). KOAc (634 g, 6.54 mol), HOAc (382 mL, 6.54 mol), acetic anhydride (655 mL, 6.54 mol), 18-crown-6 (130 g, 523 mmol) and isoamylnitrite (1.30 L, 13.4 mol) were respectively added. The mixture was heated to reflux for about 3 h. Acetic anhydride (900 mL, 9.54 mol) and isoamylnitrite (1.80 L, 13.4 mol) were added and the mixture was heated to reflux overnight. The reaction mixture was cooled to rt and then carefully poured into sat. aq. NaHCO$_3$ (80 L). The pH was carefully adjusted to basic with NaHCO$_3$. The layers were separated and the aq. phase was extracted with DCM (2×15 L). The combined organic layers were concentrated under reduced pressure. tert-Butyl methyl ether (1500 mL) was added and the resulting slurry was stirred for about 1 h. The precipitate was collected by filtration to afford 1-(5,7,8,9-tetrahydro-1H-spiro[cyclohepta[f]indazole-6,2'-[1,3]dioxolan]-1-yl)ethanone (79) (450 g, 48% yield) as a yellow solid. $^1$H NMR (300 MHz, DMSO): δ 8.38 (s, 1H), 8.05 (s, 1H), 7.72 (s, 1H), 3.95 (m, 2H), 3.82 (m, 2H), 3.16 (s, 2H), 2.96 (m, 2H), 2.64 (s, 3H), 1.84 (m, 2H), 1.62 (m, 2H).

Step 9: 1-Acetyl-5,7,8,9-tetrahydrocyclohepta[f]indazol-6(1H)-one (81)

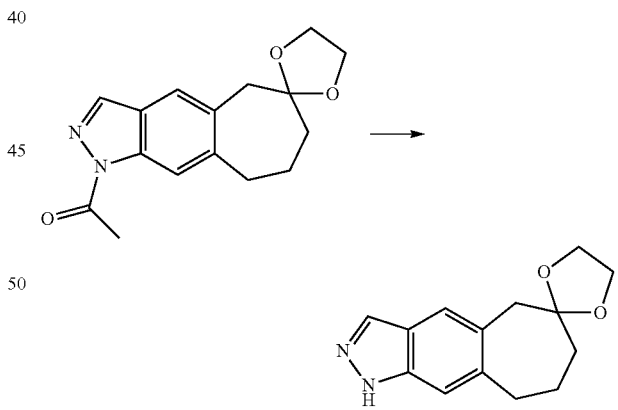

In a 10 L 3 necked flask, 1-(5,7,8,9-tetrahydro-1H-spiro[cyclohepta[f]indazole-6,2'-[1,3]dioxolan]-1-yl)ethanone (79) (440 g, 1.54 mol) was dissolved in THF (5.2 L). A solution of LiOH (143 g, 5.97 mol) in water (3.5 L) was added. The mixture was stirred at rt for about 50 min. The mixture was extracted with EtOAc (2×15 L). The combined organic layers were washed with water, dried over MgSO$_4$, filtered and concentrated under reduced pressure. The residue was recrystallized from ethanol to give 1-acetyl-5,7,8,9-tetrahydrocyclohepta[f]indazol-6(1H)-one (81) (220 g, 59% yield) as a light yellow solid. $^1$H NMR (300 MHz, CDCl$_3$): δ

10.05 (s, 1H), 7.96 (s, 1H), 7.47 (s, 1H), 7.20 (s, 1H), 4.03 (m, 4H), 3.16 (s, 2H), 2.91 (m, 2H), 2.04 (m, 2H), 1.88 (m, 2H).

Scheme 19:

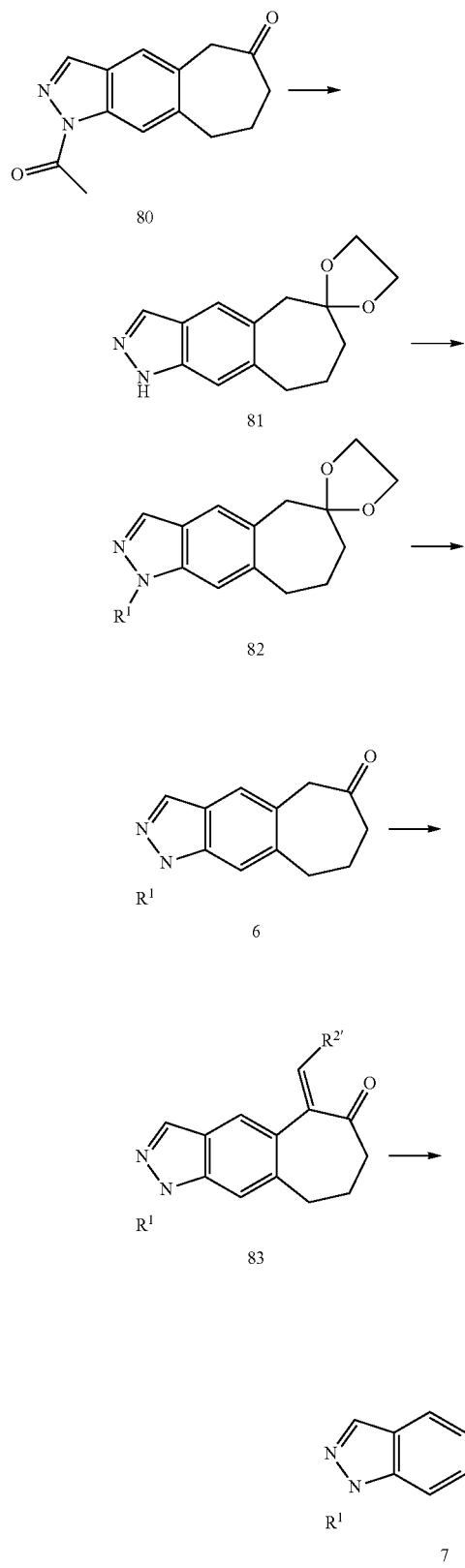

Preparation 2: 5-Ethylidene-1-(pyridin-4-yl)-5,7,8,9-tetrahydrocyclohepta indazol-6(1H)-one (83, R¹=4-Pyridyl, R²'=Methyl)

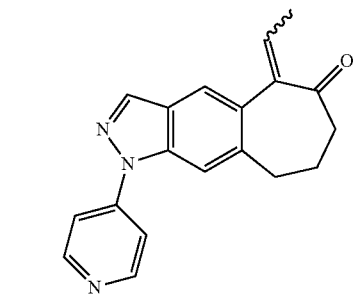

Step 1: (5,7,8,9-Tetrahydro-1H-spiro[cyclohepta[f]indazole-6,2'-[1,3]dioxolane (81)

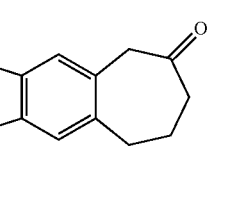

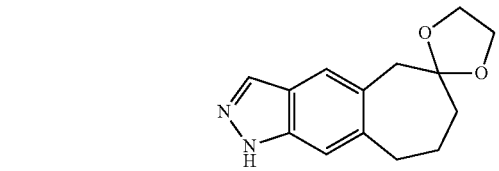

1-Acetyl-5,7,8,9-tetrahydrocyclohepta[f]indazol-6(1H)-one (79) (30 g, 124 mmol) was added to a round bottom flask, equipped with a Dean Stark trap and condenser. Ethane-1,2-diol (27.6 mL, 495 mmol), pTSA (2.36 g, 12.38 mmol) and toluene (300 mL) were added and the resulting mixture was heated to about 142° C. for about 90 min. After cooling to rt, the mixture was concentrated and sonicated with water (~50 mL). The resulting solids were collected by filtration and taken into MeOH (200 mL) and water (200 mL). Potassium hydroxide (13.9 g, 248 mmol) was added and the mixture was stirred at rt for about 30 min. The mixture was extracted with DCM (300 mL), washed with brine (200 mL), dried over MgSO₄ and concentrated to afford 5,7,8,9-tetrahydro-M-spiro[cyclohepta[f]indazole-6,2'-[1,3]dioxolane] (81), (28.3 g, 93%); LC/MS, method 1, R$_f$=1.20 min, MS m/z 245 (M+H)⁺¹H NMR (400 MHz, DMSO) δ 12.79 (bs, 1H), 7.93-

7.87 (m, 1H), 7.44 (s, 1H), 7.22 (s, 1H), 3.97-3.76 (m, 4H), 3.06 (s, 2H), 2.91-2.81 (m, 2H), 1.91-1.81 (m, 2H), 1.70-1.59 (m, 2H).

Step 2: 1-(Pyridin-4-yl)-5,7,8,9-tetrahydro-1H-spiro[cyclohepta[f]indazole-6,2'-[1,3]dioxolane] (82, R¹=4-Pyridyl)

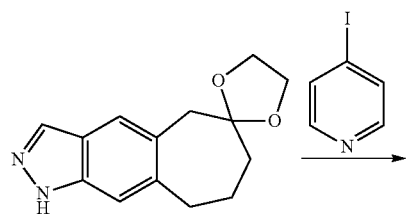

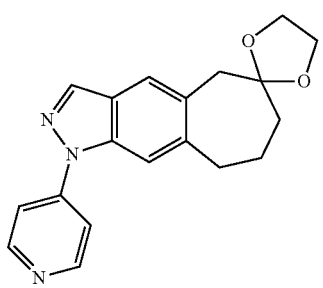

5,7,8,9-Tetrahydro-1H-spiro[cyclohepta[f]indazole-6,2'-[1,3]dioxolane] (28.283 g, 116 mmol), potassium phosphate (49.2 g, 232 mmol), copper(I) iodide (2.205 g, 11.58 mmol) and (1R,2R)-cyclohexane-1,2-diamine (2.64 g, 23.16 mmol) were added to a round bottomed flask, followed by the addition of 1,4-dioxane (300 mL). 4-Iodopyridine (35.6 g, 174 mmol) was added and the mixture was heated to about 105° C. for about 8 h. The reaction was cooled to rt and filtered. The filter cake was rinsed with excess EtOAc. The filtrate was washed with sat. a.q NH₄Cl (100 mL) followed by brine (100 mL), dried over MgSO₄, filtered and concentrated in vacuo to about ¼ the original volume. The resulting solids were collected by filtration to provide a first crop of product. The mother liquor was fully concentrated and then taken into DCM and sonicated to provide additional solids, which were collected by filtration to provide an additional crop of product. The filtrate was then purified on silica gel (120 g) eluting with a gradient of 10-100% EtOAc/DCM. The product containing fractions were concentrated in vacuo then combined with the previous collections to provide 1-(pyridin-4-yl)-5,7,8,9-tetrahydro-1H-spiro[cyclohepta[f]indazole-6,2'-[1,3]dioxolane] (82, R¹=4-Pyridyl), (31.8 g, 85%); LC/MS, method 3, $R_t$=1.98 min, MS m/z 322 (M+H)⁺, ¹H NMR (400 MHz, DMSO) δ 8.72-8.66 (m, 2H), 8.38-8.36 (m, 1H), 7.94-7.86 (m, 3H), 7.64 (s, 1H), 4.11-3.86 (m, 2H), 3.87-3.80 (m, 2H), 3.15 (s, 2H), 3.02-2.96 (m, 2H), 1.95-1.83 (m, 2H), 1.76-1.60 (m, 2H).

Step 3: 1-(Pyridin-4-yl)-5,7,8,9-tetrahydrocyclohepta[f]indazol-6(1H)-one (6, R¹=4-Pyridyl)

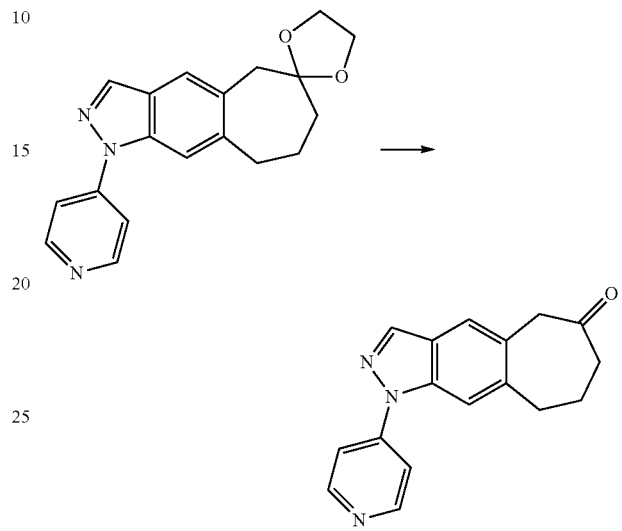

1-(Pyridin-4-yl)-5,7,8,9-tetrahydro-1H-spiro[cyclohepta[f]indazole-6,2'-[1,3]dioxolane] (31.8 g, 99 mmol) and 4-methylbenzenesulfonic acid hydrate (23.8 g, 125 mmol) were added to a round bottom flask followed by the addition of acetone (250 mL). The mixture was heated to about 60° C. for about 2 h, then about 45° C. for about 16 h. The reaction mixture was cooled to rt, filtered and the resulting solids were collected. The solids were taken into EtOAc/MeOH and neutralized with sat. aq. NaHCO₃. The mixture was extracted with EtOAc (3×100 mL) and any solids that would not dissolve were collected. The organics were dried over MgSO₄ and concentrated in vacuo. The collected solids and extracted material were combined to provided 1-(pyridin-4-yl)-5,7,8,9-tetrahydrocyclohepta[f]indazol-6(1H)-one (26.2 g, 95%); LC/MS, method 1, $R_t$=1.25 min MS m/z 278 (M+H)⁺, ¹H NMR (400 MHz, DMSO) δ 8.73-8.68 (m, 2H), 8.43-8.41 (m, 1H), 8.03 (s, 1H), 7.95-7.90 (m, 2H), 7.73 (s, 1H), 3.19 (d, J=5.5 Hz, 2H), 3.17 (d, J=4.1 Hz, 2H), 2.54-2.48 (m, 2H), 2.00-1.87 (m, 2H).

Step 4: 5-Ethylidene-1-(pyridin-4-yl)-5,7,8,9-tetrahydrocyclohepta[f]indazol-6(1H)-one (83, R¹=4-Pyridyl, R²'=Methyl)

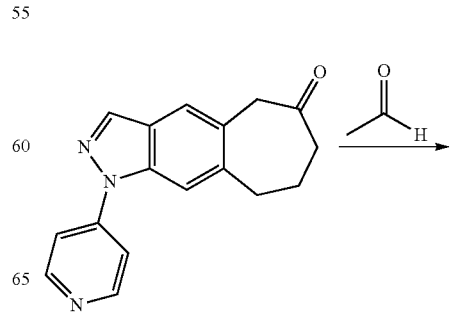

-continued

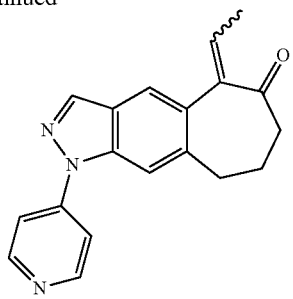

A round bottom flask was charged with 1-(pyridin-4-yl)-5,7,8,9-tetrahydrocyclohepta[f]indazol-6(1H)-one (14.419 g, 52.0 mmol) and THF (200 mL). The solution was cooled to about −77° C. and then 1 M LiHMDS solution (54.6 mL, 54.6 mmol) was added over about 30 min, keeping the internal temp below about −75° C. After complete addition of the LiHMDS the mixture was stirred for about 5 min, the cold bath was removed and the mixture was allowed to warm to about 0° C. (over about 1 h). The mixture was re-cooled to about −65° C. then acetaldehyde (14.6 mL, 260 mmol) was added. The cold bath was removed and the mixture was allowed to warm to about 0° C. brine (50 mL) and water (50 mL) were added to the mixture, then collected the organic layer. Extracted the aqueous layer with EtOAc (2×50 mL). Combined organics and dried over MgSO$_4$ and concentrated in vacuo. Purified by 120 g silica column, eluting with 20-100% EtOAc/DCM to provide 5-ethylidene-1-(pyridin-4-yl)-5,7,8,9-tetrahydrocyclohepta[f]indazol-6(1H)-one (83, R$^1$=4-Pyridyl, R$^{2'}$=Methyl) (12.3 g, 78%); LC/MS, method 3, R$_t$=2.17 min MS m/z 304 (M+H)$^+$, $^1$H NMR (400 MHz, DMSO) δ 8.75-8.72 (m, 2H), 8.50-8.49 (m, 1H), 8.13 (s, 1H), 7.98-7.95 (m, 2H), 7.75 (s, 1H), 7.18-7.11 (q, J=7.3 Hz, 1H) 2.93-2.85 (m, 2H), 2.35-2.22 (m, 2H), 2.04-1.95 (m, 2H), 1.90-1.85 (d, J=7.4 Hz, 3H).

Example 123

(3R,4aS,12bR)-12b-Ethyl-3-(methoxymethyl)-9-(pyridin-4-yl)-1,2,3,4,4a,5,6,7,9,12b-decahydrobenzo[6,7]cyclohepta[1,2-f]indazol-3-ol (13, R$^1$=4-Pyridyl, R$^2$=Ethyl, R$^3$=Methoxymethyl)

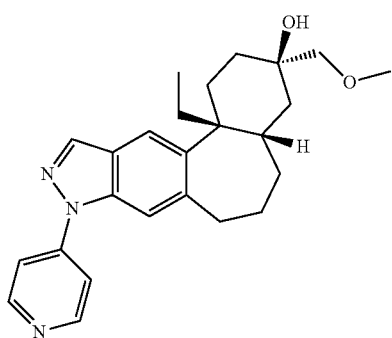 [SMILES: CC[C@@]12CC[C@](O)(COC)C[C@@H]1CCCc1cc3c(cnn3-c3ccncc3)cc12]

(3R,4aS,12bR)-12b-Ethyl-3-(methoxymethyl)-9-(pyridin-4-yl)-1,2,3,4,4a,5,6,7,9,12b-decahydrobenzo[6,7]cyclohepta[1,2-f]indazole-3-ol (13, R$^1$=4-Pyridyl, R$^2$=Ethyl, R$^3$=Methoxymethyl) was prepared from 5-ethylidene-1-(pyridin-4-yl)-5,7,8,9-tetrahydrocyclohepta[f]indazol-6(1H)-one (83, R$^1$=4-Pyridyl, R$^{2'}$=Methyl) in 5 steps in a manner similar to Example 11, Steps 1b,2,3,4 and 5 to yield (3R,4aS,12bR)-12b-ethyl-3-(methoxymethyl)-9-(pyridin-4-yl)-1,2,3,4,4a,5,6,7,9,12b-decahydrobenzo[6,7]cyclohepta[1,2-f]indazol-3-ol (13, R$^1$=4-Pyridyl, R$^2$=Ethyl, R$^3$=Methoxymethyl) as a white solid, LC/MS, method 2, R$_t$=2.40 min, MS m/z 406 (M+H)$^{+1}$H NMR (400 MHz, DMSO) δ 8.70-8.65 (m, 2H), 8.41 (m, 1H), 7.94-7.90 (m, 2H), 7.89 (s, 1H), 7.75 (s, 1H), 4.19 (s, 1H), 3.10 (s, 4H), 2.94 (s, 2H), 2.44-2.20 (m, 4H), 2.20-2.09 (m, 1H), 1.82-1.63 (m, 3H), 1.60-1.38 (m, 4H), 1.28-1.17 (m, 1H), 1.04 (d, J=11.5 Hz, 1H), 0.59 (t, J=7.3 Hz, 3H).

The enantiomers were separated using Preparative Chiral Purification Method 24. Fractions from the first peak eluted were combined and concentrated under reduced pressure. The residue was dissolved in MeOH (1 mL), treated with water (10 mL) and concentrated under reduced pressure to remove MeOH. Residue was frozen and lyophilized to afford (3R,4aS,12bR)-12b-ethyl-3-(methoxymethyl)-9-(pyridin-4-yl)-1,2,3,4,4a,5,6,7,9,12b-decahydrobenzo[6,7]cyclohepta[1,2-f]indazol-3-ol (13, R$^1$=4-Pyridyl, R$^2$=Ethyl, R$^3$=Methoxymethyl) (Example 120) LC/MS, method 2, R$_t$=2.40 min, MS m/z 406 (M+H)$^+$. $^1$H NMR (400 MHz, DMSO) δ 8.70-8.65 (m, 2H), 8.41 (m, 1H), 7.94-7.90 (m, 2H), 7.89 (s, 1H), 7.75 (s, 1H), 4.19 (s, 1H), 3.10 (s, 4H), 2.94 (s, 2H), 2.44-2.20 (m, 4H), 2.20-2.09 (m, 1H), 1.82-1.63 (m, 3H), 1.60-1.38 (m, 4H), 1.28-1.17 (m, 1H), 1.04 (d, J=11.5 Hz, 1H), 0.59 (t, J=7.3 Hz, 3H).

Example 124 rac-(3R,4aS,12bS)-3-(methoxymethyl)-9-(2-methylpyridin-4-yl)-12b-(pyridin-2-ylmethyl)-1,2,3,4,4a,5,6,7,9,12b-decahydrobenzo[6,7]cyclohepta[1,2-f]indazol-3-ol (13, R$^1$=2-methylpyridin-4-yl, R$^2$=pyridin-2-ylmethyl, R$^3$=Methoxymethyl)

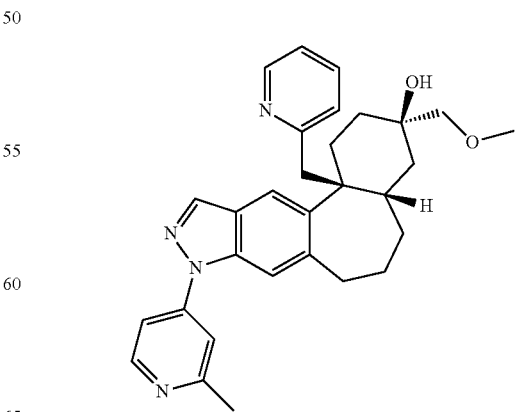

Step 1: 1-(2-methylpyridin-4-yl)-5,7,8,9-tetrahydro-1H-spiro[cyclohepta[f]indazole-6,2'-[1,3]dioxolane] (82, R¹=2-methylpyridin-4-yl)

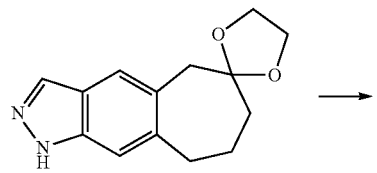

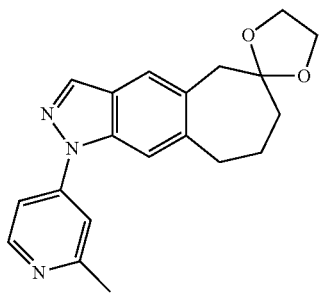

A 100 mL round-bottom flask equipped with an air cooled reflux container was charged with 5,7,8,9-tetrahydro-1H-spiro[cyclohepta[f]indazole-6,2'-[1,3]dioxolane] (81) (3.00 g, 12.3 mmol), 4-iodo-2-methylpyridine (3.84 g, 14.7 mmol), CuI (0.234 g, 1.23 mmol), (+/−)-trans-cyclohexane-1,2-diamine (0.295 mL, 2.46 mmol) and $K_3PO_4$ (5.21 g, 24.6 mmol) in 1,4-dioxane (31 mL). The reaction mixture was heated at about 100° C. for about 21 h. The reaction was allowed to cool and then it was filtered through a pad of Celite® and rinsed with EtOAc (3×10 mL). The filtrate was concentrated then the residue was purified on silica gel (120 g), using a gradient of 10-100% EtOAc in DCM). Collection and concentration of the appropriate fractions gave 1-(2-methylpyridin-4-yl)-5,7,8,9-tetrahydro-1H-spiro[cyclohepta[f]indazole-6,2'-[1,3]dioxolane] (82, R¹=2-methylpyridin-4-yl) (3.26 g, 79%); LC/MS, method 3, $R_t$=1.86 min, MS m/z 336 (M+H)⁺.

Step 2: 1-(2-methylpyridin-4-yl)-5,7,8,9-tetrahydrocyclohepta[f]indazol-6(1H)-one (83, R¹=2-methylpyridin-4-yl)

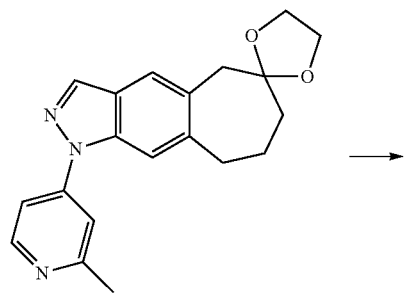

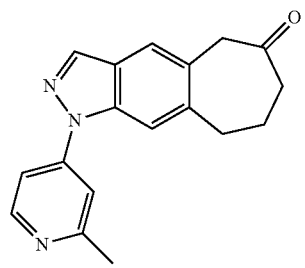

A 200 mL round-bottom flask equipped with air cooled reflux condenser outfitted with a nitrogen inlet adapter was charged with 1-(2-methylpyridin-4-yl)-5,7,8,9-tetrahydro-1H-spiro[cyclohepta[f]indazole-6,2'-[1,3]dioxolane] (82, R¹=2-methylpyridin-4-yl) (3.26 g, 9.72 mmol) and PTSA (2.31 g, 12.2 mmol) in acetone (49 mL). The mixture was heated to reflux. After 24 h, the reaction was diluted with additional acetone (50 mL) and water (2.5 mL) was added. After 1 h the reaction was cooled before adding sat. aq. $NaHCO_3$ (30 mL). The mixture was then concentrated under reduced pressure. EtOAc (70 mL) was added, and after separating the layers, the aqueous phase was extracted with EtOAc (2×25 mL). The combined organic phases were washed with brine (75 mL), dried over $Na_2SO_4$, filtered, and concentrated under reduced pressure to give 1-(2-methylpyridin-4-yl)-5,7,8,9-tetrahydrocyclohepta[f]indazol-6(1H)-one (6, R¹=2-methylpyridin-4-yl) (2.8 g, 99%); LC/MS, method 3, $R_t$=1.71 min, MS m/z 292 (M+H)⁺. ¹H NMR (400 MHz, $CDCl_3$) δ 8.65-8.60 (m, 1H), 8.20-8.16 (m, 1H), 7.71 (s, 1H), 7.69-7.65 (m, 1H), 7.63-7.59 (m, 2H), 3.85 (s, 2H), 3.21-3.11 (m, 2H), 2.71 (s, 3H), 2.62-2.54 (m, 2H), 2.14-1.94 (m, 2H).

Step 3: 1-(2-methylpyridin-4-yl)-5-(pyridin-2-ylmethylene)-5,7,8,9-tetrahydrocyclohepta[f]indazol-6(1H)-one (83, R¹=2-methylpyridin-4-yl, R²'=pyridin-2-yl)

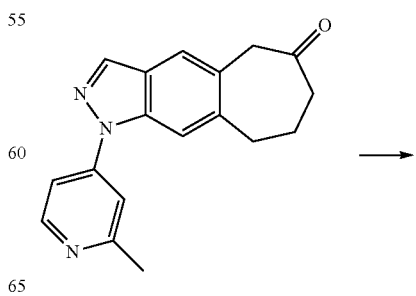

209
-continued

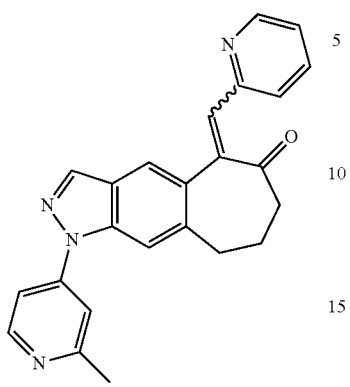

A round bottom flask was charged with 1-(2-methylpyridin-4-yl)-5,7,8,9-tetrahydrocyclohepta[f]indazol-6(1H)-one (6, $R^1$=2-methylpyridin-4-yl) (2.83 g, 9.71 mmol) and THF (43 mL). The solution was cooled to about −77° C. and then lithium bis(trimethylsilyl)amide (1.0 M in THF, 10.0 mL, 10.0 mmol) was added over about 30 min, keeping the internal temperature below about −75° C. After the addition was the mixture was stirred for about 5 min, the cold bath was removed and the mixture was allowed to warm to about 0° C. over about 1 h. The mixture was again cooled to about −75° C. then 2-pyridinecarboxaldehyde (3.2 mL, 34 mmol) was added. The mixture was allowed to warm to about −10° C. over about 1 h, and then water (40 mL) was added and the layers were separated. The aqueous layer was extracted with EtOAc (2×40 mL) and then the combined organics were washed with brine (50 mL), dried over $Na_2SO_4$ and then concentrated under reduced pressure. The crude material was purified on silica gel (120 g, eluted with 0% to 2.5% MeOH in DCM). Collection and concentration of the appropriate fractions gave 1-(2-methylpyridin-4-yl)-5-(pyridin-2-ylmethylene)-5,7,8,9-tetrahydrocyclohepta[f]indazol-6(1H-one (83, $R^1$=2-methylpyridin-4-yl, $R^{2'}$=pyridin-2-yl) (3.45 g, 93%) LC/MS, method 3, $R_t$=1.95 min, MS m/z 381 (M+H)⁺. ¹H NMR (400 MHz, $CDCl_3$) δ 8.65 (d, J=5.7 Hz, 1H), 8.61-8.53 (m, 1H), 8.11-8.08 (m, 1H), 7.95 (s, 1H), 7.82 (s, 1H), 7.80-7.64 (m, 2H), 7.53 (s, 1H), 7.44-7.35 (m, 1H), 7.14-7.06 (m, 1H), 6.92 (d, J=7.9 Hz, 1H), 3.14-3.06 (m, 2H), 2.78 (s, 3H), 2.56-2.48 (m, 2H), 2.23-2.08 (m, 2H).

210

Step 4: (3R,4aS,12bS)-3-(methoxymethyl)-9-(2-methylpyridin-4-yl)-12b-(pyridin-2-ylmethyl)-1,2,3,4,4a,5,6,7,9,12b-decahydrobenzo[6,7]cyclohepta[1,2-f]indazol-3-ol (13, $R^1$=2-methylpyridin-4-yl, $R^2$=pyridin-2-ylmethyl, $R^3$=Methoxymethyl)

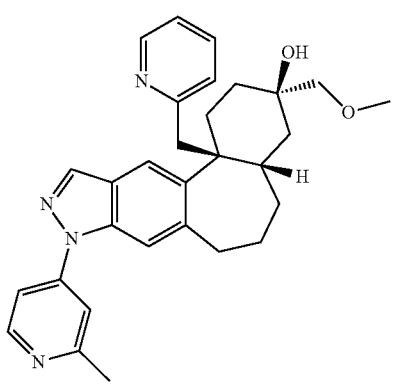 [SMILES: COC[C@@]1(O)CC[C@@]2(Cc3ccccn3)c3cc4cnn(-c5ccnc(C)c5)c4cc3CCC[C@H]2C1]

(3R,4aS,12bS)-3-(methoxymethyl)-9-(2-methylpyridin-4-yl)-12b-(pyridin-2-ylmethyl)-1,2,3,4,4a,5,6,7,9,12b-decahydrobenzo[6,7]cyclohepta[1,2-f]indazol-3-ol (13, $R^1$=2-methylpyridin-4-yl, $R^2$=pyridin-2-ylmethyl, $R^3$=Methoxymethyl) was prepared from 1-(2-methylpyridin-4-yl)-5-(pyridin-2-ylmethylene)-5,7,8,9-tetrahydrocyclohepta[f]indazol-6(1H)-one (83, $R^1$=2-methylpyridin-4-yl, $R^{2'}$=pyridin-2-yl) in 5 steps in a manner similar to Example 11, Steps 1b,2,3,4 and 5 to yield rac-(3R,4aS,12bS)-3-(methoxymethyl)-9-(2-methylpyridin-4-yl)-12b-(pyridin-2-ylmethyl)-1,2,3,4,4a,5,6,7,9,12b-decahydrobenzo[6,7]cyclohepta[1,2-f]indazol-3-ol (13, $R^1$=2-methylpyridin-4-yl, $R^2$=pyridin-2-ylmethyl, $R^3$=Methoxymethyl) (Example 124) as a white solid, LC/MS, method 2, $R_t$=1.83 min, MS m/z 483 (M+H)⁺. ¹H NMR (400 MHz, $CDCL_3$) δ 8.60 (d, J=5.8 Hz, 1H), 8.40 (d, J=4.1 Hz, 1H), 8.01 (s, 1H), 7.77-7.67 (m, 3H), 7.27-2.19 (m, 1H), 7.17 (s, 1H), 7.01-6.95 (m, 1H), 6.24 (d, J=7.7 Hz, 1H), 3.79 (d, J=12.8 Hz, 1H), 3.50-3.38 (m, 1H), 3.28 (s, 3H), 3.20-3.10 (m, 1H), 3.05-2.96 (m, 3H), 2.75 (s, 3H), 2.68-2.50 (m, 2H), 2.19-2.09 (m, 2H), 1.99-1.89 (m, 1H), 1.84-1.48 (m, 7H), 1.39-1.19 (m, 2H).

Example #125 and #126

(3R,4aS,12bS)-12b-ethyl-9-(4-fluorophenyl)-3-((((R)-1-phenylethyl)amino)methyl)-1,2,3,4,4a,5,6,7,9,12b-decahydrobenzo[6,7]cyclohepta[1,2-f]indazol-3-ol (R¹=4-Fluorophenyl, R²=Ethyl, R³=(R)-1-Phenethylaminomethyl) and (3S,4aR,12bR)-12b-ethyl-9-(4-fluorophenyl)-3-((((R)-1-phenylethyl)amino)methyl)-1,2,3,4,4a,5,6,7,9,12b-decahydrobenzo[6,7]cyclohepta[1,2-f]indazol-3-ol (R¹=4-Fluorophenyl, R²=Ethyl, R³=(R)-1-Phenethylaminomethyl)

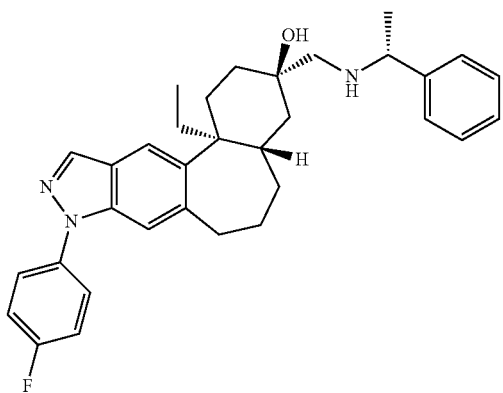

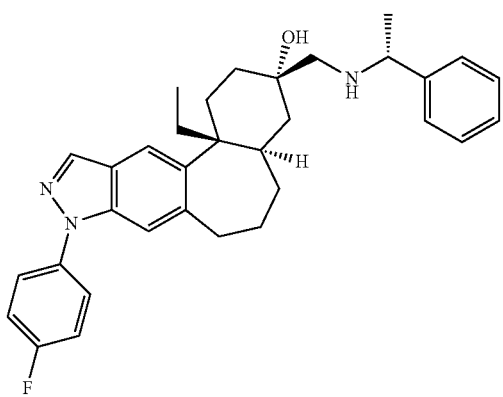

Step 1: (4aR,12bR)-12b-ethyl-9-(4-fluorophenyl)-1,4,4a,5,6,7,9,12b octahydrobenzo[6,7]cyclohepta[1,2-f]indazol-3(2H)-one and (4aS,12bS)-12b-ethyl-9-(4-fluorophenyl)-1,4,4a,5,6,7,9,12b-octahydrobenzo[6,7]cyclohepta[1,2-f]indazol-3(2H)-one

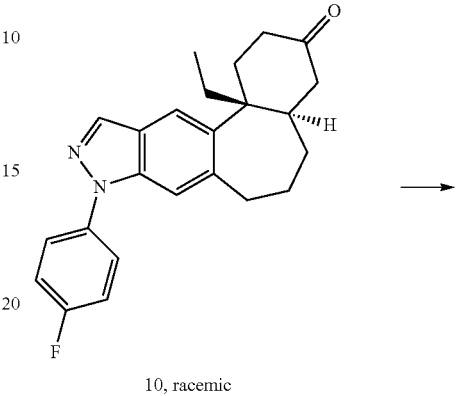

10, racemic

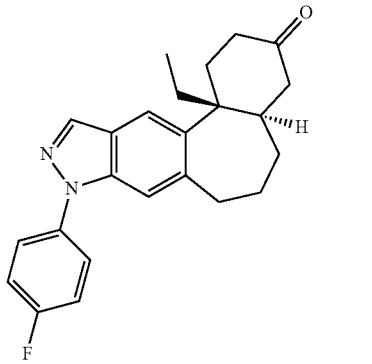

10, (4aR,12bR)

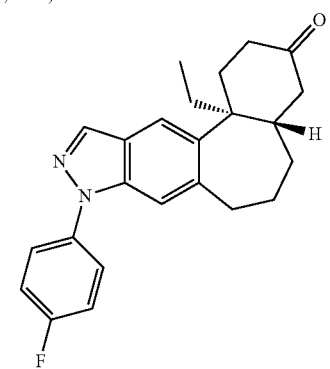

10, (4aS,12bS)

(rac)-(4aR,12bR)-12b-ethyl-9-(4-fluorophenyl)-1,4,4a,5,6,7,9,12b-octahydrobenzo[6,7]cyclohepta[1,2-f]indazol-3(2H)-one (10, R¹=4-Fluorophenyl, R²=Ethyl) (500 mg) was separated by chiral HPLC Method 34. Two enantiomers were isolated. Characterization data for the samples is as follows.

Fractions from the first peak eluted were combined and concentrated under reduced pressure. The residue was dissolved in MeCN and MeOH, treated with water, and concentrated under reduced pressure to remove the organic volatiles. The mixture was frozen then lyophilized to afford an off-white solid (137 mg, 27%). LC/MS, method 4, $R_f$=1.84 min, MS m/z 377 (M+H)⁺. ¹H NMR (400 MHz, DMSO) δ 8.30 (s, 1H), 7.87 (s, 1H), 7.83-7.76 (m, 2H), 7.58 (s, 1H), 7.45-7.35 (m, 2H), 3.25 (m, 1H under water peak), 3.05-2.95 (dd, 1H), 2.40-1.85 (m, 8H), 1.65-1.55 (m, 1H), 1.40-1.10 (m, 2H), 0.57-0.42 (t, 3H). Sign of rotation is negative.

Fractions from the second peak eluted were combined and concentrated under reduced pressure. The residue was dissolved in MeCN and MeOH, treated with water, and concentrated under reduced pressure to remove the organic volatiles. The mixture was frozen then lyophilized to afford an off-white solid (125 mg, 27%). LC/MS, method 4, $R_t$=1.84 min, MS m/z 377 (M+H)+. $^1$H NMR (400 MHz, DMSO) δ 8.30 (s, 1H), 7.87 (s, 1H), 7.83-7.76 (m, 2H), 7.58 (s, 1H), 7.45-7.35 (m, 2H), 3.25 (m, 1H under water peak), 3.05-2.95 (dd, 1H), 2.40-1.85 (m, 8H), 1.65-1.55 (m, 1H), 1.40-1.10 (m, 2H), 0.57-0.42 (t, 3H). Sign of rotation is positive.

further purified on silica gel (12 g) using DCM/EtOAc with ramp conditions of 0-100% EtOAc in DCM over 20 min followed by 10 min at 100% EtOAc. The product fractions were concentrated to colorless viscous dried on a high vacuum to yield (2'R,4aS,12bS)-12b-ethyl-9-(4-fluorophenyl)-2,4,4a,5,6,7,9,12b-octahydro-1H-spiro[benzo[6,7]cyclohepta[1,2-f]indazole-3,2'-oxirane] (14, $R^1$=4-Fluorophenyl, $R^2$=Ethyl) (131 mg, 50%) of a white crystalline solid. LC/MS, method 4, Rt=2.08 min, MS m/z 391 (M+H)+. $^1$H NMR (400 MHz, DMSO) δ 8.27 (s, 1H), 7.93 (s, 1H), 7.85-7.77 (m, 2H), 7.56 (s, 1H), 7.45-7.36 (m, 2H), 4.03 (q, J=7.1 Hz, 1H), 3.25-3.17 (m, 1H), 3.00-2.90 (m, 1H), 2.67 (d, J=4.7 Hz, 1H), 2.62 (d, J=4.7 Hz, 1H), 2.38-2.30 (m, 1H), 2.25-1.92 (m, 3H), 1.93-1.67 (m, 3H), 1.62-1.53 (m, 1H), 1.40-1.24 (m, 1H), 1.18 (t, J=7.1 Hz, 2H), 1.04-0.95 (m, 1H), 0.40 (t, J=7.3 Hz, 3H). Sign of rotation is negative.

Step 3a: (3R,4aS,12bS)-12b-ethyl-9-(4-fluorophenyl)-3-((((R)-1-phenylethyl)amino)methyl)-1,2,3,4,4a,5,6,7,9,12b-decahydrobenzo[6,7]cyclohepta[1,2-f]indazol-3-ol (16, $R^1$=4-Fluorophenyl, $R^2$=Ethyl, $R^3$=(R)-1-Phenethylaminomethyl)

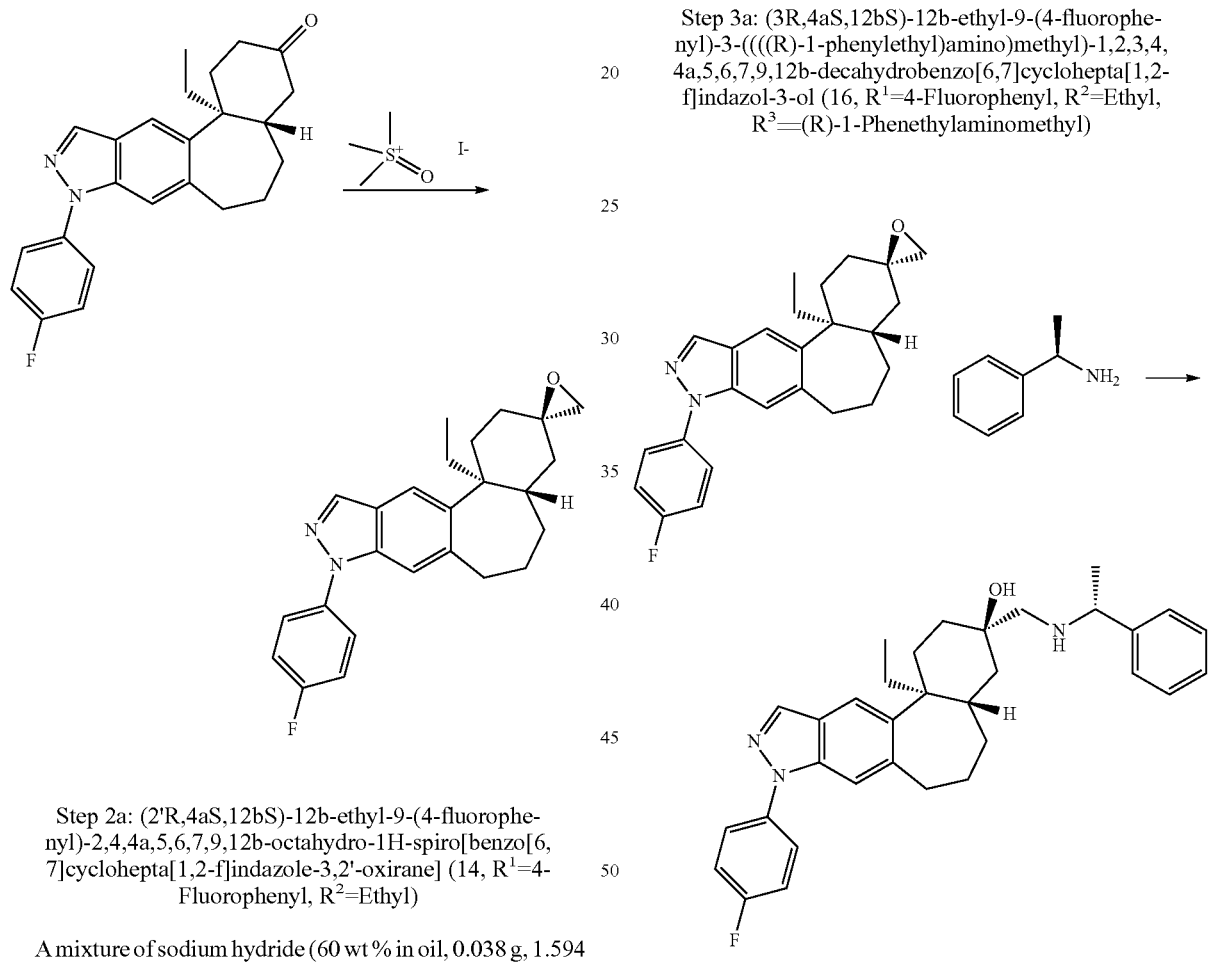

Step 2a: (2'R,4aS,12bS)-12b-ethyl-9-(4-fluorophenyl)-2,4,4a,5,6,7,9,12b-octahydro-1H-spiro[benzo[6,7]cyclohepta[1,2-f]indazole-3,2'-oxirane] (14, $R^1$=4-Fluorophenyl, $R^2$=Ethyl)

A mixture of sodium hydride (60 wt % in oil, 0.038 g, 1.594 mmol) and DMSO (5 mL) was heated to about 65° C. for about 30 min then cooled to rt and diluted with THF (2.5 mL). The reaction mixture was cooled in an ice water bath and trimethyl sulfoxonium iodide (0.149 g, 0.68 mmol) was added then stirred for about 15 min. (4aS,12bS)-12b-ethyl-9-(4-fluorophenyl)-1,4,4a,5,6,7,9,12b-octahydrobenzo[6,7]cyclohepta[1,2-f]indazol-3 (2H)-one (10, $R^1$=4-Fluorophenyl, $R^2$=Ethyl) was then added in one portion dissolved in THF (2.5 mL) and the mixture was stirred to rt for about 5 h. The solvents were removed and the residue was diluted with about 15 mL water and extracted with EtOAc (15 mL×3). The combined organics were washed with sat. aq. NaCl (15 mL). The organic layer was dried over MgSO4 filtered and concentrated to about 220 mg of a crude viscous oil. The sample was A flask was charged with 50 mg (2'R,4aS,12bS)-12b-ethyl-9-(4-fluorophenyl)-2,4,4a,5,6,7,9,12b-octahydro-1H-spiro[benzo[6,7]cyclohepta[1,2-f]indazole-3,2'-oxirane] (14, $R^1$=4-Fluorophenyl, $R^2$=Ethyl), about 0.5 mL MeCN and stirred under an atmosphere of nitrogen. To this suspension was added 0.065 mL R(+)-1-phenylethylamine followed by t 0.014 g lithium perchlorate. The reaction mixture was stirred at about 80° C. for about 4 h. The reaction was cooled and the solvents were removed under vacuum. The crude mixture was taken up in 15 mL water/15 mL DCM. The organic layer was separated and the water layer was extracted twice more with t 10 mL DCM. The combined organic layers were washed with 10 mL sat. aq. NaCl solution. The organic layer was dried over MgSO$_4$, and concentrated to a yellow oil. The crude oil was dried under high vacuum for about 1 h then recrystallized from MeCN. Upon cooling overnight, 10 mg of white needle crystals were obtained. The remaining crude material was dissolved in 2 mL DCM and submitted to chromatography on the Analogix instrument (DCM/EtOAC, 12 g column). Ramp 0-50% EtOAc over 20 min then 50-100 over 5 min and 5 min at 100% EtOAc. The product fractions were collected and concentrated to a clear oil which was further purified by crystallization from MeCN, affording (3R,4aS,12bS)-12b-ethyl-9-(4-fluorophenyl)-3-((((R)-1-phenylethyl)amino)methyl)-1,2,3,4,4a,5,6,7,9,12b-decahydrobenzo[6,7]cyclohepta[1,2-f]indazol-3-ol (35 mg of white needles) (16, R$^1$=4-Fluorophenyl, R$^2$=Ethyl, R$^3$=(R)-1-Phenethylaminomethyl) (Example 125) (53%) LC/MS, method 4, R$_t$=1.50 min, MS m/z 512 (M+H)$^+$. $^1$H NMR (400 MHz, DMSO) δ 8.27 (d, J=0.8 Hz, 1H), 7.92 (s, 1H), 7.88-7.73 (m, 2H), 7.54 (s, 1H), 7.48-7.24 (m, 7H), 7.25-7.17 (m, 1H), 3.98 (s, 1H), 3.66 (q, J=6.6 Hz, 1H), 3.23-3.12 (m, 1H), 2.96-2.87 (m, 1H), 2.36-2.29 (m, 1H), 2.29-1.68 (m, 8H), 1.69-1.20 (m, 7H), 0.34 (t, J=7.2 Hz, 3H).

Crystal structure confirms stereochemistry of (4aS,12bS)-12b-ethyl-9-(4-fluorophenyl)-1,4,4a,5,6,7,9,12b-octahydrobenzo[6,7]cyclohepta[1,2-f]indazol-3 (2H)-one (10, R$^1$=4-Fluorophenyl, R$^2$=Ethyl) [(−) optical rotation] is the inverted trans configuration as drawn for product above.

Step 2b: (2'S,4aR,12bR)-12b-ethyl-9-(4-fluorophenyl)-2,4,4a,5,6,7,9,12b-octahydro-1H-spiro[benzo[6,7]cyclohepta[1,2-f]indazole-3,2'-oxirane] (14, R$^1$=4-Fluorophenyl, R$^2$=Ethyl)

further cooled in an ice water bath and trimethylsulfoxonium iodide (0.213 g, 0.967 mmol) was added in one portion and stirred about 15 min. (4aR,12bR)-12b-ethyl-9-(4-fluorophenyl)-1,4,4a,5,6,7,9,12b-octahydrobenzo[6,7]cyclohepta[1,2-f]indazol-3 (2H)-one (9, R$^1$=4-Fluorophenyl, R$^2$=Ethyl) (0.182, 0.483 mmol) in 2 mL THF was introduced via syringe and allowed to warm to rt over about 18 hrs. THF was removed in vacuo and the residue was diluted with 15 mL water and extracted with EtOAc (15 mL×3). The combined organics were washed with sat. aq. NaCl. The organic layer was dried over MgSO$_4$ filtered and concentrated to a crude viscous oil.

The crude oil was purified on silica gel (12 g). Ramp conditions were 0-100% EtOAc in DCM over 20 min followed by 10 min at 100% EA. Product fractions were concentrated to yield (2'S,4aR,12bR)-12b-ethyl-9-(4-fluorophenyl)-2,4,4a,5,6,7,9,12b-octahydro-1H-spiro[benzo[6,7]cyclohepta[1,2-f]indazole-3,2'-oxirane] (10, R$^1$=4-Fluorophenyl, R$^2$=Ethyl) as a foam (0.153 g, 81%). LC/MS, method 4, R$_t$=2.08 min, MS m/z 391 (M+H)$^+$. $^1$H NMR (400 MHz, DMSO) δ 8.27 (d, J=0.8 Hz, 1H), 7.93 (s, 1H), 7.85-7.77 (m, 2H), 7.56 (s, 1H), 7.45-7.36 (m, 2H), 3.21 (d, J=13.3 Hz, 1H), 3.00-2.90 (m, 1H), 2.67 (d, J=4.7 Hz, 1H), 2.62 (d, J=4.6 Hz, 1H), 2.42-2.05 (m, 3H), 2.06-1.91 (m, 3H), 1.93-1.62 (m, 2H), 1.58 (dd, J=14.3, 2.6 Hz, 1H), 1.39-1.14 (m, 3H), 1.00 (dt, J=14.3, 3.1 Hz, 1H), 0.40 (t, J=7.3 Hz, 3H).

Step 3b: (3S,4aR,12bR)-12b-ethyl-9-(4-fluorophenyl)-3-((((R)-1-phenylethyl)amino)methyl)-1,2,3,4,4a,5,6,7,9,12b-decahydrobenzo[6,7]cyclohepta[1,2-f]indazol-3-ol (16, R$^1$=4-Fluorophenyl, R$^2$=Ethyl, R$^3$=(R)-1-Phenethylaminomethyl)

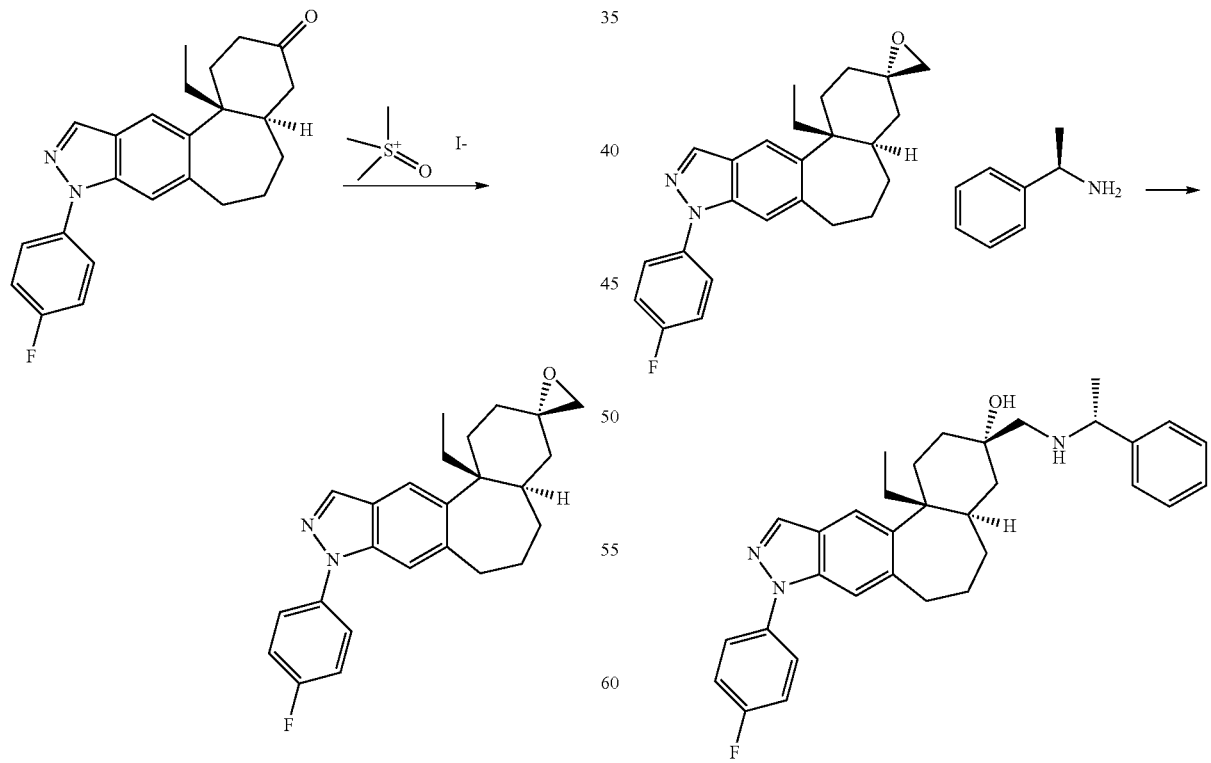

Sodium hydride (60 wt % in oil, 0.023 g, 0.967 mmol) was added carefully to a flask containing about 3 mL DMSO then heated to about 65° C. for about 30 min. The reaction was cooled to rt then diluted with 2 mL THF. The reaction was A flask was charged with 50 mg (2'S,4aR,12bR)-12b-ethyl-9-(4-fluorophenyl)-2,4,4a,5,6,7,9,12b-octahydro-1H-spiro[benzo[6,7]cyclohepta[1,2-f]indazole-3,2'-oxirane]

(14, R¹=4-Fluorophenyl, R²=Ethyl), 0.5 mL MeCN and stirred under an atmosphere of nitrogen. To this suspension was added 0.065 mL R(+)-1-phenylethylamine followed by 0.014 g lithium perchlorate. The reaction mixture was stirred at about 80° C. for about 14 h. The reaction was cooled and the solvents were removed under vacuum. The crude mixture was taken up in about 15 mL water/15 mL DCM. The organic layer was separated and the water layer was extracted with DCM. (10 mL×2) The combined organic layers were washed with about 10 mL sat. aq. NaCl solution. The organic layer was dried over MgSO₄, and concentrated to a yellow oil.

The crude material was dissolved in about 2 mL DCM and submitted to chromatography on the Analogix instrument (DCM/EtOAC, 12 g column). Ramp 0-50% EtOAc over 20 min then 10 min at 100% EtOAc. The product fractions were collected and concentrated to yield (3S,4aR,12bR)-12b-ethyl-9-(4-fluorophenyl)-3-((((R)-1-phenylethyl)amino)methyl)-1,2,3,4,4a,5,6,7,9,12b-decahydrobenzo[6,7]cyclohepta[1,2-f]indazol-3-ol (16, R¹=4-Fluorophenyl, R²=Ethyl, R³=(R)-1-Phenethylaminomethyl) (Example 126) (59.5 mg, 91%) of a clear glass which was used to obtain crystals via crystallization from MeCN. LC/MS, method 4, $R_f$=1.50 min, MS m/z 570 (M+OAc⁻)⁻. ¹H NMR (400 MHz, DMSO) δ 8.27 (d, J=0.8 Hz, 1H), 7.92 (s, 1H), 7.88-7.77 (m, 2H), 7.54 (s, 1H), 7.50-7.25 (m, 7H), 7.25-7.17 (m, 1H), 3.98 (s, 1H), 3.66 (q, J=6.6 Hz, 1H), 3.25-3.13 (m, 1H), 2.96-2.88 (m, 1H), 2.36-2.29 (m, 1H), 2.25-1.93 (m, 8H), 1.86-1.20 (m, 7H), 0.34 (t, J=7.2 Hz, 3H).

Crystal structure confirms stereochemistry of (4aR,12bR)-12b-ethyl-9-(4-fluorophenyl)-1,4,4a,5,6,7,9,12b-octahydrobenzo[6,7]cyclohepta[1,2-f]indazol-3 (2H)-one (10, R¹=4-Fluorophenyl, R²=Ethyl) [(+) optical rotation] is the trans configuration as drawn for product above.

Scheme 20:

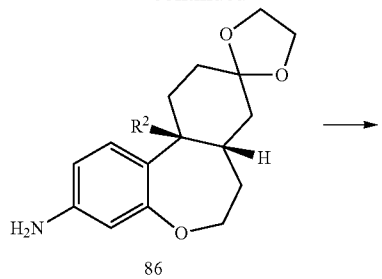

86

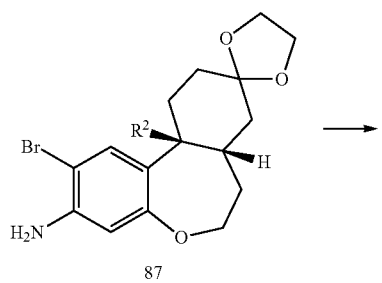

87

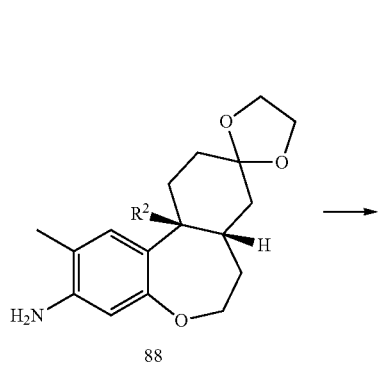

88

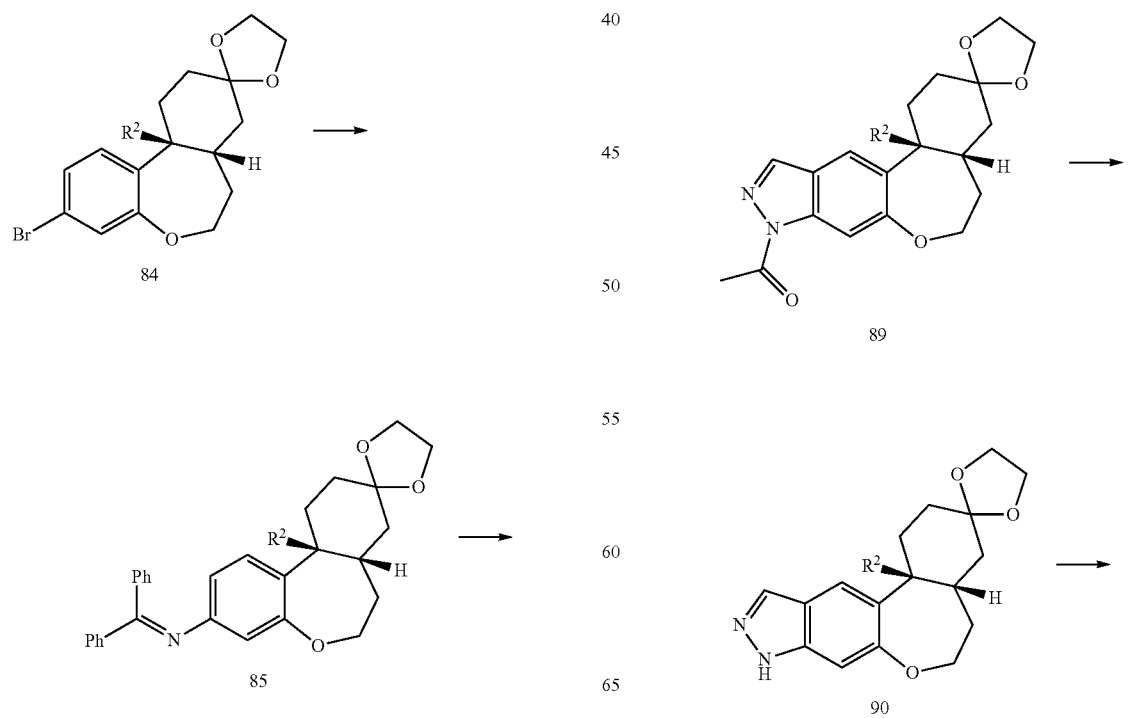

-continued

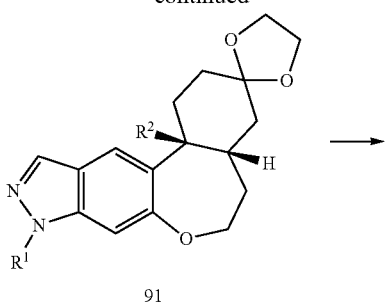
91

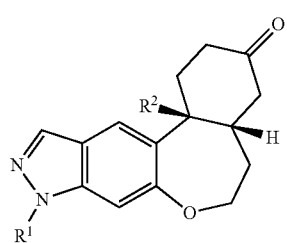
92

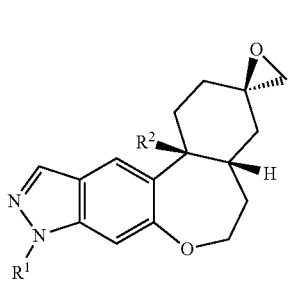
93

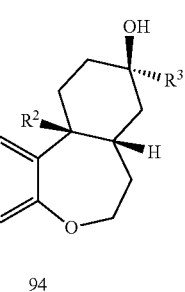
94

Examples #127 and #128

(3S,4aR,12bS)-12b-ethyl-3-(methoxymethyl)-9-(2-methylpyridin-4-yl)-2,3,4,4a,5,6,9,12b-octahydro-1H-benzo[4,5]oxepino[3,2-f]indazol-3-ol (94, $R^1$=2-methylpyridin-4-yl, $R^2$=Ethyl, $R^3$=methoxymethyl) and (3R,4aS,12bR)-12b-ethyl-3-(methoxymethyl)-9-(2-methylpyridin-4-yl)-2,3,4,4a,5,6,9,12b-octahydro-1H-benzo[4,5]oxepino[3,2-f]indazol-3-ol (94, $R^1$=2-methylpyridin-4-yl, $R^2$=Ethyl, $R^3$=methoxymethyl)

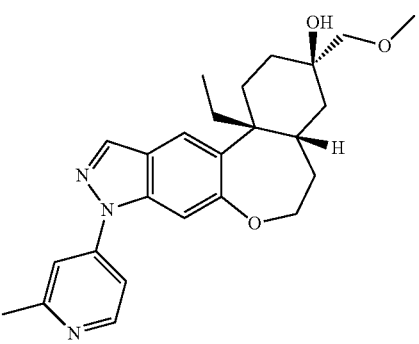

Step #1: rac-(7 aR,11aR)—N-(diphenylmethylene)-11a-vinyl-7,7a,8,10,11,11a-hexahydro-6H-spiro[dibenzo[b,d]oxepine-9,2'-[1,3]dioxolan]-3-amine (85, $R^2$=Vinyl)

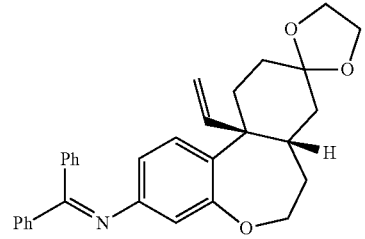

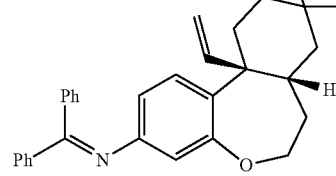

A 1 L round-bottom flask equipped with an air cooled reflux condenser outfitted with a nitrogen inlet adapter was charged with palladium(II) acetate (0.441 g, 1.97 mmol), Xantphos (1.71 g, 2.95 mmol), $Cs_2CO_3$ (22.4 g, 68.8 mmol), evacuated and filled with nitrogen (three cycles), and then 1,4-dioxane (131 mL) was added followed by an additional three cycles of evacuation and nitrogen backfilling. The suspension was stirred at rt for about 15 min and then TEA (0.41 mL, 3.0 mmol) was added. After an additional 15 min of stirring at rt, a solution of benzophenone imine (9.90 mL, 59.0 mmol) and rac-(7aS,11aS)-3-bromo-11a-vinyl-7,7a,8,10,11,11a-hexahydro-6H-spiro[dibenzo[b,d]oxepine-9,2'-[1,3]dioxolane] (18.0 g, 49.1 mmol) (prepared as described in WO 2012125797) in dioxane (65 mL) was added and the reaction mixture was heated to about 100° C. for about 18 h. The reaction mixture was diluted with EtOAc (300 mL) and filtered. The filtered solid was washed with EtOAc (2×50 mL) and the combined filtrate was concentrated under reduced pressure. The crude material was purified on silica gel (330 g, eluted with 0 to 30% EtOAc in heptane). Collection and concentration of the appropriate fractions gave rac-(7aR,11aR)—N-(diphenylmethylene)-11a-vinyl-7,7a,8,10,11,11a-hexahydro-6H-spiro[dibenzo[b,d]oxepine-9,2'-[1,3]dioxolan]-3-amine (85, R$^2$=Vinyl) (17.8 g, 78%). LC/MS, method 3, 2.98 min, MS m/z 466 (M+H)$^+$. $^1$H NMR (400 MHz, CDCL$_3$) δ 7.86-7.79 (m, 2H), 7.58-7.50 (m, 1H), 7.49-7.40 (m, 2H), 7.38-7.26 (m, 3H), 7.19-7.13 (m, 2H), 7.10-7.04 (m, 1H), 6.73-6.58 (m, 1H), 6.49-6.44 (m, 1H), 5.97-5.85 (m, 1H), 4.96-4.88 (m, 1H), 4.42-4.32 (m, 1H), 4.08-3.98 (m, 1H), 3.99-3.86 (m, 4H), 3.71-3.59 (m, 1H), 2.41-2.30 (m, 1H), 2.29-2.19 (m, 1H), 2.16-2.08 (m, 1H), 1.88-1.60 (m, 4H), 1.61-1.46 (m, 1H), 1.44-1.35 (m, 1H).

Step #2 rac-(7 aR,11aS)-11a-ethyl-7,7a,8,10,11,11a-hexahydro-6H-spiro[dibenzo[b,d]oxepine-9,2'-[1,3]dioxolan]-3-amine (86, R$^2$=Ethyl)

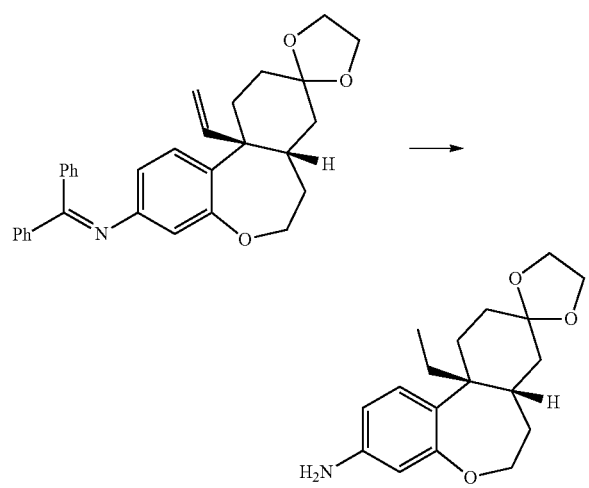

A 500 mL round-bottom flask equipped with a 3-way stopcock was charged with rac-(7 aS,11aS)—N-(diphenylmethylene)-11a-vinyl-7,7a,8,10,11,11a-hexahydro-6H-spiro[dibenzo[b,d]oxepine-9,2'-[1,3]dioxolan]-3-amine (85, R$^2$=Vinyl) (17.7 g, 38.0 mmol) and 10% palladium on carbon (2.02 g, 1.90 mmol) in EtOH (190 mL). The vessel was evacuated and backfilled with hydrogen from a balloon and the resulting suspension was allowed to stir at rt for about 22 h. The mixture was filtered through a pad of Celite® using rinses of EtOAc (3×25 mL). The combined filtrates were concentrated under reduced pressure and the resulting crude material was purified on silica gel (330 g, eluted with 0 to 50% EtOAc in heptane). Collection and concentration of the appropriate fractions gave rac-(7aR,11aS)-11a-ethyl-7,7a,8,10,11,11a-hexahydro-6H-spiro[dibenzo[b,d]oxepine-9,2'-[1,3]dioxolan]-3-amine (86, R$^2$=Ethyl) (11.24 g, 97%). LC/MS, method 3, 2.14 min, MS m/z 304 (M+H)$^+$. $^1$H NMR (400 MHz, CDCL$_3$) δ 7.00 (d, J=8.4 Hz, 1H), 6.56-6.45 (m, 2H), 5.34 (bs, 1H), 4.21-4.11 (m, 1H), 3.98-3.85 (m, 4H), 3.72-3.60 (m, 1H), 2.69-2.56 (m, 1H), 2.34-2.24 (m, 1H), 2.19-2.03 (m, 2H), 1.93-1.80 (m, 1H), 1.79-1.65 (m, 2H), 1.64-1.36 (m, 4H), 1.35-1.25 (m, 1H), 0.61 (t, J=7.4 Hz, 3H).

Step #3: rac-(7aR,11aS)-2-bromo-11a-ethyl-7,7a,8,10,11,11a-hexahydro-6H-spiro[dibenzo[b,d]oxepine-9,2'-[1,3]dioxolan]-3-amine (87, R$^2$=Ethyl)

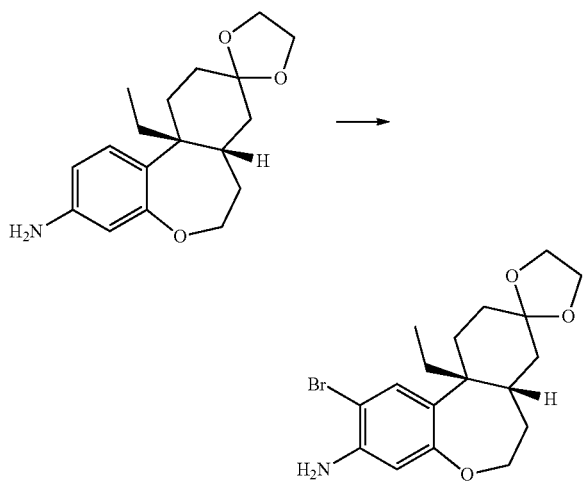

A solution of rac-(7aR,11aS)-11a-ethyl-7,7a,8,10,11,11a-hexahydro-6H-spiro[dibenzo[b,d]oxepine-9,2'-[1,3]dioxolan]-3-amine (86, R$^2$=Ethyl) (11.2 g, 37.0 mmol) in THF (370 mL) was cooled to about −10° C. in a salt/ice bath and was then treated with NBS (6.59 g, 37.0 mmol) with stirring for about 5 min. The reaction was quenched by addition of sat. aq. NaHCO$_3$ (250 mL), and the mixture was diluted with EtOAc (350 mL). The aqueous phase was extracted with EtOAc (2×50 mL) and the combined organic phases were washed with brine (350 mL), dried over Na$_2$SO$_4$, filtered, and concentrated under reduced pressure. The crude material was purified on silica gel (220 g, eluted with 0% to 40% EtOAc in heptane). Collection and concentration of the appropriate fractions gave rac-(7aR,11aS)-2-bromo-11a-ethyl-7,7a,8,10,11,11a-hexahydro-6H-spiro[dibenzo[b,d]oxepine-9,2'-[1,3]dioxolan]-3-amine (87, R$^2$=Ethyl) (13.6 g, 96%) containing about 20% of a minor regioisomer. The material was used directly in Step #4 without further purification. LC/MS, method 3, 2.49 min, MS m/z 382, 384 (M+H)$^+$.

Step #4: rac-(7aR,11aS)-11a-ethyl-2-methyl-7,7a,8,10,11,11a-hexahydro-6H-spiro[dibenzo[b,d]oxepine-9,2'-[1,3]dioxolan]-3-amine (88, R$^2$=Ethyl)

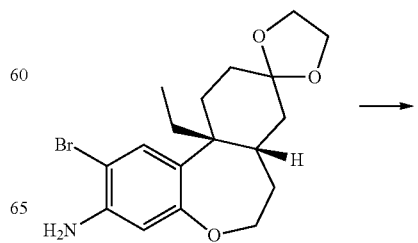

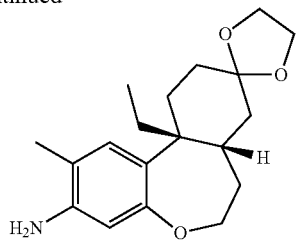

A 500 mL round-bottom flask equipped with air cooled reflux condenser outfitted with a nitrogen inlet adapter was charged with rac-(7aR,11aS)-2-bromo-11a-ethyl-7,7a,8,10,11,11a-hexahydro-6H-spiro[dibenzo[b,d]oxepine-9,2'-[1,3]dioxolan]-3-amine (87, R²=Ethyl) (9.14 g, 23.9 mmol), bis(triphenylphosphine)palladium(II) chloride (0.839 g, 1.20 mmol) and Cs₂CO₃ (23.4 g, 71.7 mmol), and then DME (180 mL), water (60 mL) and trimethylboroxine (6.67 mL, 47.8 mmol) were added. The reaction mixture was heated to about 90° C. for about 15 h. The reaction was allowed to cool to rt and then it was partitioned between EtOAc (350 mL) and water (200 mL). After separating the layers, the aqueous phase was extracted with EtOAc (2×100 mL). The combined organic phases were then washed with brine (500 mL), dried over Na₂SO₄, filtered, and concentrated under reduced pressure. The material was purified on silica gel (330 g, eluted with 0% to 50% EtOAc in heptane). Collection and concentration of the appropriate fractions gave rac-(7aR,11aS)-11a-ethyl-2-methyl-7,7a,8,10,11,11a-hexahydro-6H-spiro[dibenzo[b,d]oxepine-9,2'-[1,3]dioxolan]-3-amine (88, R²=Ethyl) (5.68 g, 74.8%) containing about 20% of a minor regioisomer. The material was used directly in Step #5 without further purification. LC/MS, method 3, 2.26 min, MS m/z 318 (M+H)⁺.

Step #5: rac-1-((4aR,12bS)-12b-ethyl-1,4,4a,5,6,12b-hexahydrospiro[benzo[4,5]oxepino[3,2-f]indazole-3,2'-[1,3]dioxolan]-9(2H)-yl)ethanone (89, R²=Ethyl)

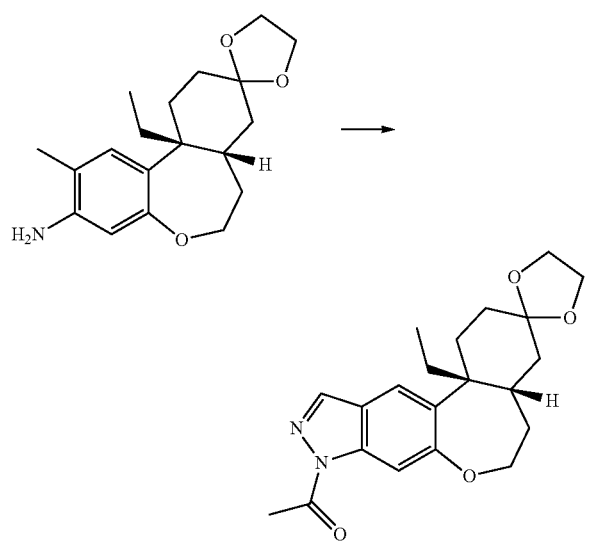

A solution of rac-(7aR,11aS)-11a-ethyl-2-methyl-7,7a,8,10,11,11a-hexahydro-6H-spiro[dibenzo[b,d]oxepine-9,2'-[1,3]dioxolan]-3-amine (88, R²=Ethyl) (6.40 g, 20.2 mmol) in chloroform (202 mL) was treated with potassium acetate (3.96 g, 40.3 mmol) and acetic anhydride (5.71 mL, 60.5 mmol) and the mixture was stirred at rt for about 10 min. 18-crown-6 (0.266 g, 1.01 mmol) and isoamyl nitrite (6.79 mL, 50.4 mmol) were each added sequentially in one portion and the reaction mixture was heated at reflux for about 68 h. The reaction was allowed to cool to rt and then the mixture was partitioned between DCM (100 mL) and a mixture of sat. aq. NaHCO₃ and water (100 mL each). After separating the layers, the organic phase was washed with brine (250 mL), dried over Na₂SO₄, filtered, and concentrated under reduced pressure. The sample was purified on silica gel (330 g, eluted with 0% to 50% EtOAc in Heptane). Collection and concentration of the appropriate fractions gave rac-1-((4aR,12bS)-12b-ethyl-1,4,4a,5,6,12b-hexahydrospiro[benzo[4,5]oxepino[3,2-f]indazole-3,2'-[1,3]dioxolan]-9(2H)-yl)ethanone (89, R²=Ethyl) (3.02 g, 40.4%). LC/MS, method 3, 2.51 min, MS m/z 371 (M+H)⁺. ¹H NMR (400 MHz, CDCl₃) δ 8.04-7.98 (m, 2H), 7.54 (s, 1H), 4.36-4.24 (m, 1H), 4.00-3.84 (m, 4H), 3.77-3.66 (m, 1H), 2.76 (s, 3H), 2.48-2.38 (m, 1H), 2.35-2.20 (m, 2H), 2.02-1.92 (m, 1H), 1.88-1.79 (m, 1H), 1.75-1.46 (m, 5H), 1.39-1.30 (m, 1H), (t, J=7.4 Hz, 3H).

Step #6: rac-(4aR,12bS)-12b-ethyl-1,2,4,4a,5,6,9,12b-octahydrospiro[benzo[4,5]oxepino[3,2-f]indazole-3,2'-[1,3]dioxolane] (90, R²=Ethyl)

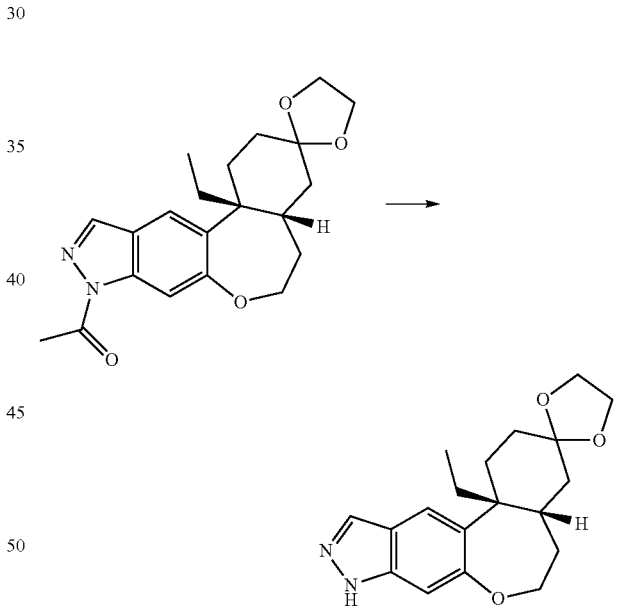

A solution of rac-1-((4aR,12bS)-12b-ethyl-1,4,4a,5,6,12b-hexahydro spiro[benzo[4,5]oxepino[3,2-f]indazole-3,2'-[1,3]dioxolan]-9(2H)-yl)ethanone (89, R²=Ethyl) (3.02 g, 8.15 mmol) in a mixture of THF (54 mL) and MeOH (27 mL) was treated with ammonia (7 M in MeOH, 3.49 mL, 24.5 mmol) and stirred at rt overnight. The reaction mixture was concentrated under reduced pressure to give rac-(4aR,12bS)-12b-ethyl-1,2,4,4a,5,6,9,12b-octahydrospiro[benzo[4,5]oxepino[3,2-f]indazole-3,2'-[1,3]dioxolane] (90, R²=Ethyl) (2.68 g, 100%). The material was used without further purification. LC/MS, method 3, 2.09 min, MS m/z 329 (M+1)⁺. ¹H NMR (400 MHz, CDCl₃) δ 7.97 (s, 1H), 7.57 (s, 1H), 7.07 (s, 1H), 4.33-4.24 (m, 1H), 4.00-3.84 (m, 4H), 3.75-3.64 (m, 1H), 2.79-2.66 (m, 1H), 2.51-2.40 (m, 1H), 2.33-2.19 (m, 2H), 2.09-1.98 (m, 1H), 1.88-1.78 (m, 1H), 1.76-1.29 (m, 5H), (t, J=7.5 Hz, 3H).

Step #7: rac-(4aR,12bS)-12b-ethyl-9-(2-methylpyridin-4-yl)-1,2,4,4a,5,6,9,12b-octahydro spiro[benzo[4,5]oxepino[3,2-f]indazole-3,2'-[1,3]dioxolane] (91, R¹=2-methylpyridin-4-yl, R²=Ethyl)

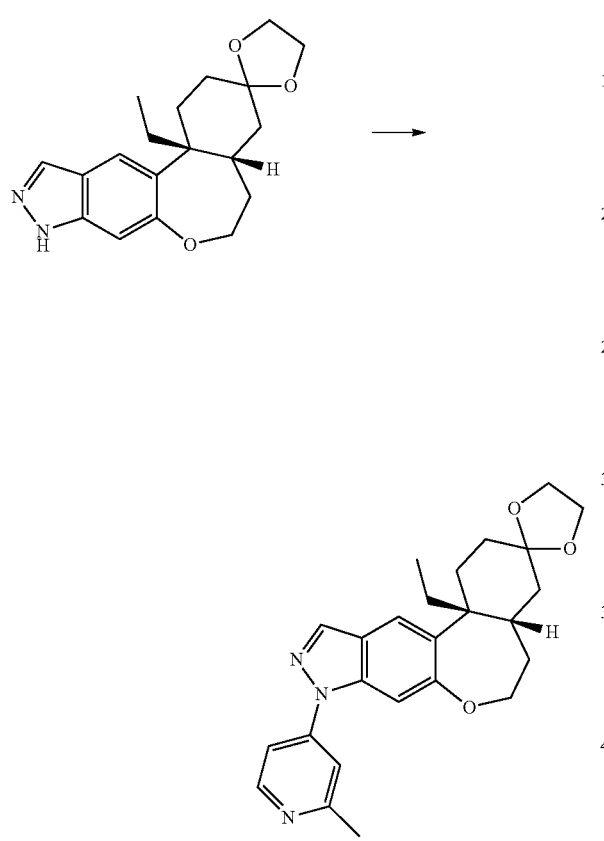

A 25 mL round-bottom flask equipped with air cooled reflux condenser was charged with rac-(4aR,12bS)-12b-ethyl-1,2,4,4a,5,6,9,12b-octahydro spiro[benzo[4,5]oxepino[3,2-f]indazole-3,2'-[1,3]dioxolane] (90, R²=Ethyl) (1.00 g, 3.05 mmol), 4-iodo-2-methylpyridine (prepared as described in US 20070287708; 1.19 g, 4.57 mmol), CuI (0.058 g, 0.30 mmol), K₃PO₄ (1.29 g, 6.09 mmol) and (+/−)-trans-cyclohexane-1,2-diamine (0.070 g, 0.61 mmol) in dioxane (7.5 mL). The reaction mixture was heated at reflux in a heating block for about 18 h. The reaction mixture was filtered through a pad of Celite® using washes of EtOAc (2×20 mL). The filtrate was concentrated under reduced pressure and the residue was purified on silica gel (40 g, eluted with 0% to 100% EtOAc in DCM). Collection and concentration of the appropriate fractions gave rac-(4aR,12bS)-12b-ethyl-9-(2-methylpyridin-4-yl)-1,2,4,4a,5,6,9,12b-octahydrospiro[benzo[4,5]oxepino[3,2-f]indazole-3,2'-[1,3]dioxolane] (91, R¹=2-methylpyridin-4-yl, R²=Ethyl) (1.11 g, 87%). LC/MS, method 3, R$_f$=2.47 min, MS m/z 420 (M+H)⁺. ¹H NMR (400 MHz, CDCl₃) δ 8.57 (d, J=5.9 Hz, 1H), 8.19 (s, 1H), 7.86-7.70 (m, 2H), 7.65 (s, 1H), 7.53 (s, 1H), 4.39-4.30 (m, 1H), 4.01-3.85 (m, 4H), 3.82-3.70 (m, 1H), 2.87-2.68 (m, 4H), 2.50-2.40 (m, 1H), 2.32-2.21 (m, 2H), 2.03-1.32 (m, 7H), (t, J=7.4 Hz, 3H).

Step #8: rac-(4aR,12bS)-12b-ethyl-9-(2-methylpyridin-4-yl)-4,4a,5,6,9,12b-hexahydro-1H-benzo[4,5]oxepino[3,2-f]indazol-3(2H)-one (92, R¹=2-methylpyridin-4-yl, R²=Ethyl)

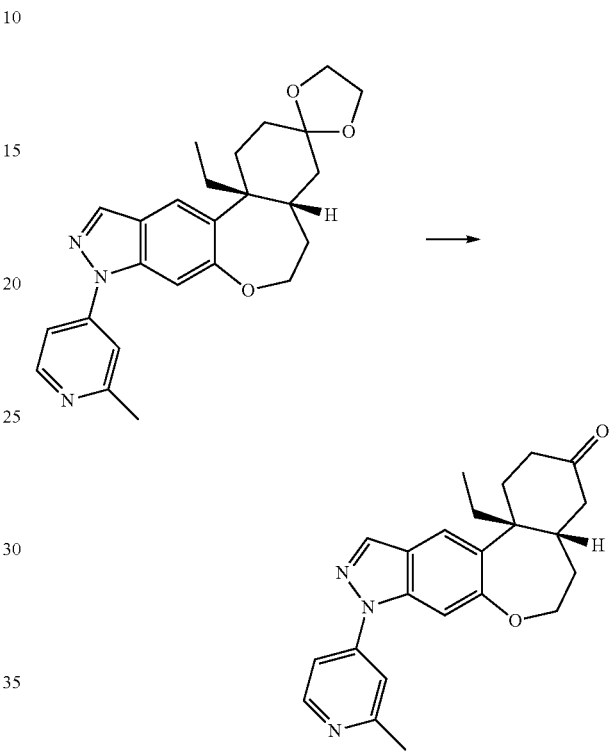

A 100 mL round-bottom flask equipped with air cooled reflux condenser and nitrogen inlet adapter was charged with rac-(4aR,12bS)-12b-ethyl-9-(2-methylpyridin-4-yl)-1,2,4,4a,5,6,9,12b-octahydrospiro[benzo[4,5]oxepino[3,2-f]indazole-3,2'-[1,3]dioxolane] (91, R¹=2-methylpyridin-4-yl, R²=Ethyl) (1.11 g, 2.65 mmol) and pTSA (0.654 g, 3.44 mmol) in acetone (26.5 mL) and the reaction mixture was heated at about reflux in a heating block for about 16 h, after which additional acetone (26.5 mL) was added and heating continued for 1 h. The reaction mixture was allowed to cool and then was quenched by careful addition of sat. aq. NaHCO₃ (25 mL). The mixture was concentrated under reduced pressure and the remainder was partitioned against EtOAc (50 mL). After separating the layers, the aqueous phase was extracted with EtOAc (2×25 mL). The combined organic phases were washed with brine (100 mL), dried over Na₂SO₄, filtered, and concentrated under reduced pressure to give (4aR,12bS)-12b-ethyl-9-(2-methylpyridin-4-yl)-4,4a,5,6,9,12b-hexahydro-1H-benzo[4,5]oxepino[3,2-f]indazol-3(2H)-one (92, R¹=2-methylpyridin-4-yl, R²=Ethyl) (1.00 g, 2.66 mmol, 101% yield), which was used without further purification. LC/MS, method 3, R$_f$=2.13 min, MS m/z 376 (M+H)⁺. ¹H NMR (400 MHz, CDCl₃) δ 8.60 (d, J=5.9 Hz, 1H), 8.25 (s, 1H), 7.95-7.75 (m, 2H), 7.72 (s, 1H), 7.61 (s, 1H), 4.45-4.36 (m, 1H), 3.88-3.71 (m, 1H), 2.93-2.54 (m, 6H), 2.51-2.29 (m, 3H), 2.23-2.06 (m, 1H), 1.96-1.83 (m, 1H), 1.72-1.42 (m, 2H), 0.68 (s, 1H), (t, J=7.5 Hz, 3H).

Step #9: rac-(2'R,4aS,12bR)-12b-ethyl-9-(2-methylpyridin-4-yl)-1,2,4,4a,5,6,9,12b-octahydro spiro[benzo[4,5]oxepino[3,2-f]indazole-3,2'-oxirane] (93, R$^1$=2-methylpyridin-4-yl, R$^2$=Ethyl)

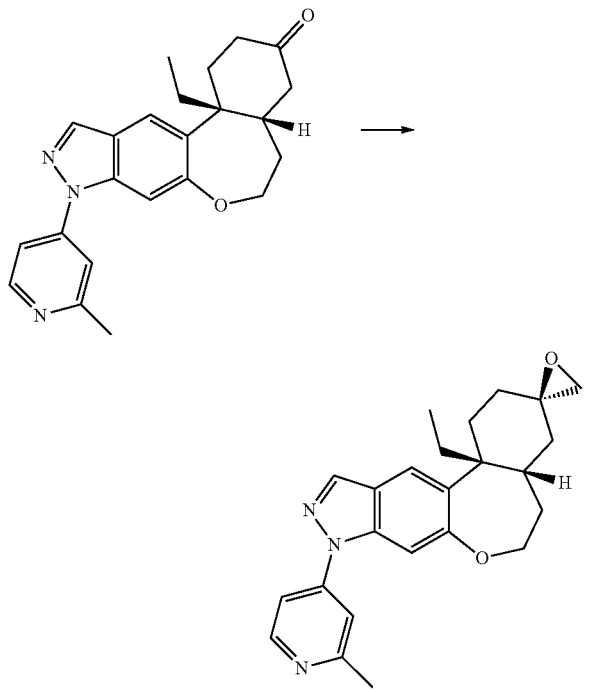

A 100 mL round-bottom flask equipped with rubber septum and nitrogen inlet needle was charged with sodium hydride (60 wt % in oil, 0.212 g, 5.29 mmol) in DMSO (13 mL) and then the mixture was heated at about 60° C. in a heating block for about 30 min. The mixture was allowed to cool to rt, at which point trimethylsulfoxonium iodide (1.16 g, 5.29 mmol) was added in one portion and the reaction mixture was stirred for about 15 min. A solution of rac-(4aR,12bS)-12b-ethyl-9-(2-methylpyridin-4-yl)-4,4a,5,6,9,12b-hexahydro-1H-benzo[4,5]oxepino[3,2-f]indazol-3 (2H)-one (92, R$^1$=2-methylpyridin-4-yl, R$^2$=Ethyl) (0.993 g, 2.64 mmol) in THF (13 mL) was added in one portion. After about 30 min the reaction was concentrated under reduced pressure and the residue was partitioned between EtOAc (50 mL) and water (50 mL). The layers were separated and the aqueous phase was extracted with EtOAc (2×10 mL). The combined organic phases were washed with brine (50 mL), dried over Na$_2$SO$_4$, filtered, and concentrated under reduced pressure. The material was purified on silica gel (40 g, EtOAc). Collection and concentration of the appropriate fractions gave rac-(2'R,4aS,12bR)-12b-ethyl-9-(2-methylpyridin-4-yl)-1,2,4,4a,5,6,9,12b-octahydrospiro[benzo[4,5]oxepino[3,2-f]indazole-3,2'-oxirane] (93, R$^1$=2-methylpyridin-4-yl, R$^2$=Ethyl) (0.844 g, 82%). LC/MS, method 3, R$_t$=2.40 min, MS m/z 390 (M+H)$^+$. $^1$H NMR (400 MHz, CDCl$_3$) δ 8.61-8.55 (m, 1H), 8.23 (s, 1H), 7.91-7.76 (m, 2H), 7.69 (s, 1H), 7.56 (s, 1H), 4.43-4.31 (m, 1H), 3.84-3.71 (m, 1H), 2.98-2.70 (m, 3H), 2.71-2.56 (m, 2H), 2.56-2.16 (m, 4H), 2.07-1.93 (m, 1H), 1.93-1.77 (m, 1H), 1.73-1.33 (m, 4H), 0.97-0.83 (m, 1H), 0.74-0.56 (t, J=7.5 Hz, 3H).

Step #10: rac-(3R,4aS,12bR)-12b-ethyl-3-(methoxymethyl)-9-(2-methylpyridin-4-yl)-2,3,4,4a,5,6,9,12b-octahydro-1H-benzo[4,5]oxepino[3,2-f]indazol-3-ol (94, R$^1$=2-methylpyridin-4-yl, R$^2$=Ethyl, R$^3$=methoxymethyl)

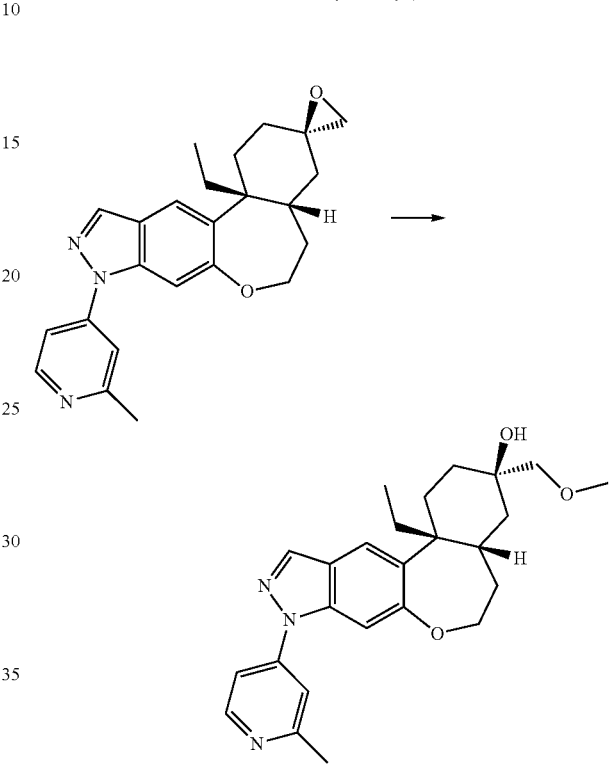

A 50 mL round-bottom flask equipped with rubber septum and nitrogen inlet needle was charged with rac-(2'R,4aS,12bR)-12b-ethyl-9-(2-methylpyridin-4-yl)-1,2,4,4a,5,6,9,12b-octahydrospiro[benzo[4,5]oxepino[3,2-f]indazole-3,2'-oxirane] (93, R$^1$=2-Methylpyridin-4-yl, R$^2$=Ethyl) (0.200 g, 0.513 mmol) and NaOMe (0.5 M in MeOH) (5.1 mL, 2.57 mmol). The resulting solution was allowed to stir at rt for about 16 h, after which the reaction solution was concentrated under reduced pressure. The residue was partitioned between a mixture of water (20 mL) with sat. aq. NH$_4$Cl (5 mL) and EtOAc (25 mL). After separating the layers, the aqueous phase was extracted with EtOAc (2×10 mL). The combined organic phases were washed with brine (25 mL), dried over Na$_2$SO$_4$, filtered, and concentrated under reduced pressure. The sample was purified on silica gel (4 g, EtOAc). Collection and concentration of the appropriate fractions gave rac-(3R,4aS,12bR)-12b-ethyl-3-(methoxymethyl)-9-(2-methylpyridin-4-yl)-2,3,4,4a,5,6,9,12b-octahydro-1H-benzo[4,5]oxepino[3,2-f]indazol-3-ol (94, R$^1$=2-methylpyridin-4-yl, R$^2$=Ethyl, R$^3$=Methoxymethyl) (198 mg, 92%). LC/MS, method 2, R$_t$=2.04 min, MS m/z 422 (M+H)$^+$. $^1$H NMR (400 MHz, CDCl$_3$) δ 8.57 (d, J=5.8 Hz, 1H), 8.20 (s, 1H), 7.86-7.72 (m, 2H), 7.64 (s, 1H), 7.53 (s, 1H), 4.39-4.30 (m, 1H), 3.81-3.71 (m, 1H), 3.33 (s, 3H), 3.19-3.02 (m, 2H), 2.87-2.70 (m, 3H), 2.53-2.45 (m, 1H), 2.38-2.20 (m, 3H), 1.96-1.85 (m, 1H), 1.82-1.65 (m, 2H), 1.63-1.36 (m, 4H), 1.34-1.22 (m, 1H), 0.60 (t, J=7.4 Hz, 3H).

Step #11: ((3S,4aR,12bS)-12b-ethyl-3-(methoxymethyl)-9-(2-methylpyridin-4-yl)-2,3,4,4a,5,6,9,12b-octahydro-1H-benzo[4,5]oxepino[3,2-f]indazol-3-ol (94, R$^1$=2-methylpyridin-4-yl, R$^2$=Ethyl, R$^3$=Methoxymethyl) and ((3R,4aS,12bR)-12b-ethyl-3-(methoxymethyl)-9-(2-methylpyridin-4-yl)-2,3,4,4a,5,6,9,12b-octahydro-1H-benzo[4,5]oxepino[3,2-f]indazol-3-ol (94, R$^1$=2-methylpyridin-4-yl, R$^2$=Ethyl, R$^3$=Methoxymethyl)

LC/MS, method 2, R$_t$=2.04 min, MS m/z 422 (M+H)$^+$. $^1$H NMR (400 MHz, CDCl$_3$) δ 8.57 (d, J=5.8 Hz, 1H), 8.20 (s, 1H), 7.86-7.72 (m, 2H), 7.64 (s, 1H), 7.53 (s, 1H), 4.39-4.30 (m, 1H), 3.81-3.71 (m, 1H), 3.33 (s, 3H), 3.19-3.02 (m, 2H), 2.87-2.70 (m, 3H), 2.53-2.45 (m, 1H), 2.38-2.20 (m, 3H), 1.96-1.85 (m, 1H), 1.82-1.65 (m, 2H), 1.63-1.36 (m, 4H), 1.34-1.22 (m, 1H), 0.60 (t, J=7.4 Hz, 3H).

The enantiomers from Step #10 were separated using Preparative Chiral Purification Method 32. Fractions from the first peak eluted were combined and concentrated under reduced pressure to give ((3S,4aR,12bS)-12b-ethyl-3-(methoxymethyl)-9-(2-methylpyridin-4-yl)-2,3,4,4a,5,6,9,12b-octahydro-1H-benzo[4,5]oxepino[3,2-f]indazol-3-ol (94, R$^1$=2-methylpyridin-4-yl, R$^2$=Ethyl, R$^3$=Methoxymethyl). (Example 127) (0.071 g, 33%). Fractions from the second peak eluted were combined and concentrated under reduced pressure to give ((3R,4aS,12bR)-12b-ethyl-3-(methoxymethyl)-9-(2-methylpyridin-4-yl)-2,3,4,4a,5,6,9,12b-octahydro-1H-benzo[4,5]oxepino[3,2-f]indazol-3-ol (94, R$^1$=2-methylpyridin-4-yl, R$^2$=Ethyl, R$^3$=Methoxymethyl). (Example 128) (0.062 g, 29%). LC/MS, method 2, R$_t$=2.04 min, MS m/z 422 (M+H)$^+$. $^1$H NMR (400 MHz, CDCl$_3$) δ 8.57 (d, J=5.8 Hz, 1H), 8.20 (s, 1H), 7.86-7.72 (m, 2H), 7.64 (s, 1H), 7.53 (s, 1H), 4.39-4.30 (m, 1H), 3.81-3.71 (m, 1H), 3.33 (s, 3H), 3.19-3.02 (m, 2H), 2.87-2.70 (m, 3H), 2.53-2.45 (m, 1H), 2.38-2.20 (m, 3H), 1.96-1.85 (m, 1H), 1.82-1.65 (m, 2H), 1.63-1.36 (m, 4H), 1.34-1.22 (m, 1H), 0.60 (t, J=7.4 Hz, 3H).

Additional examples, prepared in a manner similar to the preparation of Examples 127 and 128 are listed in Table 11.

TABLE 11

| Ex. # | Aryl halide (Step 7) | Reagent (Step 10) | Product structure | LC/MS method/ R$_t$, MH$^+$ | Chiral method | Order of elution/ sign of rotation |
|---|---|---|---|---|---|---|
| 129 | 4-fluoroiodobenzene | Sodium methoxide | 94 rac (3R,4aS,12bR) (R$^1$ = 4-fluorophenyl, R$^2$ = Ethyl, R$^3$ = methoxymethyl) | 2 2.70 min 425 | n/a | n/a |
| 130 | 4-fluoroiodobenzene | Sodium methoxide | 94 (3S,4aR,12bS) (R$^1$ = 4-fluorophenyl, R$^2$ = Ethyl, R$^3$ = methoxymethyl) | 2 2.70 min 425 | 7 | 1st/nd |
| 131 | 4-fluoroiodobenzene | Sodium methoxide | 94 (3R,4aS,12bR) (R$^1$ = 4-fluorophenyl, R$^2$ = Ethyl, R$^3$ = methoxymethyl) | 2 2.70 min 425 | 7 | 2nd/nd |
| 132 | 4-iodopyridine | Sodium methoxide | 94 (3R,4aS,12bR) compound with (3R,4aS,12bR) (R$^1$ = pyridin-4-yl, R$^2$ = Ethyl, R$^3$ = methoxymethyl) | 2 2.10 408 | n/a | n/a |
| 133 | 4-iodopyridine | Sodium methoxide | 94 (3S,4aR,12bS) (R$^1$ = pyridin-4-yl, R$^2$ = Ethyl, R$^3$ = methoxymethyl) | 2 2.10 408 | 30 | 1st/neg |
| 134 | 4-iodopyridine | Sodium methoxide | 94 (3R,4aS,12bR) (R$^1$ = pyridin-4-yl, R$^2$ = Ethyl, R$^3$ = methoxymethyl) | 2 2.10 408 | 30 | 2nd/pos |
| 135 | 4-iodopyrimidine (Synthonix, Inc.) | Sodium methoxide | 94 (3S,4aR,12bS) (R$^1$ = pyrimidin-4-yl, R$^2$ = Ethyl, R$^3$ = methoxymethyl) | 2 2.30 409 | 31 | 1st/nd |
| 136 | 4-iodopyrimidine (Synthonix, Inc.) | Sodium methoxide | 94 (3R,4aS,12bR) (R$^1$ = pyrimidin-4-yl, R$^2$ = Ethyl, R$^3$ = methoxymethyl) | 2 2.30 422 | 31 | 2nd/nd |
| 137 | 4-iodo-2-methoxypyridine | Sodium methoxide | 94 (3S,4aR,12bS) (R$^1$ = 2-MethoxyPyridin-4-yl, R$^2$ = Ethyl, R$^3$ = Methoxymethyl) | 2 2.21 min 438 MH+ | | 1$^{st}$/NA |
| 138 | 4-iodo-2-methoxypyridine | Sodium methoxide | 94 (3R,4aS,12bR) (R$^1$ = 2-MethoxyPyridin-4-yl, R$^2$ = Ethyl, R$^3$ = Methoxymethyl) | 2 2.21 min 438 MH+ | | 2$^{nd}$/NA |
| 139 | 2-Bromo-5-methyl-thiadiazole | Sodium methoxide | 94 rac-(3R,4aS,12bR) (R$^1$ = 5-Methyl-1,3,4-thiadiazol-2-yl, R$^2$ = Ethyl, R$^3$ = Methoxymethyl) | 2 2.35 min 429 MH+ | NA | NA |

TABLE 11-continued

| Ex. # | Aryl halide (Step 7) | Reagent (Step 10) | Product structure | LC/MS method/ $R_t$, MH+ | Chiral method | Order of elution/ sign of rotation |
|---|---|---|---|---|---|---|
| 140 | 4-bromo-2-trifluoromethyl-pyridine | Sodium methoxide | 94 (3S,4aR,12bS) ($R^1$ = 2-trifluoromethyl)-4-pyridyl, $R^2$ = Ethyl, $R^3$ = Methoxymethyl) | 2 2.73 min 476 MH+ | 56 | $1^{st}$/NA |
| 141 | 4-bromo-2-trifluoromethyl-pyridine | Sodium methoxide | 94 (3R,4aS,12bR) ($R^1$ = (2-trifluoromethyl)-4-pyridyl, $R^2$ = Ethyl, $R^3$ = Methoxymethyl) | 2 2.73 min 476 MH+ | 56 | $2^{nd}$/NA |

Additional examples, prepared from intermediate 93 in a manner similar to the preparation of Examples 15 and 16 are listed in Table 12.

TABLE 12

| Ex. # | Aryl iodide (Step 7) | Reagent (Step 10) | Product structure | LC/MS method/ $R_t$, MH+ | Chiral method | Order of elution/ sign of rotation |
|---|---|---|---|---|---|---|
| 142 | 4-iodo-2-methylpyridine | NaBH$_4$ | 94 (3S,4aR,12bS) ($R^1$ = 2-methylpyridin-4-yl, $R^2$ = Ethyl, $R^3$ = Methyl) | 2 2.13 392 | 33 | 1st/neg |
| 143 | 4-iodo-2-methylpyridine | NaBH$_4$ | 94 (3R,4aS,12bR) ($R^1$ = 2-methylpyridin-4-yl, $R^2$ = Ethyl, $R^3$ = Methyl) | 2 2.13 392 | 33 | 2nd/pos |

Additional examples, prepared from intermediate 93 in a manner similar to the preparation of Examples 17 and 18 are listed in Table 13.

TABLE 13

| Ex. # | Aryl iodide (Step 7) | Reagent (Step 10) | Product structure | LC/MS method/ $R_t$, MH+ | Chiral method | Order of elution/ sign of rotation |
|---|---|---|---|---|---|---|
| 144 | 4-iodo-2-methyl-pyridine | Potassium cyanide | 94 (3S,4aR,12bS) ($R^1$ = 2-methylpyridin-4-yl, $R^2$ = Ethyl, $R^3$ = cyanomethyl) | 2 1.94 417 | 54 | 1st/neg |
| 145 | 4-iodo-2-methyl-pyridine | Potassium cyanide | 94 (3R,4aS,12bR) ($R^1$ = 2-methylpyridin-4-yl, $R^2$ = Ethyl, $R^3$ = cyanomethyl) | 2 1.94 417 | 54 | 2nd/pos |

Scheme 21:

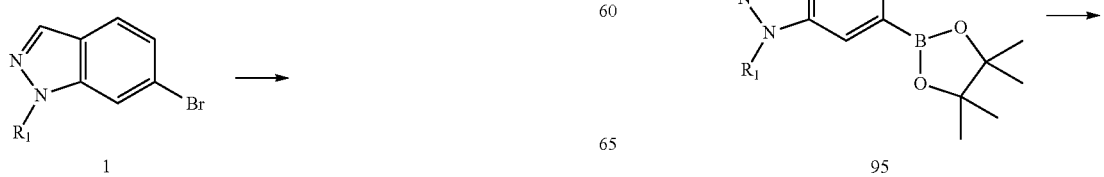

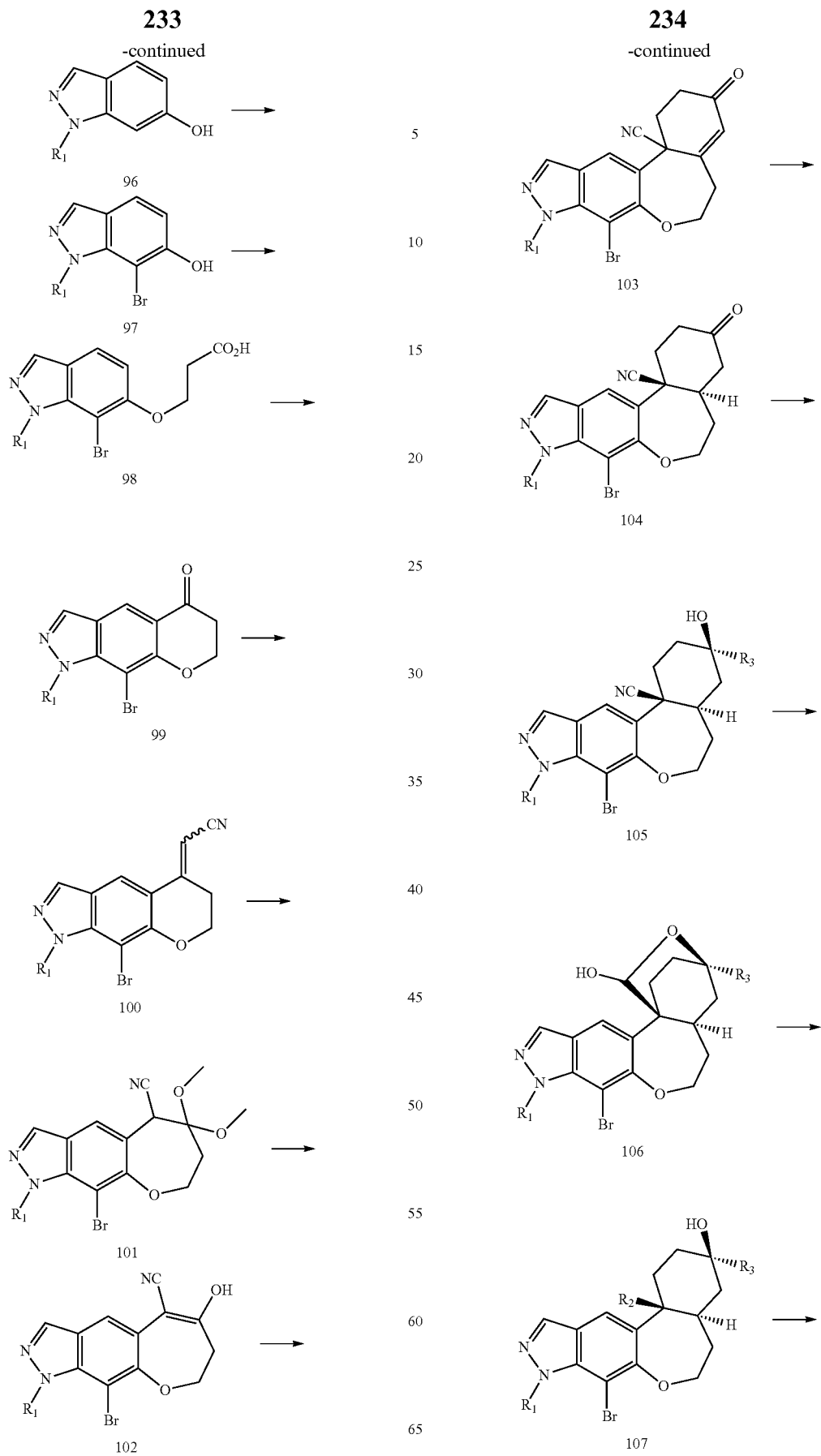

235
-continued

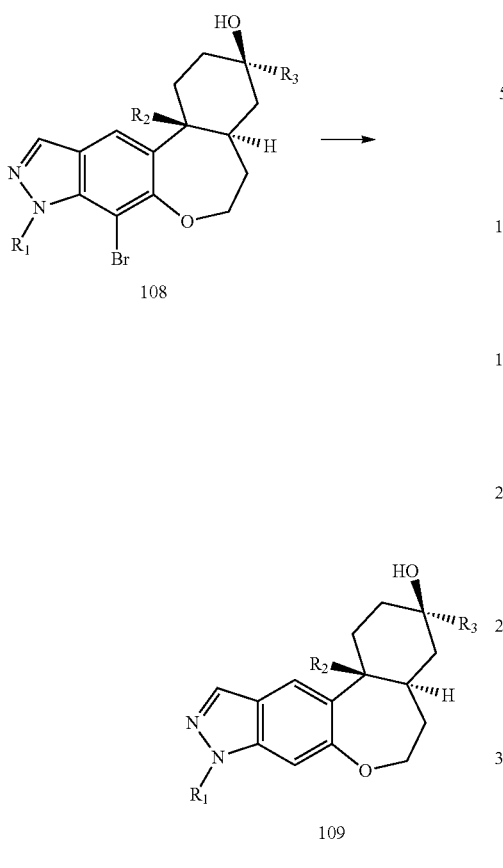

108

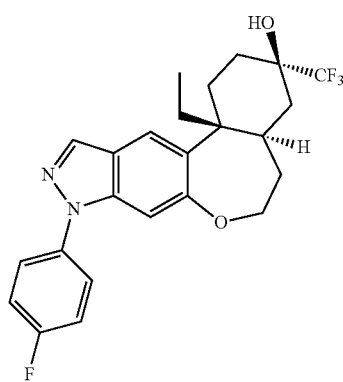 [SMILES: CC[C@@]12CC[C@](O)(C(F)(F)F)C[C@H]1CCOc1cc3c(cnn3-c3ccc(F)cc3)cc12]

109

Example #146 and #147

(3R,4aR,12bR)-12b-Ethyl-9-(4-fluorophenyl)-3-(trifluoromethyl)-2,3,4,4a,5,6,9,12b-octahydro-1H-benzo[4,5]oxepino[3,2-f]indazol-3-ol (109, R¹=4-Fluorophenyl, R²=Ethyl, R³=Trifluoromethyl) and (3S,4aS,12bS)-12b-ethyl-9-(4-fluorophenyl)-3-(trifluoromethyl)-2,3,4,4a,5,6,9,12b-octahydro-1H-benzo[4,5]oxepino[3,2-f]indazol-3-ol (109, R¹=4-Fluorophenyl, R²=Ethyl, R³=Trifluoromethyl)

236

Step #1: 1-(4-Fluorophenyl)-1H-indazol-6-ol (96, R¹=4-Fluorophenyl)

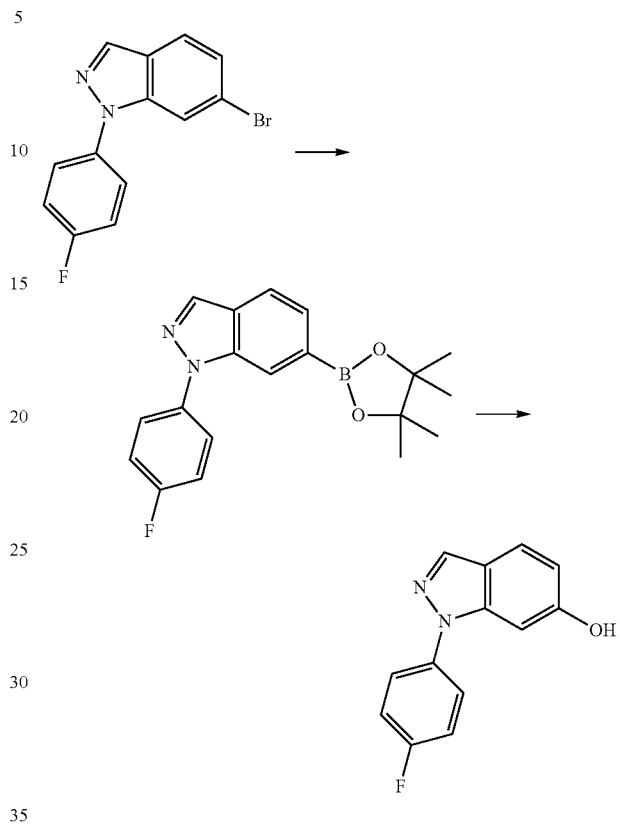

1,4-Dioxane (350 mL) was added to a mixture of 6-bromo-1-(4-fluorophenyl)-1H-indazole (1, R¹=4-Fluorophenyl) (29.6 g, 102 mmol), potassium acetate (25.0 g, 255 mmol), bis(pinacolato)diboron (31.0 g, 122 mmol), and 1,1'bis(diphenylphosphino)ferrocene-palladium(II)dichloride dichloromethane complex (2.50 g, 3.06 mmol) under a nitrogen atmosphere. The reaction vessel was evacuated then back-filled with nitrogen three times. The mixture was purged with nitrogen for about 30 min then warmed to about 90° C. After about 2 h, the reaction was allowed to cool to rt then concentrated to a volume of 100 mL. EtOAc (400 mL) and water (400 mL) were added. After stirring for about 1 h, the mixture was filtered. The layers were separated and the aqueous layer was extracted with EtOAc (100 mL). The combined organics were dried over $Na_2SO_4$, filtered and concentrated under reduced pressure to afford 1-(4-fluorophenyl)-6-(4,4,5,5-tetramethyl-1,3,2-dioxaborolan-2-yl)-1H-indazole (95, R¹=4-Fluorophenyl) as a dark drown residue. LC/MS, method 3, $R_f$=2.87 min, MS m/z 339 (M+H)⁺. ¹H NMR (400 MHz, DMSO) δ 8.41 (d, J=0.9 Hz, 1H), 7.97-7.95 (m, 1H), 7.90 (dd, J=8.0, 0.9 Hz, 1H), 7.80-7.73 (m, 2H), 7.53 (dd, J=8.0, 0.7 Hz, 1H), 7.51-7.45 (m, 2H), 1.31 (s, 12H). THF (500 mL) was added to 1-(4-fluorophenyl)-6-(4,4,5,5-tetramethyl-1,3,2-dioxaborolan-2-yl)-1H-indazole under air, then the resulting solution was cooled to about 0° C. NaOH (2 M aqueous solution, 120 mL, 240 mmol) was added. $H_2O_2$ (30% aq. solution, 30.0 mL, 294 mmol) was added dropwise over about 30 min maintaining an internal temperature of about less than 10° C. After about 30 min, the mixture was diluted with water (400 mL). The pH was adjusted to about 2 with 2 M aq. HCl. EtOAc (500 mL) was added. The layers were separated and the organic layers was washed with water (200 mL) and sat. aq. NaCl (200 mL). The aqueous layers were extracted with EtOAc (2×200 mL). The combined organics were dried over $Na_2SO_4$, filtered, and concentrated under reduced pressure. The residue was triturated with DCM resulting in 1-(4-fluorophenyl)-1H-indazol-6-ol ($R^1$=4-Fluorophenyl) (12.0 g, 52% yield) as a light tan solid. The mother liquor was purified on silica gel (220 g) using a gradient of 0-4% EtOAc in DCM. The fractions containing the first eluding diastereomer were combined and concentrated under reduced pressure to afford 1-(4-fluorophenyl)-1H-indazol-6-ol (96, $R^1$=4-Fluorophenyl) (10.1 g, 43% yield) as a light tan solid. LC/MS, method 3, $R_t$=2.01 min, MS m/z 229 (M+H)$^+$. $^1$H NMR (400 MHz, DMSO) δ 9.81 (s, 1H), 8.15 (d, J=0.9 Hz, 1H), 7.75-7.66 (m, 2H), 7.64 (d, J=9.0 Hz, 1H), 7.46-7.34 (m, 2H), 7.03-6.98 (m, 1H), 6.77 (dd, J=8.7, 2.0 Hz, 1H).

Step #2: 7-Bromo-1-(4-fluorophenyl)-1H-indazol-6-ol (97, $R^1$=4-Fluorophenyl)

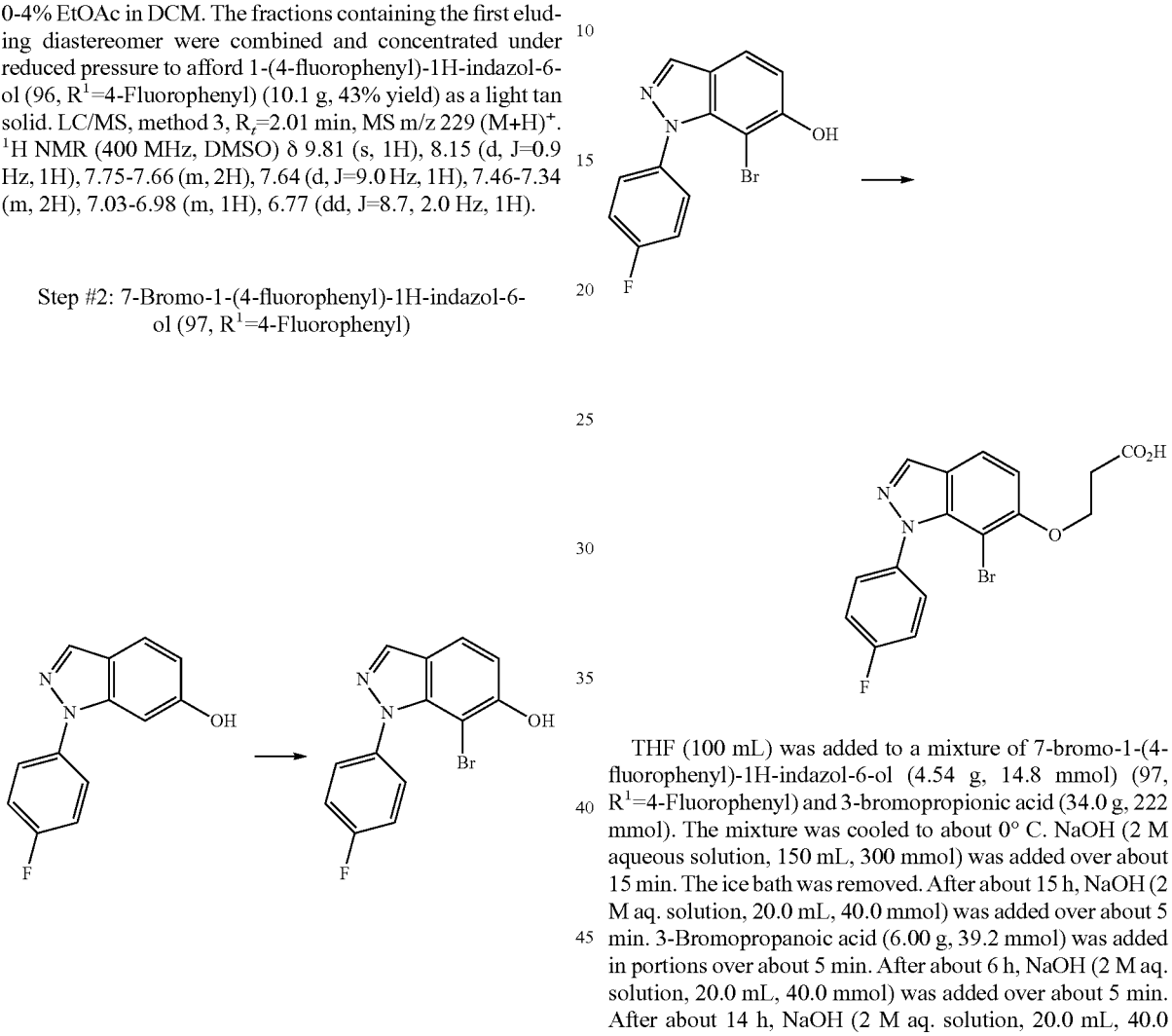

NBS (16.2 g, 91 mmol) was added in one portion to a solution of 1-(4-fluorophenyl)-1H-indazol-6-ol (96, $R^1$=4-Fluorophenyl) (20.3 g, 89 mmol) and THF (500 mL) under a nitrogen atmosphere at about 0° C. After about 1 h, water (500 mL) and EtOAc (400 mL) were added. The layers were separated and the aqueous layer was extracted with EtOAc (100 mL). The combined organics were dried over $Na_2SO_4$, filtered, and concentrated under reduced pressure. The resulting solid was slurried in DCM (50 mL) then collected by filtration rinsing with DCM (4×25 mL). The solid was dried to afford 7-bromo-1-(4-fluorophenyl)-1H-indazol-6-ol (97, $R^1$=4-Fluorophenyl) (17.2 g, 63% yield) as a faint orange solid. LC/MS, method 3, $R_t$=2.02 min, MS m/z 307 and 309 (M+H)$^+$. $^1$H NMR (400 MHz, DMSO) δ 10.52 (d, J=0.9 Hz, 1H), 8.20 (d, J=0.9 Hz, 1H), 7.67 (dd, J=8.6, 0.9 Hz, 1H), 7.54-7.47 (m, 2H), 7.38-7.29 (m, 2H), 6.95 (dd, J=8.6, 0.9 Hz, 1H).

Step #3: 3-((7-Bromo-1-(4-fluorophenyl)-1H-indazol-6-yl)oxy)propanoic acid (98, $R^1$=4-Fluorophenyl)

THF (100 mL) was added to a mixture of 7-bromo-1-(4-fluorophenyl)-1H-indazol-6-ol (4.54 g, 14.8 mmol) (97, $R^1$=4-Fluorophenyl) and 3-bromopropionic acid (34.0 g, 222 mmol). The mixture was cooled to about 0° C. NaOH (2 M aqueous solution, 150 mL, 300 mmol) was added over about 15 min. The ice bath was removed. After about 15 h, NaOH (2 M aq. solution, 20.0 mL, 40.0 mmol) was added over about 5 min. 3-Bromopropanoic acid (6.00 g, 39.2 mmol) was added in portions over about 5 min. After about 6 h, NaOH (2 M aq. solution, 20.0 mL, 40.0 mmol) was added over about 5 min. After about 14 h, NaOH (2 M aq. solution, 20.0 mL, 40.0 mmol) was added over about 5 min. After about 2 h, NaOH (2 M aq. solution, 20.0 mL, 40.0 mmol) was added over about 5 min. After about 15 h, the solution was cooled to about 0° C. 2 M aq. HCl (250 mL) and EtOAc (400 mL) were added. The layers were separated and the aqueous layer was extracted with EtOAc (100 mL). The combined organics were washed with water (400 mL) and sat. aq. NaCl (400 mL), dried over $Na_2SO_4$, filtered, and concentrated under reduced pressure. The residue was purified on silica gel (220 g) using a gradient of 0-50% EtOAc in DCM. The fractions containing the product were combined and concentrated under reduced pressure to afford a light tan solid. DCM (50 mL) was added. The solid was collected by filtration rinsing with 2×10 mL DCM (2×10 mL) then dried under reduced pressure to afford 3-((7-bromo-1-(4 fluorophenyl)-1H-indazol-6-yl)oxy)propanoic acid (98, $R^1$=4-Fluorophenyl) (7.93 g, 30% yield) as an ivory solid. LC/MS, method 3, $R_t$=1.97 min, MS m/z 379 and 381 (M+H)$^+$. $^1$H NMR (400 MHz, DMSO) δ 12.35 (s, 1H), 8.30

(s, 1H), 7.86 (d, J=8.7 Hz, 1H), 7.56-7.46 (m, 2H), 7.39-7.30 (m, 2H), 7.18 (d, J=8.8 Hz, 1H), 4.34 (t, J=6.0 Hz, 2H), 2.72 (t, J=6.0 Hz, 2H).

Step #4: 9-Bromo-1-(4-fluorophenyl)-6,7-dihydropyrano[3,2-f]indazol-5(1H)-one (99, R¹=4-Fluorophenyl)

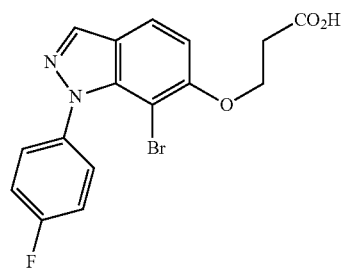

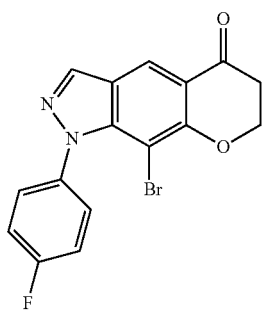

SOCl₂ (4.25 mL, 58.3 mmol) was added dropwise to a slurry of 3-((7-bromo-1-(4-fluorophenyl)-1H-indazol-6-yl)oxy)propanoic acid (98, R¹=4-Fluorophenyl) (17.0 g, 44.8 mmol) and DCM (500 mL) under a nitrogen atmosphere at about 0° C. After about 10 min, the ice bath was removed. After about 1 h, SOCl₂ (1.00 mL, 13.7 mmol) was added dropwise. After about 3 h, the solution was cooled to 0° C. and then aluminum chloride (18.0 g, 135 mmol) was added in three portions over about 15 min. The ice bath was allowed to thaw to rt over about 2 h. After about 1 h at rt, the mixture was poured into ice water (500 mL). After stirring for about 15 min, the layers were separated and the aqueous layer was extracted with DCM (100 mL). The combined organics were washed with water (100 mL), dried over Na₂SO₄, filtered, and concentrated under reduced pressure. The residue was slurried in EtOH (50 mL). The solid was collected by filtration rinsing with EtOH (2×10 mL) then dried under reduced pressure to afford 9-bromo-1-(4-fluorophenyl)-6,7-dihydropyrano[3,2-f]indazol-5(1H)-one (99, R¹=4-Fluorophenyl) (13.3 g, 82% yield) as an ivory solid. LC/MS, method 3, R$_t$=2.26 min, MS m/z 361 and 363 (M+H)⁺. ¹H NMR (400 MHz, DMSO) δ 8.50 (s, 1H), 8.42 (s, 1H), 7.61-7.54 (m, 2H), 7.42-7.33 (m, 2H), 4.66 (t, J=6.3 Hz, 2H), 2.89 (t, J=6.3 Hz, 2H).

Step #5: 2-(9-Bromo-1-(4-fluorophenyl)-6,7-dihydropyrano[3,2-f]indazol-5(1H)-ylidene)acetonitrile (100, R¹=4-Fluorophenyl)

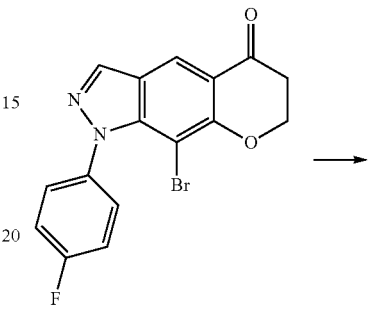

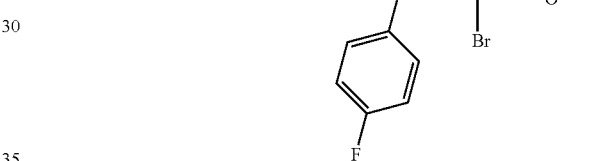

Diethyl (cyanomethyl)phosphonate (11.2 mL, 69.2 mmol) was added dropwise to a slurry of sodium hydride (60 wt % in oil, 2.76 g, 68.9 mmol) in DME (120 mL) under a nitrogen atmosphere at about 0° C. over about 15 min. After completion of addition, the ice bath was removed. After about 30 min, the solution was added to a slurry of 9-bromo-1-(4-fluorophenyl)-6,7-dihydropyrano[3,2-f]indazol-5 (1H)-one (99, R¹=4-Fluorophenyl) (12.5 g, 34.5 mmol) and DME (60 mL) rinsing with DME (60 mL). After about 43 h, the volatiles were removed under under reduced pressure and the residue was dissolved with EtOAc (300 mL) and sat. aq. NH₄Cl solution (300 mL). The layers were separated. The organic layer was washed with sat. aq. NaCl (200 mL), dried over Na₂SO₄, filtered and concentrated under reduced pressure. The residue was slurried in DCM (20 mL). The solid was collected by filtration rinsing with DCM (10 mL) then dried under reduced pressure to afford 2-(9-Bromo-1-(4-fluorophenyl)-6,7-dihydropyrano[3,2-f]indazol-5(1H)-ylidene)acetonitrile (100, R¹=4-Fluorophenyl) (2.41 g, 18% yield) as an ivory solid. The mother liquor was purified on silica gel (220 g) using a gradient of 0-2% EtOAc in DCM. The fractions containing the product were combined and concentrated under reduced pressure to afford 2-(9-Bromo-1-(4-fluorophenyl)-6,7-dihydropyrano[3,2-f]indazol-5(1H)-ylidene)acetonitrile (100, R¹=4-Fluorophenyl) (4.92 g, 37% yield) as an ivory solid. LC/MS, method 3, R$_t$=2.42 min, MS m/z 384 and 386 (M+H)⁺. ¹H NMR (400 MHz, DMSO) δ 8.69 (s, 0.33H), 8.50 (s, 0.33H), 8.46 (s, 0.67H), 8.39 (s, 0.67H), 7.60-7.51 (m, 2H), 7.42-7.30 (m, 2H), 6.50-6.46 (m, 0.67H), 5.84-5.81 (m, 0.33H), 4.48-4.42 (m, 0.67H), 4.42-4.36 (m, 1.33H), 3.06-2.98 (m, 1.33H), 2.88-2.82 (m, 0.67H).

Step #6: 10-Bromo-1-(4-fluorophenyl)-6,6-dimethoxy-5,6,7,8-tetrahydro-1H-oxepino[3,2-f]indazole-5-carbonitrile (101, R¹=4-Fluorophenyl)

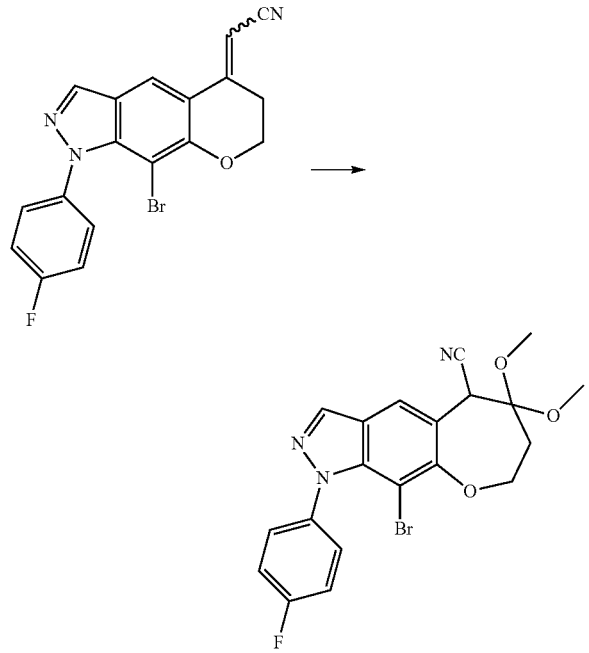

Silver(I) nitrate (7.67 g, 45.1 mmol) was added to a solution of 2-(9-bromo-1-(4-fluorophenyl)-6,7-dihydropyrano[3,2-f]indazol-5(1H)-ylidene)acetonitrile (100, R¹=4-Fluorophenyl) (6.67 g, 17.4 mmol) and 1,4-dioxane (60.0 mL). MeOH (150 mL) was added. The mixture was warmed to reflux. A solution of iodine (5.74 g, 22.6 mmol) and MeOH (22.6 mL) was added over about 20 min. After about 16 h, the mixture was allowed to cool to rt. The volatiles were removed under reduced pressure. The residue was slurried in DCM (200 mL) then filtered rinsing with 10% EtOAc/DCM (6×50 mL). The volatiles were removed under reduced pressure. The residue was purified on silica gel (220 g) using a gradient of 0-50% EtOAc in DCM. The fractions containing the product and intermediate were combined and concentrated under reduced pressure. The material was dissolved in 1,4-dioxane (30 mL). Silver(I) nitrate (2.95 g, 17.4 mmol) was added. MeOH (75 mL) was added and the mixture was warmed to reflux for about 14 h. The mixture was allowed to cool to rt then the volatiles were removed under reduced pressure. The residue was slurried in DCM (100 mL) then filtered rinsing with 10% EtOAc/DCM (4×25 mL). The organics were concentrated under reduced pressure. The residue was dissolved in DCM (100 mL) then washed with water (2×100 mL). The aqueous layers were extracted with DCM (25 mL) then dried over Na₂SO₄, filtered and concentrated under reduced pressure to afford 10-bromo-1-(4-fluorophenyl)-6,6-dimethoxy-5,6,7,8-tetrahydro-1H-oxepino[3,2-f]indazole-5-carbonitrile (101, R¹=4-Fluorophenyl) (5.75 g, 74% yield) as an orange solid. LC/MS, method 3, R$_f$=2.45 min, MS m/z 446 and 448 (M+H)⁺. ¹H NMR (400 MHz, DMSO) δ 8.40 (s, 1H), 8.06 (s, 1H), 7.64-7.55 (m, 2H), 7.42-7.31 (m, 2H), 5.04 (d, J=1.8 Hz, 1H), 4.51-4.38 (m, 1H), 3.70-3.58 (m, 1H), 3.29 (s, 3H), 3.10 (s, 3H), 2.53-2.40 (m, 1H), 2.30-2.21 (m, 1H).

Step #7: 10-Bromo-1-(4-fluorophenyl)-6-hydroxy-7,8-dihydro-1H-oxepino[3,2-f]indazole-5-carbonitrile (102, R¹=4-Fluorophenyl)

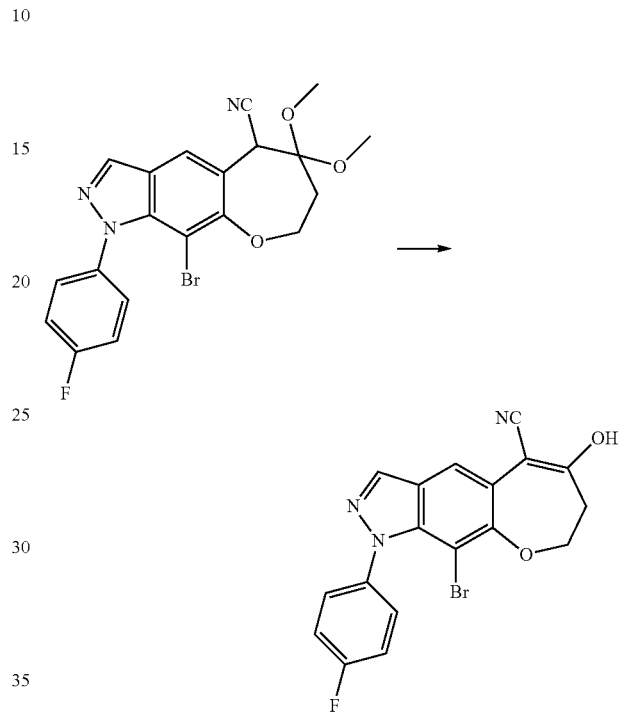

HCl (2 M aqueous solution, 18.0 mL, 36.0 mmol) was added to a solution of 10-bromo-1-(4-fluorophenyl)-6,6-dimethoxy-5,6,7,8-tetrahydro-1H-oxepino[3,2-f]indazole-5-carbonitrile (6.32 g, 14.2 mmol) and 1,4-dioxane (75 mL) under air. The reaction was vigorously stirred and warmed to about 70° C. After about 88 h, the reaction was allowed to cool to rt and then partially concentrated under reduced pressure to about 40 mL. Et₂O (60 mL) was added. After stirring for about 4 h, the solid was collected by filtration rinsing with Et₂O (10 mL) and dried under reduced pressure to afford 10-bromo-1-(4-fluorophenyl)-6-hydroxy-7,8-dihydro-M-oxepino[3,2-f]indazole-5-carbonitrile (102, R¹=4-Fluorophenyl) (2.07 g, 37% yield) as a tan solid. The organic volatiles were evaporated under reduced pressure. 1,4-Dioxane (50 mL) and HCl (2 M aqueous solution, 10.0 mL, 20.0 mmol) were added. The solution was warmed to about 70° C. After about 20 h, the solution was allowed to cool to rt and EtOAc (50 mL) was added. The layers were separated and the organics were washed with sat. aq. NaCl (25 mL). The aqueous layers were extracted with EtOAc (20 mL). The combined organics were dried over Na₂SO₄, filtered, and concentrated under reduced pressure. The residue was slurried in DCM (10 mL). The solid was collected by filtration rinsing with DCM (5 mL) then dried to afford 10-bromo-1-(4-fluorophenyl)-6-hydroxy-7,8-dihydro-M-oxepino[3,2-f]indazole-5-carbonitrile (102, R¹=4-Fluorophenyl) (1.19 g, 21% yield) as a tan solid. LC/MS, method 3, R$_f$=2.05 min, MS m/z 400 and 402 (M+H)⁺. ¹H NMR (400 MHz, DMSO) δ 11.65

(s, 1H), 8.40 (s, 1H), 7.93 (s, 1H), 7.64-7.48 (m, 2H), 7.45-7.25 (m, 2H), 4.30 (t, J=5.8 Hz, 2H), 2.92 (t, J=5.8 Hz, 2H).

Step #8: 8-Bromo-9-(4-fluorophenyl)-3-oxo-2,3,5,6,9,12b-hexahydro-1H-benzo[4,5]oxepino[3,2-f]indazole-12b-carbonitrile (103, R¹=4-Fluorophenyl)

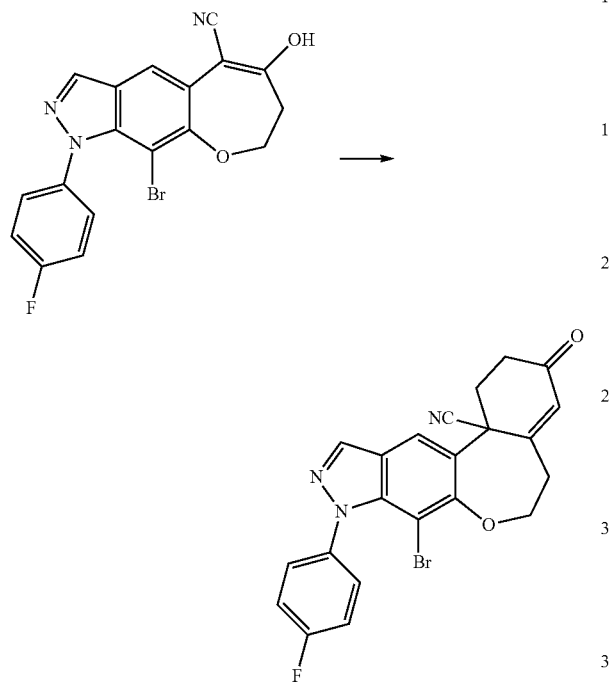

TEA (0.300 mL, 2.152 mmol) was added to a slurry of 10-bromo-1-(4-fluorophenyl)-6-hydroxy-7,8-dihydro-1H-oxepino[3,2-f]indazole-5-carbonitrile (102, R¹=4-Fluorophenyl) (3.15 g, 7.87 mmol) in DME (40.0 mL) under a nitrogen atmosphere. Methyl vinyl ketone (1.30 mL, 15.8 mmol) was added dropwise. After about 47 h, the volatiles were removed under reduced pressure to afford 10-bromo-1-(4-fluorophenyl)-6-oxo-5-(3-oxobutyl)-5,6,7,8-tetrahydro-1H-oxepino[3,2-f]indazole-5-carbonitrile as a tan foam. LC/MS, method 3, R$_f$=2.33 min, MS m/z 470 and 472 (M+H)⁺. The material was dissolved in toluene (80 mL) in a 250 mL round bottom with Dean-Stark trap and reflux condenser attached under a nitrogen atmosphere. Toluene-4-sulfonic acid hydrate (0.599 g, 3.15 mmol) was added. After about 3 h at reflux, the mixture was allowed to cool to rt. Sat. aq. NaHCO₃ (100 mL) was added.

The layers were separated and the aqueous layer was extracted with EtOAc (2×50 mL). The combined organics were dried over Na₂SO₄, filtered, and concentrated under reduced pressure. The residue was purified on silica gel (120 g) using a gradient of 0-6% EtOAc in DCM. The fractions containing the product were combined and concentrated under reduced pressure to afford 8-bromo-9-(4-fluorophenyl)-3-oxo-2,3,5,6,9,12b-hexahydro-1H-benzo[4,5]oxepino[3,2-f]indazole-12b-carbonitrile (103, R¹=4-Fluorophenyl) (2.02 g, 57% yield). LC/MS, method 3, R$_f$=2.27 min, MS m/z 452 and 454 (M+H)⁺. ¹H NMR (400 MHz, DMSO) δ 8.48 (s, 1H), 8.18 (s, 1H), 7.63-7.56 (m, 2H), 7.42-7.34 (m, 2H), 6.22 (s, 1H), 4.35-4.26 (m, 1H), 4.22-4.12 (m, 1H), 2.84-2.58 (m, 6H).

Step #9: (4aR,12bS)-8-Bromo-9-(4-fluorophenyl)-3-oxo-2,3,4,4a,5,6,9,12b-octahydro-1H-benzo[4,5]oxepino[3,2-f]indazole-12b-carbonitrile; compound with (4aS,12bR)-8-bromo-9-(4-fluorophenyl)-3-oxo-2,3,4,4a,5,6,9,12b-octahydro-1H-benzo[4,5]oxepino[3,2-f]indazole-12b-carbonitrile (104, R¹=4-Fluorophenyl)

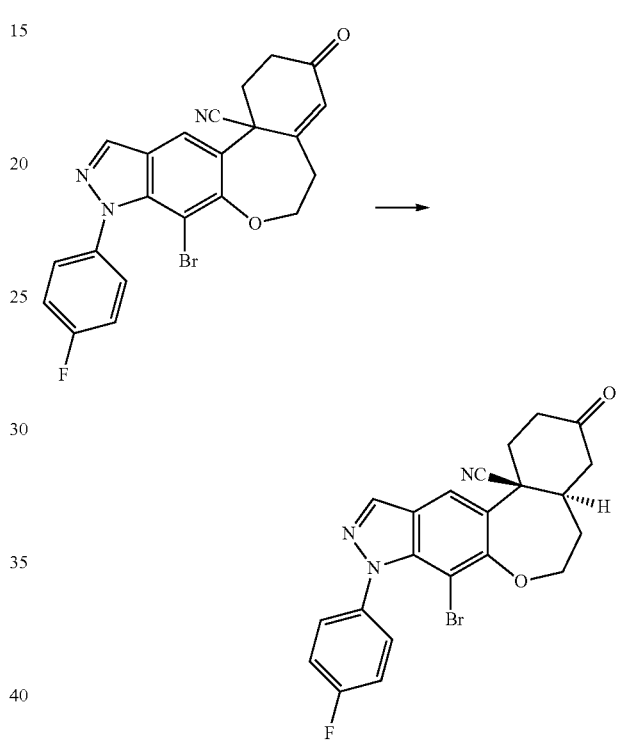

A solution of 8-bromo-9-(4-fluorophenyl)-3-oxo-2,3,5,6,9,12b-hexahydro-1H-benzo[4,5]oxepino[3,2-f]indazole-12b-carbonitrile (103, R¹=4-Fluorophenyl) (2.02 g, 4.47 mmol) and toluene (80 mL) was added to 20% palladium hydroxide on carbon (wet, Deguessa type, 0.314 g). The mixture was shaken under about 50 psi of hydrogen at about 55° C. After about 17 h, the reaction mixture was allowed to cool to rt then filtered through Celite® rinsing with 25% THF/toluene (4×50 mL) then 25% THF/DCM (6×25 mL). The volatiles were removed under reduced pressure to afford a light tan solid which was slurried in DCM (10 mL). The solid was collected by filtration rinsing with DCM (3×10 mL) then dried under reduced pressure to afford (4aR,12bS)-8-bromo-9-(4-fluorophenyl)-3-oxo-2,3,4,4a,5,6,9,12b-octahydro-1H-benzo[4,5]oxepino[3,2-f]indazole-12b-carbonitrile; compound with (4aS,12bR)-8-bromo-9-(4-fluorophenyl)-3-oxo-2,3,4,4a,5,6,9,12b-octahydro-1H-benzo[4,5]oxepino[3,2-f]indazole-12b-carbonitrile (104, R¹=4-Fluorophenyl) (0.916 g, 45% yield) as an ivory solid. The mother liquor was concentrated under reduced pressure.

The residue was dissolved in toluene (20 mL) then added to 20% palladium hydroxide on carbon (wet, Deguessa type, 0.160 g). The mixture was shaken under about 50 psi of hydrogen at about 55° C. for about 15 h. The reaction mixture was allowed to cool to rt then filtered through Celite® rinsing with 20% THF/DCM 5×30 mL). The volatiles were removed under reduced pressure. The material was slurried in DCM (5 mL). The solid was collected by filtration rinsing with DCM (3×1 mL) then dried under reduced pressure to afford (4aR, 12bS)-8-bromo-9-(4-fluorophenyl)-3-oxo-2,3,4,4a,5,6,9, 12b-octahydro-1H-benzo[4,5]oxepino[3,2-f]indazole-12b-carbonitrile; compound with (4aS,12bR)-8-bromo-9-(4-fluorophenyl)-3-oxo-2,3,4,4a,5,6,9,12b-octahydro-1H-benzo[4,5]oxepino[3,2-f]indazole-12b-carbonitrile (104, $R^1$=4-Fluorophenyl) (0.684 g, 34% yield) as an ivory solid. LC/MS, method 3, $R_t$=2.24 min, MS m/z 512 and 514 (M+AcO⁻)⁻. ¹H NMR (400 MHz, DMSO) δ 8.40 (s, 1H), 8.05 (s, 1H), 7.64-7.53 (m, 2H), 7.43-7.31 (m, 2H), 4.57-4.48 (m, 1H), 3.56-3.46 (m, 1H), 2.83-2.69 (m, 3H), 2.54-2.16 (m, 5H), 1.96-1.87 (m, 1H).

Step #10: (3R,4aR,12bS)-8-Bromo-9-(4-fluorophenyl)-3-hydroxy-3-(trifluoromethyl)-2,3,4,4a,5,6,9,12b-octahydro-1H-benzo[4,5]oxepino[3,2-f]indazole-12b-carbonitrile; compound with (3S,4aS,12bR)-8-bromo-9-(4-fluorophenyl)-3-hydroxy-3-(trifluoromethyl)-2,3,4,4a,5,6,9,12b-octahydro-1H-benzo[4,5]oxepino[3,2-f]indazole-12b-carbonitrile (105, $R^1$=4-Fluorophenyl, $R^3$=Trifluoromethyl)

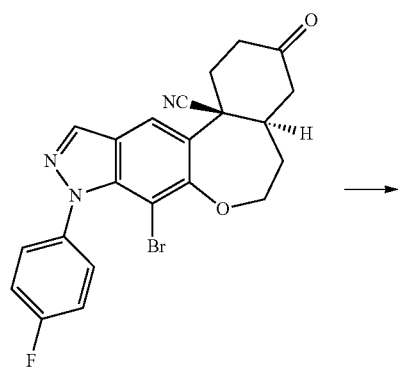

dro-1H-benzo[4,5]oxepino[3,2-f]indazole-12b-carbonitrile; compound with (4aS,12bR)-8-bromo-9-(4-fluorophenyl)-3-oxo-2,3,4,4a,5,6,9,12b-octahydro-1H-benzo[4,5]oxepino[3,2-f]indazole-12b-carbonitrile (104, $R^1$=4-Fluorophenyl) and CsF (0.060 g, 0.40 mmol) under a nitrogen atmosphere. After about 15 min, the reaction mixture was cooled to about 0° C. (Trifluoromethyl)trimethylsilane (0.720 mL, 4.87 mmol) was added dropwise over about 5 min. After about 2 h, (trifluoromethyl)trimethylsilane (0.250 mL, 1.69 mmol) was added dropwise. After about 2 h, the volatiles were removed under reduced pressure. The residue was dissolved in THF (40.0 mL). TBAF (1 M solution in THF, 5.00 mL, 5.00 mmol) was added. After about 1 h, the solution was diluted with EtOAc (100 mL) and water (50 mL). The layers were separated and the organic layer was washed with aq. NaCl (50 mL) then dried over $Na_2SO_4$, filtered and concentrated under reduced pressure. DCM (5 mL) was added and the solid was collected by filtration rinsing with DCM (2×2 mL) and dried under reduced pressure to afford (3R,4aR,12bS)-8-bromo-9-(4-fluorophenyl)-3-hydroxy-3-(trifluoromethyl)-2,3,4,4a,5,6,9,12b-octahydro-1H-benzo[4,5]oxepino[3,2-f]indazole-12b-carbonitrile; compound with (3S,4aS,12bR)-8-bromo-9-(4-fluorophenyl)-3-hydroxy-3-(trifluoromethyl)-2,3,4,4a,5,6,9,12b-octahydro-1H-benzo[4,5]oxepino[3,2-f]indazole-12b-carbonitrile (105, $R^1$=4-Fluorophenyl, $R^3$=Trifluoromethyl) (1.35 g, 68% yield) as an ivory solid. LC/MS, method 3, $R_t$=2.36 min, MS m/z 524 and 526 (M+H)⁺. ¹H NMR (400 MHz, DMSO) δ 8.36 (s, 1H), 8.09 (s, 1H), 7.62-7.53 (m, 2H), 7.42-7.32 (m, 2H), 6.30 (s, 1H), 4.54-4.43 (m, 1H), 3.59-3.47 (m, 1H), 2.57-2.40 (m, 2H), 2.41-2.29 (m, 1H), 2.25-2.03 (m, 2H), 2.01-1.83 (m, 3H), 1.63-1.51 (m, 1H).

Step #11: (3R,4aR,12bS)-8-Bromo-9-(4-fluorophenyl)-3-(trifluoromethyl)-1,2,3,4,4a,5,6,9-octahydro-3,12b-(epoxymethano)benzo[4,5]oxepino[3,2-f]indazol-13-ol; compound with (3S,4aS,12bR)-8-bromo-9-(4-fluorophenyl)-3-(trifluoromethyl)-1,2,3,4,4a,5,6,9-octahydro-3,12b-(epoxymethano)benzo[4,5]oxepino[3,2-f]indazol-13-ol (106, $R^1$=4-Fluorophenyl, $R^3$=Trifluoromethyl)

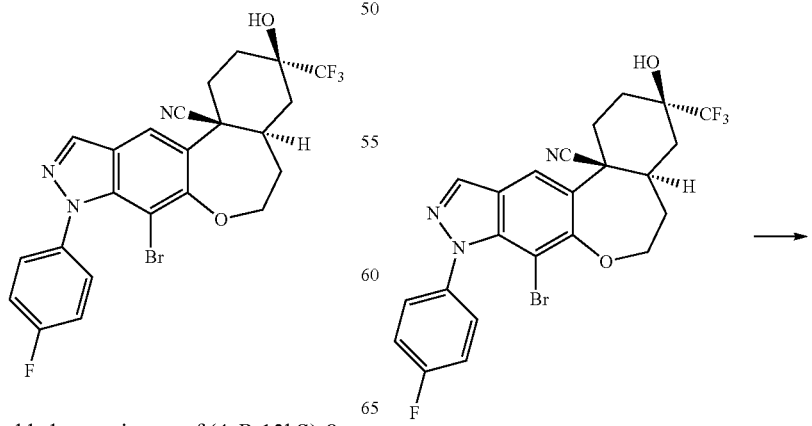

DME (40.0 mL) was added to a mixture of (4aR,12bS)-8-bromo-9-(4-fluorophenyl)-3-oxo-2,3,4,4a,5,6,9,12b-octahy-

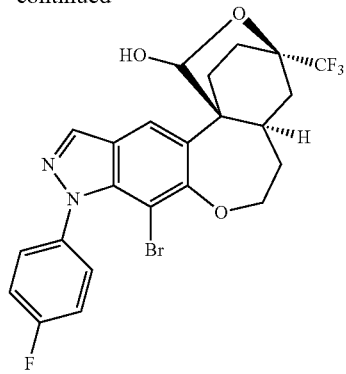

DIBAL-H (1.0 M solution in toluene, 5.40 mL, 5.40 mmol) was added dropwise over about min to a slurry of (3R,4aR,12bS)-8-bromo-9-(4-fluorophenyl)-3-hydroxy-3-(trifluoromethyl)-2,3,4,4a,5,6,9,12b-octahydro-1H-benzo[4,5]oxepino[3,2-f]indazole-12b-carbonitrile; compound with (3S,4aS,12bR)-8-bromo-9-(4-fluorophenyl)-3-hydroxy-3-(trifluoromethyl)-2,3,4,4a,5,6,9,12b-octahydro-1H-benzo[4,5]oxepino[3,2-f]indazole-12b-carbonitrile (105, R¹=4-Fluorophenyl, R³=Trifluoromethyl) (0.568 g, 1.08 mmol) in toluene (15.0 mL) at about 0° C. under a nitrogen atmosphere. After about 30 min, the resulting solution was cooled to about −40° C. Acetic acid (0.400 mL, 6.99 mmol) was added dropwise. After about 5 min, the reaction mixture was returned to about 0° C. After about 15 min, 2 M aq. HCl (20 mL) and THF (10 mL) were added. The mixture was left to vigorously stir for about 4 h. EtOAc (20 mL) was added. The layers were separated and the aqueous layer was extracted with 10% THF/EtOAc (10 mL). The combined organics were dried over Na₂SO₄, filtered, and concentrated under reduced pressure. DCM (5 mL) was added. The solid was collected by filtration rinsing with DCM (2×2 mL) and then dried under reduced pressure to afford (3R,4aR,12bS)-8-bromo-9-(4-fluorophenyl)-3-(trifluoromethyl)-1,2,3,4,4a,5,6,9-octahydro-3,12b-(epoxymethano)benzo[4,5]oxepino[3,2-f]indazol-13-ol; compound with (3S,4aS,12bR)-8-bromo-9-(4-fluorophenyl)-3-(trifluoromethyl)-1,2,3,4,4a,5,6,9-octahydro-3,12b-(epoxymethano)benzo[4,5]oxepino[3,2-f]indazol-13-ol (106, R¹=4-Fluorophenyl, R³=Trifluoromethyl) (0.270 g, 47% yield) as an ivory solid. Silica gel (2.5 g) was added to the mother liquor and the organic volatiles were removed under reduced pressure. The residue was purified on silica gel (24 g) using a gradient of 0-7% EtOAc in DCM. The fractions containing the product were combined and concentrated under reduced pressure to afford (3R,4aR,12bS)-8-bromo-9-(4-fluorophenyl)-3-(trifluoromethyl)-1,2,3,4,4a,5,6,9-octahydro-3,12b-(epoxymethano)benzo[4,5]oxepino[3,2-f]indazol-13-ol; compound with (3S,4aS,12bR)-8-bromo-9-(4-fluorophenyl)-3-(trifluoromethyl)-1,2,3,4,4a,5,6,9-octahydro-3,12b-(epoxymethano)benzo[4,5]oxepino[3,2-f]indazol-13-ol (106, R¹=4-Fluorophenyl, R³=Trifluoromethyl) (0.161 g, 24% yield) as an ivory solid. LC/MS, method 3, R$_t$=2.59 min, MS m/z 527 and 529 (M+H)⁺. ¹H NMR (400 MHz, DMSO) δ 8.32 (s, 1H), 7.84 (s, 1H), 7.60-7.48 (m, 2H), 7.42-7.29 (m, 2H), 6.68 (d, J=4.6 Hz, 1H), 5.98 (d, J=4.6 Hz, 1H), 4.47-4.35 (m, 1H), 3.45-3.34 (m, 1H), 2.71-2.58 (m, 1H), 2.40-2.24 (m, 1H), 2.24-1.96 (m, 3H), 1.96-1.74 (m, 3H), 1.50-1.41 (m, 1H).

Step #12: (3R,4aR,12bS)-8-Bromo-9-(4-fluorophenyl)-3-(trifluoromethyl)-12b-vinyl-2,3,4,4a,5,6,9,12b-octahydro-1H-benzo[4,5]oxepino[3,2-f]indazol-3-ol; compound with (3S,4aS,12bR)-8-bromo-9-(4-fluorophenyl)-3-(trifluoromethyl)-12b-vinyl-2,3,4,4a,5,6,9,12b-octahydro-1H-benzo[4,5]oxepino[3,2-f]indazol-3-ol (107, R¹=4-Fluorophenyl, R²=Vinyl, R³=Trifluoromethyl)

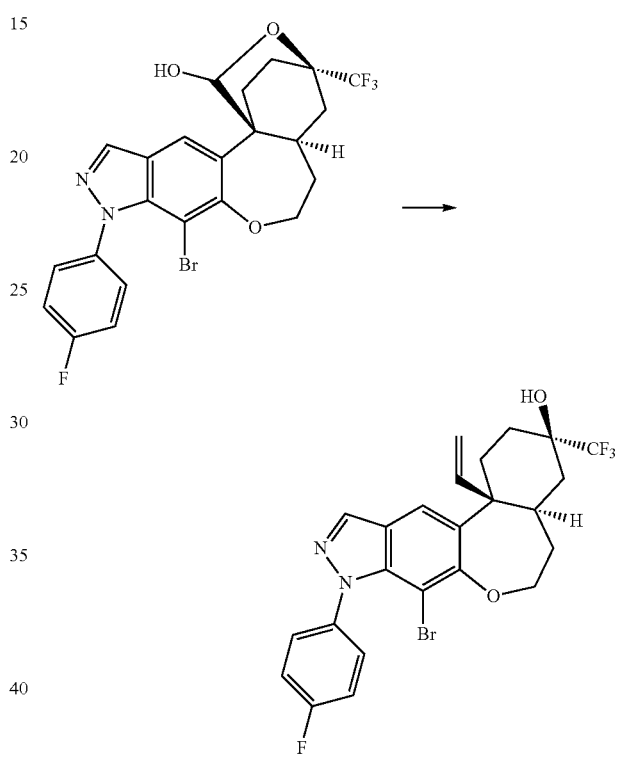

n-BuLi (1.6 M solution in hexanes, 2.90 mL, 4.64 mmol) was added dropwise to a slurry of methyltriphenylphosphonium bromide (1.70 g, 4.76 mmol) in THF (10.0 mL) at about 0° C. under a nitrogen atmosphere. After about 30 min, a solution of (3R,4aR,12bS)-8-bromo-9-(4-fluorophenyl)-3-(trifluoromethyl)-1,2,3,4,4a,5,6,9-octahydro-3,12b-(epoxymethano)benzo[4,5]oxepino[3,2-f]indazole-13-ol; compound with (3S,4aS,12bR)-8-bromo-9-(4-fluorophenyl)-3-(trifluoromethyl)-1,2,3,4,4a,5,6,9-octahydro-3,12b-(epoxymethano)benzo[4,5]oxepino[3,2-f]indazol-13-ol (106, R¹=4-Fluorophenyl, R³=Trifluoromethyl) (0.459 g, 0.871 mmol) and THF (10.0 mL) was added dropwise. After about 30 min, the ice bath was removed. After 3 h at rt, water (50 mL) and EtOAc (50 mL) were added. The layers were separated and the organics were dried over Na₂SO₄, filtered, and concentrated under reduced pressure. The residue was purified on silica gel (40 g) using a gradient of 0-5% EtOAc in DCM. The fractions containing the product were combined and concentrated under reduced pressure to afford (3R,4aR,12bS)-8-bromo-9-(4-fluorophenyl)-3-(trifluoromethyl)-12b-vinyl-2,3,4,4a,5,6,9,12b-octahydro-1H-benzo[4,5]oxepino[3,2-f]indazol-3-ol; compound with (3S,4aS,12bR)-8-bromo-9-(4-fluorophenyl)-3-(trifluoromethyl)-12b-vinyl-2, 3,4,4a,5,6,9,12b-octahydro-1H-benzo[4,5]oxepino[3,2-f]indazol-3-ol (107, $R^1$=4-Fluorophenyl, $R^2$=Vinyl, $R^3$=Trifluoromethyl) (0.443 g, 97% yield) as an ivory solid. LC/MS, method 3, $R_t$=2.63 min, MS m/z 525 and 527 $(M+H)^+$. $^1H$ NMR (400 MHz, DMSO) δ 8.30 (s, 1H), 7.95 (s, 1H), 7.58-7.50 (m, 2H), 7.39-7.29 (m, 2H), 6.62 (dd, J=17.4, 10.8 Hz, 1H), 5.98 (s, 1H), 5.08 (dd, J=10.8, 1.3 Hz, 1H), 4.64 (dd, J=17.4, 1.3 Hz, 1H), 4.41-4.32 (m, 1H), 3.54-3.43 (m, 1H), 2.31-2.04 (m, 4H), 2.01-1.58 (m, 5H).

Step #13: (3R,4aR,12bR)-8-Bromo-12b-ethyl-9-(4-fluorophenyl)-3-(trifluoromethyl)-2,3,4,4a,5,6,9,12b-octahydro-1H-benzo[4,5]oxepino[3,2-f]indazole-3-ol; compound with (3S,4aS,12bS)-8-bromo-12b-ethyl-9-(4-fluorophenyl)-3-(trifluoromethyl)-2,3,4,4a,5,6,9,12b-octahydro-1H-benzo[4,5]oxepino[3,2-f]indazol-3-ol (108, $R^1$=4-Fluorophenyl, $R^2$=Ethyl, $R^3$=Trifluoromethyl)

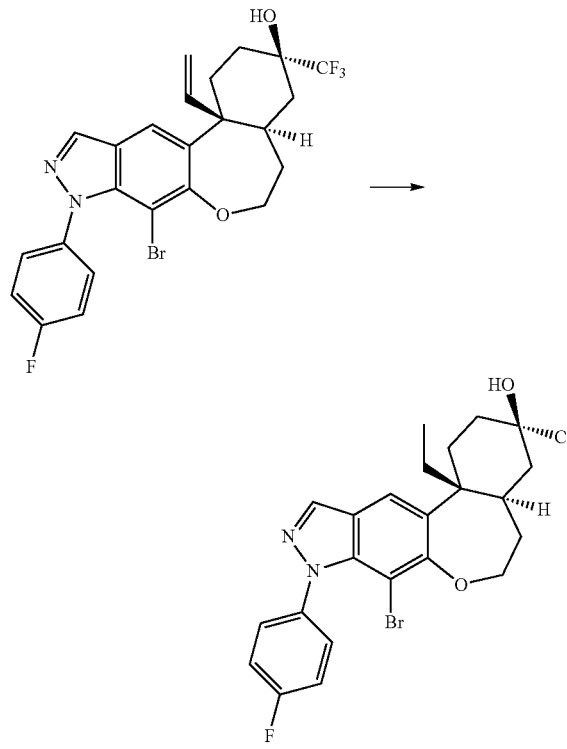

To 10% Pd/C (wet, 0.162 g) was added a solution of (3R,4aR,12bS)-8-bromo-9-(4-fluorophenyl)-3-(trifluoromethyl)-12b-vinyl-2,3,4,4a,5,6,9,12b-octahydro-1H-benzo[4,5]oxepino[3,2-f]indazol-3-ol; compound with (3S,4aS,12bR)-8-bromo-9-(4-fluorophenyl)-3-(trifluoromethyl)-12b-vinyl-2,3,4,4a,5,6,9,12b-octahydro-1H-benzo[4,5]oxepino[3,2-f]indazol-3-ol (107, $R^1$=4-Fluorophenyl, $R^2$=Vinyl, $R^3$=Trifluoromethyl) (0.443 g, 0.843 mmol) and THF (8.0 mL). The mixture was placed under an hydrogen atmosphere using a balloon. After about 4 h, the hydrogen atmosphere was evacuated and the mixture was filtered through Celite® rinsing with THF (50 mL). The volatiles were removed under reduced pressure. The residue was purified on silica gel (24 g) using a gradient of 0-5% EtOAc in DCM. The fractions containing the product were combined and concentrated under reduced pressure to afford (3R,4aR,12bR)-8-bromo-12b-ethyl-9-(4-fluorophenyl)-3-(trifluoromethyl)-2,3,4,4a,5,6,9,12b-octahydro-1H-benzo[4,5]oxepino[3,2-f]indazol-3-ol; compound with (3S,4aS,12bS)-8-bromo-12b-ethyl-9-(4-fluorophenyl)-3-(trifluoromethyl)-2,3,4,4a,5,6,9,12b-octahydro-1H-benzo[4,5]oxepino[3,2-f]indazol-3-ol (108, $R^1$=4-Fluorophenyl, $R^2$=Ethyl, $R^3$=Trifluoromethyl) (0.410 g, 92% yield) as an ivory solid. LC/MS, method 3, $R_t$=2.63 min, MS m/z 527 and 529 $(M+H)^+$. $^1H$ NMR (400 MHz, DMSO) δ 8.29 (s, 1H), 7.81 (s, 1H), 7.58-7.51 (m, 2H), 7.39-7.29 (m, 2H), 5.92 (s, 1H), 4.47-4.38 (m, 1H), 3.48-3.38 (m, 1H), 2.41-2.28 (m, 1H), 2.25-1.51 (m, 10H), 0.41 (t, J=7.3 Hz, 3H).

Step #14: Example #146 and #147: (3R,4aR,12bR)-12b-Ethyl-9-(4-fluorophenyl)-3-(trifluoromethyl)-2,3,4,4a,5,6,9,12b-octahydro-1H-benzo[4,5]oxepino[3,2-f]indazol-3-ol (109, $R^1$=4-Fluorophenyl, $R^2$=Ethyl, $R^3$=Trifluoromethyl) and (3S,4aS,12bS)-12b-ethyl-9-(4-fluorophenyl)-3-(trifluoromethyl)-2,3,4,4a,5,6,9,12b-octahydro-1H-benzo[4,5]oxepino[3,2-f]indazol-3-ol (109, $R^1$=4-Fluorophenyl, $R^2$=Ethyl, $R^3$=Trifluoromethyl)

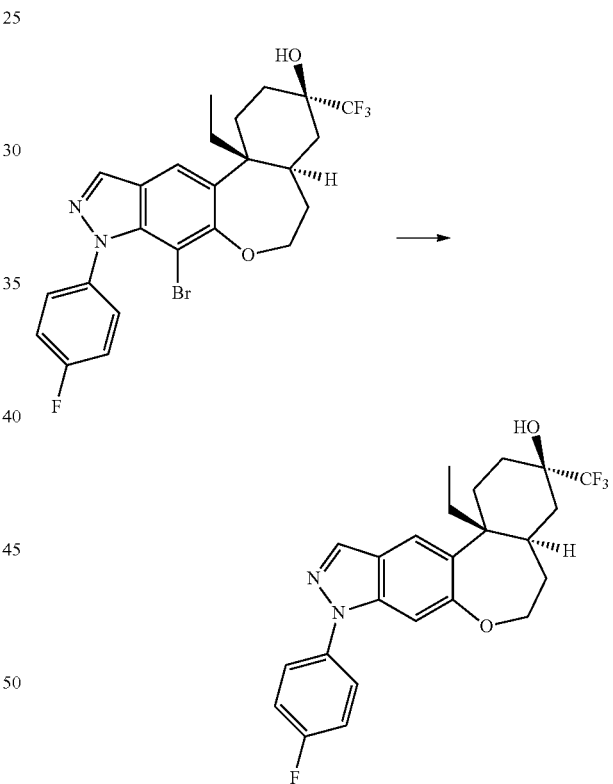

n-BuLi (1.6 M solution in hexanes, 0.900 mL, 1.440 mmol) was added dropwise to a solution of 3R,4aR,12bR)-8-bromo-12b-ethyl-9-(4-fluorophenyl)-3-(trifluoromethyl)-2,3,4,4a,5,6,9,12b-octahydro-1H-benzo[4,5]oxepino[3,2-f]indazol-3-ol; compound with 3S,4aS,12bS)-8-bromo-12b-ethyl-9-(4-fluorophenyl)-3-(trifluoromethyl)-2,3,4,4a,5,6,9,12b-octahydro-1H-benzo[4,5]oxepino[3,2-f]indazol-3-ol (108, $R^1$=4-Fluorophenyl, $R^2$=Ethyl, $R^3$=Trifluoromethyl) (0.364 g, 0.690 mmol) and THF (10.0 mL) under a nitrogen atmosphere at about −78° C. After about 45 min, n-BuLi (1.6 M solution in hexanes, 0.100 mL, 0.160 mmol) was added dropwise over about 2 min. After about 30 min, MeOH (0.4 mL)

was added dropwise. The cold bath was removed. Sat. aq. NH₄Cl (20 mL), water (5 mL) and EtOAc (20 mL) were added. The layers were separated and the organics were dried over Na₂SO₄, filtered and concentrated under reduced pressure. The residue was purified on silica gel (40 g) using a gradient of 0-2% EtOAc in DCM. The fractions containing the product were combined and concentrated under reduced pressure to afford (3R,4aR,12bR)-12b-ethyl-9-(4-fluorophenyl)-3-(trifluoromethyl)-2,3,4,4a,5,6,9,12b-octahydro-1H-benzo[4,5]oxepino[3,2-f]indazol-3-ol; compound with (3S,4aS,12bS)-12b-ethyl-9-(4-fluorophenyl)-3-(trifluoromethyl)-2,3,4,4a,5,6,9,12b-octahydro-1H-benzo[4,5]oxepino[3,2-f]indazol-3-ol (109, R¹=4-Fluorophenyl, R²=Ethyl, R³=Trifluoromethyl) (0.273 g, 88% yield) of an ivory solid. LC/MS, method 2, $R_t$=2.77 min, MS m/z 449 (M+H)⁺. ¹H NMR (400 MHz, DMSO) δ 8.27 (d, J=1.0 Hz, 1H), 7.82-7.74 (m, 3H), 7.44-7.36 (m, 2H), 7.31 (d, J=0.9 Hz, 1H), 5.91 (s, 1H), 4.45-4.34 (m, 1H), 3.60-3.47 (m, 1H), 2.40-2.25 (m, 1H), 2.23-1.49 (m, 10H), 0.38 (t, J=7.4 Hz, 3H).

The enantiomers were separated using Preparative Chiral Purification Method 44 on the racemate (0.273 g, 0.609 mmol).

Fractions from the first peak eluted were combined and concentrated under reduced pressure. The residue was dissolved in MeCN, treated with water, and concentrated under reduced pressure to remove the organic volatiles. The mixture was frozen then lyophilized to afford (3R,4aR,12bR)-12b-ethyl-9-(4-fluorophenyl)-3-(trifluoromethyl)-2,3,4,4a,5,6,9,12b-octahydro-1H-benzo[4,5]oxepino[3,2-f]indazol-3-ol Example 146, (109, R¹=4-Fluorophenyl, R²=Ethyl, R³=Trifluoromethyl) (0.117 g, 43% yield) as an ivory solid. Sign of rotation is negative. LC/MS, method 2, $R_t$=2.77 min, MS m/z 449 (M+H)⁺. ¹H NMR (400 MHz, DMSO) δ 8.27 (d, J=1.0 Hz, 1H), 7.82-7.74 (m, 3H), 7.44-7.36 (m, 2H), 7.31 (d, J=0.9 Hz, 1H), 5.91 (s, 1H), 4.45-4.34 (m, 1H), 3.60-3.47 (m, 1H), 2.40-2.25 (m, 1H), 2.23-1.49 (m, 10H), 0.38 (t, J=7.4 Hz, 3H).

Fractions from the second peak eluted were combined and concentrated under reduced pressure. The residue was dissolved in MeCN, treated with water, and concentrated under reduced pressure to remove MeOH. The mixture was frozen then lyophilized to afford (3S,4aS,12bS)-12b-ethyl-9-(4-fluorophenyl)-3-(trifluoromethyl)-2,3,4,4a,5,6,9,12b-octahydro-1H-benzo[4,5]oxepino[3,2-f]indazol-3-ol Example 147, (109, R¹=4-Fluorophenyl, R²=Ethyl, R³=Trifluoromethyl) (0.115 g, 41% yield) as an ivory solid. Sign of rotation is positive. LC/MS, method 2, $R_t$=2.77 min, MS m/z 449 (M+H)⁺. ¹H NMR (400 MHz, DMSO) δ 8.27 (d, J=1.0 Hz, 1H), 7.82-7.74 (m, 3H), 7.44-7.36 (m, 2H), 7.31 (d, J=0.9 Hz, 1H), 5.91 (s, 1H), 4.45-4.34 (m, 1H), 3.60-3.47 (m, 1H), 2.40-2.25 (m, 1H), 2.23-1.49 (m, 10H), 0.38 (t, J=7.4 Hz, 3H).

Scheme 22:

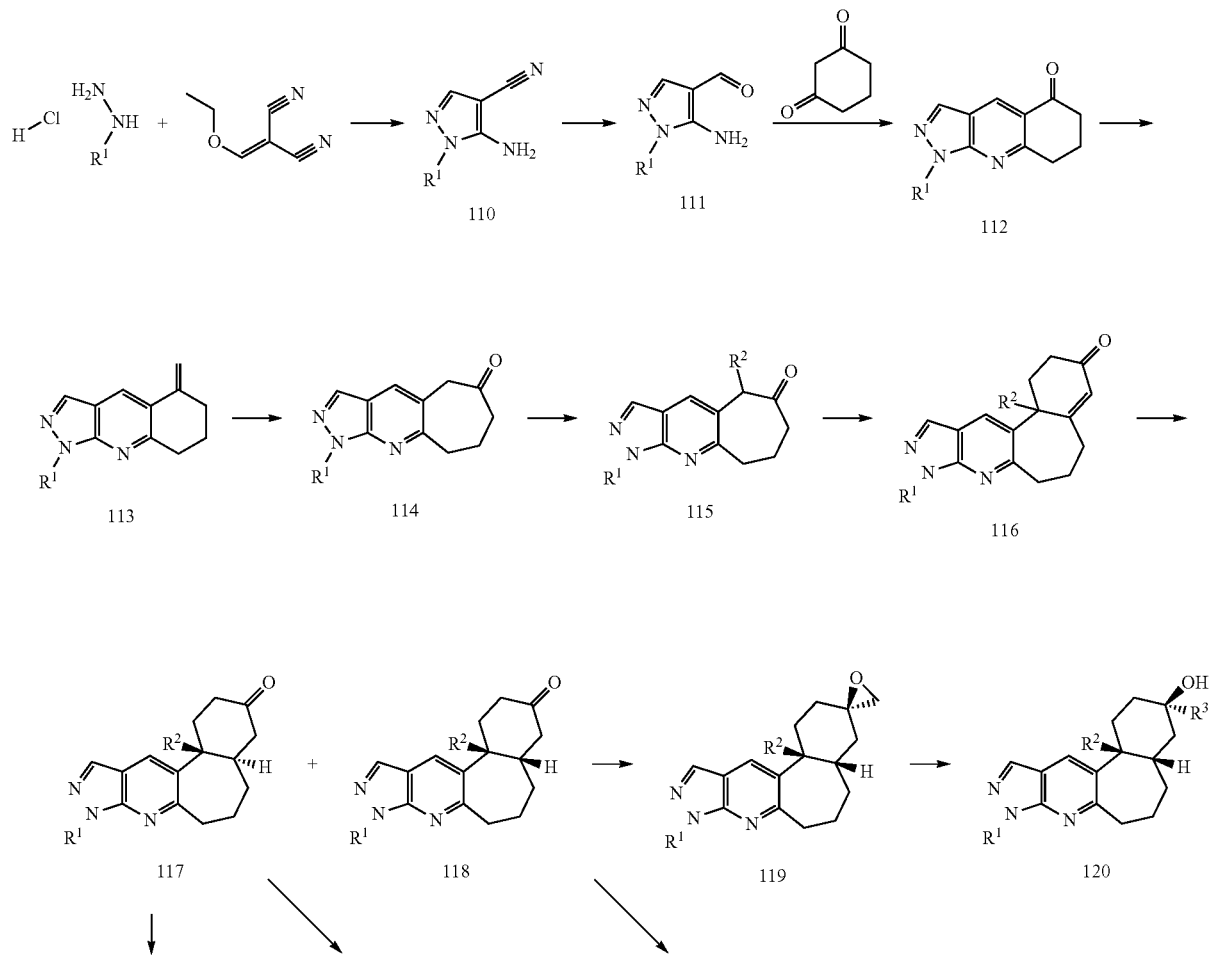

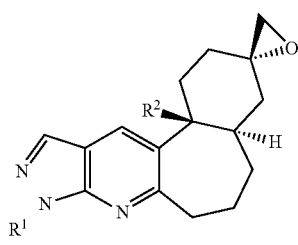
121

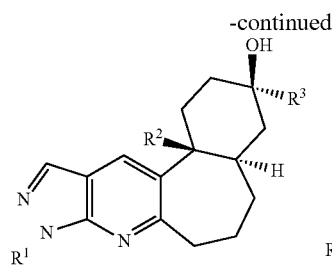
122

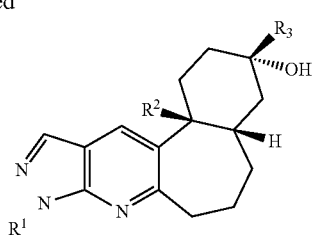
123

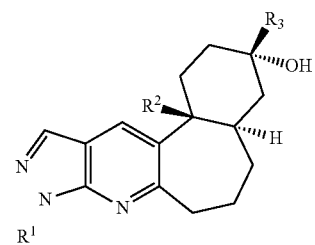
124

Example #148 rac-(3R,4aS,12bS)-9-(4-Fluorophenyl)-3-methyl-12b-(pyridin-2-ylmethyl)-1,2,3,4,4a,5,6,7,9,12b-decahydrobenzo[3,4]cyclohepta[1,2-b]pyrazolo[4,3-e]pyridin-3-ol (120, R¹=4-Fluorophenyl, R²=Pyridin-2-ylmethyl, R³=Methyl)

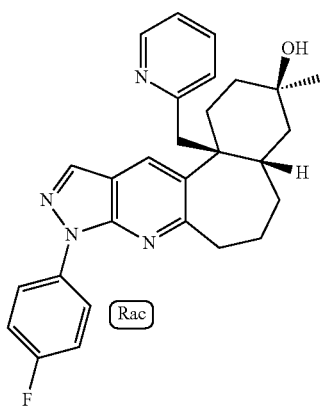 [SMILES: C[C@@]1(O)CC[C@@]2(Cc3ccccn3)c3cc4cnn(-c5ccc(F)cc5)c4nc3CCC[C@H]2C1]

Step 1: 5-Amino-1-(4-fluorophenyl)-1H-pyrazole-4-carbonitrile (110, R¹=4-Fluorophenyl)

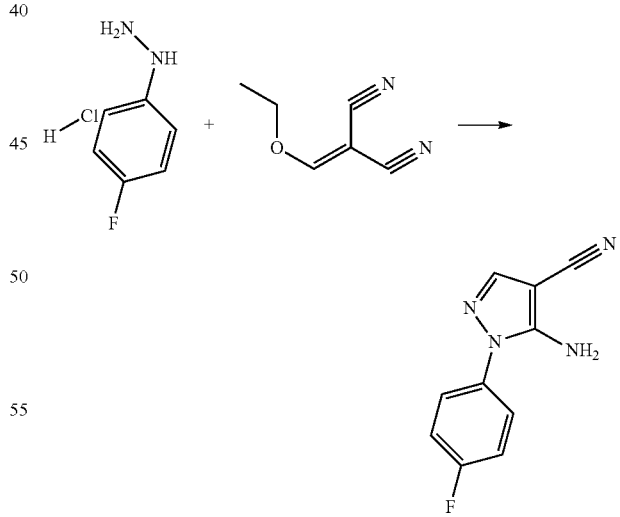

A flask was charged with (4-fluorophenyl)hydrazine hydrochloride (50.9 g, 313 mmol), EtOH (320 mL) and 2-(ethoxymethylene)malononitrile (40.1 g, 329 mmol). The stirred suspension was treated with TEA (45.8 mL, 329 mmol). After about 10 min the mixture was warmed in an oil bath heated to about 80° C. for about 1.5 h. The mixture was allowed to cool and stir overnight at rt. The solvent was removed under reduced pressure then the material was stirred with water (300 mL). After about 30 min the solids were collected by filtration, washed with water (3×100 mL) and dried under vacuum at about 65° C. to yield 5-amino-1-(4-fluorophenyl)-1H-pyrazole-4-carbonitrile (110, $R^1$=4-Fluorophenyl) (56.2 g, 89%); LC/MS, method 3, $R_t$=1.64 min, MS m/z 201 (M−H)—. $^1$H NMR (400 MHz, DMSO) δ 7.77 (s, 1H), 7.59-7.45 (m, 2H), 7.43-7.27 (m, 2H), 6.68 (s, 2H).

Step 2: 5-Amino-1-(4-fluorophenyl)-1H-pyrazole-4-carbaldehyde (111, $R^1$=4-Fluorophenyl)

5-Amino-1-(4-fluorophenyl)-1H-pyrazole-4-carbonitrile (110, $R^1$=4-Fluorophenyl) (56.2 g, 278 mmol), acetic acid (270 mL), water (75 mL) and Raney 2400 Nickel slurry in water (15 g, 278 mmol) was shaken under about 30 psi hydrogen at about 20°-25° C. for about 8 h. The mixture was filtered through a pad of Celite®. The contents of the reaction vessel were transferred with acetic acid (150 mL) and the pad was washed with an additional portion of acetic acid (200 mL). The filtrate was concentrated under reduced pressure to give a slurry. Water (300 mL) was added then the mixture was stirred for about 15 min. The mixture was cooled in an ice/water bath then basified with 5 N aq. NaOH. After stirring for about 20 min in the ice/water bath the solids were collected by filtration and washed with water (100 mL).

The material was dried under vacuum at about 70° C. to yield 5-amino-1-(4-fluorophenyl)-1H-pyrazole-4-carbaldehyde (111, $R^1$=4-Fluorophenyl) (58.15 g, 100%); LC/MS, method 3, $R_t$=1.51 min, MS m/z 206 (M+H)$^+$. $^1$H NMR (400 MHz, DMSO) δ 9.64 (s, 1H), 7.86 (s, 1H), 7.60-7.52 (m, 2H), 7.42-7.33 (m, 2H), 6.87 (s, 2H).

Step 3: 1-(4-Fluorophenyl)-7,8-dihydro-1H-pyrazolo[3,4-b]quinolin-5(6H)-one (112, $R^1$=4-Fluorophenyl)

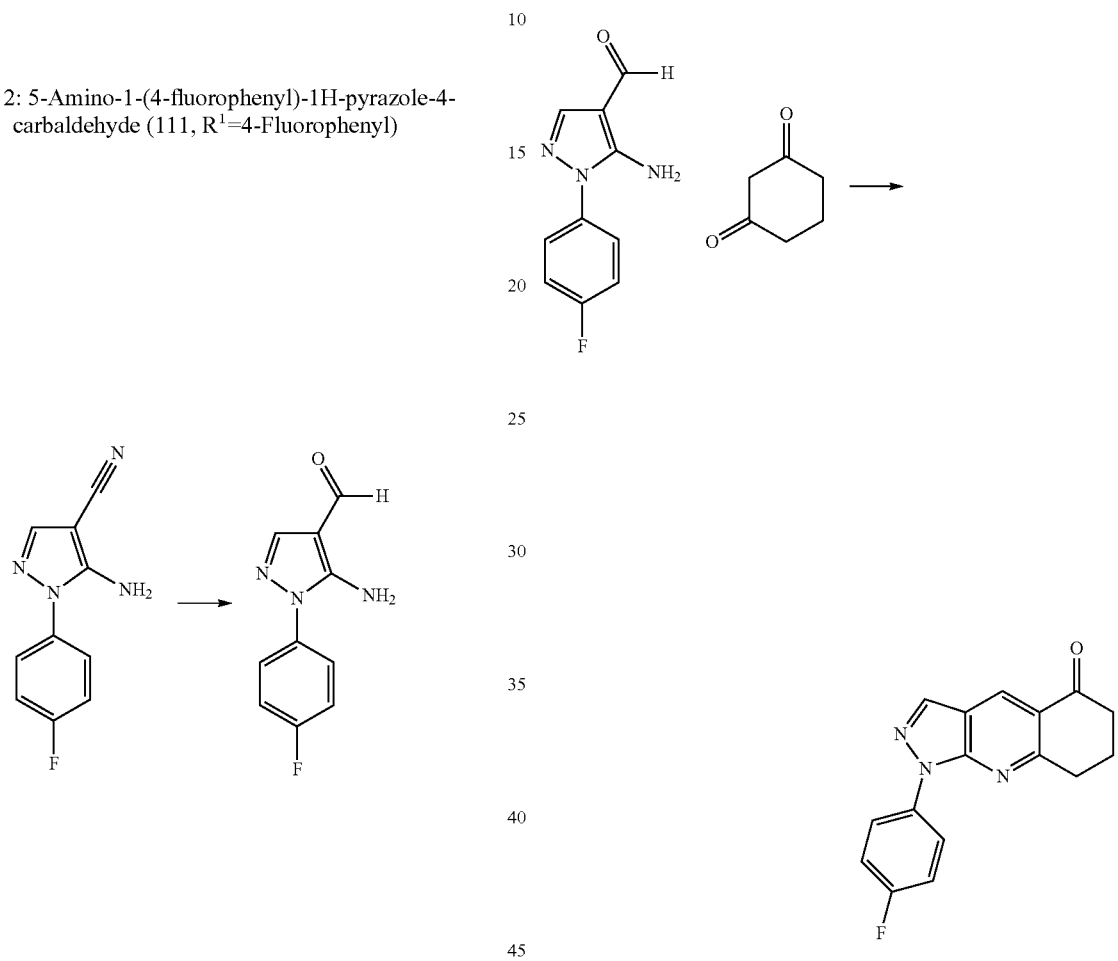

A flask was charged with 5-amino-1-(4-fluorophenyl)-1H-pyrazole-4-carbaldehyde (111, $R^1$=4-Fluorophenyl) (58.15 g, 283 mmol, cyclohexane-1,3-dione (47.7 g, 425 mmol) and toluene (600 mL). The slurry was stirred then pTSA (4.8 g, 25.2 mmol) was added. The mixture was warmed in an oil bath heated to about 100° C. for about 1 h. The mixture was allowed to cool to rt and stir overnight. The mixture was concentrated to dryness under reduced pressure. Water (400 mL), sat. aq. NaHCO$_3$ (50 mL) and ethanol (100 mL) were added to the mixture. The supernatant was decanted and the solids were triturated with water (100 mL). The supernatant was decanted and the process repeated with another portion of water (100 mL). The solids were dried under reduced pressure to remove residual water. The material was stirred with MeOH (160 mL) then the solids were collected by filtration and washed with MeOH (80 mL). The material was dried under vacuum at about 65° C. to yield 1-(4-fluorophenyl)-7,8-dihydro-1H-pyrazolo[3,4-b]quinolin-5(6H)-one (112, $R^1$=4-Fluorophenyl) (55.5 g, 70%); LC/MS, method 3, $R_t$=2.37 min, MS m/z 282 (M+H)$^+$. $^1$H NMR (400 MHz, DMSO) δ 8.82 (s, 1H), 8.56 (s, 1H), 8.32-8.23 (m, 2H), 7.51-7.39 (m, 2H), 3.22 (t, J=6.2 Hz, 2H), 2.76-2.69 (t, J=6.0 Hz, 2H), 2.20-2.11 (m, 2H).

Step 4: 1-(4-Fluorophenyl)-5-methylene-5,6,7,8-tetrahydro-1H-pyrazolo[3,4-b]quinolone (113, R¹=4-Fluorophenyl)

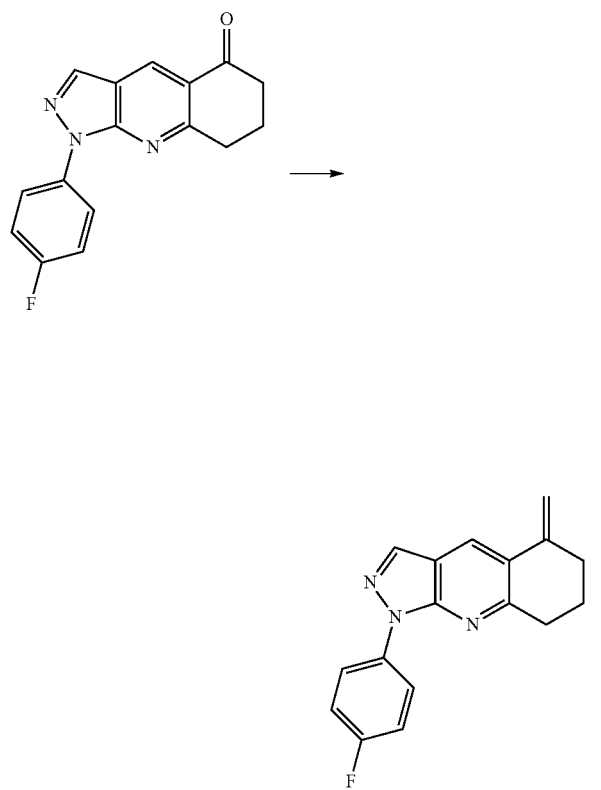

A flask was charged with potassium 2-methylpropan-2-olate (45.4 g, 404 mmol), Et₂O (1000 mL) and methyltriphenylphosphonium bromide (141 g, 395 mmol). The mixture was stirred for about 2 h at rt then 1-(4-fluorophenyl)-7,8-dihydro-1H-pyrazolo[3,4-b]quinolin-5(6H)-one (112, R¹=4-Fluorophenyl) (55.5 g, 197 mmol) was added over about 15 min. The mixture was stirred at rt for about 15 h. 1,4-Dioxane (100 mL) was added to the reaction mixture and stirring was continued for about 4 h. Solids were removed by filtration and the pad was washed with 600 mL Et₂O. The filtrate was concentrated under reduced pressure then EtOAc (250 mL) and heptane (750 mL) was added. The solids were removed by filtration then the pad was washed with 3 portions of 3:1 heptane/EtOAc (100 mL). The filtrate was concentrated under reduced pressure to yield a slurry. A mixture of 3:1 heptane/EtOAc (100 mL) was added to the material then the slurry was poured onto a pad of 600 grams of silica pre-gelled with 3:1 Heptane/EtOAc. The pad was washed with 3:1 Heptane/EtOAc (6 L) until TLC (3:1 Heptane/EtOAc, visualized by UV) showed essentially no more desired product in the filtrate. The filtrate was concentrated under reduced pressure to yield 1-(4-fluorophenyl)-5-methylene-5,6,7,8-tetrahydro-1H-pyrazolo[3,4-b]quinoline (113, R¹=4-Fluorophenyl) (44.0 g, 80%): LC/MS, method 3, R$_f$=2.87 min, MS m/z 280 (M+H)⁺. ¹H NMR (400 MHz, DMSO) δ 8.63 (s, 1H), 8.37 (s, 1H), 8.34-8.27 (m, 2H), 7.45-7.38 (m, 2H), 5.67 (d, J=0.8 Hz, 1H), 5.09 (d, J=0.9 Hz, 1H), 3.10 (t, J=6.4 Hz, 2H), 2.63-2.56 (m, 2H), 1.97-1.87 (m, 2H).

Step 5: 1-(4-Fluorophenyl)-5,7,8,9-tetrahydrocyclohepta[b]pyrazolo[4,3-e]pyridin-6(1H)-one (114, R¹=4-Fluorophenyl)

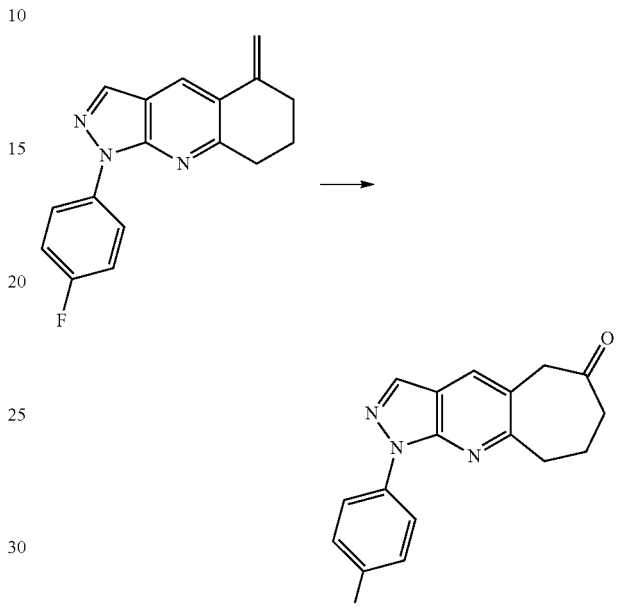

A flask was charged with 1-(4-fluorophenyl)-5-methylene-5,6,7,8-tetrahydro-1H-pyrazolo[3,4-b]quinoline (113, R¹=4-Fluorophenyl) (44.0 g, 158 mmol), MeOH (1050 mL) and water (105 mL). [Hydroxy(tosyloxy)iodo]benzene (61.8 g, 158 mmol) was dissolved in MeOH (160 mL) then the solution was added dropwise to the stirred 1-(4-fluorophenyl)-5-methylene-5,6,7,8-tetrahydro-1H-pyrazolo[3,4-b]quinolone slurry. The internal temperature of the reaction mixture was maintained at about 18 to 20° C. during the addition. The addition was carried out over about 1 h. After about 90 min [hydroxy(tosyloxy)iodo]benzene (3.09 g, 7.88 mmol) was added and the mixture was stirred for about 1 h. A third portion of [hydroxy(tosyloxy)iodo]benzene (2.5 g, 6.37 mmol) was added then after about 15 min the reaction mixture was concentrated under reduced pressure to remove about 1 L solvent (~70 torr, bath temp ~40° C.). Water (1.5 L) was added to the mixture and the resulting slurry was stirred for about 4 h at rt. The solids were collected by filtration then the pad was washed with about 150 mL water. The material was air dried then dissolved in DCM (500 mL) then washed with a mixture of water (100 mL) with sat. aq. NaHCO₃ (100 mL). The organic solution was dried over MgSO₄, filtered and the filtrate concentrated to dryness under reduced pressure. The material was treated with DCM (100 mL) then the slurry was poured onto a filter funnel containing 500 gram silica gel pre-gelled with DCM. The pad was washed with DCM (500 mL) then 9:1 DCM/EtOAc (2 L). Filtrate containing desired product was concentrated under reduced pressure then the material was treated with DCM (50 mL) and heptane (250 mL). The solids were collected by filtration and washed with heptane (100 mL). The material was dried under vacuum at about 70° C. to yield 1-(4-fluorophenyl)-5,7,8,9-tetrahydrocyclohepta[b]pyrazolo[4,3-e]pyridin-6(1H)-one (114, R¹=4-

Fluorophenyl) (36.78 g, 79%). LC/MS, method 3, $R_t$=2.31 min, MS m/z 296 (M+H)$^+$. $^1$H NMR (400 MHz, DMSO) δ 8.36 (s, 1H), 8.34-8.28 (m, 2H), 8.16 (s, 1H), 7.46-7.38 (m, 2H), 3.92 (s, 2H), 3.36-3.28 (m, 2H), 2.57 (t, J=6.9 Hz, 2H), 2.05-1.94 (m, 2H).

Step 6: (E)-1-(4-Fluorophenyl)-5-(pyridin-2-ylmethylene)-5,7,8,9-tetrahydrocyclohepta[b]pyrazolo[4,3-e]pyridin-6(1H)-one (115, R$^1$=4-Fluorophenyl, R$^2$=Pyridin-2-ylmethyl

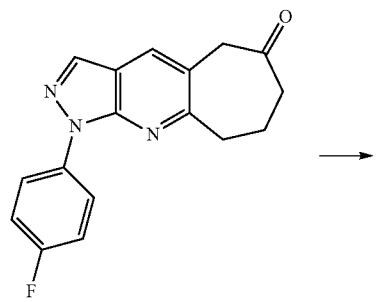

1-(4-Fluorophenyl)-5,7,8,9-tetrahydrocyclohepta[b]pyrazolo[4,3-e]pyridin-6 (1H)-one (114, R$^1$=4-Fluorophenyl) (15.0 g, 50.8 mmol) and THF (430 mL) were stirred until a solution formed. The mixture was cooled to about −70° C. then LiHMDS (1M in THF, 53 mL, 53.0 mmol) was added keeping the internal temperature between about −65 and −70° C. After about 45 min picolinaldehyde (16.32 g, 152 mmol) was added. After about 5 min the mixture was allowed to warm to about −10° C. over about 90 min. Acetic acid (5.8 mL, 102 mmol) was added to the mixture then the slurry was concentrated under reduced pressure. The material was partitioned between water (500 mL), sat. aq. NaHCO$_3$ (~75 mL) and DCM (200 mL). The aqueous layer was extracted with DCM (60 mL) then the combined organics were dried over MgSO$_4$, filtered and concentrated on the rotovap to yield (E)-1-(4-fluorophenyl)-5-(pyridin-2-ylmethylene)-5,7,8,9-tetrahydrocyclohepta[b]pyrazolo[4,3-e]pyridin-6(1H)-one which was used directly in the next step without further manipulation; LC/MS, method 3, $R_t$=2.46 min, MS m/z 385 (M+H)$^+$.

Step 7: 1-(4-Fluorophenyl)-5-(pyridin-2-ylmethyl)-5,7,8,9-tetrahydrocyclohepta[b]pyrazolo[4,3-e]pyridin-6(1H)-one (115, R$^1$=4-Fluorophenyl, R$^2$=Pyridin-2-ylmethyl)

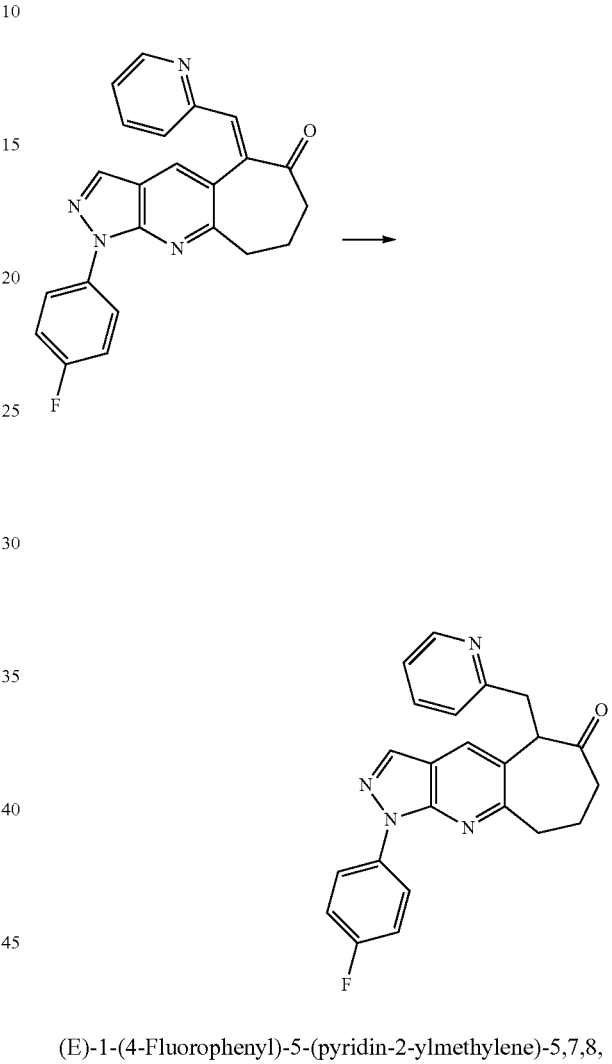

(E)-1-(4-Fluorophenyl)-5-(pyridin-2-ylmethylene)-5,7,8,9-tetrahydrocyclohepta[b]pyrazolo[4,3-e]pyridin-6(1H)-one (19.53 g, 50.8 mmol) (assumed 100% for previous reaction), in toluene (500 mL) with palladium hydroxide on carbon (20% wet) (1.784 g, 2.54 mmol) was stirred for about 22 h under an atmosphere of hydrogen provided by a balloon. The catalyst was removed by filtration through a pad of Celite® and the pad was washed with DCM (250 mL). The filtrate was concentrated under reduced pressure then the material was purified on silica gel (330 g) using a gradient from 0-100% EtOAc in DCM. Product fractions were combined and concentrated under reduced pressure to yield 1-(4-fluorophenyl)-5-(pyridin-2-ylmethyl)-5,7,8,9-tetrahydrocyclohepta[b]pyrazolo[4,3-e]pyridin-6(1H)-one (115, R$^1$=4-Fluorophenyl, R$^2$=Pyridin-2-ylmethyl) (16.47 g, 84%); LC/MS, method 3, $R_t$=1.97 min, MS m/z 387 (M+H)$^+$. $^1$H NMR (400 MHz, DMSO) δ 8.47-8.46 (m, 1H), 8.34 (s, 1H), 8.33-8.26 (m, 2H), 8.09 (s, 1H), 7.72-7.68 (m, 1H), 7.46-7.34 (m, 3H), 7.23-7.17 (m, 1H), 5.00-4.97 (m, 1H), 3.88-3.82 (m, 1H), 3.72-3.65 (m, 1H), 3.36-3.29 (m, 1H), 3.25-3.19 (m, 1H), 3.07-2.99 (m, 1H), 2.54-2.48 (m, 1H), 2.33-2.25 (m, 1H), 1.80-1.69 (m, 1H).

Step 8: 9-(4-Fluorophenyl)-12b-(pyridin-2-ylmethyl)-1,5,6,7,9,12b-hexahydrobenzo[3,4]cyclohepta[1,2-b]pyrazolo[4,3-e]pyridin-3 (2H)-one (116, R$^1$=4-Fluorophenyl, R$^2$=Pyridin-2-ylmethyl)

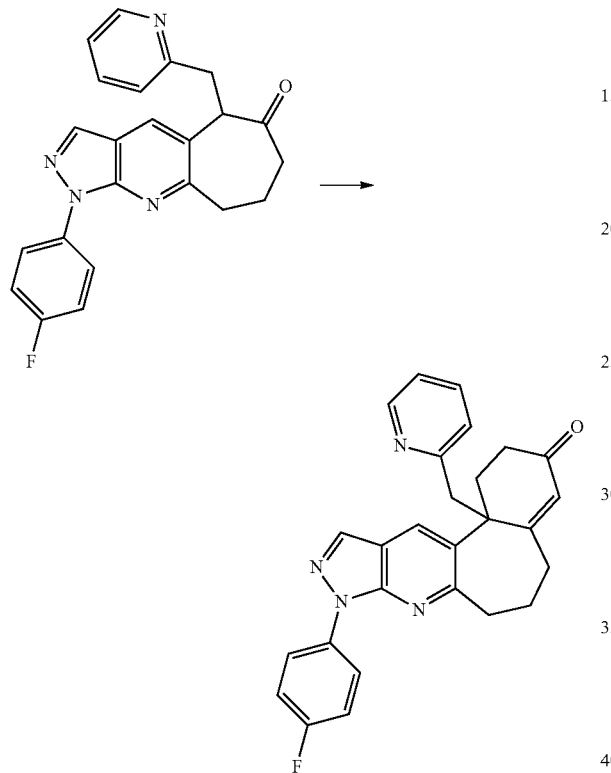

Sodium (1.09 g, 47.4 mmol) and EtOH (355 mL) were stirred together until a solution was formed then 1-(4-fluorophenyl)-5-(pyridin-2-ylmethyl)-5,7,8,9-tetrahydrocyclohepta[b]pyrazolo[4,3-e]pyridin-6(1H)-one (115, R$^1$=4-Fluorophenyl, R$^2$=Pyridin-2-ylmethyl) (16.47 g, 42.6 mmol) was added. The mixture was heated to about 60° C. then but-3-en-2-one (4.14 mL, 50.2 mmol) was added over about 50 min. The mixture was stirred at about 60° C. for about 90 min then it was cooled and concentrated under reduced pressure. The material was partitioned between EtOAc (250 mL) and water (150 mL) then the aqueous layer was extracted with EtOAc (100 mL). The combined organics were washed with brine (30 mL) then dried over MgSO$_4$, filtered and concentrated under reduced pressure. The material was purified on silica gel (330 g) using a gradient from 0-100% EtOAc in DCM. Product fractions were combined and concentrated under reduced pressure to yield rac-9-(4-fluorophenyl)-12b-(pyridin-2-ylmethyl)-1,5,6,7,9,12b-hexahydrobenzo[3,4]cyclohepta[1,2-b]pyrazolo[4,3-e]pyridin-3(2H)-one (116, R$^1$=4-Fluorophenyl, R$^2$=Pyridin-2-ylmethyl) (9.28 g, 50%); LC/MS, method 3, R$_t$=1.61, 2.40 min, MS m/z 439 (M+H)$^+$. $^1$H NMR (400 MHz, DMSO) δ 8.83 (s, 1H), 8.43 (s, 1H), 8.36-8.28 (m, 3H), 7.61-7.57 (m, 1H), 7.44-7.36 (m, 2H), 7.18-7.11 (m, 2H), 5.97 (s, 1H), 3.88 (d, J=13.4 Hz, 1H), 3.67 (d, J=13.5 Hz, 1H), 3.27-3.15 (m, 1H), 2.98-2.93 (m, 1H), 2.87-2.74 (m, 1H), 2.48-2.40 (m, 1H), 2.39-2.27 (m, 1H), 2.23-2.09 (m, 2H), 1.94-1.75 (m, 2H), 1.56-1.49 (m, 1H).

Step 9: rac-(4aR,12bR)-9-(4-Fluorophenyl)-12b-(pyridin-2-ylmethyl)-1,4,4a,5,6,7,9,12b-octahydrobenzo[3,4]cyclohepta[1,2-b]pyrazolo[4,3-e]pyridin-3 (2H)-one (118, R$^1$=4-Fluorophenyl, R$^2$=Pyridin-2-ylmethyl)

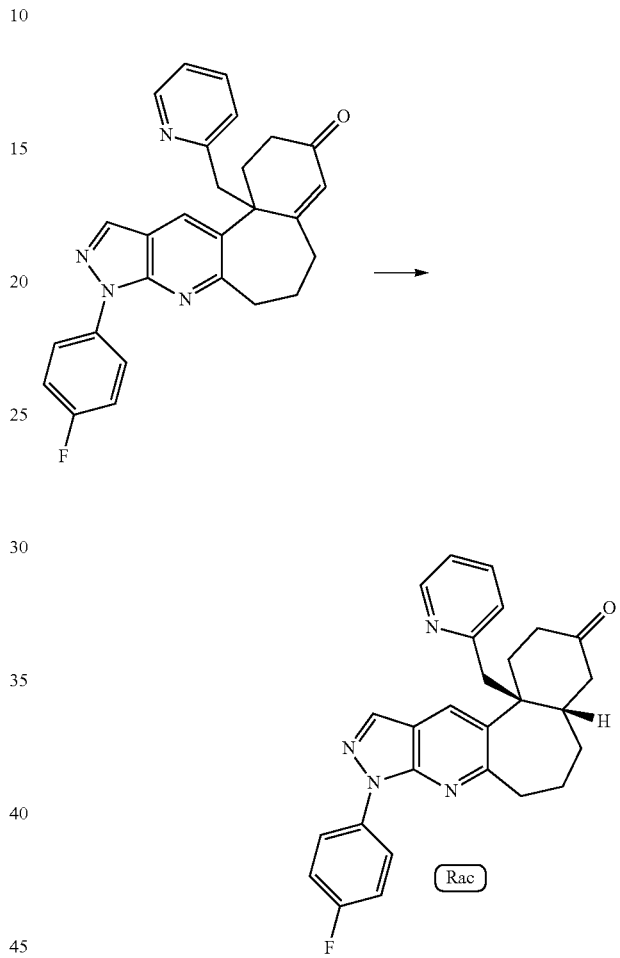

9-(4-Fluorophenyl)-12b-(pyridin-2-ylmethyl)-1,5,6,7,9,12b-hexahydrobenzo[3,4]cyclohepta[1,2-b]pyrazolo[4,3-e]pyridin-3 (2H)-one (116, R$^1$=4-Fluorophenyl, R$^2$=Pyridin-2-ylmethyl) (9.28 g, 21.16 mmol) in THF (170 mL) and pyridine (22 mL) with palladium on carbon (10%) (0.690 g, 0.648 mmol) was hydrogenated in a Parr shaker at 50 psi hydrogen and rt for about 8 h. The mixture was filtered through a pad of Celite® and the pad was washed with DCM. The filtrate was concentrated under reduced pressure and the material was purified on silica gel (330 g) using a gradient from 0-100% EtOAc in DCM. Product fractions were combined and concentrated under reduced pressure to yield rac-(4aR,12bR)-9-(4-fluorophenyl)-12b-(pyridin-2-ylmethyl)-1,4,4a,5,6,7,9,12b-octahydrobenzo[3,4]cyclohepta[1,2-b]pyrazolo[4,3-e]pyridin-3(2H)-one (118, R$^1$=4-Fluorophenyl, R$^2$=Pyridin-2-ylmethyl) (5.55 g, 59.5%); LC/MS, method 3, R$_t$=2.46 min, MS m/z 441 (M+H)$^+$. $^1$H NMR (400 MHz, DMSO) δ 8.40-8.37 (m, 2H), 8.31-8.29 (m, 1H), 8.19 (s, 1H), 7.80 (s, 1H), 7.47-7.38 (m, 3H), 7.09-7.05 (m, 1H), 6.61 (d, J=7.8 Hz, 1H), 3.83 (d, J=12.9 Hz, 1H), 3.63-3.56 (m, 1H), 3.40-3.35 (m, 1H), 2.97 (d, J=13.0 Hz, 1H), 2.62-1.81 (m, 9H), 1.75-1.65 (m, 2H).

Step 10: rac-(2'R,4aS,12bS)-9-(4-fluorophenyl)-12b-(pyridin-2-ylmethyl)-2,4,4a,5,6,7,9,12b-octahydro-1H-spiro[benzo[3,4]cyclohepta[1,2-b]pyrazolo[4,3-e]pyridine-3,2'-oxirane] (119, $R^1$=4-Fluorophenyl, $R^2$=Pyridin-2-ylmethyl)

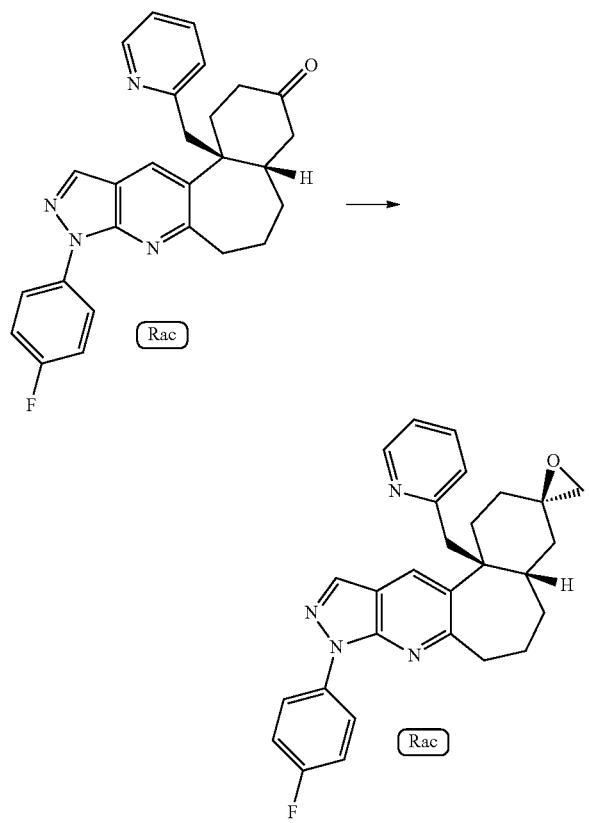

Sodium hydride (60 wt % in oil, 0.454 g, 11.35 mmol) and DMSO (25 mL) were heated to about 65° C. for about 30 min then cooled to rt. THF (50 mL) was added then the mixture was cooled to about 0° C. Trimethylsulfoxonium iodide (2.56 g, 11.63 mmol) was added then after about 30 min rac-(4aR,12bR)-9-(4-fluorophenyl)-12b-(pyridin-2-ylmethyl)-1,4,4a,5,6,7,9,12b-octahydrobenzo[3,4]cyclohepta[1,2-b]pyrazolo[4,3-e]pyridin-3 (2H)-one (118, $R^1$=4-Fluorophenyl, $R^2$=Pyridin-2-ylmethyl) (2.5 g, 5.68 mmol) was added. The mixture was allowed to warm to rt and stir for about 12 h. The mixture was concentrated under reduced pressure then the material was partitioned between water (100 mL) and EtOAc (50 mL). The aqueous layer was extracted with EtOAc (25 mL) then the organic solutions were combined and washed with water (75 mL) then brine (30 mL), dried over MgSO$_4$ then filtered. The filtrate was concentrated under reduced pressure and the material was purified on silica gel (120 g) using a gradient from 0-10% MeOH in DCM. Product fractions were combined and concentrated under reduced pressure to yield rac-(2'R,4aS,12bS)-9-(4-fluorophenyl)-12b-(pyridin-2-ylmethyl)-2,4,4a,5,6,7,9,12b-octahydro-1H-spiro[benzo[3,4]cyclohepta[1,2-b]pyrazolo[4,3-e]pyridine-3,2'-oxirane] (119, $R^1$=4-Fluorophenyl, $R^2$=Pyridin-2-ylmethyl) (1.865 g, 72.3%); LC/MS, method 3, $R_t$=2.65 min, MS m/z 455 (M+H)$^+$. $^1$H NMR (400 MHz, DMSO) δ 8.42-8.34 (m, 2H), 8.32-8.28 (m, 1H), 8.20 (s, 1H), 7.75-7.72 (m, 1H), 7.49-7.37 (m, 3H), 7.06 (ddd, J=5.2, 4.5, 0.9 Hz, 1H), 6.72-6.67 (m, 1H), 3.73 (d, J=12.8 Hz, 1H), 3.59-3.47 (m, 1H), 3.42-3.33 (m, 1H), 3.02 (d, J=12.9 Hz, 1H), 2.70-2.56 (m, 1H), 2.44-2.34 (m, 2H), 2.13-2.00 (m, 1H), 1.96-1.81 (m, 2H), 1.79-1.58 (m, 3H), 1.35-1.21 (m, 3H), 1.21-1.10 (m, 1H).

Step 11: rac-(3R,4aS,12bS)-9-(4-Fluorophenyl)-3-methyl-12b-(pyridin-2-ylmethyl)-1,2,3,4,4a,5,6,7,9,12b-decahydrobenzo[3,4]cyclohepta[1,2-b]pyrazolo[4,3-e]pyridin-3-ol (120, $R^1$=4-Fluorophenyl, $R^2$=Pyridin-2-ylmethyl, $R^3$=Methyl)

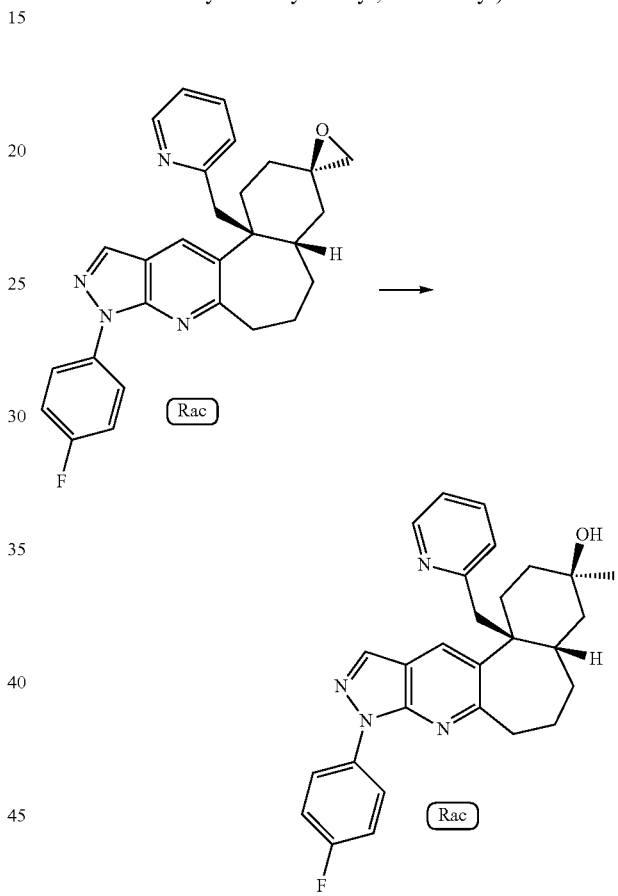

rac-(2'R,4aS,12bS)-9-(4-fluorophenyl)-12b-(pyridin-2-ylmethyl)-2,4,4a,5,6,7,9,12b-octahydro-1H-spiro[benzo[3,4]cyclohepta[1,2-b]pyrazolo[4,3-e]pyridine-3,2'-oxirane] (119, $R^1$=4-Fluorophenyl, $R^2$=Pyridin-2-ylmethyl) (1.865 g, 4.10 mmol) was suspended in EtOH (41.0 mL). NaBH$_4$ (0.776 g, 20.52 mmol) was added to the then the mixture was warmed to about 65° C. for about 2 h. The mixture was cooled then concentrated under reduced pressure. Water (50 mL) was added to the material then the solids were collected by filtration and dried the material was purified on silica gel (120 g) using a gradient from 0-10% MeOH in DCM. Product fractions were combined and concentrated under reduced pressure to yield rac-(3R,4aS,12bS)-9-(4-fluorophenyl)-3-methyl-12b-(pyridin-2-ylmethyl)-1,2,3,4,4a,5,6,7,9,12b-decahydrobenzo[3,4]cyclohepta[1,2-b]pyrazolo[4,3-e]pyridin-3-ol (120, $R^1$=4-Fluorophenyl, $R^2$=Pyridin-2-ylmethyl, $R^3$=Methyl) (1.87 g, 99%); LC/MS, method 2, $R_t$=2.65 min, MS m/z 457 (M+H)$^+$. $^1$H NMR (400 MHz, DMSO) δ 8.42-8.35 (m, 2H), 8.28-8.26 (m, 1H), 8.18 (s, 1H), 7.62 (s, 1H), 7.46-7.37 (m, 3H), 7.05-7.02 (m, 1H), 6.58 (d, J=7.8 Hz, 1H), 4.10 (s, 1H), 3.70 (d, J=12.6 Hz, 1H), 3.56-3.49 (m, 1H), 3.44-3.32 (m, 1H), 2.91 (d, J=12.8 Hz, 1H), 2.66-2.53 (m, 2H), 2.15-1.80 (m, 3H), 1.70-1.59 (m, 2H), 1.53-1.30 (m, 2H), 1.16-1.14 (m, 2H), 0.92 (s, 3H).

Example #149 and #150

(3R,4aS,12bS)-9-(4-Fluorophenyl)-3-methyl-12b-(pyridin-2-ylmethyl)-1,2,3,4,4a,5,6,7,9,12b-decahydrobenzo[3,4]cyclohepta[1,2-b]pyrazolo[4,3-e]pyridin-3-ol (120, R¹=4-Fluorophenyl, R²=Pyridin-2-ylmethyl, R³=Methyl) and (3S,4aR,12bR)-9-(4-Fluorophenyl)-3-methyl-12b-(pyridin-2-ylmethyl)-1,2,3,4,4a,5,6,7,9,12b-decahydrobenzo[3,4]cyclohepta[1,2-b]pyrazolo[4,3-e]pyridin-3-ol (120, R¹=4-Fluorophenyl, R²=Pyridin-2-ylmethyl, R³=Methyl)

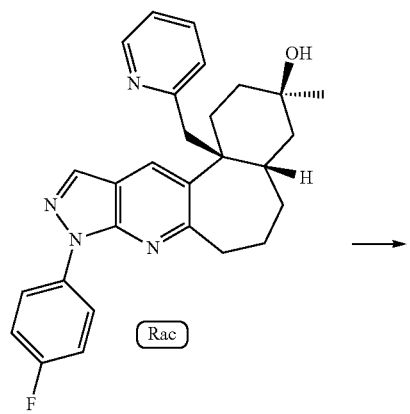

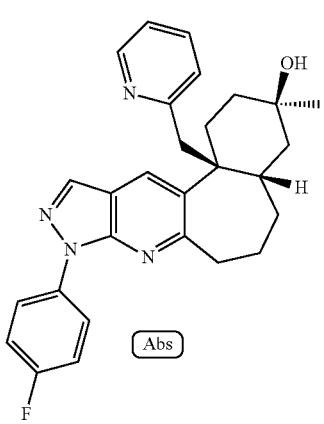

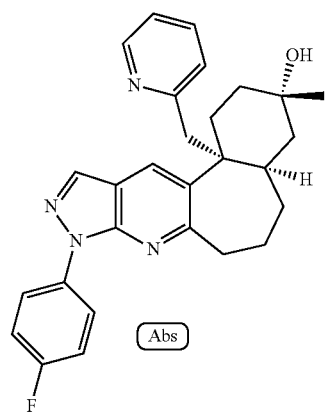

Example #148

(120, R¹=4-Fluorophenyl, R²=Pyridin-2-ylmethyl, R³=Methyl) (described above) enantiomers were separated using Preparative Chiral Purification Method 43.

Fractions from the first peak eluted were combined and concentrated under reduced pressure to yield (3R,4aS,12bS)-9-(4-Fluorophenyl)-3-methyl-12b-(pyridin-2-ylmethyl)-1,2,3,4,4a,5,6,7,9,12b-decahydrobenzo[3,4]cyclohepta[1,2-b]pyrazolo[4,3-e]pyridin-3-ol (120, R¹=4-Fluorophenyl, R²=Pyridin-2-ylmethyl, R³=Methyl) LC/MS, method 2, $R_t$=2.65 min, MS m/z 457 (M+H)⁺. ¹H NMR (400 MHz, DMSO) δ 8.42-8.35 (m, 2H), 8.28-8.26 (m, 1H), 8.18 (s, 1H), 7.62 (s, 1H), 7.46-7.37 (m, 3H), 7.05-7.02 (m, 1H), 6.58 (d, J=7.8 Hz, 1H), 4.10 (s, 1H), 3.70 (d, J=12.6 Hz, 1H), 3.56-3.49 (m, 1H), 3.44-3.32 (m, 1H), 2.91 (d, J=12.8 Hz, 1H), 2.66-2.53 (m, 2H), 2.15-1.80 (m, 3H), 1.70-1.59 (m, 2H), 1.53-1.30 (m, 2H), 1.16-1.14 (m, 2H), 0.92 (s, 3H).

Fractions from the second peak eluted were combined and concentrated under reduced pressure to yield (3S,4aR,12bR)-9-(4-Fluorophenyl)-3-methyl-12b-(pyridin-2-ylmethyl)-1,2,3,4,4a,5,6,7,9,12b-decahydrobenzo[3,4]cyclohepta[1,2-b]pyrazolo[4,3-e]pyridin-3-ol (120, R¹=4-Fluorophenyl, R²=Pyridin-2-ylmethyl, R³=Methyl) LC/MS, method 2, $R_t$=2.65 min, MS m/z 457 (M+H)⁺. ¹H NMR (400 MHz, DMSO) δ 8.42-8.35 (m, 2H), 8.28-8.26 (m, 1H), 8.18 (s, 1H), 7.62 (s, 1H), 7.46-7.37 (m, 3H), 7.05-7.02 (m, 1H), 6.58 (d, J=7.8 Hz, 1H), 4.10 (s, 1H), 3.70 (d, J=12.6 Hz, 1H), 3.56-3.49 (m, 1H), 3.44-3.32 (m, 1H), 2.91 (d, J=12.8 Hz, 1H), 2.66-2.53 (m, 2H), 2.15-1.80 (m, 3H), 1.70-1.59 (m, 2H), 1.53-1.30 (m, 2H), 1.16-1.14 (m, 2H), 0.92 (s, 3H).

Examples #151 and #152 rac-(3R,4aS,12bS)-12b-Ethyl-9-(4-fluorophenyl)-3-(trifluoromethyl)-1,2,3,4,4a,5,6,7,9,12b-decahydrobenzo[3,4]cyclohepta[1,2-b]pyrazolo[4,3-e]pyridin-3-ol (124, R¹=4-Fluorophenyl, R²=Ethyl, R³=Trifluoromethyl) and rac-(3R,4aR,12bR)-12b-ethyl-9-(4-fluorophenyl)-3-(trifluoromethyl)-1,2,3,4,4a,5,6,7,9,12b-decahydrobenzo[3,4]cyclohepta[1,2-b]pyrazolo[4,3-e]pyridin-3-ol (122, R¹=4-Fluorophenyl, R²=Ethyl, R³=Trifluoromethyl)

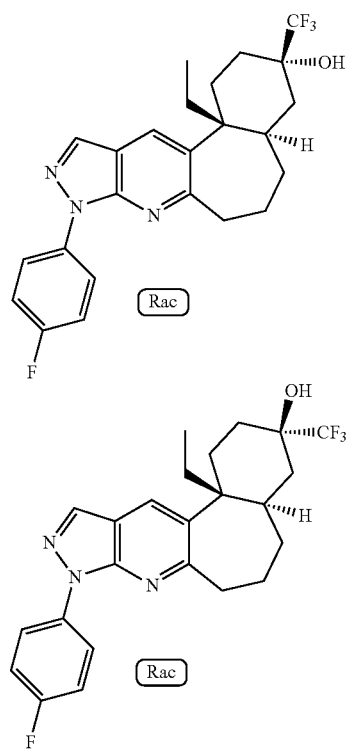

12b-Ethyl-9-(4-fluorophenyl)-1,5,6,7,9,12b-hexahydrobenzo[3,4]cyclohepta[1,2-b]pyrazolo[4,3-e]pyridin-3 (2H)-one (116, R¹=4-Fluorophenyl, R²=Ethyl) was prepared from 1-(4-fluorophenyl)-5,7,8,9-tetrahydrocyclohepta[b]pyrazolo[4,3-e]pyridin-6 (1H)-one (114, R¹=4-Fluorophenyl) in 3 steps in a manner similar to Example 148, Steps 6 (substituting acetaldehyde for pyridine-2-carboxaldehyde), 7 and 8 to yield 12b-Ethyl-9-(4-fluorophenyl)-1,5,6,7,9,12b-hexahydrobenzo[3,4]cyclohepta[1,2-b]pyrazolo[4,3-e]pyridin-3(2H)-one (116, R¹=4-Fluorophenyl, R²=Ethyl); LC/MS, method 3, $R_t$=2.65 min, MS m/z 376 (M+H)⁺. ¹H NMR (400 MHz, DMSO) δ 8.39 (s, 1H), 8.36 (s, 1H), 8.35-8.30 (m, 2H), 7.47-7.35 (m, 2H), 5.95 (s, 1H), 3.26-3.18 (m, 1H), 2.99-2.90 (m, 1H), 2.78-2.69 (m, 1H), 2.60-2.40 (m, 3H), 2.37-2.30 (m, 1H), 2.25-2.05 (m, 2H), 2.04-1.79 (m, 3H), 0.86 (t, J=7.4 Hz, 3H).

Step 2: rac-(4aR,12bR)-12b-Ethyl-9-(4-fluorophenyl)-1,4,4a,5,6,7,9,12b-octahydrobenzo[3,4]cyclohepta[1,2-b]pyrazolo[4,3-e]pyridin-3 (2H)-one (117, R¹=4-Fluorophenyl, R²=Ethyl)

Step 1: 12b-Ethyl-9-(4-fluorophenyl)-1,5,6,7,9,12b-hexahydrobenzo[3,4]cyclohepta[1,2-b]pyrazolo[4,3-e]pyridin-3(2H)-one (116, R¹=4-Fluorophenyl, R²=Ethyl)

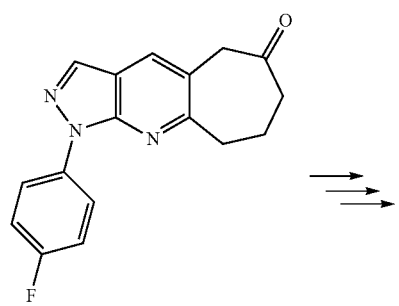

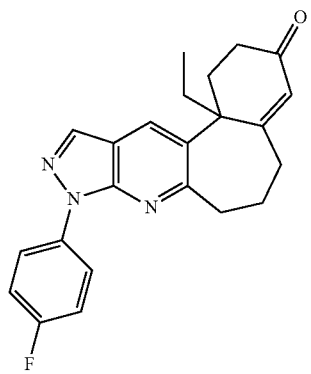

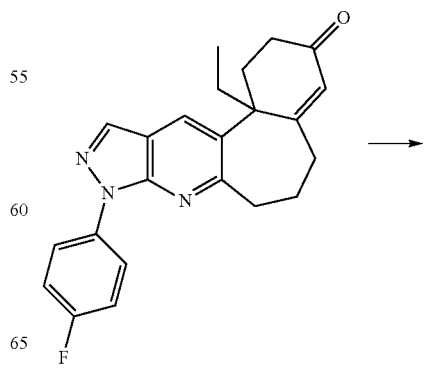

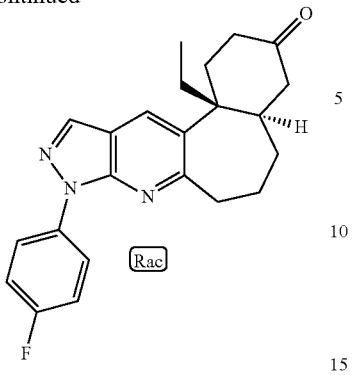

12b-Ethyl-9-(4-fluorophenyl)-1,5,6,7,9,12b-hexahydrobenzo[3,4]cyclohepta[1,2-b]pyrazolo[4,3-e]pyridin-3(2H)-one (116, R$^1$=4-Fluorophenyl, R$^2$=Ethyl) (6.97 g, 18.56 mmol) in toluene (205 mL) and heptane (20.5 mL) with palladium hydroxide on carbon (20 wt % wet) (0.925 g, 1.317 mmol) was shaken at about 55° C. under an atmosphere of about 50 psi hydrogen for about 9 h. The mixture was cooled then the reaction mixture was filtered through a pad of Celite® and the pad was rinsed with DCM (300 mL). The filtrate was concentrated under reduced pressure to yield a foam (7.98 g). EtOAc (45 mL) was added to the material and the resulting slurry was heated to reflux for about 5 min then cooled to rt and stirred for about 2 h. The mixture was cooled in an ice/water bath for about 30 min then the solids were collected by filtration and washed with ice cold EtOAc (5 mL). The material was dried under vacuum at about 70° C. to yield rac-(4aR,12bR)-12b-ethyl-9-(4-fluorophenyl)-1,4,4a,5,6,7,9,12b-octahydrobenzo[3,4]cyclohepta[1,2-b]pyrazolo[4,3-e]pyridin-3(2H)-one (117, R$^1$=4-Fluorophenyl, R$^2$=Ethyl) (4.13 g, 59%); LC/MS, method 3, R$_f$=2.78 min, MS m/z 378 (M+H)$^+$. $^1$H NMR (400 MHz, DMSO) δ 8.39-8.29 (m, 4H), 7.45-7.36 (m, 2H), 3.51-3.44 (m, 1H), 3.27-3.21 (m, 1H), 2.61-2.45 (m, 3H), 2.40-2.23 (m, 2H), 2.15-1.94 (m, 6H), 1.67-1.61 (m, 1H), 1.44-1.35 (m, 1H), 0.48 (t, J=7.4 Hz, 3H).

Step 3: rac-(3R,4aS,12bS)-12b-Ethyl-9-(4-fluorophenyl)-3-(trifluoromethyl)-1,2,3,4,4a,5,6,7,9,12b-decahydrobenzo[3,4]cyclohepta[1,2-b]pyrazolo[4,3-e]pyridin-3-ol (124, R$^1$=4-Fluorophenyl, R$^2$=Ethyl, R$^3$=Trifluoromethyl) and rac-(3R,4aR,12bR)-12b-ethyl-9-(4-fluorophenyl)-3-(trifluoromethyl)-1,2,3,4,4a,5,6,7,9,12b-decahydrobenzo[3,4]cyclohepta[1,2-b]pyrazolo[4,3-e]pyridin-3-ol (122, R$^1$=4-Fluorophenyl, R$^2$=Ethyl, R$^3$=Trifluoromethyl)

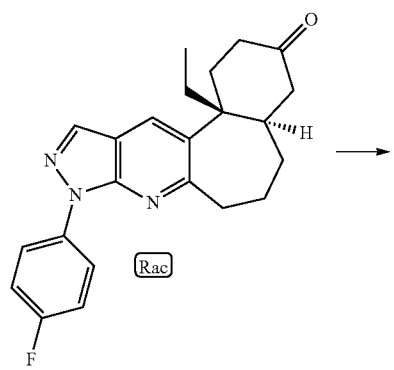

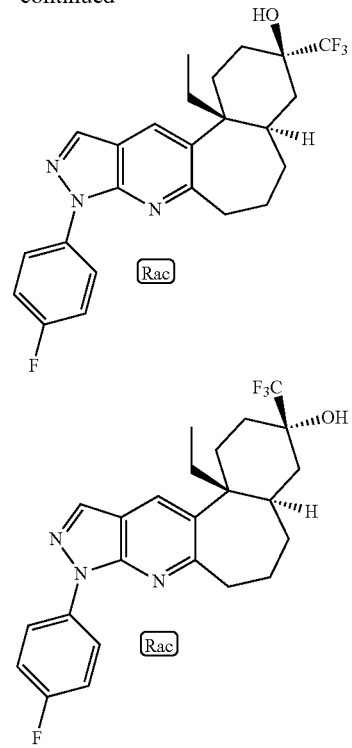

A flask equipped with stir bar, nitrogen line, septum and thermometer was charged with DME (45 mL) and CsF (0.352 g, 2.318 mmol) then the mixture was stirred for about 15 min. rac-(4aR,12bR)-12b-Ethyl-9-(4-fluorophenyl)-1,4,4a,5,6,7,9,12b-octahydrobenzo[3,4]cyclohepta[1,2-b]pyrazolo[4,3-e]pyridin-3(2H)-one (1.75 g, 4.64 mmol) was added then the suspension was cooled to about −10° C. Trimethyl(trifluoromethyl)silane (1.253 g, 8.81 mmol) was added keeping the temperature of the mixture between about −5 and −10° C. After about 30 min TBAF (5.10 mL, 5.10 mmol) was added. The mixture was stirred for about 30 min then concentrated under reduced pressure. Water (50 mL) was added to the material then the solids were collected by filtration and dried under vacuum at about 60° C. to give 2.38 grams of solid. The material was purified on silica gel (330 g) using a gradient from 10-40% EtOAc in heptane.

The high R$_f$ minor component fractions (TLC 65:35 heptane/EtOAc, visualized by UV) were combined and concentrated to yield rac-(3R,4aS,12bS)-12b-ethyl-9-(4-fluorophenyl)-3-(trifluoromethyl)-1,2,3,4,4a,5,6,7,9,12b-decahydrobenzo[3,4]cyclohepta[1,2-b]pyrazolo[4,3-e]pyridin-3-ol (124, R$^1$=4-Fluorophenyl, R$^2$=Ethyl, R$^3$=Trifluoromethyl) (0.326 g, 15.71%); LC/MS, method 2, R$_f$=3.20 min, MS m/z 448 (M+H)$^+$. $^1$H NMR (400 MHz, DMSO) δ 8.43-8.30 (m, 4H), 7.48-7.35 (m, 2H), 5.78 (s, 1H), 3.41-3.35 (m, 1H), 3.25-3.19 (m, 1H), 2.22-1.98 (m, 4H), 1.97-1.83 (m, 2H), 1.83-1.51 (m, 6H), 1.49-1.35 (m, 1H), 0.38 (t, J=7.3 Hz, 3H).

The low R$_f$ major component fractions were combined and concentrated to yield rac-(3R,4aR,12bR)-12b-ethyl-9-(4-fluorophenyl)-3-(trifluoromethyl)-1,2,3,4,4a,5,6,7,9,12b-decahydrobenzo[3,4]cyclohepta[1,2-b]pyrazolo[4,3-e]pyridin-3-ol (122, R$^1$=4-Fluorophenyl, R$^2$=Ethyl, R$^3$=Trifluoromethyl) (1.65 g 80%); LC/MS, method 2, R$_f$=3.09 min, MS m/z 448 (M+H)$^+$. $^1$H NMR (400 MHz, DMSO) δ 8.37-8.32 (m, 2H), 8.31 (s, 1H), 8.29 (s, 1H), 7.46-7.33 (m, 2H), 5.90 (s, 1H), 3.45-3.38 (m, 1H), 3.24-3.18 (m, 1H), 2.29-2.20 (m, 1H), 2.16-1.97 (m, 4H), 1.96-1.80 (m, 2H), 1.79-1.58 (m, 5H), 1.48-1.38 (m, 1H), 0.42 (t, J=7.3 Hz, 3H).

Examples #153 and #154

(3S,4aS,12bS)-12b-Ethyl-9-(4-fluorophenyl)-3-(trifluoromethyl)-1,2,3,4,4a,5,6,7,9,12b-decahydrobenzo[3,4]cyclohepta[1,2-b]pyrazolo[4,3-e]pyridin-3-ol (122, R¹=4-Fluorophenyl, R²=Ethyl, R³=Trifluoromethyl) and (3R,4aR,12bR)-12b-ethyl-9-(4-fluorophenyl)-3-(trifluoromethyl)-1,2,3,4,4a,5,6,7,9,12b-decahydrobenzo[3,4]cyclohepta[1,2-b]pyrazolo[4,3-e]pyridin-3-ol (122, R¹=4-Fluorophenyl, R²=Ethyl, R³=Trifluoromethyl)

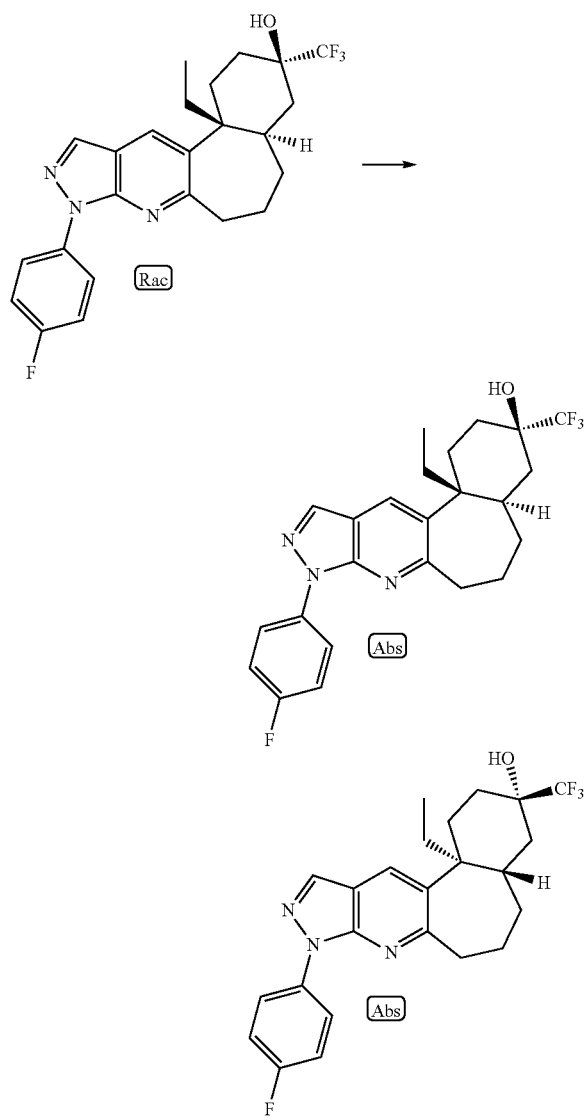

Example #151

(122, R¹=4-Fluorophenyl, R²=Ethyl, R³=Trifluoromethyl) (described above) enantiomers were separated using Preparative Chiral Purification Method 42.

Fractions from the first peak eluted were combined and concentrated under reduced pressure to yield Example #153 (3S,4aS,12bS)-12b-Ethyl-9-(4-fluorophenyl)-3-(trifluoromethyl)-1,2,3,4,4a,5,6,7,9,12b-decahydrobenzo[3,4]cyclohepta[1,2-b]pyrazolo[4,3-e]pyridin-3-ol (122, R¹=4-Fluorophenyl, R²=Ethyl, R³=Trifluoromethyl); LC/MS, method 2, $R_t$=3.10 min, MS m/z 448 (M+H)⁺.

Fractions from the second peak eluted were combined and concentrated under reduced pressure to yield Example #154 (3R,4aR,12bR)-12b-ethyl-9-(4-fluorophenyl)-3-(trifluoromethyl)-1,2,3,4,4a,5,6,7,9,12b-decahydrobenzo[3,4]cyclohepta[1,2-b]pyrazolo[4,3-e]pyridin-3-ol (122, R¹=4-Fluorophenyl, R²=Ethyl, R³=Trifluoromethyl); LC/MS, method 2, $R_t$=3.10 min, MS m/z 448 (M+H)⁺.

Examples #155 rac-(3R,4aR,12bR)-9-(4-Fluorophenyl)-12b-(pyridin-2-ylmethyl)-3-(trifluoromethyl)-1,2,3,4,4a,5,6,7,9,12b-decahydrobenzo[3,4]cyclohepta[1,2-b]pyrazolo[4,3-e]pyridin-3-ol (124, R¹=4-Fluorophenyl, R²=Pyridin-2-ylmethyl, R³=Trifluoromethyl)

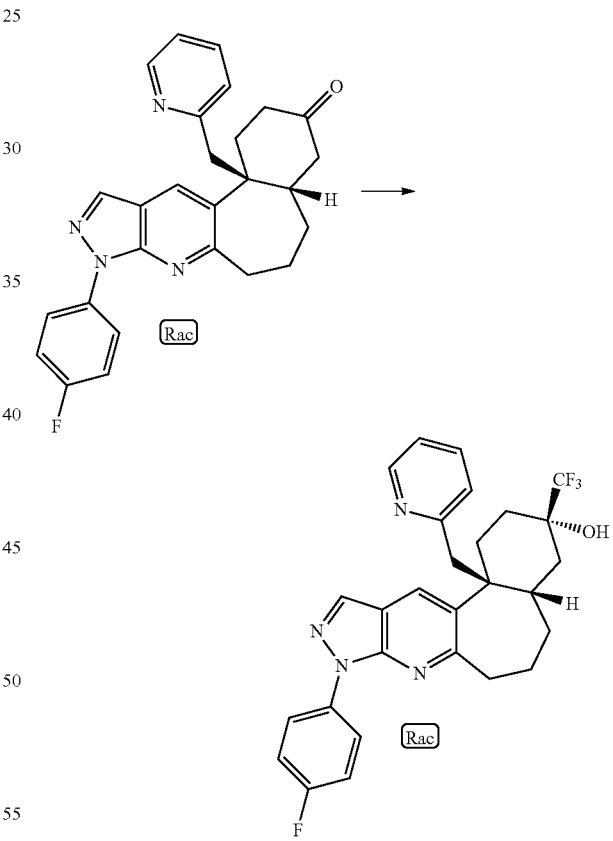

rac-(3R,4aR,12bR)-9-(4-Fluorophenyl)-12b-(pyridin-2-ylmethyl)-3-(trifluoromethyl)-1,2,3,4,4a,5,6,7,9,12b-decahydrobenzo[3,4]cyclohepta[1,2-b]pyrazolo[4,3-e]pyridin-3-ol (124, R¹=4-Fluorophenyl, R²=Pyridin-2-ylmethyl, R³=Trifluoromethyl) was prepared from rac-(4aR,12bR)-9-(4-fluorophenyl)-12b-(pyridin-2-ylmethyl)-1,4,4a,5,6,7,9,12b-octahydrobenzo[3,4]cyclohepta[1,2-b]pyrazolo[4,3-e]pyridin-3(2H)-one (118, R¹=4-Fluorophenyl, R²=Pyridin-2-ylmethyl) in 1 step in a manner similar to Example 151, Step 3 to yield rac-(3R,4aR,12bR)-9-(4-fluorophenyl)-12b-(pyridin-2-ylmethyl)-3-(trifluoromethyl)-1,2,3,4,4a,5,6,7,9,12b-decahydrobenzo[3,4]cyclohepta[1,2-b]pyrazolo[4,3-e]pyridin-3-ol (124, $R^1$=4-Fluorophenyl, $R^2$=Pyridin-2-ylmethyl, $R^3$=Trifluoromethyl); LC/MS, method 2, $R_t$=2.81 min, MS m/z 511 (M+H)$^+$. $^1$H NMR (400 MHz, DMSO) δ 8.42-8.30 (m, 3H), 8.26 (s, 1H), 8.05 (s, 1H), 7.46-7.34 (m, 3H), 7.14-7.06 (m, 1H), 6.39 (s, 1H), 5.59 (s, 1H), 3.53 (d, J=13.1 Hz, 1H), 3.04-2.82 (m, 3H), 2.28-1.98 (m, 5H), 1.82-1.53 (m, 6H).

Additional examples, prepared from compounds 119 and 121, in a manner similar to the preparation of Example 12 are listed in Table 14.

TABLE 14

| Ex. # | Reactant | Reagent | Product structure | LC/MS method/ $R_t$, MH$^+$ | Chiral method | Order of elution/ sign of rotation |
|---|---|---|---|---|---|---|
| 156 | 119 ($R^1$ = 4-Fluorophenyl, $R^2$ = Pyridin-2-ylmethyl) | Sodium methoxide | 120 (3R,4aR,12bS) ($R^1$ = 4-Fluorophenyl, $R^2$ = Pyridin-2-ylmethyl, $R^3$ = Methoxymethyl) | 2 2.54 min 487 MH$^+$ | 46 | 1$^{st}$/neg |
| 157 | 119 ($R^1$ = 4-Fluorophenyl, $R^2$ = Pyridin-2-ylmethyl) | Sodium methoxide | 120 (3S,4aS,12bR) ($R^1$ = 4-Fluorophenyl, $R^2$ = Pyridin-2-ylmethyl, $R^3$ = Methoxymethyl) | 2 2.54 min 487 MH$^+$ | 46 | 2$^{nd}$/pos |
| 158 | 119 ($R^1$ = 4-Fluorophenyl, $R^2$ = Pyrimidin-2-ylmethyl) | Sodium methoxide | 120 (3R,4aS,12bS) ($R^1$ = 4-Fluorophenyl, $R^2$ = Pyrimidin-2-ylmethyl, $R^3$ = Methoxymethyl) | 2 2.38 min 488 MH$^+$ | 47 | 1$^{st}$/neg |
| 159 | 119 ($R^1$ = 4-Fluorophenyl, $R^2$ = Pyrimidin-2-ylmethyl) | Sodium methoxide | 120 (3S,4aR,12bR) ($R^1$ = 4-Fluorophenyl, $R^2$ = Pyrimidin-2-ylmethyl, $R^3$ = Methoxymethyl) | 2 2.38 min 488 MH$^+$ | 47 | 2$^{nd}$/pos |

Additional examples, prepared from compounds 119 and 121, in a manner similar to the preparation of Example #15 are listed in Table 15.

TABLE 15

| Ex. # | Epoxide | Reagent | Product structure | LC/MS method/ $R_t$, MH$^+$ | Chiral method | Order of elution/ sign of rotation |
|---|---|---|---|---|---|---|
| 161 | 119 ($R^1$ = 4-Fluorophenyl, $R^2$ = Pyrimidin-2-ylmethyl) | NaBH$_4$ | 120 (3R,4aS,12bS) ($R^1$ = 4-Fluorophenyl, $R^2$ = Pyrimidin-2-ylmethyl, $R^3$ = Methyl) | 2 2.41 min 458 MH$^+$ | 48 | 1$^{st}$/neg |
| 162 | 119 ($R^1$ = 4-Fluorophenyl, $R^2$ = Pyrimidin-2-ylmethyl) | NaBH$_4$ | 120 (3S,4aR,12bR) ($R^1$ = 4-Fluorophenyl, $R^2$ = Pyrimidin-2-ylmethyl, $R^3$ = Methyl) | 2 2.41 min 458 MH$^+$ | 48 | 2$^{nd}$/pos |

Additional examples, prepared from compounds 119 and 121, in a manner similar to the preparation of Example #15 are listed in Table 16.

TABLE 16

| Ex. # | Epoxide | Reagent | Product structure | LC/MS method/ $R_t$, MH$^+$ | Chiral method | Order of elution/ sign of rotation |
|---|---|---|---|---|---|---|
| 160 | 119 ($R^1$ = 4-Fluorophenyl, $R^2$ = | KCN | 120 (3S,4aR,12bR) ($R^1$ = 4-Fluorophenyl, $R^2$ = Pyrimidin-2-ylmethyl, | 2 2.21 min 483 MH$^+$ | 50 | 2$^{nd}$/NA |

TABLE 16-continued

| Ex. # | Epoxide | Reagent | Product structure | LC/MS method/ $R_t$ MH$^+$ | Chiral method | Order of elution/ sign of rotation |
|---|---|---|---|---|---|---|
| | Pyrimidin-2-ylmethyl) | | R$^3$ = Cyanomethyl) | | | |
| 163 | 119 (R$^1$ = 4-Fluorophenyl, R$^2$ = Pyridin-2-ylmethyl) | KCN | 120 (3R,4aS,12bS) (R$^1$ = 4-Fluorophenyl, R$^2$ = Pyridin-2-ylmethyl, R$^3$ = Cyanomethyl) | 2 2.37 min 482 MH$^+$ | 49 | 1$^{st}$/neg |
| 164 | 119 (R$^1$ = 4-Fluorophenyl, R$^2$ = Pyridin-2-ylmethyl) | KCN | 120 (3S,4aR,12bR) (R$^1$ = 4-Fluorophenyl, R$^2$ = Pyridin-2-ylmethyl, R$^3$ = Cyanomethyl) | 2 2.37 min 482 MH$^+$ | 49 | 2$^{nd}$/pos |
| 165 | 119 (R$^1$ = 4-Fluorophenyl, R$^2$ = Pyrimidin-2-ylmethyl) | KCN | 120 (3R,4aS,12bS) (R$^1$ = 4-Fluorophenyl, R$^2$ = Pyrimidin-2-ylmethyl, R$^3$ = Cyanomethyl) | 2 2.21 min 483 MH$^+$ | 50 | 1$^{st}$/NA |

Scheme 23:

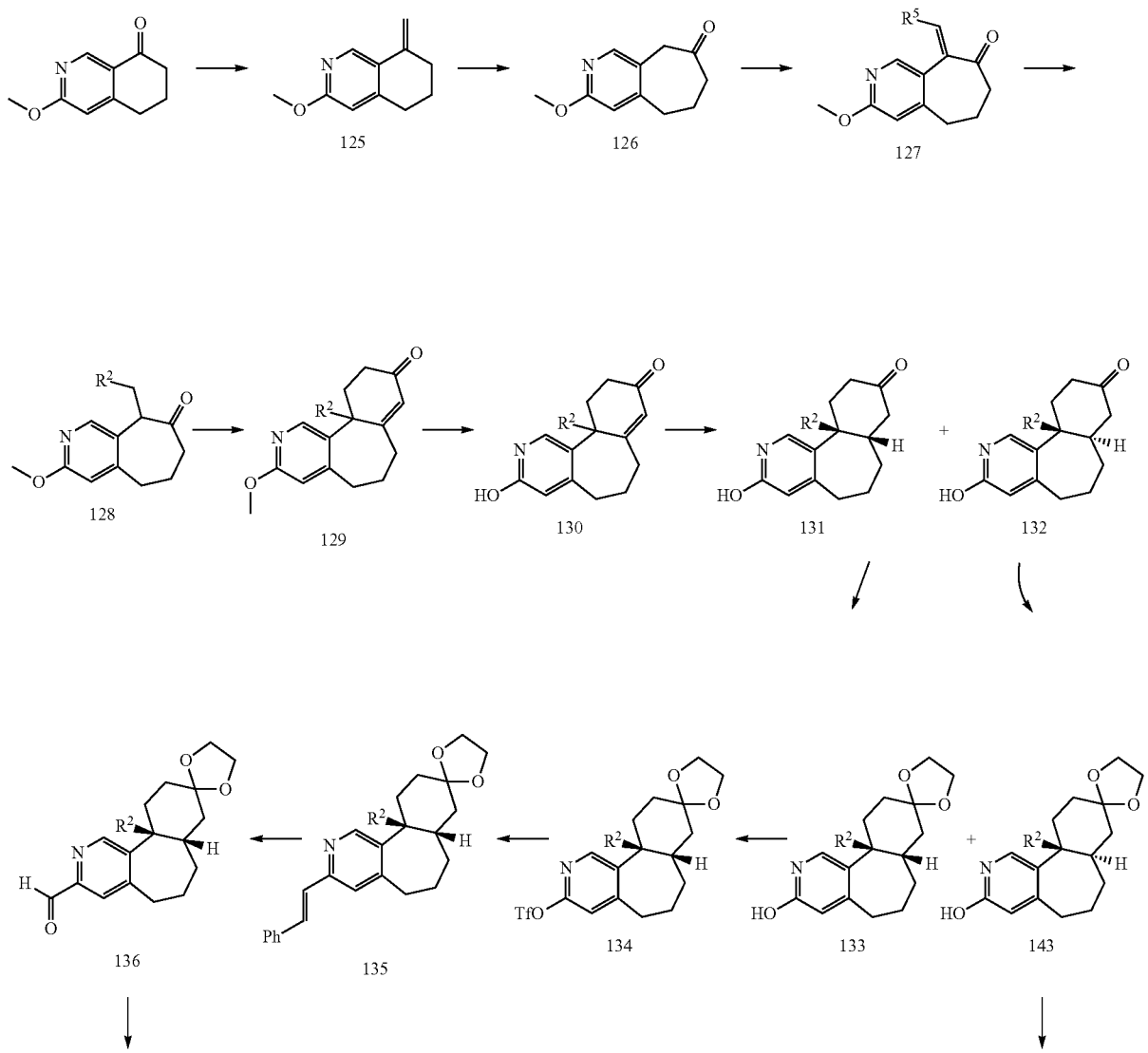

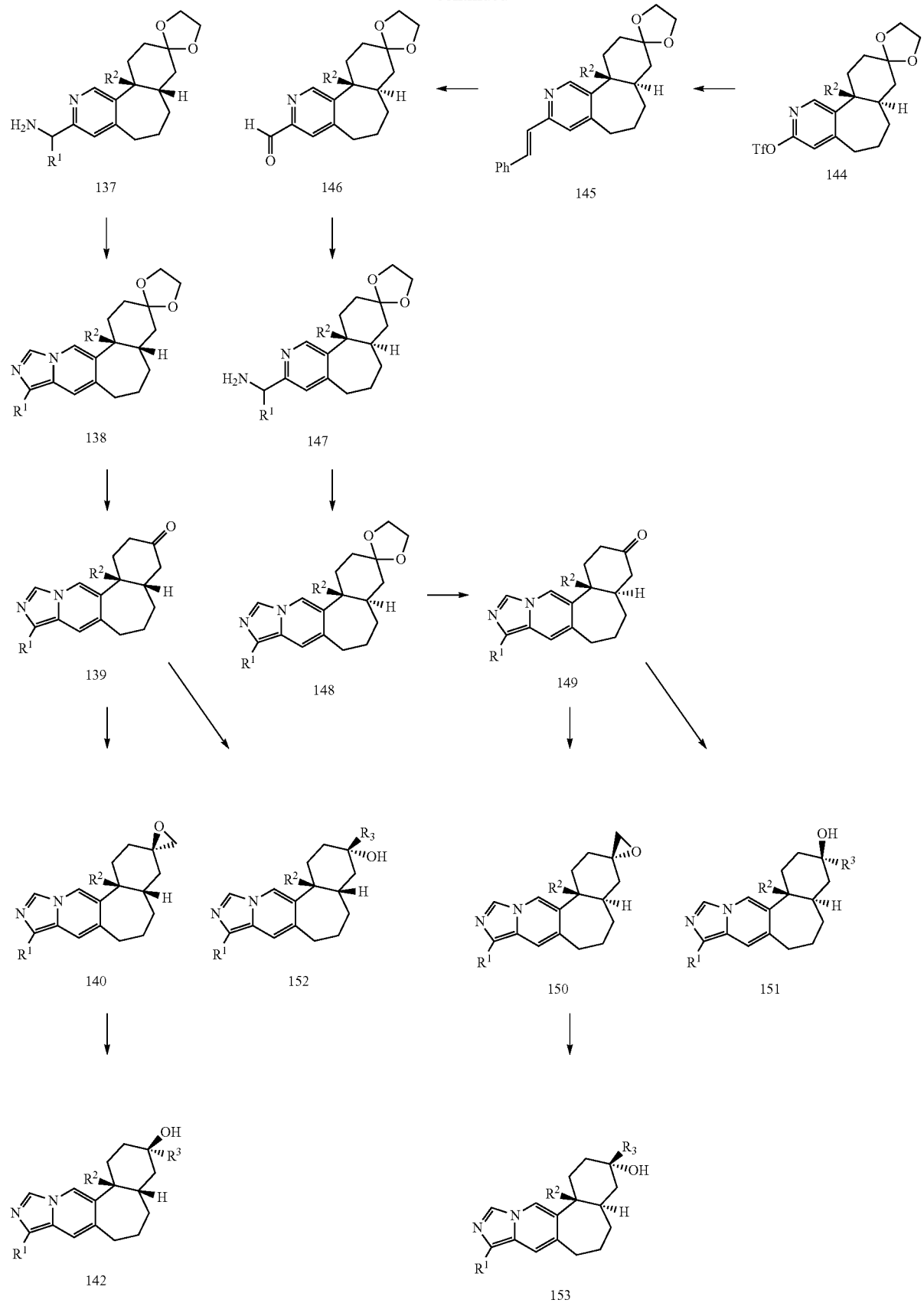

Example #166 rac-(3R,4aR,13bS)-9-(4-fluorophenyl)-13b-(pyridin-2-ylmethyl)-3-(trifluoromethyl)-2,3,4,4a,5,6,7,13b-octahydro-1H-benzo[3,4]cyclohepta[1,2-d]imidazo[1,5-a]pyridin-3-ol (151, $R^1$=4-Fluorophenyl, $R^2$=Pyridin-2-ylmethyl, $R^3$=Trifluoromethyl)

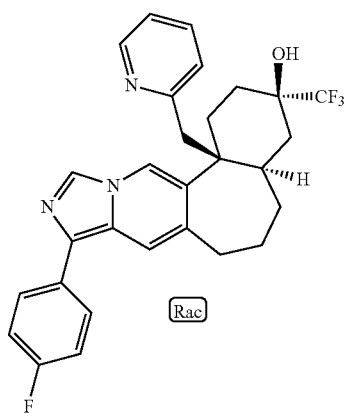 [SMILES: O[C@]1(C(F)(F)F)CC[C@@]2(Cc3ccccn3)c3cn4cnc(-c5ccc(F)cc5)c4cc3CCC[C@@H]2C1]

Step 1: 3-Methoxy-8-methylene-5,6,7,8-tetrahydroisoquinoline (125)

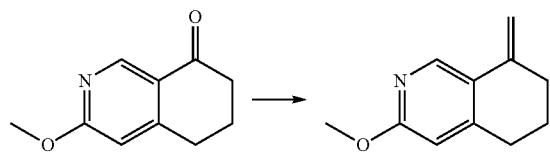

A flask with stir bar and nitrogen line was charged with methyltriphenylphosphonium bromide (3.11 g, 8.70 mmol), Et$_2$O (40 mL) and potassium 2-methylpropan-2-olate (0.976 g, 8.70 mmol). The mixture was stirred for about 45 min at rt then 3-methoxy-6,7-dihydroisoquinolin-8(5I-1)-one (prepared according to the procedure of Chorvat et. al., *J. Org. Chem.*, 1978, vol 43, no 5, pp 966-972) (1.34 g, 7.56 mmol) in Et$_2$O (10 mL) was added. After about 3 h potassium 2-methylpropan-2-olate (0.976 g, 8.70 mmol) and methyltriphenylphosphonium bromide (3.11 g, 8.70 mmol) were added. The mixture was stirred at rt overnight then the solids were removed by filtration and washed with ether (25 mL). The filtrate was concentrated under reduced pressure then the material was purified on silica gel (25 g) using a gradient of 25-100% EtOAc in heptane. Product fractions were combined and concentrated under reduced pressure to yield 3-methoxy-8-methylene-5,6,7,8-tetrahydroisoquinoline (125) (1.27 g, 96%); LC/MS, method 3, $R_t$=2.36 min, MS m/z 176 (M+H)$^+$. $^1$H NMR (400 MHz, CDCl$_3$) δ 8.46 (s, 1H), 6.47 (s, 1H), 5.42 (d, J=0.9 Hz, 1H), 4.90 (d, J=1.1 Hz, 1H), 3.92 (s, 3H), 2.79-2.76 (m, 2H), 2.55-2.48 (m, 2H), 1.91-1.80 (m, 2H).

Step 2: 3-Methoxy-6,7-dihydro-5H-cyclohepta[c]pyridin-8(9H)-one (126)

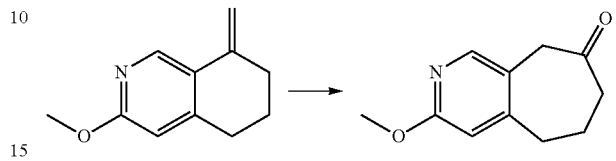

3-Methoxy-8-methylene-5,6,7,8-tetrahydroisoquinoline (125) (1.27 g, 7.25 mmol) in a mixture of water (5 mL) and MeOH (45 mL) was treated with [hydroxy(tosyloxy)iodo]benzene (2.84 g, 7.25 mmol) in MeOH (7 mL). After about 30 min water (15 mL) was added then the mixture was concentrated under reduced pressure to remove most of the MeOH. The mixture was basified to about pH 10 with sat. aq. NaHCO$_3$ then EtOAc (~30 mL) was added. Insoluble material was removed by filtration. The filtrate layers were separated then the aqueous layer was extracted with EtOAc (20 mL). The combined organic solutions were washed with brine (~25 mL) then dried over MgSO$_4$ and filtered. The filtrate was concentrated under reduced pressure then the material was purified on silica gel (40 g) using a gradient from 0-100% EtOAc in heptane. Pure product fractions were combined and concentrated under reduced pressure to yield 3-methoxy-6,7-dihydro-5H-cyclohepta[c]pyridin-8(9H)-one (126) (0.922 g, 67%); LC/MS, method 3, $R_t$=1.66 min, MS m/z 192 (M+H)$^+$. $^1$H NMR (400 MHz, CDCl$_3$) δ 7.91 (s, 1H), 6.57 (s, 1H), 3.92 (s, 3H), 3.63 (s, 2H), 2.93-2.85 (m, 2H), 2.61-2.54 (m, 2H), 2.04-1.94 (m, 2H).

Step 3: (E)-3-Methoxy-9-(pyridin-2-ylmethylene)-6,7-dihydro-5H-cyclohepta[c]pyridin-8(9H)-one (127, $R^5$=Pyridin-2-yl)

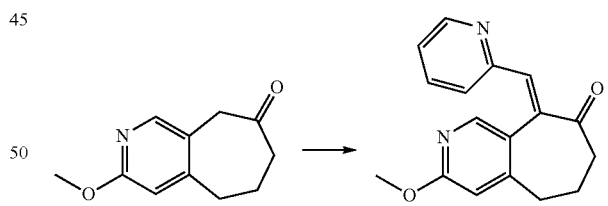

A flask was charged with 3-methoxy-6,7-dihydro-5H-cyclohepta[c]pyridin-8(9H)-one (126) (23.0 g, 120 mmol), THF (1000 mL) and picolinaldehyde (32.2 g, 301 mmol). The mixture was cooled to an internal temperature of about −70° C. then lithium bis(trimethylsilyl)amide [1 M solution] (126 mL, 126 mmol) was added over about 30 min keeping the internal temperature below about −65° C. The mixture was allowed to warm to about −10° C. in the cold bath. Acetic acid (13.8 mL, 241 mmol) then water (150 mL) were added. The mixture was concentrated under reduced pressure then partitioned between water (250 mL) and EtOAc (250 mL). The aqueous layer was extracted with EtOAc (150 mL). The combined organic solutions were with brine (100 mL) then dried over MgSO$_4$ then filtered The filtrate was concentrated under reduced pressure then the material was purified on silica gel (330 g) using a gradient from 0-75% EtOAc in DCM. Product fractions were combined and concentrated under reduced pressure to yield (E)-3-methoxy-9-(pyridin-2-ylmethylene)-6,7-dihydro-5H-cyclohepta[c]pyridin-8(9H)-one (127, $R^5$=Pyridin-2-yl) (36.15 g, 107%) $^1$H NMR showed material to contain picolinaldehyde and EtOAc. The material was used in the next step without further purification; LC/MS, method 3, $R_t$=1.90 min, MS m/z 281 (M+H)$^+$. $^1$H NMR (400 MHz, DMSO) δ 8.54-8.52 (m, 1H), 7.73 (s, 1H), 7.68-7.65 (m, 1H), 7.65 (s, 1H), 7.29-7.25 (m, 1H), 7.15 (d, J=8.0 Hz, 1H), 6.84 (s, 1H), 3.83 (s, 3H), 2.78 (t, J=7.2 Hz, 2H), 2.40 (t, J=7.1 Hz, 2H), 2.05-1.94 (m, 2H).

Step 4: 3-Methoxy-9-(pyridin-2-ylmethyl)-6,7-dihydro-5H-cyclohepta[c]pyridin-8(9H)-one (128, $R^2$=Pyridin-2-ylmethyl)

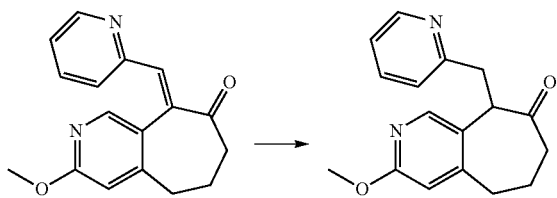 [SMILES: COc1cc2c(cn1)/C(=C\c1ccccn1)C(=O)CCC2 ; COc1cc2c(cn1)C(Cc1ccccn1)C(=O)CCC2]

(E)-3-Methoxy-9-(pyridin-2-ylmethylene)-6,7-dihydro-5H-cyclohepta[c]pyridin-8 (9H)-one (127, $R^5$=Pyridin-2-yl) (36.15 g, 129 mmol) in toluene (800 mL) with 20 wt % (wet) palladium hydroxide on carbon (4.53 g, 6.45 mmol) was stirred under a hydrogen filled balloon for about 7 h. The catalyst was removed by filtration through a pad of Celite® then the pad was washed with toluene (250 mL). The filtrate was concentrated under reduced pressure then the material was purified on silica gel (330 g) using 100% EtOAc. Product fractions were combined and concentrated under reduced pressure to yield 3-methoxy-9-(pyridin-2-ylmethyl)-6,7-dihydro-5H-cyclohepta[c]pyridin-8(9H)-one (128, $R^2$=Pyridin-2-ylmethyl) (26.64 g, 73%); LC/MS, method 3, $R_t$=1.14 min, MS m/z 283 (M+H)$^+$. $^1$H NMR (400 MHz, DMSO) δ 8.48-8.43 (m, 1H), 7.79 (s, 1H), 7.71-7.64 (m, 1H), 7.29 (d, J=7.8 Hz, 1H), 7.20-7.17 (m, 1H), 6.68 (s, 1H), 4.69-4.60 (m, 1H), 3.78 (s, 3H), 3.74-3.68 (m, 1H), 3.25-3.06 (m, 2H), 2.92-2.78 (m, 2H), 2.49-2.43 (m, 1H), 2.15-2.01 (m, 1H), 1.75-1.57 (m, 1H).

Step 5: 3-Methoxy-11a-(pyridin-2-ylmethyl)-6,7,11,11a-tetrahydro-5H-benzo[6,7]cyclohepta[1,2-c]pyridin-9(10H)-one (129, $R^2$=Pyridin-2-ylmethyl)

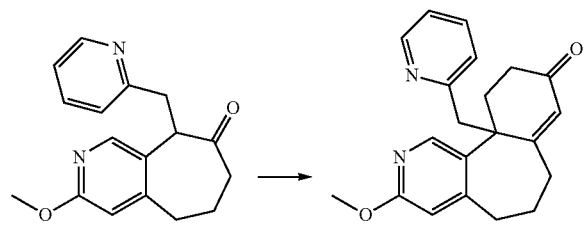 [SMILES: COc1cc2c(cn1)C(Cc1ccccn1)C(=O)CCC2 ; COc1cc2c(cn1)C1(Cc3ccccn3)CCC(=O)C=C1CCC2]

Sodium (2.21 g, 96 mmol) and EtOH (350 mL) were stirred until a solution was formed. 3-Methoxy-9-(pyridin-2-ylmethyl)-6,7-dihydro-5H-cyclohepta[c]pyridin-8 (9H)-one (128, $R^2$=Pyridin-2-ylmethyl) (26.6 g, 94 mmol) was suspended in EtOH (220 mL) then treated with the sodium ethoxide solution. The mixture was warmed to an internal temperature of about 63° C. then but-3-en-2-one (9.76 mL, 118 mmol) was added over about 2 to 3 min. The mixture was stirred at an internal temperature of about 65-70° C. for about 45 min then the mixture was cooled to rt. The solvents were removed under reduced pressure then the material was stirred with EtOH (250 mL) for about 30 min. The solids were collected by filtration then washed with EtOH (25 mL). The material was dried to yield 3-methoxy-11a-(pyridin-2-ylmethyl)-6,7,11,11a-tetrahydro-5H-benzo[6,7]cyclohepta[1,2-c]pyridin-9(10H)-one (129, $R^2$=Pyridin-2-ylmethyl) (18.89 g, 60.0%); LC/MS, method 3, $R_t$=1.12, 1.82 min, MS m/z 335 (M+H)$^+$. $^1$H NMR (400 MHz, DMSO) δ 8.44 (s, 1H), 8.42-8.37 (m, 1H), 7.63-7.58 (m, 1H), 7.18-7.14 (m, 1H), 7.13-7.08 (m, 1H), 6.58 (s, 1H), 5.88 (s, 1H), 3.83 (s, 3H), 3.70 (d, J=13.4 Hz, 1H), 3.56 (d, J=13.4 Hz, 1H), 2.87-2.75 (m, 1H), 2.74-2.59 (m, 2H), 2.41-2.05 (m, 4H), 1.85-1.65 (m, 3H).

Step 6: 3-Hydroxy-11a-(pyridin-2-ylmethyl)-6,7,11,11a-tetrahydro-5H-benzo[6,7]cyclohepta[1,2-c]pyridin-9(10H)-one (130, $R^2$=Pyridin-2-ylmethyl)

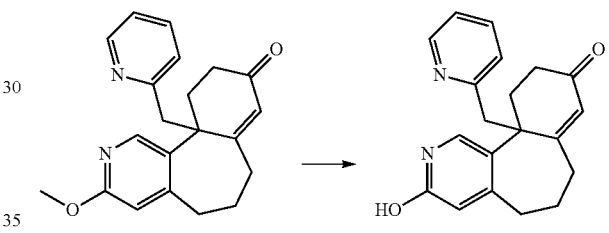

3-Methoxy-11a-(pyridin-2-ylmethyl)-6,7,11,11a-tetrahydro-5H-benzo[6,7]cyclohepta[1,2-c]pyridin-9(10H)-one (129, $R^2$=Pyridin-2-ylmethyl) (20.7 g, 61.9 mmol) in 1,4-dioxane (310 mL) was treated with hydrogen bromide (48% in water) (49.0 mL, 433 mmol). The mixture was warmed in an oil bath heated to about 100° C. After about 2 h the mixture was cooled to rt then concentrated under reduced pressure to remove most of the solvents. Water (100 mL) was added to the material then solvent was removed under reduced pressure. The material was allowed to stand at rt to form a solid mass. Water (30 mL) was added to dissolve the material then the solution was allowed to stand at rt until solids formed. The mixture was cooled in an ice/water bath for about 45 min. The solids were collected by filtration and the filtrate was used to wash residual solids from the flask onto the filter. The material was dried under vacuum at about 65° C. to give 21.0 grams of material. The filtrate was diluted with water (100 mL) then concentrated to an oil under reduced pressure. The material was dissolved in water (15 mL) then treated with about 25 mg of the solid obtained above. The mixture was cooled in ice/water bath for about 30 min. The solids were collected by filtration and the filtrate was used to wash residual solids from the flask onto filter. The material was dried under vacuum at about 65° C. to give 10.2 g of material. The two crops of solids obtained (31.2 grams total) were combined in water (155 mL) then dissolved with stirring and heating to about 40° C. The solution was cooled to rt then NaHCO$_3$ (129.6 mmol, 10.88 g) was slowly added to the stirred mixture. After about 3 h the solids were collected by filtration and washed with water (20 mL). The material was dried under vacuum at about 60° C. to yield 3-hydroxy-11a-(pyridin-2-ylmethyl)-6,7,11,11a-tetrahydro-5H-benzo[6,7]cyclohepta[1,2-c]pyridin-9(10H)-one (130, R²=Pyridin-2-ylmethyl) (16.29 g, 83%); LC/MS, method 3, R$_t$=0.43 min, MS m/z 321 (M+H)⁺. ¹H NMR (400 MHz, DMSO) δ 11.45 (s, 1H), 8.42-8.39 (m, 1H), 7.66-7.59 (m, 2H), 7.19-7.16 (m, 1H), 7.08 (d, J=7.8 Hz, 1H), 6.09 (s, 1H), 5.88 (s, 1H), 3.54-3.45 (m, 2H), 2.76-2.59 (m, 2H), 2.48-2.42 (m, 1H), 2.36-2.23 (m, 2H), 2.16-2.08 (m, 1H), 2.03-1.98 (m, 1H), 1.74-1.42 (m, 3H).

Step 7: rac-(7aR,11aR)-3-Hydroxy-11a-(pyridin-2-ylmethyl)-6,7,7a,8,11,11a-hexahydro-5H-benzo[6,7]cyclohepta[1,2-c]pyridin-9 (10H)-one (132, R²=Pyridin-2-ylmethyl) and rac-(7aR,11aS)-3-hydroxy-11a-(pyridin-2-ylmethyl)-6,7,7a,8,11,11a-hexahydro-5H-benzo[6,7]cyclohepta[1,2-c]pyridin-9 (10H)-one (131, R²=Pyridin-2-ylmethyl)

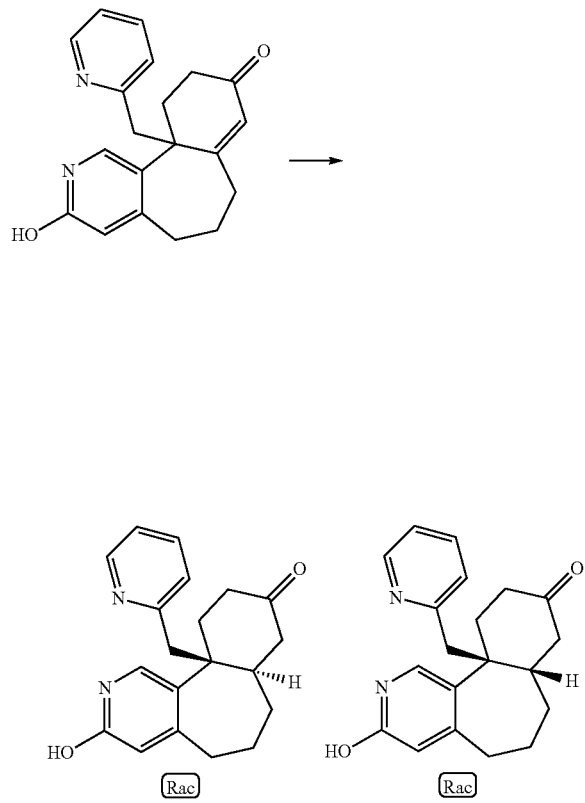

3-Hydroxy-11a-(pyridin-2-ylmethyl)-6,7,11,11a-tetrahydro-5H-benzo[6,7]cyclohepta[1,2-c]pyridin-9(10H)-one (130, R²=Pyridin-2-ylmethyl) (19.49 g, 60.8 mmol) in THF (775 mL) and pyridine (110 mL) with palladium on carbon (10 wt %) (2.92 g, 2.74 mmol) was shaken under t 50 psi hydrogen for about 18 h at rt. The catalyst was removed by filtration through a pad of Celite® then the pad was washed with EtOAc (400 mL) and DCM (400 mL). The filtrate was concentrated under reduced pressure. The material was purified in 4 portions on silica gel (330 g) using a gradient from 2-10% MeOH in DCM.

Fractions containing desired molecular weight material with a high Rf were combined and concentrated under reduced pressure to yield rac-(7aR,11aS)-3-hydroxy-11a-(pyridin-2-ylmethyl)-6,7,7a,8,11,11a-hexahydro-5H-benzo[6,7]cyclohepta[1,2-c]pyridin-9(1011)-one (132, R²=Pyridin-2-ylmethyl) (6.55 g, 33.4%); LC/MS, method 3, R$_t$=1.33 min, MS m/z 323 (M+H)⁺. ¹H NMR (400 MHz, DMSO) δ 11.01 (s, 1H), 8.43-8.38 (m, 1H), 7.54-7.49 (m, 1H), 7.14-7.10 (m, 1H), 6.59 (d, J=7.8 Hz, 1H), 6.55 (s, 1H), 6.17 (s, 1H), 3.50 (d, J=13.4 Hz, 1H), 3.32 (d, J=13.4 Hz, 1H), 3.27-3.20 (m, 1H), 3.15-3.03 (m, 1H), 2.72-2.68 (m, 1H), 2.62-2.52 (m, 1H), 2.21-2.06 (m, 2H), 2.05-1.85 (m, 4H), 1.62-1.59 (m, 2H), 1.37-1.27 (m, 1H).

Fractions containing desired molecular weight material with a low Rf were combined and concentrated under reduced pressure to yield rac-(7aR,11aR)-3-hydroxy-11a-(pyridin-2-ylmethyl)-6,7,7a,8,11,11a-hexahydro-5H-benzo[6,7]cyclohepta[1,2-c]pyridin-9(1011)-one (131, R²=Pyridin-2-ylmethyl) (6.8 g, 34.7%); LC/MS, method 3, R$_t$=1.23 min, MS m/z 323 (M+H)⁺. ¹H NMR (400 MHz, DMSO) δ 11.07 (s, 1H), 8.43-8.39 (m, 1H), 7.58-7.54 (m, 1H), 7.16-7.13 (m, 1H), 6.72 (d, J=7.8 Hz, 1H), 6.50 (s, 1H), 6.22 (s, 1H), 3.58 (d, J=12.8 Hz, 1H), 3.10-3.03 (m, 1H), 2.78 (d, J=12.8 Hz, 1H), 2.74-2.68 (m, 1H), 2.39-2.19 (m, 5H), 2.15-2.06 (m, 1H), 1.96-1.73 (m, 3H), 1.63-1.54 (m, 1H), 1.51-1.42 (m, 1H).

Step 8: rac-(7aR,11aS)-11a-(Pyridin-2-ylmethyl)-5,6,7,7a,8,10,11,11a-octahydrospiro[benzo[6,7]cyclohepta[1,2-c]pyridine-9,2'-[1,3]dioxolan]-3-ol (143, R²=Pyridin-2-ylmethyl)

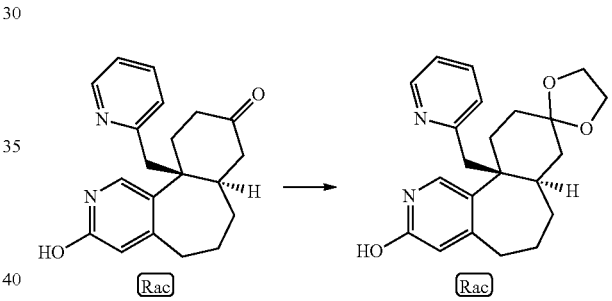

A flask fitted with a Dean-Stark apparatus was charged with rac-(7aR,11aS)-3-hydroxy-11a-(pyridin-2-ylmethyl)-6,7,7a,8,11,11a-hexahydro-5H-benzo[6,7]cyclohepta[1,2-c]pyridin-9(10H)-one (132, R²=Pyridin-2-ylmethyl) (6.8 g, 21.09 mmol), toluene (250 mL), ethane-1,2-diol (4.76 mL, 85 mmol) and pTSA (0.401 g, 2.109 mmol). The mixture was heated to reflux for about 2 h, cooled to rt then concentrated on under reduced pressure. The material was treated with sat. aq. NaHCO₃ (50 mL), water (50 mL) and EtOAc (~100 mL). The mixture was stirred for about 10 min then the solids were collected by filtration and washed with EtOAc (~15 mL). The material was dried under vacuum. The filtrate layers were separated then the aqueous layer was extracted with EtOAc (2×50 mL). The combined organic solutions were dried over MgSO₄, filtered then combined with solids from the first filtration and concentrated under reduced pressure to yield rac-(7aR,11aS)-11a-(pyridin-2-ylmethyl)-5,6,7,7a,8,10,11,11a-octahydrospiro[benzo[6,7]cyclohepta[1,2-c]pyridine-9,2'-[1,3]dioxolan]-3-ol (143, R²=Pyridin-2-ylmethyl) (7.25 g, 94%); LC/MS, method 3, R$_t$=1.49 min, MS m/z 367 (M+H)⁺. ¹H NMR (400 MHz, DMSO) δ 10.95 (s, 1H), 8.37-8.36 (m, 1H), 7.51-7.46 (m, 1H), 7.10-7.07 (m, 1H), 6.54 (s, 1H), 6.51 (d, J=7.8 Hz, 1H), 6.14 (s, 1H), 3.92-3.81 (m, 4H), 3.33 (d, J=13.3 Hz, 1H), 3.20-3.13 (m, 1H), 3.04 (d, J=13.3 Hz, 1H), 2.69-2.64 (m, 1H), 2.14-2.06 (m, 1H), 2.04-1.96 (m, 1H), 1.91-1.77 (m, 1H), 1.75-1.47 (m, 7H), 1.41-1.23 (m, 1H).

Step 9: rac-(7 aR,11aS)-11a-(Pyridin-2-ylmethyl)-5,6,7,7a,8,10,11,11a-octahydro spiro[benzo[6,7]cyclohepta[1,2-c]pyridine-9,2'-[1,3]dioxolan]-3-yl trifluoromethanesulfonate (144, R²=Pyridin-2-ylmethyl)

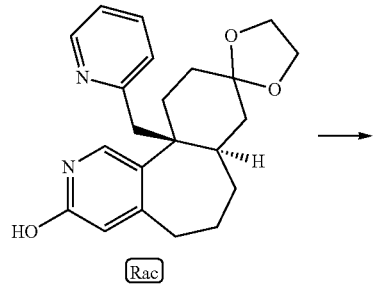

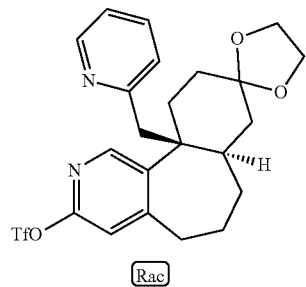

rac-(7aR,11aS)-11a-(Pyridin-2-ylmethyl)-5,6,7,7a,8,10,11,11a-octahydro spiro[benzo[6,7]cyclohepta[1,2-c]pyridine-9,2'-[1,3]dioxolan]-3-ol (143, R²=Pyridin-2-ylmethyl) (6.72 g, 18.3 mmol), DCM (150 mL) and TEA (6.39 mL, 45.8 mmol) was cooled to about 0° C. Trifluoromethanesulfonic anhydride (6.21 g, 22.0 mmol) was added keeping the internal temperature of the reaction mixture below about 5° C. After 45 min the mixture was allowed to warm to rt. After about 1 h the mixture was poured into sat. NaHCO₃ (200 mL). The layers were separated then the aqueous layer was extracted with DCM (50 mL). The organic solutions were combined, dried over MgSO₄, filtered and then concentrated under reduced pressure to yield rac-(7aR,11aS)-11a-(pyridin-2-ylmethyl)-5,6,7,7a,8,10,11,11a-octahydrospiro[benzo[6,7]cyclohepta[1,2-c]pyridine-9,2'-[1,3]dioxolan]-3-yl trifluoromethanesulfonate (144, R²=Pyridin-2-ylmethyl) (9.77 g, 107%); LC/MS, method 3, R$_t$=2.64 min, MS m/z 499 (M+H)⁺. Material was used directly in the next step without further manipulation.

Step 10: rac-(7 aR,11aS)-11a-(Pyridin-2-ylmethyl)-3-((E)-styryl)-5,6,7,7a,8,10,11,11a-octahydro spiro[benzo[6,7]cyclohepta[1,2-c]pyridine-9,2'-[1,3]dioxolane] (145, R²=Pyridin-2-ylmethyl)

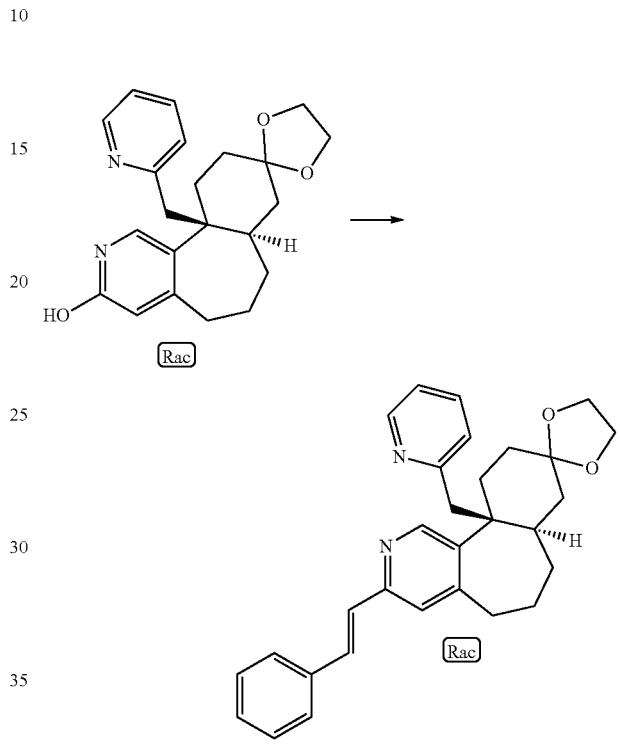

A flask with stir bar and nitrogen line was charged with rac-(7aR,11aS)-11a-(pyridin-2-ylmethyl)-5,6,7,7a,8,10,11,11a-octahydrospiro[benzo[6,7]cyclohepta[1,2-c]pyridine-9,2'-[1,3]dioxolan]-3-yl trifluoromethanesulfonate (144, R²=Pyridin-2-ylmethyl) (9.14 g, 18.34 mmol) (assumed 100% for previous reaction), (E)-styrylboronic acid (3.39 g, 22.9 mmol), cesium carbonate (14.94 g, 45.9 mmol), 1,4-dioxane (130 mL), water (32.5 mL) and bis(triphenylphosphine)palladium(II) dichloride (0.644 g, 0.917 mmol). The mixture was warmed in an oil bath heated to about 90° C. for about 30 min. The mixture was cooled then concentrated under reduced pressure. The material was partitioned between water (100 mL) and EtOAc (100 mL). The layers were separated then the organic solution was washed with brine (75 mL), dried over MgSO₄, filtered and concentrated under reduced pressure. The filtrate was concentrated under reduced pressure then the material was purified on silica gel (330 g) using 100% EtOAc. Product fractions were combined and concentrated under reduced pressure to yield (7aR,11aS)-11a-(pyridin-2-ylmethyl)-3-((E)-styryl)-5,6,7,7a,8,10,11,11a-octahydrospiro[benzo[6,7]cyclohepta[1,2-c]pyridine-9,2'-[1,3]dioxolane] (145, R²=Pyridin-2-ylmethyl) (6.15 g, 74%); LC/MS, method 3, R$_t$=2.50 min, MS m/z 453 (M+H)⁺. ¹H NMR (400 MHz, CDCl₃) δ 8.36 (s, 1H), 8.14 (s, 1H), 7.59-7.52 (m, 3H), 7.38-7.35 (m, 2H), 7.33-7.05 (m, 4H), 6.97-6.94 (m, 1H), 6.23 (s, 1H), 4.04-3.90 (m, 4H), 3.49 (d, J=13.8 Hz, 1H), 3.39-3.29 (m, 1H), 3.25 (d, J=13.3 Hz, 1H), 2.97-2.89 (m, 1H), 2.28-2.20 (m, 1H), 2.11-1.96 (m, 4H), 1.92-1.86 (m, 1H), 1.84-1.70 (m, 2H), 1.69-1.48 (m, 3H).

Step 11: rac-(7 aR,11aS)-11a-(Pyridin-2-ylmethyl)-5,6,7,7a,8,10,11,11a-octahydro spiro[benzo[6,7]cyclohepta[1,2-c]pyridine-9,2'-[1,3]dioxolane]-3-carb aldehyde (146, R²=Pyridin-2-ylmethyl)

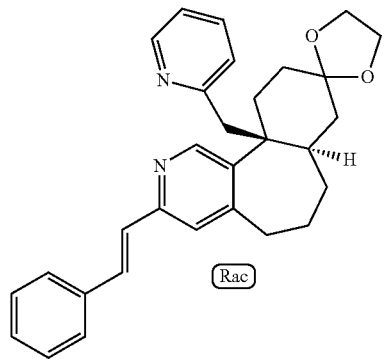

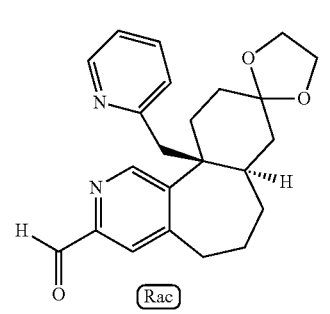

A flask with stir bar and nitrogen line was charged with rac-(7aR,11aS)-11a-(pyridin-2-ylmethyl)-3-((E)-styryl)-5,6,7,7a,8,10,11,11a-octahydro spiro[benzo[6,7]cyclohepta[1,2-c]pyridine-9,2'-[1,3]dioxolane] (145, R²=Pyridin-2-ylmethyl) (5.9 g, 13.04 mmol), 1,4-dioxane (150 mL), water (50.0 mL), 2,6-dimethylpyridine (3.04 mL, 26.1 mmol) and osmium(VIII) oxide (2.5 wt % in tert-butanol) (4.91 mL, 0.391 mmol). Sodium periodate (11.15 g, 52.1 mmol) was added and the mixture was stirred at rt for about 15 h. The mixture was diluted with water (200 mL) and EtOAc (50 mL). The layers were separated then the aqueous layer was extracted four times with EtOAc (50 mL). The combined organics were washed twice with brine (30 mL), dried over MgSO₄, filtered and concentrated under reduced pressure. The material was triturated with EtOAc and the solids collected by filtration and dried to yield rac-(7aR,11 aR)-11a-(pyridin-2-ylmethyl)-5,6,7,7a,8,10,11,11a-octahydrospiro[benzo[6,7]cyclohepta[1,2-c]pyridine-9,2'-[1,3]dioxolane]-3-carbaldehyde (146, R²=Pyridin-2-ylmethyl) (3.89 g, 79%); LC/MS, method 3, $R_t$=2.00 min, MS m/z 379 (M+H)⁺. ¹H NMR (400 MHz, DMSO) δ 9.87 (s, 1H), 8.29-8.27 (m, 1H), 8.22 (s, 1H), 7.69 (s, 1H), 7.40-7.36 (m, 1H), 7.05-7.02 (m, 1H), 6.41 (d, J=7.8 Hz, 1H), 3.94-3.84 (m, 4H), 3.50 (d, J=13.3 Hz, 1H), 3.44-3.36 (m, 1H), 3.20 (d, J=13.4 Hz, 1H), 3.07-3.02 (m, 1H), 2.19-2.11 (m, 2H), 2.06-1.94 (m, 2H), 1.94-1.83 (m, 2H), 1.75-1.66 (m, 3H), 1.62-1.57 (m, 1H), 1.49-1.34 (m, 1H).

Step 12: rac-(4-Fluorophenyl)((7aR,11aS)-11a-(pyridin-2-ylmethyl)-5,6,7,7a,8,10,11,11a-octahydrospiro[benzo[6,7]cyclohepta[1,2-c]pyridine-9,2'-[1,3]dioxolan]-3-yl)methanamine (147, R¹=4-Fluorophenyl, R²=Pyridin-2-ylmethyl)

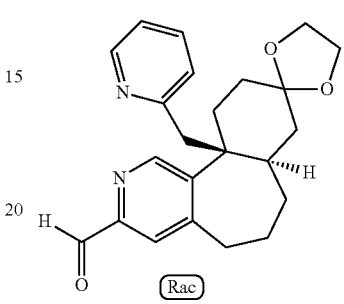

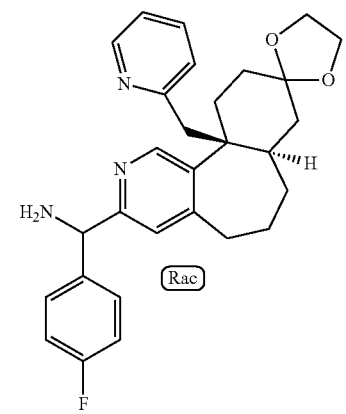

A flask with thermometer, septum, nitrogen line and stir bar was charged with rac-(7aR,11aS)-11a-(pyridin-2-ylmethyl)-5,6,7,7a,8,10,11,11a-octahydrospiro[benzo[6,7]cyclohepta[1,2-c]pyridine-9,2'-[1,3]dioxolane]-3-carb aldehyde (146, R²=Pyridin-2-ylmethyl) (0.5 g, 1.321 mmol) and THF (15 mL). The mixture was cooled to about −5° C. then LiHMDS (1 M in THF) (1.717 mL, 1.717 mmol) was added. The mixture was stirred at about −5° C. for about 30 min then (4-fluorophenyl)magnesium bromide (2 M in Et₂O) (1.321 mL, 2.64 mmol) was added. After about 1 h and 15 min water (2 mL) was added and the mixture stirred for about 15 min. The reaction mixture was diluted with EtOAc (25 mL) and water (~10 mL). The layers were separated then EtOAc (15 mL) and sat. aq. NH₄Cl (~7 mL) were added to the aqueous layer. The layers were separated then the combined organic solutions were dried over Na₂SO₄, filtered and concentrated under reduced pressure to yield crude rac-(4-fluorophenyl)((7aR,11aS)-11a-(pyridin-2-ylmethyl)-5,6,7,7a,8,10,11, 11a-octahydrospiro[benzo[6,7]cyclohepta[1,2-c]pyridine-9,2'-[1,3]dioxolan]-3-yl)methanamine (147, R¹=4-Fluorophenyl, R²=Pyridin-2-ylmethyl) (0.66 g, 105%) which was used directly in the Step 13 without further manipulation; LC/MS, method 3, $R_t$=1.67 min, MS m/z 474 (M+H)⁺.

Step 13: rac-(4aR,13bS)-9-(4-Fluorophenyl)-13b-(pyridin-2-ylmethyl)-1,2,4,4a,5,6,7,13b-octahydrospiro[benzo[3,4]cyclohepta[1,2-d]imidazo[1,5-a]pyridine-3,2'-[1,3]dioxolane] (148, R¹=4-Fluorophenyl, R²=Pyridin-2-ylmethyl)

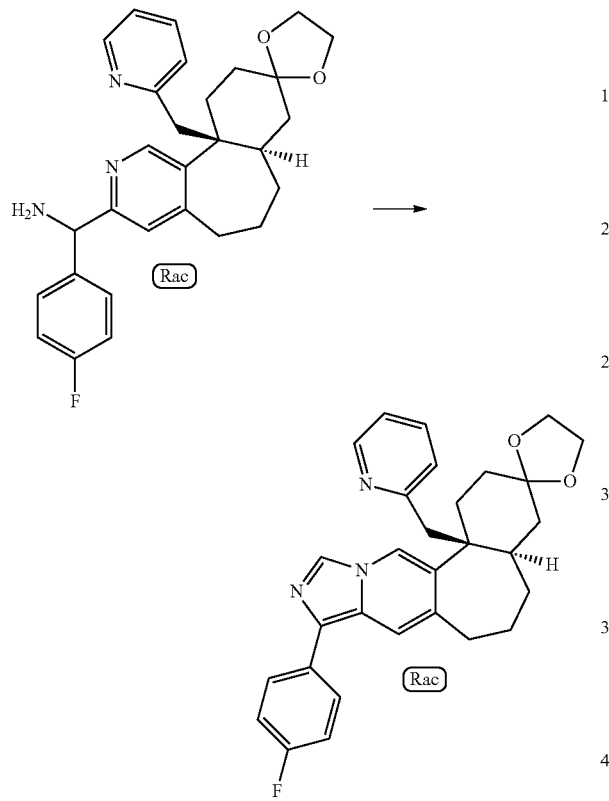

The crude rac-(4-fluorophenyl)((7 aR,11aS)— 11a-(pyridin-2-ylmethyl)-5,6,7,7a,8,10,11,11a-octahydro spiro[benzo[6,7]cyclohepta[1,2-c]pyridine-9,2'-[1,3]dioxolan]-3-yl)methanamine (147, R¹=4-Fluorophenyl, R²=Pyridin-2-ylmethyl) (0.66 g, 1.32 mmol assuming 100% yield for Step 12) from Step 12 in toluene (11 mL) was treated with diethoxymethyl acetate (1.07 g, 6.60 mmol) then the stirred mixture was placed in an oil bath preheated to about 100° C. for about 15 min. The mixture was cooled and concentrated under reduced pressure then the material was purified on silica gel (12 g) using 100% EtOAc. Product fractions were combined and concentrated under reduced pressure to yield rac-(4aR,13bS)-9-(4-fluorophenyl)-13b-(pyridin-2-ylmethyl)-1,2,4,4a,5,6,7,13b-octahydrospiro[benzo[3,4]cyclohepta[1,2-d]imidazo[1,5-a]pyridine-3,2'-[1,3]dioxolane] (148, R¹=4-Fluorophenyl, R²=Pyridin-2-ylmethyl) (0.383 g, 60.0% overall from rac-(7aR,11aS)-11a-(pyridin-2-ylmethyl)-5,6,7,7a,8,10,11,11a-octahydro spiro[benzo[6,7]cyclohepta[1,2-c]pyridine-9,2'-[1,3]dioxolane]-3-carb aldehyde (146, R²=Pyridin-2-ylmethyl) in Step 12); LC/MS, method 3, $R_t$=2.49 min, MS m/z 484 (M+H)⁺. ¹H NMR (400 MHz, DMSO) δ 8.37-8.32 (m, 1H), 8.18 (s, 1H), 7.97-7.90 (m, 3H), 7.72 (s, 1H), 7.39-7.35 (m, 1H), 7.26-7.19 (m, 2H), 7.04-7.00 (m, 1H), 6.50 (d, J=7.8 Hz, 1H), 3.94-3.86 (m, 4H), 3.53 (d, J=13.6 Hz, 1H), 3.38-3.34 (m, 1H), 3.16 (d, J=13.4 Hz, 1H), 3.07-3.00 (m, 1H), 2.23-2.16 (m, 1H), 2.12-2.06 (m, 1H), 2.01-1.52 (m, 8H), 1.45-1.33 (m, 1H).

Step 14: rac-(4aR,13bS)-9-(4-Fluorophenyl)-13b-(pyridin-2-ylmethyl)-4,4a,5,6,7,13b-hexahydro-1H-benzo[3,4]cyclohepta[1,2-d]imidazo[1,5-a]pyridin-3(2H)-one (149, R¹=4-Fluorophenyl, R²=Pyridin-2-ylmethyl)

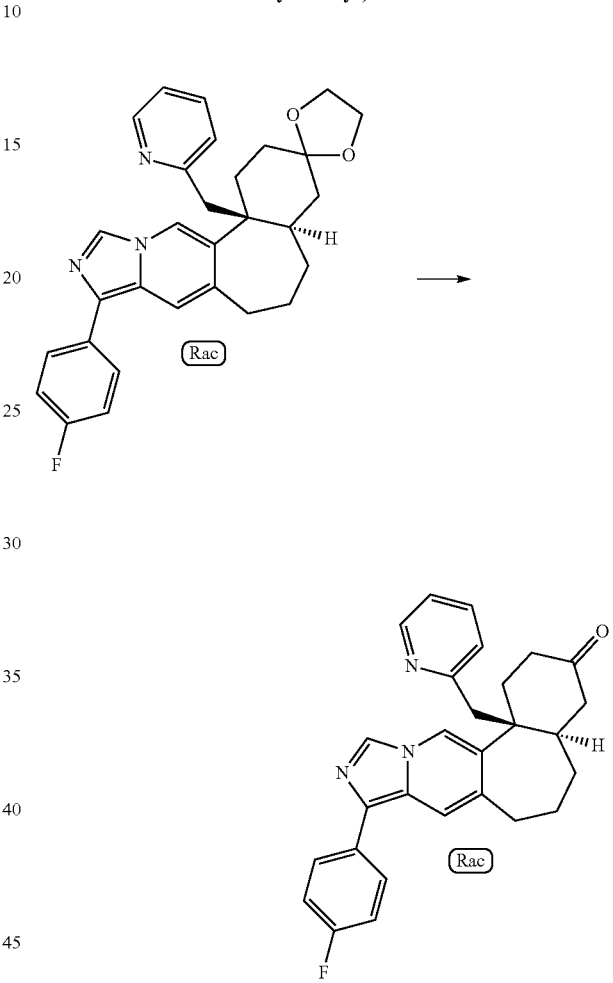

rac-(4aR,13bS)-9-(4-Fluorophenyl)-13b-(pyridin-2-ylmethyl)-1,2,4,4a,5,6,7,13b-octahydro spiro[benzo[3,4]cyclohepta[1,2-d]imidazo[1,5-a]pyridine-3,2'-[1,3]dioxolane] (148, R¹=4-Fluorophenyl, R²=Pyridin-2-ylmethyl) (0.380 g, 0.786 mmol) in 1,4-dioxane (8 mL) and water (2 mL) was treated with 6 N hydrochloric acid (0.52 mL, 3.1 mmol) then stirred at rt for about 4 h. Water (1 mL) was added and the mixture was stirred for about 12 h. Sat. aq. NaHCO₃ (~10 mL) and EtOAc (20 mL) were added to the mixture then the layers were separated. The organic layer was washed with brine (~15 mL) then dried over MgSO₄, filtered and concentrated to yield rac-(4aR,13bS)-9-(4-fluorophenyl)-13b-(pyridin-2-ylmethyl)-4,4a,5,6,7,13b-hexahydro-1H-benzo[3,4]cyclohepta[1,2-d]imidazo[1,5-a]pyridin-3(2H)-one (149, R¹=4-Fluorophenyl, R²=Pyridin-2-ylmethyl) (0.323 g, 94%); LC/MS, method 3, $R_t$=2.30 min, MS m/z 440 (M+H)⁺. ¹H NMR (400 MHz, DMSO) δ 8.38-8.36 (m, 1H), 8.18 (s, 1H), 7.96-7.90 (m, 3H), 7.75 (s, 1H), 7.43-7.39 (m, 1H), 7.27-7.19 (m, 2H), 7.08-7.04 (m, 1H), 6.59 (d, J=7.8 Hz, 1H), 3.70 (d, J=13.6 Hz, 1H), 3.45-3.38 (m, 2H), 3.20-3.02 (m, 2H), 2.69-2.62 (m, 1H), 2.29-1.87 (m, 7H), 1.72-1.63 (m, 1H), 1.46-1.32 (m, 1H).

Step 15: rac-(3R,4aR,13bS)-9-(4-Fluorophenyl)-13b-(pyridin-2-ylmethyl)-3-(trifluoromethyl)-2,3,4,4a,5,6,7,13b-octahydro-1H-benzo[3,4]cyclohepta[1,2-d]imidazo[1,5-a]pyridin-3-ol (151, R¹=4-Fluorophenyl, R²=Pyridin-2-ylmethyl, R³=Trifluoromethyl)

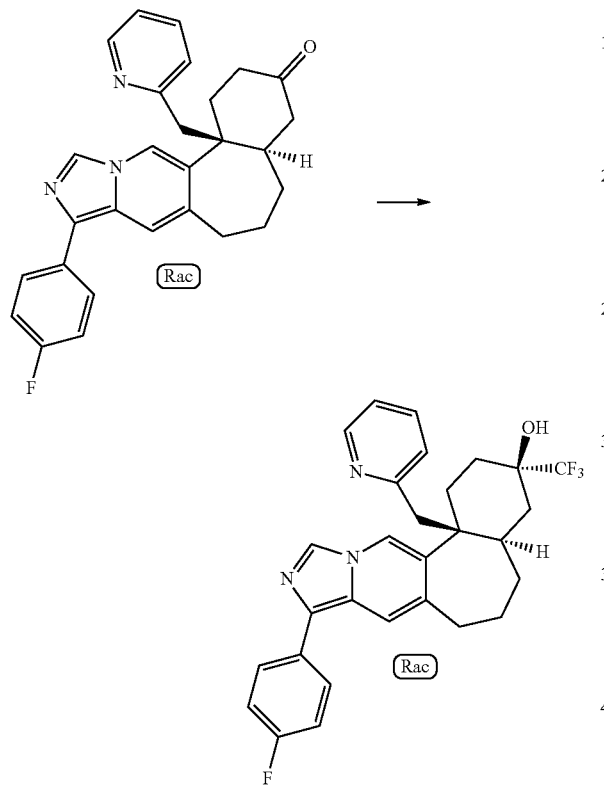

rac-(4aR,13bS)-9-(4-fluorophenyl)-13b-(pyridin-2-ylmethyl)-4,4a,5,6,7,13 b-hexahydro-1H-benzo[3,4]cyclohepta[1,2-d]imidazo[1,5-a]pyridin-3 (2H)-one (149, R¹=4-Fluorophenyl, R²=Pyridin-2-ylmethyl) (0.291 g, 0.662 mmol) was suspended in DME (7 mL) then CsF (0.060 g, 0.397 mmol) was added. The mixture was cooled to about −10° C. then trimethyl(trifluoromethyl)silane (0.185 g, 1.30 mmol) was added. After 15 min TBAF (1 M in THF) (0.695 mL, 0.695 mmol) was added and the mixture was allowed to warm to rt. The mixture was concentrated under reduced pressure then water (25 mL) was added to the material and the resulting solids collected by filtration. The material was purified on silica gel (12 g) using a gradient from 0-10% MeOH in DCM. Product fractions were combined and concentrated under reduced pressure to yield rac-(3R,4aR,13bS)-9-(4-fluorophenyl)-13b-(pyridin-2-ylmethyl)-3-(trifluoromethyl)-2,3,4,4a,5,6,7,13b-octahydro-1H-benzo[3,4]cyclohepta[1,2-d]imidazo[1,5-a]pyridin-3-ol (151, R¹=4-Fluorophenyl, R²=Pyridin-2-ylmethyl, R³=Trifluoromethyl) (0.185 g, 55%); LC/MS, method 2, $R_t$=2.54 min, MS m/z 510 (M+H)⁺. ¹H NMR (400 MHz, DMSO) δ 8.39-8.37 (m, 1H), 8.18 (s, 1H), 7.98-7.89 (m, 3H), 7.74 (s, 1H), 7.40-7.36 (m, 1H), 7.27-7.18 (m, 2H), 7.09-7.03 (m, 1H), 6.47 (d, J=7.8 Hz, 1H), 5.97 (s, 1H), 3.59 (d, J=13.2 Hz, 1H), 3.43-3.32 (m, 1H), 3.15 (d, J=13.4 Hz, 1H), 3.08-3.03 (m, 1H), 2.23-2.17 (m, 1H), 2.13-2.07 (m, 1H), 2.04-1.86 (m, 3H), 1.83-1.67 (m, 5H), 1.46-1.36 (m, 1H).

Example #167 rac-(3R,4aS,13bS)-9-(4-Fluorophenyl)-3-(methoxymethyl)-13b-(pyridin-2-ylmethyl)-2,3,4,4a,5,6,7,13b-octahydro-1H-benzo[3,4]cyclohepta[1,2-d]imidazo[1,5-a]pyridin-3-ol (142, R¹=4-Fluorophenyl, R²=Pyridin-2-ylmethyl, R³=Methoxymethyl)

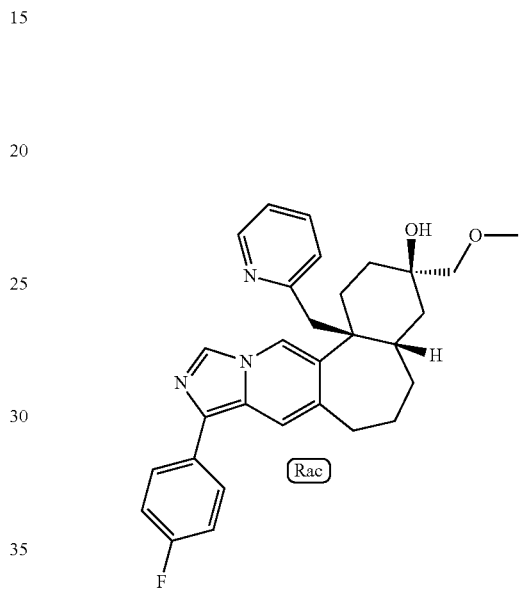

rac-(3R,4aS,13bS)-9-(4-Fluorophenyl)-3-(methoxymethyl)-13b-(pyridin-2-ylmethyl)-2,3,4,4a,5,6,7,13b-octahydro-1H-benzo[3,4]cyclohepta[1,2-d]imidazo[1,5-a]pyridin-3-ol (142, R¹=4-Fluorophenyl, R²=Pyridin-2-ylmethyl, R³=Methoxymethyl) was prepared from rac-(4aR,13bR)-9-(4-fluorophenyl)-13b-(pyridin-2-ylmethyl)-4,4a,5,6,7,13b-hexahydro-1H-benzo[3,4]cyclohepta[1,2-d]imidazo[1,5-a]pyridin-3(2H)-one (139, R¹=4 Fluorophenyl, R²=Pyridin-2-ylmethyl) [prepared in 7 steps from rac-(7aR,11aR)-3-hydroxy-11a-(pyridin-2-ylmethyl)-6,7,7a,8,11,11a-hexahydro-5H-benzo[6,7]cyclohepta[1,2-c]pyridin-9(10H)-one (131, R²=Pyridin-2-ylmethyl) in a manner similar to Example 166, steps 8, 9, 10, 11, 12, 13 and 14] in 2 steps in a manner similar to Example 11, steps 4 and 5 to yield rac-(3R,4aS,13bS)-9-(4-Fluorophenyl)-3-(methoxymethyl)-13b-(pyridin-2-ylmethyl)-2,3,4,4a,5,6,7,13b-octahydro-1H-benzo[3,4]cyclohepta[1,2-d]imidazo[1,5-a]pyridin-3-ol (142, R¹=4-Fluorophenyl, R²=Pyridin-2-ylmethyl, R³=Methoxymethyl); LC/MS, method 2, $R_t$=2.25 min, MS m/z 486 (M+H)⁺. ¹H NMR (400 MHz, DMSO) δ 8.39-8.33 (m, 1H), 8.24 (s, 1H), 7.99-7.87 (m, 2H), 7.70 (d, J=8.8 Hz, 2H), 7.46-7.43 (m, 1H), 7.28-7.19 (m, 2H), 7.10-7.07 (m, 1H), 6.65 (d, J=7.8 Hz, 1H), 4.22 (s, 1H), 3.59 (d, J=12.7 Hz, 1H), 3.19-3.03 (m, 5H), 2.98 (s, 2H), 2.87 (d, J=12.7 Hz, 1H), 2.48-2.41 (m, 1H), 1.92-1.82 (m, 3H), 1.71-1.21 (m, 6H), 1.10-1.07 (m, 1H).

Example #168

(3R,4aR,12bR)-12b-ethyl-9-(4-(methylsulfonyl)phenyl)-3-(trifluoromethyl)-1,2,3,4,4a,5,6,7,9,12b-decahydrobenzo[6,7]cyclohepta[1,2-f]indazol-3-ol (11, R$^1$=4-(Methylsulfonyl)phenyl, R$^2$=Ethyl, R$^3$=Trifluoromethyl)

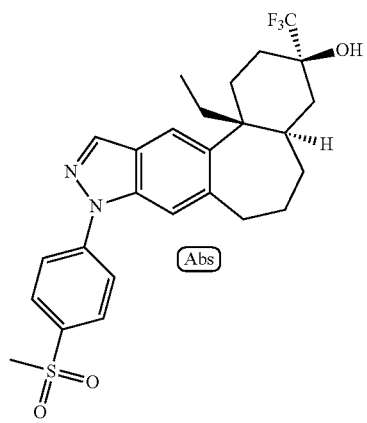 [SMILES: CC[C@@]12CC[C@](O)(C(F)(F)F)C[C@H]1CCCc1cc3c(cnn3-c3ccc(S(C)(=O)=O)cc3)cc12]

Step 1: (3R,4aR,12bR)-12b-ethyl-9-(4-(methylthio)phenyl)-3-(trifluoromethyl)-1,2,3,4,4a,5,6,7,9,12b-decahydrobenzo[6,7]cyclohepta[1,2-f]indazol-3-ol (11, R$^1$=4-(Methylthio)phenyl, R$^2$=Ethyl, R$^3$=Trifluoromethyl)

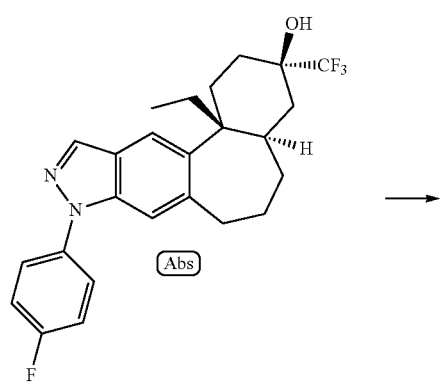

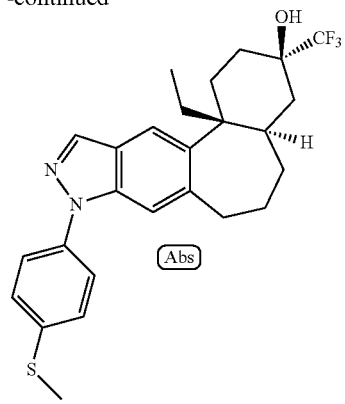

(3R,4aR,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol (11, R$^1$=4-Fluorophenyl, R$^2$=Ethyl, R$^3$=Trifluoromethyl) (0.240 g, 0.538 mmol), sodium methanethiolate (0.188 g, 2.69 mmol) and N,N-dimethylacetamide (12 mL) were heated via microwave at about 90° C. for about 1 h. The reaction mixture was purified without manipulation in two portions by preparative reverse phase HPLC using a Hypersil HS C18 column (250 mm×21.2 mm, 8 μm particle size) with a gradient of 50-100% MeCN in 0.05 N aq. ammonium acetate pH 4.5 buffer. Product fractions were concentrated under reduced pressure then basified with sat. NaHCO$_3$ then extracted with EtOAc. The organic solution was dried over MgSO$_4$, filtered and concentrated under reduced pressure to yield (3R,4aR,12bR)-12b-ethyl-9-(4-(methylthio)phenyl)-3-(trifluoromethyl)-1,2,3,4,4a,5,6,7,9,12b-decahydrobenzo[6,7]cyclohepta[1,2-f]indazol-3-ol (11, R$^1$=4-(Methylthio)phenyl, R$^2$=Ethyl, R$^3$=Trifluoromethyl) (0.230 g, 90%); LC/MS, method 3, R$_t$=2.90 min, MS m/z 475 (M+H)$^+$. $^1$H NMR (400 MHz, DMSO) δ 8.24 (d, J=1.3 Hz, 1H), 7.83 (s, 1H), 7.75-7.68 (m, 2H), 7.57 (s, 1H), 7.48-7.42 (m, 2H), 5.84 (s, 1H), 3.23-3.19 (m, 1H), 2.95-2.90 (m, 1H), 2.54 (s, 3H), 2.27-2.18 (m, 1H), 2.15-1.95 (m, 4H), 1.91-1.76 (m, 2H), 1.70-1.57 (m, 5H), 1.38-1.29 (m, 1H), 0.43 (t, J=7.3 Hz, 3H).

Step 2: (3R,4aR,12bR)-12b-ethyl-9-(4-(methylsulfonyl)phenyl)-3-(trifluoromethyl)-1,2,3,4,4a,5,6,7,9,12b-decahydrobenzo[6,7]cyclohepta[1,2-f]indazol-3-ol (11, R$^1$=4-(Methylsulfonyl)phenyl, R$^2$=Ethyl, R$^3$=Trifluoromethyl)

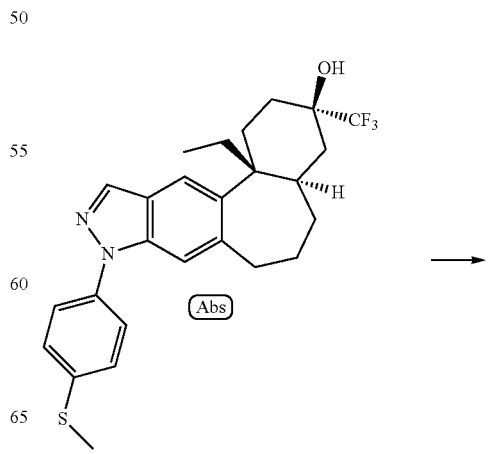

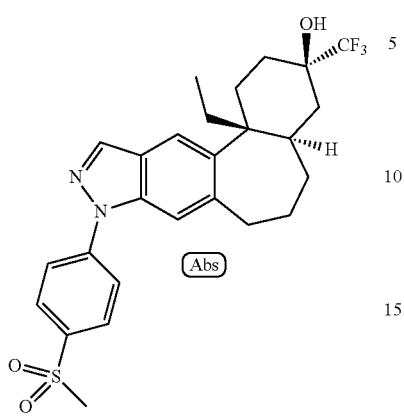

(3R,4aR,12bR)-12b-Ethyl-9-(4-(methylthio)phenyl)-3-(trifluoromethyl)-1,2,3,4,4a,5,6,7,9,12b-decahydrobenzo[6,7]cyclohepta[1,2-f]indazol-3-ol (11, R¹=4-(Methylthio)phenyl, R²=Ethyl, R³=Trifluoromethyl) (230 mg, 0.485 mmol) in acetone (10 mL) and water (2 mL) was treated with 3-chlorobenzoperoxoic acid (543 mg, 2.42 mmol) at rt. After 30 min the mixture was concentrated under reduced pressure then the material was partitioned between sat. aq. NaHCO₃ (15 mL), water (15 mL) and EtOAc (30 mL). The organic layer was washed with brine (10 mL), dried over MgSO₄ and filtered. The filtrate was concentrated under reduced pressure then the material was purified on silica gel (12 g) using 0-40% EtOAc in DCM. Product fractions were concentrated under reduced pressure then triturated with Et₂O (1.5 mL) in heptane (20 mL). The solids were collected by filtration and dried to yield (3R,4aR,12bR)-12b-ethyl-9-(4-(methylsulfonyl)phenyl)-3-(trifluoromethyl)-1,2,3,4,4a,5,6,7,9,12b-decahydrobenzo[6,7]cyclohepta[1,2-f]indazol-3-ol (11, R¹=4-(Methylsulfonyl)phenyl, R²=Ethyl, R³=Trifluoromethyl) (110.6 mg, 45.0%); LC/MS, method 2, $R_t$=2.43 min, MS m/z 507 (M+H)⁺. ¹H NMR (400 MHz, DMSO) δ 8.37 (d, J=0.8 Hz, 1H), 8.14-8.06 (m, 4H), 7.88 (s, 1H), 7.80 (s, 1H), 5.86 (s, 1H), 3.30 (s, 3H), 3.28-3.22 (m, 1H), 3.02-2.97 (m, 1H), 2.29-2.20 (m, 1H), 2.16-1.98 (m, 4H), 1.93-1.75 (m, 2H), 1.73-1.54 (m, 5H), 1.41-1.30 (m, 1H), 0.44 (t, J=7.3 Hz, 3H).

Example #169

(3S,4aS,12bS)-12b-ethyl-9-(4-(methylsulfonyl)phenyl)-3-(trifluoromethyl)-1,2,3,4,4a,5,6,7,9,12b-decahydrobenzo[6,7]cyclohepta[1,2-f]indazol-3-ol (11, R¹=4-(Methylsulfonyl)phenyl, R²=Ethyl, R³=Trifluoromethyl)

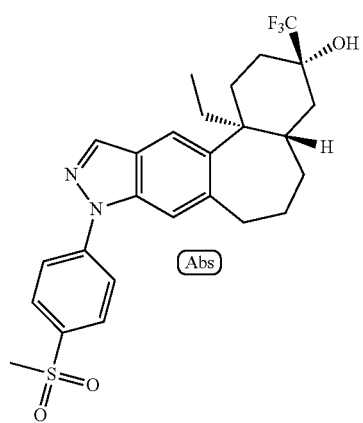 [SMILES: CC[C@]12CC[C@@](O)(C(F)(F)F)C[C@@H]1CCCc1cc3c(cnn3-c3ccc(S(C)(=O)=O)cc3)cc12]

The compound was prepared from (3S,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazole-3-ol (11, R¹=4-Fluorophenyl, R²=Ethyl, R³=Trifluoromethyl) in the manner described for the preparation of Example 168. LC/MS, method 2, $R_t$=2.43 min, MS m/z 507 (M+H)⁺.

Example #170

(3S,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-yl sulfamate

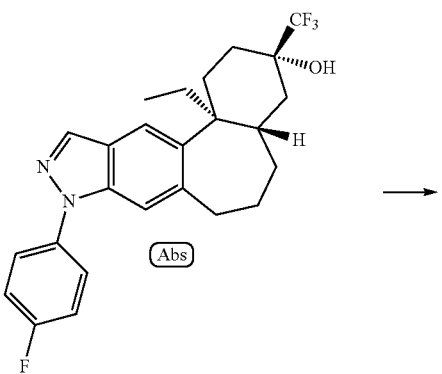

297
-continued

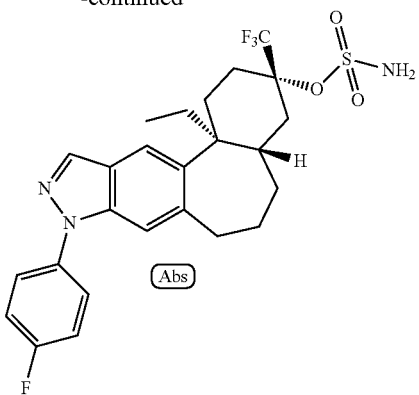

(3S,4aS,12bS)-12b-Ethyl-9-(4-fluorophenyl)-3-(trifluoromethyl)-1,2,3,4,4a,5,6,7,9,12b-decahydrobenzo[6,7]cyclohepta[1,2-f]indazol-3-ol (11, $R^1$=4-Fluorophenyl, $R^2$=Ethyl, $R^3$=Trifluoromethyl) (0.125 g, 0.280 mmol) in N,N-dimethylacetamide (3 mL) was stirred and treated with sulfamoyl chloride (0.105 g, 0.91 mmol). After about 3 h sulfamoyl chloride (0.080 g, 0.69 mmol) was added and the mixture was stirred for about 14 h at rt. The reaction mixture was purified without manipulation in one portion by preparative reverse phase HPLC using a Hypersil HS C18 column (250 mm×21.2 mm, 8 um particle size) with a gradient of 25-100% MeCN in 0.05 N aq. ammonium acetate pH 4.5 buffer. Product fractions were concentrated under reduced pressure then diluted with water (15 mL). The solids were collected by filtration then washed with water (5 mL) and dried to yield (3S,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-yl sulfamate (109 mg, 74%); LC/MS, method 2, $R_t$=2.86 min, MS m/z 526 (M+H)$^+$. $^1$H NMR (400 MHz, DMSO) δ 8.26 (d, J=0.8 Hz, 1H), 8.02 (s, 2H), 7.86 (s, 1H), 7.81-7.78 (m, 2H), 7.57 (s, 1H), 7.45-7.37 (m, 2H), 3.23-3.18 (m, 2H), 2.98-2.92 (m, 1H), 2.45-2.18 (m, 4H), 2.16-1.95 (m, 3H), 1.94-1.61 (m, 4H), 1.42-1.27 (m, 1H), 0.43 (t, J=7.3 Hz, 3H).

Example #171

2-(((3S,4aS,12bS)-12b-Ethyl-9-(4-fluorophenyl)-3-(trifluoromethyl)-1,2,3,4,4a,5,6,7,9,12b-decahydrobenzo[6,7]cyclohepta[1,2-f]indazol-3-yl)oxy)acetamide

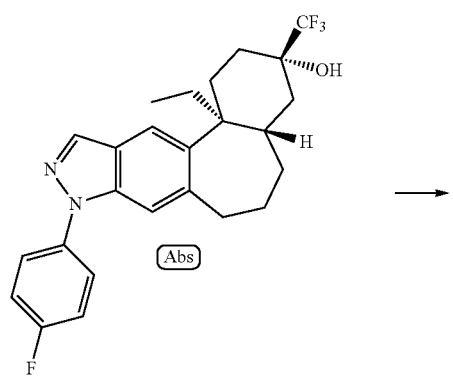

298
-continued

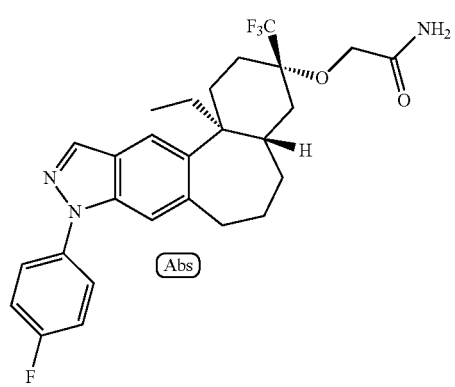

A flask with stir bar and nitrogen line was charged with (3S,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol (11, $R^1$=4-Fluorophenyl, $R^2$=Ethyl, $R^3$=Trifluoromethyl) (0.230 g, 0.515 mmol)], DMF (3 mL) and sodium hydride (60 wt % in oil, 12.0 mg, 0.30 mmol). The mixture was stirred at rt for about 20 min then cooled to about 0° C. Ethyl 2-bromoacetate (0.086 g, 0.515 mmol) was added then the mixture was allowed to warm to rt for about 12 h. Sodium hydride (60 wt % in oil, 20 mg, 0.500 mmol) was added then after about 15 min ethyl 2-bromoacetate (0.120 g, 0.719 mmol) was added dropwise over about 1 h. Sodium hydride (60 wt % in oil, 20 mg, 0.50 mmol) was added then after about 10 min ethyl 2-bromoacetate (0.120 g, 0.719 mmol) was added dropwise over about 10 min. The mixture was concentrated under reduced pressure, dissolved in 7 M ammonia in MeOH (5 mL, 35.0 mmol) transferred to a microwave vial and heated in a microwave at about 130° C. for about 1 h. The reaction mixture was purified without manipulation in one portion by preparative reverse phase HPLC using a Hypersil HS C18 column (250 mm×21.2 mm, 8 um particle size) with a gradient of 15-100% MeCN in 0.05 N aq. ammonium acetate pH 4.5 buffer. Product fractions were concentrated under reduced pressure then lyophilized to yield 2-(((3S,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-yl)oxy)acetamide (0.046 g, 18%); LC/MS, method 2, $R_t$=2.82 min, MS m/z 504 (M+H)$^+$. $^1$H NMR (400 MHz, DMSO) δ 8.26 (d, J=0.7 Hz, 1H), 7.84 (s, 1H), 7.83-7.77 (m, 2H), 7.57 (s, 1H), 7.45-7.37 (m, 2H), 7.33 (s, 1H), 7.20 (s, 1H), 4.02 (d, J=14.7 Hz, 1H), 3.95 (d, J=14.8

Hz, 1H), 3.27-3.20 (m, 1H), 2.97-2.91 (m, 1H), 2.26-1.97 (m, 5H), 1.94-1.80 (m, 4H), 1.79-1.56 (m, 3H), 1.40-1.30 (m, 1H), 0.44 (t, J=7.3 Hz, 3H).

Example #172

2-(((3S,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-yl)oxy)acetic acid

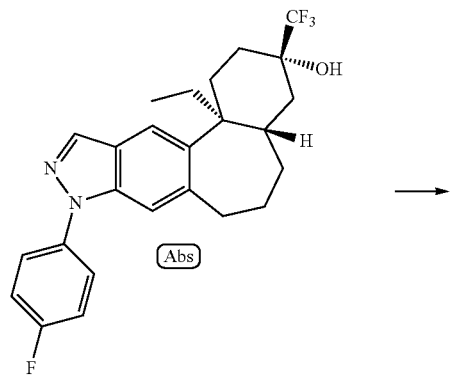

added to the mixture then after about 20 min sodium hydride (60 wt % in oil, 0.027 g, 0.672 mmol) and another portion of benzyl 2-bromoacetate (385 mg, 1.68 mmol). The mixture was transferred to a microwave vial then it was heated in a microwave at about 130° C. for about 20 min. Water (1 mL) and lithium hydroxide (200 mg, 8.33 mmol) were added then the mixture was heated in microwave at about 130° C. for about 20 min. Acetic acid (1.5 mL) was added then the reaction mixture was purified without further manipulation in one portion by preparative reverse phase HPLC using a Hypersil HS C18 column (250 mm×21.2 mm, 8 µm particle size) with a gradient of 15-100% MeCN in 0.05 N aq. ammonium acetate pH 4.5 buffer. Product fractions were concentrated under reduced pressure then the material was suspended in water (~3 mL), collected by filtration then dried to yield 2-(((3S,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-yl)oxy)acetic acid (18.3 mg, 10.80%); LC/MS, method 2, $R_t$=2.60 min, MS m/z 505 (M+H)$^+$. $^1$H NMR (400 MHz, DMSO) δ 12.72 (s, 1H), 8.26 (s, 1H), 7.83 (s, 1H), 7.82-7.78 (m, 2H), 7.57 (s, 1H), 7.43-7.37 (m, 2H), 4.21 (s, 2H), 3.27-3.20 (m, 1H), 2.96-2.91 (m, 1H), 2.31-2.09 (m, 3H), 2.08-1.98 (m, 2H), 1.89-1.76 (m, 4H), 1.70-1.61 (m, 3H), 1.40-1.29 (m, 1H), 0.44 (t, J=7.2 Hz, 3H).

Scheme 24:

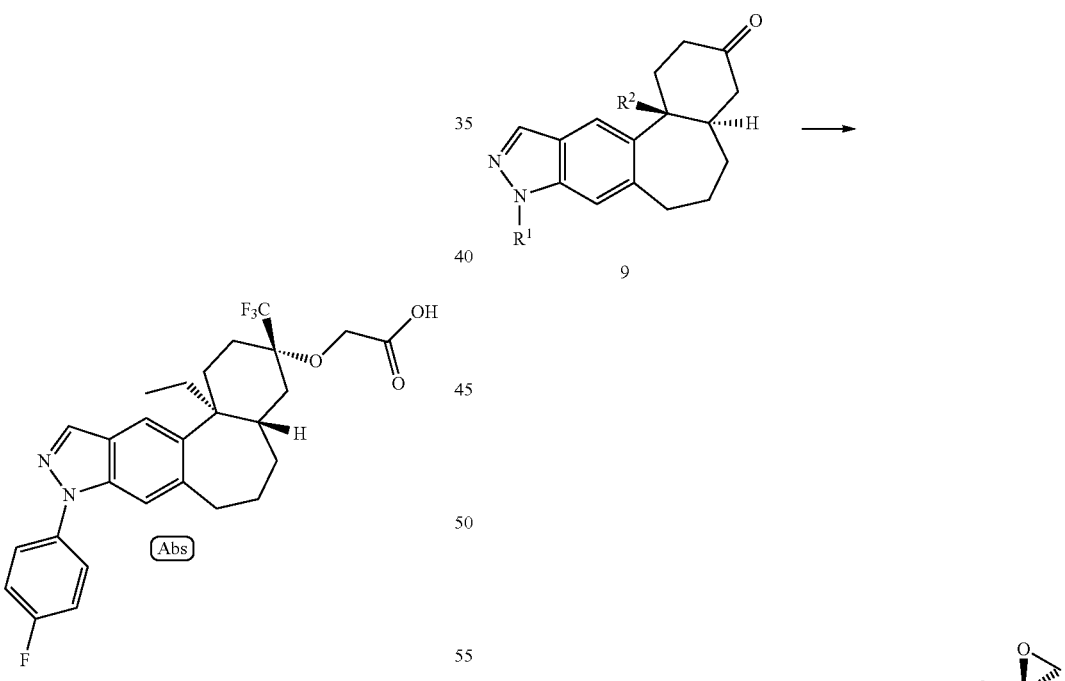

A flask with stir bar and nitrogen line was charged with (3S,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol (11, R$^1$=4-Fluorophenyl, R$^2$=Ethyl, R$^3$=Trifluoromethyl) (0.15 g, 0.336 mmol), THF (3 mL) and sodium hydride (60 wt % in oil, 0.027 g, 0.672 mmol) then warmed to about 65° C. for about 15 min. The mixture was cooled to rt then benzyl 2-bromoacetate (0.096 g, 0.420 mmol) was added and the mixture was stirred for about 20 min. Benzyl 2-bromoacetate (0.096 g, 0.420 mmol) was

301

Preparation of rac-(2'R,4aR,12bR)-12b-Ethyl-9-(4-fluorophenyl)-2,4,4a,5,6,7,9,12b-octahydro-1H-spiro[benzo[6,7]cyclohepta[1,2-f]indazole-3,2'-oxirane] (154, $R^1$=4-Fluorophenyl, $R^2$=Ethyl)

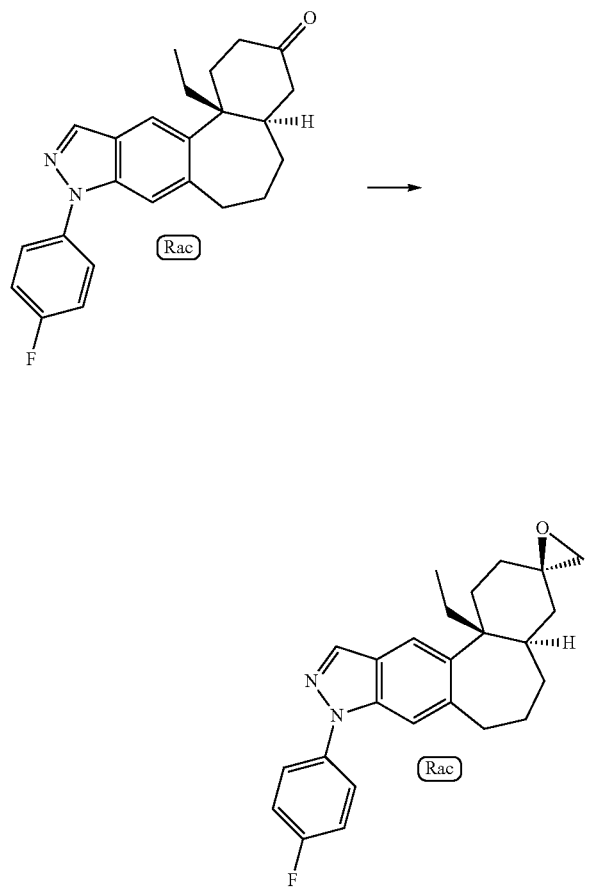

A flask with stir bar and nitrogen line was charged with sodium hydride (60 wt % in oil, 0.212 g, 5.31 mmol) and DMSO (9 mL) then the mixture was warmed in an oil bath heated to about 65° C. for about 1 h. The mixture was cooled to rt, diluted with THF (18 mL) then cooled to about 0° C. Trimethylsulfonium iodide (1.084 g, 5.31 mmol) was added then the mixture was stirred for about 15 min. rac-(4aR,12bR)-12b-Ethyl-9-(4-fluorophenyl)-1,4,4a,5,6,7,9,12b-octahydrobenzo[6,7]cyclohepta[1,2-f]indazole-3 (2H)-one (9, $R^1$=4-Fluorophenyl, $R^2$=Ethyl) (0.800 g, 2.125 mmol) was added in one portion then the mixture was stirred and allowed to warm to rt. After stirring overnight the mixture was concentrated under reduced pressure to remove THF. The mixture was partitioned between water (50 mL) and EtOAc (50 mL). The aqueous layer was extracted with EtOAc (25 mL). The combined organics were washed with water (2×25 mL) then brine (25 mL), dried over $MgSO_4$, then filtered. The filtrate was concentrated under reduced pressure then the material was purified on silica gel (40 g) using 0-10% EtOAc in DCM. Product fractions containing the epoxide isomer with the higher $R_f$ (TLC, 95:5 DCM/EtOAc, vis by UV) were collected and concentrated under reduced pressure to yield rac-(2'R,4aR,12bR)-12b-ethyl-9-(4-fluorophenyl)-2,4,4a,5,6,7,9,12b-octahydro-1H-spiro[benzo[6,7]cyclohepta[1,2-f]indazole-3,2'-oxirane] (154, $R^1$=4-Fluorophenyl, $R^2$=Ethyl) (0.308 g, 37.1%); LC/MS, method 3, $R_t$=2.94 min, MS m/z 391 (M+H)$^+$. $^1$H NMR (400 MHz, DMSO) δ 8.26 (d, J=0.8 Hz, 1H), 7.89 (s, 1H), 7.84-7.77 (m, 2H), 7.56 (s, 1H), 7.45-7.36 (m, 2H), 3.26-3.18 (m, 1H), 2.97-2.92 (m, 1H), 2.61-2.54 (m, 2H), 2.24-2.15 (m, 1H), 2.03-1.71 (m, 8H), 1.62-1.58 (m, 1H), 1.39-1.21 (m, 2H), 1.06-1.01 (m, 1H), 0.40 (t, J=7.3 Hz, 3H).

Additional examples, prepared from compounds 140 and 150, in a manner similar to the preparation of Example 167 are listed in Table 17.

TABLE 17

| Ex. # | Reactant | Reagent | Product structure | LC/MS method/ $R_t$ MH$^+$ | Chiral method | Order of elution/ sign of rotation |
|---|---|---|---|---|---|---|
| 173 | 140 ($R^1$ = 4-Fluorophenyl, $R^2$ = Pyridin-2-ylmethyl) | Sodium methoxide | 142 (3R,4aS,12bS) ($R^1$ = 4-Fluorophenyl, $R^2$ = Pyridin-2-ylmethyl, $R^3$ = Methoxymethyl) | 2 2.25 min 486 MH$^+$ | 55 | 1$^{st}$/neg |
| 174 | 140 ($R^1$ = 4-Fluorophenyl, $R^2$ = Pyridin-2-ylmethyl) | Sodium methoxide | 142 (3S,4aR,12bR) ($R^1$ = 4-Fluorophenyl, $R^2$ = Pyridin-2-ylmethyl), $R^3$ = Methoxymethyl) | 2 2.25 min 486 MH$^+$ | 55 | 2$^{nd}$/pos |

303

Scheme 25:

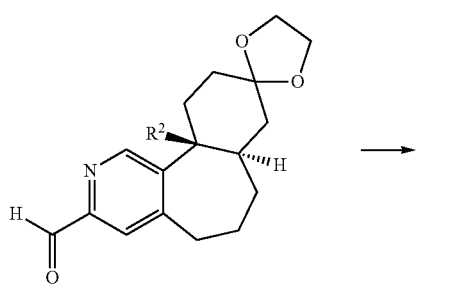
146

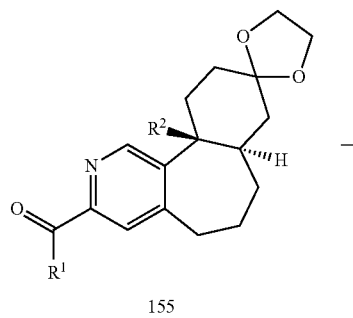
155

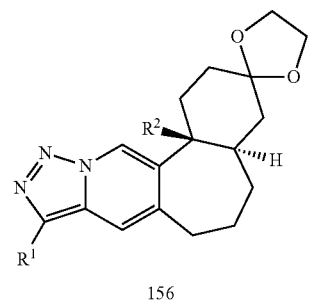
156

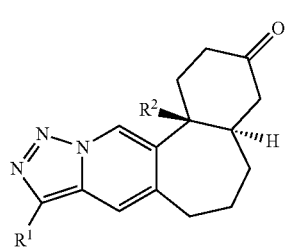
157

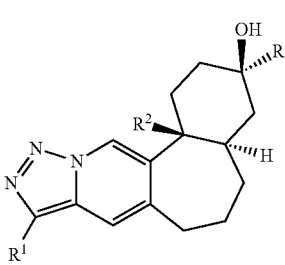
158

304

Example #175 rac-(3R,4aR,13bS)-9-(4-fluorophenyl)-13b-(pyridin-2-ylmethyl)-3-(trifluoromethyl)-2,3,4,4a,5,6,7,13b-octahydro-1H-benzo[3,4]cyclohepta[1,2-d][1,2,3]triazolo[1,5-a]pyridin-3-ol (158, R¹=4-Fluorophenyl, R²=Pyridin-2-ylmethyl, R³=Trifluoromethyl)

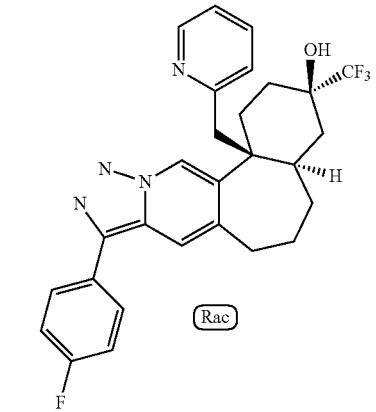 [SMILES: N/C(=C1/C=C2CCC[C@@H]3C[C@@](O)(C(F)(F)F)CC[C@@]3(Cc3ccccn3)C2=CN1N)c1ccc(F)cc1]

Step 1: rac-(4-Fluorophenyl) ((7 aR,11aS)-11a-(pyridin-2-ylmethyl)-5,6,7,7a,8,10,11,11a-octahydro spiro[benzo[6,7]cyclohepta[1,2-c]pyridine-9,2'-[1,3]dioxolan]-3-yl)methanol (155, R¹=4-Fluorophenyl, R²=Pyridin-2-ylmethyl)

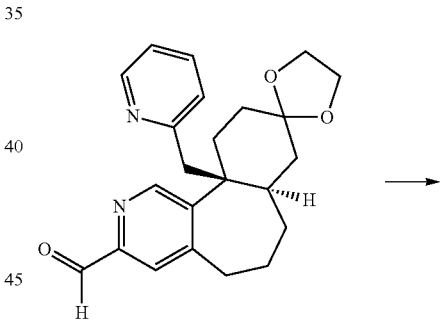

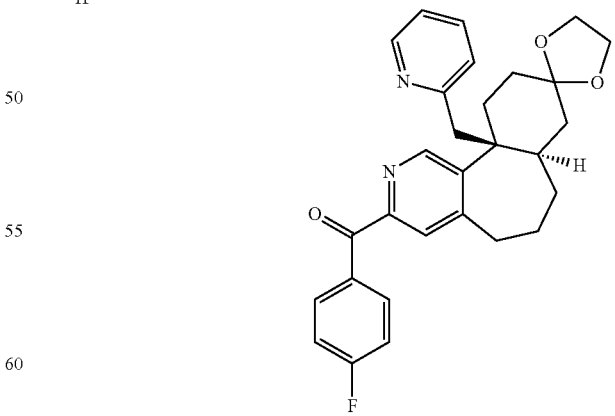

Rac-(7aR,11aS)-11a-(Pyridin-2-ylmethyl)-5,6,7,7a,8,10,11,11a-octahydro spiro[benzo[6,7]cyclohepta[1,2-c]pyridine-9,2'-[1,3]dioxolane]-3-carbaldehyde (146, R²=Pyridin-2-ylmethyl) (0.400 g, 1.06 mmol) and THF (10 mL) were added to a round bottom flask and stirred. (4-Fluorophenyl) magnesium bromide (2M in diethyl ether) (0.95 mL, 1.90 mmol) was added and the mixture was stirred at rt for about 1 h. Sat. aq. NH$_4$Cl was added and the product was extracted with EtOAc (15 mL), dried over MgSO$_4$ and concentrated in vacuo. The residue was taken into DCM (6 mL) and stirred at rt. Dess-Martin periodinane (0.556 g, 1.31 mmol) was added and mixture was stirred at rt for about 2 h. Sat. aq. NaHCO$_3$ (5 mL) and sat. aq. Na$_2$S$_2$O$_3$ (5 mL) were added and the resulting mixture was extracted with EtOAc (15 mL), dried over Na$_2$SO$_4$ and concentrated in vacuo.

The crude material was purified on silica gel (25 g), eluting with 5-100% EtOAc in heptane to provide (4-fluorophenyl) ((7aR,11aS)-11a-(pyridin-2-ylmethyl)-5,6,7,7a,8,10,11, 11a-octahydrospiro[benzo[6,7]cyclohepta[1,2-c]pyridine-9, 2'-[1,3]dioxolan]-3-yl)methanone (155, R$^1$=4-Fluorophenyl, R$^2$=Pyridin-2-ylmethyl) (0.224 g, 45%); LC/MS, method 3, R$_t$=2.49 min, MS m/z 473 (M+H)$^+$. $^1$H NMR (400 MHz, DMSO) δ 8.32-8.26 (m, 1H), 8.09 (s, 1H), 8.00-7.94 (m, 2H), 7.75 (s, 1H), 7.41-7.36 (m, 1H), 7.35-7.29 (m, 2H), 7.07-7.02 (m, 1H), 6.44-6.40 (m, 1H), 3.92-3.81 (m, 4H), 3.49 (d, J=13.2 Hz, 1H), 3.45-3.34 (m, 1H), 3.19 (d, J=13.4 Hz, 1H), 3.09-2.97 (m, 1H), 2.17-2.07 (m, 2H), 2.05-1.94 (m, 2H), 1.93-1.83 (m, 2H), 1.82-1.73 (m, 1H), 1.73-1.64 (m, 2H), 1.63-1.56 (m, 1H), 1.51-1.38 (m, 1H).

Step 2: (4aR,13bS)-9-(4-Fluorophenyl)-13b-(pyridin-2-ylmethyl)-1,2,4,4a,5,6,7,13b-octahydrospiro[benzo[3,4]cyclohepta[1,2-d][1,2,3]triazolo[1,5-a]pyridine-3,2'-[1,3]dioxolane] (156, R$^1$=4-Fluorophenyl, R$^2$=Pyridin-2-ylmethyl)

4-Methylbenzenesulfonohydrazide (0.177 g, 0.948 mmol) in MeOH (4 mL) was combined with (4-fluorophenyl)((7aR, 11aS)-11a-(pyridin-2-ylmethyl)-5,6,7,7a,8,10,11,11a-octahydrospiro[benzo[6,7]cyclohepta[1,2-c]pyridine-9,2'-[1, 3]dioxolan]-3-yl)methanone (0.224 g, 0.474 mmol) and the mixture was stirred at about 50° C. for about 48 h. The reaction mixture was cooled to rt and was washed with sat. aq. NaHCO$_3$ and extracted with DCM (10 mL). The organics were dried over MgSO$_4$ and concentrated in vacuo. The residue was purified on silica gel (12 g) using a gradient of 10-100% EtOAc in heptane to afford (4aR,13bS)-9-(4-fluorophenyl)-13b-(pyridin-2-ylmethyl)-1,2,4,4a,5,6,7,13b-octahydrospiro[benzo[3,4]cyclohepta[1,2-d][1,2,3]triazolo[1, 5-a]pyridine-3,2'-[1,3]dioxolane] (156, R$^1$=4-Fluorophenyl, R$^2$=Pyridin-2-ylmethyl) (0.230 g, 56%); LC/MS, method 3, R$_t$=2.52 min, MS m/z 485 (M+H)$^+$. $^1$H NMR (400 MHz, DMSO) δ 8.36 (s, 1H), 8.28-8.23 (m, 1H), 8.10-8.02 (m, 3H), 7.80-7.72 (m, 1H), 7.41-7.30 (m, 2H), 7.02-6.97 (m, 1H), 6.57-6.53 (m, 1H), 3.96-3.80 (m, 4H), 3.63-3.54 (m, 1H), 3.52-3.40 (m, 1H), 3.25-3.17 (m, 2H), 2.39-2.34 (m, 1H), 2.21-2.05 (m, 2H), 1.95-1.55 (m, 7H), 1.50-1.37 (m, 1H)

Step 3: rac (4aR,13bS)-9-(4-Fluorophenyl)-13b-(pyridin-2-ylmethyl)-4,4a,5,6,7,13b-hexahydro-1H-benzo[3,4]cyclohepta[1,2-d][1,2,3]triazolo[1,5-a]pyridin-3 (2H)-one (157, R$^1$=4-Fluorophenyl, R$^2$=Pyridin-2-ylmethyl)

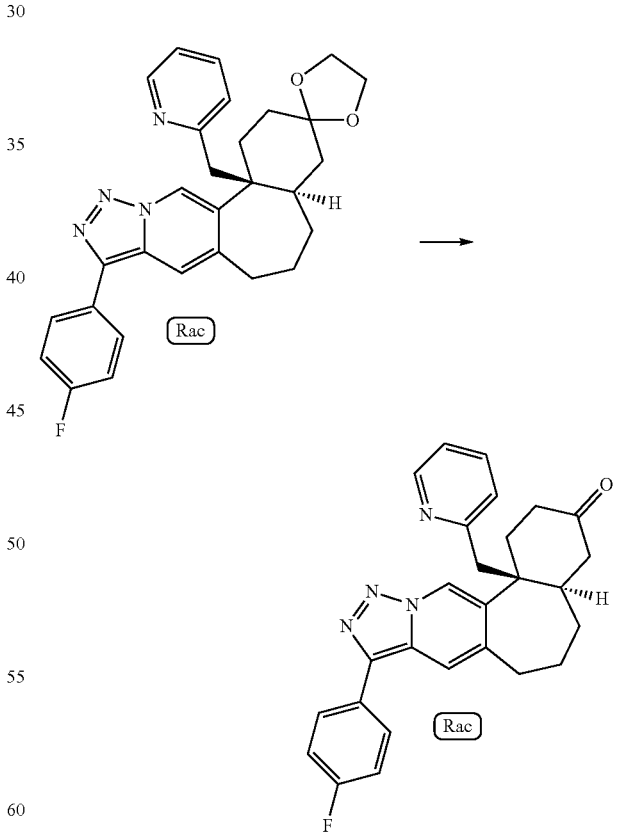

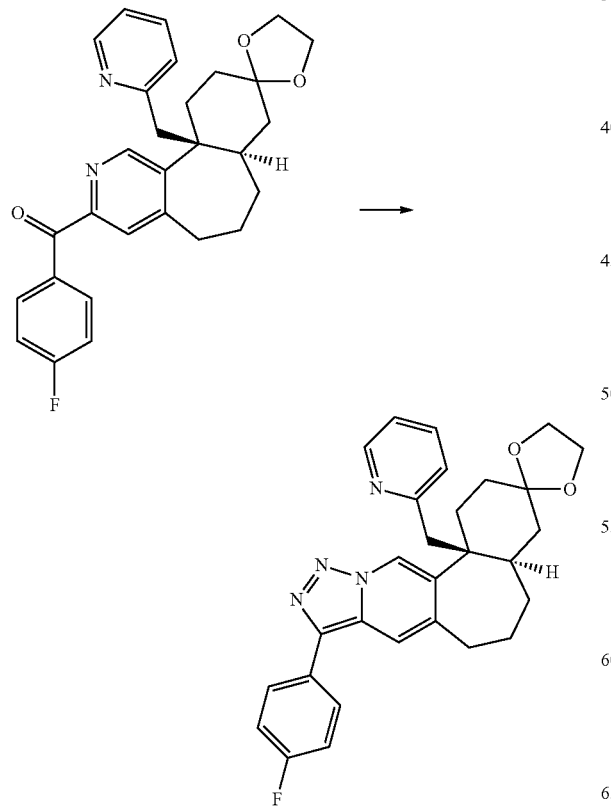

rac-(4aR,13bS)-9-(4-Fluorophenyl)-13 b-(pyridin-2-ylmethyl)-1,2,4,4a,5,6,7,13 b-octahydrospiro[benzo[3,4]cyclohepta[1,2-d][1,2,3]triazolo[1,5-a]pyridine-3,2'-[1,3]dioxolane] (156, R$^1$=4-Fluorophenyl, R$^2$=Pyridin-2-ylmethyl) (0.230 g, 0.475 mmol) in acetone (3 mL) was treated with 6 N hydrochloric acid (0.060 mL, 0.322 mmol) then stirred at rt for about 3 h. Sat. aq. NaHCO$_3$ (~5 mL) and EtOAc (15 mL) were added to the mixture then the layers were separated. The organic layer was washed with brine (~5 mL) then dried over MgSO$_4$, filtered and concentrated in vacuo to yield rac-(4aR, 13bS)-9-(4-fluorophenyl)-13b-(pyridin-2-ylmethyl)-4,4a,5,6,7,13b-hexahydro-1H-benzo[3,4]cyclohepta[1,2-d][1,2,3]triazolo[1,5-a]pyridin-3(2H)-one (157, R$^1$=4-Fluorophenyl, R$^2$=Pyridin-2-ylmethyl) (0.142 g, 68%); LC/MS, method 3, R$_t$=2.30 min, MS m/z 441 (M+H)$^+$. $^1$H NMR (400 MHz, DMSO) δ 8.40 (s, 1H), 8.36-8.27 (m, 1H), 8.12 (s, 1H), 8.11-8.03 (m, 2H), 7.48-7.30 (m, 3H), 7.08-6.98 (m, 1H), 6.64 (d, J=7.8 Hz, 1H), 3.85-3.73 (m, 1H), 3.55-3.42 (m, 2H), 2.75-2.64 (m, 1H), 2.42-2.23 (m, 3H), 2.20-2.02 (m, 5H), 1.79-1.68 (m, 1H), 1.49-1.36 (m, 1H), 1.29-1.21 (m, 1H).

Step 4: rac-(3R,4aR,13bS)-9-(4-Fluorophenyl)-13b-(pyridin-2-ylmethyl)-3-(trifluoromethyl)-2,3,4,4a,5,6,7,13b-octahydro-1H-benzo[3,4]cyclohepta[1,2-d][1,2,3]triazolo[1,5-a]pyridin-3-ol (158, R$^1$=4-Fluorophenyl, R$^2$=Pyridin-2-ylmethyl, R$^3$=Trifluoromethyl)

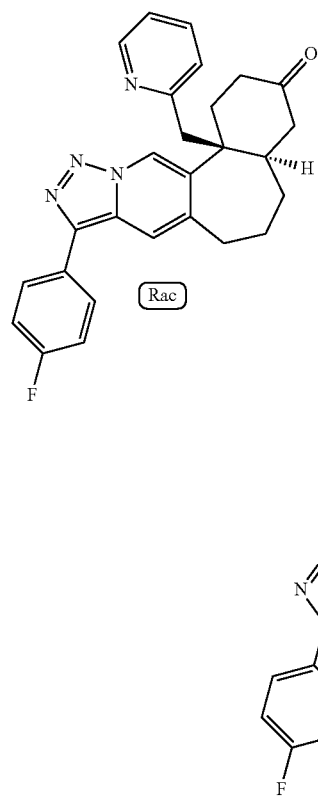

rac-(4aR,13bS)-9-(4-Fluorophenyl)-13 b-(pyridin-2-ylmethyl)-4,4a,5,6,7,13 b-hexahydro-1H-benzo[3,4]cyclohepta[1,2-d][1,2,3]triazolo[1,5-a]pyridin-3 (2H)-one (157, R$^1$=4-Fluorophenyl, R$^2$=Pyridin-2-ylmethyl) (0.139 g, 0.316 mmol) was suspended in DME (3 mL) and CsF (0.029 g, 0.19 mmol) was added. The mixture was cooled to about −10° C. then trimethyl(trifluoromethyl)silane (0.093 mL, 0.63 mmol) was added. After stirring overnight, TBAF (1 M in THF) (0.316 mL, 0.316 mmol) was added and the mixture was allowed to warm to rt. The mixture was concentrated under reduced pressure then the residue was purified on silica gel (12 g) using a gradient of 10-85% EtOAc in heptane. Product fractions were combined and concentrated under reduced pressure and then triturated with EtOAc to provide rac-(3R, 4aR,13bS)-9-(4-fluorophenyl)-13b-(pyridin-2-ylmethyl)-3-(trifluoromethyl)-2,3,4,4a,5,6,7,13b-octahydro-1H-benzo[3,4]cyclohepta[1,2-d][1,2,3]triazolo[1,5-a]pyridin-3-ol (158, R$^1$=4-Fluorophenyl, R$^2$=Pyridin-2-ylmethyl, R$^3$=Trifluoromethyl) (0.031 g, 20%); LC/MS, method 2, R$_t$=2.45 min, MS m/z 511 (M+H)$^+$. $^1$H NMR (400 MHz, DMSO) δ 8.39 (s, 1H), 8.34-8.29 (m, 1H), 8.11 (s, 1H), 8.08-8.02 (m, 2H), 7.40-7.30 (m, 3H), 7.06-7.00 (m, 1H), 6.52-6.47 (m, 1H), 5.97 (s, 1H), 3.67 (d, J=13.4 Hz, 1H), 3.56-3.42 (m, 1H), 3.27-3.15 (m, 2H), 2.22-2.07 (m, 2H), 2.07-1.67 (m, 7H), 1.55-1.38 (m, 1H), 1.30-1.20 (m, 1H).

Fluorescence polarization binding ranges measured using GR Fluorescence Polarization Assay:
A=a compound with an IC$_{50}$ less than 0.1 μM
B=a compound with an IC$_{50}$ within the range of 0.1 to 1.0 μM
C=a compound with an IC$_{50}$ within the range of 1.0 to 10.0 μM
D=a compound with an IC$_{50}$ greater than 10 μM.

| Example | GR binding | A549 cell assay | MG63 cell assay |
|---|---|---|---|
| 1 | A | A | A |
| 2 | A | A | nd |
| 3 | A | A | B |
| 4 | A | B | A |
| 5 | A | B | D |
| 6 | B | B | nd |
| 7 | A | A | D |
| 8 | B | D | nd |
| 9 | A | B | D |
| 10 | B | D | nd |
| 11 | A | A | A |
| 12 | A | A | A |
| 13 | A | A | A |
| 14 | A | D | D |
| 15 | A | A | nd |
| 16 | A | A | nd |
| 17 | A | A | nd |
| 18 | A | A | nd |
| 21 | A | A | nd |
| 22 | A | A | nd |
| 23 | A | nd | nd |
| 24 | A | A | nd |
| 25 | A | A | nd |
| 26 | A | D | nd |
| 27 | A | A | nd |
| 28 | A | A | nd |
| 29 | A | A | nd |
| 30 | A | A | nd |
| 29 | A | A | nd |
| 30 | B | A | nd |
| 31 | B | A | nd |
| 32 | A | A | nd |
| 33 | A | A | nd |
| 34 | A | D | nd |
| 35 | A | A | nd |
| 36 | A | D | nd |
| 37 | A | A | nd |
| 38 | A | A | nd |
| 39 | A | A | nd |
| 40 | A | A | nd |
| 41 | A | A | nd |
| 42 | A | A | A |
| 43 | A | D | nd |
| 44 | A | A | nd |
| 45 | A | A | nd |
| 46 | B | D | nd |
| 47 | A | A | nd |
| 48 | B | A | nd |
| 49 | A | A | nd |

| Example | GR binding | A549 cell assay | MG63 cell assay |
| --- | --- | --- | --- |
| 50 | A | A | nd |
| 51 | A | A | nd |
| 52 | B | nd | nd |
| 53 | A | A | nd |
| 54 | A | A | nd |
| 55 | A | A | nd |
| 56 | B | D | nd |
| 57 | A | A | nd |
| 58 | A | A | nd |
| 59 | | nd | nd |
| 60 | A | A | nd |
| 61 | B | nd | nd |
| 62 | A | A | nd |
| 63 | A | A | nd |
| 64 | A | A | nd |
| 65 | A | A | nd |
| 66 | A | A | nd |
| 67 | A | A | nd |
| 68 | A | A | nd |
| 69 | A | A | nd |
| 70 | | A | nd |
| 71 | A | B | nd |
| 72 | A | B | nd |
| 73 | B | D | nd |
| 74 | A | A | nd |
| 75 | A | A | nd |
| 76 | A | A | nd |
| 77 | B | nd | nd |
| 78 | A | A | nd |
| 79 | A | B | nd |
| 80 | A | A | nd |
| 81 | A | A | nd |
| 82 | A | B | nd |
| 83 | B | B | nd |
| 84 | A | A | nd |
| 85 | nd | nd | nd |
| 86 | B | nd | nd |
| 87 | A | C | nd |
| 92 | B | D | nd |
| 93 | A | D | nd |
| 94 | A | A | nd |
| 95 | B | B | nd |
| 96 | A | A | nd |
| 97 | A | A | nd |
| 98 | A | A | nd |
| 99 | A | A | nd |
| 100 | A | A | nd |
| 101 | B | nd | nd |
| 102 | A | A | nd |
| 103 | A | A | nd |
| 104 | A | A | nd |
| 105 | A | A | nd |
| 106 | A | A | nd |
| 107 | A | B | nd |
| 108 | A | A | nd |
| 109 | A | A | nd |
| 110 | A | B | nd |
| 111 | A | A | nd |
| 112 | B | A | nd |
| 113 | A | A | nd |
| 114 | B | B | nd |
| 115 | B | B | nd |
| 116 | B | B | nd |
| 117 | A | A | nd |
| 118 | A | B | nd |
| 119 | A | A | nd |
| 120 | A | B | nd |
| 121 | A | A | nd |
| 122 | A | A | nd |
| 123 | A | A | nd |
| 124 | nd | nd | nd |
| 125 | B | D | nd |
| 126 | A | D | nd |
| 127 | B | nd | nd |
| 128 | A | A | nd |
| 129 | A | A | nd |
| 130 | A | D | nd |
| 131 | A | A | nd |
| 132 | A | A | nd |
| 133 | B | D | nd |
| 134 | A | A | nd |
| 135 | C | D | nd |
| 136 | A | A | nd |
| 137 | C | nd | nd |
| 138 | A | C | nd |
| 139 | B | nd | nd |
| 140 | B | nd | nd |
| 141 | A | C | nd |
| 142 | B | nd | nd |
| 143 | A | A | nd |
| 144 | B | nd | nd |
| 145 | A | A | nd |
| 146 | A | A | nd |
| 147 | A | B | nd |
| 148 | A | A | nd |
| 149 | A | A | nd |
| 150 | B | nd | nd |
| 151 | C | B | nd |
| 152 | A | A | nd |
| 153 | B | D | nd |
| 154 | A | A | nd |
| 155 | B | D | nd |
| 156 | A | A | nd |
| 157 | B | nd | nd |
| 158 | A | A | nd |
| 159 | B | nd | nd |
| 160 | A | A | nd |
| 161 | B | nd | nd |
| 162 | B | C | nd |
| 163 | A | A | nd |
| 164 | B | nd | nd |
| 165 | A | A | nd |
| 166 | A | A | nd |
| 167 | A | A | nd |
| 168 | A | A | nd |
| 169 | B | C | nd |
| 170 | B | nd | nd |
| 171 | A | A | nd |
| 172 | A | D | nd |
| 173 | A | A | nd |
| 174 | B | nd | nd |
| 175 | nd | nd | nd |

We claim:

1. A compound of Formula (C):

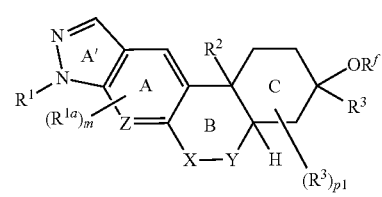

Formula (C)

or a pharmaceutically acceptable salt, isomer, or stereoisomer thereof, wherein:

Z is $CR^{1a}$ or N;

Ring B is a seven-membered ring optionally substituted with deuterium, wherein:

X is —$C(R^5)_2$— or —$C(R^5)$=; or when X is —$C(R^5)_2$—, both $R^5$ substituents, together with the carbon atom to which they are attached, optionally forms a cyclopropyl ring spiro to Ring B;

Y is —$C(R^5)_2C(R^5)_2$— or =$C(R^5)C(R^5)_2$—;

$R^1$ is independently H, deuterium, —Br, —Cl, —F, —CF$_3$, —CN, —OR$^b$, -optionally substituted (C$_1$-C$_3$)alkylene-R$^b$, optionally substituted (C$_1$-C$_3$)alkyl, optionally substituted aryl, optionally substituted (C$_3$-C$_6$)cycloalkyl, optionally substituted heteroaryl, optionally substituted heterocyclyl, —S(O)$_2$R$^b$—, =O, or —N(R$^a$)(R$^b$);

$R^{1a}$ is independently H, deuterium, —Br, —Cl, —F, —CF$_3$, —CN, optionally substituted (C$_1$-C$_6$)alkyl, optionally substituted (C$_3$-C$_6$)cycloalkyl, optionally substituted heterocyclyl, —S(O)$_2$—R$^a$, or —N(R$^a$)$_2$;

$R^2$ is —CD$_3$, —CH$_2$CD$_3$, —CN, -allyl, —CH$_2$NHC(=O)(C$_1$-C$_3$)alkyl, —CH$_2$NHSO$_2$(C$_1$-C$_3$)alkyl, —N(R)—SO$_2$-optionally substituted alkyl; —N(R)(R$^g$), —N(R)-optionally substituted cycloalkyl, —N(R)-optionally substituted aryl, —N(R)-optionally substituted heteroaryl, —N(R)-optionally substituted heterocyclyl, —N(R)C(O)-optionally substituted alkyl, —N(R)$_2$, —C(O)N(R$^a$)$_2$, —CH$_2$-optionally substituted aryl, —CH$_2$-optionally substituted (C$_3$-C$_6$)cycloalkyl, optionally substituted (C$_1$-C$_3$)alkyl, optionally substituted (C$_2$-C$_3$)alkenyl, —CH$_2$-optionally substituted heteroaryl, —(CH$_2$)$_{n1}$-optionally substituted heterocyclyl, —C(R$^d$)$_2$—R$^e$, or —C(=O)—R$^e$, provided that when $R^2$ is —C(R$^d$)$_2$—R$^e$, only one R$^d$ can be OH;

$R^3$ is independently, deuterium, —CD$_3$, —CF$_3$, —N(R$^a$)SO$_2$R$^c$, —N(R$^a$)COR$^c$, —CON(R$^a$)R$^c$, —N(R$^a$)CO-OR$^c$, —N(R$^a$)$_2$, —O—C(O)NR-optionally substituted alkyl, optionally substituted (C$_2$-C$_6$)alkynyl, =O, —OR$^a$, —OR$^f$, optionally substituted (C$_1$-C$_4$)alkyl, optionally substituted (C$_1$-C$_4$)alkyl-O—(C$_1$-C$_4$)alkyl, —(C(R$^a$)$_2$)$_r$-optionally substituted (C$_3$-C$_6$)cycloalkyl, —(C(R$^a$)$_2$)$_r$-optionally substituted aryl, —(C(R$^a$)$_2$)$_r$-optionally substituted heteroaryl, —(C(R$^a$)$_2$)$_r$—N(R$^a$)-optionally substituted heteroaryl, —(C(R$^a$)$_2$)$_r$—N(R$^a$)—(C(R$^a$)$_2$)$_r$-optionally substituted aryl, or a carbocyclic or heterocyclic spirocyclic moiety attached to ring C;

$R^5$ is independently H, deuterium, —CD$_3$, —F, —CF$_3$, —N(R$^a$), —OR$^a$, or optionally substituted (C$_1$-C$_3$) alkyl; and, $R^a$ is independently H, deuterium, optionally substituted (C$_3$-C$_6$)cycloalkyl, or optionally substituted (C$_1$-C$_3$) alkyl;

$R^b$ is H, optionally substituted (C$_1$-C$_3$)alkyl, optionally substituted aryl, optionally substituted (C$_3$-C$_6$)cycloalkyl, optionally substituted heteroaryl, or optionally substituted heterocyclyl;

$R^c$ is optionally substituted (C$_1$-C$_3$)alkyl or optionally substituted aryl;

$R^d$ is independently H, deuterium, —OH, or optionally substituted (C$_1$-C$_6$) alkyl;

$R^e$ is —CF$_3$, optionally substituted aryl, optionally substituted (C$_1$-C$_6$)alkyl, optionally substituted (C$_3$-C$_6$)cycloalkyl, optionally substituted heteroaryl, or optionally substituted heterocyclyl;

$R^f$ is —H, —SO$_2$NH$_2$, —CH$_2$CO$_2$H, —CH$_2$CONH$_2$, —P(=O)(OH)(OH), —C(O)-optionally substituted (C$_1$-C$_6$) alkyl, —C(O)N(optionally substituted (C$_1$-C$_6$)alkyl)$_2$, —C(O) (optionally substituted (C$_1$-C$_6$)alkyl)$_2$, —C(O)-optionally substituted aryl, —C(O)-optionally substituted heterocyclyl, —C(O)-optionally substituted (C$_3$-C$_6$)cycloalkyl, —C(O)—CR$_2$-optionally substituted heterocyclyl or —C(O)—CR$_2$-optionally substituted heteroaryl $R^g$ is —CH$_2$-optionally substituted (C$_3$-C$_6$)cycloalkyl, —CH$_2$-optionally substituted heteroaryl, or —CH$_2$-optionally substituted heterocyclyl;

R is independently H or (C$_1$-C$_3$)alkyl;

m is 0, 1, or 2;

n1 is independently 0 or 1;

p1 is 0, 1, or 2; and r is independently 0, 1 or 2;

wherein the optional substituents are independently selected from deuterium, CD$_3$, —CF$_3$, (C$_1$-C$_8$)alkyl groups, (C$_2$-C$_8$)alkenyl groups, (C$_2$-C$_8$)alkynyl groups, (C$_3$-C$_{10}$)cycloalkyl groups, halogen, halogenated (C$_1$-C$_8$)alkyl groups, —O—(C$_1$-C$_8$)alkyl groups, —OH, —S—(C$_1$-C$_8$)alkyl groups, —SH, —NH(C$_1$-C$_8$)alkyl groups, —N((C$_1$-C$_8$)alkyl)$_2$ groups, —NH$_2$, —NH—(C$_1$-C$_6$)alkyl-heterocycle, —NH-heterocycle, —C(O)NH$_2$, —C(O)NH(C$_1$-C$_8$)alkyl groups, —C(O)N((C$_1$-C$_8$)alkyl)$_2$, —NHC(O)H, —NHC(O)(C$_1$-C$_8$)alkyl groups, —NHC(O)(C$_3$-C$_8$)cycloalkyl groups, —N((C$_1$-C$_8$)alkyl)C(O)H, —N((C$_1$-C$_8$)alkyl)C(O)(C$_1$-C$_8$)alkyl groups, —NHC(O)NH$_2$, —NHC(O)NH(C$_1$-C$_8$)alkyl groups, —N((C$_1$-C$_8$)alkyl)C(O)NH$_2$ groups, —NHC(O)N((C$_1$-C$_8$)alkyl)$_2$ groups, —N((C$_1$-C$_8$)alkyl)C(O)N((C$_1$-C$_8$)alkyl)$_2$ groups, —N((C$_1$-C$_8$)alkyl)C(O)NH((C$_1$-C$_8$)alkyl), —C(O)H, —C(O)(C$_1$-C$_8$)alkyl groups, —CN, —NO$_2$, —S(O)(C$_1$-C$_8$)alkyl groups, —S(O)$_2$(C$_1$-C$_8$)alkyl groups, —S(O)$_2$N((C$_1$-C$_8$)alkyl)$_2$ groups, —S(O)$_2$NH(C$_1$-C$_8$)alkyl groups, —S(O)$_2$NH(C$_3$-C$_8$)cycloalkyl groups, —S(O)$_2$NH$_2$ groups, —NHS(O)$_2$(C$_1$-C$_8$)alkyl groups, —N((C$_1$-C$_8$)alkyl)S(O)$_2$(C$_1$-C$_8$) alkyl groups, —(C$_1$-C$_8$)alkyl-O—(C$_1$-C$_8$)alkyl groups, —O—(C$_1$-C$_8$)alkyl-O—(C$_1$-C$_8$)alkyl groups, —C(O)OH, —C(O)O(C$_1$-C$_8$)alkyl groups, —NHOH, —NHO(C$_1$-C$_8$)alkyl groups, —O-halogenated (C$_1$-C$_8$)alkyl groups, —OCF$_3$, —S(O)$_2$-halogenated (C$_1$-C$_8$)alkyl groups, —S(O)$_2$CF$_3$, —S-halogenated (C$_1$-C$_8$)alkyl groups, —SCF$_3$, —(C$_1$-C$_6$)alkyl-heterocycle, —(C$_1$-C$_6$)alkyl-heteroaryl, -phenyl, —NHC(O)O—(C$_1$-C$_6$) alkyl groups, —N((C$_1$-C$_6$)alkyl)C(O)O—(C$_1$-C$_6$)alkyl groups, —C(=NH)—(C$_1$-C$_6$)alkyl groups, —C(=NOH)—(C$_1$-C$_6$)alkyl groups, —NH—(C$_1$-C$_6$) alkyl-aryl groups, or —C(=N—O—(C$_1$-C$_6$)alkyl)-(C$_1$-C$_6$)alkyl groups.

2. The compound of claim 1, wherein X is —CH$_2$— or —CH=.

3. The compound of claim 2, wherein Y is —CH$_2$—CH$_2$— or =CH—CH$_2$.

4. The compound of claim 3, wherein the compound is represented by Formula (I)D1 or Formula (I)D2, and p2 is 0, 1, or 2:

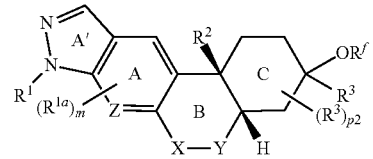

Formula (I)D1

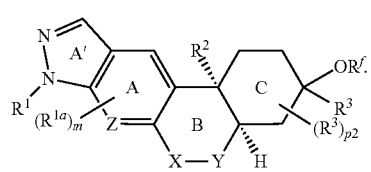

Formula (I)D2

5. The compound of claim 4, wherein the compound is represented by Formula (I)D1E1 or Formula (I)D1E2, and p2 is 0, 1, or 2:

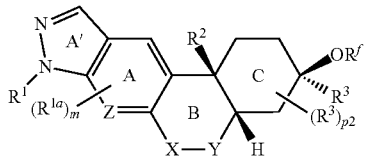
Formula (I)D1E1

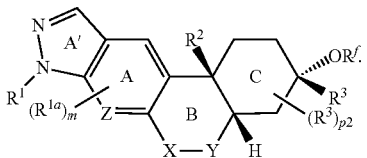
Formula (I)D1E2

6. The compound of claim 4, wherein the compound is represented by Formula (I)D2E1 or Formula (I)D2E2, and p2 is 0, 1, or 2:

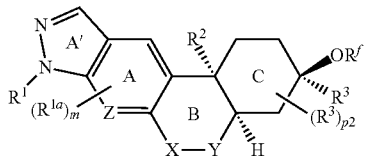
Formula (I)D2E1

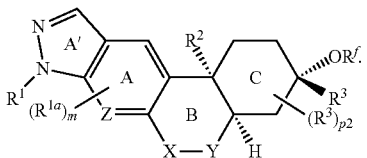
Formula (I)D2E2

7. The compound of claim 3, wherein the compound is represented by Formula (I)D3 or Formula (I)D4, and p2 is 0, 1, or 2:

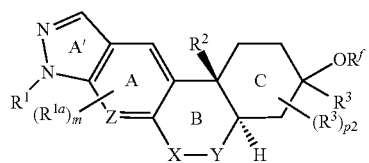
Formula (I)D3

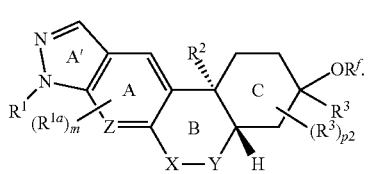
Formula (I)D4

8. The compound of claim 7, wherein the compound is represented by Formula (I)D3E1 or Formula (I)D3E2, and p2 is 0, 1, or 2:

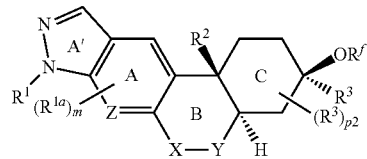
Formula (I)D3E1

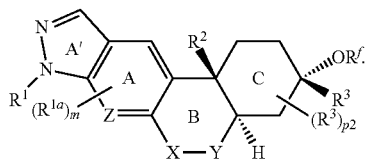
Formula (I)D3E2

9. The compound of claim 7, wherein the compound is represented by Formula (I)D4E1 or Formula (I)D4E2, and p2 is 0, 1, or 2:

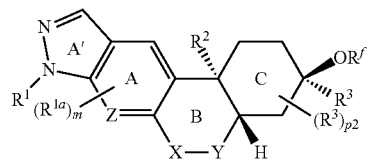
Formula (I)D4E1

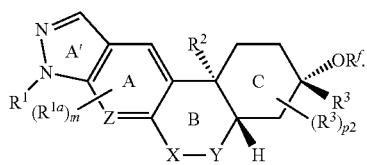
Formula (I)D4E2

10. The compound of claim 3, wherein the compound is represented by Formula (I)D1E1, Formula (I)D1E2, Formula (I)D2E1, Formula (I)D2E2, Formula (I)D3E1, Formula (I)D3E2, Formula (I)D4E1 or Formula (I)D4E2:

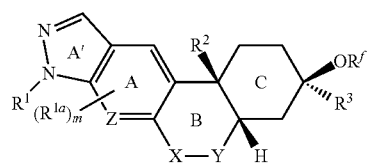
Formula (I)D1E1

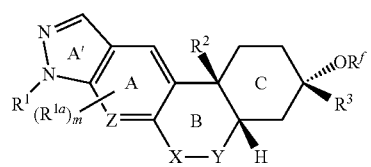
Formula (I)D1E2

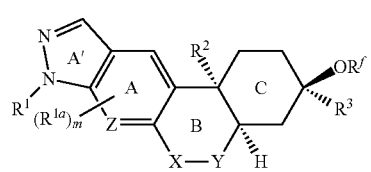
Formula (I)D2E1

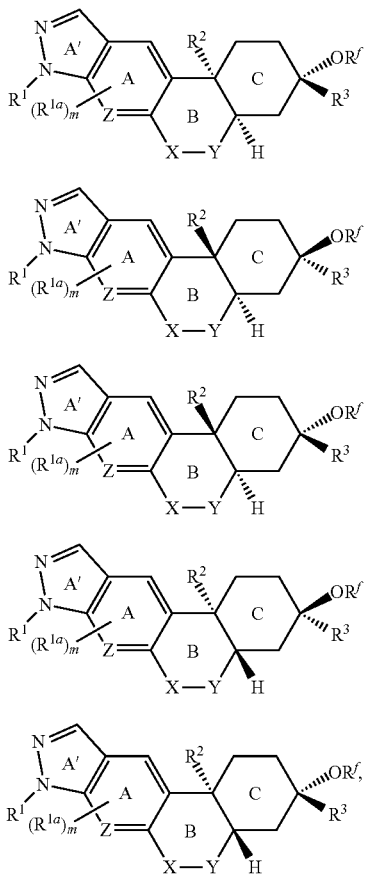

Formula (I)D2E2

Formula (I)D3E1

Formula (I)D3E2

Formula (I)D4E1

Formula (I)D4E2 wherein R¹ is independently H, —CH₂-optionally substituted heteroaryl, optionally substituted phenyl, optionally substituted benzyl, or optionally substituted heteroaryl.

11. The compound of claim 10, wherein R¹ is optionally substituted azetidinyl, optionally substituted phenyl, optionally substituted piperidinyl, optionally substituted pyrimidinyl, optionally substituted pyridinyl, optionally substituted pyrazolyl, optionally substituted pyrrolidinyl, optionally substituted tetrazolyl or optionally substituted thiadiazolyl.

12. The compound of claim 10, wherein R¹ is optionally substituted phenyl.

13. The compound of claim 12, wherein R¹ is 4-fluorophenyl or 4-(methylsulfonyl)phenyl.

14. The compound of claim 10, wherein R¹ is optionally substituted heteroaryl.

15. The compound of claim 14, wherein R¹ is 2-, 3-, or 4-pyridine, or 2-, 4-, or 5-pyrimidine, optionally substituted by $C_{1-3}$ alkyl or $C_{1-3}$ alkoxy.

16. The compound of claim 10, wherein $R^{1a}$ is independently H, deuterium, Br, Cl, F, or optionally substituted ($C_1$-$C_3$)alkyl.

17. The compound of claim 16, wherein R³ is independently H, —CF₃, —C≡CCH₃, optionally substituted ($C_1$-$C_4$)alkyl, optionally substituted —($C_1$-$C_4$)alkyl-O—($C_1$-$C_4$) alkyl, —$(C(R^a)_2)_r$-optionally substituted ($C_3$-$C_6$)cycloalkyl, optionally substituted aryl, optionally substituted heteroaryl, or —(CH₂)$_r$-optionally substituted aryl.

18. The compound of claim 16, wherein R³ is independently H, —CF₃, =O, —OR$^f$, optionally substituted ($C_1$-$C_4$) alkyl, optionally substituted ($C_2$-$C_6$)alkynyl, optionally substituted —($C_1$-$C_4$)alkyl-O—($C_1$-$C_4$)alkyl, optionally substituted aryl.

19. The compound of claim 18, wherein —OR$^f$ is independently —OH, —OSO₂NH₂, —OCH₂CO₂H, —OCH₂CONH₂, or —OP(=O)(OH)(OH).

20. The compound of claim 19, wherein one —OR$^f$ is attached to a carbon additionally substituted by an R³ selected from: —$C_{1-3}$ alkyl, —(CH₂)$_{0-3}$—CN, —CH₂—O—$C_{1-3}$ alkyl, —CF₃, —CH₂—NH—CH(CH₃)-phenyl, -phenyl, —C≡CH, or —C≡C—$C_{1-3}$ alkyl.

21. The compound of claim 20, wherein R² is —CH₂—CH₃, —CH₂—CF₃, —(CH₂)$_r$-optionally substituted aryl, or optionally substituted ($C_1$-$C_3$)alkyl.

22. The compound of claim 20, wherein R² is —CN, —CH₂-optionally substituted ($C_3$-$C_6$)cycloalkyl, —C(=O)—R$^e$, —(CH₂)$_r$-optionally substituted heteroaryl, —CH₂-optionally substituted heterocyclyl, or optionally substituted ($C_1$-$C_3$)alkyl.

23. The compound of claim 20, wherein R² is —CN, —CH₂CH₃, —CH₂OH, —CH₂CN, —CH₂NHC(=O)CH₃, —CH₂NHSO₂($C_1$-$C_3$)alkyl, —CH₂-2-pyridinyl, —CH₂-2-pyrimidinyl, —C(=O)-2-pyridinyl, —CH₂-cyclopropyl, or

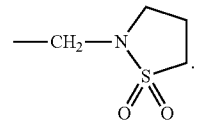

24. The compound of claim 23, wherein Z is N.

25. The compound of claim 23, wherein Z is $CR^{1a}$; m is 1; and $R^{1a}$ is H, deuterium, $C_{1-3}$ alkyl, Cl, Br, or F.

26. A compound selected from
(3S,4aS,12bR)-12b-Ethyl-9-(4-fluoro-phenyl)-3-trifluoromethyl-1,2,3,4,4a,5,6,7,9,12b-decahydro-9,10-diazabenzo[3,4]cyclohepta[1,2-f]inden-3-ol; compound with (3R,4aR,12bS)-12b-ethyl-9-(4-fluoro-phenyl)-3-trifluoromethyl-1,2,3,4,4a,5,6,7,9,12b-decahydro-9,10-diaza-benzo[3,4]cyclohepta[1,2-f]inden-3-ol;
(3R,4aR,12bS)-12b-Ethyl-9-(4-fluoro-phenyl)-3-trifluoromethyl-1,2,3,4,4a,5,6,7,9,12b-decahydro-9,10-diazabenzo[3,4]cyclohepta[1,2-f]inden-3-ol;
(3S,4aS,12bR)-12b-Ethyl-9-(4-fluoro-phenyl)-3-trifluoromethyl-1,2,3,4,4a,5,6,7,9,12b-decahydro-9,10-diazabenzo[3,4]cyclohepta[1,2-f]inden-3-ol;
(3S,4aR,12bR)-12b-Ethyl-9-(4-fluoro-phenyl)-3-propyl-1,2,3,4,4a,5,6,7,9,12b-decahydro-9,10-diaza-benzo[3,4]cyclohepta[1,2-f]inden-3-ol; compound with (3R,4aS,12bS)-12b-ethyl-9-(4-fluoro-phenyl)-3-propyl-1,2,3,4,4a,5,6,7,9,12b-decahydro-9,10-diaza-benzo[3,4]cyclohepta[1,2-f]inden-3-ol;
(3S,4aR,12bR)-12b-Ethyl-9-(4-fluoro-phenyl)-3-propyl-1,2,3,4,4a,5,6,7,9,12b-decahydro-9,10-diaza-benzo[3,4]cyclohepta[1,2-f]inden-3-ol;
(3R,4aS,12bS)-12b-ethyl-9-(4-fluoro-phenyl)-3-propyl-1,2,3,4,4a,5,6,7,9,12b-decahydro-9,10-diaza-benzo[3,4]cyclohepta[1,2-f]inden-3-ol;
(3S,4aR,12bR)-12b-Ethyl-9-(4-fluoro-phenyl)-3-methoxymethyl-1,2,3,4,4a,5,6,7,9,12b-decahydro-9,10-diaza-benzo[3,4]cyclohepta[1,2-f]inden-3-ol;
(3R,4aS,12bS)-12b-Ethyl-9-(4-fluoro-phenyl)-3-methoxymethyl-1,2,3,4,4a,5,6,7,9,12b-decahydro-9,10-diaza-benzo[3,4]cyclohepta[1,2-f]inden-3-ol;
(3S,4aR,12bR)-3-Ethoxymethyl-12b-ethyl-9-(4-fluorophenyl)-1,2,3,4,4a,5,6,7,9,12b-decahydro-9,10-diazabenzo[3,4]cyclohepta[1,2-f]inden-3-ol;

(3R,4aS,12bS)-3-Ethoxymethyl-12b-ethyl-9-(4-fluoro-phenyl)-1,2,3,4,4a,5,6,7,9,12b-decahydro-9,10-diaza-benzo[3,4]cyclohepta[1,2-f]inden-3-ol;

(3R,4aS,12bS)-9-(4-fluoro-phenyl)-3-methoxymethyl-12b-pyridin-2-ylmethyl-1,2,3,4,4a,5,6,7,9,12b-decahydro-9,10-diaza-benzo[3,4]cyclohepta[1,2-f]inden-3-ol;

(3S,4aR,12bR)-9-(4-Fluoro-phenyl)-3-methoxymethyl-12b-pyridin-2-ylmethyl-1,2,3,4,4a,5,6,7,9,12b-decahydro-9,10-diaza-benzo[3,4]cyclohepta[1,2-f]inden-3-ol;

(3R,4aS,12bR)-12b-Ethyl-3-methoxymethyl-1,2,3,4,4a,5,6,7,9,12b-decahydro-9,10-diaza-benzo[3,4]cyclohepta[1,2-f]inden-3-ol; compound with (3S,4aR,12bS)-12b-ethyl-3-methoxymethyl-1,2,3,4,4a,5,6,7,9,12b-decahydro-9,10-diaza-benzo[3,4]cyclohepta[1,2-f]inden-3-ol;

(3R,4aS,12bS)-9-(4-fluorophenyl)-3-methyl-12b-(pyridin-2-ylmethyl)-1,2,3,4,4a,5,6,7,9,12b-decahydrobenzo[6,7]cyclohepta[1,2-f]indazol-3-ol;

(3S,4aR,12bR)-9-(4-fluorophenyl)-3-methyl-12b-(pyridin-2-ylmethyl)-1,2,3,4,4a,5,6,7,9,12b-decahydrobenzo[6,7]cyclohepta[1,2-f]indazol-3-ol;

2-((3R,4aS,12bS)-9-(4-fluorophenyl)-3-hydroxy-12b-(pyridin-2-ylmethyl)-1,2,3,4,4a,5,6,7,9,12b-decahydrobenzo[6,7]cyclohepta[1,2-f]indazol-3-yl)acetonitrile;

2-((3S,4aR,12bR)-9-(4-fluorophenyl)-3-hydroxy-12b-(pyridin-2-ylmethyl)-1,2,3,4,4a,5,6,7,9,12b-decahydrobenzo[6,7]cyclohepta[1,2-f]indazol-3-yl)acetonitrile;

(3S,4aS,12bS)-9-(4-fluorophenyl)-12b-(pyridin-2-ylmethyl)-3-(trifluoromethyl)-1,2,3,4,4a,5,6,7,9,12b-decahydrobenzo[6,7]cyclohepta[1,2-f]indazol-3-ol;

(3R,4aR,12bR)-9-(4-fluorophenyl)-12b-(pyridin-2-ylmethyl)-3-(trifluoromethyl)-1,2,3,4,4a,5,6,7,9,12b-decahydrobenzo[6,7]cyclohepta[1,2-f]indazol-3-ol;

(3S,4aS,12bR)-12b-(cyclopropylmethyl)-9-(4-fluorophenyl)-3-(trifluoromethyl)-1,2,3,4,4a,5,6,7,9,12b-decahydrobenzo[6,7]cyclohepta[1,2-f]indazol-3-ol;

(3R,4aR,12bS)-12b-(cyclopropylmethyl)-9-(4-fluorophenyl)-3-(trifluoromethyl)-1,2,3,4,4a,5,6,7,9,12b-decahydrobenzo[6,7]cyclohepta[1,2-f]indazol-3-ol;

rac-(3R,4aR,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol;

(3S,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol;

(3R,4aR,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol;

(3S,4aR,12bR)-3-ethyl-9-(4-fluorophenyl)-12b-(pyridin-2-ylmethyl)-1,2,3,4,4a,5,6,7,9,12b-decahydrobenzo[6,7]cyclohepta[1,2-f]indazol-3-ol;

(3R,4aS,12bS)-3-ethyl-9-(4-fluorophenyl)-12b-(pyridin-2-ylmethyl)-1,2,3,4,4a,5,6,7,9,12b-decahydrobenzo[6,7]cyclohepta[1,2-f]indazol-3-ol;

(3R,4aS,12bS)-3-ethyl-9-(4-fluorophenyl)-12b-(pyrimidin-2-ylmethyl)-1,2,3,4,4a,5,6,7,9,12b-decahydrobenzo[6,7]cyclohepta[1,2-f]indazol-3-ol;

(3S,4aR,12bR)-3-ethyl-9-(4-fluorophenyl)-12b-(pyrimidin-2-ylmethyl)-1,2,3,4,4a,5,6,7,9,12b-decahydrobenzo[6,7]cyclohepta[1,2-f]indazol-3-ol;

(3R,4aS,12bS)-3-methyl-12b-(pyridin-2-ylmethyl)-9-(pyridin-4-yl)-1,2,3,4,4a,5,6,7,9,12b-decahydrobenzo[6,7]cyclohepta[1,2-f]indazol-3-ol;

(3S,4aR,12bR)-3-methyl-12b-(pyridin-2-ylmethyl)-9-(pyridin-4-yl)-1,2,3,4,4a,5,6,7,9,12b-decahydrobenzo[6,7]cyclohepta[1,2-f]indazol-3-ol;

(3R,4aS,12bS)-3-(ethoxymethyl)-9-(4-fluorophenyl)-12b-(pyridin-2-ylmethyl)-1,2,3,4,4a,5,6,7,9,12b-decahydrobenzo[6,7]cyclohepta[1,2-f]indazol-3-ol;

(3S,4aR,12bR)-3-(ethoxymethyl)-9-(4-fluorophenyl)-12b-(pyridin-2-ylmethyl)-1,2,3,4,4a,5,6,7,9,12b-decahydrobenzo[6,7]cyclohepta[1,2-f]indazol-3-ol;

(3S,4aR,12bS)-12b-ethyl-9-(4-fluorophenyl)-3-(methoxymethyl)-1,2,3,4,4a,5,6,7,9,12b-decahydrobenzo[6,7]cyclohepta[1,2-f]indazol-3-ol;

(3R,4aS,12bR)-12b-ethyl-9-(4-fluorophenyl)-3-(methoxymethyl)-1,2,3,4,4a,5,6,7,9,12b-decahydrobenzo[6,7]cyclohepta[1,2-f]indazol-3-ol;

(3S,4aR,12bR)-9-(4-fluorophenyl)-3-(methoxymethyl)-12b-(pyrimidin-2-ylmethyl)-1,2,3,4,4a,5,6,7,9,12b-decahydrobenzo[6,7]cyclohepta[1,2-f]indazol-3-ol;

(3R,4aR,12bR)-12b-ethyl-9-(4-fluorophenyl)-3-(methoxymethyl)-1,2,3,4,4a,5,6,7,9,12b-decahydrobenzo[6,7]cyclohepta[1,2-f]indazol-3-ol;

(3S,4aS,12bS)-12b-ethyl-9-(4-fluorophenyl)-3-(methoxymethyl)-1,2,3,4,4a,5,6,7,9,12b-decahydrobenzo[6,7]cyclohepta[1,2-f]indazol-3-ol;

(3S,4aR,12bR)-12b-(cyclopropylmethyl)-9-(4-fluorophenyl)-3-(methoxymethyl)-1,2,3,4,4a,5,6,7,9,12b-decahydrobenzo[6,7]cyclohepta[1,2-f]indazol-3-ol;

(3R,4aS,12bS)-12b-(cyclopropylmethyl)-9-(4-fluorophenyl)-3-(methoxymethyl)-1,2,3,4,4a,5,6,7,9,12b-decahydrobenzo[6,7]cyclohepta[1,2-f]indazol-3-ol;

(3R,4aS,12bS)-9-(4-fluorophenyl)-3-(methoxymethyl)-12b-(pyrimidin-2-ylmethyl)-1,2,3,4,4a,5,6,7,9,12b-decahydrobenzo[6,7]cyclohepta[1,2-f]indazol-3-ol;

rac-(3R,4aS,12bR)-12b-ethyl-3-(methoxymethyl)-9-(pyridin-4-yl)-1,2,3,4,4a,5,6,7,9,12b-decahydrobenzo[6,7]cyclohepta[1,2-f]indazol-3-ol;

(3S,4aR,12bS)-12b-ethyl-3-(methoxymethyl)-9-(pyridin-3-yl)-1,2,3,4,4a,5,6,7,9,12b-decahydrobenzo[6,7]cyclohepta[1,2-f]indazol-3-ol;

rac-(3R,4aS,12bR)-12b-ethyl-3-(methoxymethyl)-9-(2-methylpyridin-4-yl)-1,2,3,4,4a,5,6,7,9,12b-decahydrobenzo[6,7]cyclohepta[1,2-f]indazol-3-ol;

1,2,3,4,4a,5,6,7,9,12b-decahydrobenzo[6,7]cyclohepta[1,2-f]indazol-3-ol;

(3S,4aR,12bS)-12b-ethyl-3-(methoxymethyl)-9-(pyridin-2-yl)-1,2,3,4,4a,5,6,7,9,12b-decahydrobenzo[6,7]cyclohepta[1,2-f]indazol-3-ol;

(3R,4aS,12bR)-12b-ethyl-3-(methoxymethyl)-9-(pyridin-2-yl)-1,2,3,4,4a,5,6,7,9,12b-decahydrobenzo[6,7]cyclohepta[1,2-f]indazol-3-ol;

(3S,4aR,12bR)-3-(methoxymethyl)-12b-(pyridin-2-ylmethyl)-9-(pyridin-4-yl)-1,2,3,4,4a,5,6,7,9,12b-decahydrobenzo[6,7]cyclohepta[1,2-f]indazol-3-ol;

(3R,4aS,12bS)-3-(methoxymethyl)-12b-(pyridin-2-ylmethyl)-9-(pyridin-4-yl)-1,2,3,4,4a,5,6,7,9,12b-decahydrobenzo[6,7]cyclohepta[1,2-f]indazol-3-ol;

(3S,4aR,12bS)-12b-ethyl-3-(methoxymethyl)-9-(pyridin-4-yl)-1,2,3,4,4a,5,6,7,9,12b-decahydrobenzo[6,7]cyclohepta[1,2-f]indazol-3-ol;

(3R,4aS,12bS)-3-(methoxymethyl)-9-(2-methylpyridin-4-yl)-12b-(pyridin-2-ylmethyl)-1,2,3,4,4a,5,6,7,9,12b-decahydrobenzo[6,7]cyclohepta[1,2-f]indazol-3-ol;

(3S,4aR,12bR)-3-(methoxymethyl)-9-(2-methylpyridin-4-yl)-12b-(pyridin-2-ylmethyl)-1,2,3,4,4a,5,6,7,9,12b-decahydrobenzo[6,7]cyclohepta[1,2-f]indazol-3-ol;

(3S,4aR,12bS)-12b-ethyl-9-(4-fluorophenyl)-3-methyl-1,2,3,4,4a,5,6,7,9,12b-decahydrobenzo[6,7]cyclohepta[1,2-f]indazol-3-ol;

(3R,4aS,12bR)-12b-ethyl-9-(4-fluorophenyl)-3-methyl-1,2,3,4,4a,5,6,7,9,12b-decahydrobenzo[6,7]cyclohepta[1,2-f]indazol-3-ol;

(3R,4aS,12bS)-9-(4-fluorophenyl)-3-methyl-12b-(pyrimidin-2-ylmethyl)-1,2,3,4,4a,5,6,7,9,12b-decahydrobenzo[6,7]cyclohepta[1,2-f]indazol-3-ol;

(3S,4aR,12bR)-9-(4-fluorophenyl)-3-methyl-12b-(pyrimidin-2-ylmethyl)-1,2,3,4,4a,5,6,7,9,12b-decahydrobenzo[6,7]cyclohepta[1,2-f]indazol-3-ol;

(3S,4aR,12bR)-12b-(cyclopropylmethyl)-9-(4-fluorophenyl)-3-methyl-1,2,3,4,4a,5,6,7,9,12b-decahydrobenzo[6,7]cyclohepta[1,2-f]indazol-3-ol;

rac-(3R,4aS,12bS)-9-(4-fluorophenyl)-3-methyl-12b-(pyridin-2-ylmethyl)-1,2,3,4,4a,5,6,7,9,12b-decahydrobenzo[6,7]cyclohepta[1,2-f]indazol-3-ol;

(3R,4aS,12bS)-3-methyl-9-(2-methylpyridin-4-yl)-12b-(pyridin-2-ylmethyl)-1,2,3,4,4a,5,6,7,9,12b-decahydrobenzo[6,7]cyclohepta[1,2-f]indazol-3-ol;

(3S,4aR,12bR)-3-methyl-9-(2-methylpyridin-4-yl)-12b-(pyridin-2-ylmethyl)-1,2,3,4,4a,5,6,7,9,12b-decahydrobenzo[6,7]cyclohepta[1,2-f]indazol-3-ol;

2-((3R,4aS,12bS)-9-(4-fluorophenyl)-3-hydroxy-12b-(pyrimidin-2-ylmethyl)-1,2,3,4,4a,5,6,7,9,12b-decahydrobenzo[6,7]cyclohepta[1,2-f]indazol-3-yl)acetonitrile;

2-((3R,4aS,12bS)-9-(4-fluorophenyl)-3-hydroxy-12b-(pyrimidin-2-ylmethyl)-1,2,3,4,4a,5,6,7,9,12b-decahydrobenzo[6,7]cyclohepta[1,2-f]indazol-3-yl)acetonitrile;

2-((3S,4aR,12bR)-9-(4-fluorophenyl)-3-hydroxy-12b-(pyrimidin-2-ylmethyl)-1,2,3,4,4a,5,6,7,9,12b-decahydrobenzo[6,7]cyclohepta[1,2-f]indazol-3-yl)acetonitrile;

2-((3S,4aR,12bS)-12b-ethyl-9-(4-fluorophenyl)-3-hydroxy-1,2,3,4,4a,5,6,7,9,12b-decahydrobenzo[6,7]cyclohepta[1,2-f]indazol-3-yl)acetonitrile;

2-((3R,4aS,12bR)-12b-ethyl-9-(4-fluorophenyl)-3-hydroxy-1,2,3,4,4a,5,6,7,9,12b-decahydrobenzo[6,7]cyclohepta[1,2-f]indazol-3-yl)acetonitrile;

2-((3S,4aR,12bR)-12b-(cyclopropylmethyl)-9-(4-fluorophenyl)-3-hydroxy-1,2,3,4,4a,5,6,7,9,12b-decahydrobenzo[6,7]cyclohepta[1,2-f]indazol-3-yl)acetonitrile;

2-((3R,4aS,12bS)-12b-(cyclopropylmethyl)-9-(4-fluorophenyl)-3-hydroxy-1,2,3,4,4a,5,6,7,9,12b-decahydrobenzo[6,7]cyclohepta[1,2-f]indazol-3-yl)acetonitrile;

2-((3R,4aS,12bS)-3-hydroxy-12b-(pyridin-2-ylmethyl)-9-(pyridin-4-yl)-1,2,3,4,4a,5,6,7,9,12b-decahydrobenzo[6,7]cyclohepta[1,2-f]indazol-3-yl)acetonitrile;

2-((3S,4aR,12bR)-3-hydroxy-12b-(pyridin-2-ylmethyl)-9-(pyridin-4-yl)-1,2,3,4,4a,5,6,7,9,12b-decahydrobenzo[6,7]cyclohepta[1,2-f]indazol-3-yl)acetonitrile;

2-((3R,4aS,12bS)-3-hydroxy-9-(2-methylpyridin-4-yl)-12b-(pyridin-2-ylmethyl)-1,2,3,4,4a,5,6,7,9,12b-decahydrobenzo[6,7]cyclohepta[1,2-f]indazol-3-yl)acetonitrile;

2-((3S,4aR,12bR)-3-hydroxy-9-(2-methylpyridin-4-yl)-12b-(pyridin-2-ylmethyl)-1,2,3,4,4a,5,6,7,9,12b-decahydrobenzo[6,7]cyclohepta[1,2-f]indazol-3-yl)acetonitrile;

(3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carbonitrile;

(3S,4aS,12bR)-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carbonitrile;

N-(((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)methanesulfonamide;

2-(((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)isothiazolidine 1,1-dioxide;

N-(((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)ethanesulfonamide;

N-(((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)methanesulfonamide;

(3R,4aR,12bS)-9-(4-fluorophenyl)-12b-(hydroxymethyl)-3-(trifluoromethyl)-1,2,3,4,4a,5,6,7,9,12b-decahydrobenzo[6,7]cyclohepta[1,2-f]indazol-3-ol;

(3S,4aS,12bR)-9-(4-fluorophenyl)-12b-(hydroxymethyl)-3-(trifluoromethyl)-1,2,3,4,4a,5,6,7,9,12b-decahydrobenzo[6,7]cyclohepta[1,2-f]indazol-3-ol;

rac-(3R,4aR,12bS)-9-(4-fluorophenyl)-12b-(hydroxymethyl)-3-(trifluoromethyl)-1,2,3,4,4a,5,6,7,9,12b-decahydrobenzo[6,7]cyclohepta[1,2-f]indazol-3-ol;

2-((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)acetonitrile;

2-((3S,4aS,12bR)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)acetonitrile;

N-(((3S,4aS,12bR)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)acetamide;

N-(((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)methyl)acetamide;

((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)(pyridin-2-yl)methanone compound with ((3R,4aR,12bS)-9-(4-fluorophenyl)-3-hydroxy-3-(trifluoromethyl)-1,2,3,4,4a,5,6,7,9,12b-decahydrobenzo[6,7]cyclohepta[1,2-f]indazol-12b-yl)(pyridin-2-yl)methanone;

(3R,4aR,12bS)—N-Cyclopropyl-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carboxamide;

(3S,4aS,12bR)—N-cyclopropyl-9-(4-fluorophenyl)-3-hydroxy-3-(trifluoromethyl)-1,2,3,4,4a,5,6,7,9,12b-decahydrobenzo[6,7]cyclohepta[1,2-f]indazole-12b-carboxamide;

(3R,4aR,12bS)-8-Bromo-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol;

(3R,4aR,12bS)-12b-Ethyl-9-(4-fluorophenyl)-3-(trifluoromethyl)-1,2,3,4,4a,5,9,12b-octahydrobenzo[6,7]cyclohepta[1,2-f]indazol-3-ol;

(3R,4aS,12bS)-3-Ethyl-9-(4-fluorophenyl)-3-hydroxy-12b-(pyridin-2-ylmethyl)-1,2,3,4,4a,5,6,12b-octahydrobenzo[6,7]cyclohepta[1,2-f]indazol-7(9H)-one;

rac-(3S,4aR,12bR)-3-ethyl-9-(4-fluorophenyl)-3-hydroxy-12b-(pyridin-2-ylmethyl)-1,2,3,4,4a,5,6,12b-octahydrobenzo[6,7]cyclohepta[1,2-f]indazol-7(9H)-one;

(3R,4S,4aR,12bR)-12b-Ethyl-9-(4-fluorophenyl)-3-(trifluoromethyl)-1,2,3,4,4a,5,6,7,9,12b-decahydrobenzo[6,7]cyclohepta[1,2-f]indazole-3,4-diol;

(3S,4R,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazole-3,4-diol;

(2R,3S,4aS,12bR)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol;

(2S,3R,4aR,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol;

rac-(3R,4aS,12bR)-12b-Ethyl-9-(4-fluorophenyl)-3-hydroxy-3-methyl-1,3,4,4a,5,6,7,12b-octahydrobenzo[6,7]cyclohepta[1,2-f]indazol-2(9H)-one;

(3S,4aS,12bS)-12b-Ethyl-9-(4-fluorophenyl)-3-(trifluoromethyl)-1,2,3,4,4a,5,6,7,9,12b-decahydrobenzo[6,7]cyclohepta[1,2-f]indazol-3-yl dihydrogen phosphate;

(3R,4aR,12bR)-8-Bromo-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-ol;

(3R,4aR,12bR)-12b-Ethyl-9-(4-fluorophenyl)-8-methyl-3-(trifluoromethyl)-1,2,3,4,4a,5,6,7,9,12b-decahydrobenzo[6,7]cyclohepta[1,2-f]indazol-3-ol;

(3R,4aR,7S,12bR)-12b-Ethyl-9-(4-fluorophenyl)-3-(trifluoromethyl)-1,2,3,4,4a,5,6,7,9,12b-decahydrobenzo[6,7]cyclohepta[1,2-f]indazole-3,7-diol;

(3R,4aR,12bR)-12b-Ethyl-9-(4-fluorophenyl)-3-hydroxy-3-(trifluoromethyl)-1,2,3,4,4a,5,6,12b-octahydrobenzo[6,7]cyclohepta[1,2-f]indazol-7(9H)-one;

(3R,12bR)-12b-ethyl-9-(4-fluorophenyl)-3-(trifluoromethyl)-1,2,3,5,6,7,9,12b-octahydrobenzo[6,7]cyclohepta[1,2-f]indazol-3-ol;

(3S,12bS)-12b-ethyl-9-(4-fluorophenyl)-3-(trifluoromethyl)-1,2,3,5,6,7,9,12b-octahydrobenzo[6,7]cyclohepta[1,2-f]indazol-3-ol;

(2S,3R,4aR,12bR)-12b-Ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol;

(3R,4aR,12bR)-12b-Ethyl-3-ethynyl-9-(4-fluorophenyl)-1,2,3,4,4a,5,6,7,9,12b-decahydrobenzo[6,7]cyclohepta[1,2-f]indazol-3-ol;

(3S,4aS,12bS)-12b-ethyl-3-ethynyl-9-(4-fluorophenyl)-1,2,3,4,4a,5,6,7,9,12b-decahydrobenzo[6,7]cyclohepta[1,2-f]indazol-3-ol;

(3R,4aR,12bR)-12b-ethyl-9-(4-fluorophenyl)-3-(prop-1-yn-1-yl)-1,2,3,4,4a,5,6,7,9,12b-decahydrobenzo[6,7]cyclohepta[1,2-f]indazol-3-ol;

(3S,4aS,12bS)-12b-ethyl-9-(4-fluorophenyl)-3-(prop-1-yn-1-yl)-1,2,3,4,4a,5,6,7,9,12b-decahydrobenzo[6,7]cyclohepta[1,2-f]indazol-3-ol;

(3R,4aR,12bR)-3,12b-Diethyl-9-(4-fluorophenyl)-1,2,3,4,4a,5,6,7,9,12b-decahydrobenzo[6,7]cyclohepta[1,2-f]indazol-3-ol;

(3S,4aS,12bS)-3,12b-diethyl-9-(4-fluorophenyl)-1,2,3,4,4a,5,6,7,9,12b-decahydrobenzo[6,7]cyclohepta[1,2-f]indazol-3-ol;

(3S,4aR,12bR)-12b-Ethyl-9-(4-fluorophenyl)-3-hydroxy-3-(trifluoromethyl)-1,3,4,4a,5,6,7,12b-octahydrobenzo[6,7]cyclohepta[1,2-f]indazol-2(9H)-one;

(3R,4aS,12bS)-12b-ethyl-9-(4-fluorophenyl)-3-hydroxy-3-(trifluoromethyl)-1,3,4,4a,5,6,7,12b-octahydrobenzo[6,7]cyclohepta[1,2-f]indazol-2(9H)-one;

(2R,3S,4aR,12bR)-12b-Ethyl-9-(4-fluorophenyl)-2-methyl-3-(trifluoromethyl)-1,2,3,4,4a,5,6,7,9,12b-decahydrobenzo[6,7]cyclohepta[1,2-f]indazole-2,3-diol;

(2S,3R,4aS,12bS)-12b-ethyl-9-(4-fluorophenyl)-2-methyl-3-(trifluoromethyl)-1,2,3,4,4a,5,6,7,9,12b-decahydrobenzo[6,7]cyclohepta[1,2-f]indazole-2,3-diol;

(2R,3S,4aR,12bR)-12b-Ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol;

(2S,3R,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol;

(2S,3S,4aR,12bR)-12b-Ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol;

(2R,3R,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazole-2,3-diol;

(3R,4aS,12bR)-12b-Ethyl-3-(methoxymethyl)-9-(pyridin-4-yl)-1,2,3,4,4a,5,6,7,9,12b-decahydrobenzo[6,7]cyclohepta[1,2-f]indazol-3-ol;

rac-(3R,4aS,12bS)-3-(methoxymethyl)-9-(2-methylpyridin-4-yl)-12b-(pyridin-2-ylmethyl)-1,2,3,4,4a,5,6,7,9,12b-decahydrobenzo[6,7]cyclohepta[1,2-f]indazol-3-ol;

(3R,4aS,12bS)-12b-ethyl-9-(4-fluorophenyl)-3-((((R)-1-phenylethyl)amino)methyl)-1,2,3,4,4a,5,6,7,9,12b-decahydrobenzo[6,7]cyclohepta[1,2-f]indazol-3-ol;

(3S,4aR,12bR)-12b-ethyl-9-(4-fluorophenyl)-3-((((R)-1-phenylethyl)amino)methyl)-1,2,3,4,4a,5,6,7,9,12b-decahydrobenzo[6,7]cyclohepta[1,2-f]indazol-3-ol;

rac-(3R,4aS,12bS)-9-(4-Fluorophenyl)-3-methyl-12b-(pyridin-2-ylmethyl)-1,2,3,4,4a,5,6,7,9,12b-decahydrobenzo[3,4]cyclohepta[1,2-b]pyrazolo[4,3-e]pyridin-3-ol;

(3R,4aS,12bS)-9-(4-Fluorophenyl)-3-methyl-12b-(pyridin-2-ylmethyl)-1,2,3,4,4a,5,6,7,9,12b-decahydrobenzo[3,4]cyclohepta[1,2-b]pyrazolo[4,3-e]pyridin-3-ol;

(3S,4aR,12bR)-9-(4-Fluorophenyl)-3-methyl-12b-(pyridin-2-ylmethyl)-1,2,3,4,4a,5,6,7,9,12b-decahydrobenzo[3,4]cyclohepta[1,2-b]pyrazolo[4,3-e]pyridin-3-ol;

rac-(3R,4aS,12bS)-12b-Ethyl-9-(4-fluorophenyl)-3-(trifluoromethyl)-1,2,3,4,4a,5,6,7,9,12b-decahydrobenzo[3,4]cyclohepta[1,2-b]pyrazolo[4,3-e]pyridin-3-ol;

rac-(3R,4aR,12bR)-12b-ethyl-9-(4-fluorophenyl)-3-(trifluoromethyl)-1,2,3,4,4a,5,6,7,9,12b-decahydrobenzo[3,4]cyclohepta[1,2-b]pyrazolo[4,3-e]pyridin-3-ol;

(3S,4aS,12bS)-12b-Ethyl-9-(4-fluorophenyl)-3-(trifluoromethyl)-1,2,3,4,4a,5,6,7,9,12b-decahydrobenzo[3,4]cyclohepta[1,2-b]pyrazolo[4,3-e]pyridin-3-ol;

(3R,4aR,12bR)-12b-ethyl-9-(4-fluorophenyl)-3-(trifluoromethyl)-1,2,3,4,4a,5,6,7,9,12b-decahydrobenzo[3,4]cyclohepta[1,2-b]pyrazolo[4,3-e]pyridin-3-ol;

rac-(3R,4aR,12bR)-9-(4-Fluorophenyl)-12b-(pyridin-2-ylmethyl)-3-(trifluoromethyl)-1,2,3,4,4a,5,6,7,9,12b-decahydrobenzo[3,4]cyclohepta[1,2-b]pyrazolo[4,3-e]pyridin-3-ol;

(3R,4aS,12bS)-9-(4-fluorophenyl)-3-(methoxymethyl)-12b-(pyridin-2-ylmethyl)-1,2,3,4,4a,5,6,7,9,12b-decahydrobenzo[3,4]cyclohepta[1,2-b]pyrazolo[4,3-e]pyridin-3-ol;

(3S,4aR,12bR)-9-(4-fluorophenyl)-3-(methoxymethyl)-12b-(pyridin-2-ylmethyl)-1,2,3,4,4a,5,6,7,9,12b-decahydrobenzo[3,4]cyclohepta[1,2-b]pyrazolo[4,3-e]pyridin-3-ol;

(3R,4aS,12bS)-9-(4-fluorophenyl)-3-(methoxymethyl)-12b-(pyridin-2-ylmethyl)-1,2,3,4,4a,5,6,7,9,12b-decahydrobenzo[3,4]cyclohepta[1,2-b]pyrazolo[4,3-e]pyridin-3-ol;

(3S,4aR,12bR)-9-(4-fluorophenyl)-3-(methoxymethyl)-12b-(pyridin-2-ylmethyl)-1,2,3,4,4a,5,6,7,9,12b-decahydrobenzo[3,4]cyclohepta[1,2-b]pyrazolo[4,3-e]pyridin-3-ol;

2-((3S,4aR,12bR)-9-(4-fluorophenyl)-3-hydroxy-12b-(pyrimidin-2-ylmethyl)-1,2,3,4,4a,5,6,7,9,12b-decahydrobenzo[3,4]cyclohepta[1,2-b]pyrazolo[4,3-e]pyridin-3-yl)acetonitrile;

(3R,4aS,12bS)-9-(4-fluorophenyl)-3-methyl-12b-(pyrimidin-2-ylmethyl)-1,2,3,4,4a,5,6,7,9,12b-decahydrobenzo[3,4]cyclohepta[1,2-b]pyrazolo[4,3-e]pyridin-3-ol;

(3S,4aR,12bR)-9-(4-fluorophenyl)-3-methyl-12b-(pyrimidin-2-ylmethyl)-1,2,3,4,4a,5,6,7,9,12b-decahydrobenzo[3,4]cyclohepta[1,2-b]pyrazolo[4,3-e]pyridin-3-ol;

2-((3R,4aS,12bS)-9-(4-fluorophenyl)-3-hydroxy-12b-(pyrimidin-2-ylmethyl)-1,2,3,4,4a,5,6,7,9,12b-decahydrobenzo[3,4]cyclohepta[1,2-b]pyrazolo[4,3-e]pyridin-3-yl)acetonitrile;

2-((3R,4aR,12bR)-9-(4-fluorophenyl)-3-hydroxy-12b-(pyridin-2-ylmethyl)-1,2,3,4,4a,5,6,7,9,12b-decahydrobenzo[3,4]cyclohepta[1,2-b]pyrazolo[4,3-e]pyridin-3-yl)acetonitrile;

2-((3R,4aS,12bS)-9-(4-fluorophenyl)-3-hydroxy-12b-(pyridin-2-ylmethyl)-1,2,3,4,4a,5,6,7,9,12b-decahydrobenzo[3,4]cyclohepta[1,2-b]pyrazolo[4,3-e]pyridin-3-yl)acetonitrile;

(3R,4aR,12bR)-12b-ethyl-9-(4-(methylsulfonyl)phenyl)-3-(trifluoromethyl)-1,2,3,4,4a,5,6,7,9,12b-decahydrobenzo[6,7]cyclohepta[1,2-f]indazol-3-ol;

(3S,4aS,12bS)-12b-ethyl-9-(4-(methylsulfonyl)phenyl)-3-(trifluoromethyl)-1,2,3,4,4a,5,6,7,9,12b-decahydrobenzo[6,7]cyclohepta[1,2-f]indazol-3-ol;

(3S,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-yl sulfamate;

2-(((3S,4aS,12bS)-12b-Ethyl-9-(4-fluorophenyl)-3-(trifluoromethyl)-1,2,3,4,4a,5,6,7,9,12b-decahydrobenzo[6,7]cyclohepta[1,2-f]indazol-3-yl)oxy)acetamide;

2-(((3S,4aS,12bS)-12b-ethyl-9-(4-fluorophenyl)-3-(trifluoromethyl)-1,2,3,4,4a,5,6,7,9,12b-decahydrobenzo[6,7]cyclohepta[1,2-f]indazol-3-yl)oxy)acetic acid;

pharmaceutically acceptable salts, isomers, or stereoisomers thereof.

27. A pharmaceutical composition comprising the compound of claim 1, and a pharmaceutically acceptable carrier or excipient.

28. A pharmaceutical composition comprising a compound of claim 26 and a pharmaceutically acceptable carrier or excipient.

29. A method of treating a disease or condition comprising administering a therapeutically effective amount of the compound of claim 1 wherein the disease or condition to be treated is Crohn's disease, inflammatory bowel disease, juvenile idiopathic arthritis, juvenile rheumatoid arthritis, rheumatoid arthritis, ulcerative colitis, or uveitis.

30. A method of treating a disease or condition comprising administering a therapeutically effective amount of a compound of claim 26 wherein the disease or condition to be treated is Crohn's disease, inflammatory bowel disease, juvenile idiopathic arthritis, juvenile rheumatoid arthritis, rheumatoid arthritis, ulcerative colitis, or uveitis.

* * * * *